United States Patent
Zhang et al.

(10) Patent No.: US 11,713,353 B2
(45) Date of Patent: Aug. 1, 2023

(54) SINGLE-DOMAIN ANTIBODIES AND VARIANTS THEREOF AGAINST PD-1

(71) Applicant: Nanjing Legend Biotech Co., Ltd., Jiangsu (CN)

(72) Inventors: Yafeng Zhang, Jiangsu (CN); Shu Wu, Jiangsu (CN); Shuai Yang, Jiangsu (CN); Chuan-Chu Chou, Westfield, NJ (US)

(73) Assignee: Nanjing Legend Biotech Co., Ltd., Nanjing (CN)

( * ) Notice: Subject to any disclaimer, the term of this patent is extended or adjusted under 35 U.S.C. 154(b) by 51 days.

(21) Appl. No.: 16/962,023

(22) PCT Filed: Jan. 15, 2019

(86) PCT No.: PCT/CN2019/071691
§ 371 (c)(1),
(2) Date: Jul. 14, 2020

(87) PCT Pub. No.: WO2019/137541
PCT Pub. Date: Jul. 18, 2019

(65) Prior Publication Data
US 2020/0347135 A1 Nov. 5, 2020

(30) Foreign Application Priority Data
Jan. 15, 2018 (WO) ................ PCT/CN2018/072589

(51) Int. Cl.
*C07K 16/28* (2006.01)
*A61K 39/00* (2006.01)

(52) U.S. Cl.
CPC .... *C07K 16/2818* (2013.01); *A61K 2039/505* (2013.01); *C07K 2317/22* (2013.01); *C07K 2317/24* (2013.01); *C07K 2317/31* (2013.01); *C07K 2317/565* (2013.01); *C07K 2317/567* (2013.01); *C07K 2317/569* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell |
| RE30,985 E | 6/1982 | Cartaya |
| 4,419,446 A | 12/1983 | Howley |
| 4,560,655 A | 12/1985 | Baker |
| 4,601,978 A | 7/1986 | Karin |
| 4,657,866 A | 4/1987 | Kumar |
| 4,676,980 A | 6/1987 | Segal |
| 4,767,704 A | 8/1988 | Cleveland |
| 4,816,567 A | 3/1989 | Cabilly |
| 4,927,762 A | 5/1990 | Darfler |
| 4,965,199 A | 10/1990 | Capon |
| 5,122,469 A | 6/1992 | Mather |
| 5,229,275 A | 7/1993 | Goroff |
| 5,264,365 A | 11/1993 | Georgiou |
| 5,500,362 A | 3/1996 | Robinson |
| 5,508,192 A | 4/1996 | Georgiou |
| 5,545,806 A | 8/1996 | Lonberg |
| 5,545,807 A | 8/1996 | Surani |
| 5,565,332 A | 10/1996 | Hoogenboom et al. |
| 5,567,610 A | 10/1996 | Borrebaeck |
| 5,569,825 A | 10/1996 | Lonberg |
| 5,571,894 A | 11/1996 | Wels |
| 5,573,905 A | 11/1996 | Lerner |
| 5,587,458 A | 12/1996 | King |
| 5,591,669 A | 1/1997 | Krimpenfort et al. |
| 5,591,828 A | 1/1997 | Bosslet |
| 5,624,821 A | 4/1997 | Winter |
| 5,625,126 A | 4/1997 | Lonberg |
| 5,633,425 A | 5/1997 | Lonberg |
| 5,639,635 A | 6/1997 | Joly |
| 5,641,870 A | 6/1997 | Rinderknecht |
| 5,648,237 A | 7/1997 | Carter |
| 5,648,260 A | 7/1997 | Winter |
| 5,661,016 A | 8/1997 | Lonberg |
| 5,731,168 A | 3/1998 | Carter |
| 5,739,277 A | 4/1998 | Presta |
| 5,750,373 A | 5/1998 | Garrard |
| 5,770,429 A | 6/1998 | Lonberg et al. |
| 5,821,337 A | 10/1998 | Carter |
| 5,837,234 A | 11/1998 | Gentile |
| 5,840,523 A | 11/1998 | Simmons |
| 5,869,046 A | 2/1999 | Presta |
| 6,013,605 A | 1/2000 | Rees |
| 6,027,888 A | 2/2000 | Georgiou |

(Continued)

FOREIGN PATENT DOCUMENTS

| | | |
|---|---|---|
| CN | 1388136 A | 1/2003 |
| CN | 101210048 A | 7/2008 |

(Continued)

OTHER PUBLICATIONS

Almagro, J. et al. (Jan. 1, 2008). "Humanization of Antibodies," Frontiers in Bioscience 13:1619-1633.
Anderson, A. C. et al. (May 17, 2016). "Lag-3, Tim-3, and TIGIT: Co-Inhibitory Receptors with Specialized Functions in Immune Regulation," Immunity 44(5):989-1004.
Arie, J-P. et al. (Jan. 1, 2001). "Chaperone Function of FkpA, A Heat Shock Prolyl Isomerase, in the Periplasm of *Escherichia coli*," Molecular Micorbiology 39(1):199-210.
Armour, K.L. et al. (1999). "Recombinant Human IgG Molecules Lacking Fcγ Receptor I Binding and Monocyte Triggering Activities," Eur. J. Immunol. 29:2613-2624.
Baca, M. et al. (Apr. 18, 1997). "Antibody Humanization Using Monovalent Phage Display," J. Biol. Chem. 272 (16):10678-10684.

(Continued)

*Primary Examiner* — Marianne P Allen
(74) *Attorney, Agent, or Firm* — Fish & Richardson P.C.

(57) ABSTRACT

Provided are constructs comprising a single-domain antibody (sdAb) moiety that specifically recognizes PD-1. Also provided are methods of making and using these constructs.

16 Claims, 29 Drawing Sheets
Specification includes a Sequence Listing.

(56) References Cited

U.S. PATENT DOCUMENTS

| | | |
|---|---|---|
| 6,075,181 A | 6/2000 | Kucherlapati |
| 6,083,715 A | 7/2000 | Georgiou |
| 6,150,584 A | 11/2000 | Kucherlapati |
| 6,194,551 B1 | 2/2001 | Idusogie |
| 6,602,684 B1 | 8/2003 | Umana |
| 6,737,056 B1 | 5/2004 | Presta |
| 6,982,321 B2 | 1/2006 | Winter |
| 7,041,870 B2 | 5/2006 | Tomizuka |
| 7,087,409 B2 | 8/2006 | Barbas, III |
| 7,189,826 B2 | 3/2007 | Rodman |
| 7,332,581 B2 | 2/2008 | Presta |
| 7,371,826 B2 | 5/2008 | Presta |
| 7,371,849 B2 | 5/2008 | Honda |
| 7,504,256 B1 | 3/2009 | Ogawa |
| 7,521,541 B2 | 4/2009 | Eigenbrot |
| 7,527,791 B2 | 5/2009 | Adams |
| 8,754,287 B2 | 6/2014 | Macdonald |
| 9,932,412 B2 | 4/2018 | Kim et al. |
| 10,316,093 B2 | 6/2019 | Cheung et al. |
| 10,385,137 B2 | 8/2019 | Baty et al. |
| 11,447,573 B2 | 9/2022 | Chou et al. |
| 11,472,881 B2 | 10/2022 | Zhang et al. |
| 2002/0164328 A1 | 11/2002 | Shinkawa |
| 2003/0115614 A1 | 6/2003 | Kanda |
| 2003/0157108 A1 | 8/2003 | Presta |
| 2004/0093621 A1 | 5/2004 | Shitara |
| 2004/0109865 A1 | 6/2004 | Niwa |
| 2004/0110282 A1 | 6/2004 | Kanda |
| 2004/0110704 A1 | 6/2004 | Yamane |
| 2004/0132140 A1 | 7/2004 | Satoh |
| 2004/0259150 A1 | 12/2004 | Nakamura |
| 2005/0014934 A1 | 1/2005 | Hinton |
| 2005/0031613 A1 | 2/2005 | Nakamura |
| 2005/0079574 A1 | 4/2005 | Bond |
| 2005/0119455 A1 | 6/2005 | Fuh |
| 2005/0123546 A1 | 6/2005 | Umana |
| 2005/0255115 A1 | 11/2005 | Huang et al. |
| 2005/0266000 A1 | 12/2005 | Bond |
| 2005/0272916 A1 | 12/2005 | Hanai |
| 2006/0025576 A1 | 2/2006 | Miller |
| 2007/0061900 A1 | 3/2007 | Murphy |
| 2007/0071675 A1 | 3/2007 | Wu |
| 2007/0117126 A1 | 5/2007 | Sidhu |
| 2007/0134759 A1 | 6/2007 | Nishiya |
| 2007/0160598 A1 | 7/2007 | Dennis |
| 2007/0178552 A1 | 8/2007 | Arathoon |
| 2007/0237764 A1 | 10/2007 | Birtalan |
| 2007/0292936 A1 | 12/2007 | Barthelemy |
| 2008/0241884 A1 | 10/2008 | Shitara |
| 2009/0002360 A1 | 1/2009 | Chen |
| 2009/0307787 A1 | 12/2009 | Grosveld |
| 2010/0122358 A1 | 5/2010 | Brueggemann |
| 2011/0028695 A1 | 2/2011 | Revets |
| 2011/0229461 A1 | 9/2011 | Tyson |
| 2011/0287009 A1 | 11/2011 | Scheer |
| 2013/0095098 A1 | 4/2013 | Tyson |
| 2013/0156769 A1 | 6/2013 | Kufer et al. |
| 2013/0189735 A1 | 7/2013 | Zardi |
| 2014/0127210 A1 | 5/2014 | Kim |
| 2015/0086541 A1 | 3/2015 | Aguilar-cordova |
| 2015/0202291 A1 | 7/2015 | Bosch |
| 2015/0210769 A1 | 7/2015 | Freeman et al. |
| 2015/0232555 A1 | 8/2015 | Carven |
| 2015/0289489 A1 | 10/2015 | Macdonald |
| 2016/0000842 A1 | 1/2016 | Song et al. |
| 2016/0075787 A1 | 3/2016 | Zheng et al. |
| 2016/0083476 A1 | 3/2016 | Baty et al. |
| 2016/0145355 A1 | 5/2016 | Saha et al. |
| 2016/0166685 A1 | 6/2016 | Cheung et al. |
| 2016/0272708 A1 | 9/2016 | Chen |
| 2016/0272960 A1 | 9/2016 | Thanos et al. |
| 2016/0368994 A1 | 12/2016 | Kelley et al. |
| 2017/0088617 A1 | 3/2017 | Konopitzky et al. |
| 2017/0137517 A1* | 5/2017 | Bowman ................ A61P 31/04 |
| 2017/0334995 A1 | 11/2017 | Zettl et al. |
| 2018/0086831 A1 | 3/2018 | Pule et al. |
| 2019/0202935 A1 | 7/2019 | Chou |
| 2019/0233519 A1 | 8/2019 | Zhang |
| 2019/0270812 A1 | 9/2019 | Leopold et al. |
| 2020/0317787 A1 | 10/2020 | Li et al. |
| 2020/0369770 A1 | 11/2020 | Zhang et al. |
| 2021/0017279 A1 | 1/2021 | Zhang et al. |
| 2021/0054071 A1 | 2/2021 | Zhang et al. |
| 2021/0275590 A1 | 9/2021 | Zhang et al. |
| 2021/0277126 A1 | 9/2021 | Zhang et al. |

FOREIGN PATENT DOCUMENTS

| | | |
|---|---|---|
| CN | 102369215 A | 3/2012 |
| CN | 105754990 A | 7/2016 |
| CN | 106715469 | 5/2017 |
| CN | 106939050 A | 7/2017 |
| CN | 107001465 A | 8/2017 |
| CN | 108047333 A | 5/2018 |
| CN | 109897111 A | 6/2019 |
| EP | 0308936 A2 | 3/1989 |
| EP | 0368684 A1 | 5/1990 |
| EP | 0404097 A2 | 12/1990 |
| EP | 1792991 A1 | 6/2007 |
| EP | 3263702 A1 | 1/2018 |
| EP | 3459597 A1 | 3/2019 |
| EP | 3998287 A1 | 5/2022 |
| JP | 2008523795 A | 7/2008 |
| JP | 2009504191 A | 2/2009 |
| JP | 2010530753 A | 9/2010 |
| JP | 2011504742 A | 2/2011 |
| JP | 2013-505923 | 2/2013 |
| JP | 2014090721 A | 5/2014 |
| JP | 2014-515017 | 6/2014 |
| JP | 2014519029 A | 8/2014 |
| JP | 2014525918 A | 10/2014 |
| JP | 2015504306 A | 2/2015 |
| JP | 2017-506067 | 3/2017 |
| KR | 20100097720 | 9/2010 |
| KR | 2014003193 6 | 3/2014 |
| KR | 20160108568 | 9/2016 |
| TW | 201922781 A | 6/2019 |
| WO | 1987000195 A1 | 1/1987 |
| WO | 1990003430 A1 | 4/1990 |
| WO | 1991000360 A1 | 1/1991 |
| WO | 199110741 A1 | 7/1991 |
| WO | 1993001161 A1 | 1/1993 |
| WO | 1993008829 A1 | 5/1993 |
| WO | 1993011161 A1 | 6/1993 |
| WO | 1993016185 A2 | 8/1993 |
| WO | 1994004678 A1 | 3/1994 |
| WO | 1994004690 A1 | 3/1994 |
| WO | 1994011026 A2 | 5/1994 |
| WO | 1994029351 A2 | 12/1994 |
| WO | 1996016673 A1 | 6/1996 |
| WO | 1996027011 A1 | 9/1996 |
| WO | 1996033735 A1 | 10/1996 |
| WO | 1996034096 A1 | 10/1996 |
| WO | 1996034103 A1 | 10/1996 |
| WO | 1997017852 A1 | 5/1997 |
| WO | 1997030087 A1 | 8/1997 |
| WO | 1997049805 A2 | 12/1997 |
| WO | 1998022141 A2 | 5/1998 |
| WO | 1998024893 A2 | 6/1998 |
| WO | 1998050431 A2 | 11/1998 |
| WO | 1998058964 A1 | 12/1998 |
| WO | 1999022764 A1 | 5/1999 |
| WO | 1999037681 A2 | 7/1999 |
| WO | 1999051642 A1 | 10/1999 |
| WO | 2000027435 A1 | 5/2000 |
| WO | 2000043507 A1 | 7/2000 |
| WO | 2000061739 A1 | 10/2000 |
| WO | 2001014424 A2 | 3/2001 |
| WO | 2001029246 A1 | 4/2001 |
| WO | 2001077137 A1 | 10/2001 |
| WO | 2001090190 A2 | 11/2001 |
| WO | 2002031140 A1 | 4/2002 |
| WO | 2002085945 A2 | 10/2002 |
| WO | 2003011878 A2 | 2/2003 |

(56) References Cited

FOREIGN PATENT DOCUMENTS

| | | |
|---|---|---|
| WO | 2003014161 A2 | 2/2003 |
| WO | 2003025020 A1 | 3/2003 |
| WO | 2003035694 A2 | 5/2003 |
| WO | 2003084570 A1 | 10/2003 |
| WO | 2003085107 A1 | 10/2003 |
| WO | 2004042072 A2 | 5/2004 |
| WO | 2004049794 A2 | 6/2004 |
| WO | 2004056312 A2 | 7/2004 |
| WO | 2004092219 A2 | 10/2004 |
| WO | 2005035586 A1 | 4/2005 |
| WO | 2005035778 A1 | 4/2005 |
| WO | 2005053742 A1 | 6/2005 |
| WO | 2003085119 A1 | 8/2005 |
| WO | 2005100402 A1 | 10/2005 |
| WO | 2006003388 A2 | 1/2006 |
| WO | 2006008548 A2 | 1/2006 |
| WO | 2006029879 A2 | 3/2006 |
| WO | 2006030220 A1 | 3/2006 |
| WO | 2006064136 A1 | 6/2006 |
| WO | 2006138670 A2 | 12/2006 |
| WO | 2007024715 A2 | 3/2007 |
| WO | 2007112940 A2 | 10/2007 |
| WO | 2008077546 A1 | 7/2008 |
| WO | 2008156712 A1 | 12/2008 |
| WO | 2009068649 A2 | 6/2009 |
| WO | 2009089004 A1 | 7/2009 |
| WO | 2010097597 A1 | 9/2010 |
| WO | 2010112193 A1 | 10/2010 |
| WO | 2011036460 A1 | 3/2011 |
| WO | 2012155019 A1 | 11/2012 |
| WO | 2012158818 A2 | 11/2012 |
| WO | 2013019906 A1 | 2/2013 |
| WO | 2013072415 A1 | 5/2013 |
| WO | 2013112986 A1 | 8/2013 |
| WO | 2014206107 A1 | 12/2014 |
| WO | 2014209804 A1 | 12/2014 |
| WO | 2015035606 A1 | 3/2015 |
| WO | 2016024231 A1 | 2/2016 |
| WO | 2016061142 A1 | 4/2016 |
| WO | 2016077397 A2 | 5/2016 |
| WO | 2016154473 A1 | 9/2016 |
| WO | 2016168766 A1 | 10/2016 |
| WO | 2016187594 A1 | 11/2016 |
| WO | 2016200782 A1 | 12/2016 |
| WO | 2016201389 A2 | 12/2016 |
| WO | 2017024515 A1 | 2/2017 |
| WO | 2017025051 A1 | 2/2017 |
| WO | 2017037707 A1 | 3/2017 |
| WO | 2017053748 A2 | 3/2017 |
| WO | 2017132279 A1 | 3/2017 |
| WO | 2017059095 A1 | 4/2017 |
| WO | 2017059387 A1 | 4/2017 |
| WO | 2017087587 A1 | 5/2017 |
| WO | 2017087589 A2 | 5/2017 |
| WO | 2017087901 A2 | 5/2017 |
| WO | 2017125897 A1 | 7/2017 |
| WO | 2017143406 A1 | 8/2017 |
| WO | 2017165681 A1 | 9/2017 |
| WO | 2017194438 A1 | 11/2017 |
| WO | 2017196847 A1 | 11/2017 |
| WO | 2018014260 A1 | 1/2018 |
| WO | 2018014855 A1 | 1/2018 |
| WO | 2018068201 A1 | 4/2018 |
| WO | 2018068695 A1 | 4/2018 |
| WO | 2019129053 A1 | 7/2019 |
| WO | 2019129221 A1 | 7/2019 |
| WO | 2019134710 A1 | 7/2019 |
| WO | 2019137541 A1 | 7/2019 |
| WO | 2019179434 A1 | 9/2019 |
| WO | 2019185040 A1 | 10/2019 |
| WO | 2020052542 A1 | 3/2020 |
| WO | 2020052543 A1 | 3/2020 |
| WO | 2021004480 A1 | 1/2021 |

OTHER PUBLICATIONS

Bachmann, B.J. (1987). "Section G. Strains and Useful Strain Constructions. Derivations and Genotypes of Some Mutant Derivatives of *Escherichia coli* K-12," Cellular and Molecular Biology, vol. 2, Neidhardt, F. C. et al., Washington, D.C., American Society for Microbiology, pp. 1190-1219.

Balzano, C. et al. (1992). "CTLA-4 and CD28: Similar Proteins, Neighbouring Genes," Int. J. Cancer Suppl. 7:28-32. (Abstract Only).

Barbas III, C.F. et al. (Apr. 1994). "In Vitro Evolution Of A Neutralizing Human Antibody To Human Immunodeficiency Virus Type 1 To Enhance Affinity and Broaden Strain Cross-Reactivity," Proc Nat. Acad. Sci. USA 91:3809-3813.

Barnes, D. et al. (Mar. 1, 1980). "Methods for Growth of Cultured Cells In Serum-Free Medium," Anal. Biochem. 102(2):255-270.

Bass, S. et al. (1990). "Hormone Phage: An Enrichment Method for Variant Proteins With Altered Binding Properties," Proteins 8:309-314.

Bao, F. et al. (May 7, 2017) "Construction And Identification Of Natural Single Domain Antibody Library Of Bactrian Camel," Animal Husbandry and Feed Science (Inner Mongolia) 38(5):2 pages. (English Abstract Only).

Boerner, P. et al. (Jul. 1, 1991). "Production of a Antigen-Specific Human Monoclonal Antibodies from In Vitro-Primed Human Splenocytes," J. Immunol. 147(1):86-95.

Bothmann, H. et al., (Jun. 2, 2000). "The Periplasmic *Escherichia coli* Peptidylprolyl cis,trans-Isomerase FkpA," The Journal of Biological Chemistry 275(22):17100-17105.

Brennan, M. et al. (Jul. 5, 1985). "Preparation of Bispecific Antibodies by Chemical Recombination of Monoclonal Immunoglobulin G1 Fragments," Science 229:81-83.

Brown, M. et al. (1996) "Tolerance to Single, but Not Multiple, Amino Acid Replacements in Antibody VH CDR2," J. Immunol. 156:3285-3291.

Brüggemann, M. et al. (1993). "Designer Mice: The Production of Human Antibody Repertoires in Transgenic Animals," Year in Immuno. 7:33-40.

Brüggemann, M. et al. (Nov. 1, 1987). "Comparison of the Effector Functions of Human Immunoglobulins Using a Matched Set of Chimeric Antibodies," J. Exp. Med. 166:1351-1361.

Capel, P.J. et al. (Feb. 1994). "Heterogeneity of Human IgG Fc Receptors," Immunomethods 4(1):25-34.

Caron, P.C. et al. (Oct. 1, 1992). "Engineering Humanized Dimeric Forms of IgG Are More Effective Antibodies," J. Exp Med. 176:1191-1195.

Carter, L. et al. (Mar. 2002). "PD-1: PD-L Inhibitory Pathway Affects Both CD4(+) and CD8(+) T Cells And Is Overcome By IL-2," Eur. J. Immunol. 32(3):634-643.

Carter, P. et al. (Feb. 1992). "High Level *Escherichia coli* Expression and Production of a Bivalent Humanized Antibody Fragment," Bio/Technology 10:163-167.

Carter, P. et al. (May 1992). "Humanization of an Anti-p185HER2 Antibody for Human Cancer Therapy," Proc. Natl. Acad. Sci. USA 89:4285-4289.

Chen, W. et al. (2010). "A Large Human Domain Antibody Library Combining Heavy And Light Chain CDR3 Diversity," Molecular Immunology 47(4):912-921.

Chen, X.J. et al. (Dec. 31, 2007) "Construction, Expression And Functional Characterization Of Single Chain Variable Fragments (Scfv) Against Human CD33 Antigen," Xi Bao Yu Fen Zi Mian Yi Xue Za Zhi. 23(12):1147-1149, 2 pages. (English Abstract Only).

Chen, Y. et al. (1999). "Selection and Analysis of an Optimized Anti-VEGF Antibody: Crystal Structure of an Affinity-Matured Fab In Complex With Antigen," J. Mol. Biol 293:865-881.

Chothia, C. et al. (Aug. 20, 1987). "Canonical Structures for the Hypervariable Regions of Immunoglobulins," J. Mol. Biol. 196(4):901-917.

Chowdhury, P.S. (2008). "Engineering Hot Spots for Affinity Enhancement of Antibodies," Methods Mol. Biol. 207:179-196.

Clackson, T. et al. (Aug. 15, 1991). "Making Antibody Fragments Using Phage Display Libraries," Nature 352:624-628.

(56) References Cited

OTHER PUBLICATIONS

Clynes, R. et al. (Jan. 1998). "Fc Receptors are Required in Passive and Active Immunity to Melanoma," Proc. Natl. Acad. Sci. U.S.A. 95:652-656.

Cole, S.P.C. et al. (1985). "The EBV-Hybridoma Technique and Its Applicaton to Human Lung Cancer," in Monoclonal Antibodies and Cancer Therapy, Alan R. Liss, p. 77-96.

Conrath, K.E. et al. (Mar. 9, 2001). "Camel Single-domain Antibodies as Modular Building Units in Bispecific and Bivalent Antibody Constructs" J. Biol. Chem. 276(10):7346-7350.

Cragg, M.S. et al. (Apr. 1, 2004). "Antibody Specificity Controls In Vivo Effector Mechanisms Of Anti-CD20 Reagents," Blood 103(7):2738-2743.

Cragg, M.S. et al. (Feb. 1, 2003). "Complement-Mediated Lysis By Anti-CD20 Mab Correlates With Segregation Into Lipid Rafts," Blood 101(3):1045-1052.

Cunningham, B.C. et al. (Jun. 2, 1989). "High-Resolution Epitope Mapping of hGH-Receptor Interactions by Alanine-Scanning Mutagenesis," Science 244:1081-1085.

Dall'Acqua, W.F. et al. (2005). "Antibody Humanization by Framework Shuffling," Methods 36:43-60.

Davies, J. et al. (1996). "Single Antibody Domains as Small Recognition Units: Design And In Vitro Antigen Selection of Camelized, Human VH Domains with Improved Protein Stability," Protein Engineering 9(6):531-537.

Davies, J. et al. (Feb. 21, 1994). "'Camelising' Human Antibody Fragments: NMR Studies on VH Domains," FEBS Letters 339(3):285-290.

Daëron, M. (1997). "Fc Receptor Biology," Ann. Rev. Immunol. 15:203-234.

De Haas, M. et al. (Oct. 1995). "Fcγ Gamma receptors of Phagocytes," J. Lab. Clin. Med. 126:330-341.

Duncan, A.R. et al. (Apr. 21, 1988). "The Binding Site for C1q on IgG," Nature 322:738-740.

Fan, G. et al. (2015). "Bispecific Antibodies and their Applications," J. Hematol & Oncol. 8(130):1-14.

Fellouse, F.A. et al. (Aug. 24, 2004). "Synthetic Antibodies from a Four-Amino-Acid Code: A Dominant Role for Tyrosine in Antigen Recognition," Proc. Natl. Acad. Sci. USA 101(34):12467-12472.

Fishwild, D.M. et al. (Jul. 1996). "High-Avidity Human IgGκ Monoclonal Antibodies from a Novel Strain of Minilocus Transgenic Mice," Nature Biotechnol. 14:845-851.

Freeman, G.J. et al. (2000, e-pub. Oct. 2, 2000). "Engagement of the PD-1 Immunoinhibitory Receptor by a Novel B7 Family Member Leads to Negative Regulation of Lymphocyte Activation," J. Exp. Med. 192:1027-1034.

Fromentin, R. et al. (Jul. 14, 2016). "CD4+ T Cells Expressing PD-1, TIGIT and LAG-3 Contribute to HIV Persistence during ART," PLOS Athogens 12(7):1-19.

Fulkerson, P.C. et al. (2013, e-pub. Jan. 21, 2013). "Targeting Eosinophils in Allergy, Inflammation and Beyond," Nat Rev Drug Discov 12(2):117-129, 23 pages.

Gazzano-Santoro, H. et al. (Mar. 28, 1997). "A Non-Radioactive Complement-Dependent Cytotoxicity Assay for Anti-CD20 Monoclonal Antibody," J. Immunol. Methods 202:163-171.

Geering, B. et al. (Feb. 2015). "Synthetic Immunology: Modulating the Human Immune System," Trends Biotechnol. 33(2):65-79.

Ghetie, V. et al. (1997). "Increasing the Serum Persistence of an IgG Fragment by Random Mutagenesis," Nat Biotech 15:637-640.

Ghetie, V. et al. (Dec. 1997). "FcRn: the MHC Class I-related Receptor That Is More Than An IgG Transporter," Immunol. Today 18(12):592-598.

Goding, J.W. (1986). "Production of Monoclonal Antibodies," Chapter 3 in Monoclonal Antibodies: Principles and Practice, Academic Press, New York, pp. 59-103.

Graham, F.L. et al. (1977). "Characteristics Of A Human Cell Line Transformed By DNA From Human Adenovirus Type 5," Journal General Virology 36(1):59-74.

Greenberg, A.S. et al. (Mar. 9, 1995). "A New Antigen Receptor Gene Family That Undergoes Rearrangement And Extensive Somatic Diversification In Sharks" Nature 374(6518):168-173.

Griffith, A.D. et al. (1993). "Human Anti-Self Antibodies with High Specificity from Phage Display Libraries," EMBO J. 12(2):725-734.

Grosso et al., "LAG-3 regulates CD8+ T cell accumulation and effector function in murine self-and tumor-tolerance systems," J. Clin. Invest (2007) 117:3383-3392.

Gruber, M. et al. (1994). "Efficient Tumor Cell Lysis Mediated by a Bispecific Single Chain Antibody Expressed in *Escherichia coli*," J. Immunol. 152:5368-5374.

Guss, B. et al. (Jul. 1986). "Structure of the IgG-Binding Regions of Streptococcal Protein G," EMBO J. 5 (7):1567-1575.

Guyer, R.L. et al. (Aug. 1976). "Immunoglobulin Binding By Mouse Intestinal Epithelial Cell Receptors," J. Immunol. 117(2):587-593.

Ham, R.G. et al. (1979). "Media and Growth Requirements," Meth. Enzymol. 58:44-93.

Hamers-Casterman, C. et al. (Jun. 3, 1993). "Naturally Occurring Antibodies Devoid of Light Chains," Nature 363:446-448.

Hammerling, G. et al. (1981). "Monoclonal Antibodies and T-Cell Hybridomas," in Monoclonal Antibodies and T-Cell Hybridomas, Elsevier/North Holland Biomedical Press, New York, pp. 563-586.

Hara, H. et al. (1996) "Overproduction Of Penicillin-Binding Protein 7 Suppresses Thermosensitive Grovvth Defect At Low Osmolarity Due To An Spr Mutation Of *Escherichia coli*," Microhial Drug Resistance 2(1):63-72.

Harris, W.J. (1995). "Production of Humanized Monoclonal and Antibodies for in vivo Imaging and Therapy," Biochem. Soc. Transactions 23:1035-1038.

Hassanzadeh-Ghassabeh, G. et al. (2013, e-pub. Jun. 4, 2013). "Nanobodies and their Potential Applications," Nanomedicine (Lond) 8(6):1013-1026.

Hawkins, R.E. et al. (1992). "Selection of Phage Antibodies by Binding Affinity: Mimicking Affinity Maturations," J. Mol. Biol. 226:889-896.

Hellstrom, I. et al. (Mar. 1985). "Strong Antitumor Activities of IgG3 Antibodies to a Human Melanoma-associated Ganglioside," Proc. Natl. Acad. Sci. USA 82:1499-1502.

Hellstrom, I. et al. (Sep. 1986). "Antitumor Effects of L6, an IgG2a Antibody That Reacts With Most Human Carcinomas," Proc. Natl. Acad. Sci. USA 83:7059-7063.

Hinton, P.R. et al. (Feb. 20, 2004). "Engineered Human IgG Antibodies with Longer Serum Half-lives in Primates," J. Biol. Chem. 279(8):6213-6216.

Hmila, I. et al. (Aug. 2008, e-pub. Jul. 9, 2008). "VHH Bivalent Domains And Chimeric Heavy Chain-Only Antibodies With High Neutralizing Efficacy For Scorpion Toxin Aahi," Molecular Immunology 45(14):3847-3856.

Holliger, P. et al. (Jul. 1993). "Diabodies": Small Bivalent And Bispecific Antibody Fragments, Proc. Natl. Acad. Sci. USA 90:6444-6448.

Holt, L.J. et al. (Nov. 2003) "Domain Antibodies: Proteins For Therapy," Trends in Biotechnology 21(11):484-490.

Hongo, J.A.S. et al. (1995). "Development and Characterization of Murine Monoclonal Antibodies to the Latency-Associated Peptide of Transforming Growth Factor Beta1," Hybridoma, 14(3):253-260.

Hoogenboom, H.R. (2002). "Overview of Antibody Phage-Display Technology and its Applications," in Chapter 1 of Methods in Molecular Biology, O'Brien, P.M. (ed.) et al., Humana Press Inc., Totowa, NJ, 178:1-37.

Hoogenboom, H.R. et al. (Sep. 20, 1992). "By-Passing Immunisation Human Antibodies From Synthetic Repertoires Of Germline VH Gene Segments Rearranged In Vitro," J. Mol. Biol. 227(2):381-388.

Huang, C. T. et al. (Oct. 2004). "Role Of LAG-3 In Regulatory T Cells," Immunity 21(4):503-513.

Hudson, P.J. et al. (Jan. 2003). "Engineered Antibodies," Nature Medicine 9(1):129-134.

Hurle, M.R. et al. (1994). "Protein Engineering Techniques for Antibody Humanization," Curr. Op. Biotech. 5 (4):428-433.

(56) References Cited

OTHER PUBLICATIONS

Idusogie, E.E. et al. (2000). "Mapping of the C1q Binding Site on Rituxan, a Chimeric Antibody With a Human IgG1 Fc," J. Immunol. 164:4178-4184.
International Preliminary Report on Patentability dated Jun. 30, 2020, for PCT Patent Application No. PCT/CN2018/124979, filed Dec. 28, 2018, 5 pages.
International Preliminary Report on Patentability dated Jul. 14, 2020, for PCT Patent Application No. PCT/CN2019/070873, filed Jan. 8, 2019, 7 pages.
International Preliminary Report on Patentability dated Jul. 21, 2020 for PCT Application No. PCT/CN2019/071691 filed on Jan. 15, 2019, 6 pages.
International Preliminary Report on Patentability dated Apr. 16, 2019, for PCT Patent Application No. PCT/CN2017/105506, filed Oct. 10, 2017, 7 pages.
International Preliminary Report on Patentability dated Apr. 25, 2019, for PCT Patent Application No. PCT/CN2016/101777, filed Oct. 11, 2016, 9 pages.
International Preliminary Report on Patentability dated Jan. 22, 2019, for PCT Patent Application No. PCT/CN2016/090703, filed Jul. 20, 2016, 6 pages.
International Preliminary Report on Patentability dated Jan. 22, 2019, for PCT Patent Application No. PCT/CN2017/093644, filed Jul. 20, 2017, 6 pages.
International Search Report and Written Opinion dated Mar. 18, 2019, for PCT Patent Application No. PCT/CN2018/124979, filed Dec. 28, 2018, 10 pages.
International Search Report and Written Opinion dated Apr. 11, 2019, for PCT Patent Application No. PCT/CN2019/070873, filed Jan. 8, 2019, 15 pages.
International Search Report and Written Opinion of the International Searching Authority dated Apr. 19, 2019 for PCT Application No. PCT/CN2019/071691 filed on Jan. 15, 2019, 12 pages.
International Search Report dated Apr. 12, 2017, for PCT Patent Application No. PCT/CN2016/090703, filed Jul. 20, 2016, 7 pages.
International Search Report dated Jan. 19, 2018, for PCT Patent Application No. PCT/CN2017/105506, filed Oct. 10, 2017, 6 pages.
International Search Report dated Jul. 11, 2017, for PCT Patent Application No. PCT/CN2016/101777, filed Oct. 11, 2016, 7 pages.
International Search Report dated Oct. 11, 2017, for PCT Patent Application No. PCT/CN2017/093644, filed Jul. 20, 2017, 7 pages.
Iwai, Y. et al. (Feb. 2005, e-pub. Dec. 20, 2004). "PD-1 Blockade Inhibits Hematogenous Spread of Poorly Immunogenic Tumor Cells by Enhanced Recruitment of Effector T Cells," International Immunology 17(2):133-144.
Jackson, J.R. et al. (Apr. 1, 1995). "In Vitro Antibody Maturation. Improvement Of A High Affinity, Neutralizing Antibody Against IL-1 Beta," J. Immunol. 154(7):3310-3319.
Jakobovits, A. et al. (Mar. 18, 1993). "Germ-Line Transmission and Expression of a Human-Derived Yeast Artificial Chromosome," Nature 362:255-258.
Jakobovits, A. et al. (Mar. 1993). "Analysis of Homozygous Mutant Chimeric Mice: Deletion of the Immunoglobulin Heavy-Chain Joining Region Blocks B-Cell Development and Antibody Production," Proc. Natl. Acad. Sci. USA 90:2551-2555.
Janssens, R. et al. (Oct. 10, 2006). "Generation Of Heavy-Chain-Only Antibodies In Mice," Proc. Natl. Acad. Sci. USA 103(41):15130-15135.
Jin, H. (Dec. 31, 2013, e-pub. Apr. 23, 2015). "Construction and Characterization of a CTLA-4-Targeted scFv-Melittin Fusion Protein as a Potential Immunosuppressive Agent for Organ Transplant," Cell Biochemistry and Biophysics 3(67):1067-1074.
Johnson, G. et al. (2003). "The Kabat Database and a Bioinformatics Example," Methods in Molecular Biology 248:11-25, 15 pages.
Johnson, K.S. et al. (1993). "Human Antibody Engineering," Current Opinion in Structural Biology 3:564-571.
Jones, A.J.S. (1993). "Analysis of Polypeptides and Proteins," Adv. Drug Delivery Rev. 10:29-90.
Jones, P. et al. (May 29, 1986). "Replacing The Complementarity-Determining Regions In A Human Antibody With Those From A Mouse," Nature 321:522-525.
Kam, N.W.S. et al. (Aug. 16, 2005). "Carbon Nanotubes as Multifunctional Biological Transporters and Near-Infrared Agents for Selective Cancer Cell Destruction," PNAS 102(33):11600-11605, 6 pages.
Kanda, Y. et al. (Jul. 5, 2006, e-pub. Apr. 11, 2006). "Comparison of Cell Line for Stable Production of Fucose-Negative Antibodies with Enhanced ADCC," Biotechnol. Bioeng. 94(4):680-688.
Kashmiri, S.V. et al. (2005). "SDR grafting—A New Approach to Antibody Humanization," Methods 36:25-34.
Kim, J-K. et al. (1994). "Localization of the Site of the Murine IgGI Molecule That is Involved in Binding to the Murine Intestinal Fc Receptor," Eur. J. Immunol. 24:2429-2434.
Klimka, A. et al. (2000). "Human Anti-CD30 Recombinant Antibodies by Guided Phage Antibody Selection Using Cell Panning," Br. J. Cancer 83(2):252-260.
Kohler, G. et al. (Aug. 7, 1975) "Continuous Cultures Of Fused Cells Secreting Antibody Of Predefined Specificity," Nature 256:495-497.
Kostelny, S.A. et al. (Mar. 1, 1992). "Formation of a Bispecific Antibody By The Use of Leucine Zippers," J. Immunol. 148(5):1547-1553.
Kozbor, D. (Dec. 1984). "A Human Hybrid Myeloma for Production of Human Monoclonal Antibodies," J. Immunol. 133(6):3001-3005.
Lauwereys, M. et al. (Jul. 1, 1998). "Potent Enzyme Inhibitors Derived From Dromedary Heavy-Chain Antibodies," The EMBO Journal 17(13):3512-3520.
Lee, C.V. et al. (2004). "Bivalent Antibody Phage Display Mimics Natural Immunoglobulin," .J. Immunol. Methods 284 (1-2):119-132.
Lee, C.V. et al. (2004). "High-Affinity Human Antibodies From Phage-Displayed Synthetic Fab Libraries With A Single Framework Scaffold," J. Mol. Biol. 340:1073-1093.
Li, A. et al. (Apr. 26, 2016). "A Single-Domain Antibody-Linked Fab Bispecific Antibody Her2-S-Fab Has Potent Cytotoxicity Against Her2-Expressing Tumor Cells," AMB Express 6(32):1-8.
Li, J. et al. (Mar. 7, 2006). "Human Antibodies for Immunotherapy Development Generated via a Human B Cell Hybridoma Technology," Proc. Natl. Acad. Sci. USA 103:3557-3562, 6 pages.
Li, L. et al. (Nov./Dec. 2015). "A Novel Bispecific Antibody, S-Fab, Induces Potent Cancer Cell Killing", J. of Immunotherapy 38(9):350-356.
Lindmark, R. et al. (1983). "Binding of Immunoglobulins to Protein A and Immunoglobulin Levels in Mammalian Sera," J. Immunol. Meth. 62:1-13.
Lonberg, N. (Sep. 2005). "Human Antibodies From Transgenic Animals," Nat. Biotech. 23(9):1117-1125.
Lonberg, N. et al. (1995, e-pub. Jul. 10, 2009). "Human Antibodies From Transgenic Mice," Int. Rev. Immunol. 13 (1):65-93.
Lonberg, N. et al. (2008, e-pub. Jul. 21, 2008). "Fully Human Antibodies From Transgenic Mouse and Phage Display Platforms," Curr. Opin. Immunol. 20:450-459.
Lonberg, N. et al. (Apr. 28, 1994). "Antigen-Specific Human Antibodies From Mice Comprising Four Distinct Genetic Modifications," Nature 368(6474):856-859.
Mabry, R. et al. (2010, e-pub. Dec. 18, 2009). "Engineering Of Stable Bispecific Antibodies Targeting IL-17A and IL-23," Protein Engineering, Design & Selection 23(3):115-127.
Marks, J.D. et al. (1991). "By-Passing Immunization Human Antibodies from V-gene Libraries Displayed on Phage," J. Mol. Biol. 222:581-597.
Marks, J.D. et al. (2004) "Selection of Human Antibodies from Phage Display Libraries," Chapter 8 in Methods in Molecular Biology, LO, B.K.C. (ed.), Humana Press Inc., Totowa, NJ, 248:161-176, 29 pages.
Marks, J.D. et al. (Jul. 1992). "By-Passing Immunization: Building High Affinity Human Antibodies by Chain Shuffling," Bio/Technology 10:779-783.

(56) References Cited

OTHER PUBLICATIONS

Mather, J.P. (1980). "Establishment and Characterization of Two Distinct Mouse Testicular Epithelial Cell Lines," Biol. Reprod. 23:243-251.

Mather, J.P. et al. (1982). "Culture of Testicular Cells in Hormone-Supplemented Serum-Free Medium," Annals N.Y. Acad. Sci. 383:44-68.

McCafferty, J. et al. (Dec. 6, 1990). "Phage Antibodies: Filamentous Phage Displaying Antibody Variable Domains," Nature 348:552-554.

Milstein, C. et al. (Oct. 6, 1983). "Hybrid Hybridomas and Their Use in Immunohistochemistry," Nature 305:537-539.

Molhoj, M. (Sep. 2011). "Ang2/VEGF CrossMAbCH1-CL, a novel bispecific monovalent human IgG1 format aiming at neutralizing Ang2 and VEGF-A to treat solid tumors", Presentations Outline in CrossMAB Technology, 35 pages.

Mordenti, J. et al. (1989). "The Use of Interspecies Scaling in Toxicokinetics," Chapter 4 in Toxicokinetics and New Drug Development, Yacobi A. ed. et al.; Pergamon Press, New York, pp. 42-96.

Morimoto, K. et al. (1992). "Single-Step Purification of F(AB')2 Fragments of Mouse Monoclonal Antibodies (Immunoglobulins G1) By Hydrophobic Interaction High Performance Liquid Chromatography Using TSKgel Phenyl-5PW," J. Biochem. Biophys. Method 24:107-117.

Morrison, S.C. et al. (Nov. 1984). "Chimeric Human Antibody Molecules: Mouse Antigen-Binding Domains With Human Constant Region Domains," Proc. Natl. Acad. Sci. USA 81:6851-6855.

Morrison, S.L. (Apr. 28, 1994). "Success in Specification," Nature 368:812-813.

Munson, P.J. et al. (1980). "Ligand: A Versatile Computerized Approach for Characterization of Ligand-Binding Systems," Anal. Biochem. 107:220-239.

Murata, K.Y. (Aug. 1999). "Expression of the Costimulatory Molecule BB-1, the Ligands CTLA-4 and CD28, and their mRNA in Inflammatory Myopathies," Am. J. Pathol. 155(2):453-460.

Neuberger, M. (Jul. 1996) "Generating High-Avidity Human Mabs in Mice," Nature Biotechnology 14:826, 1 page.

Ni, J. (Oct. 23, 2006). "Research Progress and Future Perspectives in Antibodmics and Antibodomic Drugs," J. General Review 26(4):265-268, 3 pages.

O'Hear, C. et al. (Mar. 2015; E-pub. Dec. 5, 2014) "Anti-CD33 Chimeric Antigen Receptor Targeting Of Acute Myeloid Leukemia," Haematologica. 100(3):336-344.

Okazaki, A. et al. (Mar. 5, 2004). "Fucose Depletion From Human IgG1 Oligosaccharide Enhances Binding Enthalpy And Association Rate Between IgG1 and FcγRIIIa," J. Mol. Biol. 336(5):1239-1249.

Osbourn, J. et al. (2005). "From Rodent Regents to Human Therapeutics Using Antibody Guided Selection," Methods 36:61-68.

Padlan, E.D. (1991). "A Possible Procedure for Reducing the Immunogenicity of Antibody Variable Domains While Preserving Their Ligand-Binding Properties," Mol. Immunol. 28(4/5):489-498.

Pardoll, D.M. (Apr. 2012). "The Blockade Of Immune Checkpoints In Cancer Immunotherapy," Nat. Rev. Cancer 12 (4): 252-264.

Pardon, E. et al. (Mar. 2014, e-pub. Feb. 27, 2014). "A General Protocol for the Generation of Nanobodies for Structural Biology," Nature Protocol 9(3):674-693, 40 pages.

Perrin, P.J. et al. (Aug. 15, 1996). "CTLA-4 Blockade Enhances Clinical Disease And Cytokine Production During Experimental Allergic Encephalomyelitis," The Journal of Immunology 157(4):1333-1336.

Petkova, S.B. et al. (2006, e-pub. Oct. 31, 2006). "Enhanced Half-Life of Genetically Engineered Human IgG1 Antibodies in a Humanized FcRn Mouse Model: Potential Application in Humorally Mediated Autoimmune Disease," Int'l. Immunol. 18(12):1759-1769.

Plückthun, A. (1992). "Mono- and Bivalent Antibody Fragments Producted in *Escherichia coli*: Engineering, Folding and Antigen Binding," Immunol. Revs. 130:151-188.

Plückthun, A. (1994) "Antibodies from *Escherichia coli*," Chapter 11 in Handbook of Experimental Pharmacology 113:269-315.

Presta, L.G. (1992). "Antibody Engineering," Current Opinion in Structural Biology 2:593-596.

Presta, L.G. et al. (Oct. 15, 1997). "Humanization of an Anti-Vascular Endothelial Growth Factor Monoclonal Antibody for the Therapy of Solid Tumors and Other Disorders," Cancer Res. 57:4593-4599.

Presta, L.G. et al. (Sep. 1, 1993). "Humanization of an Antibody Directed Against IgE," J. Immunol. 151 (5):2623-2632.

Proba, K. et al. (1995). "Functional Antibody Single-chain Fragments From The Cytoplasm of *Escherichia coli*: Influence of Thioredoxin Reductase (trxb)," Gene 159(2):203-207.

Queen, C. et al. (Dec. 1989). "A Humanized Antibody That Binds to the Interleukin 2 Receptor," Proc. Natl Acad. Sci. USA 86:10029-10033.

Ramm, K. et al. (Jun. 2, 2000). "The Periplasmic *Escherichia coli* Peptidylprolyl cis,Trans-Isomerase FkpA," The Journal of Biological Chemistry 275(22):17106-17113.

Ravetch, J.V. et al. (1991). "Fc Receptors," Annu. Rev. Immunol. 9:457-492.

Reyes, G.R. et al. (Jun. 17, 1982) "Expression of Human β-interferon cDNA Under the Control of a Thymidine Kinase Promoter from Herpes Simplex Virus," Nature 297:598-601.

Richard, G. et al. (Jul. 22, 2013) "In vivo Neutralization of α-cobratoxin With High-Affinity Llama Single-Domain Antibodies (VHHs) and a VHH-Fc Antibody," PLoS One. 8(7):e69495.

Riechmann, L. (Jun. 28, 1996). "Rearrangement Of The Former VL Interface In The Solution Structure Of A Camelised, Single Antibody VH Domain," Journal of Molecular Biology 259(5):957-969.

Riechmann, L. et al. (Dec. 10, 1999). "Single Domain Antibodies: Comparison of Camel VH And Camelised Human VH Domains," Journal of Immunological Methods 231(1-2):25-38.

Riechmann, L. et al. (Mar. 1988). "Reshaping Human Antibodies for Therapy," Nature 332:323-329.

Ripka, J. et al. (Sep. 1986). "Two Chinese Hamster Ovary Glycosylation Mutants Affected in the Conversion of GDP-Mannose to GDP-Fucose," Arch Biochem Biophys. 249(2):533-545.

Rosenberg, S.A. et al. (Dec. 22, 1988). "Use Of Tumor-Infiltrating Lymphocytes And Interleukin-2 In The Immunotherapy Of Patients With Metastatic Melanoma. A Preliminary Report," N Engl J Med. 319(25):1676-1680.

Rosok, M.J. et al. (Sep. 13, 1996). "A Combinatorial Library Strategy for the Rapid Humanization of Anticarcinoma BR96 Fab," J. Biol. Chem. 271(37):22611-22618.

Schaefer, W. et al. (Jul. 5, 2011) "Immunoglobulin domain crossover as a generic approach for the production of bispecific IgG antibodies," Proc Natl Acad Sci U S A. 108(27):11187-11192.

Schier, R. et al. (1995). "Identification of Functional and Structural Amino-Acid Residues by Parsimonious Mutagenesis," Gene 169:147-155.

Sheriff, S. et al. (Sep. 1996). "Redefining the Minimal Antigen-Binding Fragment," Nature Struct. Biol. 3 (9):733-736.

Shields, R.L. et al. (Mar. 2, 2001). "High Resolution Mapping of the Binding Site on Human IgG1 for FcγRI, FcγRII. FcγRIII, and FcRn and Design of IgG1 Variants With Improved Binding to the FcγR," J. Biol.Chem. 276(9):6591-6604.

Shinkawa, T. et al. (Jan. 31, 2003). "The Absence Of Fucose But Not The Presence Of Galactose Or Bisecting N-Acetylglucosamine Of Human Lgg1 Complex-Type Oligosaccharides Shows The Critical Role Of Enhancing Antibody-Dependent Cellular Cytotoxicity," Journal of Biological Chemistry 278(5):3466-3473.

Shopes, B. et al. (May 1, 1992). "A Genetically Engineered Human IgG Mutant With Enhanced Cytolytic Activity," J. Imniunol. 148:2918-2922.

Sidhu, S.S. et al. (2004). "Phage-Displayed Antibody Libraries of Synthetic Heavy Chain Complementarity Determining Regions," J. Mol. Biol. 338(2):299-310.

Siebenlist, U. et al. (Jun. 1980). "*E. coli* RNA Polymerase Interacts Homologously With Two Different Promoters," Cell 20(2):269-281.

Simmons, L.C. et al. (May 1, 2002). "Expression of Full-Length Immunoglobulins in *Escherichia coli*: Rapid and Efficient Production of Aglycosylaled Antibodies," J. Immunol. Meth. 263(1-2):133-147.

(56) References Cited

OTHER PUBLICATIONS

Sims, M.J. et al. (Aug. 15, 1993). "A Humanized CD18 Antibody Can Block Function Without Cell Destruction," J. Immunol. 151(4):2296-2308.

Skerra, A. (1993) "Bacterial Expression of Immunoglobulin Fragments," Current Opinion in Immunology 5:256-262.

Stamova, S. et al. (Jul. 18, 2012). "Cancer Immunotherapy by Retargeting of Immune Effector Cells via Recombinant Bispecific Antibody Constructs," Antibodies 1(2):172-198.

Stevenson, G.T. et al. (Mar. 1989). "A Chimeric Antibody With Dual Fc Regions (bisFabFc) Prepared by Manipulations at the IgG Hinge," Anti-cancer Drug Des.3(4):219-230.

Streltsov, V.A. (Nov. 2005). "Structure Of A Shark Ignar Antibody Variable Domain And Modeling Of An Early-Developmental Isotype," Protein Sci. 14:2901-2909.

Suresh, M.R. et al. (1986). "Bispecific Monoclonal Antibodies From Hybrid Hybridomas," Methods in Enzymology 121:210-228, 19 pages.

Transue, T.R. et al. (1998). "Camel Single-Domain Antibody Inhibits Enzyme By Mimicking Carbohydrate Substrate," Proteins 32(4):515-522.

Traunecker, A. et al. (1991). "Bispecific Single Chain Molecules (Janusins) Target Cytotoxic Lymphocytes on HIV Infected Cells," EMBO J. 10(12):3655-3659.

Turnis, M.E. (2012, e-pub. Oct. 1, 2012). "Combinatorial Immunotherapy PD-1 May Not Be LAG-ing Behind Any More," Combinatorial Immunotherapy, OncoImmunology 1(7):1172-1174.

Tutt A. et al. (Jul. 1, 1991) "Trispecific F(ab')3 Derivatives that use Cooperative Signaling Via the TCR/CD3 Complex and CD2 to Activate and Redirect Resting Cytotoxic T Cells," J. Immunol. 147(1):60-69.

U.S. Appl. No. 16/960,521, filed Jul. 7, 2020, by Zhang et al.(U.S. Patent Application document is not submitted herewith pursuant to the waiver of 37 C.F.R. § 1.98(a)(2)(iii) issued by the Office on Sep. 21, 2004.).

Urlaub, G. et al. (Jul. 1980). "Isolation of Chinese Hamster Cell Mutants Deficient in Dihydrofolate Reductase Activity," Proc. Natl. Acad. Sci. USA 77(7):4216-4220.

Vajdos, F. et al. (2002) "Comprehensive Functional Maps of the Antigen Binding Site of an Anti-ErbB2 Antibody Obtained with Shotgun Scanning Mutagenesis," J. Mol. Biol. 320:415-428.

Van Der Linden, R. (Jun. 23, 2000, e-pub. Jun. 13, 2000). "Induction Of Immune Responses And Molecular Cloning Of The Heavy Chain Antibody Repertoire Of Lama Glama," J. Immunol. Methods 240(1-2):185-195.

Van Dijk, M.A. et al. (Aug. 2001). "Human Antibodies as Next Generation Therapeutics," Curr. Opin. Che. Biology 5(4):368-374.

Vaswani, S.K. et al. (Aug. 1998) "Humanized Antibodies as Potential Therapeutic Drugs," Annals of Allergy, Asthma, & Immunology 81:105-115.

Verhoeyen, M. et al. (Mar. 25, 1988). "Reshaping Human Antibodies: Grafting An Antilysozyme Activity," Science 239(4857):1534-1536.

Vollmers, H.P. et al. (2005) "Death by Stress: Natural IgM-induced Apoptosis," Methods Find Exp Clin Pharmacol. 27(3):1-7.

Vollmers, H.P. et al. (2005). "The 'Early Birds': Natural IgM Antibodies and Immune Surveillance," Histology and Histopathology, 20(3):927-937.

Walunas, T.L. et al. (Jun. 1996). "CTLA-4 Ligation Blocks CD28-Dependent T Cell Activation," The Journal of Experimental Medicine 183(6):2541-2550.

Ward, E.S. et al. (Oct. 12, 1989). "Binding Activities Of A Repertoire Of Single Immunoglobulin Variable Domains Secreted From *Escherichia coli*," Nature 341(6242): 544-546.

Waterhouse, P. et al. (1993). "Combinatorial Infection and In Vivo Recombination: A Strategy For Making Large Phage Antibody Repertoires," Nucleic Acids Research 21(9):2265-2266.

Weidle, U.H. et al. (Jan.-Feb. 2013). "The Intriguing Options Of Multispecific Antibody Formats For Treatment Of Cancer," Cancer Genomics Proteomics 10(1):1-18.

Weidner K. M. et al. (Nov. 1, 2010). "Anti-Angiogenic Activity of a Tetravalent Bispecific Antibody (TAvi6) Targeting VEGF and Angiopoietin-211," Blood 116(21):1746 (abstract 4303), 2 pages.

Wesolowski, J. et al. (Aug. 2009, e-pub. Jun. 16, 2009). "Single Domain Antibodies: Promising Experimental and Therapeutic Tools In Infection and Immunity," Med Microbiol Immunol 198:157-174.

Winter, G. el al. (1994). "Making Antibodies by Phage Display Technology," Ann. Rev. Immunol. 12:433-455.

Wolff, E.A. et al. (Jun. 1, 1993). "Monoclonal Antibody Homodimers: Enhanced Antitumor Activity in Nude Mice," Can Res 53:2560-2565.

Wright, A. et al. (Jan. 1997). "Effect of Glycosylation on Antibody Function: Implications for Genetics Engineering," Trends Biotechnol. 15:26-32.

Written Opinion of the International Searching Authority dated Apr. 12, 2017, for PCT Patent Application No. PCT/CN2016/090703, filed Jul. 20, 2016, 5 pages.

Written Opinion of the International Searching Authority dated Jan. 19, 2018, for PCT Patent Application No. PCT/CN2017/105506, filed Oct. 10, 2017, 6 pages.

Written Opinion of the International Searching Authority dated Jul. 11, 2017, for PCT Patent Application No. PCT/CN2016/101777, filed Oct. 11, 2016, 7 pages.

Written Opinion of the International Searching Authority dated Oct. 11, 2017, for PCT Patent Application No. PCT/CN2017/093644, filed Jul. 20, 2017, 5 pages.

Xu, J.L. et al. (Jul. 2000). "Diversity in the CDR3 Region of VH Is Sufficient for Most Antibody Specificities," Immunity 13:37-45.

Yamane-Ohnuki, N. et al. (Sep. 5, 2004, e-pub. Aug. 6, 2004). "Establishment of FUT8 Knockout Chinese hamster Ovary Cells: An Ideal Host Cell Line for Producing Completely Defucosylated Antibodies With Enhances Antibody-Dependent Cellular Cytotoxicity," Biotech. Bioeng. 87(5):614-622.

Yaniv, M. (May 6, 1982). "Enhancing Elements for Activation of Eukaryotic Promoters," Nature 297:17-18.

Yansura, D.G. et al. (1992). "Nucleotide Sequence Selection for Increased Expression of Heterologous Genes in *Escherichia coli*," Methods: A Companion to Methods in Enzymol 4:151-158.

Yelton, D.E. et al. (1995). "Affinity Maturation of the BR96 Anti-Carcinoma Antibody by Codon-Based Mutagenesis," J. Immunol. 155:1994-2004.

Zapata, G. et al. (1995). "Engineering Linear F(ab')2 Fragments For Efficient Production In *Escherichia coli* And Enhanced Antiproliferative Activity," Protein Engineering 8(10):1057-1062.

Zhu, Z. et al. (1997). "Remodeling Domain Interfaces to Enhance Heterodimer Formation," Protein Science 6:781-788.

Algazi, A. et al. (Jul. 15, 2016). "Abstract CT134: Intratumoral Electroporation of Plasmid IL-12 Can Prime Response to Anti-PDI/PD-LI Blockade in Patients with Stage III/IV-Mla Melanoma," Cancer Research 76(14):2 pages.

Asano, T. et al. (Apr. 13, 2017). "PD-1 Modulates Regulatory T-Cell Homeostasis During Low-Dose Interieukin-2 Therapy," Blood 129(15):2186-2197.

Peng. L.S. et al. (1999). "A Single-Chain IL-12 IgG3 Antibody Fusion Protein Retains Antibody Specificity and IL-12 Bioactivity and Demonstrates Antitumor Activity," The Journal of Immunology 163:250-258.

Ribas, A. (Sep. 2015). "Adaptive Immune Resistance: How Cancer Protects From Immune Attack," Cancer Discovery 5(9):915-919, 13 pages.

Tian, H.W. et al. (Nov. 18, 2016). "A Novel Cancer Vaccine with the Ability to Simultaneously Produce Anti-PD-1 Antibody and GM-CSF in Cancer Cells and Enhance Th1-Biased Antitumor Immunity," Signal Transduction and Targeted Therapy 1(16025):1-10.

Zaretsky, J. M. et al. (Sep. 1, 2016). "Mutations Associated With Acquired Resistance To PD-1 Blockade In Melanoma," New England Journal of Medicine 375(9):819-829.

Yu, J.-J. (Jan. 2017). "Single Domain Antibodies from Camel: Research Advances," J. Int. Pharm. Res. 44 (1):18-23. (English Abstract Only).

Wang, D. Y. et al. (May 2017). "Clinical Features of Acquired Resistance to Anti-PD-1 Therapy in Advanced Melanoma," Cancer Immunology Research 5(5):357-362.

(56) References Cited

OTHER PUBLICATIONS

Yao, S. et al. (2013). "Adaptive Resistance: A Tumor Strategy To Evade Immune Attack," European Journal Of Immunology 43(3):576-579.
U.S. Appl. No. 17/818,942, filed Aug. 10, 2022, by Chou et al. (U.S. Patent Application document is not submitted herewith pursuant to the waiver of 37 C.F.R. § 1.98(a)(2)(iii) issued by the Office on Sep. 21, 2004.).
Extended European Search Report in European Appln. No. 19738343.3, dated Jul. 22, 2022, 14 pages.
Scapin et al., "Structure of full-length human anti-PD1 therapeutic IgG4 antibody pembrolizumab," Nature Structural & Molecular Biology, Nov. 23, 2015, 22(12):953-958, 9 pages.

\* cited by examiner

| Analyte | $k_a$ (1/Ms) | $k_d$ (1/s) | $K_D$ (M) |
|---|---|---|---|
| AS06962_sdAb | 1.26E+07 | 5.74E-03 | 4.54E-10 |
| AS15872_sdAb | 1.98E+05 | 2.86E-03 | 1.45E-08 |
| AS15881_sdAb | 1.36E+05 | 3.13E-04 | 2.31E-09 |
| AS15883_sdAb | 9.49E+04 | 2.64E-04 | 2.78E-09 |
| AS15892_sdAb | 1.45E+05 | 3.86E-04 | 2.67E-09 |
| AS15899_sdAb | 4.25E+05 | 1.37E-03 | 3.22E-09 |

|  | AS06962 sdAb | AS07424 sdAb | A31543 sdAb |
|---|---|---|---|
| $EC_{50}$ (nM) | 79.24 | 36.7 | 41.17 |

|  | AS06962 sdAb | A31543 sdAb | Keytruda |
|---|---|---|---|
| $IC_{50}$ | 193.2 | 21.1 | 3.5 |

| Ligand | Analyte | $k_a$ (1/Ms) | $k_d$ (1/s) | $K_D$ (M) |
|---|---|---|---|---|
| AS15140_HCAb | PD-1 His | 1.79E+05 | 1.88E-03 | 1.05E-08 |
| AS15152_HCAb |  | 1.94E+05 | 3.55E-03 | 1.83E-08 |
| AS15156_HCAb |  | 6.66E+04 | 1.78E-04 | 2.67E-09 |
| AS15193_HCAb |  | 7.90E+04 | 7.51E-05 | 9.51E-10 |
| AS06962_HCAb |  | 1.80E+05 | 7.10E-03 | 3.90E-08 |
| AS15881_HCAb |  | 1.00E+05 | 3.50E-04 | 3.30E-09 |
| AS15883_HCAb |  | 8.20E+04 | 3.20E-04 | 3.90E-09 |
| AS15892_HCAb |  | 1.10E+05 | 4.30E-04 | 4.00E-09 |
| AS15899_HCAb |  | 2.20E+05 | 8.40E-04 | 3.80E-09 |
| AS25170_HCAb |  | 5.60E+04 | 5.50E-04 | 9.80E-09 |
| Keytruda |  | 2.50E+05 | 2.60E-03 | 1.00E-08 |

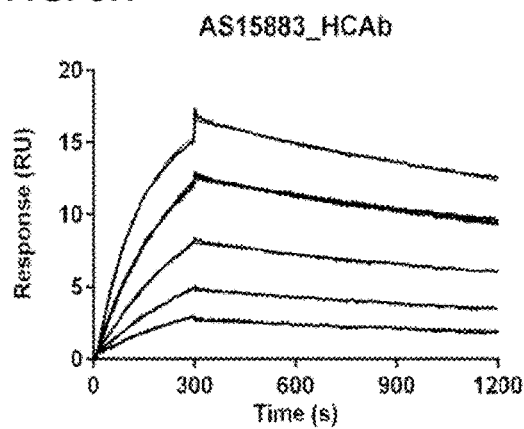
FIG. 6H AS15883_HCAb
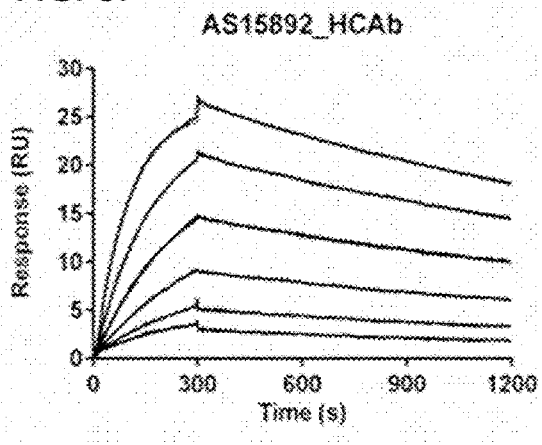
FIG. 6I AS15892_HCAb
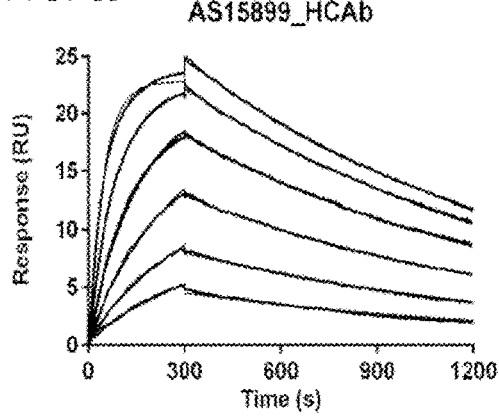
FIG. 6J AS15899_HCAb
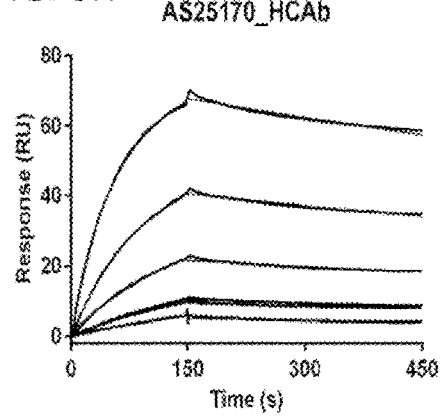
FIG. 6K AS25170_HCAb
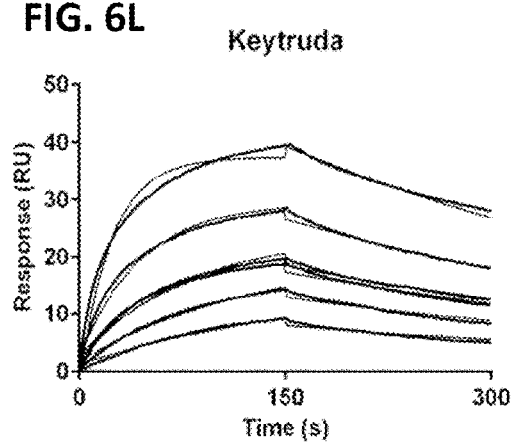
FIG. 6L Keytruda

FIG. 7X

| Sample | AS15881_HCAb | AS15899_HCAb | AS15140_HCAb | AS15156_HCAb | AS15193_HCAb |
|---|---|---|---|---|---|
| $EC_{50}$ (nM) | 2.18 | 1.48 | 2.32 | 4.91 | 1.26 |
| Sample | AS25071_HCAb | AS25115_HCAb | AS25117_HCAb | AS25119_HCAb | AS25149_HCAb |
| $EC_{50}$ (nM) | 4.74 | 4.06 | 3.22 | 3.29 | 10.65 |
| Sample | AS25396_HCAb | AS25457_HCAb | AS25487_HCAb | AS25435_HCAb | Keytruda |
| $EC_{50}$ (nM) | 3.84 | 4.04 | 8.94 | 4.91 | 2.44 |
| Sample | AS24984_HCAb | AS25037_HCAb | AS25064_HCAb | AS25067_HCAb | AS25156_HCAb |
| $EC_{50}$ (nM) | 7.22 | 6.62 | 5.46 | 4.96 | 9.18 |
| Sample | AS25164_HCAb | AS25170_HCAb | AS25222_HCAb | | |
| $EC_{50}$ (nM) | 6.15 | 7.20 | 4.59 | | |

FIG. 8X

| Sample | AS15881_HCAb | AS15899_HCAb | AS15140_HCAb | AS15156_HCAb | AS15193_HCAb |
|---|---|---|---|---|---|
| $IC_{50}$ (nM) | 1.66 | 0.91 | 0.88 | 2.20 | 0.79 |
| Sample | AS25071_HCAb | AS25115_HCAb | AS25117_HCAb | AS25119_HCAb | AS25149_HCAb |
| $IC_{50}$ (nM) | 2.41 | 2.15 | 2.06 | 1.57 | 8.00 |
| Sample | AS25396_HCAb | AS25457_HCAb | AS25487_HCAb | AS25435_HCAb | Keytruda |
| $IC_{50}$ (nM) | 1.34 | 2.44 | 7.24 | 2.70 | 0.97 |
| Sample | AS24984_HCAb | AS25037_HCAb | AS25064_HCAb | AS25067_HCAb | AS25156_HCAb |
| $IC_{50}$ (nM) | 4.59 | 6.58 | 2.91 | 3.51 | 6.04 |
| Sample | AS25164_HCAb | AS25170_HCAb | AS25222_HCAb | | |
| $IC_{50}$ (nM) | 3.25 | 3.01 | 1.66 | | |

FIG. 9A
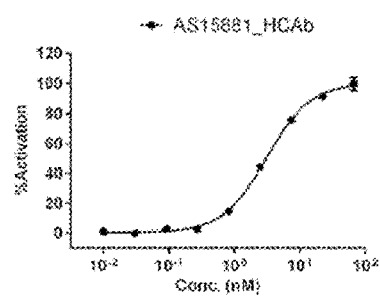
FIG. 9B
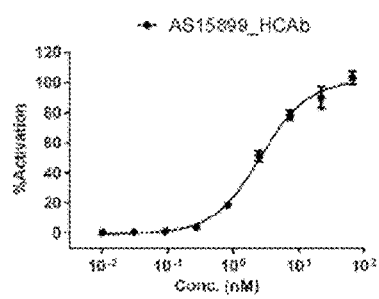
FIG. 9C
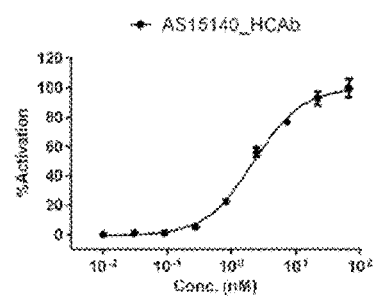
FIG. 9D
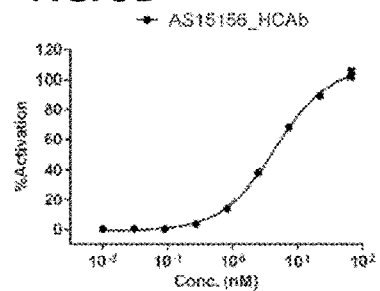
FIG. 9E
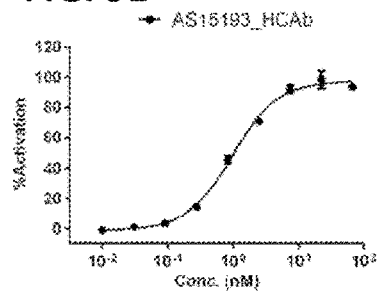
FIG. 9F
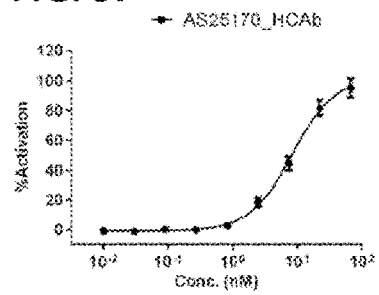
FIG. 9G
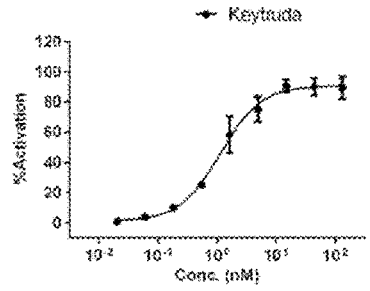
FIG. 9H
| Sample | AS15881_HCAb | AS15899_HCAb | AS15140_HCAb | AS15156_HCAb |
|---|---|---|---|---|
| $EC_{50}$ (nM) | 3.09 | 2.60 | 2.21 | 4.51 |
| Sample | AS15193_HCAb | AS25170_HCAb | Keytruda | |
| $EC_{50}$ (nM) | 0.97 | 8.36 | 1.59 | |

FIG. 10A
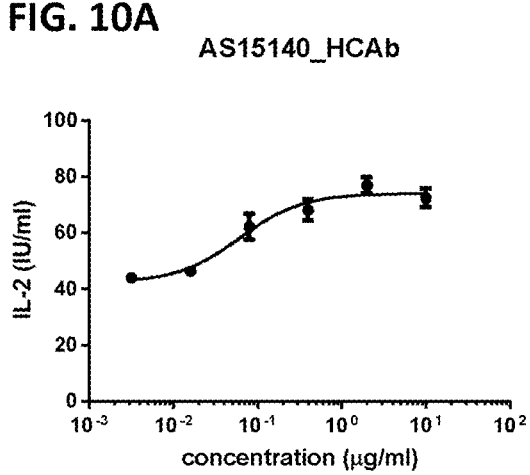
FIG. 10B
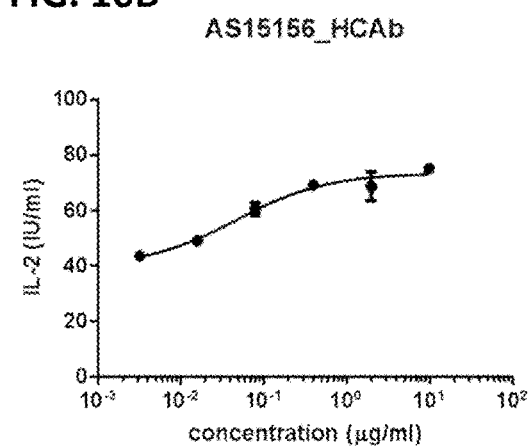
FIG. 10C
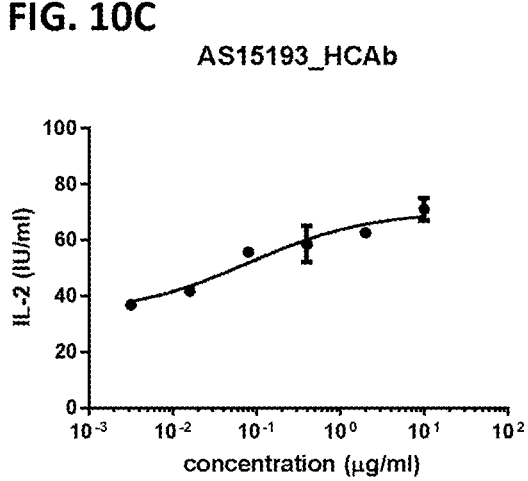
FIG. 10D
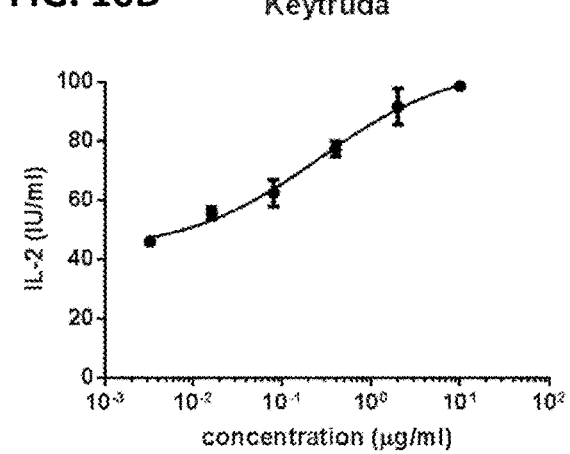
FIG. 10E
| Sample ID | Best-fit values | | |
|---|---|---|---|
| | Bottom | Top | $EC_{50}$ (μg/ml) |
| AS15140_HCAb | 42.26 | 74.11 | 0.062 |
| AS15156_HCAb | 40.08 | 73.57 | 0.048 |
| AS15193_HCAb | 33.56 | 85.39 | 0.082 |
| Keytruda | 46.59 | 98 | 0.330 |

FIG. 11

```
                                       1                  10                 20                 30                 40                 50
Camelid AS15193 SEQ ID.No 295    (1)    QVQLVESGGGSVQAGGSLRLSCVVSGNIYNHNKFGMFRQAPGKGLERVEGAAIYTGTSRTY
Var AS15193VH8 SEQ ID.No 321     (1)    EVQLVESGGGLVQPGGSLRLSCAVSGNIYNHNKFGMFRQAPGKGLERVSAIYTGTSRTY
Var AS15193VH8M1 SEQ ID.No 322   (1)    EVQLVESGGGLVQPGGSLRLSCAVSGNIYNHNKFGMFRQAPGKGLEGVSAIYTGTSRTY
Var AS15193VH18 SEQ ID.No 323    (1)    EVQLVESGGGLVQPGGSLRLSCAVSGNIYNRNFGMFRQAPGKGLEGVSAIYTGTSRTY
Var AS15193VH18M1 SEQ ID.No 324  (1)    EVQLVESGGGLVQPGGSLRLSCAVSGNIYNRNFGMFRQAPGKGLEGVSAIYTGTSRTY
human acceptor SEQ ID.No 366     (1)    QVQLVESGGGVVQPGGSLRLSAASGFTFSSYGMHWVRQAPGKGLEWLGVISGSSI 60                 70                 80                 90                100                110               123
Camelid AS15193 SEQ ID.No 295    (71)   YADSVKGRFTISRDNAKNTVYLQMSLKPEDTAMYYCAADIRDGFWDTGVWNTWGQGTQVTVSS
Var AS15193VH8 SEQ ID.No 321     (71)   YADSVKGRFTISRDNSKNTVYLQMNSLRAEDTAVYYCAADIRDGFWDTGVWNTWGQGTLVTVSS
Var AS15193VH8M1 SEQ ID.No 322   (71)   YADSVKGRFTISRDNSKNTVYLQMNSLRAEDTAVYYCAADIRDGFWDTGVWNTWGQGTLVTVSS
Var AS15193VH18 SEQ ID.No 323    (71)   YADSVKGRFTISRDNAKNTVYLQMNSLRPEDTAVYYCAADIRDGFWDTGVWNTWGQGTLVTVSS
Var AS15193VH18M1 SEQ ID.No 324  (71)   YADSVKGRFTISRDNSKNTVYLQMNSLRPEDTAVYYCAADIRDGFWDTGVWNTWGQGTLVTVSS
human acceptor SEQ ID.No 366     (71)   YADSVKGRFTISRDNSKNTLYLQMNSLRAEDTAVYYCAK---------------------
```

FIG. 12F

| Ligand | Analyte | $k_a$ (1/Ms) | $k_d$ (1/s) | $K_D$ (M) |
|---|---|---|---|---|
| AS15193_HCAb | PD-1 His | 1.2E+05 | 4.7E-04 | 4.0E-09 |
| AS15193VH8_HCAb | | 6.80E+04 | 6.60E-04 | 9.70E-09 |
| AS15193VH8M1_HCAb | | 6.10E+04 | 1.20E-03 | 2.00E-08 |
| AS15193VH18_HCAb | | 8.60E+04 | 6.00E-04 | 7.00E-09 |
| AS15193VH18M1_HCAb | | 9.20E+04 | 1.40E-03 | 1.50E-08 |

FIG. 13F

|  | AS15193_HCAb | AS15193VH8_HCAb | AS15193VH8M1_HCAb |
|---|---|---|---|
| $EC_{50}$ (nM) | 1.26 | 1.78 | 1.92 |
|  | AS15193VH18_HCAb | AS15193VH18M1_HCAb |  |
| $EC_{50}$ (nM) | 1.61 | 1.80 |  |

FIG. 14A
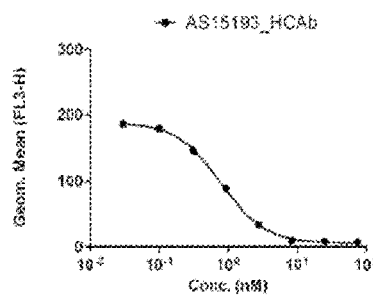
FIG. 14B
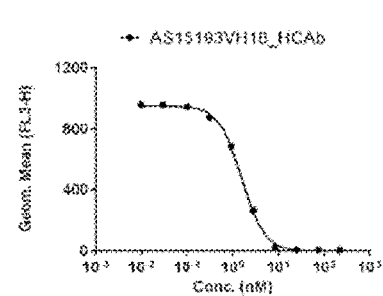
FIG. 14C
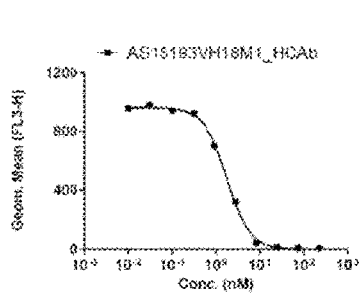
FIG. 14D
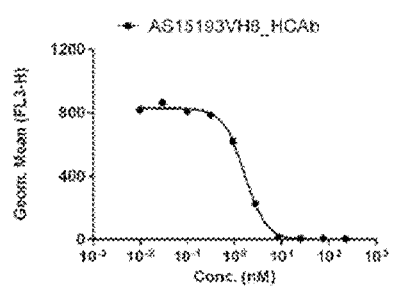
FIG. 14E
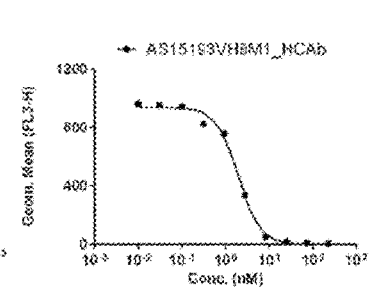
FIG. 14F
|  | AS15193_HCAb | AS15193 VH8_HCAb | AS15193 VH8M1_HCAb |
|---|---|---|---|
| IC$_{50}$ (nM) | 0.79 | 1.64 | 1.96 |
|  | AS15193 VH18_HCAb | AS15193 VH18M1_HCAb |  |
| IC$_{50}$ (nM) | 1.57 | 1.75 |  |

FIG. 15A
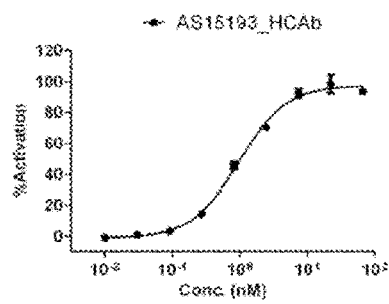
FIG. 15B
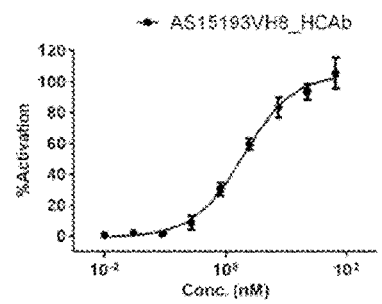
FIG. 15C
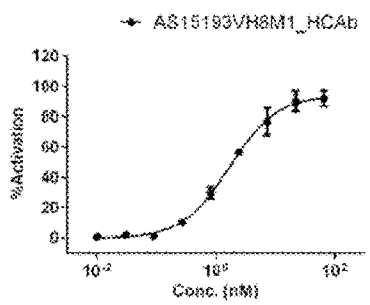
FIG. 15D
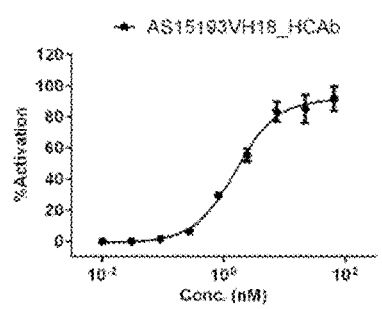
FIG. 15E
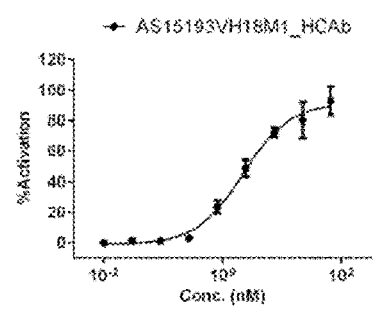
FIG. 15F
|              | AS15193_HCAb       | AS15193VH8_HCAb     | AS15193VH8M1_HCAb |
|--------------|--------------------|---------------------|-------------------|
| $EC_{50}$ (nM) | 0.97               | 1.97                | 1.72              |
|              | AS15193VH18_HCAb   | AS15193VH18M1_HCAb  |                   |
| $EC_{50}$ (nM) | 1.58               | 2.21                |                   |

FIG. 28

| Sample | AS06962_sdAb | AS15872_sdAb | AS15881_sdAb | AS15883_sdAb | AS15892_sdAb | AS15899_sdAb | AS07424_sdAb | AS31543_sdAb |
|---|---|---|---|---|---|---|---|---|
| Amount(mg) | 4.39 | 17.79 | 8.29 | 2.22 | 2.78 | 0.74 | 2.34 | 4.09 |
| Purity | >85% | >90% | >90% | >80% | >90% | 80% | >90% | >85% |
| Endotoxin level(EU/μg) | <0.01 | <0.01 | <0.01 | <0.01 | <0.01 | <0.01 | <0.01 | <0.01 |

FIG. 29

| Sample | AS15881_HCAb | AS15899_HCAb | AS15140-HCAb | AS15156_HCAb | AS15193_HCAb | AS25071_HCAb | AS25115_HCAb | AS25117_HCAb |
|---|---|---|---|---|---|---|---|---|
| Conc.(mg/ml) | 1.92 | 1.58 | 1.73 | 2.13 | 0.96 | 1.48 | 1.33 | 1.24 |
| Amount(mg) | 6.73 | 5.54 | 6.06 | 11.70 | 3.77 | 4.18 | 5.06 | 4.72 |
| Purity | >90% | >90% | >90% | >90% | >90% | >85% | >90% | >90% |
| Endotoxin level(EU/μg) | <0.01 | <0.01 | <0.01 | <0.01 | <0.01 | <0.01 | <0.1 | <0.1 |
| Sample | AS25119_HCAb | AS25149_HCAb | AS25396_HCAb | AS25457_HCAb | AS25487_HCAb | AS25435_HCAb | AS24984_HCAb | AS25037_HCAb |
| Conc.(mg/ml) | 1.15 | 1.23 | 1.12 | 1.47 | 1.64 | 1.41 | 0.65 | 0.62 |
| Amount(mg) | 4.39 | 4.68 | 4.05 | 7.20 | 9.10 | 8.86 | 1.35 | 1.90 |
| Purity | >90% | >90% | >90% | >90% | >90% | >85% | >85% | >85% |
| Endotoxin level(EU/μg) | <0.1 | <0.1 | <0.01 | <0.01 | <0.01 | <0.01 | <0.01 | <0.01 |
| Sample | AS25064_HCAb | AS25067_HCAb | AS25156_HCAb | AS25164_HCAb | AS25170_HCAb | AS2522_HCAb | | |
| Conc.(mg/ml) | 1.35 | 1.37 | 1.18 | 1.18 | 1.26 | 1.00 | | |
| Amount(mg) | 5.57 | 4.68 | 4.60 | 6.10 | 5.93 | 5.22 | | |
| Purity | >90% | >85% | >90% | >90% | >90% | >90% | | |
| Endotoxin level(EU/μg) | <0.01 | <0.01 | <0.01 | <0.01 | <0.01 | <0.01 | | |

SEQUENCE LISTING

<160> NUMBER OF SEQ ID NOS: 386

<210> SEQ ID NO 1
<211> LENGTH: 25
<212> TYPE: PRT
<213> ORGANISM: Artificial Sequence
<220> FEATURE:
<223> OTHER INFORMATION: Synthetic Construct

<400> SEQUENCE: 1

Gln Val Gln Leu Val Glu Ser Gly Gly Gly Lys Val Gln Pro Gly Gly
1               5                   10                  15

Ser Leu Arg Leu Ser Cys Ala Ala Ser
            20                  25

<210> SEQ ID NO 2
<211> LENGTH: 25
<212> TYPE: PRT
<213> ORGANISM: Artificial Sequence
<220> FEATURE:
<223> OTHER INFORMATION: Synthetic Construct

<400> SEQUENCE: 2

Gln Val His Leu Val Asp Ser Gly Gly Gly Leu Val Gln Pro Gly Gly
1               5                   10                  15

Ser Leu Arg Leu Ser Cys Ala Ala Ser
            20                  25

<210> SEQ ID NO 3
<211> LENGTH: 25
<212> TYPE: PRT
<213> ORGANISM: Artificial Sequence
<220> FEATURE:
<223> OTHER INFORMATION: Synthetic Construct

<400> SEQUENCE: 3

Gln Val Gln Leu Val Glu Ser Gly Gly Gly Ser Val Gln Ala Gly Gly
1               5                   10                  15

Ser Leu Arg Leu Ser Cys Ala Ala Ser
            20                  25

<210> SEQ ID NO 4
<211> LENGTH: 25
<212> TYPE: PRT
<213> ORGANISM: Artificial Sequence
<220> FEATURE:
<223> OTHER INFORMATION: Synthetic Construct

<400> SEQUENCE: 4

Gln Val Gln Leu Val Glu Ser Gly Gly Gly Ser Val Gln Ala Gly Gly
1               5                   10                  15

Ser Leu Arg Leu Ser Cys Thr Ala Ser

```
                20                  25

<210> SEQ ID NO 5
<211> LENGTH: 25
<212> TYPE: PRT
<213> ORGANISM: Artificial Sequence
<220> FEATURE:
<223> OTHER INFORMATION: Synthetic Construct

<400> SEQUENCE: 5

Gln Met Gln Leu Val Glu Ser Gly Gly Gly Ser Val Gln Ala Gly Gly
1               5                   10                  15

Ser Leu Arg Leu Ser Cys Ala Val Ser
            20                  25

<210> SEQ ID NO 6
<211> LENGTH: 25
<212> TYPE: PRT
<213> ORGANISM: Artificial Sequence
<220> FEATURE:
<223> OTHER INFORMATION: Synthetic Construct

<400> SEQUENCE: 6

Gln Val Gln Leu Val Glu Ser Gly Gly Gly Ser Ala Gln Ala Gly Gly
1               5                   10                  15

Ser Leu Arg Leu Ser Cys Ala Val Ser
            20                  25

<210> SEQ ID NO 7
<211> LENGTH: 25
<212> TYPE: PRT
<213> ORGANISM: Artificial Sequence
<220> FEATURE:
<223> OTHER INFORMATION: Synthetic Construct

<400> SEQUENCE: 7

Gln Ile Gln Leu Val Glu Ser Gly Gly Gly Ser Ala Gln Ala Gly Gly
1               5                   10                  15

Ser Leu Arg Leu Ser Cys Val Val Ser
            20                  25

<210> SEQ ID NO 8
<211> LENGTH: 25
<212> TYPE: PRT
<213> ORGANISM: Artificial Sequence
<220> FEATURE:
<223> OTHER INFORMATION: Synthetic Construct

<400> SEQUENCE: 8

Gln Val Gln Leu Val Glu Ser Gly Gly Gly Leu Val Gln Pro Gly Gly
1               5                   10                  15

Ser Leu Thr Leu Ser Cys Ala Ala Ser
            20                  25

<210> SEQ ID NO 9
<211> LENGTH: 25
<212> TYPE: PRT
<213> ORGANISM: Artificial Sequence
<220> FEATURE:
<223> OTHER INFORMATION: Synthetic Construct

<400> SEQUENCE: 9

Gln Val Gln Leu Val Glu Ser Gly Gly Gly Ser Val Gln Ala Gly Gly
1               5                   10                  15
```

```
Ser Leu Arg Leu Ser Cys Ala Ala Ser
        20                  25

<210> SEQ ID NO 10
<211> LENGTH: 25
<212> TYPE: PRT
<213> ORGANISM: Artificial Sequence
<220> FEATURE:
<223> OTHER INFORMATION: Synthetic Construct

<400> SEQUENCE: 10

Gln Val His Leu Met Glu Ser Gly Gly Gly Ser Val Gln Ala Gly Gly
1               5                   10                  15

Ser Leu Thr Leu Ser Cys Ala Ala Ser
        20                  25

<210> SEQ ID NO 11
<211> LENGTH: 25
<212> TYPE: PRT
<213> ORGANISM: Artificial Sequence
<220> FEATURE:
<223> OTHER INFORMATION: Synthetic Construct

<400> SEQUENCE: 11

Gln Ile Gln Leu Val Glu Ser Gly Gly Gly Ser Val Gln Ala Gly Gly
1               5                   10                  15

Ser Leu Arg Leu Ser Cys Ala Ala Ser
        20                  25

<210> SEQ ID NO 12
<211> LENGTH: 25
<212> TYPE: PRT
<213> ORGANISM: Artificial Sequence
<220> FEATURE:
<223> OTHER INFORMATION: Synthetic Construct

<400> SEQUENCE: 12

Gln Val Gln Leu Val Glu Ser Gly Gly Gly Ser Val Gln Ala Gly Gly
1               5                   10                  15

Ser Leu Arg Leu Ser Cys Ala Ala Ser
        20                  25

<210> SEQ ID NO 13
<211> LENGTH: 25
<212> TYPE: PRT
<213> ORGANISM: Artificial Sequence
<220> FEATURE:
<223> OTHER INFORMATION: Synthetic Construct

<400> SEQUENCE: 13

Gln Val Lys Leu Val Glu Ser Gly Gly Gly Ser Val Gln Ala Gly Gly
1               5                   10                  15

Tyr Leu Arg Leu Ser Cys Ala Ala Ser
        20                  25

<210> SEQ ID NO 14
<211> LENGTH: 25
<212> TYPE: PRT
<213> ORGANISM: Artificial Sequence
<220> FEATURE:
<223> OTHER INFORMATION: Synthetic Construct

<400> SEQUENCE: 14

Gln Val Gln Leu Val Glu Ser Gly Gly Gly Ser Val Gln Ala Gly Gly
1               5                   10                  15
```

Ser Leu Arg Leu Ser Cys Ala Gly Ser
            20                  25

<210> SEQ ID NO 15
<211> LENGTH: 25
<212> TYPE: PRT
<213> ORGANISM: Artificial Sequence
<220> FEATURE:
<223> OTHER INFORMATION: Synthetic Construct

<400> SEQUENCE: 15

Gln Val His Leu Met Glu Ser Gly Gly Gly Ser Val Pro Ser Gly Gly
1               5                   10                  15

Ser Leu Arg Leu Ser Cys Ala Val Ser
            20                  25

<210> SEQ ID NO 16
<211> LENGTH: 25
<212> TYPE: PRT
<213> ORGANISM: Artificial Sequence
<220> FEATURE:
<223> OTHER INFORMATION: Synthetic Construct

<400> SEQUENCE: 16

Glu Val Gln Leu Ala Glu Ser Gly Gly Gly Ser Val Gln Ala Gly Gly
1               5                   10                  15

Ser Leu Lys Leu Ser Cys Leu Ala Ser
            20                  25

<210> SEQ ID NO 17
<211> LENGTH: 25
<212> TYPE: PRT
<213> ORGANISM: Artificial Sequence
<220> FEATURE:
<223> OTHER INFORMATION: Synthetic Construct

<400> SEQUENCE: 17

Gln Val Gln Leu Val Glu Ser Gly Gly Gly Ser Val Gln Ala Gly Gly
1               5                   10                  15

Ser Leu Arg Leu Thr Cys Ala Ala Thr
            20                  25

<210> SEQ ID NO 18
<211> LENGTH: 25
<212> TYPE: PRT
<213> ORGANISM: Artificial Sequence
<220> FEATURE:
<223> OTHER INFORMATION: Synthetic Construct

<400> SEQUENCE: 18

Gln Val His Leu Met Glu Ser Gly Gly Gly Ala Val Gln Thr Gly Gly
1               5                   10                  15

Ser Leu Arg Leu Ser Cys Ala Val Ser
            20                  25

<210> SEQ ID NO 19
<211> LENGTH: 25
<212> TYPE: PRT
<213> ORGANISM: Artificial Sequence
<220> FEATURE:
<223> OTHER INFORMATION: Synthetic Construct

<400> SEQUENCE: 19

Glu Val Gln Leu Ala Glu Ser Gly Gly Gly Ser Val Gln Ser Gly Gly

```
1               5                   10                  15

Ser Leu Arg Leu Ser Cys Ala Val Ser
            20                  25

<210> SEQ ID NO 20
<211> LENGTH: 25
<212> TYPE: PRT
<213> ORGANISM: Artificial Sequence
<220> FEATURE:
<223> OTHER INFORMATION: Synthetic Construct

<400> SEQUENCE: 20

Gln Val His Leu Val Glu Ser Gly Gly Ala Ser Val Gln Ala Gly Gly
1               5                   10                  15

Ser Leu Arg Leu Ser Cys Ala Ala Thr
            20                  25

<210> SEQ ID NO 21
<211> LENGTH: 25
<212> TYPE: PRT
<213> ORGANISM: Artificial Sequence
<220> FEATURE:
<223> OTHER INFORMATION: Synthetic Construct

<400> SEQUENCE: 21

Glu Val Gln Leu Ala Glu Ser Gly Gly Gly Ser Val Gln Ala Gly Gly
1               5                   10                  15

Ser Leu Arg Leu Ser Cys Val Ile Ser
            20                  25

<210> SEQ ID NO 22
<211> LENGTH: 25
<212> TYPE: PRT
<213> ORGANISM: Artificial Sequence
<220> FEATURE:
<223> OTHER INFORMATION: Synthetic Construct

<400> SEQUENCE: 22

Gln Val Gln Leu Val Glu Ser Gly Gly Gly Ser Val Gln Ala Gly Gly
1               5                   10                  15

Pro Leu Arg Leu Thr Cys Ala Ala Thr
            20                  25

<210> SEQ ID NO 23
<211> LENGTH: 25
<212> TYPE: PRT
<213> ORGANISM: Artificial Sequence
<220> FEATURE:
<223> OTHER INFORMATION: Synthetic Construct

<400> SEQUENCE: 23

Gln Val Gln Leu Val Glu Ser Gly Gly Gly Ser Val Gln Ser Gly Gly
1               5                   10                  15

Ser Leu Lys Leu Ser Cys Ala Val Ser
            20                  25

<210> SEQ ID NO 24
<211> LENGTH: 25
<212> TYPE: PRT
<213> ORGANISM: Artificial Sequence
<220> FEATURE:
<223> OTHER INFORMATION: Synthetic Construct

<400> SEQUENCE: 24
```

```
Glu Val Gln Leu Val Glu Ser Gly Gly Gly Ser Val Gln Ser Gly Gly
1               5                   10                  15

Ser Leu Arg Leu Ser Cys Ala Val Ser
            20                  25
```

<210> SEQ ID NO 25
<211> LENGTH: 25
<212> TYPE: PRT
<213> ORGANISM: Artificial Sequence
<220> FEATURE:
<223> OTHER INFORMATION: Synthetic Construct

<400> SEQUENCE: 25

```
Glu Val Gln Leu Val Glu Ser Gly Gly Gly Ser Val Gln Ser Gly Gly
1               5                   10                  15

Ser Leu Arg Leu Ser Cys Ala Val Ser
            20                  25
```

<210> SEQ ID NO 26
<211> LENGTH: 25
<212> TYPE: PRT
<213> ORGANISM: Artificial Sequence
<220> FEATURE:
<223> OTHER INFORMATION: Synthetic Construct

<400> SEQUENCE: 26

```
Gln Val Lys Leu Val Glu Ser Gly Gly Gly Leu Val Gln Ser Gly Gly
1               5                   10                  15

Ser Leu Arg Leu Ser Cys Ala Val Ser
            20                  25
```

<210> SEQ ID NO 27
<211> LENGTH: 25
<212> TYPE: PRT
<213> ORGANISM: Artificial Sequence
<220> FEATURE:
<223> OTHER INFORMATION: Synthetic Construct

<400> SEQUENCE: 27

```
Gln Ile Gln Leu Val Glu Ser Gly Gly Gly Ser Val Gln Ala Gly Gly
1               5                   10                  15

Ser Leu Arg Leu Ser Cys Ala Val Thr
            20                  25
```

<210> SEQ ID NO 28
<211> LENGTH: 25
<212> TYPE: PRT
<213> ORGANISM: Artificial Sequence
<220> FEATURE:
<223> OTHER INFORMATION: Synthetic Construct

<400> SEQUENCE: 28

```
Gln Val His Leu Met Glu Ser Gly Gly Gly Ser Val Gln Ala Gly Gly
1               5                   10                  15

Ser Leu Arg Leu Ser Cys Val Val Ser
            20                  25
```

<210> SEQ ID NO 29
<211> LENGTH: 25
<212> TYPE: PRT
<213> ORGANISM: Artificial Sequence
<220> FEATURE:
<223> OTHER INFORMATION: Synthetic Construct

<400> SEQUENCE: 29

Gln Val Gln Leu Val Glu Ser Gly Gly Gly Ser Val Gln Ala Gly Gly
1               5                   10                  15

Ser Leu Arg Leu Ser Cys Ala Val Ser
            20                  25

<210> SEQ ID NO 30
<211> LENGTH: 25
<212> TYPE: PRT
<213> ORGANISM: Artificial Sequence
<220> FEATURE:
<223> OTHER INFORMATION: Synthetic Construct

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 31
<211> LENGTH: 25
<212> TYPE: PRT
<213> ORGANISM: Artificial Sequence
<220> FEATURE:
<223> OTHER INFORMATION: Synthetic Construct

<400> SEQUENCE: 31

Gln Val Gln Leu Val Glu Ser Gly Gly Gly Leu Met Gln Pro Gly Gly
1               5                   10                  15

Ser Leu Arg Leu Ser Cys Ala Ala Ser
            20                  25

<210> SEQ ID NO 32
<211> LENGTH: 25
<212> TYPE: PRT
<213> ORGANISM: Artificial Sequence
<220> FEATURE:
<223> OTHER INFORMATION: Synthetic Construct

<400> SEQUENCE: 32

Gln Val Gln Leu Val Glu Ser Gly Gly Gly Ser Val Gln Ala Gly Gly
1               5                   10                  15

Ser Leu Arg Leu Ser Cys Ala Ala Thr
            20                  25

<210> SEQ ID NO 33
<211> LENGTH: 25
<212> TYPE: PRT
<213> ORGANISM: Artificial Sequence
<220> FEATURE:
<223> OTHER INFORMATION: Synthetic Construct

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Val Ser
            20                  25

<210> SEQ ID NO 34
<211> LENGTH: 25
<212> TYPE: PRT
<213> ORGANISM: Artificial Sequence
<220> FEATURE:
<223> OTHER INFORMATION: Synthetic Construct

```
<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Val Ser
            20                  25

<210> SEQ ID NO 35
<211> LENGTH: 25
<212> TYPE: PRT
<213> ORGANISM: Artificial Sequence
<220> FEATURE:
<223> OTHER INFORMATION: Synthetic Construct

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Val Ser
            20                  25

<210> SEQ ID NO 36
<211> LENGTH: 25
<212> TYPE: PRT
<213> ORGANISM: Artificial Sequence
<220> FEATURE:
<223> OTHER INFORMATION: Synthetic Construct

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Val Ser
            20                  25

<210> SEQ ID NO 37
<211> LENGTH: 10
<212> TYPE: PRT
<213> ORGANISM: Artificial Sequence
<220> FEATURE:
<223> OTHER INFORMATION: Synthetic Construct

<400> SEQUENCE: 37

Gly Gly Thr Leu Asp Tyr Tyr Ala Ile Gly
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Synthetic Construct

<400> SEQUENCE: 38

Gly Ser Ile Thr Ser Arg Asn Thr Met Gly
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Synthetic Construct

<400> SEQUENCE: 39

Gly Tyr Thr Tyr Ile Pro Asn Cys Met Ala
1               5                   10
```

<210> SEQ ID NO 40
<211> LENGTH: 10
<212> TYPE: PRT
<213> ORGANISM: Artificial Sequence
<220> FEATURE:
<223> OTHER INFORMATION: Synthetic Construct

<400> SEQUENCE: 40

Ala Tyr Thr Tyr Ser Asn Ile Cys Leu Gly
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Synthetic Construct

<400> SEQUENCE: 41

Gly Tyr Ile Tyr Asn Arg Asn Phe Met Gly
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Synthetic Construct

<400> SEQUENCE: 42

Gly Tyr Ile Tyr Asn Arg Asn Phe Met Gly
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Synthetic Construct

<400> SEQUENCE: 43

Gly Asn Ile Tyr Asn Arg Asn Phe Met Gly
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Synthetic Construct

<400> SEQUENCE: 44

Gly Phe Thr Phe Ser Thr Ala Ala Met Ser
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Synthetic Construct

<400> SEQUENCE: 45

Gly Phe Thr Asp Ser Ser Tyr Cys Gly Ala
1               5                   10

```
<210> SEQ ID NO 46
<211> LENGTH: 10
<212> TYPE: PRT
<213> ORGANISM: Artificial Sequence
<220> FEATURE:
<223> OTHER INFORMATION: Synthetic Construct

<400> SEQUENCE: 46

Val Phe Thr Asp Ser Asn Tyr Cys Met Ala
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Synthetic Construct

<400> SEQUENCE: 47

Gly Phe Thr Asp Ser Ser Tyr Cys Gly Ala
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Synthetic Construct

<400> SEQUENCE: 48

Gly Tyr Thr Ala Gly Ser Leu Cys Met Gly
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Synthetic Construct

<400> SEQUENCE: 49

Gly Asp Thr Asn Asn Leu Asn Phe Arg Gly
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Synthetic Construct

<400> SEQUENCE: 50

Gly Phe Thr Phe Asn Asn Tyr Ala Met Gly
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Synthetic Construct

<400> SEQUENCE: 51

Gly Ser Gly Tyr Ser Tyr Ser Arg Gly Cys Phe Ala
1               5                   10

<210> SEQ ID NO 52
```

```
<211> LENGTH: 10
<212> TYPE: PRT
<213> ORGANISM: Artificial Sequence
<220> FEATURE:
<223> OTHER INFORMATION: Synthetic Construct

<400> SEQUENCE: 52

Gln Trp Ile Ser Ser Asp Cys Gly Met Ala
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Synthetic Construct

<400> SEQUENCE: 53

Gly Tyr Ser Trp Arg Pro Asp Cys Met Gly
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Synthetic Construct

<400> SEQUENCE: 54

Gly Ile Ser Ile Ser Pro Asp Cys Met Gly
1               5                   10

<210> SEQ ID NO 55
<211> LENGTH: 12
<212> TYPE: PRT
<213> ORGANISM: Artificial Sequence
<220> FEATURE:
<223> OTHER INFORMATION: Synthetic Construct

<400> SEQUENCE: 55

Gly Ser Gly Tyr Ser Tyr Ser Arg Gly Cys Phe Ala
1               5                   10

<210> SEQ ID NO 56
<211> LENGTH: 10
<212> TYPE: PRT
<213> ORGANISM: Artificial Sequence
<220> FEATURE:
<223> OTHER INFORMATION: Synthetic Construct

<400> SEQUENCE: 56

Ala Tyr Thr Ala Ser Asn Tyr Cys Met Gly
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Synthetic Construct

<400> SEQUENCE: 57

Gly Thr Ser Ile Ser Pro Asp Cys Met Gly
1               5                   10

<210> SEQ ID NO 58
<211> LENGTH: 10
```

```
<212> TYPE: PRT
<213> ORGANISM: Artificial Sequence
<220> FEATURE:
<223> OTHER INFORMATION: Synthetic Construct

<400> SEQUENCE: 58

Gly Tyr Ser Trp Arg Pro Asp Cys Met Gly
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Synthetic Construct

<400> SEQUENCE: 59

Gly Ser Gly Tyr Ser Tyr Ser Arg Gly Cys Phe Ala
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Synthetic Construct

<400> SEQUENCE: 60

Gly Ser Gly Tyr Ser Tyr Ser Arg Gly Cys Phe Ala
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Synthetic Construct

<400> SEQUENCE: 61

Gly Ser Gly Tyr Ser Tyr Asn Arg Gly Cys Phe Ala
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Synthetic Construct

<400> SEQUENCE: 62

Gly Ser Gly Tyr Ser Tyr Ser Arg Gly Cys Phe Ala
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Synthetic Construct

<400> SEQUENCE: 63

Gly Ile Ser Ile Ser Pro Asp Cys Met Gly
1               5                   10

<210> SEQ ID NO 64
<211> LENGTH: 10
<212> TYPE: PRT
```

```
<213> ORGANISM: Artificial Sequence
<220> FEATURE:
<223> OTHER INFORMATION: Synthetic Construct

<400> SEQUENCE: 64

Gly Ile Ser Ile Ser Pro Asp Cys Met Gly
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Synthetic Construct

<400> SEQUENCE: 65

Gly Ile Ser Ile Ser Pro Asp Cys Met Gly
1               5                   10

<210> SEQ ID NO 66
<211> LENGTH: 10
<212> TYPE: PRT
<213> ORGANISM: Artificial Sequence
<220> FEATURE:
<223> OTHER INFORMATION: Synthetic Construct

<400> SEQUENCE: 66

Gly Phe Thr Phe Ser Val Trp Ser Met Ser
1               5                   10

<210> SEQ ID NO 67
<211> LENGTH: 10
<212> TYPE: PRT
<213> ORGANISM: Artificial Sequence
<220> FEATURE:
<223> OTHER INFORMATION: Synthetic Construct

<400> SEQUENCE: 67

Gly Phe Thr Phe Ser Ser Tyr Trp Met Tyr
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Synthetic Construct

<400> SEQUENCE: 68

Ala Tyr Thr Ala Ser Phe Tyr Cys Met Gly
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Synthetic Construct

<400> SEQUENCE: 69

Gly Asn Ile Tyr Asn Arg Asn Phe Met Gly
1               5                   10

<210> SEQ ID NO 70
<211> LENGTH: 10
<212> TYPE: PRT
<213> ORGANISM: Artificial Sequence
```

```
<220> FEATURE:
<223> OTHER INFORMATION: Synthetic Construct

<400> SEQUENCE: 70

Gly Asn Ile Tyr Asn Arg Asn Phe Met Gly
1               5                   10

<210> SEQ ID NO 71
<211> LENGTH: 10
<212> TYPE: PRT
<213> ORGANISM: Artificial Sequence
<220> FEATURE:
<223> OTHER INFORMATION: Synthetic Construct

<400> SEQUENCE: 71

Gly Asn Ile Tyr Asn Arg Asn Phe Met Gly
1               5                   10

<210> SEQ ID NO 72
<211> LENGTH: 10
<212> TYPE: PRT
<213> ORGANISM: Artificial Sequence
<220> FEATURE:
<223> OTHER INFORMATION: Synthetic Construct

<400> SEQUENCE: 72

Gly Asn Ile Tyr Asn Arg Asn Phe Met Gly
1               5                   10

<210> SEQ ID NO 73
<211> LENGTH: 14
<212> TYPE: PRT
<213> ORGANISM: Artificial Sequence
<220> FEATURE:
<223> OTHER INFORMATION: Synthetic Construct

<400> SEQUENCE: 73

Trp Phe Arg Gln Ala Pro Gly Lys Glu Arg Glu Ala Val Ser
1               5                   10

<210> SEQ ID NO 74
<211> LENGTH: 14
<212> TYPE: PRT
<213> ORGANISM: Artificial Sequence
<220> FEATURE:
<223> OTHER INFORMATION: Synthetic Construct

<400> SEQUENCE: 74

Trp Tyr Arg Gln Val Pro Gly Lys Gln Arg Glu Leu Val Ala
1               5                   10

<210> SEQ ID NO 75
<211> LENGTH: 14
<212> TYPE: PRT
<213> ORGANISM: Artificial Sequence
<220> FEATURE:
<223> OTHER INFORMATION: Synthetic Construct

<400> SEQUENCE: 75

Trp Phe Arg Gln Ala Pro Gly Lys Glu Arg Glu Gly Val Thr
1               5                   10

<210> SEQ ID NO 76
<211> LENGTH: 14
<212> TYPE: PRT
<213> ORGANISM: Artificial Sequence
<220> FEATURE:
```

```
<223> OTHER INFORMATION: Synthetic Construct

<400> SEQUENCE: 76

Trp Leu Arg Gln Ala Pro Gly Gly Gly Leu Glu Ala Val Ala
1               5                   10

<210> SEQ ID NO 77
<211> LENGTH: 14
<212> TYPE: PRT
<213> ORGANISM: Artificial Sequence
<220> FEATURE:
<223> OTHER INFORMATION: Synthetic Construct

<400> SEQUENCE: 77

Trp Phe Arg Gln Ala Pro Gly Lys Glu Arg Glu Gly Val Ala
1               5                   10

<210> SEQ ID NO 78
<211> LENGTH: 14
<212> TYPE: PRT
<213> ORGANISM: Artificial Sequence
<220> FEATURE:
<223> OTHER INFORMATION: Synthetic Construct

<400> SEQUENCE: 78

Trp Phe Arg Gln Val Pro Gly Lys Val Arg Glu Gly Val Ala
1               5                   10

<210> SEQ ID NO 79
<211> LENGTH: 14
<212> TYPE: PRT
<213> ORGANISM: Artificial Sequence
<220> FEATURE:
<223> OTHER INFORMATION: Synthetic Construct

<400> SEQUENCE: 79

Trp Phe Arg Gln Ala Pro Gly Lys Val Arg Glu Gly Val Ala
1               5                   10

<210> SEQ ID NO 80
<211> LENGTH: 14
<212> TYPE: PRT
<213> ORGANISM: Artificial Sequence
<220> FEATURE:
<223> OTHER INFORMATION: Synthetic Construct

<400> SEQUENCE: 80

Trp Val Arg Gln Val Pro Glu Glu Gly Leu Glu Trp Val Ala
1               5                   10

<210> SEQ ID NO 81
<211> LENGTH: 14
<212> TYPE: PRT
<213> ORGANISM: Artificial Sequence
<220> FEATURE:
<223> OTHER INFORMATION: Synthetic Construct

<400> SEQUENCE: 81

Trp Phe Arg Gln Val Pro Gly Lys Glu Arg Glu Gly Val Ala
1               5                   10

<210> SEQ ID NO 82
<211> LENGTH: 14
<212> TYPE: PRT
<213> ORGANISM: Artificial Sequence
<220> FEATURE:
<223> OTHER INFORMATION: Synthetic Construct
```

```
<400> SEQUENCE: 82

Trp Phe Arg Gln Val Pro Gly Lys Glu Arg Glu Gly Val Ala
1               5                   10

<210> SEQ ID NO 83
<211> LENGTH: 14
<212> TYPE: PRT
<213> ORGANISM: Artificial Sequence
<220> FEATURE:
<223> OTHER INFORMATION: Synthetic Construct

<400> SEQUENCE: 83

Trp Phe Arg Gln Val Pro Gly Lys Glu Arg Glu Gly Val Ala
1               5                   10

<210> SEQ ID NO 84
<211> LENGTH: 14
<212> TYPE: PRT
<213> ORGANISM: Artificial Sequence
<220> FEATURE:
<223> OTHER INFORMATION: Synthetic Construct

<400> SEQUENCE: 84

Trp Phe Arg Gln Ala Pro Gly Lys Glu Arg Glu Gly Val Ala
1               5                   10

<210> SEQ ID NO 85
<211> LENGTH: 14
<212> TYPE: PRT
<213> ORGANISM: Artificial Sequence
<220> FEATURE:
<223> OTHER INFORMATION: Synthetic Construct

<400> SEQUENCE: 85

Trp Phe Arg Gln Ala Pro Gly Lys Glu Arg Glu Gly Val Ala
1               5                   10

<210> SEQ ID NO 86
<211> LENGTH: 14
<212> TYPE: PRT
<213> ORGANISM: Artificial Sequence
<220> FEATURE:
<223> OTHER INFORMATION: Synthetic Construct

<400> SEQUENCE: 86

Trp Phe Arg Gln Ala Pro Gly Lys Glu Arg Glu Gly Ile Ala
1               5                   10

<210> SEQ ID NO 87
<211> LENGTH: 14
<212> TYPE: PRT
<213> ORGANISM: Artificial Sequence
<220> FEATURE:
<223> OTHER INFORMATION: Synthetic Construct

<400> SEQUENCE: 87

Trp Phe Gln Gln Arg Pro Gly Lys Glu Arg Glu Gly Val Ala
1               5                   10

<210> SEQ ID NO 88
<211> LENGTH: 14
<212> TYPE: PRT
<213> ORGANISM: Artificial Sequence
<220> FEATURE:
<223> OTHER INFORMATION: Synthetic Construct
```

```
<400> SEQUENCE: 88

Trp Tyr Arg Gln Ala Pro Gly Lys Glu Arg Glu Leu Val Ser
1               5                   10

<210> SEQ ID NO 89
<211> LENGTH: 14
<212> TYPE: PRT
<213> ORGANISM: Artificial Sequence
<220> FEATURE:
<223> OTHER INFORMATION: Synthetic Construct

<400> SEQUENCE: 89

Trp Tyr Arg Gln Ala Ala Glu Lys Glu Arg Glu Gly Val Ala
1               5                   10

<210> SEQ ID NO 90
<211> LENGTH: 14
<212> TYPE: PRT
<213> ORGANISM: Artificial Sequence
<220> FEATURE:
<223> OTHER INFORMATION: Synthetic Construct

<400> SEQUENCE: 90

Trp Phe Arg Gln Ala Pro Gly Lys Lys Arg Glu Ala Val Thr
1               5                   10

<210> SEQ ID NO 91
<211> LENGTH: 14
<212> TYPE: PRT
<213> ORGANISM: Artificial Sequence
<220> FEATURE:
<223> OTHER INFORMATION: Synthetic Construct

<400> SEQUENCE: 91

Trp Phe Gln Gln Arg Pro Gly Lys Glu Arg Glu Gly Val Ala
1               5                   10

<210> SEQ ID NO 92
<211> LENGTH: 14
<212> TYPE: PRT
<213> ORGANISM: Artificial Sequence
<220> FEATURE:
<223> OTHER INFORMATION: Synthetic Construct

<400> SEQUENCE: 92

Trp Phe Arg Gln Ser Pro Gly Lys Glu Arg Glu Ala Val Ala
1               5                   10

<210> SEQ ID NO 93
<211> LENGTH: 14
<212> TYPE: PRT
<213> ORGANISM: Artificial Sequence
<220> FEATURE:
<223> OTHER INFORMATION: Synthetic Construct

<400> SEQUENCE: 93

Trp Phe Arg Gln Ala Pro Gly Lys Lys Arg Glu Ala Val Met
1               5                   10

<210> SEQ ID NO 94
<211> LENGTH: 14
<212> TYPE: PRT
<213> ORGANISM: Artificial Sequence
<220> FEATURE:
<223> OTHER INFORMATION: Synthetic Construct

<400> SEQUENCE: 94
```

Trp Tyr Arg Gln Ala Ala Glu Lys Glu Arg Glu Gly Val Ala
1               5                   10

<210> SEQ ID NO 95
<211> LENGTH: 14
<212> TYPE: PRT
<213> ORGANISM: Artificial Sequence
<220> FEATURE:
<223> OTHER INFORMATION: Synthetic Construct

<400> SEQUENCE: 95

Trp Phe Gln Gln Arg Pro Gly Lys Glu Arg Glu Gly Val Ala
1               5                   10

<210> SEQ ID NO 96
<211> LENGTH: 14
<212> TYPE: PRT
<213> ORGANISM: Artificial Sequence
<220> FEATURE:
<223> OTHER INFORMATION: Synthetic Construct

<400> SEQUENCE: 96

Trp Phe Gln Gln Arg Pro Gly Lys Glu Arg Glu Gly Val Ala
1               5                   10

<210> SEQ ID NO 97
<211> LENGTH: 14
<212> TYPE: PRT
<213> ORGANISM: Artificial Sequence
<220> FEATURE:
<223> OTHER INFORMATION: Synthetic Construct

<400> SEQUENCE: 97

Trp Phe Gln Gln Arg Pro Gly Lys Glu Arg Glu Gly Val Ala
1               5                   10

<210> SEQ ID NO 98
<211> LENGTH: 14
<212> TYPE: PRT
<213> ORGANISM: Artificial Sequence
<220> FEATURE:
<223> OTHER INFORMATION: Synthetic Construct

<400> SEQUENCE: 98

Trp Phe Gln Gln Arg Pro Gly Lys Glu Arg Glu Gly Val Ala
1               5                   10

<210> SEQ ID NO 99
<211> LENGTH: 14
<212> TYPE: PRT
<213> ORGANISM: Artificial Sequence
<220> FEATURE:
<223> OTHER INFORMATION: Synthetic Construct

<400> SEQUENCE: 99

Trp Phe Arg Gln Ala Pro Gly Lys Lys Arg Glu Ala Val Ala
1               5                   10

<210> SEQ ID NO 100
<211> LENGTH: 14
<212> TYPE: PRT
<213> ORGANISM: Artificial Sequence
<220> FEATURE:
<223> OTHER INFORMATION: Synthetic Construct

<400> SEQUENCE: 100

Trp Phe Arg Gln Ala Pro Gly Lys Lys Arg Glu Ala Val Ala
1               5                   10

<210> SEQ ID NO 101
<211> LENGTH: 14
<212> TYPE: PRT
<213> ORGANISM: Artificial Sequence
<220> FEATURE:
<223> OTHER INFORMATION: Synthetic Construct

<400> SEQUENCE: 101

Trp Phe Arg Gln Ala Pro Gly Lys Lys Arg Glu Ala Val Ala
1               5                   10

<210> SEQ ID NO 102
<211> LENGTH: 14
<212> TYPE: PRT
<213> ORGANISM: Artificial Sequence
<220> FEATURE:
<223> OTHER INFORMATION: Synthetic Construct

<400> SEQUENCE: 102

Trp Val Arg Gln Ala Pro Gly Glu Gly Leu Glu Trp Val Ser
1               5                   10

<210> SEQ ID NO 103
<211> LENGTH: 14
<212> TYPE: PRT
<213> ORGANISM: Artificial Sequence
<220> FEATURE:
<223> OTHER INFORMATION: Synthetic Construct

<400> SEQUENCE: 103

Trp Val Arg Gln Ala Pro Gly Lys Gly Leu Glu Trp Val Ser
1               5                   10

<210> SEQ ID NO 104
<211> LENGTH: 14
<212> TYPE: PRT
<213> ORGANISM: Artificial Sequence
<220> FEATURE:
<223> OTHER INFORMATION: Synthetic Construct

<400> SEQUENCE: 104

Trp Phe Arg Gln Ala Pro Gly Lys Glu Arg Glu Ala Val Ala
1               5                   10

<210> SEQ ID NO 105
<211> LENGTH: 14
<212> TYPE: PRT
<213> ORGANISM: Artificial Sequence
<220> FEATURE:
<223> OTHER INFORMATION: Synthetic Construct

<400> SEQUENCE: 105

Trp Phe Arg Gln Ala Pro Gly Lys Gly Leu Glu Gly Val Ser
1               5                   10

<210> SEQ ID NO 106
<211> LENGTH: 14
<212> TYPE: PRT
<213> ORGANISM: Artificial Sequence
<220> FEATURE:
<223> OTHER INFORMATION: Synthetic Construct

<400> SEQUENCE: 106

Trp Phe Arg Gln Ala Pro Gly Lys Gly Leu Glu Gly Val Ser

```
<210> SEQ ID NO 107
<211> LENGTH: 14
<212> TYPE: PRT
<213> ORGANISM: Artificial Sequence
<220> FEATURE:
<223> OTHER INFORMATION: Synthetic Construct

<400> SEQUENCE: 107

Trp Phe Arg Gln Ala Pro Gly Lys Gly Arg Glu Gly Val Ser
1               5                   10

<210> SEQ ID NO 108
<211> LENGTH: 14
<212> TYPE: PRT
<213> ORGANISM: Artificial Sequence
<220> FEATURE:
<223> OTHER INFORMATION: Synthetic Construct

<400> SEQUENCE: 108

Trp Phe Arg Gln Ala Pro Gly Lys Gly Arg Glu Gly Val Ser
1               5                   10

<210> SEQ ID NO 109
<211> LENGTH: 17
<212> TYPE: PRT
<213> ORGANISM: Artificial Sequence
<220> FEATURE:
<223> OTHER INFORMATION: Synthetic Construct

<400> SEQUENCE: 109

Cys Ile Ser Ser Ser Asp Gly Ser Thr Tyr Tyr Ala Asp Ser Val Lys
1               5                   10                  15

Gly

<210> SEQ ID NO 110
<211> LENGTH: 15
<212> TYPE: PRT
<213> ORGANISM: Artificial Sequence
<220> FEATURE:
<223> OTHER INFORMATION: Synthetic Construct

<400> SEQUENCE: 110

Leu Ile Ala Thr Phe Val Thr His Tyr Ala Asp Ser Val Lys Gly
1               5                   10                  15

<210> SEQ ID NO 111
<211> LENGTH: 17
<212> TYPE: PRT
<213> ORGANISM: Artificial Sequence
<220> FEATURE:
<223> OTHER INFORMATION: Synthetic Construct

<400> SEQUENCE: 111

Leu Ile Phe Thr Gly Asp Gly Thr Ser Thr Tyr Val Asp Ser Val Lys
1               5                   10                  15

Gly

<210> SEQ ID NO 112
<211> LENGTH: 17
<212> TYPE: PRT
<213> ORGANISM: Artificial Sequence
<220> FEATURE:
<223> OTHER INFORMATION: Synthetic Construct
```

```
<400> SEQUENCE: 112

Thr Ile Tyr Ile Ala Asp Gln Thr Ser Tyr Tyr Ala Asp Ser Val Lys
1               5                   10                  15

Gly

<210> SEQ ID NO 113
<211> LENGTH: 17
<212> TYPE: PRT
<213> ORGANISM: Artificial Sequence
<220> FEATURE:
<223> OTHER INFORMATION: Synthetic Construct

<400> SEQUENCE: 113

Ala Ile Tyr Thr Gly Gly Pro Tyr Thr Tyr Tyr Thr Asp Ser Val Gln
1               5                   10                  15

Gly

<210> SEQ ID NO 114
<211> LENGTH: 17
<212> TYPE: PRT
<213> ORGANISM: Artificial Sequence
<220> FEATURE:
<223> OTHER INFORMATION: Synthetic Construct

<400> SEQUENCE: 114

Ala Ile Tyr Thr Gly Thr Glu Arg Thr Tyr Tyr Ala Asp Ser Val Lys
1               5                   10                  15

Gly

<210> SEQ ID NO 115
<211> LENGTH: 17
<212> TYPE: PRT
<213> ORGANISM: Artificial Sequence
<220> FEATURE:
<223> OTHER INFORMATION: Synthetic Construct

<400> SEQUENCE: 115

Ala Ile Tyr Thr Gly Thr Ser Arg Thr Tyr Tyr Ala Asp Ser Val Lys
1               5                   10                  15

Gly

<210> SEQ ID NO 116
<211> LENGTH: 17
<212> TYPE: PRT
<213> ORGANISM: Artificial Sequence
<220> FEATURE:
<223> OTHER INFORMATION: Synthetic Construct

<400> SEQUENCE: 116

Ser Ile Asp Ser Ser Gly Ser Arg Thr Tyr Tyr Ala Gly Ser Val Lys
1               5                   10                  15

Gly

<210> SEQ ID NO 117
<211> LENGTH: 16
<212> TYPE: PRT
<213> ORGANISM: Artificial Sequence
<220> FEATURE:
<223> OTHER INFORMATION: Synthetic Construct

<400> SEQUENCE: 117

Ile Ile Asp Arg Tyr Gly Gly Thr Met Tyr Lys Asp Ser Val Lys Gly
1               5                   10                  15
```

<210> SEQ ID NO 118
<211> LENGTH: 16
<212> TYPE: PRT
<213> ORGANISM: Artificial Sequence
<220> FEATURE:
<223> OTHER INFORMATION: Synthetic Construct

<400> SEQUENCE: 118

Ile Ile Asp Arg Tyr Gly Gly Thr Met Tyr Lys Asp Ser Val Lys Gly
1               5                   10                  15

<210> SEQ ID NO 119
<211> LENGTH: 16
<212> TYPE: PRT
<213> ORGANISM: Artificial Sequence
<220> FEATURE:
<223> OTHER INFORMATION: Synthetic Construct

<400> SEQUENCE: 119

Ile Ile Asp Arg Tyr Gly Gly Thr Met Tyr Lys Asp Ser Val Lys Gly
1               5                   10                  15

<210> SEQ ID NO 120
<211> LENGTH: 17
<212> TYPE: PRT
<213> ORGANISM: Artificial Sequence
<220> FEATURE:
<223> OTHER INFORMATION: Synthetic Construct

<400> SEQUENCE: 120

Ala Ile Tyr Thr Gly Gly Gly Ser Thr Tyr Tyr Ala Asp Ser Val Lys
1               5                   10                  15
Gly

<210> SEQ ID NO 121
<211> LENGTH: 16
<212> TYPE: PRT
<213> ORGANISM: Artificial Sequence
<220> FEATURE:
<223> OTHER INFORMATION: Synthetic Construct

<400> SEQUENCE: 121

Val Ile Thr His Ser Gly Ser Thr Tyr Tyr Ala Glu Ser Val Lys Gly
1               5                   10                  15

<210> SEQ ID NO 122
<211> LENGTH: 17
<212> TYPE: PRT
<213> ORGANISM: Artificial Sequence
<220> FEATURE:
<223> OTHER INFORMATION: Synthetic Construct

<400> SEQUENCE: 122

Gly Ile Trp Thr Gly Gly Gly Ser Thr Tyr Tyr Ala Asp Ser Val Lys
1               5                   10                  15
Gly

<210> SEQ ID NO 123
<211> LENGTH: 16
<212> TYPE: PRT
<213> ORGANISM: Artificial Sequence
<220> FEATURE:
<223> OTHER INFORMATION: Synthetic Construct

<400> SEQUENCE: 123

```
Ile Ile Asn Met Asp Gly His Thr Arg Tyr Ser Asp Ser Val Gln Gly
1               5                   10                  15

<210> SEQ ID NO 124
<211> LENGTH: 16
<212> TYPE: PRT
<213> ORGANISM: Artificial Sequence
<220> FEATURE:
<223> OTHER INFORMATION: Synthetic Construct

<400> SEQUENCE: 124

Arg Ile Ser Ser Asp Asp Thr Thr Thr Tyr Ala Asp Ser Val Lys Gly
1               5                   10                  15

<210> SEQ ID NO 125
<211> LENGTH: 16
<212> TYPE: PRT
<213> ORGANISM: Artificial Sequence
<220> FEATURE:
<223> OTHER INFORMATION: Synthetic Construct

<400> SEQUENCE: 125

Val Ile Asp Ala Asp Gly Ile Thr Ser Tyr Ala Asp Ala Ala Lys Gly
1               5                   10                  15

<210> SEQ ID NO 126
<211> LENGTH: 17
<212> TYPE: PRT
<213> ORGANISM: Artificial Sequence
<220> FEATURE:
<223> OTHER INFORMATION: Synthetic Construct

<400> SEQUENCE: 126

Thr Ile Phe Ala Asn Thr Gly Ser Ala Arg Tyr Gly Asp Ser Val Lys
1               5                   10                  15

Gly

<210> SEQ ID NO 127
<211> LENGTH: 16
<212> TYPE: PRT
<213> ORGANISM: Artificial Sequence
<220> FEATURE:
<223> OTHER INFORMATION: Synthetic Construct

<400> SEQUENCE: 127

Ile Ile Asn Ser Asp Gly His Thr Ala Tyr Ser Asp Ser Val Gln Gly
1               5                   10                  15

<210> SEQ ID NO 128
<211> LENGTH: 16
<212> TYPE: PRT
<213> ORGANISM: Artificial Sequence
<220> FEATURE:
<223> OTHER INFORMATION: Synthetic Construct

<400> SEQUENCE: 128

Ser Ile Asn Asp Asp Gly Val Thr Ser Tyr Ala Asp Ser Val Lys Gly
1               5                   10                  15

<210> SEQ ID NO 129
<211> LENGTH: 17
<212> TYPE: PRT
<213> ORGANISM: Artificial Sequence
<220> FEATURE:
<223> OTHER INFORMATION: Synthetic Construct
```

```
<400> SEQUENCE: 129

Ser Ile Phe Thr Asn Thr Gly Ser Thr Arg Tyr Gly Asp Ser Val Lys
1               5                   10                  15

Gly

<210> SEQ ID NO 130
<211> LENGTH: 16
<212> TYPE: PRT
<213> ORGANISM: Artificial Sequence
<220> FEATURE:
<223> OTHER INFORMATION: Synthetic Construct

<400> SEQUENCE: 130

Val Ile Asp Ala Asp Gly Ile Thr Ser Tyr Ala Asp Ala Ala Lys Gly
1               5                   10                  15

<210> SEQ ID NO 131
<211> LENGTH: 16
<212> TYPE: PRT
<213> ORGANISM: Artificial Sequence
<220> FEATURE:
<223> OTHER INFORMATION: Synthetic Construct

<400> SEQUENCE: 131

Ile Ile Asn Ser Asp Gly His Thr Arg Tyr Ser Asp Ser Val Gln Gly
1               5                   10                  15

<210> SEQ ID NO 132
<211> LENGTH: 16
<212> TYPE: PRT
<213> ORGANISM: Artificial Sequence
<220> FEATURE:
<223> OTHER INFORMATION: Synthetic Construct

<400> SEQUENCE: 132

Ile Ile Asn Ser Asp Gly His Thr Arg Tyr Ser Asp Ser Val Gln Gly
1               5                   10                  15

<210> SEQ ID NO 133
<211> LENGTH: 16
<212> TYPE: PRT
<213> ORGANISM: Artificial Sequence
<220> FEATURE:
<223> OTHER INFORMATION: Synthetic Construct

<400> SEQUENCE: 133

Ile Ile Asn Ser Asp Gly His Thr Thr Tyr Gly Asp Ser Val Gln Gly
1               5                   10                  15

<210> SEQ ID NO 134
<211> LENGTH: 16
<212> TYPE: PRT
<213> ORGANISM: Artificial Sequence
<220> FEATURE:
<223> OTHER INFORMATION: Synthetic Construct

<400> SEQUENCE: 134

Ile Ile Asn Met Asp Gly His Thr Met Tyr Ser Asp Leu Ala Gln Gly
1               5                   10                  15

<210> SEQ ID NO 135
<211> LENGTH: 17
<212> TYPE: PRT
<213> ORGANISM: Artificial Sequence
<220> FEATURE:
<223> OTHER INFORMATION: Synthetic Construct
```

<400> SEQUENCE: 135

Thr Ile Phe Thr Asn Thr Ala Ser Thr Arg Tyr Gly Asp Ser Val Lys
1               5                   10                  15

Gly

<210> SEQ ID NO 136
<211> LENGTH: 17
<212> TYPE: PRT
<213> ORGANISM: Artificial Sequence
<220> FEATURE:
<223> OTHER INFORMATION: Synthetic Construct

<400> SEQUENCE: 136

Thr Ile Phe Thr Asn Thr Arg Arg Thr Arg Tyr Gly Asp Ser Val Lys
1               5                   10                  15

Gly

<210> SEQ ID NO 137
<211> LENGTH: 17
<212> TYPE: PRT
<213> ORGANISM: Artificial Sequence
<220> FEATURE:
<223> OTHER INFORMATION: Synthetic Construct

<400> SEQUENCE: 137

Thr Ile Phe Thr Asn Thr Arg Ser Thr Arg Tyr Gly Asp Ser Val Lys
1               5                   10                  15

Gly

<210> SEQ ID NO 138
<211> LENGTH: 17
<212> TYPE: PRT
<213> ORGANISM: Artificial Sequence
<220> FEATURE:
<223> OTHER INFORMATION: Synthetic Construct

<400> SEQUENCE: 138

Thr Ile Thr Gly Ser Gly Ala Gln Thr Tyr Tyr Ala Ser Ser Val Arg
1               5                   10                  15

Gly

<210> SEQ ID NO 139
<211> LENGTH: 17
<212> TYPE: PRT
<213> ORGANISM: Artificial Sequence
<220> FEATURE:
<223> OTHER INFORMATION: Synthetic Construct

<400> SEQUENCE: 139

Val Ile Asn Arg Ala Gly Asp Ser Ala Trp Tyr Ala Asp Ser Val Thr
1               5                   10                  15

Gly

<210> SEQ ID NO 140
<211> LENGTH: 16
<212> TYPE: PRT
<213> ORGANISM: Artificial Sequence
<220> FEATURE:
<223> OTHER INFORMATION: Synthetic Construct

<400> SEQUENCE: 140

Ser Ile Asn Asp Asp Gly Val Thr Met Tyr Ala Asp Ser Val Lys Gly

```
<210> SEQ ID NO 141
<211> LENGTH: 17
<212> TYPE: PRT
<213> ORGANISM: Artificial Sequence
<220> FEATURE:
<223> OTHER INFORMATION: Synthetic Construct

<400> SEQUENCE: 141

Ala Ile Tyr Thr Gly Thr Ser Arg Thr Tyr Tyr Ala Asp Ser Val Lys
1               5                   10                  15

Gly

<210> SEQ ID NO 142
<211> LENGTH: 17
<212> TYPE: PRT
<213> ORGANISM: Artificial Sequence
<220> FEATURE:
<223> OTHER INFORMATION: Synthetic Construct

<400> SEQUENCE: 142

Ala Ile Tyr Thr Gly Thr Ser Arg Thr Tyr Tyr Ala Asp Ser Val Lys
1               5                   10                  15

Gly

<210> SEQ ID NO 143
<211> LENGTH: 17
<212> TYPE: PRT
<213> ORGANISM: Artificial Sequence
<220> FEATURE:
<223> OTHER INFORMATION: Synthetic Construct

<400> SEQUENCE: 143

Ala Ile Tyr Thr Gly Thr Ser Arg Thr Tyr Tyr Ala Asp Ser Val Lys
1               5                   10                  15

Gly

<210> SEQ ID NO 144
<211> LENGTH: 17
<212> TYPE: PRT
<213> ORGANISM: Artificial Sequence
<220> FEATURE:
<223> OTHER INFORMATION: Synthetic Construct

<400> SEQUENCE: 144

Ala Ile Tyr Thr Gly Thr Ser Arg Thr Tyr Tyr Ala Asp Ser Val Lys
1               5                   10                  15

Gly

<210> SEQ ID NO 145
<211> LENGTH: 32
<212> TYPE: PRT
<213> ORGANISM: Artificial Sequence
<220> FEATURE:
<223> OTHER INFORMATION: Synthetic Construct

<400> SEQUENCE: 145

Arg Phe Thr Ile Ser Arg Asp Asn Ala Lys Asn Thr Val Tyr Leu Gln
1               5                   10                  15

Met Asn Ser Leu Lys Pro Gly Asp Thr Ala Val Tyr His Cys Ala Thr
            20                  25                  30
```

```
<210> SEQ ID NO 146
<211> LENGTH: 32
<212> TYPE: PRT
<213> ORGANISM: Artificial Sequence
<220> FEATURE:
<223> OTHER INFORMATION: Synthetic Construct

<400> SEQUENCE: 146

Arg Phe Thr Ile Ser Arg Asp Asn Ala Arg Lys Met Val Phe Leu Glu
1               5                   10                  15

Met Asn Ser Leu Gln Pro Glu Asp Thr Gly Ala Tyr Tyr Cys Tyr Val
            20                  25                  30

<210> SEQ ID NO 147
<211> LENGTH: 32
<212> TYPE: PRT
<213> ORGANISM: Artificial Sequence
<220> FEATURE:
<223> OTHER INFORMATION: Synthetic Construct

<400> SEQUENCE: 147

Arg Phe Thr Ile Ser Gln Asp Asn Ala Lys Asn Thr Val Tyr Leu Gln
1               5                   10                  15

Met Asn Ser Leu Lys Pro Glu Asp Thr Ala Leu Tyr Tyr Cys Ala Ala
            20                  25                  30

<210> SEQ ID NO 148
<211> LENGTH: 32
<212> TYPE: PRT
<213> ORGANISM: Artificial Sequence
<220> FEATURE:
<223> OTHER INFORMATION: Synthetic Construct

<400> SEQUENCE: 148

Arg Phe Arg Ile Ser Lys Asp Ala Ala Lys Asn Ala Val Tyr Leu Gln
1               5                   10                  15

Met Ser Ser Leu Arg Pro Glu Asp Thr Ala Met Tyr Tyr Cys Ala Ser
            20                  25                  30

<210> SEQ ID NO 149
<211> LENGTH: 32
<212> TYPE: PRT
<213> ORGANISM: Artificial Sequence
<220> FEATURE:
<223> OTHER INFORMATION: Synthetic Construct

<400> SEQUENCE: 149

Arg Phe Thr Ile Ser Gln Asp Asn Thr Lys Asn Thr Val Tyr Leu Gln
1               5                   10                  15

Met Asn Ser Leu Lys Pro Glu Asp Thr Ala Met Tyr Tyr Cys Val Ser
            20                  25                  30

<210> SEQ ID NO 150
<211> LENGTH: 32
<212> TYPE: PRT
<213> ORGANISM: Artificial Sequence
<220> FEATURE:
<223> OTHER INFORMATION: Synthetic Construct

<400> SEQUENCE: 150

Arg Phe Thr Ile Ser Gln Asp Asn Ala Lys Asn Thr Val Tyr Leu Gln
1               5                   10                  15

Met Asn Ser Leu Lys Pro Glu Asp Thr Ala Met Tyr Tyr Cys Val Ala
            20                  25                  30
```

```
<210> SEQ ID NO 151
<211> LENGTH: 32
<212> TYPE: PRT
<213> ORGANISM: Artificial Sequence
<220> FEATURE:
<223> OTHER INFORMATION: Synthetic Construct

<400> SEQUENCE: 151

Arg Phe Thr Ile Ser Gln Asp Asn Ala Lys Asn Thr Val Tyr Leu Gln
1               5                   10                  15

Met Asn Ser Leu Lys Pro Glu Asp Thr Ala Met Tyr Tyr Cys Ala Ala
            20                  25                  30

<210> SEQ ID NO 152
<211> LENGTH: 32
<212> TYPE: PRT
<213> ORGANISM: Artificial Sequence
<220> FEATURE:
<223> OTHER INFORMATION: Synthetic Construct

<400> SEQUENCE: 152

Arg Phe Thr Ile Ser Arg Asp Asn Ala Lys Asn Thr Leu Tyr Leu Gln
1               5                   10                  15

Leu Asn Ser Leu Lys Ala Glu Asp Thr Ala Met Tyr Tyr Cys Ala Lys
            20                  25                  30

<210> SEQ ID NO 153
<211> LENGTH: 32
<212> TYPE: PRT
<213> ORGANISM: Artificial Sequence
<220> FEATURE:
<223> OTHER INFORMATION: Synthetic Construct

<400> SEQUENCE: 153

Arg Phe Thr Ile Ser Lys Asp Thr Ala Lys Asn Ile Leu Tyr Leu Gln
1               5                   10                  15

Met Asn Ser Leu Lys Leu Glu Asp Thr Ala Met Tyr Tyr Cys Ala Ala
            20                  25                  30

<210> SEQ ID NO 154
<211> LENGTH: 32
<212> TYPE: PRT
<213> ORGANISM: Artificial Sequence
<220> FEATURE:
<223> OTHER INFORMATION: Synthetic Construct

<400> SEQUENCE: 154

Arg Phe Thr Ile Ser Lys Asp Thr Ala Lys Asn Ile Leu Tyr Leu Gln
1               5                   10                  15

Met Asn Ser Leu Lys Leu Glu Asp Thr Ala Met Tyr Tyr Cys Ala Ala
            20                  25                  30

<210> SEQ ID NO 155
<211> LENGTH: 32
<212> TYPE: PRT
<213> ORGANISM: Artificial Sequence
<220> FEATURE:
<223> OTHER INFORMATION: Synthetic Construct

<400> SEQUENCE: 155

Arg Phe Thr Ile Ser Lys Asp Thr Ala Lys Asn Ile Leu Tyr Leu Gln
1               5                   10                  15

Met Asn Ser Leu Lys Leu Glu Asp Thr Ala Met Tyr Tyr Cys Ala Ala
            20                  25                  30
```

<210> SEQ ID NO 156
<211> LENGTH: 32
<212> TYPE: PRT
<213> ORGANISM: Artificial Sequence
<220> FEATURE:
<223> OTHER INFORMATION: Synthetic Construct

<400> SEQUENCE: 156

Arg Phe Thr Ile Ser Gln Asp Asn Ala Lys Asn Thr Val Tyr Leu Gln
1               5                   10                  15

Met Asn Ser Leu Lys Pro Glu Asp Thr Ala Gln Tyr Tyr Cys Gly Ala
            20                  25                  30

<210> SEQ ID NO 157
<211> LENGTH: 32
<212> TYPE: PRT
<213> ORGANISM: Artificial Sequence
<220> FEATURE:
<223> OTHER INFORMATION: Synthetic Construct

<400> SEQUENCE: 157

Arg Phe Thr Ile Ser Gln Asp Leu Ala Lys Asn Thr Met Tyr Leu Gln
1               5                   10                  15

Met Asn Ser Leu Lys Pro Glu Asp Thr Ala Met Tyr Tyr Cys Ala Ala
            20                  25                  30

<210> SEQ ID NO 158
<211> LENGTH: 32
<212> TYPE: PRT
<213> ORGANISM: Artificial Sequence
<220> FEATURE:
<223> OTHER INFORMATION: Synthetic Construct

<400> SEQUENCE: 158

Arg Phe Thr Ile Ser Glu Asp Val Ala Lys Asn Thr Val Tyr Leu Gln
1               5                   10                  15

Met Asp Ser Leu Lys Pro Glu Asp Thr Ala Met Tyr Tyr Cys Ala Ala
            20                  25                  30

<210> SEQ ID NO 159
<211> LENGTH: 32
<212> TYPE: PRT
<213> ORGANISM: Artificial Sequence
<220> FEATURE:
<223> OTHER INFORMATION: Synthetic Construct

<400> SEQUENCE: 159

Arg Phe Ile Ile Ser Gln Asp Lys Ala Lys Asn Thr Leu His Leu Gln
1               5                   10                  15

Met Asn Thr Leu Arg Pro Asp Asp Thr Ala Met Tyr Tyr Cys Ala Tyr
            20                  25                  30

<210> SEQ ID NO 160
<211> LENGTH: 32
<212> TYPE: PRT
<213> ORGANISM: Artificial Sequence
<220> FEATURE:
<223> OTHER INFORMATION: Synthetic Construct

<400> SEQUENCE: 160

Arg Phe Thr Ile Ser Gln Asp Ser Ala Lys Asn Thr Leu Tyr Leu Gln
1               5                   10                  15

Met Asn Lys Leu Lys Thr Glu Asp Thr Gly Val Tyr Tyr Cys Ala Ala

```
            20                  25                  30
```

<210> SEQ ID NO 161
<211> LENGTH: 30
<212> TYPE: PRT
<213> ORGANISM: Artificial Sequence
<220> FEATURE:
<223> OTHER INFORMATION: Synthetic Construct

<400> SEQUENCE: 161

```
Arg Phe Thr Ile Ser Arg Asp Asn Asn Lys Ile Thr Leu Tyr Leu Gln
1               5                  10                  15

Met Leu Lys Pro Asp Asp Thr Gly Met Tyr Val Cys Val Val
            20                  25                  30
```

<210> SEQ ID NO 162
<211> LENGTH: 32
<212> TYPE: PRT
<213> ORGANISM: Artificial Sequence
<220> FEATURE:
<223> OTHER INFORMATION: Synthetic Construct

<400> SEQUENCE: 162

```
Arg Phe Thr Ser Ser Gln Gly Asn Ala Lys Asn Thr Leu Tyr Leu Gln
1               5                  10                  15

Met Asp Ser Val Lys Leu Asp Asp Thr Gly Thr Tyr Tyr Cys Ala Ala
            20                  25                  30
```

<210> SEQ ID NO 163
<211> LENGTH: 32
<212> TYPE: PRT
<213> ORGANISM: Artificial Sequence
<220> FEATURE:
<223> OTHER INFORMATION: Synthetic Construct

<400> SEQUENCE: 163

```
Arg Phe Ile Ile Ser Gln Asp Lys Ala Lys Asn Thr Leu Tyr Leu Gln
1               5                  10                  15

Met Asn Ser Leu Lys Pro Asp Asp Thr Ala Met Tyr Tyr Cys Ala Tyr
            20                  25                  30
```

<210> SEQ ID NO 164
<211> LENGTH: 32
<212> TYPE: PRT
<213> ORGANISM: Artificial Sequence
<220> FEATURE:
<223> OTHER INFORMATION: Synthetic Construct

<400> SEQUENCE: 164

```
Arg Phe Thr Ile Ser Gln Asp Ser Ala Lys Lys Thr Leu Tyr Leu Gln
1               5                  10                  15

Met Asn Arg Leu Lys Pro Glu Asp Thr Ala Met Tyr Tyr Cys Ala Ala
            20                  25                  30
```

<210> SEQ ID NO 165
<211> LENGTH: 32
<212> TYPE: PRT
<213> ORGANISM: Artificial Sequence
<220> FEATURE:
<223> OTHER INFORMATION: Synthetic Construct

<400> SEQUENCE: 165

```
Arg Phe Thr Ser Ser Gln Gly Asn Ala Lys Asn Thr Leu Tyr Leu Gln
1               5                  10                  15
```

Met Asp Ser Leu Lys Leu Asp Asp Thr Ala Thr Tyr Tyr Cys Ala Ala
            20                  25                  30

<210> SEQ ID NO 166
<211> LENGTH: 30
<212> TYPE: PRT
<213> ORGANISM: Artificial Sequence
<220> FEATURE:
<223> OTHER INFORMATION: Synthetic Construct

<400> SEQUENCE: 166

Arg Phe Thr Ile Ser Arg Asp Asn Asn Ile Thr Leu Tyr Leu Gln
1               5                   10                  15

Met Leu Lys Pro Asp Asp Thr Gly Met Tyr Val Cys Val Ile
            20                  25                  30

<210> SEQ ID NO 167
<211> LENGTH: 32
<212> TYPE: PRT
<213> ORGANISM: Artificial Sequence
<220> FEATURE:
<223> OTHER INFORMATION: Synthetic Construct

<400> SEQUENCE: 167

Arg Phe Ile Ile Ser Gln Asp Lys Ala Lys Asn Thr Leu Tyr Leu Gln
1               5                   10                  15

Met Asn Ser Leu Lys Pro Asp Asp Ala Ala Met Tyr Tyr Cys Ala Tyr
            20                  25                  30

<210> SEQ ID NO 168
<211> LENGTH: 32
<212> TYPE: PRT
<213> ORGANISM: Artificial Sequence
<220> FEATURE:
<223> OTHER INFORMATION: Synthetic Construct

<400> SEQUENCE: 168

Arg Phe Ile Ile Ser Gln Asp Lys Ala Lys Asn Thr Leu Tyr Leu Gln
1               5                   10                  15

Met Asn Ser Leu Lys Pro Asp Asp Thr Ala Met Tyr Tyr Cys Ala Tyr
            20                  25                  30

<210> SEQ ID NO 169
<211> LENGTH: 32
<212> TYPE: PRT
<213> ORGANISM: Artificial Sequence
<220> FEATURE:
<223> OTHER INFORMATION: Synthetic Construct

<400> SEQUENCE: 169

Arg Phe Ile Ile Ser Gln Asp Lys Ala Lys Asn Thr Leu Asp Leu Gln
1               5                   10                  15

Met Asn Ser Leu Lys Pro Asp Asp Thr Ala Met Tyr Tyr Cys Ala Tyr
            20                  25                  30

<210> SEQ ID NO 170
<211> LENGTH: 32
<212> TYPE: PRT
<213> ORGANISM: Artificial Sequence
<220> FEATURE:
<223> OTHER INFORMATION: Synthetic Construct

<400> SEQUENCE: 170

Arg Phe Ile Ile Ser Gln Asp Lys Ala Lys Asn Thr Leu Tyr Leu Gln
1               5                   10                  15

```
Met Asn Ser Leu Lys Pro Asp Asp Thr Ala Met Tyr Tyr Cys Ala Tyr
            20                  25                  30
```

<210> SEQ ID NO 171
<211> LENGTH: 32
<212> TYPE: PRT
<213> ORGANISM: Artificial Sequence
<220> FEATURE:
<223> OTHER INFORMATION: Synthetic Construct

<400> SEQUENCE: 171

```
Arg Phe Thr Ser Ser Gln Gly Asn Gly Lys Asn Thr Leu Tyr Leu Gln
1               5                   10                  15

Met Asp Ser Leu Asn Val Asp Asp Thr Ala Thr Tyr Tyr Cys Ala Ala
            20                  25                  30
```

<210> SEQ ID NO 172
<211> LENGTH: 32
<212> TYPE: PRT
<213> ORGANISM: Artificial Sequence
<220> FEATURE:
<223> OTHER INFORMATION: Synthetic Construct

<400> SEQUENCE: 172

```
Arg Val Thr Ser Ser Gln Gly Asn Ala Lys Asn Thr Leu Tyr Leu Lys
1               5                   10                  15

Met Asp Asn Leu Arg His Asp Asp Thr Ala Thr Tyr Tyr Cys Ala Ala
            20                  25                  30
```

<210> SEQ ID NO 173
<211> LENGTH: 32
<212> TYPE: PRT
<213> ORGANISM: Artificial Sequence
<220> FEATURE:
<223> OTHER INFORMATION: Synthetic Construct

<400> SEQUENCE: 173

```
Arg Phe Thr Ser Ser Gln Gly Asn Ala Lys Asn Thr Leu Tyr Leu Gln
1               5                   10                  15

Met Asp Ser Leu Lys Leu Asp Asp Thr Ala Thr Tyr Tyr Cys Ala Ala
            20                  25                  30
```

<210> SEQ ID NO 174
<211> LENGTH: 32
<212> TYPE: PRT
<213> ORGANISM: Artificial Sequence
<220> FEATURE:
<223> OTHER INFORMATION: Synthetic Construct

<400> SEQUENCE: 174

```
Arg Phe Thr Thr Ser Arg Asp Asn Ala Lys Asn Thr Val Tyr Leu Gln
1               5                   10                  15

Met Asn Ser Leu Lys Ser Asp Asp Thr Ala Val Tyr Tyr Cys Glu Arg
            20                  25                  30
```

<210> SEQ ID NO 175
<211> LENGTH: 32
<212> TYPE: PRT
<213> ORGANISM: Artificial Sequence
<220> FEATURE:
<223> OTHER INFORMATION: Synthetic Construct

<400> SEQUENCE: 175

```
Arg Phe Thr Ile Ser Arg Asp Asn Ala Lys Asn Thr Val Tyr Leu Gln
```

```
                1               5                   10                  15
Met Asp Ser Leu Lys Pro Glu Asp Thr Ala Met Tyr Tyr Cys Ala Ala
                20                  25                  30

<210> SEQ ID NO 176
<211> LENGTH: 32
<212> TYPE: PRT
<213> ORGANISM: Artificial Sequence
<220> FEATURE:
<223> OTHER INFORMATION: Synthetic Construct

<400> SEQUENCE: 176

Gln Phe Thr Ile Ser Gln Asp Ser Ala Thr Lys Thr Leu Tyr Leu Gln
1               5                   10                  15
Met Asn Arg Leu Lys Pro Glu Asp Thr Ala Met Tyr Tyr Cys Ala Ala
                20                  25                  30

<210> SEQ ID NO 177
<211> LENGTH: 32
<212> TYPE: PRT
<213> ORGANISM: Artificial Sequence
<220> FEATURE:
<223> OTHER INFORMATION: Synthetic Construct

<400> SEQUENCE: 177

Arg Phe Thr Ile Ser Arg Asp Asn Ser Lys Asn Thr Val Tyr Leu Gln
1               5                   10                  15
Met Asn Ser Leu Arg Ala Glu Asp Thr Ala Val Tyr Tyr Cys Ala Ala
                20                  25                  30

<210> SEQ ID NO 178
<211> LENGTH: 32
<212> TYPE: PRT
<213> ORGANISM: Artificial Sequence
<220> FEATURE:
<223> OTHER INFORMATION: Synthetic Construct

<400> SEQUENCE: 178

Arg Phe Thr Ile Ser Arg Asp Asn Ser Lys Asn Thr Val Tyr Leu Gln
1               5                   10                  15
Met Asn Ser Leu Arg Ala Glu Asp Thr Ala Val Tyr Tyr Cys Ala Ala
                20                  25                  30

<210> SEQ ID NO 179
<211> LENGTH: 32
<212> TYPE: PRT
<213> ORGANISM: Artificial Sequence
<220> FEATURE:
<223> OTHER INFORMATION: Synthetic Construct

<400> SEQUENCE: 179

Arg Phe Thr Ile Ser Arg Asp Asn Ala Lys Asn Thr Val Tyr Leu Gln
1               5                   10                  15
Met Asn Ser Leu Arg Pro Glu Asp Thr Ala Val Tyr Tyr Cys Ala Ala
                20                  25                  30

<210> SEQ ID NO 180
<211> LENGTH: 32
<212> TYPE: PRT
<213> ORGANISM: Artificial Sequence
<220> FEATURE:
<223> OTHER INFORMATION: Synthetic Construct

<400> SEQUENCE: 180
```

```
Arg Phe Thr Ile Ser Arg Asp Asn Ala Lys Asn Thr Val Tyr Leu Gln
1               5                   10                  15

Met Asn Ser Leu Arg Pro Glu Asp Thr Ala Val Tyr Tyr Cys Ala Ala
            20                  25                  30
```

<210> SEQ ID NO 181
<211> LENGTH: 13
<212> TYPE: PRT
<213> ORGANISM: Artificial Sequence
<220> FEATURE:
<223> OTHER INFORMATION: Synthetic Construct

<400> SEQUENCE: 181

```
Asp Arg Ala Cys Gly Ser Ser Trp Leu Gly Ala Glu Ser
1               5                   10
```

<210> SEQ ID NO 182
<211> LENGTH: 5
<212> TYPE: PRT
<213> ORGANISM: Artificial Sequence
<220> FEATURE:
<223> OTHER INFORMATION: Synthetic Construct

<400> SEQUENCE: 182

```
Asp Val Ser Pro Tyr
1               5
```

<210> SEQ ID NO 183
<211> LENGTH: 18
<212> TYPE: PRT
<213> ORGANISM: Artificial Sequence
<220> FEATURE:
<223> OTHER INFORMATION: Synthetic Construct

<400> SEQUENCE: 183

```
Ala Glu Arg Cys Ser Gly Ser Asn Asp Arg Ile Ser Phe Trp Gly Ile
1               5                   10                  15

Ser Tyr
```

<210> SEQ ID NO 184
<211> LENGTH: 15
<212> TYPE: PRT
<213> ORGANISM: Artificial Sequence
<220> FEATURE:
<223> OTHER INFORMATION: Synthetic Construct

<400> SEQUENCE: 184

```
Arg Tyr Gly Ser Thr Cys Gly Glu Tyr Leu Ala Asp Tyr Thr Ser
1               5                   10                  15
```

<210> SEQ ID NO 185
<211> LENGTH: 14
<212> TYPE: PRT
<213> ORGANISM: Artificial Sequence
<220> FEATURE:
<223> OTHER INFORMATION: Synthetic Construct

<400> SEQUENCE: 185

```
Asp Leu Ser Asp Gly Thr Trp Asp Gln Gly Arg Trp Asn Tyr
1               5                   10
```

<210> SEQ ID NO 186
<211> LENGTH: 14
<212> TYPE: PRT
<213> ORGANISM: Artificial Sequence
<220> FEATURE:

```
<223> OTHER INFORMATION: Synthetic Construct

<400> SEQUENCE: 186

Asp Leu Arg Asp Gly Thr Trp Asp Thr Gly Val Trp Asn Thr
1               5                   10

<210> SEQ ID NO 187
<211> LENGTH: 14
<212> TYPE: PRT
<213> ORGANISM: Artificial Sequence
<220> FEATURE:
<223> OTHER INFORMATION: Synthetic Construct

<400> SEQUENCE: 187

Asp Leu Arg Asp Gly Phe Trp Asp Thr Gly Val Trp Asn Thr
1               5                   10

<210> SEQ ID NO 188
<211> LENGTH: 7
<212> TYPE: PRT
<213> ORGANISM: Artificial Sequence
<220> FEATURE:
<223> OTHER INFORMATION: Synthetic Construct

<400> SEQUENCE: 188

Asp His Met Ser Trp Leu Pro
1               5

<210> SEQ ID NO 189
<211> LENGTH: 14
<212> TYPE: PRT
<213> ORGANISM: Artificial Sequence
<220> FEATURE:
<223> OTHER INFORMATION: Synthetic Construct

<400> SEQUENCE: 189

Ala Glu Tyr Arg Gly Ser Ser Cys Asp Ala Glu Ser Gly Tyr
1               5                   10

<210> SEQ ID NO 190
<211> LENGTH: 14
<212> TYPE: PRT
<213> ORGANISM: Artificial Sequence
<220> FEATURE:
<223> OTHER INFORMATION: Synthetic Construct

<400> SEQUENCE: 190

Ala Gly Tyr Arg Gly Ser Ser Cys Asp Ala Asp Ser Gly Tyr
1               5                   10

<210> SEQ ID NO 191
<211> LENGTH: 14
<212> TYPE: PRT
<213> ORGANISM: Artificial Sequence
<220> FEATURE:
<223> OTHER INFORMATION: Synthetic Construct

<400> SEQUENCE: 191

Ala Glu Tyr Arg Gly Ser Ser Cys Asp Ala Glu Ser Gly Tyr
1               5                   10

<210> SEQ ID NO 192
<211> LENGTH: 15
<212> TYPE: PRT
<213> ORGANISM: Artificial Sequence
<220> FEATURE:
<223> OTHER INFORMATION: Synthetic Construct
```

<400> SEQUENCE: 192

Gly Ser Arg Glu Asp Tyr Cys Asp Arg Gly Tyr Ile Tyr Asp His
1               5                   10                  15

<210> SEQ ID NO 193
<211> LENGTH: 17
<212> TYPE: PRT
<213> ORGANISM: Artificial Sequence
<220> FEATURE:
<223> OTHER INFORMATION: Synthetic Construct

<400> SEQUENCE: 193

Ala Asp Val Trp Arg Ile Ser Trp Ser Phe Val Pro Glu Leu Phe Ser
1               5                   10                  15

Tyr

<210> SEQ ID NO 194
<211> LENGTH: 18
<212> TYPE: PRT
<213> ORGANISM: Artificial Sequence
<220> FEATURE:
<223> OTHER INFORMATION: Synthetic Construct

<400> SEQUENCE: 194

Glu Arg Trp Asp Tyr Ser Asp Trp Arg Arg Leu Lys Arg Gly Asp Tyr
1               5                   10                  15

Asn Tyr

<210> SEQ ID NO 195
<211> LENGTH: 20
<212> TYPE: PRT
<213> ORGANISM: Artificial Sequence
<220> FEATURE:
<223> OTHER INFORMATION: Synthetic Construct

<400> SEQUENCE: 195

Asp Arg Ser Gln Cys Tyr Val Leu Ser Asp Arg Leu Arg Leu Pro Gly
1               5                   10                  15

Thr Phe Ser Asp
            20

<210> SEQ ID NO 196
<211> LENGTH: 15
<212> TYPE: PRT
<213> ORGANISM: Artificial Sequence
<220> FEATURE:
<223> OTHER INFORMATION: Synthetic Construct

<400> SEQUENCE: 196

Glu Ala Lys Ser Thr Ile Thr Ser Leu Cys Tyr Pro Leu Asn Tyr
1               5                   10                  15

<210> SEQ ID NO 197
<211> LENGTH: 15
<212> TYPE: PRT
<213> ORGANISM: Artificial Sequence
<220> FEATURE:
<223> OTHER INFORMATION: Synthetic Construct

<400> SEQUENCE: 197

Gly Trp Arg Val Ser Ser Gly Gly Asn Cys Gln Phe Asn Asp Tyr
1               5                   10                  15

```
<210> SEQ ID NO 198
<211> LENGTH: 14
<212> TYPE: PRT
<213> ORGANISM: Artificial Sequence
<220> FEATURE:
<223> OTHER INFORMATION: Synthetic Construct

<400> SEQUENCE: 198

Arg Phe Thr Gly Gly Asp Cys Phe Asp His Gln Pro Leu Ala
1               5                   10

<210> SEQ ID NO 199
<211> LENGTH: 20
<212> TYPE: PRT
<213> ORGANISM: Artificial Sequence
<220> FEATURE:
<223> OTHER INFORMATION: Synthetic Construct

<400> SEQUENCE: 199

Asp Arg Ser Gln Cys Tyr Val Leu Arg Asp Arg Leu Arg Leu Pro Asp
1               5                   10                  15

Thr Phe Thr Asp
            20

<210> SEQ ID NO 200
<211> LENGTH: 18
<212> TYPE: PRT
<213> ORGANISM: Artificial Sequence
<220> FEATURE:
<223> OTHER INFORMATION: Synthetic Construct

<400> SEQUENCE: 200

Thr Pro Asp Gly Tyr Cys Tyr Ala Glu Arg Leu Ser Arg Trp Arg Tyr
1               5                   10                  15

Glu Phe

<210> SEQ ID NO 201
<211> LENGTH: 17
<212> TYPE: PRT
<213> ORGANISM: Artificial Sequence
<220> FEATURE:
<223> OTHER INFORMATION: Synthetic Construct

<400> SEQUENCE: 201

Arg Tyr Thr Gly Gly Asp Cys Phe Asn Leu Glu Pro Leu Ala Trp Arg
1               5                   10                  15

Phe

<210> SEQ ID NO 202
<211> LENGTH: 15
<212> TYPE: PRT
<213> ORGANISM: Artificial Sequence
<220> FEATURE:
<223> OTHER INFORMATION: Synthetic Construct

<400> SEQUENCE: 202

Gly Trp Arg Val Ser Ser Gly Gly Asn Cys Gln Phe Asn Asp Tyr
1               5                   10                  15

<210> SEQ ID NO 203
<211> LENGTH: 20
<212> TYPE: PRT
<213> ORGANISM: Artificial Sequence
<220> FEATURE:
<223> OTHER INFORMATION: Synthetic Construct
```

```
<400> SEQUENCE: 203

Asp Arg Asn Gln Cys Tyr Val Leu Leu Asp Arg Leu Arg Leu Pro Gly
1               5                   10                  15

Thr Phe Ser Asp
            20

<210> SEQ ID NO 204
<211> LENGTH: 20
<212> TYPE: PRT
<213> ORGANISM: Artificial Sequence
<220> FEATURE:
<223> OTHER INFORMATION: Synthetic Construct

<400> SEQUENCE: 204

Asp Cys Ser Gln Cys Tyr Val Leu Arg Asp Arg Leu Arg Leu Pro Asp
1               5                   10                  15

Thr Phe Thr Asp
            20

<210> SEQ ID NO 205
<211> LENGTH: 20
<212> TYPE: PRT
<213> ORGANISM: Artificial Sequence
<220> FEATURE:
<223> OTHER INFORMATION: Synthetic Construct

<400> SEQUENCE: 205

Asp Arg Asn Gln Cys Tyr Val Leu Arg Asp Arg Leu Arg Leu Pro Asp
1               5                   10                  15

Thr Phe Thr Asp
            20

<210> SEQ ID NO 206
<211> LENGTH: 20
<212> TYPE: PRT
<213> ORGANISM: Artificial Sequence
<220> FEATURE:
<223> OTHER INFORMATION: Synthetic Construct

<400> SEQUENCE: 206

Asp Arg Asp Gln Cys Tyr Val Leu Arg Asp Arg Leu Arg Leu Pro Asp
1               5                   10                  15

Thr Phe Asn Asp
            20

<210> SEQ ID NO 207
<211> LENGTH: 17
<212> TYPE: PRT
<213> ORGANISM: Artificial Sequence
<220> FEATURE:
<223> OTHER INFORMATION: Synthetic Construct

<400> SEQUENCE: 207

Arg Tyr Thr Gly Gly Asn Cys Phe Asn Leu Glu Pro Leu Ala Trp His
1               5                   10                  15

Phe

<210> SEQ ID NO 208
<211> LENGTH: 17
<212> TYPE: PRT
<213> ORGANISM: Artificial Sequence
<220> FEATURE:
<223> OTHER INFORMATION: Synthetic Construct
```

```
<400> SEQUENCE: 208

Arg Tyr Thr Gly Gly Asp Cys Phe Asn Leu Asp Pro Leu Ser Trp Arg
1               5                   10                  15

Phe

<210> SEQ ID NO 209
<211> LENGTH: 17
<212> TYPE: PRT
<213> ORGANISM: Artificial Sequence
<220> FEATURE:
<223> OTHER INFORMATION: Synthetic Construct

<400> SEQUENCE: 209

Arg Tyr Thr Gly Gly Asp Cys Phe Asn Leu Glu Pro Val Ala Trp Arg
1               5                   10                  15

Phe

<210> SEQ ID NO 210
<211> LENGTH: 14
<212> TYPE: PRT
<213> ORGANISM: Artificial Sequence
<220> FEATURE:
<223> OTHER INFORMATION: Synthetic Construct

<400> SEQUENCE: 210

Gly Asn Gly Gln Thr Ala Met Glu Ala Leu Ile Asn Pro Pro
1               5                   10

<210> SEQ ID NO 211
<211> LENGTH: 18
<212> TYPE: PRT
<213> ORGANISM: Artificial Sequence
<220> FEATURE:
<223> OTHER INFORMATION: Synthetic Construct

<400> SEQUENCE: 211

Asp Ser Arg Gly Tyr Gly Gly Asp Trp Tyr Lys Leu Leu Ser Asp Phe
1               5                   10                  15

Asn Tyr

<210> SEQ ID NO 212
<211> LENGTH: 18
<212> TYPE: PRT
<213> ORGANISM: Artificial Sequence
<220> FEATURE:
<223> OTHER INFORMATION: Synthetic Construct

<400> SEQUENCE: 212

Thr Pro Glu Gly Tyr Cys Tyr Ala Glu Arg Leu Ser Thr Trp Arg Tyr
1               5                   10                  15

Thr Phe

<210> SEQ ID NO 213
<211> LENGTH: 14
<212> TYPE: PRT
<213> ORGANISM: Artificial Sequence
<220> FEATURE:
<223> OTHER INFORMATION: Synthetic Construct

<400> SEQUENCE: 213

Asp Leu Arg Asp Gly Phe Trp Asp Thr Gly Val Trp Asn Thr
1               5                   10
```

```
<210> SEQ ID NO 214
<211> LENGTH: 14
<212> TYPE: PRT
<213> ORGANISM: Artificial Sequence
<220> FEATURE:
<223> OTHER INFORMATION: Synthetic Construct

<400> SEQUENCE: 214

Asp Leu Arg Glu Gly Phe Trp Asp Thr Gly Val Trp Asn Thr
1               5                   10

<210> SEQ ID NO 215
<211> LENGTH: 14
<212> TYPE: PRT
<213> ORGANISM: Artificial Sequence
<220> FEATURE:
<223> OTHER INFORMATION: Synthetic Construct

<400> SEQUENCE: 215

Asp Leu Arg Asp Gly Phe Trp Asp Thr Gly Val Trp Asn Thr
1               5                   10

<210> SEQ ID NO 216
<211> LENGTH: 14
<212> TYPE: PRT
<213> ORGANISM: Artificial Sequence
<220> FEATURE:
<223> OTHER INFORMATION: Synthetic Construct

<400> SEQUENCE: 216

Asp Leu Arg Glu Gly Phe Trp Asp Thr Gly Val Trp Asn Thr
1               5                   10

<210> SEQ ID NO 217
<211> LENGTH: 11
<212> TYPE: PRT
<213> ORGANISM: Artificial Sequence
<220> FEATURE:
<223> OTHER INFORMATION: Synthetic Construct

<400> SEQUENCE: 217

Trp Ala Gln Gly Thr Gln Val Thr Val Ser Ser
1               5                   10

<210> SEQ ID NO 218
<211> LENGTH: 11
<212> TYPE: PRT
<213> ORGANISM: Artificial Sequence
<220> FEATURE:
<223> OTHER INFORMATION: Synthetic Construct

<400> SEQUENCE: 218

Trp Gly Arg Gly Thr Gln Val Thr Val Ser Ser
1               5                   10

<210> SEQ ID NO 219
<211> LENGTH: 11
<212> TYPE: PRT
<213> ORGANISM: Artificial Sequence
<220> FEATURE:
<223> OTHER INFORMATION: Synthetic Construct

<400> SEQUENCE: 219

Trp Gly Gln Gly Thr Gln Val Thr Val Ser Ser
1               5                   10

<210> SEQ ID NO 220
```

```
<211> LENGTH: 11
<212> TYPE: PRT
<213> ORGANISM: Artificial Sequence
<220> FEATURE:
<223> OTHER INFORMATION: Synthetic Construct

<400> SEQUENCE: 220

Arg Ala Gln Gly Thr Gln Val Thr Val Ser Ser
1               5                   10

<210> SEQ ID NO 221
<211> LENGTH: 11
<212> TYPE: PRT
<213> ORGANISM: Artificial Sequence
<220> FEATURE:
<223> OTHER INFORMATION: Synthetic Construct

<400> SEQUENCE: 221

Trp Gly Gln Gly Thr Gln Val Thr Val Ser Ser
1               5                   10

<210> SEQ ID NO 222
<211> LENGTH: 11
<212> TYPE: PRT
<213> ORGANISM: Artificial Sequence
<220> FEATURE:
<223> OTHER INFORMATION: Synthetic Construct

<400> SEQUENCE: 222

Trp Gly Gln Gly Thr Gln Val Thr Val Ser Ser
1               5                   10

<210> SEQ ID NO 223
<211> LENGTH: 11
<212> TYPE: PRT
<213> ORGANISM: Artificial Sequence
<220> FEATURE:
<223> OTHER INFORMATION: Synthetic Construct

<400> SEQUENCE: 223

Trp Gly Gln Gly Thr Gln Val Thr Val Ser Ser
1               5                   10

<210> SEQ ID NO 224
<211> LENGTH: 11
<212> TYPE: PRT
<213> ORGANISM: Artificial Sequence
<220> FEATURE:
<223> OTHER INFORMATION: Synthetic Construct

<400> SEQUENCE: 224

Arg Gly Gln Gly Thr Gln Val Thr Val Ser Ser
1               5                   10

<210> SEQ ID NO 225
<211> LENGTH: 11
<212> TYPE: PRT
<213> ORGANISM: Artificial Sequence
<220> FEATURE:
<223> OTHER INFORMATION: Synthetic Construct

<400> SEQUENCE: 225

Trp Gly Gln Gly Thr Gln Val Thr Val Ser Ser
1               5                   10

<210> SEQ ID NO 226
<211> LENGTH: 11
```

```
<212> TYPE: PRT
<213> ORGANISM: Artificial Sequence
<220> FEATURE:
<223> OTHER INFORMATION: Synthetic Construct

<400> SEQUENCE: 226

Trp Gly Gln Gly Thr Gln Val Thr Val Ser Ser
1               5                   10

<210> SEQ ID NO 227
<211> LENGTH: 11
<212> TYPE: PRT
<213> ORGANISM: Artificial Sequence
<220> FEATURE:
<223> OTHER INFORMATION: Synthetic Construct

<400> SEQUENCE: 227

Trp Gly Gln Gly Thr Gln Val Thr Val Ser Ser
1               5                   10

<210> SEQ ID NO 228
<211> LENGTH: 11
<212> TYPE: PRT
<213> ORGANISM: Artificial Sequence
<220> FEATURE:
<223> OTHER INFORMATION: Synthetic Construct

<400> SEQUENCE: 228

Trp Gly Gln Gly Thr Gln Val Thr Val Ser Ser
1               5                   10

<210> SEQ ID NO 229
<211> LENGTH: 11
<212> TYPE: PRT
<213> ORGANISM: Artificial Sequence
<220> FEATURE:
<223> OTHER INFORMATION: Synthetic Construct

<400> SEQUENCE: 229

Trp Gly Gln Gly Thr Gln Val Thr Val Ser Ser
1               5                   10

<210> SEQ ID NO 230
<211> LENGTH: 11
<212> TYPE: PRT
<213> ORGANISM: Artificial Sequence
<220> FEATURE:
<223> OTHER INFORMATION: Synthetic Construct

<400> SEQUENCE: 230

Trp Gly Gln Gly Thr Gln Val Thr Val Ser Ser
1               5                   10

<210> SEQ ID NO 231
<211> LENGTH: 11
<212> TYPE: PRT
<213> ORGANISM: Artificial Sequence
<220> FEATURE:
<223> OTHER INFORMATION: Synthetic Construct

<400> SEQUENCE: 231

Trp Gly Gln Gly Thr Gln Val Thr Val Ser Ser
1               5                   10

<210> SEQ ID NO 232
<211> LENGTH: 11
<212> TYPE: PRT
```

<213> ORGANISM: Artificial Sequence
<220> FEATURE:
<223> OTHER INFORMATION: Synthetic Construct

<400> SEQUENCE: 232

Trp Gly Gln Gly Thr Gln Val Thr Val Ser Ser
1               5                   10

<210> SEQ ID NO 233
<211> LENGTH: 11
<212> TYPE: PRT
<213> ORGANISM: Artificial Sequence
<220> FEATURE:
<223> OTHER INFORMATION: Synthetic Construct

<400> SEQUENCE: 233

Trp Gly Gln Gly Thr Gln Val Thr Val Ser Ser
1               5                   10

<210> SEQ ID NO 234
<211> LENGTH: 14
<212> TYPE: PRT
<213> ORGANISM: Artificial Sequence
<220> FEATURE:
<223> OTHER INFORMATION: Synthetic Construct

<400> SEQUENCE: 234

Trp Arg Phe Trp Gly Gln Gly Thr Gln Val Thr Val Ser Ser
1               5                   10

<210> SEQ ID NO 235
<211> LENGTH: 11
<212> TYPE: PRT
<213> ORGANISM: Artificial Sequence
<220> FEATURE:
<223> OTHER INFORMATION: Synthetic Construct

<400> SEQUENCE: 235

Trp Gly Gln Gly Thr Gln Val Thr Val Ser Ser
1               5                   10

<210> SEQ ID NO 236
<211> LENGTH: 11
<212> TYPE: PRT
<213> ORGANISM: Artificial Sequence
<220> FEATURE:
<223> OTHER INFORMATION: Synthetic Construct

<400> SEQUENCE: 236

Trp Gly Gln Gly Thr Gln Val Thr Val Ser Ser
1               5                   10

<210> SEQ ID NO 237
<211> LENGTH: 11
<212> TYPE: PRT
<213> ORGANISM: Artificial Sequence
<220> FEATURE:
<223> OTHER INFORMATION: Synthetic Construct

<400> SEQUENCE: 237

Trp Gly Gln Gly Thr Gln Val Thr Val Ser Ser
1               5                   10

<210> SEQ ID NO 238
<211> LENGTH: 11
<212> TYPE: PRT
<213> ORGANISM: Artificial Sequence

```
<220> FEATURE:
<223> OTHER INFORMATION: Synthetic Construct

<400> SEQUENCE: 238

Trp Gly Gln Gly Thr Gln Val Thr Val Ser Ser
1               5                   10

<210> SEQ ID NO 239
<211> LENGTH: 11
<212> TYPE: PRT
<213> ORGANISM: Artificial Sequence
<220> FEATURE:
<223> OTHER INFORMATION: Synthetic Construct

<400> SEQUENCE: 239

Trp Gly Gln Gly Thr Gln Val Thr Val Ser Ser
1               5                   10

<210> SEQ ID NO 240
<211> LENGTH: 11
<212> TYPE: PRT
<213> ORGANISM: Artificial Sequence
<220> FEATURE:
<223> OTHER INFORMATION: Synthetic Construct

<400> SEQUENCE: 240

Trp Gly Gln Gly Thr Gln Val Thr Val Ser Ser
1               5                   10

<210> SEQ ID NO 241
<211> LENGTH: 11
<212> TYPE: PRT
<213> ORGANISM: Artificial Sequence
<220> FEATURE:
<223> OTHER INFORMATION: Synthetic Construct

<400> SEQUENCE: 241

Trp Gly Gln Gly Thr Gln Val Thr Val Ser Ser
1               5                   10

<210> SEQ ID NO 242
<211> LENGTH: 11
<212> TYPE: PRT
<213> ORGANISM: Artificial Sequence
<220> FEATURE:
<223> OTHER INFORMATION: Synthetic Construct

<400> SEQUENCE: 242

Trp Gly Gln Gly Thr Gln Val Thr Val Ser Ser
1               5                   10

<210> SEQ ID NO 243
<211> LENGTH: 11
<212> TYPE: PRT
<213> ORGANISM: Artificial Sequence
<220> FEATURE:
<223> OTHER INFORMATION: Synthetic Construct

<400> SEQUENCE: 243

Trp Gly Gln Gly Thr Gln Val Thr Val Ser Ser
1               5                   10

<210> SEQ ID NO 244
<211> LENGTH: 11
<212> TYPE: PRT
<213> ORGANISM: Artificial Sequence
<220> FEATURE:
```

```
<223> OTHER INFORMATION: Synthetic Construct

<400> SEQUENCE: 244

Trp Gly Gln Gly Thr Gln Val Thr Val Ser Ser
1               5                   10

<210> SEQ ID NO 245
<211> LENGTH: 11
<212> TYPE: PRT
<213> ORGANISM: Artificial Sequence
<220> FEATURE:
<223> OTHER INFORMATION: Synthetic Construct

<400> SEQUENCE: 245

Trp Gly Gln Gly Thr Gln Val Thr Val Ser Ser
1               5                   10

<210> SEQ ID NO 246
<211> LENGTH: 11
<212> TYPE: PRT
<213> ORGANISM: Artificial Sequence
<220> FEATURE:
<223> OTHER INFORMATION: Synthetic Construct

<400> SEQUENCE: 246

Glu Arg Pro Gly Thr Gln Val Thr Val Ser Ser
1               5                   10

<210> SEQ ID NO 247
<211> LENGTH: 11
<212> TYPE: PRT
<213> ORGANISM: Artificial Sequence
<220> FEATURE:
<223> OTHER INFORMATION: Synthetic Construct

<400> SEQUENCE: 247

Cys Gly Gln Gly Thr Gln Val Thr Val Ser Ser
1               5                   10

<210> SEQ ID NO 248
<211> LENGTH: 11
<212> TYPE: PRT
<213> ORGANISM: Artificial Sequence
<220> FEATURE:
<223> OTHER INFORMATION: Synthetic Construct

<400> SEQUENCE: 248

Trp Gly Gln Gly Thr Gln Val Thr Val Ser Ser
1               5                   10

<210> SEQ ID NO 249
<211> LENGTH: 11
<212> TYPE: PRT
<213> ORGANISM: Artificial Sequence
<220> FEATURE:
<223> OTHER INFORMATION: Synthetic Construct

<400> SEQUENCE: 249

Trp Gly Gln Gly Thr Leu Val Thr Val Ser Ser
1               5                   10

<210> SEQ ID NO 250
<211> LENGTH: 11
<212> TYPE: PRT
<213> ORGANISM: Artificial Sequence
<220> FEATURE:
<223> OTHER INFORMATION: Synthetic Construct
```

<400> SEQUENCE: 250

Trp Gly Gln Gly Thr Leu Val Thr Val Ser Ser
1               5                   10

<210> SEQ ID NO 251
<211> LENGTH: 11
<212> TYPE: PRT
<213> ORGANISM: Artificial Sequence
<220> FEATURE:
<223> OTHER INFORMATION: Synthetic Construct

<400> SEQUENCE: 251

Trp Gly Gln Gly Thr Leu Val Thr Val Ser Ser
1               5                   10

<210> SEQ ID NO 252
<211> LENGTH: 11
<212> TYPE: PRT
<213> ORGANISM: Artificial Sequence
<220> FEATURE:
<223> OTHER INFORMATION: Synthetic Construct

<400> SEQUENCE: 252

Trp Gly Gln Gly Thr Leu Val Thr Val Ser Ser
1               5                   10

<210> SEQ ID NO 253
<211> LENGTH: 366
<212> TYPE: DNA
<213> ORGANISM: Artificial Sequence
<220> FEATURE:
<223> OTHER INFORMATION: Synthetic Construct

<400> SEQUENCE: 253

```
caggtacagc tggtggagtc tgggggaggc aaggtgcagc ctggggggtc tctgagactc      60
tcctgtgcag cctctggagg cactttggat tattatgcca taggctggtt ccgccaggcc     120
ccagggaagg agcgcgaggc cgtgtcatgt attagtagta gcgatggtag cacatactat     180
gcagactccg tgaagggccg attcaccatc tccagagaca tgccaagaa cacggtgtat      240
cttcaaatga acagcctgaa acctggggac acggccgttt atcactgtgc gacagatcgg     300
gcgtgcggta gtagctggtt aggggccgaa tcatgggccc aggggaccca ggtcaccgtc     360
tcctca                                                                366
```

<210> SEQ ID NO 254
<211> LENGTH: 336
<212> TYPE: DNA
<213> ORGANISM: Artificial Sequence
<220> FEATURE:
<223> OTHER INFORMATION: Synthetic Construct

<400> SEQUENCE: 254

```
caggtgcacc tggtggattc tgggggaggc ttggtgcagc ctggggggtc tctgagactc      60
tcctgtgcag cctctggaag catcaccagt agaaatacca tgggctggta ccggcaggtt     120
ccagggaagc agcgcgaatt ggtcgcgcta attgcgactt ttgtcacaca ttatgcggac     180
tccgtgaagg gccgattcac catctccaga gataacgcca ggaagatggt gtttctagag     240
atgaacagcc tgcaacctga ggacacgggc gcgtattatt gttatgtcga tgtctcgccc     300
tattggggcc gggggaccca ggtcaccgtc tcctca                              336
```

```
<210> SEQ ID NO 255
<211> LENGTH: 381
<212> TYPE: DNA
<213> ORGANISM: Artificial Sequence
<220> FEATURE:
<223> OTHER INFORMATION: Synthetic Construct

<400> SEQUENCE: 255
caggtgcaac tggtggagtc tgggggaggc tcggtgcagg ctggagggtc tctgagactc      60
tcctgtgcag cctctggata cacctatatt cccaactgca tggcctggtt ccgccaggct     120
ccagggaagg agcgcgaggg ggtcacactt attttactg gtgatggtac ctcaacctat      180
gtcgactccg tgaagggccg attcaccatc tcccaagaca acgccaagaa cacggtgtat     240
ctgcaaatga acagcctgaa acccgaggac actgccttgt actactgtgc ggcagccgaa     300
cgttgtagtg gttcaaacga cagaatatcc ttttggggaa ttagctactg gggccagggg     360
acccaggtca ccgtctcctc a                                               381

<210> SEQ ID NO 256
<211> LENGTH: 372
<212> TYPE: DNA
<213> ORGANISM: Artificial Sequence
<220> FEATURE:
<223> OTHER INFORMATION: Synthetic Construct

<400> SEQUENCE: 256
caggtgcaac tggtggagtc tgggggaggc tcggtgcagg ctgggggggtc tttgagactc     60 tcctgtacag cctctgcata cacctacagt aacatctgtt tgggctggct ccgccaggct     120 caggggggg ggctcgaggc tgtcgcaacg atttatattg cggatcagac atcatactat      180
gccgactccg tgaagggccg attccgcatc tctaaagacg ccgccaagaa cgcggtgtat     240
ctgcaaatga gcagcctgag acctgaggac actgccatgt actactgtgc gtcccggtac     300
ggtagtacct gcggcgaata tttagctgac tatacctccc gggcccaggg gacccaggtc     360
accgtctcct ca                                                         372

<210> SEQ ID NO 257
<211> LENGTH: 369
<212> TYPE: DNA
<213> ORGANISM: Artificial Sequence
<220> FEATURE:
<223> OTHER INFORMATION: Synthetic Construct

<400> SEQUENCE: 257
cagatgcagc tggtggagtc tgggggaggc tcggtgcagg ctggagggtc tctgagactc     60
tcttgtgcag tctctggata catctacaat cgcaacttca tgggctggtt ccgccaggct    120
cccgggaagg agcgcgaggg ggtcgcggct atttatactg gtggcccata cacatactat    180
accgactccg tgcagggccg attcaccatc tcccaagaca caccaagaa cacggtgtat    240 ctgcaaatga acagcctgaa acctgaggac actgccatgt attactgtgt gtcagatctt    300
tcggacggta cttgggacca gggccgatgg aactactggg gccaggggac ccaggtcacc    360
gtctcctca                                                            369

<210> SEQ ID NO 258
<211> LENGTH: 369
<212> TYPE: DNA
<213> ORGANISM: Artificial Sequence
<220> FEATURE:
<223> OTHER INFORMATION: Synthetic Construct
```

<400> SEQUENCE: 258

```
caggtgcaac tggtggagtc tgggggaggc tcggcgcagg ctggagggtc tctgagactc    60
tcctgtgcag tctctggata catttacaat cgtaacttca tgggctggtt ccgccaggtt   120
ccaggaaagg tgcgcgaggg ggtcgcagca atttatactg gtactgaacg cacgtactat   180
gccgactccg tgaagggccg attcaccatc tcccaagaca cgccaagaa cacggtgtat    240
ctgcagatga atagtctgaa acctgaggac actgccatgt actactgtgt ggcggatttg   300
cgggatggta cttgggatac gggcgtatgg aacacctggg gccaggggac ccaggtcacc   360
gtctcctca                                                           369
```

<210> SEQ ID NO 259
<211> LENGTH: 369
<212> TYPE: DNA
<213> ORGANISM: Artificial Sequence
<220> FEATURE:
<223> OTHER INFORMATION: Synthetic Construct

<400> SEQUENCE: 259

```
cagattcagc tggtggagtc tgggggaggc tcggcgcagg ctggagggtc tctgagactc    60
tcctgtgtag tctctggaaa catctacaat cgtaacttca tgggctggtt ccgccaggct   120
ccagggaagg tgcgcgaggg ggtcgcagca atttatactg gtactagtcg cacgtactat   180
gccgactccg tgaagggccg attcaccatc tcccaagaca cgccaagaa tacggtgtat    240
ctgcaaatga atagtctgaa acctgaggac actgccatgt actactgtgc ggcggatttg   300
cgggatggtt ctgggatac gggcgtatgg aacacctggg gccaggggac ccaggtcacc    360
gtctcctca                                                           369
```

<210> SEQ ID NO 260
<211> LENGTH: 348
<212> TYPE: DNA
<213> ORGANISM: Artificial Sequence
<220> FEATURE:
<223> OTHER INFORMATION: Synthetic Construct

<400> SEQUENCE: 260

```
caggtgcaac tggtggagtc tgggggaggc ttggtgcagc ctgggggggtc tctgacactc    60
tcctgtgcag cctctggatt cacgttcagt accgccgcca tgagctgggt ccgccaggtt   120
ccagaggagg gactcgagtg ggtcgcatct attgatagta gtggtagtcg cacatactat   180
gcgggctccg tgaagggccg attcaccatc tccagagaca cgccaagaa cacgctgtat    240
ttgcaattga acagcctgaa agctgaggac acggccatgt attactgtgc aaaagatcac   300
atgagctggt tgccgcgggg ccaggggacc caggtcaccg tctcctca                348
```

<210> SEQ ID NO 261
<211> LENGTH: 366
<212> TYPE: DNA
<213> ORGANISM: Artificial Sequence
<220> FEATURE:
<223> OTHER INFORMATION: Synthetic Construct

<400> SEQUENCE: 261

```
caggtgcaac tggtggagtc tgggggagga tcggtgcagg ctggagggtc tctgagactc    60
tcctgtgcag cctctggatt caccgacagt tcgtactgcg gggcctggtt tcgccaggtt   120
ccagggaagg agcgcgaggg ggtcgcgatt atcgatagat atggtgggac aatgtacaaa   180
gactccgtga agggccgatt caccatctcc aaagacactg ccaagaatat tctgtatctg   240
```

```
caaatgaaca gcctgaaact tgaggacact gccatgtact actgtgcggc agccgaatat    300
cgaggctctt cgtgtgacgc ggagagtggc tactggggcc aggggaccca ggtcaccgtc    360
tcctca                                                               366
```

<210> SEQ ID NO 262
<211> LENGTH: 366
<212> TYPE: DNA
<213> ORGANISM: Artificial Sequence
<220> FEATURE:
<223> OTHER INFORMATION: Synthetic Construct

<400> SEQUENCE: 262

```
caggtgcacc tgatggagtc tgggggaggt tcggtgcagg ctggagggtc cctgactctc    60
tcctgtgcag cctctgtatt caccgacagt aactactgca tggcctggtt ccgccaggtt   120
ccagggaagg agcgcgaggg ggtcgcaatt atcgatagat atggtggtac gatgtacaaa   180
gactccgtga agggccgatt caccatctcc aaagacactg ccaagaatat tctgtatctg   240
caaatgaaca gcctgaaact tgaggacact gccatgtact actgtgcggc agccgggtat   300
cgaggctctt cgtgtgacgc ggatagtggc tactggggcc aggggaccca ggtcaccgtc   360
tcctca                                                               366
```

<210> SEQ ID NO 263
<211> LENGTH: 366
<212> TYPE: DNA
<213> ORGANISM: Artificial Sequence
<220> FEATURE:
<223> OTHER INFORMATION: Synthetic Construct

<400> SEQUENCE: 263

```
cagattcagc tggtggagtc tgggggagga tcggtgcagg ctggagggtc tctgagactc    60
tcctgtgcag cctctggatt caccgacagt tcgtactgcg gggcctggtt tcgccaggtt   120
ccagggaagg agcgcgaggg ggtcgcgatt atcgatagat atggtgggac aatgtacaaa   180
gactccgtga agggccgatt caccatctcc aaagacactg ccaagaatat tctgtatctg   240
caaatgaaca gcctgaaact tgaggacact gccatgtact actgtgcggc agccgaatat   300
cgaggctctt cgtgtgacgc ggagagtggc tactggggcc aggggaccca ggtcaccgtc   360
tcctca                                                               366
```

<210> SEQ ID NO 264
<211> LENGTH: 372
<212> TYPE: DNA
<213> ORGANISM: Artificial Sequence
<220> FEATURE:
<223> OTHER INFORMATION: Synthetic Construct

<400> SEQUENCE: 264

```
caggtgcaac tggtggagtc tgggggaggc tcggtgcagg ctggagggtc tctgagactc    60
tcctgtgcag cctctggata caccgccggt agcctctgca tgggctggtt ccgccaggct   120
ccagggaagg agcgcgaggg ggtcgcagct atttatactg gtggtggtag cacatactat   180
gccgactccg tgaagggccg attcaccatc tcccaagaca cgccaagaa cacggtgtat   240 ctgcaaatga acagcctgaa acctgaggac actgcccagt actactgcgg ggcgggtagt   300
agggaagact actgcgacag gggttacatc tatgatcact ggggccaggg gacccaggtc   360
accgtctcct ca                                                        372
```

<210> SEQ ID NO 265
<211> LENGTH: 375
<212> TYPE: DNA
<213> ORGANISM: Artificial Sequence
<220> FEATURE:
<223> OTHER INFORMATION: Synthetic Construct

<400> SEQUENCE: 265

```
caggtgaagt tagtggagtc tgggggaggc tcggtgcagg ctggagggta cctgagactc      60
tcctgtgcag cctctggaga caccaacaac ttgaacttca ggggctggtt ccgccaggct     120
ccagggaagg agcgcgaggg ggtcgcagtt atcactcact ctggtagcac atactatgcc     180
gaatccgtga agggccgatt caccatctcc aagacctcg ccaagaacac gatgtatctg      240
caaatgaaca gtctgaaacc tgaggacact gctatgtact actgtgcggc agcagatgtg     300
tggcgtatta gctggtcctt tgttccggaa ctctttagtt actggggcca ggggacccag     360
gtcaccgtct cctca                                                      375
```

<210> SEQ ID NO 266
<211> LENGTH: 381
<212> TYPE: DNA
<213> ORGANISM: Artificial Sequence
<220> FEATURE:
<223> OTHER INFORMATION: Synthetic Construct

<400> SEQUENCE: 266

```
caggtgcagc tggtggagtc tgggggaggc tcggtgcagg ctggagggtc tctgagactc      60
tcttgtgcag gctctggatt taccttcaat aactacgcca tgggctggtt ccgccaggct     120
ccagggaagg agcgcgaggg aatcgcggga atttggactg gtggtggtag tacatactat     180
gccgactccg tgaagggccg attcaccatc tccgaagacg tcgccaagaa cacggtgtat     240
ctgcaaatgg acagcctgaa acctgaggac actgccatgt actactgtgc ggccgagcgc     300
tgggactata gcgactggcg acgcctaaag agggggact ataactactg gggccagggg      360
acccaggtca ccgtctcctc a                                               381
```

<210> SEQ ID NO 267
<211> LENGTH: 390
<212> TYPE: DNA
<213> ORGANISM: Artificial Sequence
<220> FEATURE:
<223> OTHER INFORMATION: Synthetic Construct

<400> SEQUENCE: 267

```
caggtgcacc tgatggagtc tgggggaggg tcggtgccgt ctggagggtc tctgagactc      60
tcctgtgcag tctctggatc tggatacagc tatagtcgcg gctgcttcgc atggttccag     120
cagcgtccag ggaaggagcg cgaggggtc gcaattatta atatggatgg cacacaaga       180
tactcagact ccgtgcaggg ccgattcatc atctcccaag acaaggccaa gaacacacta     240
catctgcaaa tgaacaccct gagacctgac gacacggcca tgtattactg tgcgtacgat     300
cgcagtcagt gttacgtgct aagcgaccgc ttacgcctcc caggtacctt tagtgactgg     360
ggccagggga cccaggtcac cgtctcctca                                      390
```

<210> SEQ ID NO 268
<211> LENGTH: 369
<212> TYPE: DNA
<213> ORGANISM: Artificial Sequence
<220> FEATURE:
<223> OTHER INFORMATION: Synthetic Construct

<400> SEQUENCE: 268

```
gaggtgcaac tggcggagtc tgggggaggc tcggtgcagg ctggagggtc tctgaaactc      60
tcctgtttag cctcgcaatg gatcagtagt gattgcggaa tggcctggta ccgccaggct     120
ccagggaagg agcgcgaatt ggtctcacgc attagtagtg atgataccac aacctatgca     180
gactccgtga agggccgatt caccatctcc aagacagtg ccaagaacac gctgtatctg      240
caaatgaaca agctgaaaac tgaagacacg ggcgtgtatt attgtgcggc agaagccaag     300
agcactataa cgagcctgtg ctaccccttg aactactggg gccaggggac ccaggtcacc     360
gtctcctca                                                             369
```

<210> SEQ ID NO 269
<211> LENGTH: 363
<212> TYPE: DNA
<213> ORGANISM: Artificial Sequence
<220> FEATURE:
<223> OTHER INFORMATION: Synthetic Construct

<400> SEQUENCE: 269

```
caggtgcagc tggtggagtc tgggggaggc tccgtgcagg ctggagggtc tctgagactc      60
acctgtgcag ccactggata ctcttggaga cccgactgca tgggctggta ccgccaggct     120
gcagagaagg agcgcgaggg ggtcgcagtt attgatgctg atggtatcac aagctacgca     180
gacgccgcga agggccgatt caccatctcc cgagacaaca caagatcac tctatatctg      240
caaatgctga aacctgacga cactggcatg tacgtctgtg tggtaggatg gagagtaagc     300
agtggtggta actgccaatt caatgactac tggggtcagg gacccaggt caccgtctcc      360
tca                                                                    363
```

<210> SEQ ID NO 270
<211> LENGTH: 378
<212> TYPE: DNA
<213> ORGANISM: Artificial Sequence
<220> FEATURE:
<223> OTHER INFORMATION: Synthetic Construct

<400> SEQUENCE: 270

```
caggtgcacc tgatggagtc tgggggaggc gcggtgcaga ccggagggtc tctgaggctc      60
tcctgtgcag tatcgggaat ctccatcagt ccagactgca tgggctggtt ccgccaggct     120
ccagggaaga agcgcgaggc ggtcacgaca attttgcta atactggtag cgcgcgctat      180
ggcgactccg tgaagggccg attcaccagc tcccaaggca acgccaagaa tacgctgtat     240
ctgcaaatgg acagcgtgaa acttgatgac actggcacgt actactgtgc ggcacggttt     300
acggggggtg actgctttga tcatcagcca ttggcgtggc gcttctgggg ccaggggacc     360
caggtcaccg tctcctca                                                    378
```

<210> SEQ ID NO 271
<211> LENGTH: 390
<212> TYPE: DNA
<213> ORGANISM: Artificial Sequence
<220> FEATURE:
<223> OTHER INFORMATION: Synthetic Construct

<400> SEQUENCE: 271

```
gaggtgcaac tggcggagtc tgggggaggg tcggtgcagt ctggagggtc tctgagactc      60
tcctgtgcag tctctggatc tggatacagc tatagtcgcg gctgcttcgc gtggttccag     120
```

```
cagcgtccag gaaaggagcg cgaggggtc gcaattatta atagtgatgg gcacacagca      180
tactcagact ccgtgcaggg ccgattcatc atctcccaag acaaggccaa gaacacacta      240
tatctgcaaa tgaacagcct gaaacctgac gacacggcca tgtattactg tgcgtacgat      300
cgcagtcagt gttacgtgct tcgcgaccgc ttacgcctcc cagataccct tactgactgg      360
ggccagggga cccaggtcac cgtctcctca                                       390

<210> SEQ ID NO 272
<211> LENGTH: 378
<212> TYPE: DNA
<213> ORGANISM: Artificial Sequence
<220> FEATURE:
<223> OTHER INFORMATION: Synthetic Construct

<400> SEQUENCE: 272
caggtgcacc tggtggagtc tgggggagcc tcggtgcagg ctggagggtc tctgagactc       60
tcctgtgcag ccactgcgta caccgccagt aattattgca tgggctggtt ccgccagtct      120
ccagggaagg agcgcgaggc agtcgcaagt attaatgatg acggcgtcac aagctacgca      180
gactccgtga agggccgatt caccatctcc caagacagcg ccaagaagac tctgtatctc      240
caaatgaacc gcctgaaacc tgaggacact gccatgtact actgtgcggc caccccggat      300
ggttactgct acgccgagag actttcccgg tggagatatg agttctgggg ccaggggacc      360
caggtcaccg tctcctca                                                    378

<210> SEQ ID NO 273
<211> LENGTH: 378
<212> TYPE: DNA
<213> ORGANISM: Artificial Sequence
<220> FEATURE:
<223> OTHER INFORMATION: Synthetic Construct

<400> SEQUENCE: 273
gaggtgcagc tggcggagtc tgggggaggc tcggtgcagg ctggagggtc tctgaggctc       60
tcctgtgtaa tatcaggaac ctccatcagt ccagactgca tgggctggtt ccgccaggct      120
ccagggaaga gcgcgaggc agtcatgagt atttttacaa atactggtag cacgcgctat      180
ggcgactccg tgaagggccg attcaccagc tcccaaggca acgccaagaa tacgctgtat      240
ctgcaaatgg acagcttgaa acttgatgac actgccacgt actactgtgc ggcccggtat      300 acgggggtg actgctttaa tcttgaacca ttggcgtggc gcttctgggg ccaggggacc      360
caggtcaccg tctcctca                                                    378

<210> SEQ ID NO 274
<211> LENGTH: 363
<212> TYPE: DNA
<213> ORGANISM: Artificial Sequence
<220> FEATURE:
<223> OTHER INFORMATION: Synthetic Construct

<400> SEQUENCE: 274
caggttcagc tggtggagtc tgggggaggc tccgtgcagg ctggagggcc tctgagactc       60
acctgtgcag ccactggata ctcttggaga cccgactgca tgggctggta ccgccaggct      120
gcagagaagg agcgcgaggg ggtcgcagtt attgatgctg atggtatcac aagttacgca      180
gacgccgcga agggccgatt caccatctcc cgagacaaca acaacatcac tctatatctg      240
caaatgctga aacctgacga cactggcatg tacgtctgtg tgataggatg gagagtaagc      300
agtggtggta actgccaatt caatgactac tggggtcagg gacccaggt caccgtctcc      360
```

```
tca                                                                  363

<210> SEQ ID NO 275
<211> LENGTH: 390
<212> TYPE: DNA
<213> ORGANISM: Artificial Sequence
<220> FEATURE:
<223> OTHER INFORMATION: Synthetic Construct

<400> SEQUENCE: 275
caggttcagc tggtggagtc tgggggaggg tcggtgcagt ctggagggtc tctgaaactc      60
tcctgtgcag tctctggatc tggatacagc tatagtcgcg gctgcttcgc atggttccaa     120
cagcgtccag ggaaggagcg cgaggggtc gcaattatta atagcgatgg acacacaaga     180
tactcagact ccgtgcaggg ccgattcatc atctcccaag acaaggccaa gaacacacta     240
tatctccaaa tgaacagcct gaaacctgac gacgcggcca tgtattactg tgcgtacgat     300
cgcaatcagt gttacgttct tctcgaccgc ttacgcctcc caggtacctt tagtgactgg     360
ggccagggga cccaggtcac cgtctcctca                                      390

<210> SEQ ID NO 276
<211> LENGTH: 390
<212> TYPE: DNA
<213> ORGANISM: Artificial Sequence
<220> FEATURE:
<223> OTHER INFORMATION: Synthetic Construct

<400> SEQUENCE: 276
gaggtgcagc tggtggagtc tgggggaggg tcggtgcagt ctggagggtc tctgagactc      60
tcctgtgcag tctctggatc tggatacagc tataatcgcg gctgcttcgc gtggttccag     120
cagcgtccag ggaaggagcg cgaggggtc gcaattatta atagcgatgg gcacacaacg     180
tacggagact ccgtgcaggg ccgattcatc atctcccaag acaaggccaa gaacacacta     240
gatctgcaaa tgaacagcct gaaacctgac gacacggcca tgtattactg tgcgtacgat     300
cgcaatcagt gttacgtgct tcgcgaccgc ttacgcctcc cagataccct tactgactgg     360
ggccagggga cccaggtcac cgtctcctca                                      390

<210> SEQ ID NO 277
<211> LENGTH: 390
<212> TYPE: DNA
<213> ORGANISM: Artificial Sequence
<220> FEATURE:
<223> OTHER INFORMATION: Synthetic Construct

<400> SEQUENCE: 277
caggtgaagt tggtggagtc tgggggaggg ttggtgcagt ctggagggtc tctgagactc      60
tcctgtgcag tctctggatc tggatacagc tatagtcgcg gctgcttcgc atggttccag     120
cagcgtccag ggaaggagcg cgaggggtc gcaattatta atatggatgg gcacacaatg     180
tactcagact tggcgcaggg ccgattcatc atctcccaag acaaggccaa gaacacacta     240
tatctgcaaa tgaacagcct gaaacctgac gacacggcca tgtattactg tgcgtacgat     300
cgcgatcagt gttacgtact tcgggaccgc ttacgcctcc cagatacctt taatgactgg     360
ggccagggga cccaggtcac cgtctcctca                                      390

<210> SEQ ID NO 278
<211> LENGTH: 378
<212> TYPE: DNA
```

<213> ORGANISM: Artificial Sequence
<220> FEATURE:
<223> OTHER INFORMATION: Synthetic Construct

<400> SEQUENCE: 278

```
cagattcagc tggtggagtc tggggggaggc tcggtgcagg ctggagggtc tctgaggctc      60
tcctgtgcag tgacaggaat ctccatcagt ccagactgca tgggctggtt ccgccaggct     120
ccagggaaga agcgcgaggc agtcgcgact attttacta atactgcgag cacgcgctat      180
ggcgactccg tgaagggccg attcaccagc tcccaaggga acggcaagaa tacgctgtat     240
ctgcaaatgg acagcttgaa cgttgatgac actgccacgt actactgtgc ggcccgctat     300
acgggggta actgctttaa tcttgagcca ttggcgtggc acttctgggg ccaggggacc      360
caggtcaccg tctcctca                                                   378
```

<210> SEQ ID NO 279
<211> LENGTH: 378
<212> TYPE: DNA
<213> ORGANISM: Artificial Sequence
<220> FEATURE:
<223> OTHER INFORMATION: Synthetic Construct

<400> SEQUENCE: 279

```
caggtgcacc tgatggagtc tggggggaggc tcggtgcagg ctggagggtc tctgaggctc     60
tcctgtgtag tatcaggaat ctccatcagt ccagactgta tggggtggtt ccgccaggct    120
ccagggaaga agcgcgaggc agtcgcgact attttacta atactcgtag gacgcgctat      180
ggcgactccg tgaagggccg agtcaccagc tcccaaggca acgccaagaa tacgctgtat    240
ctaaaaatgg acaacttgag gcacgatgac actgccacgt actactgtgc ggcccggtat    300
acgggggtg actgctttaa tcttgaccca ttgtcctggc gcttctgggg ccaggggacc     360
caggtcaccg tctcctca                                                  378
```

<210> SEQ ID NO 280
<211> LENGTH: 378
<212> TYPE: DNA
<213> ORGANISM: Artificial Sequence
<220> FEATURE:
<223> OTHER INFORMATION: Synthetic Construct

<400> SEQUENCE: 280

```
caggtgcagc tggtggagtc tggggggaggc tcggtgcagg ctggagggtc tctgaggctc     60
tcctgtgcag tatcaggaat ctccatcagt ccagactgca tgggctggtt ccgccaggct    120
ccagggaaga agcgcgaggc agtcgcgact attttacta atactcgtag cacgcgctat      180
ggcgactccg tgaagggccg attcaccagc tcccaaggca acgccaagaa tacgctgtat    240
ctgcaaatgg acagcttgaa acttgatgac actgccacgt actactgtgc ggcccggtat    300
acgggggtg actgctttaa tcttgagcct gtggcgtggc gcttctgggg ccaggggacc     360
caggtcaccg tctcctca                                                  378
```

<210> SEQ ID NO 281
<211> LENGTH: 369
<212> TYPE: DNA
<213> ORGANISM: Artificial Sequence
<220> FEATURE:
<223> OTHER INFORMATION: Synthetic Construct

<400> SEQUENCE: 281

```
gaggtgcagc tggtggagtc tgggggaggc ttggtgcagc ctgggggtc tctgagactc       60
```

```
tcctgtgcag cctctggctt caccttcagt gtttggtcga tgtcctgggt ccgccaggct    120
ccaggggagg gactcgagtg gtctcaact  atcactggga gtggcgcaca aacatattat    180
gcaagctcag tgaggggccg attcaccacc tccagagaca acgccaagaa cacggtatat    240
ctgcaaatga acagcctgaa atctgacgac acggccgtgt attattgtga gagaggaaat    300
ggtcagactg ctatggaggc tctcattaac ccgcccgagc gtccggggac ccaggtcacc    360
gtctcctca                                                            369
```

```
<210> SEQ ID NO 282
<211> LENGTH: 381
<212> TYPE: DNA
<213> ORGANISM: Artificial Sequence
<220> FEATURE:
<223> OTHER INFORMATION: Synthetic Construct

<400> SEQUENCE: 282
caggtgcagc tggtggagtc tgggggaggc ttgatgcagc ctgggggtc  tttgagactc     60 tcctgtgcag cctctggatt caccttcagt agttactgga tgtactgggt ccgccaggct    120
ccagggaagg ggcttgagtg gtctcggtt  attaatagag ctggtgattc cgcctggtat    180
gcagactcag tgacgggccg attcaccatc tccagagaca acgccaagaa cacggtgtat    240
ctgcaaatgg acagcctgaa acctgaggac acggccatgt actactgtgc ggcagactcg    300 aggggtacg  gtggtgactg gtacaagctc ctctcagact ttaattattg cggccagggg    360
acccaggtca ccgtctcctc a                                              381
```

```
<210> SEQ ID NO 283
<211> LENGTH: 378
<212> TYPE: DNA
<213> ORGANISM: Artificial Sequence
<220> FEATURE:
<223> OTHER INFORMATION: Synthetic Construct

<400> SEQUENCE: 283
caggtgcagc tggtggagtc tgggggaggc tcggtgcagg ctggagggtc tctgagactc     60
tcctgtgcag ccactgcgta caccgccagt ttctactgca tgggctggtt ccgccaggct    120
ccagggaagg agcgcgaggc ggtcgcaagt attaatgatg acggcgtcac aatgtacgca    180
gactccgtga agggccaatt caccatctcc aagacagcg  ccacgaagac tctgtatctg    240
caaatgaacc gcctgaaacc tgaggacacc gccatgtact actgtgcggc cacccggaa    300 ggttactgct acgccgagag actttccacg tggagatata cgttctgggg ccaggggacc    360
caggtcaccg tctcctca                                                  378
```

```
<210> SEQ ID NO 284
<211> LENGTH: 390
<212> TYPE: DNA
<213> ORGANISM: Artificial Sequence
<220> FEATURE:
<223> OTHER INFORMATION: Synthetic Construct

<400> SEQUENCE: 284
gaggtgcagc tggtggagtc tggggagggg tcggtgcagt ctggagggtc tctgagactc     60
tcctgtgcag tctctggatc tggatacagc tatagtcgcg gctgcttcgc gtggttccag    120
cagcgtccag gaaaggagcg cgaggggggtc gcaattatta atagcgatgg gcacacaaga    180
tactcagact ccgtgcaggg ccgattcatc atctcccaag acaaggccaa gaacacacta    240
```

| | |
|---|---|
| tatctgcaaa tgaacagcct gaaacctgac gacacggcca tgtattactg tgcgtacgat | 300 |
| tgcagtcagt gttacgtgct cgcgaccgc ttacgcctcc cagataccctt tactgactgg | 360 |
| ggccagggga cccaggtcac cgtctcctca | 390 |

<210> SEQ ID NO 285
<211> LENGTH: 369
<212> TYPE: DNA
<213> ORGANISM: Artificial Sequence
<220> FEATURE:
<223> OTHER INFORMATION: Synthetic Construct

<400> SEQUENCE: 285

| | |
|---|---|
| gaggtgcagc tggtggagag cggaggagga ctggtgcagc caggaggctc tctgagactg | 60 |
| tcctgcgccg tgagcggcaa catctacaac agaaatttca tgggatggtt taggcaggct | 120 |
| cctggcaagg gactggaggg cgtgtccgcc atctataccg gcacatctcg cacctactat | 180 |
| gctgactccg tgaagggcag gttcaccatc tctcgggata actccaagaa tacagtgtac | 240 |
| ctgcagatga actctctgag ggccgaggac acagccgtgt actattgtgc cgctgacctg | 300 |
| cgggatggct tttgggatac cggcgtgtgg aatacatggg gccagggcac cctggtgaca | 360 |
| gtgtccagc | 369 |

<210> SEQ ID NO 286
<211> LENGTH: 369
<212> TYPE: DNA
<213> ORGANISM: Artificial Sequence
<220> FEATURE:
<223> OTHER INFORMATION: Synthetic Construct

<400> SEQUENCE: 286

| | |
|---|---|
| gaggtgcagc tggtggagag cggaggagga ctggtgcagc caggaggctc tctgagactg | 60 |
| tcctgcgccg tgagcggcaa catctacaac agaaatttca tgggatggtt taggcaggct | 120 |
| cctggcaagg gactggaggg cgtgtccgcc atctataccg gcacatctcg cacctactat | 180 |
| gctgactccg tgaagggcag gttcaccatc tctcgggata actccaagaa tacagtgtac | 240 |
| ctgcagatga actctctgag ggccgaggac acagccgtgt actattgtgc cgctgacctg | 300 |
| cgggagggct tttgggatac cggcgtgtgg aatacatggg gccagggcac cctggtgaca | 360 |
| gtgtccagc | 369 |

<210> SEQ ID NO 287
<211> LENGTH: 369
<212> TYPE: DNA
<213> ORGANISM: Artificial Sequence
<220> FEATURE:
<223> OTHER INFORMATION: Synthetic Construct

<400> SEQUENCE: 287

| | |
|---|---|
| gaggtgcagc tggtggagtc cggaggagga ctggtgcagc caggaggctc tctgaggctg | 60 |
| tcctgcgccg tgagcggaaa catctacaac agaaatttca tgggatggtt taggcaggct | 120 |
| cctggcaagg gaagggaggg cgtgtctgct atctataccg gcacatccag gacctactat | 180 |
| gccgacagcg tgaagggcag gttcaccatc tctcgggata cgctaagaa tacagtgtac | 240 |
| ctgcagatga actccctgcg gccagaggac acagccgtgt actattgtgc cgctgacctg | 300 |
| agagatggct tttgggatac cggcgtgtgg aatacatggg gccagggcac cctggtgaca | 360 |
| gtgtccagc | 369 |

```
<210> SEQ ID NO 288
<211> LENGTH: 369
<212> TYPE: DNA
<213> ORGANISM: Artificial Sequence
<220> FEATURE:
<223> OTHER INFORMATION: Synthetic Construct

<400> SEQUENCE: 288
gaggtgcagc tggtggagtc cggaggagga ctggtgcagc aggaggctc tctgaggctg      60 tcctgcgccg tgagcggaaa catctacaac agaaatttca tgggatggtt taggcaggct    120
cctggcaagg gaagggaggg cgtgtctgct atctataccg gcacatccag gacctactat    180
gccgacagcg tgaagggcag gttcaccatc tctcgggata cgctaagaa tacagtgtac     240 ctgcagatga actccctgcg gccagaggac acagccgtgt actattgtgc cgctgacctg    300
agagagggct tttgggatac cggcgtgtgg aatacatggg gccagggcac cctggtgaca    360
gtgtccagc                                                            369

<210> SEQ ID NO 289
<211> LENGTH: 122
<212> TYPE: PRT
<213> ORGANISM: Artificial Sequence
<220> FEATURE:
<223> OTHER INFORMATION: Synthetic Construct

<400> SEQUENCE: 289

Gln Val Gln Leu Val Glu Ser Gly Gly Gly Lys Val Gln Pro Gly Gly
1               5                   10                  15

Ser Leu Arg Leu Ser Cys Ala Ala Ser Gly Gly Thr Leu Asp Tyr Tyr
            20                  25                  30

Ala Ile Gly Trp Phe Arg Gln Ala Pro Gly Lys Glu Arg Glu Ala Val
        35                  40                  45

Ser Cys Ile Ser Ser Ser Asp Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Gly Asp Thr Ala Val Tyr His Cys
                85                  90                  95

Ala Thr Asp Arg Ala Cys Gly Ser Ser Trp Leu Gly Ala Glu Ser Trp
            100                 105                 110

Ala Gln Gly Thr Gln Val Thr Val Ser Ser
        115                 120

<210> SEQ ID NO 290
<211> LENGTH: 112
<212> TYPE: PRT
<213> ORGANISM: Artificial Sequence
<220> FEATURE:
<223> OTHER INFORMATION: Synthetic Construct

<400> SEQUENCE: 290

Gln Val His Leu Val Asp Ser Gly Gly Gly Leu Val Gln Pro Gly Gly
1               5                   10                  15

Ser Leu Arg Leu Ser Cys Ala Ala Ser Gly Ser Ile Thr Ser Arg Asn
            20                  25                  30

Thr Met Gly Trp Tyr Arg Gln Val Pro Gly Lys Gln Arg Glu Leu Val
        35                  40                  45

Ala Leu Ile Ala Thr Phe Val Thr His Tyr Ala Asp Ser Val Lys Gly
    50                  55                  60
```

```
Arg Phe Thr Ile Ser Arg Asp Asn Ala Arg Lys Met Val Phe Leu Glu
 65                  70                  75                  80

Met Asn Ser Leu Gln Pro Glu Asp Thr Gly Ala Tyr Tyr Cys Tyr Val
                 85                  90                  95

Asp Val Ser Pro Tyr Trp Gly Arg Gly Thr Gln Val Thr Val Ser Ser
            100                 105                 110
```

<210> SEQ ID NO 291
<211> LENGTH: 127
<212> TYPE: PRT
<213> ORGANISM: Artificial Sequence
<220> FEATURE:
<223> OTHER INFORMATION: Synthetic Construct

<400> SEQUENCE: 291

```
Gln Val Gln Leu Val Glu Ser Gly Gly Gly Ser Val Gln Ala Gly Gly
  1               5                  10                  15

Ser Leu Arg Leu Ser Cys Ala Ala Ser Gly Tyr Thr Tyr Ile Pro Asn
                 20                  25                  30

Cys Met Ala Trp Phe Arg Gln Ala Pro Gly Lys Glu Arg Glu Gly Val
             35                  40                  45

Thr Leu Ile Phe Thr Gly Asp Gly Thr Ser Thr Tyr Val Asp Ser Val
     50                  55                  60

Lys Gly Arg Phe Thr Ile Ser Gln Asp Asn Ala Lys Asn Thr Val Tyr
 65                  70                  75                  80

Leu Gln Met Asn Ser Leu Lys Pro Glu Asp Thr Ala Leu Tyr Tyr Cys
                 85                  90                  95

Ala Ala Ala Glu Arg Cys Ser Gly Ser Asn Asp Arg Ile Ser Phe Trp
            100                 105                 110

Gly Ile Ser Tyr Trp Gly Gln Gly Thr Gln Val Thr Val Ser Ser
            115                 120                 125
```

<210> SEQ ID NO 292
<211> LENGTH: 124
<212> TYPE: PRT
<213> ORGANISM: Artificial Sequence
<220> FEATURE:
<223> OTHER INFORMATION: Synthetic Construct

<400> SEQUENCE: 292

```
Gln Val Gln Leu Val Glu Ser Gly Gly Gly Ser Val Gln Ala Gly Gly
  1               5                  10                  15

Ser Leu Arg Leu Ser Cys Thr Ala Ser Ala Tyr Thr Tyr Ser Asn Ile
                 20                  25                  30

Cys Leu Gly Trp Leu Arg Gln Ala Pro Gly Gly Leu Glu Ala Val
             35                  40                  45

Ala Thr Ile Tyr Ile Ala Asp Gln Thr Ser Tyr Tyr Ala Asp Ser Val
     50                  55                  60

Lys Gly Arg Phe Arg Ile Ser Lys Asp Ala Ala Lys Asn Ala Val Tyr
 65                  70                  75                  80

Leu Gln Met Ser Ser Leu Arg Pro Glu Asp Thr Ala Met Tyr Tyr Cys
                 85                  90                  95

Ala Ser Arg Tyr Gly Ser Thr Cys Gly Glu Tyr Leu Ala Asp Tyr Thr
            100                 105                 110

Ser Arg Ala Gln Gly Thr Gln Val Thr Val Ser Ser
            115                 120
```

<210> SEQ ID NO 293

```
<211> LENGTH: 123
<212> TYPE: PRT
<213> ORGANISM: Artificial Sequence
<220> FEATURE:
<223> OTHER INFORMATION: Synthetic Construct

<400> SEQUENCE: 293

Gln Met Gln Leu Val Glu Ser Gly Gly Gly Ser Val Gln Ala Gly Gly
1               5                   10                  15

Ser Leu Arg Leu Ser Cys Ala Val Ser Gly Tyr Ile Tyr Asn Arg Asn
            20                  25                  30

Phe Met Gly Trp Phe Arg Gln Ala Pro Gly Lys Glu Arg Glu Gly Val
        35                  40                  45

Ala Ala Ile Tyr Thr Gly Gly Pro Tyr Thr Tyr Thr Asp Ser Val
    50                  55                  60

Gln Gly Arg Phe Thr Ile Ser Gln Asp Asn Thr Lys Asn Thr Val Tyr
65                  70                  75                  80

Leu Gln Met Asn Ser Leu Lys Pro Glu Asp Thr Ala Met Tyr Tyr Cys
                85                  90                  95

Val Ser Asp Leu Ser Asp Gly Thr Trp Asp Gln Gly Arg Trp Asn Tyr
            100                 105                 110

Trp Gly Gln Gly Thr Gln Val Thr Val Ser Ser
        115                 120

<210> SEQ ID NO 294
<211> LENGTH: 123
<212> TYPE: PRT
<213> ORGANISM: Artificial Sequence
<220> FEATURE:
<223> OTHER INFORMATION: Synthetic Construct

<400> SEQUENCE: 294

Gln Val Gln Leu Val Glu Ser Gly Gly Gly Ser Ala Gln Ala Gly Gly
1               5                   10                  15

Ser Leu Arg Leu Ser Cys Ala Val Ser Gly Tyr Ile Tyr Asn Arg Asn
            20                  25                  30

Phe Met Gly Trp Phe Arg Gln Val Pro Gly Lys Val Arg Glu Gly Val
        35                  40                  45

Ala Ala Ile Tyr Thr Gly Thr Glu Arg Thr Tyr Tyr Ala Asp Ser Val
    50                  55                  60

Lys Gly Arg Phe Thr Ile Ser Gln Asp Asn Ala Lys Asn Thr Val Tyr
65                  70                  75                  80

Leu Gln Met Asn Ser Leu Lys Pro Glu Asp Thr Ala Met Tyr Tyr Cys
                85                  90                  95

Val Ala Asp Leu Arg Asp Gly Thr Trp Asp Thr Gly Val Trp Asn Thr
            100                 105                 110

Trp Gly Gln Gly Thr Gln Val Thr Val Ser Ser
        115                 120

<210> SEQ ID NO 295
<211> LENGTH: 123
<212> TYPE: PRT
<213> ORGANISM: Artificial Sequence
<220> FEATURE:
<223> OTHER INFORMATION: Synthetic Construct

<400> SEQUENCE: 295

Gln Ile Gln Leu Val Glu Ser Gly Gly Gly Ser Ala Gln Ala Gly Gly
1               5                   10                  15
```

```
Ser Leu Arg Leu Ser Cys Val Val Ser Gly Asn Ile Tyr Asn Arg Asn
            20                  25                  30

Phe Met Gly Trp Phe Arg Gln Ala Pro Gly Lys Val Arg Glu Gly Val
        35                  40                  45

Ala Ala Ile Tyr Thr Gly Thr Ser Arg Thr Tyr Tyr Ala Asp Ser Val
    50                  55                  60

Lys Gly Arg Phe Thr Ile Ser Gln Asp Asn Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Asp Leu Arg Asp Gly Phe Trp Asp Thr Gly Val Trp Asn Thr
            100                 105                 110

Trp Gly Gln Gly Thr Gln Val Thr Val Ser Ser
        115                 120
```

<210> SEQ ID NO 296
<211> LENGTH: 116
<212> TYPE: PRT
<213> ORGANISM: Artificial Sequence
<220> FEATURE:
<223> OTHER INFORMATION: Synthetic Construct

<400> SEQUENCE: 296

```
Gln Val Gln Leu Val Glu Ser Gly Gly Gly Leu Val Gln Pro Gly Gly
1               5                   10                  15

Ser Leu Thr Leu Ser Cys Ala Ala Ser Gly Phe Thr Phe Ser Thr Ala
            20                  25                  30

Ala Met Ser Trp Val Arg Gln Pro Glu Gly Leu Glu Trp Val
        35                  40                  45

Ala Ser Ile Asp Ser Ser Gly Ser Arg Thr Tyr Tyr Ala Gly Ser Val
    50                  55                  60

Lys Gly Arg Phe Thr Ile Ser Arg Asp Asn Ala Lys Asn Thr Leu Tyr
65                  70                  75                  80

Leu Gln Leu Asn Ser Leu Lys Ala Glu Asp Thr Ala Met Tyr Tyr Cys
                85                  90                  95

Ala Lys Asp His Met Ser Trp Leu Pro Arg Gly Gln Gly Thr Gln Val
            100                 105                 110

Thr Val Ser Ser
        115
```

<210> SEQ ID NO 297
<211> LENGTH: 122
<212> TYPE: PRT
<213> ORGANISM: Artificial Sequence
<220> FEATURE:
<223> OTHER INFORMATION: Synthetic Construct

<400> SEQUENCE: 297

```
Gln Val Gln Leu Val Glu Ser Gly Gly Gly Ser Val Gln Ala Gly Gly
1               5                   10                  15

Ser Leu Arg Leu Ser Cys Ala Ala Ser Gly Phe Thr Asp Ser Ser Tyr
            20                  25                  30

Cys Gly Ala Trp Phe Arg Gln Val Pro Gly Lys Glu Arg Glu Gly Val
        35                  40                  45

Ala Ile Ile Asp Arg Tyr Gly Gly Thr Met Tyr Lys Asp Ser Val Lys
    50                  55                  60

Gly Arg Phe Thr Ile Ser Lys Asp Thr Ala Lys Asn Ile Leu Tyr Leu
65                  70                  75                  80
```

Gln Met Asn Ser Leu Lys Leu Glu Asp Thr Ala Met Tyr Tyr Cys Ala
                    85                  90                  95

Ala Ala Glu Tyr Arg Gly Ser Ser Cys Asp Ala Glu Ser Gly Tyr Trp
                100                 105                 110

Gly Gln Gly Thr Gln Val Thr Val Ser Ser
            115                 120

<210> SEQ ID NO 298
<211> LENGTH: 122
<212> TYPE: PRT
<213> ORGANISM: Artificial Sequence
<220> FEATURE:
<223> OTHER INFORMATION: Synthetic Construct

<400> SEQUENCE: 298

Gln Val His Leu Met Glu Ser Gly Gly Gly Ser Val Gln Ala Gly Gly
1               5                   10                  15

Ser Leu Thr Leu Ser Cys Ala Ala Ser Val Phe Thr Asp Ser Asn Tyr
                20                  25                  30

Cys Met Ala Trp Phe Arg Gln Val Pro Gly Lys Glu Arg Glu Gly Val
            35                  40                  45

Ala Ile Ile Asp Arg Tyr Gly Gly Thr Met Tyr Lys Asp Ser Val Lys
        50                  55                  60

Gly Arg Phe Thr Ile Ser Lys Asp Thr Ala Lys Asn Ile Leu Tyr Leu
65                  70                  75                  80

Gln Met Asn Ser Leu Lys Leu Glu Asp Thr Ala Met Tyr Tyr Cys Ala
                85                  90                  95

Ala Ala Gly Tyr Arg Gly Ser Ser Cys Asp Ala Asp Ser Gly Tyr Trp
                100                 105                 110

Gly Gln Gly Thr Gln Val Thr Val Ser Ser
            115                 120

<210> SEQ ID NO 299
<211> LENGTH: 122
<212> TYPE: PRT
<213> ORGANISM: Artificial Sequence
<220> FEATURE:
<223> OTHER INFORMATION: Synthetic Construct

<400> SEQUENCE: 299

Gln Ile Gln Leu Val Glu Ser Gly Gly Gly Ser Val Gln Ala Gly Gly
1               5                   10                  15

Ser Leu Arg Leu Ser Cys Ala Ala Ser Gly Phe Thr Asp Ser Ser Tyr
                20                  25                  30

Cys Gly Ala Trp Phe Arg Gln Val Pro Gly Lys Glu Arg Glu Gly Val
            35                  40                  45

Ala Ile Ile Asp Arg Tyr Gly Gly Thr Met Tyr Lys Asp Ser Val Lys
        50                  55                  60

Gly Arg Phe Thr Ile Ser Lys Asp Thr Ala Lys Asn Ile Leu Tyr Leu
65                  70                  75                  80

Gln Met Asn Ser Leu Lys Leu Glu Asp Thr Ala Met Tyr Tyr Cys Ala
                85                  90                  95

Ala Ala Glu Tyr Arg Gly Ser Ser Cys Asp Ala Glu Ser Gly Tyr Trp
                100                 105                 110

Gly Gln Gly Thr Gln Val Thr Val Ser Ser
            115                 120

```
<210> SEQ ID NO 300
<211> LENGTH: 124
<212> TYPE: PRT
<213> ORGANISM: Artificial Sequence
<220> FEATURE:
<223> OTHER INFORMATION: Synthetic Construct

<400> SEQUENCE: 300
```

Gln Val Gln Leu Val Glu Ser Gly Gly Gly Ser Val Gln Ala Gly Gly
1               5                   10                  15

Ser Leu Arg Leu Ser Cys Ala Ala Ser Gly Tyr Thr Ala Gly Ser Leu
            20                  25                  30

Cys Met Gly Trp Phe Arg Gln Ala Pro Gly Lys Glu Arg Glu Gly Val
        35                  40                  45

Ala Ala Ile Tyr Thr Gly Gly Ser Thr Tyr Ala Asp Ser Val
    50                  55                  60

Lys Gly Arg Phe Thr Ile Ser Gln Asp Asn Ala Lys Asn Thr Val Tyr
65                  70                  75                  80

Leu Gln Met Asn Ser Leu Lys Pro Glu Asp Thr Ala Gly Tyr Tyr Cys
                85                  90                  95

Gly Ala Gly Ser Arg Glu Asp Tyr Cys Asp Arg Gly Tyr Ile Tyr Asp
            100                 105                 110

His Trp Gly Gln Gly Thr Gln Val Thr Val Ser Ser
        115                 120

```
<210> SEQ ID NO 301
<211> LENGTH: 125
<212> TYPE: PRT
<213> ORGANISM: Artificial Sequence
<220> FEATURE:
<223> OTHER INFORMATION: Synthetic Construct

<400> SEQUENCE: 301
```

Gln Val Lys Leu Val Glu Ser Gly Gly Gly Ser Val Gln Ala Gly Gly
1               5                   10                  15

Tyr Leu Arg Leu Ser Cys Ala Ala Ser Gly Asp Thr Asn Asn Leu Asn
            20                  25                  30

Phe Arg Gly Trp Phe Arg Gln Ala Pro Gly Lys Glu Arg Glu Gly Val
        35                  40                  45

Ala Val Ile Thr His Ser Gly Ser Thr Tyr Ala Glu Ser Val Lys
    50                  55                  60

Gly Arg Phe Thr Ile Ser Gln Asp Leu Ala Lys Asn Thr Met Tyr Leu
65                  70                  75                  80

Gln Met Asn Ser Leu Lys Pro Glu Asp Thr Ala Met Tyr Tyr Cys Ala
                85                  90                  95

Ala Ala Asp Val Trp Arg Ile Ser Trp Ser Phe Val Pro Glu Leu Phe
            100                 105                 110

Ser Tyr Trp Gly Gln Gly Thr Gln Val Thr Val Ser Ser
        115                 120                 125

```
<210> SEQ ID NO 302
<211> LENGTH: 127
<212> TYPE: PRT
<213> ORGANISM: Artificial Sequence
<220> FEATURE:
<223> OTHER INFORMATION: Synthetic Construct

<400> SEQUENCE: 302
```

Gln Val Gln Leu Val Glu Ser Gly Gly Gly Ser Val Gln Ala Gly Gly
1               5                   10                  15

Ser Leu Arg Leu Ser Cys Ala Gly Ser Gly Phe Thr Phe Asn Asn Tyr
            20                  25                  30

Ala Met Gly Trp Phe Arg Gln Ala Pro Gly Lys Glu Arg Glu Gly Ile
        35                  40                  45

Ala Gly Ile Trp Thr Gly Gly Ser Thr Tyr Tyr Ala Asp Ser Val
    50                  55                  60

Lys Gly Arg Phe Thr Ile Ser Glu Asp Val Ala Lys Asn Thr Val Tyr
65                  70                  75                  80

Leu Gln Met Asp Ser Leu Lys Pro Glu Asp Thr Ala Met Tyr Tyr Cys
                85                  90                  95

Ala Ala Glu Arg Trp Asp Tyr Ser Asp Trp Arg Arg Leu Lys Arg Gly
            100                 105                 110

Asp Tyr Asn Tyr Trp Gly Gln Gly Thr Gln Val Thr Val Ser Ser
            115                 120                 125

<210> SEQ ID NO 303
<211> LENGTH: 130
<212> TYPE: PRT
<213> ORGANISM: Artificial Sequence
<220> FEATURE:
<223> OTHER INFORMATION: Synthetic Construct

<400> SEQUENCE: 303

Gln Val His Leu Met Glu Ser Gly Gly Gly Ser Val Pro Ser Gly Gly
1               5                   10                  15

Ser Leu Arg Leu Ser Cys Ala Val Ser Gly Ser Gly Tyr Ser Tyr Ser
            20                  25                  30

Arg Gly Cys Phe Ala Trp Phe Gln Gln Arg Pro Gly Lys Glu Arg Glu
        35                  40                  45

Gly Val Ala Ile Ile Asn Met Asp Gly His Thr Arg Tyr Ser Asp Ser
    50                  55                  60

Val Gln Gly Arg Phe Ile Ile Ser Gln Asp Lys Ala Lys Asn Thr Leu
65                  70                  75                  80

His Leu Gln Met Asn Thr Leu Arg Pro Asp Asp Thr Ala Met Tyr Tyr
                85                  90                  95

Cys Ala Tyr Asp Arg Ser Gln Cys Tyr Val Leu Ser Asp Arg Leu Arg
            100                 105                 110

Leu Pro Gly Thr Phe Ser Asp Trp Gly Gln Gly Thr Gln Val Thr Val
            115                 120                 125

Ser Ser
    130

<210> SEQ ID NO 304
<211> LENGTH: 123
<212> TYPE: PRT
<213> ORGANISM: Artificial Sequence
<220> FEATURE:
<223> OTHER INFORMATION: Synthetic Construct

<400> SEQUENCE: 304

Glu Val Gln Leu Ala Glu Ser Gly Gly Gly Ser Val Gln Ala Gly Gly
1               5                   10                  15

Ser Leu Lys Leu Ser Cys Leu Ala Ser Gln Trp Ile Ser Asp Cys
            20                  25                  30

Gly Met Ala Trp Tyr Arg Gln Ala Pro Gly Lys Glu Arg Glu Leu Val
        35                  40                  45

Ser Arg Ile Ser Ser Asp Asp Thr Thr Thr Tyr Ala Asp Ser Val Lys

```
                 50                  55                  60

Gly Arg Phe Thr Ile Ser Gln Asp Ser Ala Lys Asn Thr Leu Tyr Leu
 65                  70                  75                  80

Gln Met Asn Lys Leu Lys Thr Glu Asp Thr Gly Val Tyr Tyr Cys Ala
                 85                  90                  95

Ala Glu Ala Lys Ser Thr Ile Thr Ser Leu Cys Tyr Pro Leu Asn Tyr
            100                 105                 110

Trp Gly Gln Gly Thr Gln Val Thr Val Ser Ser
        115                 120

<210> SEQ ID NO 305
<211> LENGTH: 121
<212> TYPE: PRT
<213> ORGANISM: Artificial Sequence
<220> FEATURE:
<223> OTHER INFORMATION: Synthetic Construct

<400> SEQUENCE: 305

Gln Val Gln Leu Val Glu Ser Gly Gly Ser Val Gln Ala Gly Gly
 1               5                  10                  15

Ser Leu Arg Leu Thr Cys Ala Ala Thr Gly Tyr Ser Trp Arg Pro Asp
                 20                  25                  30

Cys Met Gly Trp Tyr Arg Gln Ala Ala Glu Lys Glu Arg Glu Gly Val
             35                  40                  45

Ala Val Ile Asp Ala Asp Gly Ile Thr Ser Tyr Ala Asp Ala Ala Lys
         50                  55                  60

Gly Arg Phe Thr Ile Ser Arg Asp Asn Lys Ile Thr Leu Tyr Leu
 65                  70                  75                  80

Gln Met Leu Lys Pro Asp Asp Thr Gly Met Tyr Val Cys Val Gly
                 85                  90                  95

Trp Arg Val Ser Ser Gly Gly Asn Cys Gln Phe Asn Asp Tyr Trp Gly
             100                 105                 110

Gln Gly Thr Gln Val Thr Val Ser Ser
         115                 120

<210> SEQ ID NO 306
<211> LENGTH: 126
<212> TYPE: PRT
<213> ORGANISM: Artificial Sequence
<220> FEATURE:
<223> OTHER INFORMATION: Synthetic Construct

<400> SEQUENCE: 306

Gln Val His Leu Met Glu Ser Gly Gly Gly Ala Val Gln Thr Gly Gly
 1               5                  10                  15

Ser Leu Arg Leu Ser Cys Ala Val Ser Gly Ile Ser Ile Ser Pro Asp
                 20                  25                  30

Cys Met Gly Trp Phe Arg Gln Ala Pro Gly Lys Lys Arg Glu Ala Val
             35                  40                  45

Thr Thr Ile Phe Ala Asn Thr Gly Ser Ala Arg Tyr Gly Asp Ser Val
         50                  55                  60

Lys Gly Arg Phe Thr Ser Ser Gln Gly Asn Ala Lys Asn Thr Leu Tyr
 65                  70                  75                  80

Leu Gln Met Asp Ser Val Lys Leu Asp Asp Thr Gly Thr Tyr Tyr Cys
                 85                  90                  95

Ala Ala Arg Phe Thr Gly Gly Asp Cys Phe Asp His Gln Pro Leu Ala
             100                 105                 110
```

```
Trp Arg Phe Trp Gly Gln Gly Thr Gln Val Thr Val Ser Ser
        115                 120                 125
```

<210> SEQ ID NO 307
<211> LENGTH: 130
<212> TYPE: PRT
<213> ORGANISM: Artificial Sequence
<220> FEATURE:
<223> OTHER INFORMATION: Synthetic Construct

<400> SEQUENCE: 307

```
Glu Val Gln Leu Ala Glu Ser Gly Gly Gly Val Gln Ser Gly Gly
1               5                   10                  15

Ser Leu Arg Leu Ser Cys Ala Val Ser Gly Ser Gly Tyr Ser Tyr Ser
            20                  25                  30

Arg Gly Cys Phe Ala Trp Phe Gln Gln Arg Pro Gly Lys Glu Arg Glu
        35                  40                  45

Gly Val Ala Ile Ile Asn Ser Asp Gly His Thr Ala Tyr Ser Asp Ser
    50                  55                  60

Val Gln Gly Arg Phe Ile Ile Ser Gln Asp Lys Ala Lys Asn Thr Leu
65                  70                  75                  80

Tyr Leu Gln Met Asn Ser Leu Lys Pro Asp Asp Thr Ala Met Tyr Tyr
                85                  90                  95

Cys Ala Tyr Asp Arg Ser Gln Cys Tyr Val Leu Arg Asp Arg Leu Arg
            100                 105                 110

Leu Pro Asp Thr Phe Thr Asp Trp Gly Gln Gly Thr Gln Val Thr Val
        115                 120                 125

Ser Ser
    130
```

<210> SEQ ID NO 308
<211> LENGTH: 126
<212> TYPE: PRT
<213> ORGANISM: Artificial Sequence
<220> FEATURE:
<223> OTHER INFORMATION: Synthetic Construct

<400> SEQUENCE: 308

```
Gln Val His Leu Val Glu Ser Gly Gly Ala Ser Val Gln Ala Gly Gly
1               5                   10                  15

Ser Leu Arg Leu Ser Cys Ala Ala Thr Ala Tyr Thr Ala Ser Asn Tyr
            20                  25                  30

Cys Met Gly Trp Phe Arg Gln Ser Pro Gly Lys Glu Arg Glu Ala Val
        35                  40                  45

Ala Ser Ile Asn Asp Asp Gly Val Thr Ser Tyr Ala Asp Ser Val Lys
    50                  55                  60

Gly Arg Phe Thr Ile Ser Gln Asp Ser Ala Lys Lys Thr Leu Tyr Leu
65                  70                  75                  80

Gln Met Asn Arg Leu Lys Pro Glu Asp Thr Ala Met Tyr Tyr Cys Ala
                85                  90                  95

Ala Thr Pro Asp Gly Tyr Cys Tyr Ala Glu Arg Leu Ser Arg Trp Arg
            100                 105                 110

Tyr Glu Phe Trp Gly Gln Gly Thr Gln Val Thr Val Ser Ser
        115                 120                 125
```

<210> SEQ ID NO 309
<211> LENGTH: 126
<212> TYPE: PRT
<213> ORGANISM: Artificial Sequence
<220> FEATURE:
<223> OTHER INFORMATION: Synthetic Construct

<400> SEQUENCE: 309

Glu Val Gln Leu Ala Glu Ser Gly Gly Gly Ser Val Gln Ala Gly Gly
1               5                   10                  15

Ser Leu Arg Leu Ser Cys Val Ile Ser Gly Thr Ser Ile Ser Pro Asp
            20                  25                  30

Cys Met Gly Trp Phe Arg Gln Ala Pro Gly Lys Lys Arg Glu Ala Val
        35                  40                  45

Met Ser Ile Phe Thr Asn Thr Gly Ser Thr Arg Tyr Gly Asp Ser Val
    50                  55                  60

Lys Gly Arg Phe Thr Ser Ser Gln Gly Asn Ala Lys Asn Thr Leu Tyr
65                  70                  75                  80

Leu Gln Met Asp Ser Leu Lys Leu Asp Asp Thr Ala Thr Tyr Tyr Cys
                85                  90                  95

Ala Ala Arg Tyr Thr Gly Gly Asp Cys Phe Asn Leu Glu Pro Leu Ala
            100                 105                 110

Trp Arg Phe Trp Gly Gln Gly Thr Gln Val Thr Val Ser Ser
        115                 120                 125

<210> SEQ ID NO 310
<211> LENGTH: 121
<212> TYPE: PRT
<213> ORGANISM: Artificial Sequence
<220> FEATURE:
<223> OTHER INFORMATION: Synthetic Construct

<400> SEQUENCE: 310

Gln Val Gln Leu Val Glu Ser Gly Gly Gly Ser Val Gln Ala Gly Gly
1               5                   10                  15

Pro Leu Arg Leu Thr Cys Ala Ala Thr Gly Tyr Ser Trp Arg Pro Asp
            20                  25                  30

Cys Met Gly Trp Tyr Arg Gln Ala Ala Glu Lys Glu Arg Glu Gly Val
        35                  40                  45

Ala Val Ile Asp Ala Asp Gly Ile Thr Ser Tyr Ala Asp Ala Ala Lys
    50                  55                  60

Gly Arg Phe Thr Ile Ser Arg Asp Asn Asn Ile Thr Leu Tyr Leu
65                  70                  75                  80

Gln Met Leu Lys Pro Asp Asp Thr Gly Met Tyr Val Cys Val Ile Gly
                85                  90                  95

Trp Arg Val Ser Ser Gly Gly Asn Cys Gln Phe Asn Asp Tyr Trp Gly
            100                 105                 110

Gln Gly Thr Gln Val Thr Val Ser Ser
        115                 120

<210> SEQ ID NO 311
<211> LENGTH: 130
<212> TYPE: PRT
<213> ORGANISM: Artificial Sequence
<220> FEATURE:
<223> OTHER INFORMATION: Synthetic Construct

<400> SEQUENCE: 311

Gln Val Gln Leu Val Glu Ser Gly Gly Gly Ser Val Gln Ser Gly Gly
1               5                   10                  15

Ser Leu Lys Leu Ser Cys Ala Val Ser Gly Ser Gly Tyr Ser Tyr Ser
            20                  25                  30

```
Arg Gly Cys Phe Ala Trp Phe Gln Gln Arg Pro Gly Lys Glu Arg Glu
            35                  40                  45

Gly Val Ala Ile Ile Asn Ser Asp Gly His Thr Arg Tyr Ser Asp Ser
 50                  55                  60

Val Gln Gly Arg Phe Ile Ile Ser Gln Asp Lys Ala Lys Asn Thr Leu
 65                  70                  75                  80

Tyr Leu Gln Met Asn Ser Leu Lys Pro Asp Asp Ala Ala Met Tyr Tyr
                85                  90                  95

Cys Ala Tyr Asp Arg Asn Gln Cys Tyr Val Leu Leu Asp Arg Leu Arg
                100                 105                 110

Leu Pro Gly Thr Phe Ser Asp Trp Gly Gln Gly Thr Gln Val Thr Val
                115                 120                 125

Ser Ser
    130

<210> SEQ ID NO 312
<211> LENGTH: 130
<212> TYPE: PRT
<213> ORGANISM: Artificial Sequence
<220> FEATURE:
<223> OTHER INFORMATION: Synthetic Construct

<400> SEQUENCE: 312

Glu Val Gln Leu Val Glu Ser Gly Gly Gly Ser Val Gln Ser Gly Gly
 1               5                  10                  15

Ser Leu Arg Leu Ser Cys Ala Val Ser Gly Ser Gly Tyr Ser Tyr Ser
                20                  25                  30

Arg Gly Cys Phe Ala Trp Phe Gln Gln Arg Pro Gly Lys Glu Arg Glu
            35                  40                  45

Gly Val Ala Ile Ile Asn Ser Asp Gly His Thr Arg Tyr Ser Asp Ser
 50                  55                  60

Val Gln Gly Arg Phe Ile Ile Ser Gln Asp Lys Ala Lys Asn Thr Leu
 65                  70                  75                  80

Tyr Leu Gln Met Asn Ser Leu Lys Pro Asp Asp Thr Ala Met Tyr Tyr
                85                  90                  95

Cys Ala Tyr Asp Cys Ser Gln Cys Tyr Val Leu Arg Asp Arg Leu Arg
                100                 105                 110

Leu Pro Asp Thr Phe Thr Asp Trp Gly Gln Gly Thr Gln Val Thr Val
                115                 120                 125

Ser Ser
    130

<210> SEQ ID NO 313
<211> LENGTH: 130
<212> TYPE: PRT
<213> ORGANISM: Artificial Sequence
<220> FEATURE:
<223> OTHER INFORMATION: Synthetic Construct

<400> SEQUENCE: 313

Glu Val Gln Leu Val Glu Ser Gly Gly Gly Ser Val Gln Ser Gly Gly
 1               5                  10                  15

Ser Leu Arg Leu Ser Cys Ala Val Ser Gly Ser Gly Tyr Ser Tyr Asn
                20                  25                  30

Arg Gly Cys Phe Ala Trp Phe Gln Gln Arg Pro Gly Lys Glu Arg Glu
            35                  40                  45

Gly Val Ala Ile Ile Asn Ser Asp Gly His Thr Thr Tyr Gly Asp Ser
 50                  55                  60
```

Val Gln Gly Arg Phe Ile Ile Ser Gln Asp Lys Ala Lys Asn Thr Leu
65                  70                  75                  80

Asp Leu Gln Met Asn Ser Leu Lys Pro Asp Thr Ala Met Tyr Tyr
                85                  90                  95

Cys Ala Tyr Asp Arg Asn Gln Cys Tyr Val Leu Arg Asp Arg Leu Arg
            100                 105                 110

Leu Pro Asp Thr Phe Thr Asp Trp Gly Gln Gly Thr Gln Val Thr Val
        115                 120                 125

Ser Ser
    130

<210> SEQ ID NO 314
<211> LENGTH: 130
<212> TYPE: PRT
<213> ORGANISM: Artificial Sequence
<220> FEATURE:
<223> OTHER INFORMATION: Synthetic Construct

<400> SEQUENCE: 314

Gln Val Lys Leu Val Glu Ser Gly Gly Gly Leu Val Gln Ser Gly Gly
1               5                   10                  15

Ser Leu Arg Leu Ser Cys Ala Val Ser Gly Ser Gly Tyr Ser Tyr Ser
            20                  25                  30

Arg Gly Cys Phe Ala Trp Phe Gln Gln Arg Pro Gly Lys Glu Arg Glu
        35                  40                  45

Gly Val Ala Ile Ile Asn Met Asp Gly His Thr Met Tyr Ser Asp Leu
    50                  55                  60

Ala Gln Gly Arg Phe Ile Ile Ser Gln Asp Lys Ala Lys Asn Thr Leu
65                  70                  75                  80

Tyr Leu Gln Met Asn Ser Leu Lys Pro Asp Thr Ala Met Tyr Tyr
                85                  90                  95

Cys Ala Tyr Asp Arg Asp Gln Cys Tyr Val Leu Arg Asp Arg Leu Arg
            100                 105                 110

Leu Pro Asp Thr Phe Asn Asp Trp Gly Gln Gly Thr Gln Val Thr Val
        115                 120                 125

Ser Ser
    130

<210> SEQ ID NO 315
<211> LENGTH: 126
<212> TYPE: PRT
<213> ORGANISM: Artificial Sequence
<220> FEATURE:
<223> OTHER INFORMATION: Synthetic Construct

<400> SEQUENCE: 315

Gln Ile Gln Leu Val Glu Ser Gly Gly Gly Ser Val Gln Ala Gly Gly
1               5                   10                  15

Ser Leu Arg Leu Ser Cys Ala Val Thr Gly Ile Ser Ile Ser Pro Asp
            20                  25                  30

Cys Met Gly Trp Phe Arg Gln Ala Pro Gly Lys Lys Arg Glu Ala Val
        35                  40                  45

Ala Thr Ile Phe Thr Asn Thr Ala Ser Thr Arg Tyr Gly Asp Ser Val
    50                  55                  60

Lys Gly Arg Phe Thr Ser Ser Gln Gly Asn Gly Lys Asn Thr Leu Tyr
65                  70                  75                  80

Leu Gln Met Asp Ser Leu Asn Val Asp Asp Thr Ala Thr Tyr Tyr Cys 85                  90                  95

Ala Ala Arg Tyr Thr Gly Gly Asn Cys Phe Asn Leu Glu Pro Leu Ala
            100                 105                 110

Trp His Phe Trp Gly Gln Gly Thr Gln Val Thr Val Ser Ser
            115                 120                 125

<210> SEQ ID NO 316
<211> LENGTH: 126
<212> TYPE: PRT
<213> ORGANISM: Artificial Sequence
<220> FEATURE:
<223> OTHER INFORMATION: Synthetic Construct

<400> SEQUENCE: 316

Gln Val His Leu Met Glu Ser Gly Gly Gly Ser Val Gln Ala Gly Gly
1               5                   10                  15

Ser Leu Arg Leu Ser Cys Val Val Ser Gly Ile Ser Ile Ser Pro Asp
            20                  25                  30

Cys Met Gly Trp Phe Arg Gln Ala Pro Gly Lys Lys Arg Glu Ala Val
        35                  40                  45

Ala Thr Ile Phe Thr Asn Thr Arg Arg Thr Arg Tyr Gly Asp Ser Val
    50                  55                  60

Lys Gly Arg Val Thr Ser Ser Gln Gly Asn Ala Lys Asn Thr Leu Tyr
65                  70                  75                  80

Leu Lys Met Asp Asn Leu Arg His Asp Asp Thr Ala Thr Tyr Tyr Cys
                85                  90                  95

Ala Ala Arg Tyr Thr Gly Gly Asp Cys Phe Asn Leu Asp Pro Leu Ser
            100                 105                 110

Trp Arg Phe Trp Gly Gln Gly Thr Gln Val Thr Val Ser Ser
            115                 120                 125

<210> SEQ ID NO 317
<211> LENGTH: 126
<212> TYPE: PRT
<213> ORGANISM: Artificial Sequence
<220> FEATURE:
<223> OTHER INFORMATION: Synthetic Construct

<400> SEQUENCE: 317

Gln Val Gln Leu Val Glu Ser Gly Gly Gly Ser Val Gln Ala Gly Gly
1               5                   10                  15

Ser Leu Arg Leu Ser Cys Ala Val Ser Gly Ile Ser Ile Ser Pro Asp
            20                  25                  30

Cys Met Gly Trp Phe Arg Gln Ala Pro Gly Lys Lys Arg Glu Ala Val
        35                  40                  45

Ala Thr Ile Phe Thr Asn Thr Arg Ser Thr Arg Tyr Gly Asp Ser Val
    50                  55                  60

Lys Gly Arg Phe Thr Ser Ser Gln Gly Asn Ala Lys Asn Thr Leu Tyr
65                  70                  75                  80

Leu Gln Met Asp Ser Leu Lys Leu Asp Asp Thr Ala Thr Tyr Tyr Cys
                85                  90                  95

Ala Ala Arg Tyr Thr Gly Gly Asp Cys Phe Asn Leu Glu Pro Val Ala
            100                 105                 110

Trp Arg Phe Trp Gly Gln Gly Thr Gln Val Thr Val Ser Ser
            115                 120                 125

<210> SEQ ID NO 318
<211> LENGTH: 123

<212> TYPE: PRT
<213> ORGANISM: Artificial Sequence
<220> FEATURE:
<223> OTHER INFORMATION: Synthetic Construct

<400> SEQUENCE: 318

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Val Trp
            20                  25                  30

Ser Met Ser Trp Val Arg Gln Ala Pro Gly Glu Gly Leu Glu Trp Val
        35                  40                  45

Ser Thr Ile Thr Gly Ser Gly Ala Gln Thr Tyr Tyr Ala Ser Ser Val
    50                  55                  60

Arg Gly Arg Phe Thr Thr Ser Arg Asp Asn Ala Lys Asn Thr Val Tyr
65                  70                  75                  80

Leu Gln Met Asn Ser Leu Lys Ser Asp Asp Thr Ala Val Tyr Tyr Cys
                85                  90                  95

Glu Arg Gly Asn Gly Gln Thr Ala Met Glu Ala Leu Ile Asn Pro Pro
            100                 105                 110

Glu Arg Pro Gly Thr Gln Val Thr Val Ser Ser
        115                 120

<210> SEQ ID NO 319
<211> LENGTH: 127
<212> TYPE: PRT
<213> ORGANISM: Artificial Sequence
<220> FEATURE:
<223> OTHER INFORMATION: Synthetic Construct

<400> SEQUENCE: 319

Gln Val Gln Leu Val Glu Ser Gly Gly Gly Leu Met Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ser Val Ile Asn Arg Ala Gly Asp Ser Ala Trp Tyr Ala Asp Ser Val
    50                  55                  60

Thr Gly Arg Phe Thr Ile Ser Arg Asp Asn Ala Lys Asn Thr Val Tyr
65                  70                  75                  80

Leu Gln Met Asp Ser Leu Lys Pro Glu Asp Thr Ala Met Tyr Tyr Cys
                85                  90                  95

Ala Ala Asp Ser Arg Gly Tyr Gly Asp Trp Tyr Lys Leu Leu Ser
            100                 105                 110

Asp Phe Asn Tyr Cys Gly Gln Gly Thr Gln Val Thr Val Ser Ser
        115                 120                 125

<210> SEQ ID NO 320
<211> LENGTH: 126
<212> TYPE: PRT
<213> ORGANISM: Artificial Sequence
<220> FEATURE:
<223> OTHER INFORMATION: Synthetic Construct

<400> SEQUENCE: 320

Gln Val Gln Leu Val Glu Ser Gly Gly Gly Ser Val Gln Ala Gly Gly
1               5                   10                  15

Ser Leu Arg Leu Ser Cys Ala Ala Thr Ala Tyr Thr Ala Ser Phe Tyr

```
                    20                  25                  30
Cys Met Gly Trp Phe Arg Gln Ala Pro Gly Lys Glu Arg Glu Ala Val
                35                  40                  45

Ala Ser Ile Asn Asp Asp Gly Val Thr Met Tyr Ala Asp Ser Val Lys
        50                  55                  60

Gly Gln Phe Thr Ile Ser Gln Asp Ser Ala Thr Lys Thr Leu Tyr Leu
65                  70                  75                  80

Gln Met Asn Arg Leu Lys Pro Glu Asp Thr Ala Met Tyr Tyr Cys Ala
                85                  90                  95

Ala Thr Pro Glu Gly Tyr Cys Tyr Ala Glu Arg Leu Ser Thr Trp Arg
                100                 105                 110

Tyr Thr Phe Trp Gly Gln Gly Thr Gln Val Thr Val Ser Ser
                115                 120                 125

<210> SEQ ID NO 321
<211> LENGTH: 123
<212> TYPE: PRT
<213> ORGANISM: Artificial Sequence
<220> FEATURE:
<223> OTHER INFORMATION: Synthetic Construct

<400> SEQUENCE: 321

Glu Val Gln Leu Val Glu Ser Gly Gly Gly Leu Val Gln Pro Gly Gly
1               5                   10                  15

Ser Leu Arg Leu Ser Cys Ala Val Ser Gly Asn Ile Tyr Asn Arg Asn
                20                  25                  30

Phe Met Gly Trp Phe Arg Gln Ala Pro Gly Lys Gly Leu Glu Gly Val
                35                  40                  45

Ser Ala Ile Tyr Thr Gly Thr Ser Arg Thr Tyr Tyr Ala Asp Ser Val
        50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Asp Leu Arg Asp Gly Phe Trp Asp Thr Gly Val Trp Asn Thr
                100                 105                 110

Trp Gly Gln Gly Thr Leu Val Thr Val Ser Ser
        115                 120

<210> SEQ ID NO 322
<211> LENGTH: 123
<212> TYPE: PRT
<213> ORGANISM: Artificial Sequence
<220> FEATURE:
<223> OTHER INFORMATION: Synthetic Construct

<400> SEQUENCE: 322

Glu Val Gln Leu Val Glu Ser Gly Gly Gly Leu Val Gln Pro Gly Gly
1               5                   10                  15

Ser Leu Arg Leu Ser Cys Ala Val Ser Gly Asn Ile Tyr Asn Arg Asn
                20                  25                  30

Phe Met Gly Trp Phe Arg Gln Ala Pro Gly Lys Gly Leu Glu Gly Val
                35                  40                  45

Ser Ala Ile Tyr Thr Gly Thr Ser Arg Thr Tyr Tyr Ala Asp Ser Val
        50                  55                  60

Lys Gly Arg Phe Thr Ile Ser Arg Asp Asn Ser Lys Asn Thr Val Tyr
65                  70                  75                  80
```

```
Leu Gln Met Asn Ser Leu Arg Ala Glu Asp Thr Ala Val Tyr Tyr Cys
                85                  90                  95

Ala Ala Asp Leu Arg Glu Gly Phe Trp Asp Thr Gly Val Trp Asn Thr
            100                 105                 110

Trp Gly Gln Gly Thr Leu Val Thr Val Ser Ser
        115                 120

<210> SEQ ID NO 323
<211> LENGTH: 123
<212> TYPE: PRT
<213> ORGANISM: Artificial Sequence
<220> FEATURE:
<223> OTHER INFORMATION: Synthetic Construct

<400> SEQUENCE: 323

Glu Val Gln Leu Val Glu Ser Gly Gly Gly Leu Val Gln Pro Gly Gly
1               5                   10                  15

Ser Leu Arg Leu Ser Cys Ala Val Ser Gly Asn Ile Tyr Asn Arg Asn
            20                  25                  30

Phe Met Gly Trp Phe Arg Gln Ala Pro Gly Lys Gly Arg Glu Gly Val
            35                  40                  45

Ser Ala Ile Tyr Thr Gly Thr Ser Arg Thr Tyr Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Asp Leu Arg Asp Gly Phe Trp Asp Thr Gly Val Trp Asn Thr
            100                 105                 110

Trp Gly Gln Gly Thr Leu Val Thr Val Ser Ser
        115                 120

<210> SEQ ID NO 324
<211> LENGTH: 123
<212> TYPE: PRT
<213> ORGANISM: Artificial Sequence
<220> FEATURE:
<223> OTHER INFORMATION: Synthetic Construct

<400> SEQUENCE: 324

Glu Val Gln Leu Val Glu Ser Gly Gly Gly Leu Val Gln Pro Gly Gly
1               5                   10                  15

Ser Leu Arg Leu Ser Cys Ala Val Ser Gly Asn Ile Tyr Asn Arg Asn
            20                  25                  30

Phe Met Gly Trp Phe Arg Gln Ala Pro Gly Lys Gly Arg Glu Gly Val
            35                  40                  45

Ser Ala Ile Tyr Thr Gly Thr Ser Arg Thr Tyr Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Asp Leu Arg Glu Gly Phe Trp Asp Thr Gly Val Trp Asn Thr
            100                 105                 110

Trp Gly Gln Gly Thr Leu Val Thr Val Ser Ser
        115                 120

<210> SEQ ID NO 325
```

<211> LENGTH: 351
<212> TYPE: PRT
<213> ORGANISM: Artificial Sequence
<220> FEATURE:
<223> OTHER INFORMATION: Synthetic Construct

<400> SEQUENCE: 325

```
Gln Val Gln Leu Val Glu Ser Gly Gly Gly Lys Val Gln Pro Gly Gly
 1               5                  10                  15

Ser Leu Arg Leu Ser Cys Ala Ala Ser Gly Gly Thr Leu Asp Tyr Tyr
            20                  25                  30

Ala Ile Gly Trp Phe Arg Gln Ala Pro Gly Lys Glu Arg Glu Ala Val
        35                  40                  45

Ser Cys Ile Ser Ser Ser Asp Gly Ser Thr Tyr Tyr Ala Asp Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Gly Asp Thr Ala Val Tyr His Cys
                85                  90                  95

Ala Thr Asp Arg Ala Cys Gly Ser Ser Trp Leu Gly Ala Glu Ser Trp
            100                 105                 110

Ala Gln Gly Thr Gln Val Thr Val Ser Ser Glu Ser Lys Tyr Gly Pro
        115                 120                 125

Pro Cys Pro Pro Cys Pro Ala Pro Glu Phe Leu Gly Gly Pro Ser Val
130                 135                 140

Phe Leu Phe Pro Pro Lys Pro Lys Asp Thr Leu Met Ile Ser Arg Thr
145                 150                 155                 160

Pro Glu Val Thr Cys Val Val Val Asp Val Ser Gln Glu Asp Pro Glu
                165                 170                 175

Val Gln Phe Asn Trp Tyr Val Asp Gly Val Glu Val His Asn Ala Lys
            180                 185                 190

Thr Lys Pro Arg Glu Glu Gln Phe Asn Ser Thr Tyr Arg Val Val Ser
        195                 200                 205

Val Leu Thr Val Leu His Gln Asp Trp Leu Asn Gly Lys Glu Tyr Lys
210                 215                 220

Cys Lys Val Ser Asn Lys Gly Leu Pro Ser Ser Ile Glu Lys Thr Ile
225                 230                 235                 240

Ser Lys Ala Lys Gly Gln Pro Arg Glu Pro Gln Val Tyr Thr Leu Pro
                245                 250                 255

Pro Ser Gln Glu Glu Met Thr Lys Asn Gln Val Ser Leu Thr Cys Leu
            260                 265                 270

Val Lys Gly Phe Tyr Pro Ser Asp Ile Ala Val Glu Trp Glu Ser Asn
        275                 280                 285

Gly Gln Pro Glu Asn Asn Tyr Lys Thr Thr Pro Pro Val Leu Asp Ser
290                 295                 300

Asp Gly Ser Phe Phe Leu Tyr Ser Arg Leu Thr Val Asp Lys Ser Arg
305                 310                 315                 320

Trp Gln Glu Gly Asn Val Phe Ser Cys Ser Val Met His Glu Ala Leu
                325                 330                 335

His Asn His Tyr Thr Gln Lys Ser Leu Ser Leu Ser Leu Gly Lys
            340                 345                 350
```

<210> SEQ ID NO 326
<211> LENGTH: 341
<212> TYPE: PRT
<213> ORGANISM: Artificial Sequence
<220> FEATURE:
<223> OTHER INFORMATION: Synthetic Construct

<400> SEQUENCE: 326

```
Gln Val His Leu Val Asp Ser Gly Gly Gly Leu Val Gln Pro Gly Gly
1               5                   10                  15

Ser Leu Arg Leu Ser Cys Ala Ala Ser Gly Ser Ile Thr Ser Arg Asn
            20                  25                  30

Thr Met Gly Trp Tyr Arg Gln Val Pro Gly Lys Gln Arg Glu Leu Val
        35                  40                  45

Ala Leu Ile Ala Thr Phe Val Thr His Tyr Ala Asp Ser Val Lys Gly
    50                  55                  60

Arg Phe Thr Ile Ser Arg Asp Asn Ala Arg Lys Met Val Phe Leu Glu
65                  70                  75                  80

Met Asn Ser Leu Gln Pro Glu Asp Thr Gly Ala Tyr Tyr Cys Tyr Val
                85                  90                  95

Asp Val Ser Pro Tyr Trp Gly Arg Gly Thr Gln Val Thr Val Ser Ser
            100                 105                 110

Glu Ser Lys Tyr Gly Pro Pro Cys Pro Pro Cys Pro Ala Pro Glu Phe
        115                 120                 125

Leu Gly Gly Pro Ser Val Phe Leu Phe Pro Pro Lys Pro Lys Asp Thr
    130                 135                 140

Leu Met Ile Ser Arg Thr Pro Glu Val Thr Cys Val Val Val Asp Val
145                 150                 155                 160

Ser Gln Glu Asp Pro Glu Val Gln Phe Asn Trp Tyr Val Asp Gly Val
                165                 170                 175

Glu Val His Asn Ala Lys Thr Lys Pro Arg Glu Glu Gln Phe Asn Ser
            180                 185                 190

Thr Tyr Arg Val Val Ser Val Leu Thr Val Leu His Gln Asp Trp Leu
        195                 200                 205

Asn Gly Lys Glu Tyr Lys Cys Lys Val Ser Asn Lys Gly Leu Pro Ser
    210                 215                 220

Ser Ile Glu Lys Thr Ile Ser Lys Ala Lys Gly Gln Pro Arg Glu Pro
225                 230                 235                 240

Gln Val Tyr Thr Leu Pro Pro Ser Gln Glu Glu Met Thr Lys Asn Gln
                245                 250                 255

Val Ser Leu Thr Cys Leu Val Lys Gly Phe Tyr Pro Ser Asp Ile Ala
            260                 265                 270

Val Glu Trp Glu Ser Asn Gly Gln Pro Glu Asn Asn Tyr Lys Thr Thr
        275                 280                 285

Pro Pro Val Leu Asp Ser Asp Gly Ser Phe Phe Leu Tyr Ser Arg Leu
    290                 295                 300

Thr Val Asp Lys Ser Arg Trp Gln Glu Gly Asn Val Phe Ser Cys Ser
305                 310                 315                 320

Val Met His Glu Ala Leu His Asn His Tyr Thr Gln Lys Ser Leu Ser
                325                 330                 335

Leu Ser Leu Gly Lys
            340
```

<210> SEQ ID NO 327
<211> LENGTH: 356
<212> TYPE: PRT
<213> ORGANISM: Artificial Sequence
<220> FEATURE:
<223> OTHER INFORMATION: Synthetic Construct

<400> SEQUENCE: 327

```
Gln Val Gln Leu Val Glu Ser Gly Gly Gly Ser Val Gln Ala Gly Gly
1               5                   10                  15

Ser Leu Arg Leu Ser Cys Ala Ala Ser Gly Tyr Thr Tyr Ile Pro Asn
            20                  25                  30

Cys Met Ala Trp Phe Arg Gln Ala Pro Gly Lys Glu Arg Glu Gly Val
        35                  40                  45

Thr Leu Ile Phe Thr Gly Asp Gly Thr Ser Thr Tyr Val Asp Ser Val
    50                  55                  60

Lys Gly Arg Phe Thr Ile Ser Gln Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Ala Ala Ala Glu Arg Cys Ser Gly Ser Asn Asp Arg Ile Ser Phe Trp
            100                 105                 110

Gly Ile Ser Tyr Trp Gly Gln Gly Thr Gln Val Thr Val Ser Ser Glu
        115                 120                 125

Ser Lys Tyr Gly Pro Pro Cys Pro Pro Cys Pro Ala Pro Glu Phe Leu
    130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

Gln Glu Asp Pro Glu Val Gln Phe Asn Trp Tyr Val Asp Gly Val Glu
            180                 185                 190

Val His Asn Ala Lys Thr Lys Pro Arg Glu Glu Gln Phe Asn Ser Thr
        195                 200                 205

Tyr Arg Val Val Ser Val Leu Thr Val Leu His Gln Asp Trp Leu Asn
    210                 215                 220

Gly Lys Glu Tyr Lys Cys Lys Val Ser Asn Lys Gly Leu Pro Ser Ser
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Gln Glu Glu Met Thr Lys Asn Gln Val
            260                 265                 270

Ser Leu Thr Cys Leu Val Lys Gly Phe Tyr Pro Ser Asp Ile Ala Val
        275                 280                 285

Glu Trp Glu Ser Asn Gly Gln Pro Glu Asn Asn Tyr Lys Thr Thr Pro
    290                 295                 300

Pro Val Leu Asp Ser Asp Gly Ser Phe Phe Leu Tyr Ser Arg Leu Thr
305                 310                 315                 320

Val Asp Lys Ser Arg Trp Gln Glu Gly Asn Val Phe Ser Cys Ser Val
                325                 330                 335

Met His Glu Ala Leu His Asn His Tyr Thr Gln Lys Ser Leu Ser Leu
            340                 345                 350

Ser Leu Gly Lys
    355
```

<210> SEQ ID NO 328
<211> LENGTH: 353
<212> TYPE: PRT
<213> ORGANISM: Artificial Sequence
<220> FEATURE:
<223> OTHER INFORMATION: Synthetic Construct

<400> SEQUENCE: 328

```
Gln Val Gln Leu Val Glu Ser Gly Gly Gly Ser Val Gln Ala Gly Gly
1               5                   10                  15

Ser Leu Arg Leu Ser Cys Thr Ala Ser Ala Tyr Thr Tyr Ser Asn Ile
            20                  25                  30

Cys Leu Gly Trp Leu Arg Gln Ala Pro Gly Gly Leu Glu Ala Val
        35                  40                  45

Ala Thr Ile Tyr Ile Ala Asp Gln Thr Ser Tyr Tyr Ala Asp Ser Val
    50                  55                  60

Lys Gly Arg Phe Arg Ile Ser Lys Asp Ala Ala Lys Asn Ala Val Tyr
65                  70                  75                  80

Leu Gln Met Ser Ser Leu Arg Pro Glu Asp Thr Ala Met Tyr Tyr Cys
                85                  90                  95

Ala Ser Arg Tyr Gly Ser Thr Cys Gly Glu Tyr Leu Ala Asp Tyr Thr
            100                 105                 110

Ser Arg Ala Gln Gly Thr Gln Val Thr Val Ser Ser Glu Ser Lys Tyr
        115                 120                 125

Gly Pro Pro Cys Pro Pro Cys Pro Ala Pro Glu Phe Leu Gly Gly Pro
    130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser Gln Glu Asp
                165                 170                 175

Pro Glu Val Gln Phe Asn Trp Tyr Val Asp Gly Val Glu Val His Asn
            180                 185                 190

Ala Lys Thr Lys Pro Arg Glu Glu Gln Phe Asn Ser Thr Tyr Arg Val
        195                 200                 205

Val Ser Val Leu Thr Val Leu His Gln Asp Trp Leu Asn Gly Lys Glu
    210                 215                 220

Tyr Lys Cys Lys Val Ser Asn Lys Gly Leu Pro Ser Ser Ile Glu Lys
225                 230                 235                 240

Thr Ile Ser Lys Ala Lys Gly Gln Pro Arg Glu Pro Gln Val Tyr Thr
                245                 250                 255

Leu Pro Pro Ser Gln Glu Glu Met Thr Lys Asn Gln Val Ser Leu Thr
            260                 265                 270

Cys Leu Val Lys Gly Phe Tyr Pro Ser Asp Ile Ala Val Glu Trp Glu
        275                 280                 285

Ser Asn Gly Gln Pro Glu Asn Asn Tyr Lys Thr Thr Pro Pro Val Leu
    290                 295                 300

Asp Ser Asp Gly Ser Phe Phe Leu Tyr Ser Arg Leu Thr Val Asp Lys
305                 310                 315                 320

Ser Arg Trp Gln Glu Gly Asn Val Phe Ser Cys Ser Val Met His Glu
                325                 330                 335

Ala Leu His Asn His Tyr Thr Gln Lys Ser Leu Ser Leu Ser Leu Gly
            340                 345                 350

Lys
```

<210> SEQ ID NO 329
<211> LENGTH: 352
<212> TYPE: PRT
<213> ORGANISM: Artificial Sequence
<220> FEATURE:
<223> OTHER INFORMATION: Synthetic Construct

<400> SEQUENCE: 329

Gln Met Gln Leu Val Glu Ser Gly Gly Gly Ser Val Gln Ala Gly Gly
1               5                   10                  15

Ser Leu Arg Leu Ser Cys Ala Val Ser Gly Tyr Ile Tyr Asn Arg Asn
            20                  25                  30

Phe Met Gly Trp Phe Arg Gln Ala Pro Gly Lys Glu Arg Glu Gly Val
        35                  40                  45

Ala Ala Ile Tyr Thr Gly Gly Pro Tyr Thr Tyr Tyr Thr Asp Ser Val
50                  55                  60

Gln Gly Arg Phe Thr Ile Ser Gln Asp Asn Thr Lys Asn Thr Val Tyr
65                  70                  75                  80

Leu Gln Met Asn Ser Leu Lys Pro Glu Asp Thr Ala Met Tyr Tyr Cys
                85                  90                  95

Val Ser Asp Leu Ser Asp Gly Thr Trp Asp Gln Gly Arg Trp Asn Tyr
            100                 105                 110

Trp Gly Gln Gly Thr Gln Val Thr Val Ser Ser Glu Ser Lys Tyr Gly
        115                 120                 125

Pro Pro Cys Pro Pro Cys Pro Ala Pro Glu Phe Leu Gly Gly Pro Ser
130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser Gln Glu Asp Pro
                165                 170                 175

Glu Val Gln Phe Asn Trp Tyr Val Asp Gly Val Glu Val His Asn Ala
            180                 185                 190

Lys Thr Lys Pro Arg Glu Glu Gln Phe Asn Ser Thr Tyr Arg Val Val
        195                 200                 205

Ser Val Leu Thr Val Leu His Gln Asp Trp Leu Asn Gly Lys Glu Tyr
210                 215                 220

Lys Cys Lys Val Ser Asn Lys Gly Leu Pro Ser Ser Ile Glu Lys Thr
225                 230                 235                 240

Ile Ser Lys Ala Lys Gly Gln Pro Arg Glu Pro Gln Val Tyr Thr Leu
                245                 250                 255

Pro Pro Ser Gln Glu Glu Met Thr Lys Asn Gln Val Ser Leu Thr Cys
            260                 265                 270

Leu Val Lys Gly Phe Tyr Pro Ser Asp Ile Ala Val Glu Trp Glu Ser
        275                 280                 285

Asn Gly Gln Pro Glu Asn Asn Tyr Lys Thr Thr Pro Pro Val Leu Asp
290                 295                 300

Ser Asp Gly Ser Phe Phe Leu Tyr Ser Arg Leu Thr Val Asp Lys Ser
305                 310                 315                 320

Arg Trp Gln Glu Gly Asn Val Phe Ser Cys Ser Val Met His Glu Ala
                325                 330                 335

Leu His Asn His Tyr Thr Gln Lys Ser Leu Ser Leu Ser Leu Gly Lys
            340                 345                 350

<210> SEQ ID NO 330
<211> LENGTH: 352
<212> TYPE: PRT
<213> ORGANISM: Artificial Sequence
<220> FEATURE:
<223> OTHER INFORMATION: Synthetic Construct

<400> SEQUENCE: 330

Gln Val Gln Leu Val Glu Ser Gly Gly Gly Ser Ala Gln Ala Gly Gly
1               5                   10                  15

Ser Leu Arg Leu Ser Cys Ala Val Ser Gly Tyr Ile Tyr Asn Arg Asn
            20                  25                  30

Phe Met Gly Trp Phe Arg Gln Val Pro Gly Lys Val Arg Glu Gly Val
        35                  40                  45

Ala Ala Ile Tyr Thr Gly Thr Glu Arg Thr Tyr Tyr Ala Asp Ser Val
50                  55                  60

Lys Gly Arg Phe Thr Ile Ser Gln Asp Asn Ala Lys Asn Thr Val Tyr
65                  70                  75                  80

Leu Gln Met Asn Ser Leu Lys Pro Glu Asp Thr Ala Met Tyr Tyr Cys
                85                  90                  95

Val Ala Asp Leu Arg Asp Gly Thr Trp Asp Thr Gly Val Trp Asn Thr
            100                 105                 110

Trp Gly Gln Gly Thr Gln Val Thr Val Ser Ser Glu Ser Lys Tyr Gly
        115                 120                 125

Pro Pro Cys Pro Pro Cys Pro Ala Pro Glu Phe Leu Gly Gly Pro Ser
130                 135                 140

Val Phe Leu Phe Pro Pro Lys Pro Lys Asp Thr Leu Met Ile Ser Arg
145                 150                 155                 160

Thr Pro Glu Val Thr Cys Val Val Asp Val Ser Gln Glu Asp Pro
                165                 170                 175

Glu Val Gln Phe Asn Trp Tyr Val Asp Gly Val Glu Val His Asn Ala
            180                 185                 190

Lys Thr Lys Pro Arg Glu Glu Gln Phe Asn Ser Thr Tyr Arg Val Val
        195                 200                 205

Ser Val Leu Thr Val Leu His Gln Asp Trp Leu Asn Gly Lys Glu Tyr
            210                 215                 220

Lys Cys Lys Val Ser Asn Lys Gly Leu Pro Ser Ser Ile Glu Lys Thr
225                 230                 235                 240

Ile Ser Lys Ala Lys Gly Gln Pro Arg Glu Pro Gln Val Tyr Thr Leu
                245                 250                 255

Pro Pro Ser Gln Glu Glu Met Thr Lys Asn Gln Val Ser Leu Thr Cys
            260                 265                 270

Leu Val Lys Gly Phe Tyr Pro Ser Asp Ile Ala Val Glu Trp Glu Ser
        275                 280                 285

Asn Gly Gln Pro Glu Asn Asn Tyr Lys Thr Thr Pro Pro Val Leu Asp
290                 295                 300

Ser Asp Gly Ser Phe Phe Leu Tyr Ser Arg Leu Thr Val Asp Lys Ser
305                 310                 315                 320

Arg Trp Gln Glu Gly Asn Val Phe Ser Cys Ser Val Met His Glu Ala
                325                 330                 335

Leu His Asn His Tyr Thr Gln Lys Ser Leu Ser Leu Ser Leu Gly Lys
            340                 345                 350

<210> SEQ ID NO 331
<211> LENGTH: 352
<212> TYPE: PRT
<213> ORGANISM: Artificial Sequence
<220> FEATURE:
<223> OTHER INFORMATION: Synthetic Construct

<400> SEQUENCE: 331

Gln Ile Gln Leu Val Glu Ser Gly Gly Gly Ser Ala Gln Ala Gly Gly
1               5                   10                  15

Ser Leu Arg Leu Ser Cys Val Val Ser Gly Asn Ile Tyr Asn Arg Asn
            20                  25                  30

```
Phe Met Gly Trp Phe Arg Gln Ala Pro Gly Lys Val Arg Glu Gly Val
            35                  40                  45

Ala Ala Ile Tyr Thr Gly Thr Ser Arg Thr Tyr Tyr Ala Asp Ser Val
    50                  55                  60

Lys Gly Arg Phe Thr Ile Ser Gln Asp Asn Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Asp Leu Arg Asp Gly Phe Trp Asp Thr Gly Val Trp Asn Thr
            100                 105                 110

Trp Gly Gln Gly Thr Gln Val Thr Val Ser Ser Glu Ser Lys Tyr Gly
            115                 120                 125

Pro Pro Cys Pro Pro Cys Pro Ala Pro Glu Phe Leu Gly Gly Pro Ser
        130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser Gln Glu Asp Pro
                165                 170                 175

Glu Val Gln Phe Asn Trp Tyr Val Asp Gly Val Glu Val His Asn Ala
            180                 185                 190

Lys Thr Lys Pro Arg Glu Glu Gln Phe Asn Ser Thr Tyr Arg Val Val
            195                 200                 205

Ser Val Leu Thr Val Leu His Gln Asp Trp Leu Asn Gly Lys Glu Tyr
    210                 215                 220

Lys Cys Lys Val Ser Asn Lys Gly Leu Pro Ser Ser Ile Glu Lys Thr
225                 230                 235                 240

Ile Ser Lys Ala Lys Gly Gln Pro Arg Glu Pro Gln Val Tyr Thr Leu
                245                 250                 255

Pro Pro Ser Gln Glu Glu Met Thr Lys Asn Gln Val Ser Leu Thr Cys
            260                 265                 270

Leu Val Lys Gly Phe Tyr Pro Ser Asp Ile Ala Val Glu Trp Glu Ser
            275                 280                 285

Asn Gly Gln Pro Glu Asn Asn Tyr Lys Thr Thr Pro Pro Val Leu Asp
        290                 295                 300

Ser Asp Gly Ser Phe Phe Leu Tyr Ser Arg Leu Thr Val Asp Lys Ser
305                 310                 315                 320

Arg Trp Gln Glu Gly Asn Val Phe Ser Cys Ser Val Met His Glu Ala
                325                 330                 335

Leu His Asn His Tyr Thr Gln Lys Ser Leu Ser Leu Ser Leu Gly Lys
            340                 345                 350

<210> SEQ ID NO 332
<211> LENGTH: 345
<212> TYPE: PRT
<213> ORGANISM: Artificial Sequence
<220> FEATURE:
<223> OTHER INFORMATION: Synthetic Construct

<400> SEQUENCE: 332

Gln Val Gln Leu Val Glu Ser Gly Gly Gly Leu Val Gln Pro Gly Gly
1               5                   10                  15

Ser Leu Thr Leu Ser Cys Ala Ala Ser Gly Phe Thr Phe Ser Thr Ala
            20                  25                  30

Ala Met Ser Trp Val Arg Gln Val Pro Glu Glu Gly Leu Glu Trp Val
            35                  40                  45
```

```
Ala Ser Ile Asp Ser Ser Gly Ser Arg Thr Tyr Tyr Ala Gly Ser Val
 50                  55                  60

Lys Gly Arg Phe Thr Ile Ser Arg Asp Asn Ala Lys Asn Thr Leu Tyr
 65                  70                  75                  80

Leu Gln Leu Asn Ser Leu Lys Ala Glu Asp Thr Ala Met Tyr Tyr Cys
                 85                  90                  95

Ala Lys Asp His Met Ser Trp Leu Pro Arg Gly Gln Gly Thr Gln Val
            100                 105                 110

Thr Val Ser Ser Glu Ser Lys Tyr Gly Pro Pro Cys Pro Cys Pro
            115                 120                 125

Ala Pro Glu Phe Leu Gly Gly Pro Ser Val Phe Leu Phe Pro Pro Lys
        130                 135                 140

Pro Lys Asp Thr Leu Met Ile Ser Arg Thr Pro Glu Val Thr Cys Val
145                 150                 155                 160

Val Val Asp Val Ser Gln Glu Asp Pro Glu Val Gln Phe Asn Trp Tyr
                165                 170                 175

Val Asp Gly Val Glu Val His Asn Ala Lys Thr Lys Pro Arg Glu Glu
            180                 185                 190

Gln Phe Asn Ser Thr Tyr Arg Val Val Ser Val Leu Thr Val Leu His
        195                 200                 205

Gln Asp Trp Leu Asn Gly Lys Glu Tyr Lys Cys Lys Val Ser Asn Lys
210                 215                 220

Gly Leu Pro Ser Ser Ile Glu Lys Thr Ile Ser Lys Ala Lys Gly Gln
225                 230                 235                 240

Pro Arg Glu Pro Gln Val Tyr Thr Leu Pro Pro Ser Gln Glu Glu Met
                245                 250                 255

Thr Lys Asn Gln Val Ser Leu Thr Cys Leu Val Lys Gly Phe Tyr Pro
            260                 265                 270

Ser Asp Ile Ala Val Glu Trp Glu Ser Asn Gly Gln Pro Glu Asn Asn
        275                 280                 285

Tyr Lys Thr Thr Pro Pro Val Leu Asp Ser Asp Gly Ser Phe Phe Leu
290                 295                 300

Tyr Ser Arg Leu Thr Val Asp Lys Ser Arg Trp Gln Glu Gly Asn Val
305                 310                 315                 320

Phe Ser Cys Ser Val Met His Glu Ala Leu His Asn His Tyr Thr Gln
                325                 330                 335

Lys Ser Leu Ser Leu Ser Leu Gly Lys
            340                 345

<210> SEQ ID NO 333
<211> LENGTH: 351
<212> TYPE: PRT
<213> ORGANISM: Artificial Sequence
<220> FEATURE:
<223> OTHER INFORMATION: Synthetic Construct

<400> SEQUENCE: 333

Gln Val Gln Leu Val Glu Ser Gly Gly Gly Ser Val Gln Ala Gly Gly
1               5                   10                  15

Ser Leu Arg Leu Ser Cys Ala Ala Ser Gly Phe Thr Asp Ser Ser Tyr
            20                  25                  30

Cys Gly Ala Trp Phe Arg Gln Val Pro Gly Lys Glu Arg Glu Gly Val
        35                  40                  45

Ala Ile Ile Asp Arg Tyr Gly Gly Thr Met Tyr Lys Asp Ser Val Lys
 50                  55                  60
```

Gly Arg Phe Thr Ile Ser Lys Asp Thr Ala Lys Asn Ile Leu Tyr Leu
65                  70                  75                  80

Gln Met Asn Ser Leu Lys Leu Glu Asp Thr Ala Met Tyr Tyr Cys Ala
                85                  90                  95

Ala Ala Glu Tyr Arg Gly Ser Ser Cys Asp Ala Glu Ser Gly Tyr Trp
            100                 105                 110

Gly Gln Gly Thr Gln Val Thr Val Ser Ser Glu Ser Lys Tyr Gly Pro
        115                 120                 125

Pro Cys Pro Pro Cys Pro Ala Pro Glu Phe Leu Gly Gly Pro Ser Val
    130                 135                 140

Phe Leu Phe Pro Pro Lys Pro Lys Asp Thr Leu Met Ile Ser Arg Thr
145                 150                 155                 160

Pro Glu Val Thr Cys Val Val Val Asp Val Ser Gln Glu Asp Pro Glu
                165                 170                 175

Val Gln Phe Asn Trp Tyr Val Asp Gly Val Glu Val His Asn Ala Lys
            180                 185                 190

Thr Lys Pro Arg Glu Glu Gln Phe Asn Ser Thr Tyr Arg Val Val Ser
        195                 200                 205

Val Leu Thr Val Leu His Gln Asp Trp Leu Asn Gly Lys Glu Tyr Lys
    210                 215                 220

Cys Lys Val Ser Asn Lys Gly Leu Pro Ser Ser Ile Glu Lys Thr Ile
225                 230                 235                 240

Ser Lys Ala Lys Gly Gln Pro Arg Glu Pro Gln Val Tyr Thr Leu Pro
                245                 250                 255

Pro Ser Gln Glu Glu Met Thr Lys Asn Gln Val Ser Leu Thr Cys Leu
            260                 265                 270

Val Lys Gly Phe Tyr Pro Ser Asp Ile Ala Val Glu Trp Glu Ser Asn
        275                 280                 285

Gly Gln Pro Glu Asn Asn Tyr Lys Thr Thr Pro Pro Val Leu Asp Ser
    290                 295                 300

Asp Gly Ser Phe Phe Leu Tyr Ser Arg Leu Thr Val Asp Lys Ser Arg
305                 310                 315                 320

Trp Gln Glu Gly Asn Val Phe Ser Cys Ser Val Met His Glu Ala Leu
                325                 330                 335

His Asn His Tyr Thr Gln Lys Ser Leu Ser Leu Ser Leu Gly Lys
            340                 345                 350

<210> SEQ ID NO 334
<211> LENGTH: 351
<212> TYPE: PRT
<213> ORGANISM: Artificial Sequence
<220> FEATURE:
<223> OTHER INFORMATION: Synthetic Construct

<400> SEQUENCE: 334

Gln Val His Leu Met Glu Ser Gly Gly Gly Ser Val Gln Ala Gly Gly
1               5                   10                  15

Ser Leu Thr Leu Ser Cys Ala Ala Ser Val Phe Thr Asp Ser Asn Tyr
            20                  25                  30

Cys Met Ala Trp Phe Arg Gln Val Pro Gly Lys Glu Arg Glu Gly Val
        35                  40                  45

Ala Ile Ile Asp Arg Tyr Gly Gly Thr Met Tyr Lys Asp Ser Val Lys
    50                  55                  60

Gly Arg Phe Thr Ile Ser Lys Asp Thr Ala Lys Asn Ile Leu Tyr Leu
65                  70                  75                  80

```
Gln Met Asn Ser Leu Lys Leu Glu Asp Thr Ala Met Tyr Tyr Cys Ala
                85                  90                  95

Ala Ala Gly Tyr Arg Gly Ser Ser Cys Asp Ala Asp Ser Gly Tyr Trp
            100                 105                 110

Gly Gln Gly Thr Gln Val Thr Val Ser Ser Glu Ser Lys Tyr Gly Pro
        115                 120                 125

Pro Cys Pro Pro Cys Pro Ala Pro Glu Phe Leu Gly Gly Pro Ser Val
    130                 135                 140

Phe Leu Phe Pro Pro Lys Pro Lys Asp Thr Leu Met Ile Ser Arg Thr
145                 150                 155                 160

Pro Glu Val Thr Cys Val Val Val Asp Val Ser Gln Glu Asp Pro Glu
                165                 170                 175

Val Gln Phe Asn Trp Tyr Val Asp Gly Val Glu Val His Asn Ala Lys
            180                 185                 190

Thr Lys Pro Arg Glu Glu Gln Phe Asn Ser Thr Tyr Arg Val Val Ser
        195                 200                 205

Val Leu Thr Val Leu His Gln Asp Trp Leu Asn Gly Lys Glu Tyr Lys
    210                 215                 220

Cys Lys Val Ser Asn Lys Gly Leu Pro Ser Ser Ile Glu Lys Thr Ile
225                 230                 235                 240

Ser Lys Ala Lys Gly Gln Pro Arg Glu Pro Gln Val Tyr Thr Leu Pro
                245                 250                 255

Pro Ser Gln Glu Glu Met Thr Lys Asn Gln Val Ser Leu Thr Cys Leu
            260                 265                 270

Val Lys Gly Phe Tyr Pro Ser Asp Ile Ala Val Glu Trp Glu Ser Asn
        275                 280                 285

Gly Gln Pro Glu Asn Asn Tyr Lys Thr Thr Pro Pro Val Leu Asp Ser
    290                 295                 300

Asp Gly Ser Phe Phe Leu Tyr Ser Arg Leu Thr Val Asp Lys Ser Arg
305                 310                 315                 320

Trp Gln Glu Gly Asn Val Phe Ser Cys Ser Val Met His Glu Ala Leu
                325                 330                 335

His Asn His Tyr Thr Gln Lys Ser Leu Ser Leu Ser Leu Gly Lys
            340                 345                 350

<210> SEQ ID NO 335
<211> LENGTH: 351
<212> TYPE: PRT
<213> ORGANISM: Artificial Sequence
<220> FEATURE:
<223> OTHER INFORMATION: Synthetic Construct

<400> SEQUENCE: 335

Gln Ile Gln Leu Val Glu Ser Gly Gly Gly Ser Val Gln Ala Gly Gly
1               5                   10                  15

Ser Leu Arg Leu Ser Cys Ala Ala Ser Gly Phe Thr Asp Ser Ser Tyr
            20                  25                  30

Cys Gly Ala Trp Phe Arg Gln Val Pro Gly Lys Glu Arg Glu Gly Val
        35                  40                  45

Ala Ile Ile Asp Arg Tyr Gly Thr Met Tyr Lys Asp Ser Val Lys
    50                  55                  60

Gly Arg Phe Thr Ile Ser Lys Asp Thr Ala Lys Asn Ile Leu Tyr Leu
65                  70                  75                  80

Gln Met Asn Ser Leu Lys Leu Glu Asp Thr Ala Met Tyr Tyr Cys Ala
                85                  90                  95
```

-continued

Ala Ala Glu Tyr Arg Gly Ser Ser Cys Asp Ala Glu Ser Gly Tyr Trp
            100                 105                 110

Gly Gln Gly Thr Gln Val Thr Val Ser Ser Glu Ser Lys Tyr Gly Pro
            115                 120                 125

Pro Cys Pro Pro Cys Pro Ala Pro Glu Phe Leu Gly Gly Pro Ser Val
        130                 135                 140

Phe Leu Phe Pro Pro Lys Pro Lys Asp Thr Leu Met Ile Ser Arg Thr
145                 150                 155                 160

Pro Glu Val Thr Cys Val Val Val Asp Val Ser Gln Glu Asp Pro Glu
                165                 170                 175

Val Gln Phe Asn Trp Tyr Val Asp Gly Val Glu Val His Asn Ala Lys
            180                 185                 190

Thr Lys Pro Arg Glu Glu Gln Phe Asn Ser Thr Tyr Arg Val Val Ser
        195                 200                 205

Val Leu Thr Val Leu His Gln Asp Trp Leu Asn Gly Lys Glu Tyr Lys
    210                 215                 220

Cys Lys Val Ser Asn Lys Gly Leu Pro Ser Ser Ile Glu Lys Thr Ile
225                 230                 235                 240

Ser Lys Ala Lys Gly Gln Pro Arg Glu Pro Gln Val Tyr Thr Leu Pro
                245                 250                 255

Pro Ser Gln Glu Glu Met Thr Lys Asn Gln Val Ser Leu Thr Cys Leu
            260                 265                 270

Val Lys Gly Phe Tyr Pro Ser Asp Ile Ala Val Glu Trp Glu Ser Asn
        275                 280                 285

Gly Gln Pro Glu Asn Asn Tyr Lys Thr Thr Pro Pro Val Leu Asp Ser
    290                 295                 300

Asp Gly Ser Phe Phe Leu Tyr Ser Arg Leu Thr Val Asp Lys Ser Arg
305                 310                 315                 320

Trp Gln Glu Gly Asn Val Phe Ser Cys Ser Val Met His Glu Ala Leu
                325                 330                 335

His Asn His Tyr Thr Gln Lys Ser Leu Ser Leu Ser Leu Gly Lys
            340                 345                 350

<210> SEQ ID NO 336
<211> LENGTH: 353
<212> TYPE: PRT
<213> ORGANISM: Artificial Sequence
<220> FEATURE:
<223> OTHER INFORMATION: Synthetic Construct

<400> SEQUENCE: 336

Gln Val Gln Leu Val Glu Ser Gly Gly Gly Ser Val Gln Ala Gly Gly
1               5                   10                  15

Ser Leu Arg Leu Ser Cys Ala Ala Ser Gly Tyr Thr Ala Gly Ser Leu
            20                  25                  30

Cys Met Gly Trp Phe Arg Gln Ala Pro Gly Lys Glu Arg Glu Gly Val
        35                  40                  45

Ala Ala Ile Tyr Thr Gly Gly Ser Thr Tyr Tyr Ala Asp Ser Val
    50                  55                  60

Lys Gly Arg Phe Thr Ile Ser Gln Asp Asn Ala Lys Asn Thr Val Tyr
65                  70                  75                  80

Leu Gln Met Asn Ser Leu Lys Pro Glu Asp Thr Ala Gln Tyr Tyr Cys
                85                  90                  95

Gly Ala Gly Ser Arg Glu Asp Tyr Cys Asp Arg Gly Tyr Ile Tyr Asp
            100                 105                 110

His Trp Gly Gln Gly Thr Gln Val Thr Val Ser Ser Glu Ser Lys Tyr
            115                 120                 125

Gly Pro Pro Cys Pro Pro Cys Pro Ala Pro Glu Phe Leu Gly Gly Pro
    130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser Gln Glu Asp
                165                 170                 175

Pro Glu Val Gln Phe Asn Trp Tyr Val Asp Gly Val Glu Val His Asn
            180                 185                 190

Ala Lys Thr Lys Pro Arg Glu Gln Phe Asn Ser Thr Tyr Arg Val
        195                 200                 205

Val Ser Val Leu Thr Val Leu His Gln Asp Trp Leu Asn Gly Lys Glu
    210                 215                 220

Tyr Lys Cys Lys Val Ser Asn Lys Gly Leu Pro Ser Ser Ile Glu Lys
225                 230                 235                 240

Thr Ile Ser Lys Ala Lys Gly Gln Pro Arg Glu Pro Gln Val Tyr Thr
                245                 250                 255

Leu Pro Pro Ser Gln Glu Glu Met Thr Lys Asn Gln Val Ser Leu Thr
            260                 265                 270

Cys Leu Val Lys Gly Phe Tyr Pro Ser Asp Ile Ala Val Glu Trp Glu
        275                 280                 285

Ser Asn Gly Gln Pro Glu Asn Asn Tyr Lys Thr Thr Pro Pro Val Leu
    290                 295                 300

Asp Ser Asp Gly Ser Phe Phe Leu Tyr Ser Arg Leu Thr Val Asp Lys
305                 310                 315                 320

Ser Arg Trp Gln Glu Gly Asn Val Phe Ser Cys Ser Val Met His Glu
                325                 330                 335

Ala Leu His Asn His Tyr Thr Gln Lys Ser Leu Ser Leu Ser Leu Gly
            340                 345                 350

Lys

<210> SEQ ID NO 337
<211> LENGTH: 354
<212> TYPE: PRT
<213> ORGANISM: Artificial Sequence
<220> FEATURE:
<223> OTHER INFORMATION: Synthetic Construct

<400> SEQUENCE: 337

Gln Val Lys Leu Val Glu Ser Gly Gly Gly Ser Val Gln Ala Gly Gly
1               5                   10                  15

Tyr Leu Arg Leu Ser Cys Ala Ala Ser Gly Asp Thr Asn Asn Leu Asn
            20                  25                  30

Phe Arg Gly Trp Phe Arg Gln Ala Pro Gly Lys Glu Arg Glu Gly Val
        35                  40                  45

Ala Val Ile Thr His Ser Gly Ser Thr Tyr Tyr Ala Glu Ser Val Lys
    50                  55                  60

Gly Arg Phe Thr Ile Ser Gln Asp Leu Ala Lys Asn Thr Met Tyr Leu
65                  70                  75                  80

Gln Met Asn Ser Leu Lys Pro Glu Asp Thr Ala Met Tyr Tyr Cys Ala
                85                  90                  95

Ala Ala Asp Val Trp Arg Ile Ser Trp Ser Phe Val Pro Glu Leu Phe
            100                 105                 110

```
Ser Tyr Trp Gly Gln Gly Thr Gln Val Thr Val Ser Ser Glu Ser Lys
            115                 120                 125

Tyr Gly Pro Pro Cys Pro Pro Cys Pro Ala Pro Glu Phe Leu Gly Gly
        130                 135                 140

Pro Ser Val Phe Leu Phe Pro Pro Lys Pro Lys Asp Thr Leu Met Ile
145                 150                 155                 160

Ser Arg Thr Pro Glu Val Thr Cys Val Val Val Asp Val Ser Gln Glu
                165                 170                 175

Asp Pro Glu Val Gln Phe Asn Trp Tyr Val Asp Gly Val Glu Val His
            180                 185                 190

Asn Ala Lys Thr Lys Pro Arg Glu Glu Gln Phe Asn Ser Thr Tyr Arg
        195                 200                 205

Val Val Ser Val Leu Thr Val Leu His Gln Asp Trp Leu Asn Gly Lys
210                 215                 220

Glu Tyr Lys Cys Lys Val Ser Asn Lys Gly Leu Pro Ser Ser Ile Glu
225                 230                 235                 240

Lys Thr Ile Ser Lys Ala Lys Gly Gln Pro Arg Glu Pro Gln Val Tyr
                245                 250                 255

Thr Leu Pro Pro Ser Gln Glu Glu Met Thr Lys Asn Gln Val Ser Leu
            260                 265                 270

Thr Cys Leu Val Lys Gly Phe Tyr Pro Ser Asp Ile Ala Val Glu Trp
        275                 280                 285

Glu Ser Asn Gly Gln Pro Glu Asn Asn Tyr Lys Thr Thr Pro Pro Val
290                 295                 300

Leu Asp Ser Asp Gly Ser Phe Phe Leu Tyr Ser Arg Leu Thr Val Asp
305                 310                 315                 320

Lys Ser Arg Trp Gln Glu Gly Asn Val Phe Ser Cys Ser Val Met His
                325                 330                 335

Glu Ala Leu His Asn His Tyr Thr Gln Lys Ser Leu Ser Leu Ser Leu
            340                 345                 350

Gly Lys

<210> SEQ ID NO 338
<211> LENGTH: 356
<212> TYPE: PRT
<213> ORGANISM: Artificial Sequence
<220> FEATURE:
<223> OTHER INFORMATION: Synthetic Construct

<400> SEQUENCE: 338

Gln Val Gln Leu Val Glu Ser Gly Gly Gly Ser Val Gln Ala Gly Gly
1               5                   10                  15

Ser Leu Arg Leu Ser Cys Ala Gly Ser Gly Phe Thr Phe Asn Asn Tyr
            20                  25                  30

Ala Met Gly Trp Phe Arg Gln Ala Pro Gly Lys Glu Arg Glu Gly Ile
        35                  40                  45

Ala Gly Ile Trp Thr Gly Gly Ser Thr Tyr Tyr Ala Asp Ser Val
    50                  55                  60

Lys Gly Arg Phe Thr Ile Ser Glu Asp Val Ala Lys Asn Thr Val Tyr
65                  70                  75                  80

Leu Gln Met Asp Ser Leu Lys Pro Glu Asp Thr Ala Met Tyr Tyr Cys
                85                  90                  95

Ala Ala Glu Arg Trp Asp Tyr Ser Asp Trp Arg Arg Leu Lys Arg Gly
            100                 105                 110

Asp Tyr Asn Tyr Trp Gly Gln Gly Thr Gln Val Thr Val Ser Ser Glu
```

```
                  115                 120                 125
Ser Lys Tyr Gly Pro Cys Pro Cys Pro Ala Pro Glu Phe Leu
130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

Gln Glu Asp Pro Glu Val Gln Phe Asn Trp Tyr Val Asp Gly Val Glu
            180                 185                 190

Val His Asn Ala Lys Thr Lys Pro Arg Glu Glu Gln Phe Asn Ser Thr
        195                 200                 205

Tyr Arg Val Val Ser Val Leu Thr Val Leu His Gln Asp Trp Leu Asn
    210                 215                 220

Gly Lys Glu Tyr Lys Cys Lys Val Ser Asn Lys Gly Leu Pro Ser Ser
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Gln Glu Glu Met Thr Lys Asn Gln Val
            260                 265                 270

Ser Leu Thr Cys Leu Val Lys Gly Phe Tyr Pro Ser Asp Ile Ala Val
        275                 280                 285

Glu Trp Glu Ser Asn Gly Gln Pro Glu Asn Asn Tyr Lys Thr Thr Pro
    290                 295                 300

Pro Val Leu Asp Ser Asp Gly Ser Phe Phe Leu Tyr Ser Arg Leu Thr
305                 310                 315                 320

Val Asp Lys Ser Arg Trp Gln Glu Gly Asn Val Phe Ser Cys Ser Val
                325                 330                 335

Met His Glu Ala Leu His Asn His Tyr Thr Gln Lys Ser Leu Ser Leu
            340                 345                 350

Ser Leu Gly Lys
        355

<210> SEQ ID NO 339
<211> LENGTH: 359
<212> TYPE: PRT
<213> ORGANISM: Artificial Sequence
<220> FEATURE:
<223> OTHER INFORMATION: Synthetic Construct

<400> SEQUENCE: 339

Gln Val His Leu Met Glu Ser Gly Gly Gly Ser Val Pro Ser Gly Gly
1               5                   10                  15

Ser Leu Arg Leu Ser Cys Ala Val Ser Gly Ser Gly Tyr Ser Tyr Ser
                20                  25                  30

Arg Gly Cys Phe Ala Trp Phe Gln Gln Arg Pro Gly Lys Glu Arg Glu
            35                  40                  45

Gly Val Ala Ile Ile Asn Met Asp Gly His Thr Arg Tyr Ser Asp Ser
        50                  55                  60

Val Gln Gly Arg Phe Ile Ile Ser Gln Asp Lys Ala Lys Asn Thr Leu
65                  70                  75                  80

His Leu Gln Met Asn Thr Leu Arg Pro Asp Asp Thr Ala Met Tyr Tyr
                85                  90                  95

Cys Ala Tyr Asp Arg Ser Gln Cys Tyr Val Leu Ser Asp Arg Leu Arg
            100                 105                 110

Leu Pro Gly Thr Phe Ser Asp Trp Gly Gln Gly Thr Gln Val Thr Val
```

```
            115                 120                 125
Ser Ser Glu Ser Lys Tyr Gly Pro Pro Cys Pro Pro Cys Pro Ala Pro
        130                 135                 140

Glu Phe Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser Gln Glu Asp Pro Glu Val Gln Phe Asn Trp Tyr Val Asp
            180                 185                 190

Gly Val Glu Val His Asn Ala Lys Thr Lys Pro Arg Glu Glu Gln Phe
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Gly Leu
225                 230                 235                 240

Pro Ser Ser Ile Glu Lys Thr Ile Ser Lys Ala Lys Gly Gln Pro Arg
                245                 250                 255

Glu Pro Gln Val Tyr Thr Leu Pro Pro Ser Gln Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Arg Leu Thr Val Asp Lys Ser Arg Trp Gln Glu Gly Asn Val Phe Ser
                325                 330                 335

Cys Ser Val Met His Glu Ala Leu His Asn His Tyr Thr Gln Lys Ser
            340                 345                 350

Leu Ser Leu Ser Leu Gly Lys
        355

<210> SEQ ID NO 340
<211> LENGTH: 352
<212> TYPE: PRT
<213> ORGANISM: Artificial Sequence
<220> FEATURE:
<223> OTHER INFORMATION: Synthetic Construct

<400> SEQUENCE: 340

Glu Val Gln Leu Ala Glu Ser Gly Gly Gly Ser Val Gln Ala Gly Gly
1               5                   10                  15

Ser Leu Lys Leu Ser Cys Leu Ala Ser Gln Trp Ile Ser Ser Asp Cys
            20                  25                  30

Gly Met Ala Trp Tyr Arg Gln Ala Pro Gly Lys Glu Arg Glu Leu Val
        35                  40                  45

Ser Arg Ile Ser Ser Asp Asp Thr Thr Tyr Ala Asp Ser Val Lys
    50                  55                  60

Gly Arg Phe Thr Ile Ser Gln Asp Ser Ala Lys Asn Thr Leu Tyr Leu
65                  70                  75                  80

Gln Met Asn Lys Leu Lys Thr Glu Asp Thr Gly Val Tyr Tyr Cys Ala
                85                  90                  95

Ala Glu Ala Lys Ser Thr Ile Thr Ser Leu Cys Tyr Pro Leu Asn Tyr
            100                 105                 110

Trp Gly Gln Gly Thr Gln Val Thr Val Ser Ser Glu Ser Lys Tyr Gly
```

```
                115                 120                 125
Pro Pro Cys Pro Pro Cys Pro Ala Pro Glu Phe Leu Gly Gly Pro Ser
        130                 135                 140

Val Phe Leu Phe Pro Lys Pro Lys Asp Thr Leu Met Ile Ser Arg
145                 150                 155                 160

Thr Pro Glu Val Thr Cys Val Val Val Asp Val Ser Gln Glu Asp Pro
                    165                 170                 175

Glu Val Gln Phe Asn Trp Tyr Val Asp Gly Val Glu Val His Asn Ala
            180                 185                 190

Lys Thr Lys Pro Arg Glu Glu Gln Phe Asn Ser Thr Tyr Arg Val Val
                195                 200                 205

Ser Val Leu Thr Val Leu His Gln Asp Trp Leu Asn Gly Lys Glu Tyr
        210                 215                 220

Lys Cys Lys Val Ser Asn Lys Gly Leu Pro Ser Ser Ile Glu Lys Thr
225                 230                 235                 240

Ile Ser Lys Ala Lys Gly Gln Pro Arg Glu Pro Gln Val Tyr Thr Leu
                    245                 250                 255

Pro Pro Ser Gln Glu Glu Met Thr Lys Asn Gln Val Ser Leu Thr Cys
            260                 265                 270

Leu Val Lys Gly Phe Tyr Pro Ser Asp Ile Ala Val Glu Trp Glu Ser
                275                 280                 285

Asn Gly Gln Pro Glu Asn Asn Tyr Lys Thr Thr Pro Pro Val Leu Asp
        290                 295                 300

Ser Asp Gly Ser Phe Phe Leu Tyr Ser Arg Leu Thr Val Asp Lys Ser
305                 310                 315                 320

Arg Trp Gln Glu Gly Asn Val Phe Ser Cys Ser Val Met His Glu Ala
                    325                 330                 335

Leu His Asn His Tyr Thr Gln Lys Ser Leu Ser Leu Ser Leu Gly Lys
            340                 345                 350

<210> SEQ ID NO 341
<211> LENGTH: 350
<212> TYPE: PRT
<213> ORGANISM: Artificial Sequence
<220> FEATURE:
<223> OTHER INFORMATION: Synthetic Construct

<400> SEQUENCE: 341

Gln Val Gln Leu Val Glu Ser Gly Gly Gly Ser Val Gln Ala Gly Gly
1               5                   10                  15

Ser Leu Arg Leu Thr Cys Ala Ala Thr Gly Tyr Ser Trp Arg Pro Asp
            20                  25                  30

Cys Met Gly Trp Tyr Arg Gln Ala Ala Glu Lys Glu Arg Glu Gly Val
        35                  40                  45

Ala Val Ile Asp Ala Asp Gly Ile Thr Ser Tyr Ala Asp Ala Ala Lys
    50                  55                  60

Gly Arg Phe Thr Ile Ser Arg Asp Asn Asn Lys Ile Thr Leu Tyr Leu
65                  70                  75                  80

Gln Met Leu Lys Pro Asp Asp Thr Gly Met Tyr Val Cys Val Val Gly
                85                  90                  95

Trp Arg Val Ser Ser Gly Gly Asn Cys Gln Phe Asn Asp Tyr Trp Gly
            100                 105                 110

Gln Gly Thr Gln Val Thr Val Ser Ser Glu Ser Lys Tyr Gly Pro Pro
        115                 120                 125

Cys Pro Pro Cys Pro Ala Pro Glu Phe Leu Gly Gly Pro Ser Val Phe
```

```
                130             135             140
Leu Phe Pro Pro Lys Pro Lys Asp Thr Leu Met Ile Ser Arg Thr Pro
145                 150                 155                 160

Glu Val Thr Cys Val Val Val Asp Val Ser Gln Glu Asp Pro Glu Val
                165                 170                 175

Gln Phe Asn Trp Tyr Val Asp Gly Val Glu Val His Asn Ala Lys Thr
            180                 185                 190

Lys Pro Arg Glu Glu Gln Phe Asn Ser Thr Tyr Arg Val Val Ser Val
        195                 200                 205

Leu Thr Val Leu His Gln Asp Trp Leu Asn Gly Lys Glu Tyr Lys Cys
210                 215                 220

Lys Val Ser Asn Lys Gly Leu Pro Ser Ser Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Gln Glu Glu Met Thr Lys Asn Gln Val Ser Leu Thr Cys Leu Val
            260                 265                 270

Lys Gly Phe Tyr Pro Ser Asp Ile Ala Val Glu Trp Glu Ser Asn Gly
        275                 280                 285

Gln Pro Glu Asn Asn Tyr Lys Thr Thr Pro Pro Val Leu Asp Ser Asp
    290                 295                 300

Gly Ser Phe Phe Leu Tyr Ser Arg Leu Thr Val Asp Lys Ser Arg Trp
305                 310                 315                 320

Gln Glu Gly Asn Val Phe Ser Cys Ser Val Met His Glu Ala Leu His
                325                 330                 335

Asn His Tyr Thr Gln Lys Ser Leu Ser Leu Ser Leu Gly Lys
            340                 345                 350

<210> SEQ ID NO 342
<211> LENGTH: 355
<212> TYPE: PRT
<213> ORGANISM: Artificial Sequence
<220> FEATURE:
<223> OTHER INFORMATION: Synthetic Construct

<400> SEQUENCE: 342

Gln Val His Leu Met Glu Ser Gly Gly Gly Ala Val Gln Thr Gly Gly
1               5                   10                  15

Ser Leu Arg Leu Ser Cys Ala Val Ser Gly Ile Ser Ile Ser Pro Asp
            20                  25                  30

Cys Met Gly Trp Phe Arg Gln Ala Pro Gly Lys Lys Arg Glu Ala Val
        35                  40                  45

Thr Thr Ile Phe Ala Asn Thr Gly Ser Ala Arg Tyr Gly Asp Ser Val
    50                  55                  60

Lys Gly Arg Phe Thr Ser Ser Gln Gly Asn Ala Lys Asn Thr Leu Tyr
65                  70                  75                  80

Leu Gln Met Asp Ser Val Lys Leu Asp Asp Thr Gly Thr Tyr Tyr Cys
                85                  90                  95

Ala Ala Arg Phe Thr Gly Gly Asp Cys Phe Asp His Gln Pro Leu Ala
            100                 105                 110

Trp Arg Phe Trp Gly Gln Gly Thr Gln Val Thr Val Ser Ser Glu Ser
        115                 120                 125

Lys Tyr Gly Pro Pro Cys Pro Pro Cys Pro Ala Pro Glu Phe Leu Gly
    130                 135                 140

Gly Pro Ser Val Phe Leu Phe Pro Pro Lys Pro Lys Asp Thr Leu Met
```

```
              145                 150                 155                 160
Ile Ser Arg Thr Pro Glu Val Thr Cys Val Val Asp Val Ser Gln
              165                 170                 175

Glu Asp Pro Glu Val Gln Phe Asn Trp Tyr Val Asp Gly Val Glu Val
                180                 185                 190

His Asn Ala Lys Thr Lys Pro Arg Glu Glu Gln Phe Asn Ser Thr Tyr
                195                 200                 205

Arg Val Val Ser Val Leu Thr Val Leu His Gln Asp Trp Leu Asn Gly
            210                 215                 220

Lys Glu Tyr Lys Cys Lys Val Ser Asn Lys Gly Leu Pro Ser Ser Ile
225                 230                 235                 240

Glu Lys Thr Ile Ser Lys Ala Lys Gly Gln Pro Arg Glu Pro Gln Val
                245                 250                 255

Tyr Thr Leu Pro Pro Ser Gln Glu Glu Met Thr Lys Asn Gln Val Ser
                260                 265                 270

Leu Thr Cys Leu Val Lys Gly Phe Tyr Pro Ser Asp Ile Ala Val Glu
            275                 280                 285

Trp Glu Ser Asn Gly Gln Pro Glu Asn Asn Tyr Lys Thr Thr Pro Pro
        290                 295                 300

Val Leu Asp Ser Asp Gly Ser Phe Phe Leu Tyr Ser Arg Leu Thr Val
305                 310                 315                 320

Asp Lys Ser Arg Trp Gln Glu Gly Asn Val Phe Ser Cys Ser Val Met
                325                 330                 335

His Glu Ala Leu His Asn His Tyr Thr Gln Lys Ser Leu Ser Leu Ser
                340                 345                 350

Leu Gly Lys
        355

<210> SEQ ID NO 343
<211> LENGTH: 359
<212> TYPE: PRT
<213> ORGANISM: Artificial Sequence
<220> FEATURE:
<223> OTHER INFORMATION: Synthetic Construct

<400> SEQUENCE: 343

Glu Val Gln Leu Ala Glu Ser Gly Gly Gly Ser Val Gln Ser Gly Gly
1               5                   10                  15

Ser Leu Arg Leu Ser Cys Ala Val Ser Gly Ser Gly Tyr Ser Tyr Ser
                20                  25                  30

Arg Gly Cys Phe Ala Trp Phe Gln Gln Arg Pro Gly Lys Glu Arg Glu
            35                  40                  45

Gly Val Ala Ile Ile Asn Ser Asp Gly His Thr Ala Tyr Ser Asp Ser
        50                  55                  60

Val Gln Gly Arg Phe Ile Ile Ser Gln Asp Lys Ala Lys Asn Thr Leu
65                  70                  75                  80

Tyr Leu Gln Met Asn Ser Leu Lys Pro Asp Asp Thr Ala Met Tyr Tyr
                85                  90                  95

Cys Ala Tyr Asp Arg Ser Gln Cys Tyr Val Leu Arg Asp Arg Leu Arg
            100                 105                 110

Leu Pro Asp Thr Phe Thr Asp Trp Gly Gln Gly Thr Gln Val Thr Val
        115                 120                 125

Ser Ser Glu Ser Lys Tyr Gly Pro Pro Cys Pro Pro Cys Pro Ala Pro
    130                 135                 140

Glu Phe Leu Gly Gly Pro Ser Val Phe Leu Phe Pro Pro Lys Pro Lys
```

```
            145                 150                 155                 160
Asp Thr Leu Met Ile Ser Arg Thr Pro Glu Val Thr Cys Val Val Val
                165                 170                 175

Asp Val Ser Gln Glu Asp Pro Glu Val Gln Phe Asn Trp Tyr Val Asp
            180                 185                 190

Gly Val Glu Val His Asn Ala Lys Thr Lys Pro Arg Glu Glu Gln Phe
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Gly Leu
225                 230                 235                 240

Pro Ser Ser Ile Glu Lys Thr Ile Ser Lys Ala Lys Gly Gln Pro Arg
                245                 250                 255

Glu Pro Gln Val Tyr Thr Leu Pro Pro Ser Gln Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Arg Leu Thr Val Asp Lys Ser Arg Trp Gln Glu Gly Asn Val Phe Ser
                325                 330                 335

Cys Ser Val Met His Glu Ala Leu His Asn His Tyr Thr Gln Lys Ser
            340                 345                 350

Leu Ser Leu Ser Leu Gly Lys
        355

<210> SEQ ID NO 344
<211> LENGTH: 355
<212> TYPE: PRT
<213> ORGANISM: Artificial Sequence
<220> FEATURE:
<223> OTHER INFORMATION: Synthetic Construct

<400> SEQUENCE: 344

Gln Val His Leu Val Glu Ser Gly Gly Ala Val Gln Ala Gly Gly
1               5                   10                  15

Ser Leu Arg Leu Ser Cys Ala Ala Thr Ala Tyr Thr Ala Ser Asn Tyr
            20                  25                  30

Cys Met Gly Trp Phe Arg Gln Ser Pro Gly Lys Glu Arg Glu Ala Val
        35                  40                  45

Ala Ser Ile Asn Asp Asp Gly Val Thr Ser Tyr Ala Asp Ser Val Lys
    50                  55                  60

Gly Arg Phe Thr Ile Ser Gln Asp Ser Ala Lys Lys Thr Leu Tyr Leu
65                  70                  75                  80

Gln Met Asn Arg Leu Lys Pro Glu Asp Thr Ala Met Tyr Tyr Cys Ala
                85                  90                  95

Ala Thr Pro Asp Gly Tyr Cys Tyr Ala Glu Arg Leu Ser Arg Trp Arg
            100                 105                 110

Tyr Glu Phe Trp Gly Gln Gly Thr Gln Val Thr Val Ser Ser Glu Ser
        115                 120                 125

Lys Tyr Gly Pro Pro Cys Pro Pro Cys Pro Ala Pro Glu Phe Leu Gly
    130                 135                 140

Gly Pro Ser Val Phe Leu Phe Pro Pro Lys Pro Lys Asp Thr Leu Met
```

```
            145                 150                 155                 160
        Ile Ser Arg Thr Pro Glu Val Thr Cys Val Val Asp Val Ser Gln
                        165                 170                 175

Glu Asp Pro Glu Val Gln Phe Asn Trp Tyr Val Asp Gly Val Glu Val
                        180                 185                 190

His Asn Ala Lys Thr Lys Pro Arg Glu Glu Gln Phe Asn Ser Thr Tyr
                        195                 200                 205

Arg Val Val Ser Val Leu Thr Val Leu His Gln Asp Trp Leu Asn Gly
                        210                 215                 220

Lys Glu Tyr Lys Cys Lys Val Ser Asn Lys Gly Leu Pro Ser Ser Ile
        225                 230                 235                 240

Glu Lys Thr Ile Ser Lys Ala Lys Gly Gln Pro Arg Glu Pro Gln Val
                        245                 250                 255

Tyr Thr Leu Pro Pro Ser Gln Glu Glu Met Thr Lys Asn Gln Val Ser
                        260                 265                 270

Leu Thr Cys Leu Val Lys Gly Phe Tyr Pro Ser Asp Ile Ala Val Glu
                        275                 280                 285

Trp Glu Ser Asn Gly Gln Pro Glu Asn Asn Tyr Lys Thr Thr Pro Pro
                        290                 295                 300

Val Leu Asp Ser Asp Gly Ser Phe Phe Leu Tyr Ser Arg Leu Thr Val
        305                 310                 315                 320

Asp Lys Ser Arg Trp Gln Glu Gly Asn Val Phe Ser Cys Ser Val Met
                        325                 330                 335

His Glu Ala Leu His Asn His Tyr Thr Gln Lys Ser Leu Ser Leu Ser
                        340                 345                 350

Leu Gly Lys
                355

<210> SEQ ID NO 345
<211> LENGTH: 355
<212> TYPE: PRT
<213> ORGANISM: Artificial Sequence
<220> FEATURE:
<223> OTHER INFORMATION: Synthetic Construct

<400> SEQUENCE: 345

Glu Val Gln Leu Ala Glu Ser Gly Gly Gly Ser Val Gln Ala Gly Gly
        1               5                   10                  15

Ser Leu Arg Leu Ser Cys Val Ile Ser Gly Thr Ser Ile Ser Pro Asp
                        20                  25                  30

Cys Met Gly Trp Phe Arg Gln Ala Pro Gly Lys Lys Arg Glu Ala Val
                        35                  40                  45

Met Ser Ile Phe Thr Asn Thr Gly Ser Thr Arg Tyr Gly Asp Ser Val
                        50                  55                  60

Lys Gly Arg Phe Thr Ser Ser Gln Gly Asn Ala Lys Asn Thr Leu Tyr
        65                  70                  75                  80

Leu Gln Met Asp Ser Leu Lys Leu Asp Asp Thr Ala Thr Tyr Tyr Cys
                        85                  90                  95

Ala Ala Arg Tyr Thr Gly Gly Asp Cys Phe Asn Leu Glu Pro Leu Ala
                        100                 105                 110

Trp Arg Phe Trp Gly Gln Gly Thr Gln Val Thr Val Ser Ser Glu Ser
                        115                 120                 125

Lys Tyr Gly Pro Pro Cys Pro Pro Cys Pro Ala Pro Glu Phe Leu Gly
                        130                 135                 140

Gly Pro Ser Val Phe Leu Phe Pro Pro Lys Pro Lys Asp Thr Leu Met
```

```
145                 150                 155                 160
Ile Ser Arg Thr Pro Glu Val Thr Cys Val Val Val Asp Val Ser Gln
                165                 170                 175

Glu Asp Pro Glu Val Gln Phe Asn Trp Tyr Val Asp Gly Val Glu Val
            180                 185                 190

His Asn Ala Lys Thr Lys Pro Arg Glu Glu Gln Phe Asn Ser Thr Tyr
                195                 200                 205

Arg Val Val Ser Val Leu Thr Val Leu His Gln Asp Trp Leu Asn Gly
            210                 215                 220

Lys Glu Tyr Lys Cys Lys Val Ser Asn Lys Gly Leu Pro Ser Ser Ile
225                 230                 235                 240

Glu Lys Thr Ile Ser Lys Ala Lys Gly Gln Pro Arg Glu Pro Gln Val
                245                 250                 255

Tyr Thr Leu Pro Pro Ser Gln Glu Glu Met Thr Lys Asn Gln Val Ser
            260                 265                 270

Leu Thr Cys Leu Val Lys Gly Phe Tyr Pro Ser Asp Ile Ala Val Glu
            275                 280                 285

Trp Glu Ser Asn Gly Gln Pro Glu Asn Asn Tyr Lys Thr Thr Pro Pro
    290                 295                 300

Val Leu Asp Ser Asp Gly Ser Phe Phe Leu Tyr Ser Arg Leu Thr Val
305                 310                 315                 320

Asp Lys Ser Arg Trp Gln Glu Gly Asn Val Phe Ser Cys Ser Val Met
                325                 330                 335

His Glu Ala Leu His Asn His Tyr Thr Gln Lys Ser Leu Ser Leu Ser
            340                 345                 350

Leu Gly Lys
        355

<210> SEQ ID NO 346
<211> LENGTH: 350
<212> TYPE: PRT
<213> ORGANISM: Artificial Sequence
<220> FEATURE:
<223> OTHER INFORMATION: Synthetic Construct

<400> SEQUENCE: 346

Gln Val Gln Leu Val Glu Ser Gly Gly Gly Val Gln Ala Gly Gly
1               5                   10                  15

Pro Leu Arg Leu Thr Cys Ala Ala Thr Gly Tyr Ser Trp Arg Pro Asp
            20                  25                  30

Cys Met Gly Trp Tyr Arg Gln Ala Ala Glu Lys Glu Arg Glu Gly Val
        35                  40                  45

Ala Val Ile Asp Ala Asp Gly Ile Thr Ser Tyr Ala Asp Ala Ala Lys
    50                  55                  60

Gly Arg Phe Thr Ile Ser Arg Asp Asn Asn Asn Ile Thr Leu Tyr Leu
65                  70                  75                  80

Gln Met Leu Lys Pro Asp Asp Thr Gly Met Tyr Val Cys Val Ile Gly
                85                  90                  95

Trp Arg Val Ser Ser Gly Gly Asn Cys Gln Phe Asn Asp Tyr Trp Gly
            100                 105                 110

Gln Gly Thr Gln Val Thr Val Ser Glu Ser Lys Tyr Gly Pro Pro
        115                 120                 125

Cys Pro Pro Cys Pro Ala Pro Glu Phe Leu Gly Gly Pro Ser Val Phe
    130                 135                 140

Leu Phe Pro Pro Lys Pro Lys Asp Thr Leu Met Ile Ser Arg Thr Pro
```

```
145                 150                 155                 160
Glu Val Thr Cys Val Val Asp Val Ser Gln Glu Asp Pro Glu Val
                165                 170                 175
Gln Phe Asn Trp Tyr Val Asp Gly Val Glu Val His Asn Ala Lys Thr
            180                 185                 190
Lys Pro Arg Glu Glu Gln Phe Asn Ser Thr Tyr Arg Val Val Ser Val
            195                 200                 205
Leu Thr Val Leu His Gln Asp Trp Leu Asn Gly Lys Glu Tyr Lys Cys
        210                 215                 220
Lys Val Ser Asn Lys Gly Leu Pro Ser Ser Ile Glu Lys Thr Ile Ser
225                 230                 235                 240
Lys Ala Lys Gly Gln Pro Arg Glu Pro Gln Val Tyr Thr Leu Pro Pro
                245                 250                 255
Ser Gln Glu Glu Met Thr Lys Asn Gln Val Ser Leu Thr Cys Leu Val
            260                 265                 270
Lys Gly Phe Tyr Pro Ser Asp Ile Ala Val Glu Trp Glu Ser Asn Gly
        275                 280                 285
Gln Pro Glu Asn Asn Tyr Lys Thr Thr Pro Pro Val Leu Asp Ser Asp
    290                 295                 300
Gly Ser Phe Phe Leu Tyr Ser Arg Leu Thr Val Asp Lys Ser Arg Trp
305                 310                 315                 320
Gln Glu Gly Asn Val Phe Ser Cys Ser Val Met His Glu Ala Leu His
                325                 330                 335
Asn His Tyr Thr Gln Lys Ser Leu Ser Leu Ser Leu Gly Lys
            340                 345                 350

<210> SEQ ID NO 347
<211> LENGTH: 359
<212> TYPE: PRT
<213> ORGANISM: Artificial Sequence
<220> FEATURE:
<223> OTHER INFORMATION: Synthetic Construct

<400> SEQUENCE: 347

Gln Val Gln Leu Val Glu Ser Gly Gly Gly Ser Val Gln Ser Gly Gly
1               5                   10                  15
Ser Leu Lys Leu Ser Cys Ala Val Ser Gly Ser Gly Tyr Ser Tyr Ser
            20                  25                  30
Arg Gly Cys Phe Ala Trp Phe Gln Gln Arg Pro Gly Lys Glu Arg Glu
        35                  40                  45
Gly Val Ala Ile Ile Asn Ser Asp Gly His Thr Arg Tyr Ser Asp Ser
    50                  55                  60
Val Gln Gly Arg Phe Ile Ile Ser Gln Asp Lys Ala Lys Asn Thr Leu
65                  70                  75                  80
Tyr Leu Gln Met Asn Ser Leu Lys Pro Asp Asp Ala Ala Met Tyr Tyr
                85                  90                  95
Cys Ala Tyr Asp Arg Asn Gln Cys Tyr Val Leu Leu Asp Arg Leu Arg
            100                 105                 110
Leu Pro Gly Thr Phe Ser Asp Trp Gly Gln Gly Thr Gln Val Thr Val
        115                 120                 125
Ser Ser Glu Ser Lys Tyr Gly Pro Pro Cys Pro Pro Cys Pro Ala Pro
    130                 135                 140
Glu Phe Leu Gly Gly Pro Ser Val Phe Leu Phe Pro Pro Lys Pro Lys
145                 150                 155                 160
Asp Thr Leu Met Ile Ser Arg Thr Pro Glu Val Thr Cys Val Val Val
```

```
                      165                 170                 175
Asp Val Ser Gln Glu Asp Pro Glu Val Gln Phe Asn Trp Tyr Val Asp
            180                 185                 190

Gly Val Glu Val His Asn Ala Lys Thr Lys Pro Arg Glu Glu Gln Phe
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Gly Leu
225                 230                 235                 240

Pro Ser Ser Ile Glu Lys Thr Ile Ser Lys Ala Lys Gly Gln Pro Arg
                245                 250                 255

Glu Pro Gln Val Tyr Thr Leu Pro Pro Ser Gln Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Arg Leu Thr Val Asp Lys Ser Arg Trp Gln Glu Gly Asn Val Phe Ser
                325                 330                 335

Cys Ser Val Met His Glu Ala Leu His Asn His Tyr Thr Gln Lys Ser
            340                 345                 350

Leu Ser Leu Ser Leu Gly Lys
            355

<210> SEQ ID NO 348
<211> LENGTH: 359
<212> TYPE: PRT
<213> ORGANISM: Artificial Sequence
<220> FEATURE:
<223> OTHER INFORMATION: Synthetic Construct

<400> SEQUENCE: 348

Glu Val Gln Leu Val Glu Ser Gly Gly Gly Ser Val Gln Ser Gly Gly
1               5                   10                  15

Ser Leu Arg Leu Ser Cys Ala Val Ser Gly Ser Gly Tyr Ser Tyr Ser
            20                  25                  30

Arg Gly Cys Phe Ala Trp Phe Gln Gln Arg Pro Gly Lys Glu Arg Glu
        35                  40                  45

Gly Val Ala Ile Ile Asn Ser Asp Gly His Thr Arg Tyr Ser Asp Ser
    50                  55                  60

Val Gln Gly Arg Phe Ile Ile Ser Gln Asp Lys Ala Lys Asn Thr Leu
65                  70                  75                  80

Tyr Leu Gln Met Asn Ser Leu Lys Pro Asp Asp Thr Ala Met Tyr Tyr
                85                  90                  95

Cys Ala Tyr Asp Cys Ser Gln Cys Tyr Val Leu Arg Asp Arg Leu Arg
            100                 105                 110

Leu Pro Asp Thr Phe Thr Asp Trp Gly Gln Gly Thr Gln Val Thr Val
        115                 120                 125

Ser Ser Glu Ser Lys Tyr Gly Pro Pro Cys Pro Cys Pro Ala Pro
    130                 135                 140

Glu Phe Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
```

```
                    165                 170                 175
Asp Val Ser Gln Glu Asp Pro Glu Val Gln Phe Asn Trp Tyr Val Asp
            180                 185                 190
Gly Val Glu Val His Asn Ala Lys Thr Lys Pro Arg Glu Glu Gln Phe
        195                 200                 205
Asn Ser Thr Tyr Arg Val Val Ser Val Leu Thr Val Leu His Gln Asp
    210                 215                 220
Trp Leu Asn Gly Lys Glu Tyr Lys Cys Lys Val Ser Asn Lys Gly Leu
225                 230                 235                 240
Pro Ser Ser Ile Glu Lys Thr Ile Ser Lys Ala Lys Gly Gln Pro Arg
                245                 250                 255
Glu Pro Gln Val Tyr Thr Leu Pro Pro Ser Gln Glu Glu Met Thr Lys
            260                 265                 270
Asn Gln Val Ser Leu Thr Cys Leu Val Lys Gly Phe Tyr Pro Ser Asp
        275                 280                 285
Ile Ala Val Glu Trp Glu Ser Asn Gly Gln Pro Glu Asn Asn Tyr Lys
    290                 295                 300
Thr Thr Pro Pro Val Leu Asp Ser Asp Gly Ser Phe Phe Leu Tyr Ser
305                 310                 315                 320
Arg Leu Thr Val Asp Lys Ser Arg Trp Gln Glu Gly Asn Val Phe Ser
                325                 330                 335
Cys Ser Val Met His Glu Ala Leu His Asn His Tyr Thr Gln Lys Ser
            340                 345                 350
Leu Ser Leu Ser Leu Gly Lys
            355

<210> SEQ ID NO 349
<211> LENGTH: 359
<212> TYPE: PRT
<213> ORGANISM: Artificial Sequence
<220> FEATURE:
<223> OTHER INFORMATION: Synthetic Construct

<400> SEQUENCE: 349

Glu Val Gln Leu Val Glu Ser Gly Gly Gly Ser Val Gln Ser Gly Gly
1               5                   10                  15
Ser Leu Arg Leu Ser Cys Ala Val Ser Gly Ser Gly Tyr Ser Tyr Asn
            20                  25                  30
Arg Gly Cys Phe Ala Trp Phe Gln Gln Arg Pro Gly Lys Glu Arg Glu
        35                  40                  45
Gly Val Ala Ile Ile Asn Ser Asp Gly His Thr Thr Tyr Gly Asp Ser
    50                  55                  60
Val Gln Gly Arg Phe Ile Ile Ser Gln Asp Lys Ala Lys Asn Thr Leu
65                  70                  75                  80
Asp Leu Gln Met Asn Ser Leu Lys Pro Asp Asp Thr Ala Met Tyr Tyr
                85                  90                  95
Cys Ala Tyr Asp Arg Asn Gln Cys Tyr Val Leu Arg Asp Arg Leu Arg
            100                 105                 110
Leu Pro Asp Thr Phe Thr Asp Trp Gly Gln Gly Thr Gln Val Thr Val
        115                 120                 125
Ser Ser Glu Ser Lys Tyr Gly Pro Pro Cys Pro Pro Cys Pro Ala Pro
    130                 135                 140
Glu Phe Leu Gly Gly Pro Ser Val Phe Leu Phe Pro Pro Lys Pro Lys
145                 150                 155                 160
Asp Thr Leu Met Ile Ser Arg Thr Pro Glu Val Thr Cys Val Val Val
```

```
                165                 170                 175
Asp Val Ser Gln Glu Asp Pro Glu Val Gln Phe Asn Trp Tyr Val Asp
            180                 185                 190

Gly Val Glu Val His Asn Ala Lys Thr Lys Pro Arg Glu Glu Gln Phe
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Gly Leu
225                 230                 235                 240

Pro Ser Ser Ile Glu Lys Thr Ile Ser Lys Ala Lys Gly Gln Pro Arg
                245                 250                 255

Glu Pro Gln Val Tyr Thr Leu Pro Pro Ser Gln Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Arg Leu Thr Val Asp Lys Ser Arg Trp Gln Glu Gly Asn Val Phe Ser
                325                 330                 335

Cys Ser Val Met His Glu Ala Leu His Asn His Tyr Thr Gln Lys Ser
            340                 345                 350

Leu Ser Leu Ser Leu Gly Lys
        355

<210> SEQ ID NO 350
<211> LENGTH: 359
<212> TYPE: PRT
<213> ORGANISM: Artificial Sequence
<220> FEATURE:
<223> OTHER INFORMATION: Synthetic Construct

<400> SEQUENCE: 350

Gln Val Lys Leu Val Glu Ser Gly Gly Gly Leu Val Gln Ser Gly Gly
1               5                   10                  15

Ser Leu Arg Leu Ser Cys Ala Val Ser Gly Ser Gly Tyr Ser Tyr Ser
            20                  25                  30

Arg Gly Cys Phe Ala Trp Phe Gln Gln Arg Pro Gly Lys Glu Arg Glu
        35                  40                  45

Gly Val Ala Ile Ile Asn Met Asp Gly His Thr Met Tyr Ser Asp Leu
    50                  55                  60

Ala Gln Gly Arg Phe Ile Ile Ser Gln Asp Lys Ala Lys Asn Thr Leu
65                  70                  75                  80

Tyr Leu Gln Met Asn Ser Leu Lys Pro Asp Asp Thr Ala Met Tyr Tyr
                85                  90                  95

Cys Ala Tyr Asp Arg Asp Gln Cys Tyr Val Leu Arg Asp Arg Leu Arg
            100                 105                 110

Leu Pro Asp Thr Phe Asn Asp Trp Gly Gln Gly Thr Gln Val Thr Val
        115                 120                 125

Ser Ser Glu Ser Lys Tyr Gly Pro Pro Cys Pro Pro Cys Pro Ala Pro
    130                 135                 140

Glu Phe Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
```

```
                165                 170                 175
Asp Val Ser Gln Glu Asp Pro Glu Val Gln Phe Asn Trp Tyr Val Asp
            180                 185                 190
Gly Val Glu Val His Asn Ala Lys Thr Lys Pro Arg Glu Glu Gln Phe
        195                 200                 205
Asn Ser Thr Tyr Arg Val Val Ser Val Leu Thr Val Leu His Gln Asp
    210                 215                 220
Trp Leu Asn Gly Lys Glu Tyr Lys Cys Lys Val Ser Asn Lys Gly Leu
225                 230                 235                 240
Pro Ser Ser Ile Glu Lys Thr Ile Ser Lys Ala Lys Gly Gln Pro Arg
                245                 250                 255
Glu Pro Gln Val Tyr Thr Leu Pro Pro Ser Gln Glu Glu Met Thr Lys
            260                 265                 270
Asn Gln Val Ser Leu Thr Cys Leu Val Lys Gly Phe Tyr Pro Ser Asp
        275                 280                 285
Ile Ala Val Glu Trp Glu Ser Asn Gly Gln Pro Glu Asn Asn Tyr Lys
    290                 295                 300
Thr Thr Pro Pro Val Leu Asp Ser Asp Gly Ser Phe Phe Leu Tyr Ser
305                 310                 315                 320
Arg Leu Thr Val Asp Lys Ser Arg Trp Gln Gln Gly Asn Val Phe Ser
                325                 330                 335
Cys Ser Val Met His Glu Ala Leu His Asn His Tyr Thr Gln Lys Ser
            340                 345                 350
Leu Ser Leu Ser Leu Gly Lys
            355

<210> SEQ ID NO 351
<211> LENGTH: 355
<212> TYPE: PRT
<213> ORGANISM: Artificial Sequence
<220> FEATURE:
<223> OTHER INFORMATION: Synthetic Construct

<400> SEQUENCE: 351

Gln Ile Gln Leu Val Glu Ser Gly Gly Gly Ser Val Gln Ala Gly Gly
1               5                   10                  15
Ser Leu Arg Leu Ser Cys Ala Val Thr Gly Ile Ser Ile Ser Pro Asp
            20                  25                  30
Cys Met Gly Trp Phe Arg Gln Ala Pro Gly Lys Lys Arg Glu Ala Val
        35                  40                  45
Ala Thr Ile Phe Thr Asn Thr Ala Ser Thr Arg Tyr Gly Asp Ser Val
    50                  55                  60
Lys Gly Arg Phe Thr Ser Ser Gln Gly Asn Gly Lys Asn Thr Leu Tyr
65                  70                  75                  80
Leu Gln Met Asp Ser Leu Asn Val Asp Asp Thr Ala Thr Tyr Tyr Cys
                85                  90                  95
Ala Ala Arg Tyr Thr Gly Gly Asn Cys Phe Asn Leu Glu Pro Leu Ala
            100                 105                 110
Trp His Phe Trp Gly Gln Gly Thr Gln Val Thr Val Ser Ser Glu Ser
        115                 120                 125
Lys Tyr Gly Pro Pro Cys Pro Pro Cys Pro Ala Pro Glu Phe Leu Gly
    130                 135                 140
Gly Pro Ser Val Phe Leu Phe Pro Pro Lys Pro Lys Asp Thr Leu Met
145                 150                 155                 160
Ile Ser Arg Thr Pro Glu Val Thr Cys Val Val Val Asp Val Ser Gln
```

```
                165                 170                 175
Glu Asp Pro Glu Val Gln Phe Asn Trp Tyr Val Asp Gly Val Glu Val
            180                 185                 190

His Asn Ala Lys Thr Lys Pro Arg Glu Glu Gln Phe Asn Ser Thr Tyr
        195                 200                 205

Arg Val Val Ser Val Leu Thr Val Leu His Gln Asp Trp Leu Asn Gly
    210                 215                 220

Lys Glu Tyr Lys Cys Lys Val Ser Asn Lys Gly Leu Pro Ser Ser Ile
225                 230                 235                 240

Glu Lys Thr Ile Ser Lys Ala Lys Gly Gln Pro Arg Glu Pro Gln Val
                245                 250                 255

Tyr Thr Leu Pro Pro Ser Gln Glu Glu Met Thr Lys Asn Gln Val Ser
            260                 265                 270

Leu Thr Cys Leu Val Lys Gly Phe Tyr Pro Ser Asp Ile Ala Val Glu
        275                 280                 285

Trp Glu Ser Asn Gly Gln Pro Glu Asn Asn Tyr Lys Thr Thr Pro Pro
    290                 295                 300

Val Leu Asp Ser Asp Gly Ser Phe Phe Leu Tyr Ser Arg Leu Thr Val
305                 310                 315                 320

Asp Lys Ser Arg Trp Gln Glu Gly Asn Val Phe Ser Cys Ser Val Met
                325                 330                 335

His Glu Ala Leu His Asn His Tyr Thr Gln Lys Ser Leu Ser Leu Ser
            340                 345                 350

Leu Gly Lys
        355

<210> SEQ ID NO 352
<211> LENGTH: 355
<212> TYPE: PRT
<213> ORGANISM: Artificial Sequence
<220> FEATURE:
<223> OTHER INFORMATION: Synthetic Construct

<400> SEQUENCE: 352

Gln Val His Leu Met Glu Ser Gly Gly Gly Ser Val Gln Ala Gly Gly
1               5                   10                  15

Ser Leu Arg Leu Ser Cys Val Val Ser Gly Ile Ser Ile Ser Pro Asp
            20                  25                  30

Cys Met Gly Trp Phe Arg Gln Ala Pro Gly Lys Lys Arg Glu Ala Val
        35                  40                  45

Ala Thr Ile Phe Thr Asn Thr Arg Arg Thr Arg Tyr Gly Asp Ser Val
    50                  55                  60

Lys Gly Arg Val Thr Ser Ser Gln Gly Asn Ala Lys Asn Thr Leu Tyr
65                  70                  75                  80

Leu Lys Met Asp Asn Leu Arg His Asp Asp Thr Ala Thr Tyr Tyr Cys
                85                  90                  95

Ala Ala Arg Tyr Thr Gly Gly Asp Cys Phe Asn Leu Asp Pro Leu Ser
            100                 105                 110

Trp Arg Phe Trp Gly Gln Gly Thr Gln Val Thr Val Ser Ser Glu Ser
        115                 120                 125

Lys Tyr Gly Pro Pro Cys Pro Pro Cys Pro Ala Pro Glu Phe Leu Gly
    130                 135                 140

Gly Pro Ser Val Phe Leu Phe Pro Pro Lys Pro Lys Asp Thr Leu Met
145                 150                 155                 160

Ile Ser Arg Thr Pro Glu Val Thr Cys Val Val Val Asp Val Ser Gln
```

```
                      165                 170                 175
Glu Asp Pro Glu Val Gln Phe Asn Trp Tyr Val Asp Gly Val Glu Val
            180                 185                 190

His Asn Ala Lys Thr Lys Pro Arg Glu Glu Gln Phe Asn Ser Thr Tyr
        195                 200                 205

Arg Val Val Ser Val Leu Thr Val Leu His Gln Asp Trp Leu Asn Gly
    210                 215                 220

Lys Glu Tyr Lys Cys Lys Val Ser Asn Lys Gly Leu Pro Ser Ser Ile
225                 230                 235                 240

Glu Lys Thr Ile Ser Lys Ala Lys Gly Gln Pro Arg Glu Pro Gln Val
                245                 250                 255

Tyr Thr Leu Pro Pro Ser Gln Glu Glu Met Thr Lys Asn Gln Val Ser
            260                 265                 270

Leu Thr Cys Leu Val Lys Gly Phe Tyr Pro Ser Asp Ile Ala Val Glu
        275                 280                 285

Trp Glu Ser Asn Gly Gln Pro Glu Asn Asn Tyr Lys Thr Thr Pro Pro
    290                 295                 300

Val Leu Asp Ser Asp Gly Ser Phe Phe Leu Tyr Ser Arg Leu Thr Val
305                 310                 315                 320

Asp Lys Ser Arg Trp Gln Glu Gly Asn Val Phe Ser Cys Ser Val Met
                325                 330                 335

His Glu Ala Leu His Asn His Tyr Thr Gln Lys Ser Leu Ser Leu Ser
            340                 345                 350

Leu Gly Lys
        355

<210> SEQ ID NO 353
<211> LENGTH: 355
<212> TYPE: PRT
<213> ORGANISM: Artificial Sequence
<220> FEATURE:
<223> OTHER INFORMATION: Synthetic Construct

<400> SEQUENCE: 353

Gln Val Gln Leu Val Glu Ser Gly Gly Gly Ser Val Gln Ala Gly Gly
1               5                   10                  15

Ser Leu Arg Leu Ser Cys Ala Val Ser Gly Ile Ser Ile Ser Pro Asp
            20                  25                  30

Cys Met Gly Trp Phe Arg Gln Ala Pro Gly Lys Lys Arg Glu Ala Val
        35                  40                  45

Ala Thr Ile Phe Thr Asn Thr Arg Ser Thr Arg Tyr Gly Asp Ser Val
    50                  55                  60

Lys Gly Arg Phe Thr Ser Ser Gln Gly Asn Ala Lys Asn Thr Leu Tyr
65                  70                  75                  80

Leu Gln Met Asp Ser Leu Lys Leu Asp Asp Thr Ala Thr Tyr Tyr Cys
                85                  90                  95

Ala Ala Arg Tyr Thr Gly Gly Asp Cys Phe Asn Leu Glu Pro Val Ala
            100                 105                 110

Trp Arg Phe Trp Gly Gln Gly Thr Gln Val Thr Val Ser Ser Glu Ser
        115                 120                 125

Lys Tyr Gly Pro Pro Cys Pro Pro Cys Pro Ala Pro Glu Phe Leu Gly
    130                 135                 140

Gly Pro Ser Val Phe Leu Phe Pro Pro Lys Pro Lys Asp Thr Leu Met
145                 150                 155                 160

Ile Ser Arg Thr Pro Glu Val Thr Cys Val Val Val Asp Val Ser Gln
```

```
                165                 170                 175
Glu Asp Pro Glu Val Gln Phe Asn Trp Tyr Val Asp Gly Val Glu Val
            180                 185                 190

His Asn Ala Lys Thr Lys Pro Arg Glu Glu Gln Phe Asn Ser Thr Tyr
        195                 200                 205

Arg Val Val Ser Val Leu Thr Val Leu His Gln Asp Trp Leu Asn Gly
    210                 215                 220

Lys Glu Tyr Lys Cys Lys Val Ser Asn Lys Gly Leu Pro Ser Ser Ile
225                 230                 235                 240

Glu Lys Thr Ile Ser Lys Ala Lys Gly Gln Pro Arg Glu Pro Gln Val
            245                 250                 255

Tyr Thr Leu Pro Pro Ser Gln Glu Glu Met Thr Lys Asn Gln Val Ser
        260                 265                 270

Leu Thr Cys Leu Val Lys Gly Phe Tyr Pro Ser Asp Ile Ala Val Glu
    275                 280                 285

Trp Glu Ser Asn Gly Gln Pro Glu Asn Asn Tyr Lys Thr Thr Pro Pro
290                 295                 300

Val Leu Asp Ser Asp Gly Ser Phe Phe Leu Tyr Ser Arg Leu Thr Val
305                 310                 315                 320

Asp Lys Ser Arg Trp Gln Glu Gly Asn Val Phe Ser Cys Ser Val Met
            325                 330                 335

His Glu Ala Leu His Asn His Tyr Thr Gln Lys Ser Leu Ser Leu Ser
        340                 345                 350

Leu Gly Lys
        355

<210> SEQ ID NO 354
<211> LENGTH: 352
<212> TYPE: PRT
<213> ORGANISM: Artificial Sequence
<220> FEATURE:
<223> OTHER INFORMATION: Synthetic Construct

<400> SEQUENCE: 354

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Val Trp
            20                  25                  30

Ser Met Ser Trp Val Arg Gln Ala Pro Gly Glu Gly Leu Glu Trp Val
        35                  40                  45

Ser Thr Ile Thr Gly Ser Gly Ala Gln Thr Tyr Tyr Ala Ser Ser Val
    50                  55                  60

Arg Gly Arg Phe Thr Thr Ser Arg Asp Asn Ala Lys Asn Thr Val Tyr
65                  70                  75                  80

Leu Gln Met Asn Ser Leu Lys Ser Asp Asp Thr Ala Val Tyr Tyr Cys
            85                  90                  95

Glu Arg Gly Asn Gly Gln Thr Ala Met Glu Ala Leu Ile Asn Pro Pro
        100                 105                 110

Glu Arg Pro Gly Thr Gln Val Thr Val Ser Ser Glu Ser Lys Tyr Gly
    115                 120                 125

Pro Pro Cys Pro Pro Cys Pro Ala Pro Glu Phe Leu Gly Gly Pro Ser
130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser Gln Glu Asp Pro
```

```
                        165                 170                 175
Glu Val Gln Phe Asn Trp Tyr Val Asp Gly Val Glu Val His Asn Ala
                180                 185                 190
Lys Thr Lys Pro Arg Glu Glu Gln Phe Asn Ser Thr Tyr Arg Val Val
            195                 200                 205
Ser Val Leu Thr Val Leu His Gln Asp Trp Leu Asn Gly Lys Glu Tyr
        210                 215                 220
Lys Cys Lys Val Ser Asn Lys Gly Leu Pro Ser Ser Ile Glu Lys Thr
225                 230                 235                 240
Ile Ser Lys Ala Lys Gly Gln Pro Arg Glu Pro Gln Val Tyr Thr Leu
                245                 250                 255
Pro Pro Ser Gln Glu Glu Met Thr Lys Asn Gln Val Ser Leu Thr Cys
            260                 265                 270
Leu Val Lys Gly Phe Tyr Pro Ser Asp Ile Ala Val Glu Trp Glu Ser
        275                 280                 285
Asn Gly Gln Pro Glu Asn Asn Tyr Lys Thr Thr Pro Pro Val Leu Asp
        290                 295                 300
Ser Asp Gly Ser Phe Phe Leu Tyr Ser Arg Leu Thr Val Asp Lys Ser
305                 310                 315                 320
Arg Trp Gln Glu Gly Asn Val Phe Ser Cys Ser Val Met His Glu Ala
                325                 330                 335
Leu His Asn His Tyr Thr Gln Lys Ser Leu Ser Leu Ser Leu Gly Lys
            340                 345                 350

<210> SEQ ID NO 355
<211> LENGTH: 356
<212> TYPE: PRT
<213> ORGANISM: Artificial Sequence
<220> FEATURE:
<223> OTHER INFORMATION: Synthetic Construct

<400> SEQUENCE: 355

Gln Val Gln Leu Val Glu Ser Gly Gly Gly Leu Met Gln Pro Gly Gly
1               5                   10                  15
Ser Leu Arg Leu Ser Cys Ala Ala Ser Gly Phe Thr Phe Ser Ser Tyr
            20                  25                  30
Trp Met Tyr Trp Val Arg Gln Ala Pro Gly Lys Gly Leu Glu Trp Val
        35                  40                  45
Ser Val Ile Asn Arg Ala Gly Asp Ser Ala Trp Tyr Ala Asp Ser Val
    50                  55                  60
Thr Gly Arg Phe Thr Ile Ser Arg Asp Asn Ala Lys Asn Thr Val Tyr
65                  70                  75                  80
Leu Gln Met Asp Ser Leu Lys Pro Glu Asp Thr Ala Met Tyr Tyr Cys
                85                  90                  95
Ala Ala Asp Ser Arg Gly Tyr Gly Gly Asp Trp Tyr Lys Leu Leu Ser
            100                 105                 110
Asp Phe Asn Tyr Cys Gly Gln Gly Thr Gln Val Thr Val Ser Ser Glu
        115                 120                 125
Ser Lys Tyr Gly Pro Pro Cys Pro Pro Cys Pro Ala Pro Glu Phe Leu
    130                 135                 140
Gly Gly Pro Ser Val Phe Leu Phe Pro Pro Lys Pro Lys Asp Thr Leu
145                 150                 155                 160
Met Ile Ser Arg Thr Pro Glu Val Thr Cys Val Val Val Asp Val Ser
                165                 170                 175
Gln Glu Asp Pro Glu Val Gln Phe Asn Trp Tyr Val Asp Gly Val Glu
```

```
                180                 185                 190
Val His Asn Ala Lys Thr Lys Pro Arg Glu Glu Gln Phe Asn Ser Thr
            195                 200                 205

Tyr Arg Val Val Ser Val Leu Thr Val Leu His Gln Asp Trp Leu Asn
        210                 215                 220

Gly Lys Glu Tyr Lys Cys Lys Val Ser Asn Lys Gly Leu Pro Ser Ser
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Gln Glu Glu Met Thr Lys Asn Gln Val
            260                 265                 270

Ser Leu Thr Cys Leu Val Lys Gly Phe Tyr Pro Ser Asp Ile Ala Val
        275                 280                 285

Glu Trp Glu Ser Asn Gly Gln Pro Glu Asn Asn Tyr Lys Thr Thr Pro
    290                 295                 300

Pro Val Leu Asp Ser Asp Gly Ser Phe Phe Leu Tyr Ser Arg Leu Thr
305                 310                 315                 320

Val Asp Lys Ser Arg Trp Gln Glu Gly Asn Val Phe Ser Cys Ser Val
                325                 330                 335

Met His Glu Ala Leu His Asn His Tyr Thr Gln Lys Ser Leu Ser Leu
            340                 345                 350

Ser Leu Gly Lys
        355

<210> SEQ ID NO 356
<211> LENGTH: 355
<212> TYPE: PRT
<213> ORGANISM: Artificial Sequence
<220> FEATURE:
<223> OTHER INFORMATION: Synthetic Construct

<400> SEQUENCE: 356

Gln Val Gln Leu Val Glu Ser Gly Gly Gly Ser Val Gln Ala Gly Gly
1               5                   10                  15

Ser Leu Arg Leu Ser Cys Ala Ala Thr Ala Tyr Thr Ala Ser Phe Tyr
            20                  25                  30

Cys Met Gly Trp Phe Arg Gln Ala Pro Gly Lys Glu Arg Glu Ala Val
        35                  40                  45

Ala Ser Ile Asn Asp Asp Gly Val Thr Met Tyr Ala Asp Ser Val Lys
    50                  55                  60

Gly Gln Phe Thr Ile Ser Gln Asp Ser Ala Thr Lys Thr Leu Tyr Leu
65                  70                  75                  80

Gln Met Asn Arg Leu Lys Pro Glu Asp Thr Ala Met Tyr Tyr Cys Ala
                85                  90                  95

Ala Thr Pro Glu Gly Tyr Cys Tyr Ala Glu Arg Leu Ser Thr Trp Arg
            100                 105                 110

Tyr Thr Phe Trp Gly Gln Gly Thr Gln Val Thr Val Ser Ser Glu Ser
        115                 120                 125

Lys Tyr Gly Pro Pro Cys Pro Pro Cys Pro Ala Pro Glu Phe Leu Gly
    130                 135                 140

Gly Pro Ser Val Phe Leu Phe Pro Pro Lys Pro Lys Asp Thr Leu Met
145                 150                 155                 160

Ile Ser Arg Thr Pro Glu Val Thr Cys Val Val Val Asp Val Ser Gln
                165                 170                 175

Glu Asp Pro Glu Val Gln Phe Asn Trp Tyr Val Asp Gly Val Glu Val
```

```
            180                 185                 190
His Asn Ala Lys Thr Lys Pro Arg Glu Glu Gln Phe Asn Ser Thr Tyr
        195                 200                 205

Arg Val Val Ser Val Leu Thr Val Leu His Gln Asp Trp Leu Asn Gly
    210                 215                 220

Lys Glu Tyr Lys Cys Lys Val Ser Asn Lys Gly Leu Pro Ser Ser Ile
225                 230                 235                 240

Glu Lys Thr Ile Ser Lys Ala Lys Gly Gln Pro Arg Glu Pro Gln Val
                245                 250                 255

Tyr Thr Leu Pro Pro Ser Gln Glu Glu Met Thr Lys Asn Gln Val Ser
            260                 265                 270

Leu Thr Cys Leu Val Lys Gly Phe Tyr Pro Ser Asp Ile Ala Val Glu
        275                 280                 285

Trp Glu Ser Asn Gly Gln Pro Glu Asn Asn Tyr Lys Thr Thr Pro Pro
    290                 295                 300

Val Leu Asp Ser Asp Gly Ser Phe Phe Leu Tyr Ser Arg Leu Thr Val
305                 310                 315                 320

Asp Lys Ser Arg Trp Gln Glu Gly Asn Val Phe Ser Cys Ser Val Met
                325                 330                 335

His Glu Ala Leu His Asn His Tyr Thr Gln Lys Ser Leu Ser Leu Ser
            340                 345                 350

Leu Gly Lys
        355

<210> SEQ ID NO 357
<211> LENGTH: 352
<212> TYPE: PRT
<213> ORGANISM: Artificial Sequence
<220> FEATURE:
<223> OTHER INFORMATION: Synthetic Construct

<400> SEQUENCE: 357

Glu Val Gln Leu Val Glu Ser Gly Gly Gly Leu Val Gln Pro Gly Gly
1               5                   10                  15

Ser Leu Arg Leu Ser Cys Ala Val Ser Gly Asn Ile Tyr Asn Arg Asn
            20                  25                  30

Phe Met Gly Trp Phe Arg Gln Ala Pro Gly Lys Gly Leu Glu Gly Val
        35                  40                  45

Ser Ala Ile Tyr Thr Gly Thr Ser Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
            85                  90                  95

Ala Ala Asp Leu Arg Asp Gly Phe Trp Asp Thr Gly Val Trp Asn Thr
        100                 105                 110

Trp Gly Gln Gly Thr Leu Val Thr Val Ser Ser Glu Ser Lys Tyr Gly
        115                 120                 125

Pro Pro Cys Pro Pro Cys Pro Ala Pro Glu Phe Leu Gly Gly Pro Ser
        130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser Gln Glu Asp Pro
                165                 170                 175

Glu Val Gln Phe Asn Trp Tyr Val Asp Gly Val Glu Val His Asn Ala
```

```
                    180                 185                 190
Lys Thr Lys Pro Arg Glu Glu Gln Phe Asn Ser Thr Tyr Arg Val Val
                195                 200                 205
Ser Val Leu Thr Val Leu His Gln Asp Trp Leu Asn Gly Lys Glu Tyr
            210                 215                 220
Lys Cys Lys Val Ser Asn Lys Gly Leu Pro Ser Ser Ile Glu Lys Thr
225                 230                 235                 240
Ile Ser Lys Ala Lys Gly Gln Pro Arg Glu Pro Gln Val Tyr Thr Leu
                245                 250                 255
Pro Pro Ser Gln Glu Glu Met Thr Lys Asn Gln Val Ser Leu Thr Cys
            260                 265                 270
Leu Val Lys Gly Phe Tyr Pro Ser Asp Ile Ala Val Glu Trp Glu Ser
            275                 280                 285
Asn Gly Gln Pro Glu Asn Asn Tyr Lys Thr Thr Pro Pro Val Leu Asp
            290                 295                 300
Ser Asp Gly Ser Phe Phe Leu Tyr Ser Arg Leu Thr Val Asp Lys Ser
305                 310                 315                 320
Arg Trp Gln Glu Gly Asn Val Phe Ser Cys Ser Val Met His Glu Ala
                325                 330                 335
Leu His Asn His Tyr Thr Gln Lys Ser Leu Ser Leu Ser Leu Gly Lys
            340                 345                 350

<210> SEQ ID NO 358
<211> LENGTH: 352
<212> TYPE: PRT
<213> ORGANISM: Artificial Sequence
<220> FEATURE:
<223> OTHER INFORMATION: Synthetic Construct

<400> SEQUENCE: 358

Glu Val Gln Leu Val Glu Ser Gly Gly Gly Leu Val Gln Pro Gly Gly
1               5                   10                  15
Ser Leu Arg Leu Ser Cys Ala Val Ser Gly Asn Ile Tyr Asn Arg Asn
                20                  25                  30
Phe Met Gly Trp Phe Arg Gln Ala Pro Gly Lys Gly Leu Glu Gly Val
            35                  40                  45
Ser Ala Ile Tyr Thr Gly Thr Ser Arg Thr Tyr Tyr Ala Asp Ser Val
        50                  55                  60
Lys Gly Arg Phe Thr Ile Ser Arg Asp Asn Ser Lys Asn Thr Val Tyr
65                  70                  75                  80
Leu Gln Met Asn Ser Leu Arg Ala Glu Asp Thr Ala Val Tyr Tyr Cys
                85                  90                  95
Ala Ala Asp Leu Arg Glu Gly Phe Trp Asp Thr Gly Val Trp Asn Thr
            100                 105                 110
Trp Gly Gln Gly Thr Leu Val Thr Val Ser Ser Glu Ser Lys Tyr Gly
        115                 120                 125
Pro Pro Cys Pro Pro Cys Pro Ala Pro Glu Phe Leu Gly Gly Pro Ser
    130                 135                 140
Val Phe Leu Phe Pro Pro Lys Pro Lys Asp Thr Leu Met Ile Ser Arg
145                 150                 155                 160
Thr Pro Glu Val Thr Cys Val Val Val Asp Val Ser Gln Glu Asp Pro
                165                 170                 175
Glu Val Gln Phe Asn Trp Tyr Val Asp Gly Val Glu Val His Asn Ala
            180                 185                 190
Lys Thr Lys Pro Arg Glu Glu Gln Phe Asn Ser Thr Tyr Arg Val Val
```

195                 200                 205
Ser Val Leu Thr Val Leu His Gln Asp Trp Leu Asn Gly Lys Glu Tyr
210                 215                 220

Lys Cys Lys Val Ser Asn Lys Gly Leu Pro Ser Ser Ile Glu Lys Thr
225                 230                 235                 240

Ile Ser Lys Ala Lys Gly Gln Pro Arg Glu Pro Gln Val Tyr Thr Leu
                245                 250                 255

Pro Pro Ser Gln Glu Glu Met Thr Lys Asn Gln Val Ser Leu Thr Cys
                260                 265                 270

Leu Val Lys Gly Phe Tyr Pro Ser Asp Ile Ala Val Glu Trp Glu Ser
                275                 280                 285

Asn Gly Gln Pro Glu Asn Asn Tyr Lys Thr Thr Pro Pro Val Leu Asp
                290                 295                 300

Ser Asp Gly Ser Phe Phe Leu Tyr Ser Arg Leu Thr Val Asp Lys Ser
305                 310                 315                 320

Arg Trp Gln Glu Gly Asn Val Phe Ser Cys Ser Val Met His Glu Ala
                325                 330                 335

Leu His Asn His Tyr Thr Gln Lys Ser Leu Ser Leu Ser Leu Gly Lys
                340                 345                 350

<210> SEQ ID NO 359
<211> LENGTH: 352
<212> TYPE: PRT
<213> ORGANISM: Artificial Sequence
<220> FEATURE:
<223> OTHER INFORMATION: Synthetic Construct

<400> SEQUENCE: 359

Glu Val Gln Leu Val Glu Ser Gly Gly Gly Leu Val Gln Pro Gly Gly
1               5                   10                  15

Ser Leu Arg Leu Ser Cys Ala Val Ser Gly Asn Ile Tyr Asn Arg Asn
                20                  25                  30

Phe Met Gly Trp Phe Arg Gln Ala Pro Gly Lys Gly Arg Glu Gly Val
                35                  40                  45

Ser Ala Ile Tyr Thr Gly Thr Ser Arg Thr Tyr Tyr Ala Asp Ser Val
50                  55                  60

Lys Gly Arg Phe Thr Ile Ser Arg Asp Asn Ala Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Asp Leu Arg Asp Gly Phe Trp Asp Thr Gly Val Trp Asn Thr
                100                 105                 110

Trp Gly Gln Gly Thr Leu Val Thr Val Ser Ser Glu Ser Lys Tyr Gly
                115                 120                 125

Pro Pro Cys Pro Pro Cys Pro Ala Pro Glu Phe Leu Gly Gly Pro Ser
130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser Gln Glu Asp Pro
                165                 170                 175

Glu Val Gln Phe Asn Trp Tyr Val Asp Gly Val Glu Val His Asn Ala
                180                 185                 190

Lys Thr Lys Pro Arg Glu Glu Gln Phe Asn Ser Thr Tyr Arg Val Val
                195                 200                 205

Ser Val Leu Thr Val Leu His Gln Asp Trp Leu Asn Gly Lys Glu Tyr

```
            210                 215                 220
Lys Cys Lys Val Ser Asn Lys Gly Leu Pro Ser Ser Ile Glu Lys Thr
225                 230                 235                 240

Ile Ser Lys Ala Lys Gly Gln Pro Arg Glu Pro Gln Val Tyr Thr Leu
                245                 250                 255

Pro Pro Ser Gln Glu Met Thr Lys Asn Gln Val Ser Leu Thr Cys
                260                 265                 270

Leu Val Lys Gly Phe Tyr Pro Ser Asp Ile Ala Val Glu Trp Glu Ser
                275                 280                 285

Asn Gly Gln Pro Glu Asn Asn Tyr Lys Thr Thr Pro Pro Val Leu Asp
                290                 295                 300

Ser Asp Gly Ser Phe Phe Leu Tyr Ser Arg Leu Thr Val Asp Lys Ser
305                 310                 315                 320

Arg Trp Gln Glu Gly Asn Val Phe Ser Cys Ser Val Met His Glu Ala
                325                 330                 335

Leu His Asn His Tyr Thr Gln Lys Ser Leu Ser Leu Ser Leu Gly Lys
                340                 345                 350
```

<210> SEQ ID NO 360
<211> LENGTH: 352
<212> TYPE: PRT
<213> ORGANISM: Artificial Sequence
<220> FEATURE:
<223> OTHER INFORMATION: Synthetic Construct

<400> SEQUENCE: 360

```
Glu Val Gln Leu Val Glu Ser Gly Gly Gly Leu Val Gln Pro Gly Gly
1               5                   10                  15

Ser Leu Arg Leu Ser Cys Ala Val Ser Gly Asn Ile Tyr Asn Arg Asn
                20                  25                  30

Phe Met Gly Trp Phe Arg Gln Ala Pro Gly Lys Gly Arg Glu Gly Val
            35                  40                  45

Ser Ala Ile Tyr Thr Gly Thr Ser Arg Thr Tyr Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Asp Leu Arg Glu Gly Phe Trp Asp Thr Gly Val Trp Asn Thr
            100                 105                 110

Trp Gly Gln Gly Thr Leu Val Thr Val Ser Ser Glu Ser Lys Tyr Gly
        115                 120                 125

Pro Pro Cys Pro Pro Cys Pro Ala Pro Glu Phe Leu Gly Gly Pro Ser
130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser Gln Glu Asp Pro
                165                 170                 175

Glu Val Gln Phe Asn Trp Tyr Val Asp Gly Val Glu Val His Asn Ala
            180                 185                 190

Lys Thr Lys Pro Arg Glu Glu Gln Phe Asn Ser Thr Tyr Arg Val Val
        195                 200                 205

Ser Val Leu Thr Val Leu His Gln Asp Trp Leu Asn Gly Lys Glu Tyr
    210                 215                 220

Lys Cys Lys Val Ser Asn Lys Gly Leu Pro Ser Ser Ile Glu Lys Thr
```

```
                225                 230                 235                 240
Ile Ser Lys Ala Lys Gly Gln Pro Arg Glu Pro Gln Val Tyr Thr Leu
                245                 250                 255

Pro Pro Ser Gln Glu Glu Met Thr Lys Asn Gln Val Ser Leu Thr Cys
                260                 265                 270

Leu Val Lys Gly Phe Tyr Pro Ser Asp Ile Ala Val Glu Trp Glu Ser
                275                 280                 285

Asn Gly Gln Pro Glu Asn Asn Tyr Lys Thr Thr Pro Pro Val Leu Asp
                290                 295                 300

Ser Asp Gly Ser Phe Phe Leu Tyr Ser Arg Leu Thr Val Asp Lys Ser
305                 310                 315                 320

Arg Trp Gln Glu Gly Asn Val Phe Ser Cys Ser Val Met His Glu Ala
                325                 330                 335

Leu His Asn His Tyr Thr Gln Lys Ser Leu Ser Leu Ser Leu Gly Lys
                340                 345                 350

<210> SEQ ID NO 361
<211> LENGTH: 268
<212> TYPE: PRT
<213> ORGANISM: Homo sapiens

<400> SEQUENCE: 361

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe Val Leu Asn Trp Tyr
                35                  40                  45

Arg Met Ser Pro Ser Asn Gln Thr Asp Lys Leu Ala Ala Phe Pro Glu
                50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
                100                 105                 110

Gln Ile Lys Glu Ser Leu Arg Ala Glu Leu Arg Val Thr Glu Arg Arg
                115                 120                 125

Ala Glu Val Pro Thr Ala His Pro Ser Pro Ser Pro Arg Pro Ala Gly
130                 135                 140

Gln Phe Gln Thr Leu Val Val Gly Val Val Gly Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Pro Leu Lys Glu Asp
                180                 185                 190

Pro Ser Ala Val Pro Val Phe Ser Val Asp Tyr Gly Glu Leu Asp Phe
                195                 200                 205

Gln Trp Arg Glu Lys Thr Pro Glu Pro Pro Val Pro Cys Val Pro Glu
                210                 215                 220

Gln Thr Glu Tyr Ala Thr Ile Val Phe Pro Ser Gly Met Gly Thr Ser
225                 230                 235                 240

Ser Pro Ala Arg Arg Gly Ser Ala Asp Gly Pro Arg Ser Ala Gln Pro
                245                 250                 255
```

-continued

Leu Arg Pro Glu Asp Gly His Cys Ser Trp Pro Leu
        260                 265

<210> SEQ ID NO 362
<211> LENGTH: 150
<212> TYPE: PRT
<213> ORGANISM: Homo sapiens

<400> SEQUENCE: 362

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 363
<211> LENGTH: 217
<212> TYPE: PRT
<213> ORGANISM: Artificial Sequence
<220> FEATURE:
<223> OTHER INFORMATION: Synthetic Construct

<400> SEQUENCE: 363

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn 145              150              155              160

Tyr Lys Thr Thr Pro Val Leu Asp Ser Asp Gly Ser Phe Phe Leu
                165              170              175

Tyr Ser Arg Leu Thr Val Asp Lys Ser Arg Trp Gln Glu Gly Asn Val
            180              185              190

Phe Ser Cys Ser Val Met His Glu Ala Leu His Asn His Tyr Thr Gln
        195              200              205

Lys Ser Leu Ser Leu Ser Leu Gly Lys
    210              215

<210> SEQ ID NO 364
<211> LENGTH: 217
<212> TYPE: PRT
<213> ORGANISM: Artificial Sequence
<220> FEATURE:
<223> OTHER INFORMATION: Synthetic Construct

<400> SEQUENCE: 364

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Ala Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 365
<211> LENGTH: 217
<212> TYPE: PRT
<213> ORGANISM: Artificial Sequence
<220> FEATURE:
<223> OTHER INFORMATION: Synthetic Construct

<400> SEQUENCE: 365

Ala Pro Glu Leu Leu Gly Gly Pro Ser Val Phe Leu Phe Pro Pro Lys
1               5                   10                  15

```
Pro Lys Asp Thr Leu Met Ile Ser Arg Thr Pro Glu Val Thr Cys Val
                 20                  25                  30

Val Val Asp Val Ser His Glu Asp Pro Glu Val Lys Phe Asn Trp Tyr
             35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
210                 215

<210> SEQ ID NO 366
<211> LENGTH: 98
<212> TYPE: PRT
<213> ORGANISM: Homo sapiens

<400> SEQUENCE: 366

Gln Val Gln Leu Val Glu Ser Gly Gly Gly Val Val Gln Pro Gly Gly
1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ser Val Ile Tyr Ser Gly Gly Ser Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys

<210> SEQ ID NO 367
<211> LENGTH: 12
<212> TYPE: PRT
<213> ORGANISM: Artificial Sequence
<220> FEATURE:
<223> OTHER INFORMATION: Synthetic Construct

<400> SEQUENCE: 367

Glu Ser Lys Tyr Gly Pro Pro Cys Pro Pro Cys Pro
1               5                  10
```

<210> SEQ ID NO 368
<211> LENGTH: 15
<212> TYPE: PRT
<213> ORGANISM: Artificial Sequence
<220> FEATURE:
<223> OTHER INFORMATION: Synthetic Construct

<400> SEQUENCE: 368

Glu Pro Lys Ser Ser Asp Lys Thr His Thr Ser Pro Pro Ser Pro
1               5                   10                  15

<210> SEQ ID NO 369
<211> LENGTH: 15
<212> TYPE: PRT
<213> ORGANISM: Artificial Sequence
<220> FEATURE:
<223> OTHER INFORMATION: Synthetic Construct

<400> SEQUENCE: 369

Glu Pro Lys Ser Cys Asp Lys Thr His Thr Cys Pro Pro Cys Pro
1               5                   10                  15

<210> SEQ ID NO 370
<211> LENGTH: 9
<212> TYPE: PRT
<213> ORGANISM: Artificial Sequence
<220> FEATURE:
<223> OTHER INFORMATION: Synthetic Construct

<400> SEQUENCE: 370

Gly Gly Gly Gly Ser Gly Gly Gly Ser
1               5

<210> SEQ ID NO 371
<211> LENGTH: 15
<212> TYPE: PRT
<213> ORGANISM: Artificial Sequence
<220> FEATURE:
<223> OTHER INFORMATION: Synthetic Construct

<400> SEQUENCE: 371

Gly Gly Gly Gly Ser Gly Gly Gly Gly Ser Gly Gly Gly Gly Ser
1               5                   10                  15

<210> SEQ ID NO 372
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Can be present in repeats
      of at least one

<400> SEQUENCE: 372

Gly
1

<210> SEQ ID NO 373
<211> LENGTH: 2
<212> TYPE: PRT
<213> ORGANISM: Artificial Sequence
<220> FEATURE:
<223> OTHER INFORMATION: Synthetic Construct
<220> FEATURE:

```
<221> NAME/KEY: VARIANT
<222> LOCATION: (1)...(2)
<223> OTHER INFORMATION: Can be present in repeats
      of at least one

<400> SEQUENCE: 373

Gly Ser
1

<210> SEQ ID NO 374
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)...(5)
<223> OTHER INFORMATION: Can be present in repeats
      of at least one

<400> SEQUENCE: 374

Gly Ser Gly Gly Ser
1               5

<210> SEQ ID NO 375
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)...(4)
<223> OTHER INFORMATION: Can be present in repeats
      of at least one

<400> SEQUENCE: 375

Gly Gly Gly Ser
1

<210> SEQ ID NO 376
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)...(5)
<223> OTHER INFORMATION: Can be present in repeats
      of at least one

<400> SEQUENCE: 376

Gly Gly Gly Gly Ser
1               5

<210> SEQ ID NO 377
<211> LENGTH: 456
<212> TYPE: PRT
<213> ORGANISM: Artificial Sequence
<220> FEATURE:
<223> OTHER INFORMATION: Synthetic Construct

<400> SEQUENCE: 377

Glu Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30
```

```
Ser Ala Ala Trp Asn Trp Ile Arg Gln Ser Pro Ser Arg Gly Leu Glu
        35                  40                  45

Trp Leu Gly Lys Thr Tyr Tyr Arg Phe Lys Trp Tyr Ser Asp Tyr Ala
    50                  55                  60

Val Ser Val Lys Gly Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Phe Tyr Cys Thr Arg Glu Ser Thr Thr Tyr Asp Leu Leu Ala Gly Pro
            100                 105                 110

Phe Asp Tyr Trp Gly Gln Gly Thr Leu Val Thr Val Ser Ser Ala Ser
            115                 120                 125

Thr Lys Gly Pro Ser Val Phe Pro Leu Ala Pro Ser Ser Lys Ser Thr
        130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
            195                 200                 205

Cys Asn Val Asn His Lys Pro Ser Asn Thr Lys Val Asp Lys Lys Val
        210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
            275                 280                 285

Asp Gly Val Glu Val His Asn Ala Lys Thr Lys Pro Arg Glu Glu Gln
        290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
            355                 360                 365

Lys Asn Gln Val Ser Leu Thr Cys Leu Val Lys Gly Phe Tyr Pro Ser
        370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445
```

```
Ser Leu Ser Leu Ser Pro Gly Lys
    450                 455
```

\<210\> SEQ ID NO 378
\<211\> LENGTH: 220
\<212\> TYPE: PRT
\<213\> ORGANISM: Artificial Sequence
\<220\> FEATURE:
\<223\> OTHER INFORMATION: Synthetic Construct

\<400\> SEQUENCE: 378

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Val Leu Tyr Ser
            20                  25                  30

Ser Asn Asn Lys Lys Tyr Leu Ala Trp Tyr Gln Gln Lys Pro Gly Gln
        35                  40                  45

Pro Pro Asn Leu Leu Ile Tyr Trp Ala Ser Thr Arg Glu Ser Gly Val
    50                  55                  60

Pro Asp Arg Glu Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Phe Thr Phe Gly Pro Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

\<210\> SEQ ID NO 379
\<211\> LENGTH: 446
\<212\> TYPE: PRT
\<213\> ORGANISM: Artificial Sequence
\<220\> FEATURE:
\<223\> OTHER INFORMATION: Synthetic Construct

\<400\> SEQUENCE: 379

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Asn Trp Ile Arg Gln Pro Pro Gly Lys Gly Leu Glu Trp Ile
        35                  40                  45

Gly Glu Ile Asn His Arg Gly Ser Thr Asn Ser Asn Pro Ser Leu Lys
    50                  55                  60

Ser Arg Val Thr Leu Ser Leu Asp Thr Ser Lys Asn Gln Phe Ser Leu
65                  70                  75                  80
```

Lys Leu Arg Ser Val Thr Ala Ala Asp Thr Ala Val Tyr Tyr Cys Ala
                85                  90                  95

Phe Gly Tyr Ser Asp Tyr Glu Tyr Asn Trp Phe Asp Pro Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445

<210> SEQ ID NO 380
<211> LENGTH: 214
<212> TYPE: PRT
<213> ORGANISM: Artificial Sequence
<220> FEATURE:
<223> OTHER INFORMATION: Synthetic Construct

<400> SEQUENCE: 380

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Asn Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 381
<211> LENGTH: 445
<212> TYPE: PRT
<213> ORGANISM: Artificial Sequence
<220> FEATURE:
<223> OTHER INFORMATION: Synthetic Construct

<400> SEQUENCE: 381

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Gln Gly Leu Glu Trp Ile
        35                  40                  45

Gly Asp Ile Tyr Pro Gly Gln Gly Asp Thr Ser Tyr Asn Gln Lys Phe
50                  55                  60

Lys Gly Arg Ala Thr Met Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Gly Gly Ala Phe Pro Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
130                 135                 140
```

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
            195                 200                 205

Asn Thr Lys Val Asp Lys Arg Val Glu Ser Lys Tyr Gly Pro Pro Cys
210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
            435                 440                 445

<210> SEQ ID NO 382
<211> LENGTH: 218
<212> TYPE: PRT
<213> ORGANISM: Artificial Sequence
<220> FEATURE:
<223> OTHER INFORMATION: Synthetic Construct

<400> SEQUENCE: 382

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Glu Tyr Tyr
            20                  25                  30

Gly Thr Ser Leu Met Gln Trp Tyr Gln Gln Lys Pro Gly Gln Pro Pro
        35                  40                  45

Lys Leu Leu Ile Tyr Ala Ala Ser Asn Val Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Arg
            85                  90                  95

Lys Asp Pro Ser Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
                195                 200                 205

Val Thr Lys Ser Phe Asn Arg Gly Glu Cys
210                 215

<210> SEQ ID NO 383
<211> LENGTH: 448
<212> TYPE: PRT
<213> ORGANISM: Artificial Sequence
<220> FEATURE:
<223> OTHER INFORMATION: Synthetic Construct

<400> SEQUENCE: 383

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
            35                  40                  45

Thr Phe Ile Ser Tyr Asp Gly Asn Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
            85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

-continued

```
Asn Thr Lys Val Asp Lys Arg Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 384
<211> LENGTH: 215
<212> TYPE: PRT
<213> ORGANISM: Artificial Sequence
<220> FEATURE:
<223> OTHER INFORMATION: Synthetic Construct

<400> SEQUENCE: 384

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125
```

```
Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 385
<211> LENGTH: 447
<212> TYPE: PRT
<213> ORGANISM: Artificial Sequence
<220> FEATURE:
<223> OTHER INFORMATION: Synthetic Construct

<400> SEQUENCE: 385

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270
```

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 386
<211> LENGTH: 218
<212> TYPE: PRT
<213> ORGANISM: Artificial Sequence
<220> FEATURE:
<223> OTHER INFORMATION: Synthetic Construct

<400> SEQUENCE: 386

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

```
His Lys Val Tyr Ala Cys Glu Val Thr His Gln Gly Leu Ser Ser Pro
        195                 200                 205
Val Thr Lys Ser Phe Asn Arg Gly Glu Cys
    210                 215
```

US 11,713,353 B2

SINGLE-DOMAIN ANTIBODIES AND VARIANTS THEREOF AGAINST PD-1

CROSS REFERENCE TO RELATED APPLICATIONS

This application is a national stage application under 35 U.S.C. § 371 of International Patent Application No. PCT/CN2019/071691, filed internationally on Jan. 15, 2019, which claims priority benefit of International Patent Application No. PCT/CN2018/072589 filed on Jan. 15, 2018, the contents of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 761422000800SEQLIST.TXT, date recorded: May 14, 2020, size: 277,346 bytes).

FIELD OF THE INVENTION

The present invention relates to constructs comprising a single-domain antibody (sdAb) moiety that specifically recognize PD-1, and methods of making and using thereof.

BACKGROUND OF THE INVENTION

An immunoinhibitory receptor that is primarily expressed on activated T and B cells, Programmed Cell Death Receptor 1 (PD-1; also referred to as Programmed Death Receptor 1, Programmed cell death protein 1, CD279), is a member of the immunoglobulin superfamily related to CD28 and cytotoxic T-lymphocyte associated protein-4 (CTLA-4, CD152). PD-1 (and the family members alike) is a type I transmembrane glycoprotein containing an extracellular Ig Variable-type (V-type) domain that binds its ligands and a cytoplasmic tail that binds signaling molecules. The cytoplasmic tail of PD-1 contains two tyrosine-based signaling motifs, an ITIM (immunoreceptor tyrosine-based inhibition motif) and an ITSM (immunoreceptor tyrosine-based switch motif).

PD-1 attenuates T-cell responses when bound by Programmed Cell Death Ligand 1, also referred to as Programmed Death Ligand 1 (PD-L1, CD274, B7-H1), and/or Programmed Cell Death Ligand 2, also referred to as Programmed Death Ligand 2 (PD-L2. CD273, B7-DC). The binding of either of these ligands to PD-1 transduces a signal that inhibits T-cell proliferation, cytokine production, and cytolytic function. Blocking the binding of PD-L1 to PD-1 enhances tumor-specific CD8+ T-cell immunity, facilitating the clearance of tumor cells by the immune system.

Antibody-mediated blockade of PD-1/PD-L1 interaction has entered clinical trials in the treatment of refractory solid tumors, including melanoma, renal cell carcinoma, colorectal cancer, non-small cell lung cancer, and hematologic malignancies. However, there remains a need of an optimal therapy for treating, stabilizing, preventing, and/or delaying the development of various cancers, especially in view of the resistance or relapse upon PD-1/PD-L1 blockade.

The disclosures of all publications, patents, patent applications and published patent applications referred to herein are hereby incorporated herein by reference in their entirety.

BRIEF SUMMARY OF THE INVENTION

The present invention relates to anti-PD-1 constructs comprising an sdAb moiety that specifically recognizes PD-1 (hereinafter referred to as "anti-PD-1 sdAb"), such as anti-PD-1 sdAb, anti-PD-1 HCAb e.g., anti-PD-1 sdAb-Fc fusion protein comprising an anti-PD-1 sdAb fused to a crystalline fragment (Fc) fragment of human immunoglobulin G (IgG), and multispecific (such as bispecific) antigen binding proteins comprising an anti-PD-1 sdAb fused to, for example, other sdAbs, a full-length four-chain antibody or antigen binding fragments thereof (e.g., Fab or scFv), and methods of making and using thereof.

One aspect of the present application provides an isolated anti-PD-1 construct comprising an sdAb moiety specifically recognizing PD-1, wherein the sdAb moiety comprises a CDR1 comprising the amino acid sequence of any one of SEQ ID NOs: 37-72, or a variant thereof comprising up to about 3 (such as about any of 1, 2, or 3) amino acid substitutions; a CDR2 comprising the amino acid sequence of any one of SEQ ID NOs: 109-144, or a variant thereof comprising up to about 3 (such as about any of 1, 2, or 3) amino acid substitutions; and a CDR3 comprising the amino acid sequence of any one of SEQ ID NOs: 181-216, or a variant thereof comprising up to about 3 (such as about any of 1, 2, or 3) amino acid substitutions. In some embodiments, the isolated anti-PD-1 construct comprises an sdAb moiety specifically recognizing PD-1, wherein the sdAb moiety comprises a CDR1 comprising the amino acid sequence of any one of SEQ ID NOs: 37-72, or a variant thereof comprising up to about 3 (such as about any of 1, 2, or 3) amino acid substitutions; a CDR2 comprising the amino acid sequence of any one of SEQ ID NOs: 109-144, or a variant thereof comprising up to about 3 (such as about any of 1, 2, or 3) amino acid substitutions; and a CDR3 comprising the amino acid sequence of any one of SEQ ID NOs: 181-216. In some embodiments, the sdAb moiety specifically recognizing PD-1 comprises a CDR1 comprising the amino acid sequence of any one of SEQ ID NOs: 37-72; a CDR2 comprising the amino acid sequence of any one of SEQ ID NOs: 109-144; and a CDR3 comprising the amino acid sequence of any one of SEQ ID NOs: 181-216; or a variant thereof comprising up to about any of 1, 2, or 3) amino acid substitutions in the CDR regions. In some embodiments, the amino acid substitutions are in CDR1 and/or CDR2, wherein CDR3 comprises the amino acid sequence of any one of SEQ ID NOs: 181-216. In some embodiments, the sdAb moiety specifically recognizing PD-1 comprises a CDR1 comprising the amino acid sequence of any one of SEQ ID NOs: 37-72; a CDR2 comprising the amino acid sequence of any one of SEQ ID NOs: 109-144; and a CDR3 comprising the amino acid sequence of any one of SEQ ID NOs: 181-216.

In some embodiments according to any one of the isolated anti-PD-1 constructs described above, the sdAb moiety specifically recognizing PD-1 comprises any one of the following:

(1) a CDR1 comprising the amino acid sequence of SEQ ID NO: 37, or a variant thereof comprising up to about 3 (such as about any of 1, 2, or 3) amino acid substitutions; a CDR2 comprising the amino acid sequence of SEQ ID NO: 109, or a variant thereof comprising up to about any of 1, 2, or 3) amino acid substitutions; and a CDR3 comprising the amino acid sequence of SEQ ID NO: 181, or a variant thereof comprising up to about 3 (such as about any of 1, 2, or 3) amino acid substitutions;

(2) a CDR1 comprising the amino acid sequence of SEQ ID NO: 38, or a variant thereof comprising up to about 3 (such as about any of 1, 2, or 3) amino acid substitutions; a CDR2 comprising the amino acid sequence of SEQ ID NO: 110, or a variant thereof comprising up to about 3 (such as about any of 1, 2, or 3) amino acid substitutions; and a CDR3 comprising the amino acid sequence of SEQ ID NO: 182, or a variant thereof comprising up to about 3 (such as about any of 1, 2, or 3) amino acid substitutions;
(3) a CDR1 comprising the amino acid sequence of SEQ ID NO: 39, or a variant thereof comprising up to about 3 (such as about any of 1, 2, or 3) amino acid substitutions; a CDR2 comprising the amino acid sequence of SEQ ID NO: 111, or a variant thereof comprising up to about 3 (such as about any of 1, 2, or 3) amino acid substitutions; and a CDR3 comprising the amino acid sequence of SEQ ID NO: 183, or a variant thereof comprising up to about 3 (such as about any of 1, 2, or 3) amino acid substitutions;
(4) a CDR1 comprising the amino acid sequence of SEQ ID NO: 40, or a variant thereof comprising up to about 3 (such as about any of 1, 2, or 3) amino acid substitutions; a CDR2 comprising the amino acid sequence of SEQ ID NO: 112, or a variant thereof comprising up to about 3 (such as about any of 1, 2, or 3) amino acid substitutions; and a CDR3 comprising the amino acid sequence of SEQ ID NO: 184, or a variant thereof comprising up to about 3 (such as about any of 1, 2, or 3) amino acid substitutions;
(5) a CDR1 comprising the amino acid sequence of SEQ ID NO: 41, or a variant thereof comprising up to about 3 (such as about any of 1, 2, or 3) amino acid substitutions; a CDR2 comprising the amino acid sequence of SEQ ID NO: 113, or a variant thereof comprising up to about 3 (such as about any of 1, 2, or 3) amino acid substitutions; and a CDR3 comprising the amino acid sequence of SEQ ID NO: 185, or a variant thereof comprising up to about 3 (such as about any of 1, 2, or 3) amino acid substitutions;
(6) a CDR1 comprising the amino acid sequence of SEQ ID NO: 42, or a variant thereof comprising up to about 3 (such as about any of 1, 2, or 3) amino acid substitutions; a CDR2 comprising the amino acid sequence of SEQ ID NO: 114, or a variant thereof comprising up to about 3 (such as about any of 1, 2, or 3) amino acid substitutions; and a CDR3 comprising the amino acid sequence of SEQ ID NO: 186, or a variant thereof comprising up to about 3 (such as about any of 1, 2, or 3) amino acid substitutions;
(7) a CDR1 comprising the amino acid sequence of SEQ ID NO: 43, or a variant thereof comprising up to about 3 (such as about any of 1, 2, or 3) amino acid substitutions; a CDR2 comprising the amino acid sequence of SEQ ID NO: 115, or a variant thereof comprising up to about 3 (such as about any of 1, 2, or 3) amino acid substitutions; and a CDR3 comprising the amino acid sequence of SEQ ID NO: 187, or a variant thereof comprising up to about 3 (such as about any of 1, 2, or 3) amino acid substitutions;
(8) a CDR1 comprising the amino acid sequence of SEQ ID NO: 44, or a variant thereof comprising up to about 3 (such as about any of 1, 2, or 3) amino acid substitutions; a CDR2 comprising the amino acid sequence of SEQ ID NO: 116, or a variant thereof comprising up to about 3 (such as about any of 1, 2, or 3) amino acid substitutions; and a CDR3 comprising the amino acid sequence of SEQ ID NO: 188, or a variant thereof comprising up to about 3 (such as about any of 1, 2, or 3) amino acid substitutions;
(9) a CDR1 comprising the amino acid sequence of SEQ ID NO: 45, or a variant thereof comprising up to about 3 (such as about any of 1, 2, or 3) amino acid substitutions; a CDR2 comprising the amino acid sequence of SEQ ID NO: 117, or a variant thereof comprising up to about 3 (such as about any of 1, 2, or 3) amino acid substitutions; and a CDR3 comprising the amino acid sequence of SEQ ID NO: 189, or a variant thereof comprising up to about 3 (such as about any of 1, 2, or 3) amino acid substitutions;
(10) a CDR1 comprising the amino acid sequence of SEQ ID NO: 46, or a variant thereof comprising up to about 3 (such as about any of 1, 2, or 3) amino acid substitutions; a CDR2 comprising the amino acid sequence of SEQ ID NO: 118, or a variant thereof comprising up to about 3 (such as about any of 1, 2, or 3) amino acid substitutions; and a CDR3 comprising the amino acid sequence of SEQ ID NO: 190, or a variant thereof comprising up to about 3 (such as about any of 1, 2, or 3) amino acid substitutions;
(11) a CDR1 comprising the amino acid sequence of SEQ ID NO: 47, or a variant thereof comprising up to about 3 (such as about any of 1, 2, or 3) amino acid substitutions; a CDR2 comprising the amino acid sequence of SEQ ID NO: 119, or a variant thereof comprising up to about 3 (such as about any of 1, 2, or 3) amino acid substitutions; and a CDR3 comprising the amino acid sequence of SEQ ID NO: 191, or a variant thereof comprising up to about 3 (such as about any of 1, 2, or 3) amino acid substitutions;
(12) a CDR1 comprising the amino acid sequence of SEQ ID NO: 48, or a variant thereof comprising up to about 3 (such as about any of 1, 2, or 3) amino acid substitutions; a CDR2 comprising the amino acid sequence of SEQ ID NO: 120, or a variant thereof comprising up to about 3 (such as about any of 1, 2, or 3) amino acid substitutions; and a CDR3 comprising the amino acid sequence of SEQ ID NO: 192, or a variant thereof comprising up to about 3 (such as about any of 1, 2, or 3) amino acid substitutions;
(13) a CDR1 comprising the amino acid sequence of SEQ ID NO: 49, or a variant thereof comprising up to about 3 (such as about any of 1, 2, or 3) amino acid substitutions; a CDR2 comprising the amino acid sequence of SEQ ID NO: 121, or a variant thereof comprising up to about 3 (such as about any of 1, 2, or 3) amino acid substitutions; and a CDR3 comprising the amino acid sequence of SEQ ID NO: 193, or a variant thereof comprising up to about 3 (such as about any of 1, 2, or 3) amino acid substitutions;
(14) a CDR1 comprising the amino acid sequence of SEQ ID NO: 50, or a variant thereof comprising up to about 3 (such as about any of 1, 2, or 3) amino acid substitutions; a CDR2 comprising the amino acid sequence of SEQ ID NO: 122, or a variant thereof comprising up to about 3 (such as about any of 1, 2, or 3) amino acid substitutions; and a CDR3 comprising the amino acid sequence of SEQ ID NO: 194, or a variant thereof comprising up to about 3 (such as about any of 1, 2, or 3) amino acid substitutions;
(15) a CDR1 comprising the amino acid sequence of SEQ ID NO: 51, or a variant thereof comprising up to about 3 (such as about any of 1, 2, or 3) amino acid substitutions; a CDR2 comprising the amino acid sequence of SEQ ID NO: 123, or a variant thereof comprising up to about 3 (such as about any of 1, 2, or 3) amino acid substitutions; and a CDR3 comprising the amino acid sequence of SEQ ID NO: 195, or a variant thereof comprising up to about 3 (such as about any of 1, 2, or 3) amino acid substitutions;
(16) a CDR1 comprising the amino acid sequence of SEQ ID NO: 52, or a variant thereof comprising up to about 3 (such as about any of 1, 2, or 3) amino acid substitutions; a CDR2 comprising the amino acid sequence of SEQ ID NO: 124, or a variant thereof comprising up to about 3 (such as about any of 1, 2, or 3) amino acid substitutions; and a CDR3 comprising the amino acid sequence of SEQ ID NO: 196, or a variant thereof comprising up to about 3 (such as about any of 1, 2, or 3) amino acid substitutions;
(17) a CDR1 comprising the amino acid sequence of SEQ ID NO: 53, or a variant thereof comprising up to about 3 (such as about any of 1, 2, or 3) amino acid substitutions; a CDR2 comprising the amino acid sequence of SEQ ID NO: 125, or a variant thereof comprising up to about 3 (such as about any of 1, 2, or 3) amino acid substitutions; and a CDR3 comprising the amino acid sequence of SEQ ID NO: 197, or a variant thereof comprising up to about 3 (such as about any of 1, 2, or 3) amino acid substitutions;

(18) a CDR1 comprising the amino acid sequence of SEQ ID NO: 54, or a variant thereof comprising up to about 3 (such as about any of 1, 2, or 3) amino acid substitutions; a CDR2 comprising the amino acid sequence of SEQ ID NO: 126, or a variant thereof comprising up to about 3 (such as about any of 1, 2, or 3) amino acid substitutions; and a CDR3 comprising the amino acid sequence of SEQ ID NO: 198, or a variant thereof comprising up to about 3 (such as about any of 1, 2, or 3) amino acid substitutions;

(19) a CDR1 comprising the amino acid sequence of SEQ ID NO: 55, or a variant thereof comprising up to about 3 (such as about any of 1, 2, or 3) amino acid substitutions; a CDR2 comprising the amino acid sequence of SEQ ID NO: 127, or a variant thereof comprising up to about 3 (such as about any of 1, 2, or 3) amino acid substitutions; and a CDR3 comprising the amino acid sequence of SEQ ID NO: 199, or a variant thereof comprising up to about 3 (such as about any of 1, 2, or 3) amino acid substitutions;

(20) a CDR1 comprising the amino acid sequence of SEQ ID NO: 56, or a variant thereof comprising up to about 3 (such as about any of 1, 2, or 3) amino acid substitutions; a CDR2 comprising the amino acid sequence of SEQ ID NO: 128, or a variant thereof comprising up to about 3 (such as about any of 1, 2, or 3) amino acid substitutions; and a CDR3 comprising the amino acid sequence of SEQ ID NO: 200, or a variant thereof comprising up to about 3 (such as about any of 1, 2, or 3) amino acid substitutions;

(21) a CDR1 comprising the amino acid sequence of SEQ ID NO: 57, or a variant thereof comprising up to about 3 (such as about any of 1, 2, or 3) amino acid substitutions; a CDR2 comprising the amino acid sequence of SEQ ID NO: 129, or a variant thereof comprising up to about 3 (such as about any of 1, 2, or 3) amino acid substitutions; and a CDR3 comprising the amino acid sequence of SEQ ID NO: 201, or a variant thereof comprising up to about 3 (such as about any of 1, 2, or 3) amino acid substitutions;

(22) a CDR1 comprising the amino acid sequence of SEQ ID NO: 58, or a variant thereof comprising up to about 3 (such as about any of 1, 2, or 3) amino acid substitutions; a CDR2 comprising the amino acid sequence of SEQ ID NO: 130, or a variant thereof comprising up to about 3 (such as about any of 1, 2, or 3) amino acid substitutions; and a CDR3 comprising the amino acid sequence of SEQ ID NO: 202, or a variant thereof comprising up to about 3 (such as about any of 1, 2, or 3) amino acid substitutions;

(23) a CDR1 comprising the amino acid sequence of SEQ ID NO: 59, or a variant thereof comprising up to about 3 (such as about any of 1, 2, or 3) amino acid substitutions; a CDR2 comprising the amino acid sequence of SEQ ID NO: 131, or a variant thereof comprising up to about 3 (such as about any of 1, 2, or 3) amino acid substitutions; and a CDR3 comprising the amino acid sequence of SEQ ID NO: 203, or a variant thereof comprising up to about 3 (such as about any of 1, 2, or 3) amino acid substitutions;

(24) a CDR1 comprising the amino acid sequence of SEQ ID NO: 60, or a variant thereof comprising up to about 3 (such as about any of 1, 2, or 3) amino acid substitutions; a CDR2 comprising the amino acid sequence of SEQ ID NO: 132, or a variant thereof comprising up to about 3 (such as about any of 1, 2, or 3) amino acid substitutions; and a CDR3 comprising the amino acid sequence of SEQ ID NO: 204, or a variant thereof comprising up to about 3 (such as about any of 1, 2, or 3) amino acid substitutions;

(25) a CDR1 comprising the amino acid sequence of SEQ ID NO: 61, or a variant thereof comprising up to about 3 (such as about any of 1, 2, or 3) amino acid substitutions; a CDR2 comprising the amino acid sequence of SEQ ID NO: 133, or a variant thereof comprising up to about 3 (such as about any of 1, 2, or 3) amino acid substitutions; and a CDR3 comprising the amino acid sequence of SEQ ID NO: 205, or a variant thereof comprising up to about 3 (such as about any of 1, 2, or 3) amino acid substitutions;

(26) a CDR1 comprising the amino acid sequence of SEQ ID NO: 62, or a variant thereof comprising up to about 3 (such as about any of 1, 2, or 3) amino acid substitutions; a CDR2 comprising the amino acid sequence of SEQ ID NO: 134, or a variant thereof comprising up to about 3 (such as about any of 1, 2, or 3) amino acid substitutions; and a CDR3 comprising the amino acid sequence of SEQ ID NO: 206, or a variant thereof comprising up to about 3 (such as about any of 1, 2, or 3) amino acid substitutions;

(27) a CDR1 comprising the amino acid sequence of SEQ ID NO: 63, or a variant thereof comprising up to about 3 (such as about any of 1, 2, or 3) amino acid substitutions; a CDR2 comprising the amino acid sequence of SEQ ID NO: 135, or a variant thereof comprising up to about 3 (such as about any of 1, 2, or 3) amino acid substitutions; and a CDR3 comprising the amino acid sequence of SEQ ID NO: 207, or a variant thereof comprising up to about 3 (such as about any of 1, 2, or 3) amino acid substitutions;

(28) a CDR1 comprising the amino acid sequence of SEQ ID NO: 64, or a variant thereof comprising up to about 3 (such as about any of 1, 2, or 3) amino acid substitutions; a CDR2 comprising the amino acid sequence of SEQ ID NO: 136, or a variant thereof comprising up to about 3 (such as about any of 1, 2, or 3) amino acid substitutions; and a CDR3 comprising the amino acid sequence of SEQ ID NO: 208, or a variant thereof comprising up to about 3 (such as about any of 1, 2, or 3) amino acid substitutions;

(29) a CDR1 comprising the amino acid sequence of SEQ ID NO: 65, or a variant thereof comprising up to about 3 (such as about any of 1, 2, or 3) amino acid substitutions; a CDR2 comprising the amino acid sequence of SEQ ID NO: 137, or a variant thereof comprising up to about 3 (such as about any of 1, 2, or 3) amino acid substitutions; and a CDR3 comprising the amino acid sequence of SEQ ID NO: 209, or a variant thereof comprising up to about 3 (such as about any of 1, 2, or 3) amino acid substitutions;

(30) a CDR1 comprising the amino acid sequence of SEQ ID NO: 66, or a variant thereof comprising up to about 3 (such as about any of 1, 2, or 3) amino acid substitutions; a CDR2 comprising the amino acid sequence of SEQ ID NO: 138, or a variant thereof comprising up to about 3 (such as about any of 1, 2, or 3) amino acid substitutions; and a CDR3 comprising the amino acid sequence of SEQ ID NO: 210, or a variant thereof comprising up to about 3 (such as about any of 1, 2, or 3) amino acid substitutions;

(31) a CDR1 comprising the amino acid sequence of SEQ ID NO: 67, or a variant thereof comprising up to about 3 (such as about any of 1, 2, or 3) amino acid substitutions; a CDR2 comprising the amino acid sequence of SEQ ID NO: 139, or a variant thereof comprising up to about 3 (such as about any of 1, 2, or 3) amino acid substitutions; and a CDR3 comprising the amino acid sequence of SEQ ID NO: 211, or a variant thereof comprising up to about 3 (such as about any of 1, 2, or 3) amino acid substitutions;

(32) a CDR1 comprising the amino acid sequence of SEQ ID NO: 68, or a variant thereof comprising up to about 3 (such as about any of 1, 2, or 3) amino acid substitutions; a CDR2 comprising the amino acid sequence of SEQ ID NO: 140, or a variant thereof comprising up to about 3 (such as about any of 1, 2, or 3) amino acid substitutions; and a CDR3 comprising the amino acid sequence of SEQ ID NO: 212, or a variant thereof comprising up to about 3 (such as about any of 1, 2, or 3) amino acid substitutions;

(33) a CDR1 comprising the amino acid sequence of SEQ ID NO: 69, or a variant thereof comprising up to about 3 (such as about any of 1, 2, or 3) amino acid substitutions; a CDR2 comprising the amino acid sequence of SEQ ID NO: 141, or a variant thereof comprising up to about 3 (such as about any of 1, 2, or 3) amino acid substitutions; and a CDR3 comprising the amino acid sequence of SEQ ID NO: 213, or a variant thereof comprising up to about 3 (such as about any of 1, 2, or 3) amino acid substitutions;

(34) a CDR1 comprising the amino acid sequence of SEQ ID NO: 70, or a variant thereof comprising up to about 3 (such as about any of 1, 2, or 3) amino acid substitutions; a CDR2 comprising the amino acid sequence of SEQ ID NO: 142, or a variant thereof comprising up to about 3 (such as about any of 1, 2, or 3) amino acid substitutions; and a CDR3 comprising the amino acid sequence of SEQ ID NO: 214, or a variant thereof comprising up to about 3 (such as about any of 1, 2, or 3) amino acid substitutions;

(35) a CDR1 comprising the amino acid sequence of SEQ ID NO: 71, or a variant thereof comprising up to about 3 (such as about any of 1, 2, or 3) amino acid substitutions; a CDR2 comprising the amino acid sequence of SEQ ID NO: 143, or a variant thereof comprising up to about 3 (such as about any of 1, 2, or 3) amino acid substitutions; and a CDR3 comprising the amino acid sequence of SEQ ID NO: 215, or a variant thereof comprising up to about 3 (such as about any of 1, 2, or 3) amino acid substitutions; or

(35) a CDR1 comprising the amino acid sequence of SEQ ID NO: 72, or a variant thereof comprising up to about 3 (such as about any of 1, 2, or 3) amino acid substitutions; a CDR2 comprising the amino acid sequence of SEQ ID NO: 144, or a variant thereof comprising up to about 3 (such as about any of 1, 2, or 3) amino acid substitutions; and a CDR3 comprising the amino acid sequence of SEQ ID NO: 216, or a variant thereof comprising up to about 3 (such as about any of 1, 2, or 3) amino acid substitutions.

In some embodiments according to any one of the isolated anti-PD-1 constructs described above, the sdAb moiety specifically recognizing PD-1 comprises any one of the following:

(1) a CDR1 comprising the amino acid sequence of SEQ ID NO: 37; a CDR2 comprising the amino acid sequence of SEQ ID NO: 109; and a CDR3 comprising the amino acid sequence of SEQ ID NO: 181; or a variant thereof comprising up to about 3 (such as about any of 1, 2, or 3) amino acid substitutions in the CDR regions;

(2) a CDR1 comprising the amino acid sequence of SEQ ID NO: 38; a CDR2 comprising the amino acid sequence of SEQ ID NO: 110; and a CDR3 comprising the amino acid sequence of SEQ ID NO: 182; or a variant thereof comprising up to about 3 (such as about any of 1, 2, or 3) amino acid substitutions in the CDR regions;

(3) a CDR1 comprising the amino acid sequence of SEQ ID NO: 39; a CDR2 comprising the amino acid sequence of SEQ ID NO: 111; and a CDR3 comprising the amino acid sequence of SEQ ID NO: 183; or a variant thereof comprising up to about 3 (such as about any of 1, 2, or 3) amino acid substitutions in the CDR regions;

(4) a CDR1 comprising the amino acid sequence of SEQ ID NO: 40; a CDR2 comprising the amino acid sequence of SEQ ID NO: 112; and a CDR3 comprising the amino acid sequence of SEQ ID NO: 184; or a variant thereof comprising up to about 3 (such as about any of 1, 2, or 3) amino acid substitutions in the CDR regions;

(5) a CDR1 comprising the amino acid sequence of SEQ ID NO: 41; a CDR2 comprising the amino acid sequence of SEQ ID NO: 113; and a CDR3 comprising the amino acid sequence of SEQ ID NO: 185; or a variant thereof comprising up to about 3 (such as about any of 1, 2, or 3) amino acid substitutions in the CDR regions;

(6) a CDR1 comprising the amino acid sequence of SEQ ID NO: 42; a CDR2 comprising the amino acid sequence of SEQ ID NO: 114; and a CDR3 comprising the amino acid sequence of SEQ ID NO: 186; or a variant thereof comprising up to about 3 (such as about any of 1, 2, or 3) amino acid substitutions in the CDR regions;

(7) a CDR1 comprising the amino acid sequence of SEQ ID NO: 43; a CDR2 comprising the amino acid sequence of SEQ ID NO: 115; and a CDR3 comprising the amino acid sequence of SEQ ID NO: 187; or a variant thereof comprising up to about 3 (such as about any of 1, 2, or 3) amino acid substitutions in the CDR regions;

(8) a CDR1 comprising the amino acid sequence of SEQ ID NO: 44; a CDR2 comprising the amino acid sequence of SEQ ID NO: 116; and a CDR3 comprising the amino acid sequence of SEQ ID NO: 188; or a variant thereof comprising up to about 3 (such as about any of 1, 2, or 3) amino acid substitutions in the CDR regions;

(9) a CDR1 comprising the amino acid sequence of SEQ ID NO: 45; a CDR2 comprising the amino acid sequence of SEQ ID NO: 117; and a CDR3 comprising the amino acid sequence of SEQ ID NO: 189; or a variant thereof comprising up to about 3 (such as about any of 1, 2, or 3) amino acid substitutions in the CDR regions;

(10) a CDR1 comprising the amino acid sequence of SEQ ID NO: 46; a CDR2 comprising the amino acid sequence of SEQ ID NO: 118; and a CDR3 comprising the amino acid sequence of SEQ ID NO: 190; or a variant thereof comprising up to about 3 (such as about any of 1, 2, or 3) amino acid substitutions in the CDR regions;

(11) a CDR1 comprising the amino acid sequence of SEQ ID NO: 47; a CDR2 comprising the amino acid sequence of SEQ ID NO: 119; and a CDR3 comprising the amino acid sequence of SEQ ID NO: 191; or a variant thereof comprising up to about 3 (such as about any of 1, 2, or 3) amino acid substitutions in the CDR regions;

(12) a CDR1 comprising the amino acid sequence of SEQ ID NO: 48; a CDR2 comprising the amino acid sequence of SEQ ID NO: 120; and a CDR3 comprising the amino acid sequence of SEQ ID NO: 192; or a variant thereof comprising up to about 3 (such as about any of 1, 2, or 3) amino acid substitutions in the CDR regions;

(13) a CDR1 comprising the amino acid sequence of SEQ ID NO: 49; a CDR2 comprising the amino acid sequence of SEQ ID NO: 121; and a CDR3 comprising the amino acid sequence of SEQ ID NO: 193; or a variant thereof comprising up to about 3 (such as about any of 1, 2, or 3) amino acid substitutions in the CDR regions;

(14) a CDR1 comprising the amino acid sequence of SEQ ID NO: 50; a CDR2 comprising the amino acid sequence of SEQ ID NO: 122; and a CDR3 comprising the amino acid sequence of SEQ ID NO: 194; or a variant thereof comprising up to about 3 (such as about any of 1, 2, or 3) amino acid substitutions in the CDR regions;

(15) a CDR1 comprising the amino acid sequence of SEQ ID NO: 51; a CDR2 comprising the amino acid sequence of SEQ ID NO: 123; and a CDR3 comprising the amino acid sequence of SEQ ID NO: 195; or a variant thereof comprising up to about 3 (such as about any of 1, 2, or 3) amino acid substitutions in the CDR regions;

(16) a CDR1 comprising the amino acid sequence of SEQ ID NO: 52; a CDR2 comprising the amino acid sequence of SEQ ID NO: 124; and a CDR3 comprising the amino acid sequence of SEQ ID NO: 196; or a variant thereof comprising up to about 3 (such as about any of 1, 2, or 3) amino acid substitutions in the CDR regions;

(17) a CDR1 comprising the amino acid sequence of SEQ ID NO: 53; a CDR2 comprising the amino acid sequence of SEQ ID NO: 125; and a CDR3 comprising the amino acid sequence of SEQ ID NO: 197; or a variant thereof comprising up to about 3 (such as about any of 1, 2, or 3) amino acid substitutions in the CDR regions;

(18) a CDR1 comprising the amino acid sequence of SEQ ID NO: 54; a CDR2 comprising the amino acid sequence of SEQ ID NO: 126; and a CDR3 comprising the amino acid sequence of SEQ ID NO: 198; or a variant thereof comprising up to about 3 (such as about any of 1, 2, or 3) amino acid substitutions in the CDR regions;

(19) a CDR1 comprising the amino acid sequence of SEQ ID NO: 55; a CDR2 comprising the amino acid sequence of SEQ ID NO: 127; and a CDR3 comprising the amino acid sequence of SEQ ID NO: 199; or a variant thereof comprising up to about 3 (such as about any of 1, 2, or 3) amino acid substitutions in the CDR regions;

(20) a CDR1 comprising the amino acid sequence of SEQ ID NO: 56; a CDR2 comprising the amino acid sequence of SEQ ID NO: 128; and a CDR3 comprising the amino acid sequence of SEQ ID NO: 200; or a variant thereof comprising up to about 3 (such as about any of 1, 2, or 3) amino acid substitutions in the CDR regions;

(21) a CDR1 comprising the amino acid sequence of SEQ ID NO: 57; a CDR2 comprising the amino acid sequence of SEQ ID NO: 129; and a CDR3 comprising the amino acid sequence of SEQ ID NO: 201; or a variant thereof comprising up to about 3 (such as about any of 1, 2, or 3) amino acid substitutions in the CDR regions;

(22) a CDR1 comprising the amino acid sequence of SEQ ID NO: 58; a CDR2 comprising the amino acid sequence of SEQ ID NO: 130; and a CDR3 comprising the amino acid sequence of SEQ ID NO: 202; or a variant thereof comprising up to about 3 (such as about any of 1, 2, or 3) amino acid substitutions in the CDR regions;

(23) a CDR1 comprising the amino acid sequence of SEQ ID NO: 59; a CDR2 comprising the amino acid sequence of SEQ ID NO: 131; and a CDR3 comprising the amino acid sequence of SEQ ID NO: 203; or a variant thereof comprising up to about 3 (such as about any of 1, 2, or 3) amino acid substitutions in the CDR regions;

(24) a CDR1 comprising the amino acid sequence of SEQ ID NO: 60; a CDR2 comprising the amino acid sequence of SEQ ID NO: 132; and a CDR3 comprising the amino acid sequence of SEQ ID NO: 204; or a variant thereof comprising up to about 3 (such as about any of 1, 2, or 3) amino acid substitutions in the CDR regions;

(25) a CDR1 comprising the amino acid sequence of SEQ ID NO: 61; a CDR2 comprising the amino acid sequence of SEQ ID NO: 133; and a CDR3 comprising the amino acid sequence of SEQ ID NO: 205; or a variant thereof comprising up to about 3 (such as about any of 1, 2, or 3) amino acid substitutions in the CDR regions;

(26) a CDR1 comprising the amino acid sequence of SEQ ID NO: 62; a CDR2 comprising the amino acid sequence of SEQ ID NO: 134; and a CDR3 comprising the amino acid sequence of SEQ ID NO: 206; or a variant thereof comprising up to about 3 (such as about any of 1, 2, or 3) amino acid substitutions in the CDR regions;

(27) a CDR1 comprising the amino acid sequence of SEQ ID NO: 63; a CDR2 comprising the amino acid sequence of SEQ ID NO: 135; and a CDR3 comprising the amino acid sequence of SEQ ID NO: 207; or a variant thereof comprising up to about 3 (such as about any of 1, 2, or 3) amino acid substitutions in the CDR regions;

(28) a CDR1 comprising the amino acid sequence of SEQ ID NO: 64; a CDR2 comprising the amino acid sequence of SEQ ID NO: 136; and a CDR3 comprising the amino acid sequence of SEQ ID NO: 208; or a variant thereof comprising up to about 3 (such as about any of 1, 2, or 3) amino acid substitutions in the CDR regions;

(29) a CDR1 comprising the amino acid sequence of SEQ ID NO: 65; a CDR2 comprising the amino acid sequence of SEQ ID NO: 137; and a CDR3 comprising the amino acid sequence of SEQ ID NO: 209; or a variant thereof comprising up to about 3 (such as about any of 1, 2, or 3) amino acid substitutions in the CDR regions;

(30) a CDR1 comprising the amino acid sequence of SEQ ID NO: 66; a CDR2 comprising the amino acid sequence of SEQ ID NO: 138; and a CDR3 comprising the amino acid sequence of SEQ ID NO: 210; or a variant thereof comprising up to about 3 (such as about any of 1, 2, or 3) amino acid substitutions in the CDR regions;

(31) a CDR1 comprising the amino acid sequence of SEQ ID NO: 67; a CDR2 comprising the amino acid sequence of SEQ ID NO: 139; and a CDR3 comprising the amino acid sequence of SEQ ID NO: 211; or a variant thereof comprising up to about 3 (such as about any of 1, 2, or 3) amino acid substitutions in the CDR regions;

(32) a CDR1 comprising the amino acid sequence of SEQ ID NO: 68; a CDR2 comprising the amino acid sequence of SEQ ID NO: 140; and a CDR3 comprising the amino acid sequence of SEQ ID NO: 212; or a variant thereof comprising up to about 3 (such as about any of 1, 2, or 3) amino acid substitutions in the CDR regions;

(33) a CDR1 comprising the amino acid sequence of SEQ ID NO: 69; a CDR2 comprising the amino acid sequence of SEQ ID NO: 141; and a CDR3 comprising the amino acid sequence of SEQ ID NO: 213; or a variant thereof comprising up to about 3 (such as about any of 1, 2, or 3) amino acid substitutions in the CDR regions;

(34) a CDR1 comprising the amino acid sequence of SEQ ID NO: 70; a CDR2 comprising the amino acid sequence of SEQ ID NO: 142; and a CDR3 comprising the amino acid sequence of SEQ ID NO: 214; or a variant thereof comprising up to about 3 (such as about any of 1, 2, or 3) amino acid substitutions in the CDR regions;

(35) a CDR1 comprising the amino acid sequence of SEQ ID NO: 71; a CDR2 comprising the amino acid sequence of SEQ ID NO: 143; and a CDR3 comprising the amino acid sequence of SEQ ID NO: 215; or a variant thereof comprising up to about 3 (such as about any of 1, 2, or 3) amino acid substitutions in the CDR regions; or

(36) a CDR1 comprising the amino acid sequence of SEQ ID NO: 72; a CDR2 comprising the amino acid sequence of SEQ ID NO: 144; and a CDR3 comprising the amino acid sequence of SEQ ID NO: 216; or a variant thereof comprising up to about 3 (such as about any of 1, 2, or 3) amino acid substitutions in the CDR regions.

In some embodiments according to any one of the isolated anti-PD-1 constructs described above, the sdAb moiety specifically recognizing PD-1 comprises a $V_H H$ domain comprising the amino acid sequence of any one of the following: a-1) the amino acid residue at position 37 is selected from the group consisting of F, Y, L, I, and V (such as F, Y or V, or such as F); a-2) the amino acid residue at position 44 is selected from the group consisting of A, G, E, D, G, Q, R, S, and L (such as E, Q, or G, or such as E); a-3) the amino acid residue at position 45 is selected from the group consisting of L, R, and C (such as L or R); a-4) the amino acid residue at position 103 is selected from the group consisting of W, R, G, and S (such as W, G, or R, or such as W); and a-5) the amino acid residue at position 108 is Q; or b-1) the amino acid residue at position 37 is selected from the group consisting of F, Y, L, I, and V (such as F, V or Y, or such as F); b-2) the amino acid residue at position 44 is selected from the group consisting of E, Q, and G; b-3) the amino acid residue at position 45 is R; b-4) the amino acid residue at position 103 is selected from the group consisting of W, R, and S (such as W); and b-5) the amino acid residue at position 108 is selected from the group consisting of Q and L (such as Q); wherein the amino acid position is according to Kabat numbering, and wherein position 108 can be optionally humanized to L when position 108 is Q.

In some embodiments according to any one of the isolated anti-PD-1 constructs described above, the sdAb moiety specifically recognizing PD-1 comprises a $V_HH$ domain comprising the amino acid sequence of any one of SEQ ID NOs: 289-324, or a variant thereof having at least about 80% (such as at least about any of 80%, 85%, 90%, 91%, 92%, 93%, 94%, 95%, 96%, 97%, 98%, or 99%) sequence identify to any one of SEQ ID NOs: 289-324. In some embodiments, the sdAb moiety specifically recognizing PD-1 comprises a $V_HH$ domain comprising the amino acid sequence of any one of SEQ ID NOs: 289-324, or a variant thereof comprising up to about 3 (such as about any of 1, 2, or 3) amino acid substitutions in the $V_HH$ domain. In some embodiments, the amino acid substitutions are in the CDRs, such as the CDR1, and/or the CDR2, and/or the CDR3 of any one of SEQ ID NOs: 289-324. In some embodiments, the amino acid substitutions are in the FRs, such as the FR1, and/or the FR2, and/or the FR3, and/or the FR4 of any one of SEQ ID NOs: 289-324. In some embodiments, the amino acid substitutions are in both CDRs and FRs. In some embodiments, the sdAb moiety specifically recognizing PD-1 comprises a $V_HH$ domain comprising the amino acid sequence of any one of SEQ ID NOs: 289-324.

In some embodiments according to any one of the isolated anti-PD-1 constructs described above, the $K_d$ of the binding between the sdAb moiety specifically recognizing PD-1 and PD-1 is about $10^{-5}$ M to about $10^{-12}$ M (such as about $10^{-5}$ M to about $10^{-12}$ M, about $10^{-7}$ M to about $10^{-12}$ M, or about $10^{-8}$ M to about $10^{-12}$ M).

In some embodiments according to any one of the isolated anti-PD-1 constructs described above, the sdAb moiety specifically recognizing PD-1 is camelid, chimeric, human, partially humanized, or fully humanized.

In some embodiments according to any one of the isolated anti-PD-1 constructs described above, the isolated anti-PD-1 construct is a heavy chain-only antibody (HCAb) comprising the sdAb moiety specifically recognizing PD-1 fused to an Fc fragment via an optional linker. In some embodiments, HCAb is monomeric. In some embodiments, the HCAb is dimeric. In some embodiments, the Fc fragment is a human IgG1 (hIgG1) Fc, effectorless (inert) hIgG1 Fc, hIgG4 Fc, or hIgG4 Fc (S228P). In some embodiments, the Fc fragment comprises the amino acid sequence of any one of SEQ ID NOs: 363-365. In some embodiments, the Fc fragment is hIgG4 Fc (S228P). In some embodiments, the optional linker comprises the amino acid sequence of any one of SEQ ID NOs: 367-376. In some embodiments, the HCAb comprises the amino acid sequence of any one of SEQ ID NOs: 325-360.

In some embodiments according to any one of the isolated anti-PD-1 construct described above, the isolated anti-PD-1 construct further comprises a second antibody moiety specifically recognizing a second epitope. In some embodiments, the second antibody moiety is a full-length antibody, a Fab, a Fab', a (Fab')$_2$, an Fv, a single chain Fv (scFv), an scFv-scFv, a minibody, a diabody, or an sdAb. In some embodiments, the anti-PD-1 construct is monospecific. In some embodiments, the anti-PD-1 construct is multispecific (such as bispecific). In some embodiments, the second epitope is not from PD-1. In some embodiments, the second epitope is from PD-1 but different from that specifically recognized by the anti-PD-1 sdAb moiety. In some embodiments, the second epitope is the same as that specifically recognized by the anti-PD-1 sdAb moiety. In some embodiments, the sdAb moiety specifically recognizing PD-1 and the second antibody moiety are optionally connected by a peptide linker, such as peptide linker comprising the amino acid sequence of any one of SEQ ID NOs: 367-376. In some embodiments, the second antibody moiety is an sdAb, such as an sdAb specifically recognizing PD-1 or CTLA-4. In some embodiments, the second antibody moiety is a Fab. In some embodiments, the second antibody moiety is an scFv. In some embodiments, the second antibody moiety is a full-length antibody consisting of two heavy chains and two light chains. In some embodiments, the Fc fragment of the heavy chain is IgG1 Fc, effectorless IgG1 Fc, IgG2 Fc, IgG4 Fc, or IgG4 Fc (S228P), such as any of SEQ ID NOs: 363-365. In some embodiments, the N-terminus of the sdAb moiety specifically recognizing PD-1 is fused to the C-terminus of at least one of the heavy chains of the full-length antibody. In some embodiments, the C-terminus of the sdAb moiety specifically recognizing PD-1 is fused to the N-terminus of at least one of the heavy chains of the full-length antibody. In some embodiments, the N-terminus of the sdAb moiety specifically recognizing PD-1 is fused to the C-terminus of at least one of the light chains of the full-length antibody. In some embodiments, the C-terminus of the sdAb moiety specifically recognizing PD-1 is fused to the N-terminus of at least one of the light chains of the full-length antibody. In some embodiments, the isolated anti-PD-1 construct comprises four identical sdAb moieties specifically recognizing PD-1 as described above, the C-terminus of each anti-PD-1 sdAb moiety is fused to the N-terminus of each chain of the full-length antibody via an optional peptide linker. In some embodiments, the isolated anti-PD-1 construct comprises four identical sdAb moieties specifically recognizing PD-1 as described above, two anti-PD-1 sdAb moieties are fused to each other via an optional peptide linker, the other two anti-PD-1 sdAb moieties are fused to each other via an optional peptide linker, and the C-terminus of each of the anti-PD-1 sdAb moiety fusion polypeptide is fused to the N-terminus of each heavy chain of the full-length antibody via an optional peptide linker. In some embodiments the isolated anti-PD-1 construct consists of four polypeptide chains with structures from the N-terminus to the C-terminus as follows: (1) $V_L$—$C_L$; (2) anti-PD-1 sdAb-$V_H$—$C_H1$-$C_H2$-$C_H3$; (3) anti-PD-1 sdAb-$V_H$—$C_H1$-$C_H2$-$C_H3$; and (4) $V_L$—$C_L$, wherein $V_H$ and $V_L$ of polypeptide chains (1) and (2) forms an antigen binding site that specifically binds a first copy of the second epitope (e.g., TIGIT, LAG-3, TIM-3, CTLA-4, PD-1 (such as a second PD-1 epitope different from that recognized by the anti-PD-1 sdAb moiety described herein)), $V_H$ and $V_L$ of polypeptide chains (3) and (4) forms an antigen binding site that specifically binds a second copy of the second epitope (e.g., TIGIT, LAG-3, TIM-3, CTLA-4, PD-1 (such as a second PD-1 epitope different from that recognized by the anti-PD-1 sdAb moiety described herein)), and each anti-PD-1 sdAb specifically binds a copy of PD-1. In some embodiments the isolated anti-PD-1 construct consists of four polypeptide chains with structures from the N-terminus to the C-terminus as follows: (1) $V_L$—$C_L$; (2) $V_H$—$C_H1$-$C_H2$-$C_H3$-anti-PD-1 sdAb; (3) $V_H$—$C_H1$-$C_H2$-$C_H3$-anti-PD-1 sdAb; and (4) $V_L$—$C_L$, wherein $V_H$ and $V_L$ of polypeptide chains (1) and (2) forms an antigen binding site that specifically binds a first copy of the second epitope (e.g., TIGIT, LAG-3, TIM-3, CTLA-4, PD-1 (such as a second PD-1 epitope different from that recognized by the anti-PD-1 sdAb moiety described herein)), $V_H$ and $V_L$ of polypeptide chains (3) and (4) forms an antigen binding site that specifically binds a second copy of the second epitope (e.g., TIGIT, LAG-3, TIM-3, CTLA-4, PD-1 (such as a second PD-1 epitope different from that recognized by the anti-PD-1 sdAb moiety described herein)), and each anti-PD-1 sdAb specifically binds a copy of PD-1. In some embodiments the isolated anti-PD-1 construct consists of four polypeptide chains with structures from the N-terminus to the C-terminus as follows: (1) anti-PD-1 sdAb-$V_L$—$C_L$; (2) $V_H$—$C_H1$-$C_H2$-$C_H3$; (3) $V_H$—$C_H1$-$C_H2$-$C_H3$; and (4) anti-PD-1 sdAb-$V_L$—$C_L$, wherein $V_H$ and $V_L$ of polypeptide chains (1) and (2) forms an antigen binding site that specifically binds a first copy of the second epitope (e.g., TIGIT, LAG-3, TIM-3, CTLA-4, PD-1 (such as a second PD-1 epitope different from that recognized by the anti-PD-1 sdAb moiety described herein)), $V_H$ and $V_L$ of polypeptide chains (3) and (4) forms an antigen binding site that specifically binds a second copy of the second epitope (e.g., TIGIT, LAG-3, TIM-3, CTLA-4, PD-1 (such as a second PD-1 epitope different from that recognized by the anti-PD-1 sdAb moiety described herein)), and each anti-PD-1 sdAb specifically binds a copy of PD-1. In some embodiments the isolated anti-PD-1 construct consists of four polypeptide chains with structures from the N-terminus to the C-terminus as follows: (1) $V_L$—$C_L$-anti-PD-1 sdAb; (2) $V_H$—$C_H1$-$C_H2$-$C_H3$; (3) $V_H$—$C_H1$-$C_H2$-$C_H3$; and (4) $V_L$—$C_L$-anti-PD-1 sdAb, wherein $V_H$ and $V_L$ of polypeptide chains (1) and (2) forms an antigen binding site that specifically binds a first copy of the second epitope (e.g., TIGIT, LAG-3, TIM-3, CTLA-4, PD-1 (such as a second PD-1 epitope different from that recognized by the anti-PD-1 sdAb moiety described herein)), $V_H$ and $V_L$ of polypeptide chains (3) and (4) forms an antigen binding site that specifically binds a second copy of the second epitope (e.g., TIGIT, LAG-3, TIM-3, CTLA-4, PD-1 (such as a second PD-1 epitope different from that recognized by the anti-PD-1 sdAb moiety described herein)), and each anti-PD-1 sdAb specifically binds a copy of PD-1. In some embodiments the isolated anti-PD-1 construct consists of four polypeptide chains with structures from the N-terminus to the C-terminus as follows: (1) anti-PD-1 sdAb-$V_L$—$C_L$; (2) anti-PD-1 sdAb-$V_H$—$C_H1$-$C_H2$-$C_H3$; (3) anti-PD-1 sdAb-$V_H$—$C_H1$-$C_H2$-$C_H3$; and (4) anti-PD-1 sdAb-$V_L$—$C_L$, wherein $V_H$ and $V_L$ of polypeptide chains (1) and (2) forms an antigen binding site that specifically binds a first copy of the second epitope (e.g., TIGIT, LAG-3, TIM-3, CTLA-4, PD-1 (such as a second PD-1 epitope different from that recognized by the anti-PD-1 sdAb moiety described herein)), $V_H$ and $V_L$ of polypeptide chains (3) and (4) forms an antigen binding site that specifically binds a second copy of the second epitope (e.g., TIGIT, LAG-3, TIM-3, CTLA-4, PD-1 (such as a second PD-1 epitope different from that recognized by the anti-PD-1 sdAb moiety described herein)), and each anti-PD-1 sdAb specifically binds a copy of PD-1. In some embodiments the isolated anti-PD-1 construct consists of four polypeptide chains with structures from the N-terminus to the C-terminus as follows: (1) $V_L$—$C_L$; (2) anti-PD-1 sdAb-anti-PD-1 sdAb-$V_H$—$C_H1$-$C_H2$-$C_H3$; (3) anti-PD-1 sdAb-anti-PD-1 sdAb-$V_H$—$C_H1$-$C_H2$-$C_H3$; and (4) $V_L$—$C_L$, wherein $V_H$ and $V_L$ of polypeptide chains (1) and (2) forms an antigen binding site that specifically binds a first copy of the second epitope (e.g., TIGIT, LAG-3, TIM-3, CTLA-4, PD-1 (such as a second PD-1 epitope different from that recognized by the anti-PD-1 sdAb moiety described herein)), $V_H$ and $V_L$ of polypeptide chains (3) and (4) forms an antigen binding site that specifically binds a second copy of the second epitope (e.g., TIGIT, LAG-3, TIM-3, CTLA-4, PD-1 (such as a second PD-1 epitope different from that recognized by the anti-PD-1 sdAb moiety described herein)), and each anti-PD-1 sdAb specifically binds a copy of PD-1. In some embodiments the isolated anti-PD-1 construct consists of four polypeptide chains with structures from the N-terminus to the C-terminus as follows: (1) $V_L$—$C_L$; (2) $V_H$—$C_H1$-anti-PD-1 sdAb-$C_H2$-$C_H3$; (3) $V_H$—$C_H1$-anti-PD-1 sdAb-$C_H2$-$C_H3$; and (4) $V_L$—$C_L$, wherein $V_H$ and $V_L$ of polypeptide chains (1) and (2) forms an antigen binding site that specifically binds a first copy of the second epitope (e.g., TIGIT, LAG-3, TIM-3, CTLA-4, PD-1 (such as a second PD-1 epitope different from that recognized by the anti-PD-1 sdAb moiety described herein)), $V_H$ and $V_L$ of polypeptide chains (3) and (4) forms an antigen binding site that specifically binds a second copy of the second epitope (e.g., TIGIT, LAG-3, TIM-3, CTLA-4, PD-1 (such as a second PD-1 epitope different from that recognized by the anti-PD-1 sdAb moiety described herein)), and each anti-PD-1 sdAb specifically binds a copy of PD-1. In some embodiments the isolated anti-PD-1 construct consists of two polypeptide chains each with a structure from the N-terminus to the C-terminus as follows: $V_L$—$V_H$-anti-PD-1 sdAb-$C_H2$-$C_H3$, wherein $V_H$ and $V_L$ of each polypeptide chain forms a scFv domain that specifically binds a copy of the second epitope (e.g., TIGIT, LAG-3, TIM-3, CTLA-4, PD-1 (such as a second PD-1 epitope different from that recognized by the anti-PD-1 sdAb moiety described herein)), and each anti-PD-1 sdAb specifically binds a copy of PD-1. In some embodiments the isolated anti-PD-1 construct consists of four polypeptide chains with structures from the N-terminus to the C-terminus as follows: (1) $V_L$—$C_L$-anti-PD-1 sdAb-$C_L$; (2) $V_H$—$C_H1$-anti-PD-1 sdAb-$C_H1$-$C_H2$-$C_H3$; (3) $V_H$—$C_H1$-anti-PD-1 sdAb-$C_H1$-$C_H2$-$C_H3$; and (4) $V_L$—$C_L$-anti-PD-1 sdAb-$C_L$, wherein $V_H$ and $V_L$ of polypeptide chains (1) and (2) forms an antigen binding site that specifically binds a first copy of the second epitope (e.g., TIGIT, LAG-3, TIM-3, CTLA-4, PD-1 (such as a second PD-1 epitope different from that recognized by the anti-PD-1 sdAb moiety described herein)), $V_H$ and $V_L$ of polypeptide chains (3) and (4) forms an antigen binding site that specifically binds a second copy of the second epitope (e.g., TIGIT, LAG-3, TIM-3, CTLA-4, PD-1 (such as a second PD-1 epitope different from that recognized by the anti-PD-1 sdAb moiety described herein)), and each anti-PD-1 sdAb specifically binds a copy of PD-1. In some embodiments the isolated anti-PD-1 construct consists of four polypeptide chains with structures from the N-terminus to the C-terminus as follows: (1) anti-PD-1 sdAb-$C_L$; (2) $V_L$—$V_H$-anti-PD-1 sdAb-$C_H1$-$C_H2$-$C_H3$; (3) $V_L$—$V_H$-anti-PD-1 sdAb-$C_H1$-$C_H2$-$C_H3$; and (4) anti-PD-1 sdAb-$C_L$, wherein $V_H$ and $V_L$ of polypeptide chains (2) and (3) each forms an scFv that specifically binds a copy of the second epitope (e.g., TIGIT, LAG-3, TIM-3, CTLA-4, PD-1 (such as a second PD-1 epitope different from that recognized by the anti-PD-1 sdAb moiety described herein)), and each anti-PD-1 sdAb specifically binds a copy of PD-1. In some embodiments, the full-length antibody (or antigen binding portion comprising a $V_H$ and a $V_L$) specifically recognizes TIGIT. In some embodiments, the anti-TIGIT full-length antibody (or antigen binding portion comprising a $V_H$ and a $V_L$) comprises a $V_H$ comprising HC-CDR1, HC-CDR2, and HC-CDR3 of a heavy chain comprising the amino acid sequence of SEQ ID NO: 377, and a $V_L$ comprising LC-CDR1, LC-CDR2, and LC-CDR3 of a light chain comprising the amino acid sequence of SEQ ID NO: 378. In some embodiments, the anti-TIGIT full-length antibody comprises a heavy chain comprising the amino acid sequence of SEQ ID NO: 377, and a light chain comprising the amino acid sequence of SEQ ID NO: 378. In some embodiments, the full-length antibody (or antigen binding portion comprising a $V_H$ and a $V_L$) specifically recognizing TIGIT is derived from tiragolumab. In some embodiments, the full-length antibody (or antigen binding portion comprising a $V_H$ and a $V_L$) specifically recognizes LAG-3. In some embodiments, the anti-LAG-3 full-length antibody (or antigen binding portion comprising a $V_H$ and a $V_L$) comprises a $V_H$ comprising HC-CDR1, HC-CDR2, and HC-CDR3 of a heavy chain comprising the amino acid sequence of SEQ ID NO: 379, and a $V_L$ comprising LC-CDR1, LC-CDR2, and LC-CDR3 of a light chain comprising the amino acid sequence of SEQ ID NO: 380. In some embodiments, the anti-LAG-3 full-length antibody comprises a heavy chain comprising the amino acid sequence of SEQ ID NO: 379, and a light chain comprising the amino acid sequence of SEQ ID NO: 380. In some embodiments, the full-length antibody (or antigen binding portion comprising a $V_H$ and a $V_L$) specifically recognizing LAG-3 is derived from relatlimab. In some embodiments, the full-length antibody (or antigen binding portion comprising a $V_H$ and a $V_L$) specifically recognizes TIM-3. In some embodiments, the anti-TIM-3 full-length antibody (or antigen binding portion comprising a $V_H$ and a $V_L$) comprises a $V_H$ comprising HC-CDR1, HC-CDR2, and HC-CDR3 of a heavy chain comprising the amino acid sequence of SEQ ID NO: 381, and a $V_L$ comprising LC-CDR1, LC-CDR2, and LC-CDR3 of a light chain comprising the amino acid sequence of SEQ ID NO: 382. In some embodiments, the anti-TIM-3 full-length antibody comprises a heavy chain comprising the amino acid sequence of SEQ ID NO: 381, and a light chain comprising the amino acid sequence of SEQ ID NO: 382. In some embodiments, the full-length antibody (or antigen binding portion comprising a $V_H$ and a $V_L$) specifically recognizing TIM-3 is derived from MBG453. In some embodiments, the full-length antibody (or antigen binding portion comprising a $V_H$ and a $V_L$) specifically recognizes CTLA-4. In some embodiments, the anti-CTLA-4 full-length antibody (or antigen binding portion comprising a $V_H$ and a $V_L$) comprises a $V_H$ comprising HC-CDR1, HC-CDR2, and HC-CDR3 of a heavy chain comprising the amino acid sequence of SEQ ID NO: 383, and a $V_L$ comprising LC-CDR1, LC-CDR2, and LC-CDR3 of a light chain comprising the amino acid sequence of SEQ ID NO: 384. In some embodiments, the anti-CTLA-4 full-length antibody comprises a heavy chain comprising the amino acid sequence of SEQ ID NO: 383, and a light chain comprising the amino acid sequence of SEQ ID NO: 384. In some embodiments, the full-length antibody (or antigen binding portion comprising a $V_H$ and a $V_L$) specifically recognizing CTLA-4 is derived from ipilimumab (e.g., Yervoy®). In some embodiments, the full-length antibody (or antigen binding portion comprising a $V_H$ and a $V_L$) specifically recognizes PD-1 (such as a second PD-1 epitope different from that recognized by the anti-PD-1 sdAb moiety described herein). In some embodiments, the anti-PD-1 full-length antibody (or antigen binding portion comprising a $V_H$ and a $V_L$) comprises a $V_H$ comprising HC-CDR1, HC-CDR2, and HC-CDR3 of a heavy chain comprising the amino acid sequence of SEQ ID NO: 385, and a $V_L$ comprising LC-CDR1, LC-CDR2, and LC-CDR3 of a light chain comprising the amino acid sequence of SEQ ID NO: 386. In some embodiments, the anti-PD-1 full-length antibody comprises a heavy chain comprising the amino acid sequence of SEQ ID NO: 385, and a light chain comprising the amino acid sequence of SEQ ID NO: 386. In some embodiments, the full-length antibody (or antigen binding portion comprising a $V_H$ and a $V_L$) specifically recognizing PD-1 is derived from pembrolizumab (e.g., Keytruda®) or nivolumab (e.g., Opdivo®).

In some embodiments according to any one of the isolated anti-PD-1 constructs described above, the isolated anti-PD-1 construct further comprises a biologically active protein or fragments thereof.

Further provided is an isolated anti-PD-1 construct comprising an sdAb moiety specifically recognizing PD-1, wherein the sdAb moiety comprises CDR1, CDR2, and CDR3 of any one of SEQ ID NOs: 289-324.

Further provided is an isolated anti-PD-1 construct (e.g., anti-PD-1 sdAb, anti-PD-1 HCAb (e.g., anti-PD-1 sdAb-Fc fusion), PD-1×TIGIT BABP, PD-1×LAG-3 BABP, PD-1× TIM-3 BABP, PD-1×CTLA-4 BABP, or PD-1×PD-1 BABP) that specifically binds to PD-1 competitively with the any of the isolated anti-PD-1 constructs described above.

Further provided is a pharmaceutical composition comprising any one of the isolated anti-PD-1 constructs described above, and optionally a pharmaceutical acceptable carrier.

Another aspect of the present application provides a method of treating an individual having a PD-1-related disease (such as cancer, or immune-related disease), comprising administering to the individual an effective amount of any one of the pharmaceutical compositions described above. In some embodiments, the PD-1-related disease is cancer. In some embodiments, the cancer is a solid tumor, such as a colon cancer. In some embodiments, the PD-1-related disease is an immune-related disease. In some embodiments, immune-related disease is associated with a T cell dysfunctional disorder. In some embodiments, the T cell dysfunctional disorder is characterized by T cell anergy or decreased ability to secrete cytokines, proliferate or execute cytolytic activity. In some embodiments, the T cell dysfunctional disorder is characterized by T cell exhaustion. In some embodiments, the immune-related disease is selected from the group consisting of unresolved acute infection, chronic infection, and tumor immunity. In some embodiments, the PD-1 related disease is a pathogenic infection. In some embodiments, the method further comprises administering to the individual an additional therapy (e.g., cancer therapy), such as surgery, radiation, chemotherapy, immunotherapy, hormone therapy, or a combination thereof. In some embodiments, the additional therapy is immunotherapy. In some embodiments, the immunotherapy comprises administering to the individual an effective amount of a second pharmaceutical composition comprising an immunomodulator, such as an immune checkpoint inhibitor (e.g., antibody specifically recognizing TIGIT, LAG-3, TIM-3, CTLA-4, PD-1, or PD-L1). In some embodiments, the pharmaceutical composition is administered systemically, such as intravenously (i.v.) or intraperitoneally (i.p.). In some embodiments, the pharmaceutical composition is administered locally, such as intratumorally. In some embodiments, the individual is a human.

Further provided is an isolated nucleic acid encoding any one of the isolated anti-PD-1 constructs described above. In some embodiments, the isolated nucleic acid comprises the nucleic acid sequence of any one of SEQ ID NOs: 253-288.

Further provided is a vector comprising any one of the isolated nucleic acids described above.

Further provided is an isolated host cell comprising any one of the isolated nucleic acid or vector described above.

Further provided is a kit comprising any one of the isolated anti-PD-1 construct, isolated nucleic acid, vector, or isolated host cell described above.

Another aspect of the present application provides a method of producing any one of isolated anti-PD-1 constructs described above, comprising culturing a host cell comprising any one of the isolated nucleic acid or vector described above, or culturing any one of the isolated host cell described above, under conditions effective to express the encoded anti-PD-1 construct; and obtaining the expressed anti-PD-1 construct from said host cell. In some embodiments, the method further comprises producing a host cell comprising any one of the isolated nucleic acid or vector described above.

BRIEF DESCRIPTION OF THE DRAWINGS

FIG. 1A depicts immune response evaluation of pre-immune serum and immune serum of the first camel after the 6$^{th}$ immunization. FIG. 1B depicts immune response evaluation of heavy chain antibodies (IgG2 and IgG3) after the 6$^{th}$ immunization (terminal bleed). Heavy chain antibodies fractionated from pre-immune serum were used as negative controls.

FIG. 2A depicts immune response evaluation of pre-immune serum and immune serum of the 2$^{nd}$ camel after the 6$^{th}$ immunization. FIG. 2B depicts immune response evaluation of heavy chain antibodies (IgG2 and IgG3) after the 6$^{th}$ immunization (terminal bleed). Heavy chain antibodies fractionated from pre-immune serum were used as negative controls.

FIG. 4A depicts the binding of AS06962 sdAb, AS07424 sdAb and A31543 sdAb to human PD-1 expressing cells by flow cytometry. EC$_{50}$ data are summarized in FIG. 4B.

FIG. 5A depicts ligand competition activity evaluation of AS06962 sdAb and A31543 sdAb measured by flow cytometry, using PD-L1 Fc ligand and PD-1 expressing cell line. Keytruda® was used as a positive anti-PD-1 control antibody. IC$_{50}$ is summarized in FIG. 5B.

FIGS. 6B-6L depict the affinities of generated camelid HCAbs measured by surface plasma resonance. Keytruda® was used as a positive anti-PD-1 control antibody (FIG. 6K). The $k_{on}$, $k_{off}$ and $K_D$ parameters are summarized in FIG. 6A.

FIGS. 7A-7X depict binding abilities of generated camelid HCAbs to human PD-1 expressing cells by flow cytometry. FIGS. 7A-7V depict FACS based binding of generated camelid HCAbs to human PD-1 expressing cells. Keytruda® was used as a positive anti-PD-1 control antibody (FIG. 7W). EC$_{50}$ is summarized in FIG. 7X.

FIGS. 8A-8X depict ligand competition activity evaluation of generated camelid HCAbs measured by flow cytometry. FIGS. 8A-8V depict FACS based ligand competition assay of generated camelid HCAbs using PD-L1 Fc ligand and PD-1 expressing cell line. Keytruda® was used as a positive anti-PD-1 control antibody (FIG. 8W). IC$_{50}$ is summarized in FIG. 8X.

FIGS. 9A-9H depict biological activity evaluation of generated camelid HCAbs measured by NFAT-induced luciferase reporter activity. FIGS. 9A-9F depict RLU induction through NFAT response elements from the IL-2 promoter in the presence of generated camelid HCAbs during PD-1 effector cells and PD-L1 cells incubation. Keytruda® was used as a positive anti-PD-1 control antibody (FIG. 9G). EC$_{50}$ is summarized in FIG. 9H.

FIGS. 10A-10C depict functional activity evaluation of camelid HCAbs AS15140_HCAb, AS15156_HCAb, and AS15193_HCAb by mixed lymphocyte reaction (MLR) assay. Keytruda® was used as a positive anti-PD-1 control antibody (FIG. 10D). EC$_{50}$ is summarized in FIG. 10E.

FIG. 11 depicts sequence alignment of parent AS15193 sdAb, its corresponding four humanized versions, and the human acceptor.

FIGS. 14A-14F depict ligand competition activity evaluation of four humanized HCAbs measured by flow cytometry. FIGS. 14B-14E depict FACS based ligand competition assay of humanized HCAbs using PD-L1-Fc ligand and PD-1 expressing cell line. Parent HCAb AS15193_HCAb was used as a positive anti-PD-1 control antibody (FIG. 14A). IC$_{50}$ is summarized in FIG. 14F.

FIGS. 15A-15F depict biological activity evaluation of four humanized HCAbs and their parent HCAb measured by NFAT-induced luciferase reporter activity. FIGS. 15B-15E depict RLU induction through NFAT response elements from the IL-2 promoter in the presence of humanized HCAbs during PD-1 effector cells and PD-L1 cells incubation. Parent HCAb AS15193_HCAb was used as a positive anti-PD-1 control antibody (FIG. 15A). EC$_{50}$ is summarized in FIG. 15F.

FIG. 26A depicts a schematic structure of an exemplary monospecific bivalent anti-PD-1 HCAb. FIG. 26B depicts a schematic structure of an exemplary bispecific bivalent anti-PD-1 HCAb.

FIG. 28 depicts the purification summary of selected sdAbs.

FIG. 29 depicts the purification summary of selected HCAbs.

DETAILED DESCRIPTION OF THE INVENTION

Figure 1A:
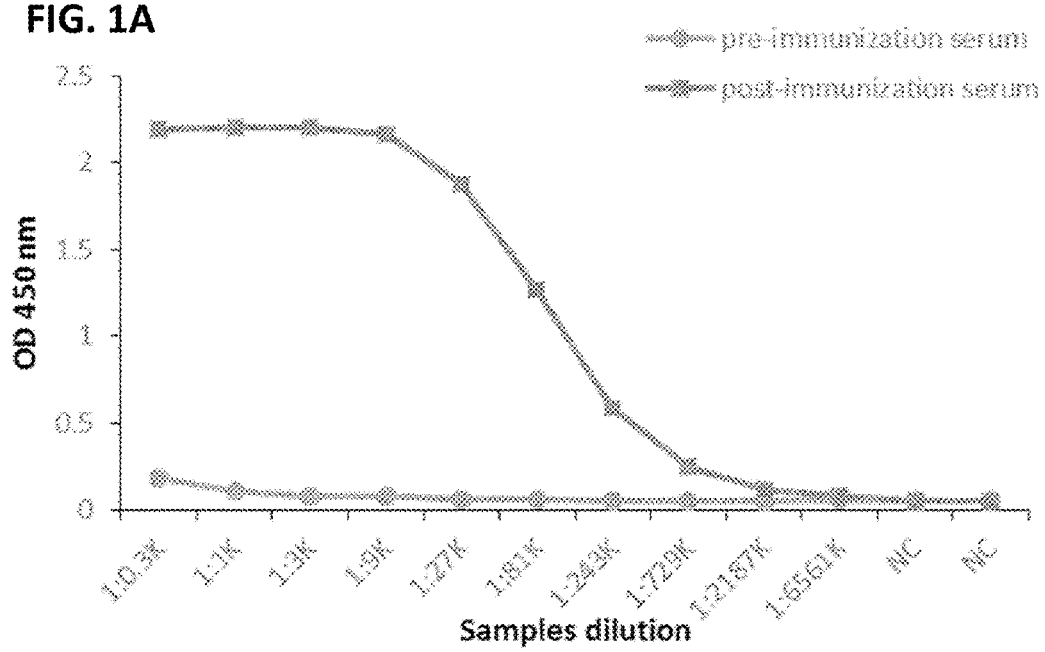
FIGS. 1A-1B depict immune response evaluation of the first camel after PD-1 immunization.
Figure 1B:
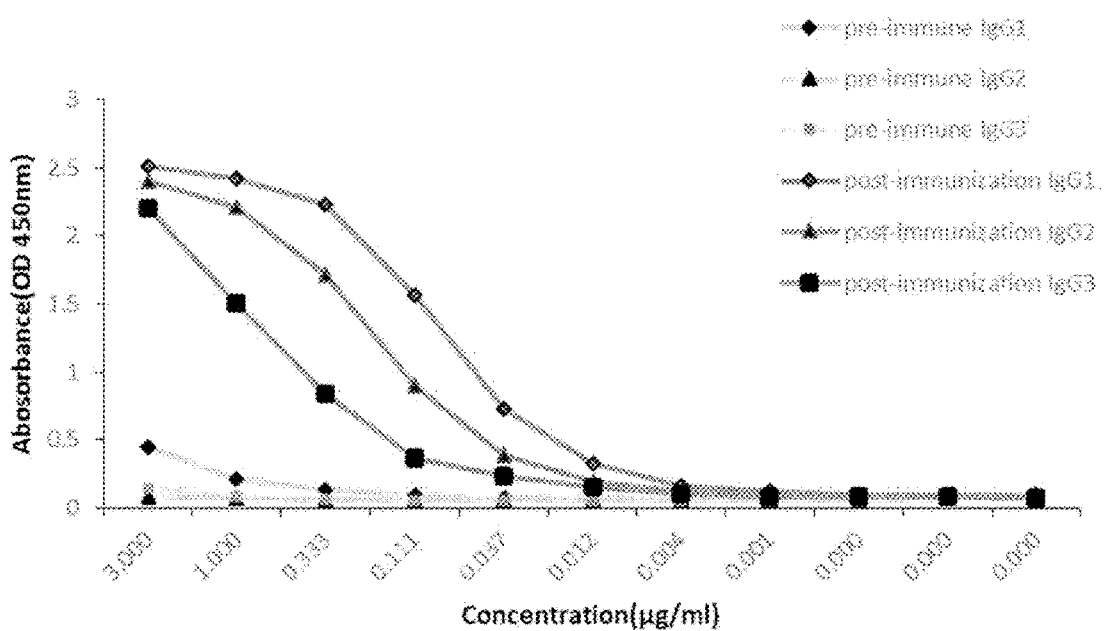
Figure 2A:
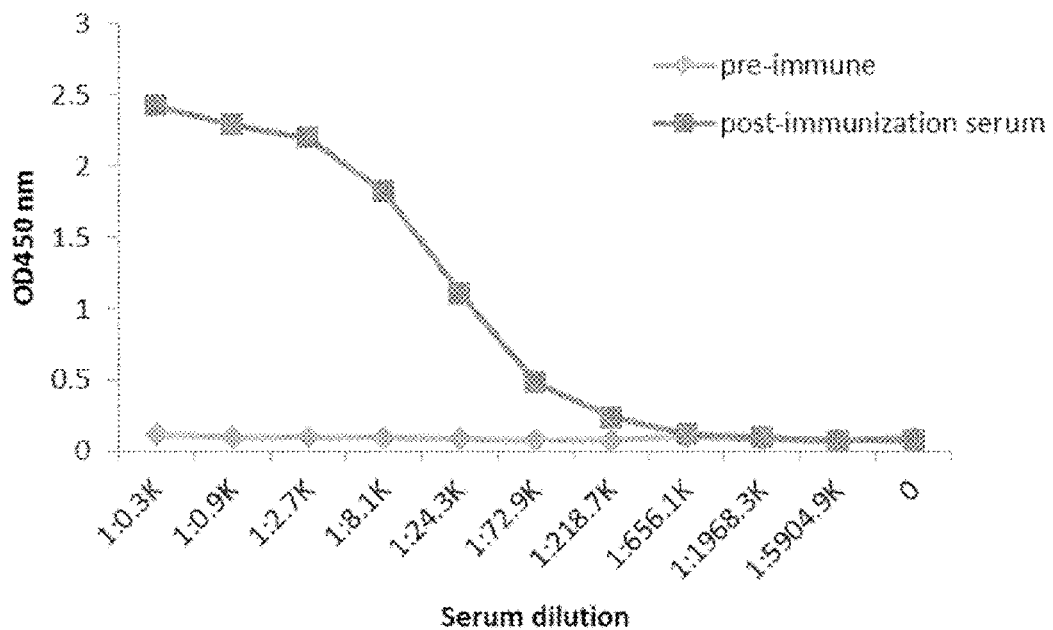
FIGS. 2A-2B depict immune response evaluation of the second camel after PD-1 immunization.
Figure 2B:
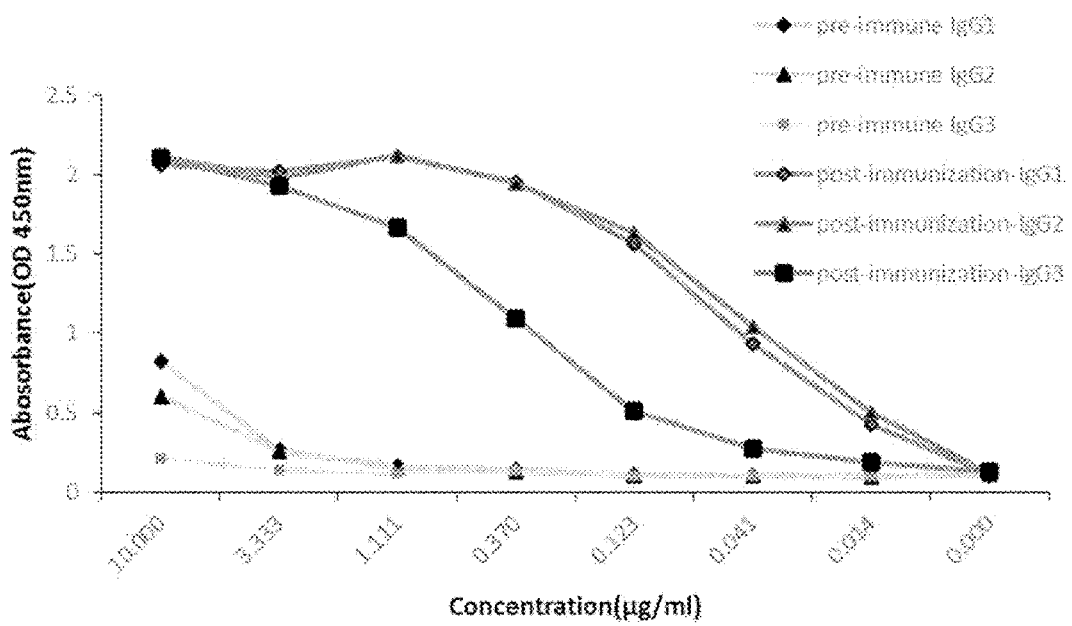

The present invention provides novel sdAbs specifically recognizing PD-1 (hereinafter also referred to as "anti-PD-1 sdAb") and its antibody variants (for example, a larger protein or polypeptide comprising the anti-PD-1 sdAb, such as anti-PD-1 sdAb-Fc fusion protein (e.g., anti-PD-1 HCAb), anti-PD-1 sdAb fused to a full-length antibody, Fab, or scFv, or multispecific antigen binding proteins (MABPs, such as bispecific antigen binding proteins (BABPs)) comprising the anti-PD-1 sdAb), uses thereof for treating PD-1-related diseases (such as cancer) and methods of making thereof.

sdAbs are different from conventional 4-chain antibodies by having a single monomeric antibody variable domain, such as heavy chain variable domain ($V_HH$), which can exhibit high affinity to an antigen without the aid of a light chain. Camelid $V_HH$ is known as the smallest functional antigen-binding fragment with a molecular weight of approximately 15 kDa.

Accordingly, one aspect of the present application provides an isolated anti-PD-1 construct comprising an sdAb moiety specifically recognizing PD-1. The isolated anti-PD-1 construct can be, for example, an anti-PD-1 sdAb (e.g. natural, humanized, or human), a polypeptide comprising multiple anti-PD-1 sdAbs described herein fused together, an anti-PD-1 sdAb-Fc fusion protein (e.g., anti-PD-1 HCAb) comprising an anti-PD-1 sdAb described herein fused to an Fc fragment (e.g., a human IgG1 Fc, effectorless (inert) hIgG1 Fc, hIgG4 Fc, or hIgG4 Fc (S228P)), or a MABP comprising the anti-PD-1 sdAb described herein fused to a full-length antibody (such as an antibody specifically recognizing TIGIT, LAG-3, TIM-3, CTLA-4, or PD-1 (e.g., a second PD-1 epitope different from that recognized by the anti-PD-1 sdAb moiety described herein)) or antigen binding fragment thereof that comprises a heavy chain variable domain ($V_H$) and a light chain variable domain ($V_L$). The anti-PD-1 construct can be monospecific or multispecific (such as bispecific), monovalent or multivalent (such as bivalent).

Also provided are compositions (such as pharmaceutical compositions), kits and articles of manufacture comprising the anti-PD-1 construct described herein, methods of making thereof, and methods of treating PD-1-related disease (such as cancer) using the anti-PD-1 construct described herein.

I. Definitions

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing the quality of life, and/or prolonging survival. Also encompassed by "treatment" is a reduction of pathological consequence of cancer. The methods of the invention contemplate any one or more of these aspects of treatment.

The term "prevent," and similar words such as "prevented," "preventing" etc., indicate an approach for preventing, inhibiting, or reducing the likelihood of the recurrence of, a disease or condition, e.g., cancer. It also refers to delaying the recurrence of a disease or condition or delaying the recurrence of the symptoms of a disease or condition. As used herein, "prevention" and similar words also includes reducing the intensity, effect, symptoms and/or burden of a disease or condition prior to recurrence of the disease or condition.

As used herein, "delaying" the development of cancer means to defer, hinder, slow, retard, stabilize, and/or postpone development of the disease. This delay can be of varying lengths of time, depending on the history of the disease and/or individual being treated. A method that "delays" development of cancer is a method that reduces probability of disease development in a given time frame and/or reduces the extent of the disease in a given time frame, when compared to not using the method. Such comparisons are typically based on clinical studies, using a statistically significant number of individuals. Cancer development can be detectable using standard methods, including, but not limited to, computerized axial tomography (CAT Scan), Magnetic Resonance Imaging (MRI), abdominal ultrasound, clotting tests, arteriography, or biopsy. Development may also refer to cancer progression that may be initially undetectable and includes occurrence, recurrence, and onset.

The term "effective amount" used herein refers to an amount of an agent or a combination of agents, sufficient to treat a specified disorder, condition or disease such as ameliorate, palliate, lessen, and/or delay one or more of its symptoms. In reference to cancer, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay recurrence. An effective amount can be administered in one or more administrations. The effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

As used herein, an "individual" or a "subject" refers to a mammal, including, but not limited to, human, bovine, horse, feline, canine, rodent, or primate. In some embodiments, the individual is a human.

The terms "antibody," "antigen binding portion," or "antibody moiety" are used in their broadest sense and encompasses various antibody structures, including but not limited to monoclonal antibodies, polyclonal antibodies, multispecific antibodies (e.g., bispecific antibodies), full-length antibodies and antigen-binding fragments thereof, so long as they exhibit the desired antigen-binding activity.

The basic 4-chain antibody unit is a heterotetrameric glycoprotein composed of two identical light (L) chains and two identical heavy (H) chains. An IgM antibody consists of 5 of the basic heterotetramer units along with an additional polypeptide called a J chain, and contains 10 antigen-binding sites, while IgA antibodies comprise from 2-5 of the basic 4-chain units which can polymerize to form polyvalent assemblages in combination with the J chain. In the case of IgGs, the 4-chain unit is generally about 150,000 Daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see e.g., *Basic and Clinical Immunology*, 8th Edition, Daniel P. Sties, Abba I. Terr and Tristram G. Parsolw (eds), Appleton & Lange, Norwalk, Conn. 1994, page 71 and Chapter 6. The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG and IgM, having heavy chains designated α, δ, ε, γ and μ, respectively. The γ and α classes are further divided into subclasses on the basis of relatively minor differences in the $C_H$ sequence and function, e.g., humans express the following subclasses: IgG1, IgG2A, IgG2B, IgG3, IgG4, IgA1 and IgA2.

The term "heavy chain-only antibody" or "HCAb" refers to a functional antibody, which comprises heavy chains, but lacks the light chains usually found in 4-chain antibodies. *Camelid* animals (such as camels, llamas, or alpacas) are known to produce HCAbs.

The term "single-domain antibody" or "sdAb" refers to a single antigen-binding polypeptide having three complementary determining regions (CDRs). The sdAb alone is capable of binding to the antigen without pairing with a corresponding CDR-containing polypeptide. In some cases, single-domain antibodies are engineered from camelid HCAbs, and their heavy chain variable domains are referred herein as "$V_HHs$" (Variable domain of the heavy chain of the Heavy chain antibody). *Camelid* sdAb is one of the smallest known antigen-binding antibody fragments (see, e.g., Hamers-Casterman et al., Nature 363:446-8 (1993); Greenberg et al., Nature 374:168-73 (1995); Hassanzadeh-Ghassabeh et al., Nanomedicine (Lond), 8:1013-26 (2013)). A basic $V_HH$ has the following structure from the N-terminus to the C-terminus: FR1-CDR1-FR2-CDR2-FR3-CDR3-FR4, in which FR1 to FR4 refer to framework regions 1 to 4, respectively, and in which CDR1 to CDR3 refer to the complementarity determining regions 1 to 3.

An "isolated" antibody (or construct) is one that has been identified, separated and/or recovered from a component of its production environment (e.g., natural or recombinant). Preferably, the isolated polypeptide is free of association with all other components from its production environment. Contaminant components of its production environment, such as that resulting from recombinant transfected cells, are materials that would typically interfere with research, diagnostic or therapeutic uses for the antibody, and may include enzymes, hormones, and other proteinaceous or non-proteinaceous solutes. In preferred embodiments, the polypeptide will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator; or (3) to homogeneity by SDS-PAGE under non-reducing or reducing conditions using Coomassie Blue or, preferably, silver stain. Isolated antibody (or construct) includes the antibody in situ within recombinant cells since at least one component of the antibody's natural environment will not be present. Ordinarily, however, an isolated polypeptide, antibody, or construct will be prepared by at least one purification step.

The "variable region" or "variable domain" of an antibody refers to the amino-terminal domains of the heavy or light chain of the antibody. The variable domains of the heavy chain and light chain may be referred to as "$V_H$" and "$V_L$", respectively. These domains are generally the most variable parts of the antibody (relative to other antibodies of the same class) and contain the antigen binding sites. Heavy-chain only antibodies from the *Camelid* species have a single heavy chain variable region, which is referred to as "$V_HH$". $V_HH$ is thus a special type of $V_H$.

The term "variable" refers to the fact that certain segments of the variable domains differ extensively in sequence among antibodies. The V domain mediates antigen binding and defines the specificity of a particular antibody for its particular antigen. However, the variability is not evenly distributed across the entire span of the variable domains. Instead, it is concentrated in three segments called complementary determining regions (CDRs) or hypervariable regions (HVRs) both in the heavy chain and light chain variable domains. The more highly conserved portions of variable domains are called the framework regions (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies (see Kabat et al., *Sequences of Immunological Interest*, Fifth Edition, National Institute of Health, Bethesda, Md. (1991)). The constant domains are not involved directly in the binding of antibody to an antigen, but exhibit various effector functions, such as participation of the antibody in antibody-dependent cellular toxicity.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein., *Nature*, 256:495-97 (1975); Hongo et al., *Hybridoma*, 14 (3): 253-260 (1995), Harlow et al., *Antibodies: A Laboratory Manual*, (Cold Spring Harbor Laboratory Press, $2^{nd}$ ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature*, 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993);

U.S. Pat. Nos. 5,545,807; 5,545,806; 5,569,825; 5,625,126; 5,633,425; and 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg and Huszar, *Intern. Rev. Immunol.* 13: 65-93 (1995).

The terms "full-length antibody", "intact antibody", or "whole antibody" are used interchangeably to refer to an antibody in its substantially intact form, as opposed to an antibody fragment. Specifically, full-length 4-chain antibodies include those with heavy and light chains including an Fc region. Full-length heavy-chain only antibodies include the heavy chain variable domain (such as $V_HH$) and an Fc region. The constant domains may be native sequence constant domains (e.g., human native sequence constant domains) or amino acid sequence variants thereof. In some cases, the intact antibody may have one or more effector functions.

An "antibody fragment" or "antigen-binding fragment" comprises a portion of an intact antibody, preferably the antigen binding and/or the variable region of the intact antibody. Examples of antibody fragments include, but are not limited to Fab, Fab', F(ab')$_2$ and Fv fragments; diabodies; linear antibodies (see U.S. Pat. No. 5,641,870, Example 2; Zapata et al., *Protein Eng.* 8(10): 1057-1062 (1995)); single-chain antibody (scFv) molecules; single-domain antibodies (such as $V_HH$), and multispecific antibodies formed from antibody fragments. Papain digestion of antibodies produced two identical antigen-binding fragments, called "Fab" fragments, and a residual "Fc" fragment, a designation reflecting the ability to crystallize readily. The Fab fragment consists of an entire L chain along with the variable domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy-terminus of the $C_H1$ domain including one or more cysteines from the antibody hinge region. Fab'—SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The term "constant domain" refers to the portion of an immunoglobulin molecule having a more conserved amino acid sequence relative to the other portion of the immunoglobulin, the variable domain, which contains the antigen-binding site. The constant domain contains the $C_H1$, $C_H2$ and $C_H3$ domains (collectively, $C_H$) of the heavy chain and the CHL (or $C_L$) domain of the light chain.

The "light chains" of antibodies (immunoglobulins) from any mammalian species can be assigned to one of two clearly distinct types, called kappa ("κ") and lambda ("λ"), based on the amino acid sequences of their constant domains.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the scFv polypeptide further comprises a polypeptide linker between the $V_H$ and $V_L$ domains which enables the scFv to form the desired structure for antigen binding. For a review of the scFv, see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains. Diabodies are described in greater detail in, for example, EP 404,097; WO 93/11161; Hollinger et al., *Proc. Natl. Acad. Sci. USA* 90: 6444-6448 (1993).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA,* 81:6851-6855 (1984)). "Humanized antibody" is used as a subset of "chimeric antibodies".

"Humanized" forms of non-human (e.g., llama or camelid) antibodies are chimeric antibodies that contain minimal sequence derived from non-human immunoglobulin. In some embodiments, a humanized antibody is a human immunoglobulin (recipient antibody) in which residues from an CDR (hereinafter defined) of the recipient are replaced by residues from an CDR of a non-human species (donor antibody) such as mouse, rat, rabbit, camel, llama, alpaca, or non-human primate having the desired specificity, affinity, and/or capacity. In some instances, framework ("FR") residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, etc. The number of these amino acid substitutions in the FR is typically no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, for example, Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is an antibody that possesses an amino-acid sequence corresponding to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.*, 227: 381 (1991); Marks et al., *J. Mol. Biol.*, 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.*, 147(1):86-95 (1991). See also van Dijk and van de Winkel, *Curr. Opin. Pharmacol.*, 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Natl. Acad. Sci. USA*, 103:3557-3562 (2006) regarding human antibodies generated via a human B-cell hybridoma technology.

The term "hypervariable region," "HVR," or "HV," when used herein refers to the regions of an antibody variable domain which are hypervariable in sequence and/or form structurally defined loops. Generally, single-domain antibodies comprise three HVRs (or CDRs): HVR1 (or CDR1), HVR2 (or CDR2), and HVR3 (or CDR3). HVR3 (or CDR3) displays the most diversity of the three HVRs, and is believed to play a unique role in conferring fine specificity to antibodies. See, e.g., Hamers-Casterman et al., *Nature* 363:446-448 (1993); Sheriff et al., *Nature Struct. Biol.* 3:733-736 (1996).

The term "Complementarity Determining Region" or "CDR" are used to refer to hypervariable regions as defined by the Kabat system. See Kabat et al., *Sequences of Proteins of Immunological Interest,* 5th Ed. Public Health Service, National Institutes of Health, Bethesda, Md. (1991).

A number of HVR delineations are in use and are encompassed herein. The Kabat Complementarity Determining Regions (CDRs) are based on sequence variability and are the most commonly used (Kabat et al., *Sequences of Proteins of Immunological Interest,* 5th Ed. Public Health Service, National Institutes of Health, Bethesda, Md. (1991)). Chothia refers instead to the location of the structural loops (Chothia and Lesk, *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below in Table 1.

TABLE 1

HVR delineations.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B |
| | | (Kabat Numbering) | | |
| H1 | H31-H35 | H26-H35 | H26-H32 | H30-H35 |
| | | (Chothia Numbering) | | |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the $V_L$ and 26-35 (H1), 50-65 or 49-65 (H2) and 93-102, 94-102, or 95-102 (H3) in the $V_H$. The variable domain residues are numbered according to Kabat et al., supra, for each of these definitions.

The amino acid residues of a single-domain antibody (such as $V_HH$) are numbered according to the general numbering for $V_H$ domains given by Kabat et al. ("Sequence of proteins of immunological interest", US Public Health Services, NIH Bethesda, Md., Publication No. 91), as applied to $V_HH$ domains from Camelids in the article of Riechmann and Muyldermans, J. Immunol. Methods 2000 Jun. 23; 240 (1-2): 185-195. According to this numbering, FR1 of a $V_HH$ comprises the amino acid residues at positions 1-30, CDR1 of a $V_HH$ comprises the amino acid residues at positions 31-35, FR2 of a $V_HH$ comprises the amino acids at positions 36-49, CDR2 of a $V_HH$ comprises the amino acid residues at positions 50-65, FR3 of a $V_HH$ comprises the amino acid residues at positions 66-94, CDR3 of a $V_HH$ comprises the amino acid residues at positions 95-102, and FR4 of a $V_HH$ comprises the amino acid residues at positions 103-113. In this respect, it should be noted that—as is well known in the art for $V_H$ domains and for $V_HH$ domains—the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering).

The expression "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g. residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

Unless indicated otherwise herein, the numbering of the residues in an immunoglobulin heavy chain is that of the EU index as in Kabat et al., supra. The "EU index as in Kabat" refers to the residue numbering of the human IgG1 EU antibody.

"Framework" or "FR" residues are those variable-domain residues other than the HVR residues as herein defined.

A "human consensus framework" or "acceptor human framework" is a framework that represents the most commonly occurring amino acid residues in a selection of human immunoglobulin $V_L$ or $V_H$ framework sequences. Generally, the selection of human immunoglobulin $V_L$ or $V_H$ sequences is from a subgroup of variable domain sequences. Generally, the subgroup of sequences is a subgroup as in Kabat et al., *Sequences of Proteins of Immunological Interest*, 5$^{th}$ Ed. Public Health Service, National Institutes of Health, Bethesda, Md. (1991). Examples include for the $V_L$, the subgroup may be subgroup kappa I, kappa II, kappa III or kappa IV as in Kabat et al., supra. Additionally, for the VH, the subgroup may be subgroup I, subgroup II, or subgroup III as in Kabat et al. Alternatively, a human consensus framework can be derived from the above in which particular residues, such as when a human framework residue is selected based on its homology to the donor framework by aligning the donor framework sequence with a collection of various human framework sequences. An acceptor human framework "derived from" a human immunoglobulin framework or a human consensus framework may comprise the same amino acid sequence thereof, or it may contain pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less.

An "affinity-matured" antibody is one with one or more alterations in one or more CDRs thereof that result in an improvement in the affinity of the antibody for antigen, compared to a parent antibody that does not possess those alteration(s). In some embodiments, an affinity-matured antibody has nanomolar or even picomolar affinities for the target antigen. Affinity-matured antibodies are produced by procedures known in the art. For example, Marks et al., *Bio/Technology* 10:779-783 (1992) describes affinity maturation by $V_H$- and $V_L$-domain shuffling. Random mutagenesis of CDR and/or framework residues is described by, for example: Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

As used herein, the term "specifically binds," "specifically recognizes," or is "specific for" refers to measurable and reproducible interactions such as binding between a target and an antigen binding protein (such as an sdAb), which is determinative of the presence of the target in the presence of a heterogeneous population of molecules including biological molecules. For example, an antigen binding protein (such as an sdAb) that specifically binds a target (which can be an epitope) is an antigen binding protein (such as an sdAb) that binds this target with greater affinity, avidity, more readily, and/or with greater duration than it binds other targets. In some embodiments, the extent of binding of an antigen binding protein (such as an sdAb) to an unrelated target is less than about 10% of the binding of the antigen binding protein (such as an sdAb) to the target as measured, e.g., by a radioimmunoassay (RIA). In some embodiments, an antigen binding protein (such as an sdAb) that specifically binds a target has a dissociation constant ($K_d$) of $\leq 10^{-5}$ M, $\leq 10^{-6}$ M, $\leq 10^{-7}$ M, $\leq 10^{-8}$ M, $\leq 10^{-9}$ M, $\leq 10^{-10}$ M, $\leq 10^{-11}$ M, or $\leq 10^{-12}$ M. In some embodiments, an antigen binding protein specifically binds an epitope on a protein that is conserved among the protein from different species. In some embodiments, specific binding can include, but does not require exclusive binding. Binding specificity of the antibody or antigen-binding domain can be determined experimentally by methods known in the art. Such methods comprise, but are not limited to Western blots, ELISA-, RIA-, ECL-, IRMA-, EIA-, BIAcore-tests and peptide scans.

The term "specificity" refers to selective recognition of an antigen binding protein (such as an sdAb) for a particular epitope of an antigen. Natural antibodies, for example, are monospecific. The term "multispecific" as used herein denotes that an antigen binding protein has polyepitopic specificity (i.e., is capable of specifically binding to two, three, or more, different epitopes on one biological molecule or is capable of specifically binding to epitopes on two, three, or more, different biological molecules). "Bispecific" as used herein denotes that an antigen binding protein has two different antigen-binding specificities. Unless otherwise indicated, the order in which the antigens bound by a bispecific antibody listed is arbitrary. That is, for example, the terms "anti-TIGIT/PD-1," "anti-PD-1/TIGIT," "TIGIT× PD-1," "PD-1×TIGIT," "PD-1/TIGIT," "TIGIT/PD-1," "PD-1-TIGIT," and "TIGIT-PD-1" may be used interchangeably to refer to bispecific antibodies that specifically bind to both TIGIT and PD-1. The term "monospecific" as used herein denotes an antigen binding protein (such as an sdAb) that has one or more binding sites each of which bind the same epitope of the same antigen.

The term "valent" as used herein denotes the presence of a specified number of binding sites in an antigen binding protein. A natural antibody for example or a full length antibody has two binding sites and is bivalent. As such, the terms "trivalent", "tetravalent", "pentavalent" and "hexavalent" denote the presence of two binding site, three binding sites, four binding sites, five binding sites, and six binding sites, respectively, in an antigen binding protein.

"Antibody effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptors); and B cell activation. "Reduced or minimized" antibody effector function means that which is reduced by at least 50% (alternatively 60%, 65%, 70%, 75%, 80%, 85%, 90%, 95%, 96%, 97%, 98%, 99%) from the wild type or unmodified antibody. The determination of antibody effector function is readily determinable and measurable by one of ordinary skill in the art. In a preferred embodiment, the antibody effector functions of complement binding, complement dependent cytotoxicity and antibody dependent cytotoxicity are affected. In some embodiments, effector function is eliminated through a mutation in the constant region that eliminated glycosylation, e.g., "effectorless mutation." In one aspect, the effectorless mutation is an N297A or DANA mutation (D265A+N297A) in the $C_H2$ region. Shields et al., *J. Biol. Chem.* 276 (9): 6591-6604 (2001). Alternatively, additional mutations resulting in reduced or eliminated effector function include: K322A and L234A/L235A (LALA). Alternatively, effector function can be reduced or eliminated through production techniques, such as expression in host cells that do not glycosylate (e.g., *E. coli*) or in which result in an altered glycosylation pattern that is ineffective or less effective at promoting effector function (e.g., Shinkawa et al., *J. Biol. Chem.* 278(5): 3466-3473 (2003).

"Antibody-dependent cell-mediated cytotoxicity" or ADCC refers to a form of cytotoxicity in which secreted Ig bound onto Fc receptors (FcRs) present on certain cytotoxic cells (e.g., natural killer (NK) cells, neutrophils and macrophages) enable these cytotoxic effector cells to bind specifically to an antigen-bearing target cell and subsequently kill the target cell with cytotoxins. The antibodies "arm" the cytotoxic cells and are required for killing of the target cell by this mechanism. The primary cells for mediating ADCC, NK cells, express FcγRIII only, whereas monocytes express FcγRI, FcγRII and FcγRIII. Fc expression on hematopoietic cells is summarized in Table 2 on page 464 of Ravetch and Kinet, *Annu. Rev. Immunol.* 9: 457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and natural killer (NK) cells. Alternatively, or additionally, ADCC activity of the molecule of interest may be assessed in vivo, e.g., in an animal model such as that disclosed in Clynes et al., *PNAS USA* 95:652-656 (1998).

The term "Fc region" or "fragment crystallizable region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies described herein include human IgG1, IgG2 (IgG2A, IgG2B), IgG3 and IgG4.

"Fc receptor" or "FcR" describes a receptor that binds the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (See M. Daëron, *Annu. Rev. Immunol.* 15:203-234 (1997). FcRs are reviewed in Ravetch and Kinet, *Annu. Rev. Immunol.* 9: 457-92 (1991); Capel et al., *Immunomethods* 4: 25-34 (1994); and de Haas et al., *J. Lab. Clin. Med.* 126: 330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus. Guyer et al., *J. Immunol.* 117: 587 (1976) and Kim et al., *J. Immunol.* 24: 249 (1994). Methods of measuring binding to FcRn are known (see, e.g., Ghetie and Ward, *Immunol. Today* 18: (12): 592-8 (1997); Ghetie et al., *Nature Biotechnology* 15 (7): 637-40 (1997); Hinton et al., *J. Biol. Chem.* 279 (8): 6213-6 (2004); WO 2004/92219 (Hinton et al.). Binding to FcRn in vivo and serum half-life of human FcRn high-affinity binding polypeptides can be assayed, e.g., in transgenic mice or transfected human cell lines expressing human FcRn, or in primates to which the polypeptides having a variant Fc region are administered. WO 2004/42072 (Presta) describes antibody variants which improved or diminished binding to FcRs. See also, e.g., Shields et al., *J. Biol. Chem.* 9(2): 6591-6604 (2001).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., *J. Immunol. Methods* 202: 163 (1996), may be performed. Antibody variants with altered Fc region amino acid sequences and increased or decreased C1q binding capability are described in U.S. Pat. No. 6,194,551B1 and WO99/51642. The contents of those patent publications are specifically incorporated herein by reference. See, also, Idusogie et al. *J. Immunol.* 164: 4178-4184 (2000).

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity that reflects a 1:1 interaction between members of a binding pair. Binding affinity can be indicated by $K_d$, $K_{off}$, $K_{on}$, or $K_a$. The term "$K_{off}$", as used herein, is intended to refer to the off rate constant for dissociation of an antibody (or antigen-binding domain) from the antibody/antigen complex, as determined from a kinetic selection set up, expressed in units of $s^{-1}$. The term "$K_{on}$", as used herein, is intended to refer to the on rate constant for association of an antibody (or antigen-binding domain) to the antigen to form the antibody/antigen complex, expressed in units of $M^{-1} s^{-1}$. The term equilibrium dissociation constant "$K_D$" or "$K_d$", as used herein, refers to the dissociation constant of a particular antibody-antigen interaction, and describes the concentration of antigen required to occupy one half of all of the antibody-binding domains present in a solution of antibody molecules at equilibrium, and is equal to $K_{off}/K_{on}$, expressed in units of M. The measurement of $K_d$ presupposes that all binding agents are in solution. In the case where the antibody is tethered to a cell wall, e.g., in a yeast expression system, the corresponding equilibrium rate constant is expressed as EC50, which gives a good approximation of $K_d$. The affinity constant, $K_a$, is the inverse of the dissociation constant, $K_d$, expressed in units of $M^{-1}$. The dissociation constant ($K_D$ or $K_d$) is used as an indicator showing affinity of antibodies to antigens. For example, easy analysis is possible by the Scatchard method using antibodies marked with a variety of marker agents, as well as by using BiacoreX (made by Amersham Biosciences), which is an over-the-counter, measuring kit, or similar kit, according to the user's manual and experiment operation method attached with the kit. The $K_D$ value that can be derived using these methods is expressed in units of M (Mols). An antibody or antigen-binding fragment thereof that specifically binds to a target may have a dissociation constant ($K_d$) of, for example, $\leq 10^{-5}$ M, $\leq 10^{-6}$ M, $\leq 10^{-7}$ M, $\leq 10^{-8}$ M, $\leq 10^{-9}$ M, $\leq 10^{-10}$ M, $\leq 10^{-11}$ M, or $\leq 10^{-12}$ M.

Half maximal inhibitory concentration ($IC_{50}$) is a measure of the effectiveness of a substance (such as an antibody) in inhibiting a specific biological or biochemical function. It indicates how much of a particular drug or other substance (inhibitor, such as an antibody) is needed to inhibit a given biological process (e.g., the binding between PD-1 and PD-L1/PD-L2, or component of a process, i.e. an enzyme, cell, cell receptor or microorganism) by half. The values are typically expressed as molar concentration. $IC_{50}$ is comparable to an "$EC_{50}$" for agonist drug or other substance (such as an antibody). $EC_{50}$ also represents the plasma concentration required for obtaining 50% of a maximum effect in vivo. As used herein, an "$IC_{50}$" is used to indicate the effective concentration of an antibody (such as an anti-PD-1 sdAb) needed to neutralize 50% of the antigen bioactivity (such as PD-1 bioactivity) in vitro. $IC_{50}$ or $EC_{50}$ can be measured by bioassays such as inhibition of ligand binding by FACS analysis (competition binding assay), cell based cytokine release assay, or amplified luminescent proximity homogeneous assay (AlphaLISA).

"Percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

An "isolated" nucleic acid molecule encoding a construct, antibody, or antigen-binding fragment thereof described herein is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies described herein is in a form other than in the form or setting in which it is found in nature. Isolated nucleic acid molecules therefore are distinguished from nucleic acid encoding the polypeptides and antibodies described herein existing naturally in cells. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

"Adjuvant setting" refers to a clinical setting in which an individual has had a history of cancer, and generally (but not necessarily) been responsive to therapy, which includes, but is not limited to, surgery (e.g., surgery resection), radiotherapy, and chemotherapy. However, because of their history of cancer, these individuals are considered at risk of development of the disease. Treatment or administration in the "adjuvant setting" refers to a subsequent mode of treatment. The degree of risk (e.g., when an individual in the adjuvant setting is considered as "high risk" or "low risk") depends upon several factors, most usually the extent of disease when first treated.

"Neoadjuvant setting" refers to a clinical setting in which the method is carried out before the primary/definitive therapy.

The term "pharmaceutical formulation" of "pharmaceutical composition" refers to a preparation that is in such form as to permit the biological activity of the active ingredient to be effective, and that contains no additional components that are unacceptably toxic to a subject to which the formulation would be administered. Such formulations are sterile. A "sterile" formulation is aseptic or free from all living microorganisms and their spores.

It is understood that embodiments of the invention described herein include "consisting" and/or "consisting essentially of" embodiments.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter. For example, the method is not used to treat cancer of type X means the method is used to treat cancer of types other than X.

As used herein and in the appended claims, the singular forms "a," "or," and "the" include plural referents unless the context clearly dictates otherwise.

II. Anti-PD-1 Construct (I) Anti-PD-1 Single-Domain Antibody Moiety

The isolated anti-PD-1 construct described herein comprises a single-domain antibody (sdAb) moiety that specifically recognizes PD-1 (or "anti-PD-1 sdAb"). In some embodiments, the isolated anti-PD-1 construct is an anti-PD-1 sdAb.

In some embodiments, there is provided an anti-PD-1 sdAb moiety comprising a CDR1 comprising the amino acid sequence of any one of SEQ ID NOs: 37-72, or a variant thereof comprising up to about 3 (such as about any of 1, 2, or 3) amino acid substitutions; a CDR2 comprising the amino acid sequence of any one of SEQ ID NOs: 109-144, or a variant thereof comprising up to about 3 (such as about any of 1, 2, or 3) amino acid substitutions; and a CDR3 comprising the amino acid sequence of any one of SEQ ID NOs: 181-216, or a variant thereof comprising up to about 3 (such as about any of 1, 2, or 3) amino acid substitutions. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized.

In some embodiments, the anti-PD-1 sdAb moiety comprises a CDR3 comprising the amino acid sequence of any one of SEQ ID NOs: 181-216, and the amino acid substitutions are in CDR1 and/or CDR2. Thus, in some embodiments, there is provided an anti-PD-1 sdAb moiety comprising a CDR1 comprising the amino acid sequence of any one of SEQ ID NOs: 37-72, or a variant thereof comprising up to about 3 (such as about any of 1, 2, or 3) amino acid substitutions; a CDR2 comprising the amino acid sequence of any one of SEQ ID NOs: 109-144, or a variant thereof comprising up to about 3 (such as about any of 1, 2, or 3) amino acid substitutions; and a CDR3 comprising the amino acid sequence of any one of SEQ ID NOs: 181-216. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized.

In some embodiments, there is provided an anti-PD-1 sdAb moiety comprising a CDR1 comprising the amino acid sequence of any one of SEQ ID NOs: 37-72; a CDR2 comprising the amino acid sequence of any one of SEQ ID NOs: 109-144; and a CDR3 comprising the amino acid sequence of any one of SEQ ID NOs: 181-216; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-PD-1 sdAb moiety comprising a CDR1 comprising the amino acid sequence of any one of SEQ ID NOs: 37-72; a CDR2 comprising the amino acid sequence of any one of SEQ ID NOs: 109-144; and a CDR3 comprising the amino acid sequence of any one of SEQ ID NOs: 181-216; or a variant thereof comprising up to about 3 (such as about any of 1, 2, or 3) amino acid substitutions in the CDR regions, wherein the amino acid substitutions are in CDR1 and/or CDR2. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized.

In some embodiments, there is provided an anti-PD-1 sdAb moiety comprising a CDR1 comprising the amino acid sequence of any one of SEQ ID NOs: 37-72; a CDR2 comprising the amino acid sequence of any one of SEQ ID NOs: 109-144; and a CDR3 comprising the amino acid sequence of any one of SEQ ID NOs: 181-216. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized.

The sequences of the CDRs noted herein are provided in Table 3. The CDRs can be combined in various pair-wise combinations to generate a number of anti-PD-1 sdAb moieties.

For example, in some embodiments, there is provided an anti-PD-1 sdAb moiety comprising a CDR1 comprising the amino acid sequence of SEQ ID NO: 37, or a variant thereof comprising up to about 3 (such as about any of 1, 2, or 3) amino acid substitutions; a CDR2 comprising the amino acid sequence of SEQ ID NO: 109, or a variant thereof comprising up to about 3 (such as about any of 1, 2, or 3) amino acid substitutions; and a CDR3 comprising the amino acid sequence of SEQ ID NO: 181, or a variant thereof comprising up to about 3 (such as about any of 1, 2, or 3) amino acid substitutions. In some embodiments, there is provided an anti-PD-1 sdAb moiety comprising a CDR1 comprising the amino acid sequence of SEQ ID NO: 37; a CDR2 comprising the amino acid sequence of SEQ ID NO: 109; and a CDR3 comprising the amino acid sequence of SEQ ID NO: 181; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-PD-1 sdAb moiety comprising a CDR1 comprising the amino acid sequence of SEQ ID NO: 37; a CDR2 comprising the amino acid sequence of SEQ ID NO: 109; and a CDR3 comprising the amino acid sequence of SEQ ID NO: 181. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$M). In some embodiments, the anti-PD-1 sdAb moiety is camelid, chimeric, human, partially humanized, or fully humanized.

In some embodiments, there is provided an anti-PD-1 sdAb moiety comprising a CDR1 comprising the amino acid sequence of SEQ ID NO: 38, or a variant thereof comprising up to about 3 (such as about any of 1, 2, or 3) amino acid substitutions; a CDR2 comprising the amino acid sequence of SEQ ID NO: 110, or a variant thereof comprising up to about 3 (such as about any of 1, 2, or 3) amino acid substitutions; and a CDR3 comprising the amino acid sequence of SEQ ID NO: 182, or a variant thereof comprising up to about 3 (such as about any of 1, 2, or 3) amino acid substitutions. In some embodiments, there is provided an anti-PD-1 sdAb moiety comprising a CDR1 comprising the amino acid sequence of SEQ ID NO: 38; a CDR2 comprising the amino acid sequence of SEQ ID NO: 110; and a CDR3 comprising the amino acid sequence of SEQ ID NO: 182; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-PD-1 sdAb moiety comprising a CDR1 comprising the amino acid sequence of SEQ ID NO: 38; a CDR2 comprising the amino acid sequence of SEQ ID NO: 110; and a CDR3 comprising the amino acid sequence of SEQ ID NO: 182. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized.

In some embodiments, there is provided an anti-PD-1 sdAb moiety comprising a CDR1 comprising the amino acid sequence of SEQ ID NO: 39, or a variant thereof comprising up to about 3 (such as about any of 1, 2, or 3) amino acid substitutions; a CDR2 comprising the amino acid sequence of SEQ ID NO: 111, or a variant thereof comprising up to about 3 (such as about any of 1, 2, or 3) amino acid substitutions; and a CDR3 comprising the amino acid sequence of SEQ ID NO: 183, or a variant thereof comprising up to about 3 (such as about any of 1, 2, or 3) amino acid substitutions. In some embodiments, there is provided an anti-PD-1 sdAb moiety comprising a CDR1 comprising the amino acid sequence of SEQ ID NO: 39; a CDR2 comprising the amino acid sequence of SEQ ID NO: 111; and a CDR3 comprising the amino acid sequence of SEQ ID NO: 183; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-PD-1 sdAb moiety comprising a CDR1 comprising the amino acid sequence of SEQ ID NO: 39; a CDR2 comprising the amino acid sequence of SEQ ID NO: 111; and a CDR3 comprising the amino acid sequence of SEQ ID NO: 183. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized.

In some embodiments, there is provided an anti-PD-1 sdAb moiety comprising a CDR1 comprising the amino acid sequence of SEQ ID NO: 40, or a variant thereof comprising up to about 3 (such as about any of 1, 2, or 3) amino acid substitutions; a CDR2 comprising the amino acid sequence of SEQ ID NO: 112, or a variant thereof comprising up to about 3 (such as about any of 1, 2, or 3) amino acid substitutions; and a CDR3 comprising the amino acid sequence of SEQ ID NO: 184, or a variant thereof comprising up to about 3 (such as about any of 1, 2, or 3) amino acid substitutions. In some embodiments, there is provided an anti-PD-1 sdAb moiety comprising a CDR1 comprising the amino acid sequence of SEQ ID NO: 40; a CDR2 comprising the amino acid sequence of SEQ ID NO: 112; and a CDR3 comprising the amino acid sequence of SEQ ID NO: 184; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-PD-1 sdAb moiety comprising a CDR1 comprising the amino acid sequence of SEQ ID NO: 40; a CDR2 comprising the amino acid sequence of SEQ ID NO: 112; and a CDR3 comprising the amino acid sequence of SEQ ID NO: 184. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized.

In some embodiments, there is provided an anti-PD-1 sdAb moiety comprising a CDR1 comprising the amino acid sequence of SEQ ID NO: 41, or a variant thereof comprising up to about 3 (such as about any of 1, 2, or 3) amino acid substitutions; a CDR2 comprising the amino acid sequence of SEQ ID NO: 113, or a variant thereof comprising up to about 3 (such as about any of 1, 2, or 3) amino acid substitutions; and a CDR3 comprising the amino acid sequence of SEQ ID NO: 185, or a variant thereof comprising up to about 3 (such as about any of 1, 2, or 3) amino acid substitutions. In some embodiments, there is provided an anti-PD-1 sdAb moiety comprising a CDR1 comprising the amino acid sequence of SEQ ID NO: 41; a CDR2 comprising the amino acid sequence of SEQ ID NO: 113; and a CDR3 comprising the amino acid sequence of SEQ ID NO: 185; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-PD-1 sdAb moiety comprising a CDR1 comprising the amino acid sequence of SEQ ID NO: 41; a CDR2 comprising the amino acid sequence of SEQ ID NO: 113; and a CDR3 comprising the amino acid sequence of SEQ ID NO: 185. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized.

In some embodiments, there is provided an anti-PD-1 sdAb moiety comprising a CDR1 comprising the amino acid sequence of SEQ ID NO: 42, or a variant thereof comprising up to about 3 (such as about any of 1, 2, or 3) amino acid substitutions; a CDR2 comprising the amino acid sequence of SEQ ID NO: 114, or a variant thereof comprising up to about 3 (such as about any of 1, 2, or 3) amino acid substitutions; and a CDR3 comprising the amino acid sequence of SEQ ID NO: 186, or a variant thereof comprising up to about 3 (such as about any of 1, 2, or 3) amino acid substitutions. In some embodiments, there is provided an anti-PD-1 sdAb moiety comprising a CDR1 comprising the amino acid sequence of SEQ ID NO: 42; a CDR2 comprising the amino acid sequence of SEQ ID NO: 114; and a CDR3 comprising the amino acid sequence of SEQ ID NO: 186; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-PD-1 sdAb moiety comprising a CDR1 comprising the amino acid sequence of SEQ ID NO: 42; a CDR2 comprising the amino acid sequence of SEQ ID NO: 114; and a CDR3 comprising the amino acid sequence of SEQ ID NO: 186. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized.

In some embodiments, there is provided an anti-PD-1 sdAb moiety comprising a CDR1 comprising the amino acid sequence of SEQ ID NO: 43, or a variant thereof comprising up to about 3 (such as about any of 1, 2, or 3) amino acid substitutions; a CDR2 comprising the amino acid sequence of SEQ ID NO: 115, or a variant thereof comprising up to about 3 (such as about any of 1, 2, or 3) amino acid substitutions; and a CDR3 comprising the amino acid sequence of SEQ ID NO: 187, or a variant thereof comprising up to about 3 (such as about any of 1, 2, or 3) amino acid substitutions. In some embodiments, there is provided an anti-PD-1 sdAb moiety comprising a CDR1 comprising the amino acid sequence of SEQ ID NO: 43; a CDR2 comprising the amino acid sequence of SEQ ID NO: 115; and a CDR3 comprising the amino acid sequence of SEQ ID NO: 187; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-PD-1 sdAb moiety comprising a CDR1 comprising the amino acid sequence of SEQ ID NO: 43; a CDR2 comprising the amino acid sequence of SEQ ID NO: 115; and a CDR3 comprising the amino acid sequence of SEQ ID NO: 187. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized.

In some embodiments, there is provided an anti-PD-1 sdAb moiety comprising a CDR1 comprising the amino acid sequence of SEQ ID NO: 44, or a variant thereof comprising up to about 3 (such as about any of 1, 2, or 3) amino acid substitutions; a CDR2 comprising the amino acid sequence of SEQ ID NO: 116, or a variant thereof comprising up to about 3 (such as about any of 1, 2, or 3) amino acid substitutions; and a CDR3 comprising the amino acid sequence of SEQ ID NO: 188, or a variant thereof comprising up to about 3 (such as about any of 1, 2, or 3) amino acid substitutions. In some embodiments, there is provided an anti-PD-1 sdAb moiety comprising a CDR1 comprising the amino acid sequence of SEQ ID NO: 44; a CDR2 comprising the amino acid sequence of SEQ ID NO: 116; and a CDR3 comprising the amino acid sequence of SEQ ID NO: 188; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-PD-1 sdAb moiety comprising a CDR1 comprising the amino acid sequence of SEQ ID NO: 44; a CDR2 comprising the amino acid sequence of SEQ ID NO: 116; and a CDR3 comprising the amino acid sequence of SEQ ID NO: 188. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized.

In some embodiments, there is provided an anti-PD-1 sdAb moiety comprising a CDR1 comprising the amino acid sequence of SEQ ID NO: 45, or a variant thereof comprising up to about 3 (such as about any of 1, 2, or 3) amino acid substitutions; a CDR2 comprising the amino acid sequence of SEQ ID NO: 117, or a variant thereof comprising up to about 3 (such as about any of 1, 2, or 3) amino acid substitutions; and a CDR3 comprising the amino acid sequence of SEQ ID NO: 189, or a variant thereof comprising up to about 3 (such as about any of 1, 2, or 3) amino acid substitutions. In some embodiments, there is provided an anti-PD-1 sdAb moiety comprising a CDR1 comprising the amino acid sequence of SEQ ID NO: 45; a CDR2 comprising the amino acid sequence of SEQ ID NO: 117; and a CDR3 comprising the amino acid sequence of SEQ ID NO: 189; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-PD-1 sdAb moiety comprising a CDR1 comprising the amino acid sequence of SEQ ID NO: 45; a CDR2 comprising the amino acid sequence of SEQ ID NO: 117; and a CDR3 comprising the amino acid sequence of SEQ ID NO: 189. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized.

In some embodiments, there is provided an anti-PD-1 sdAb moiety comprising a CDR1 comprising the amino acid sequence of SEQ ID NO: 46, or a variant thereof comprising up to about 3 (such as about any of 1, 2, or 3) amino acid substitutions; a CDR2 comprising the amino acid sequence of SEQ ID NO: 118, or a variant thereof comprising up to about 3 (such as about any of 1, 2, or 3) amino acid substitutions; and a CDR3 comprising the amino acid sequence of SEQ ID NO: 190, or a variant thereof comprising up to about 3 (such as about any of 1, 2, or 3) amino acid substitutions. In some embodiments, there is provided an anti-PD-1 sdAb moiety comprising a CDR1 comprising the amino acid sequence of SEQ ID NO: 46; a CDR2 comprising the amino acid sequence of SEQ ID NO: 118; and a CDR3 comprising the amino acid sequence of SEQ ID NO: 190; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-PD-1 sdAb moiety comprising a CDR1 comprising the amino acid sequence of SEQ ID NO: 46; a CDR2 comprising the amino acid sequence of SEQ ID NO: 118; and a CDR3 comprising the amino acid sequence of SEQ ID NO: 190. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized.

In some embodiments, there is provided an anti-PD-1 sdAb moiety comprising a CDR1 comprising the amino acid sequence of SEQ ID NO: 47, or a variant thereof comprising up to about 3 (such as about any of 1, 2, or 3) amino acid substitutions; a CDR2 comprising the amino acid sequence of SEQ ID NO: 119, or a variant thereof comprising up to about 3 (such as about any of 1, 2, or 3) amino acid substitutions; and a CDR3 comprising the amino acid sequence of SEQ ID NO: 191, or a variant thereof comprising up to about 3 (such as about any of 1, 2, or 3) amino acid substitutions. In some embodiments, there is provided an anti-PD-1 sdAb moiety comprising a CDR1 comprising the amino acid sequence of SEQ ID NO: 47; a CDR2 comprising the amino acid sequence of SEQ ID NO: 119; and a CDR3 comprising the amino acid sequence of SEQ ID NO: 191; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-PD-1 sdAb moiety comprising a CDR1 comprising the amino acid sequence of SEQ ID NO: 47; a CDR2 comprising the amino acid sequence of SEQ ID NO: 119; and a CDR3 comprising the amino acid sequence of SEQ ID NO: 191. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized.

In some embodiments, there is provided an anti-PD-1 sdAb moiety comprising a CDR1 comprising the amino acid sequence of SEQ ID NO: 48, or a variant thereof comprising up to about 3 (such as about any of 1, 2, or 3) amino acid substitutions; a CDR2 comprising the amino acid sequence of SEQ ID NO: 120, or a variant thereof comprising up to about 3 (such as about any of 1, 2, or 3) amino acid substitutions; and a CDR3 comprising the amino acid sequence of SEQ ID NO: 192, or a variant thereof comprising up to about 3 (such as about any of 1, 2, or 3) amino acid substitutions. In some embodiments, there is provided an anti-PD-1 sdAb moiety comprising a CDR1 comprising the amino acid sequence of SEQ ID NO: 48; a CDR2 comprising the amino acid sequence of SEQ ID NO: 120; and a CDR3 comprising the amino acid sequence of SEQ ID NO: 192; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-PD-1 sdAb moiety comprising a CDR1 comprising the amino acid sequence of SEQ ID NO: 48; a CDR2 comprising the amino acid sequence of SEQ ID NO: 120; and a CDR3 comprising the amino acid sequence of SEQ ID NO: 192. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized.

In some embodiments, there is provided an anti-PD-1 sdAb moiety comprising a CDR1 comprising the amino acid sequence of SEQ ID NO: 49, or a variant thereof comprising up to about 3 (such as about any of 1, 2, or 3) amino acid substitutions; a CDR2 comprising the amino acid sequence of SEQ ID NO: 121, or a variant thereof comprising up to about 3 (such as about any of 1, 2, or 3) amino acid substitutions; and a CDR3 comprising the amino acid sequence of SEQ ID NO: 193, or a variant thereof comprising up to about 3 (such as about any of 1, 2, or 3) amino acid substitutions. In some embodiments, there is provided an anti-PD-1 sdAb moiety comprising a CDR1 comprising the amino acid sequence of SEQ ID NO: 49; a CDR2 comprising the amino acid sequence of SEQ ID NO: 121; and a CDR3 comprising the amino acid sequence of SEQ ID NO: 193; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-PD-1 sdAb moiety comprising a CDR1 comprising the amino acid sequence of SEQ ID NO: 49; a CDR2 comprising the amino acid sequence of SEQ ID NO: 121; and a CDR3 comprising the amino acid sequence of SEQ ID NO: 193. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized.

In some embodiments, there is provided an anti-PD-1 sdAb moiety comprising a CDR1 comprising the amino acid sequence of SEQ ID NO: 50, or a variant thereof comprising up to about 3 (such as about any of 1, 2, or 3) amino acid substitutions; a CDR2 comprising the amino acid sequence of SEQ ID NO: 122, or a variant thereof comprising up to about 3 (such as about any of 1, 2, or 3) amino acid substitutions; and a CDR3 comprising the amino acid sequence of SEQ ID NO: 194, or a variant thereof comprising up to about 3 (such as about any of 1, 2, or 3) amino acid substitutions. In some embodiments, there is provided an anti-PD-1 sdAb moiety comprising a CDR1 comprising the amino acid sequence of SEQ ID NO: 50; a CDR2 comprising the amino acid sequence of SEQ ID NO: 122; and a CDR3 comprising the amino acid sequence of SEQ ID NO: 194; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-PD-1 sdAb moiety comprising a CDR1 comprising the amino acid sequence of SEQ ID NO: 50; a CDR2 comprising the amino acid sequence of SEQ ID NO: 122; and a CDR3 comprising the amino acid sequence of SEQ ID NO: 194. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized.

In some embodiments, there is provided an anti-PD-1 sdAb moiety comprising a CDR1 comprising the amino acid sequence of SEQ ID NO: 51, or a variant thereof comprising up to about 3 (such as about any of 1, 2, or 3) amino acid substitutions; a CDR2 comprising the amino acid sequence of SEQ ID NO: 123, or a variant thereof comprising up to about 3 (such as about any of 1, 2, or 3) amino acid substitutions; and a CDR3 comprising the amino acid sequence of SEQ ID NO: 195, or a variant thereof comprising up to about 3 (such as about any of 1, 2, or 3) amino acid substitutions. In some embodiments, there is provided an anti-PD-1 sdAb moiety comprising a CDR1 comprising the amino acid sequence of SEQ ID NO: 51; a CDR2 comprising the amino acid sequence of SEQ ID NO: 123; and a CDR3 comprising the amino acid sequence of SEQ ID NO: 195; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-PD-1 sdAb moiety comprising a CDR1 comprising the amino acid sequence of SEQ ID NO: 51; a CDR2 comprising the amino acid sequence of SEQ ID NO: 123; and a CDR3 comprising the amino acid sequence of SEQ ID NO: 195. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized.

In some embodiments, there is provided an anti-PD-1 sdAb moiety comprising a CDR1 comprising the amino acid sequence of SEQ ID NO: 52, or a variant thereof comprising up to about 3 (such as about any of 1, 2, or 3) amino acid substitutions; a CDR2 comprising the amino acid sequence of SEQ ID NO: 124, or a variant thereof comprising up to about 3 (such as about any of 1, 2, or 3) amino acid substitutions; and a CDR3 comprising the amino acid sequence of SEQ ID NO: 196, or a variant thereof comprising up to about 3 (such as about any of 1, 2, or 3) amino acid substitutions. In some embodiments, there is provided an anti-PD-1 sdAb moiety comprising a CDR1 comprising the amino acid sequence of SEQ ID NO: 52; a CDR2 comprising the amino acid sequence of SEQ ID NO: 124; and a CDR3 comprising the amino acid sequence of SEQ ID NO: 196; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-PD-1 sdAb moiety comprising a CDR1 comprising the amino acid sequence of SEQ ID NO: 52; a CDR2 comprising the amino acid sequence of SEQ ID NO: 124; and a CDR3 comprising the amino acid sequence of SEQ ID NO: 196. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized.

In some embodiments, there is provided an anti-PD-1 sdAb moiety comprising a CDR1 comprising the amino acid sequence of SEQ ID NO: 53, or a variant thereof comprising up to about 3 (such as about any of 1, 2, or 3) amino acid substitutions; a CDR2 comprising the amino acid sequence of SEQ ID NO: 125, or a variant thereof comprising up to about 3 (such as about any of 1, 2, or 3) amino acid substitutions; and a CDR3 comprising the amino acid sequence of SEQ ID NO: 197, or a variant thereof comprising up to about 3 (such as about any of 1, 2, or 3) amino acid substitutions. In some embodiments, there is provided an anti-PD-1 sdAb moiety comprising a CDR1 comprising the amino acid sequence of SEQ ID NO: 53; a CDR2 comprising the amino acid sequence of SEQ ID NO: 125; and a CDR3 comprising the amino acid sequence of SEQ ID NO: 197; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-PD-1 sdAb moiety comprising a CDR1 comprising the amino acid sequence of SEQ ID NO: 53; a CDR2 comprising the amino acid sequence of SEQ ID NO: 125; and a CDR3 comprising the amino acid sequence of SEQ ID NO: 197. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized.

In some embodiments, there is provided an anti-PD-1 sdAb moiety comprising a CDR1 comprising the amino acid sequence of SEQ ID NO: 54, or a variant thereof comprising up to about 3 (such as about any of 1, 2, or 3) amino acid substitutions; a CDR2 comprising the amino acid sequence of SEQ ID NO: 126, or a variant thereof comprising up to about 3 (such as about any of 1, 2, or 3) amino acid substitutions; and a CDR3 comprising the amino acid sequence of SEQ ID NO: 198, or a variant thereof comprising up to about 3 (such as about any of 1, 2, or 3) amino acid substitutions. In some embodiments, there is provided an anti-PD-1 sdAb moiety comprising a CDR1 comprising the amino acid sequence of SEQ ID NO: 54; a CDR2 comprising the amino acid sequence of SEQ ID NO: 126; and a CDR3 comprising the amino acid sequence of SEQ ID NO: 198; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-PD-1 sdAb moiety comprising a CDR1 comprising the amino acid sequence of SEQ ID NO: 54; a CDR2 comprising the amino acid sequence of SEQ ID NO: 126; and a CDR3 comprising the amino acid sequence of SEQ ID NO: 198. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized.

In some embodiments, there is provided an anti-PD-1 sdAb moiety comprising a CDR1 comprising the amino acid sequence of SEQ ID NO: 55, or a variant thereof comprising up to about 3 (such as about any of 1, 2, or 3) amino acid substitutions; a CDR2 comprising the amino acid sequence of SEQ ID NO: 127, or a variant thereof comprising up to about 3 (such as about any of 1, 2, or 3) amino acid substitutions; and a CDR3 comprising the amino acid sequence of SEQ ID NO: 199, or a variant thereof comprising up to about 3 (such as about any of 1, 2, or 3) amino acid substitutions. In some embodiments, there is provided an anti-PD-1 sdAb moiety comprising a CDR1 comprising the amino acid sequence of SEQ ID NO: 55; a CDR2 comprising the amino acid sequence of SEQ ID NO: 127; and a CDR3 comprising the amino acid sequence of SEQ ID NO: 199; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-PD-1 sdAb moiety comprising a CDR1 comprising the amino acid sequence of SEQ ID NO: 55; a CDR2 comprising the amino acid sequence of SEQ ID NO: 127; and a CDR3 comprising the amino acid sequence of SEQ ID NO: 199. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized.

In some embodiments, there is provided an anti-PD-1 sdAb moiety comprising a CDR1 comprising the amino acid sequence of SEQ ID NO: 56, or a variant thereof comprising up to about 3 (such as about any of 1, 2, or 3) amino acid substitutions; a CDR2 comprising the amino acid sequence of SEQ ID NO: 128, or a variant thereof comprising up to about 3 (such as about any of 1, 2, or 3) amino acid substitutions; and a CDR3 comprising the amino acid sequence of SEQ ID NO: 200, or a variant thereof comprising up to about 3 (such as about any of 1, 2, or 3) amino acid substitutions. In some embodiments, there is provided an anti-PD-1 sdAb moiety comprising a CDR1 comprising the amino acid sequence of SEQ ID NO: 56; a CDR2 comprising the amino acid sequence of SEQ ID NO: 128; and a CDR3 comprising the amino acid sequence of SEQ ID NO: 200; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-PD-1 sdAb moiety comprising a CDR1 comprising the amino acid sequence of SEQ ID NO: 56; a CDR2 comprising the amino acid sequence of SEQ ID NO: 128; and a CDR3 comprising the amino acid sequence of SEQ ID NO: 200. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized.

In some embodiments, there is provided an anti-PD-1 sdAb moiety comprising a CDR1 comprising the amino acid sequence of SEQ ID NO: 57, or a variant thereof comprising up to about 3 (such as about any of 1, 2, or 3) amino acid substitutions; a CDR2 comprising the amino acid sequence of SEQ ID NO: 129, or a variant thereof comprising up to about 3 (such as about any of 1, 2, or 3) amino acid substitutions; and a CDR3 comprising the amino acid sequence of SEQ ID NO: 201, or a variant thereof comprising up to about 3 (such as about any of 1, 2, or 3) amino acid substitutions. In some embodiments, there is provided an anti-PD-1 sdAb moiety comprising a CDR1 comprising the amino acid sequence of SEQ ID NO: 57; a CDR2 comprising the amino acid sequence of SEQ ID NO: 129; and a CDR3 comprising the amino acid sequence of SEQ ID NO: 201; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-PD-1 sdAb moiety comprising a CDR1 comprising the amino acid sequence of SEQ ID NO: 57; a CDR2 comprising the amino acid sequence of SEQ ID NO: 129; and a CDR3 comprising the amino acid sequence of SEQ ID NO: 201. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized.

In some embodiments, there is provided an anti-PD-1 sdAb moiety comprising a CDR1 comprising the amino acid sequence of SEQ ID NO: 58, or a variant thereof comprising up to about 3 (such as about any of 1, 2, or 3) amino acid substitutions; a CDR2 comprising the amino acid sequence of SEQ ID NO: 130, or a variant thereof comprising up to about 3 (such as about any of 1, 2, or 3) amino acid substitutions; and a CDR3 comprising the amino acid sequence of SEQ ID NO: 202, or a variant thereof comprising up to about 3 (such as about any of 1, 2, or 3) amino acid substitutions. In some embodiments, there is provided an anti-PD-1 sdAb moiety comprising a CDR1 comprising the amino acid sequence of SEQ ID NO: 58; a CDR2 comprising the amino acid sequence of SEQ ID NO: 130; and a CDR3 comprising the amino acid sequence of SEQ ID NO: 202; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-PD-1 sdAb moiety comprising a CDR1 comprising the amino acid sequence of SEQ ID NO: 58; a CDR2 comprising the amino acid sequence of SEQ ID NO: 130; and a CDR3 comprising the amino acid sequence of SEQ ID NO: 202. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized.

In some embodiments, there is provided an anti-PD-1 sdAb moiety comprising a CDR1 comprising the amino acid sequence of SEQ ID NO: 59, or a variant thereof comprising up to about 3 (such as about any of 1, 2, or 3) amino acid substitutions; a CDR2 comprising the amino acid sequence of SEQ ID NO: 131, or a variant thereof comprising up to about 3 (such as about any of 1, 2, or 3) amino acid substitutions; and a CDR3 comprising the amino acid sequence of SEQ ID NO: 203, or a variant thereof comprising up to about 3 (such as about any of 1, 2, or 3) amino acid substitutions. In some embodiments, there is provided an anti-PD-1 sdAb moiety comprising a CDR1 comprising the amino acid sequence of SEQ ID NO: 59; a CDR2 comprising the amino acid sequence of SEQ ID NO: 131; and a CDR3 comprising the amino acid sequence of SEQ ID NO: 203; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-PD-1 sdAb moiety comprising a CDR1 comprising the amino acid sequence of SEQ ID NO: 59; a CDR2 comprising the amino acid sequence of SEQ ID NO: 131; and a CDR3 comprising the amino acid sequence of SEQ ID NO: 203. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized.

In some embodiments, there is provided an anti-PD-1 sdAb moiety comprising a CDR1 comprising the amino acid sequence of SEQ ID NO: 60, or a variant thereof comprising up to about 3 (such as about any of 1, 2, or 3) amino acid substitutions; a CDR2 comprising the amino acid sequence of SEQ ID NO: 132, or a variant thereof comprising up to about 3 (such as about any of 1, 2, or 3) amino acid substitutions; and a CDR3 comprising the amino acid sequence of SEQ ID NO: 204, or a variant thereof comprising up to about 3 (such as about any of 1, 2, or 3) amino acid substitutions. In some embodiments, there is provided an anti-PD-1 sdAb moiety comprising a CDR1 comprising the amino acid sequence of SEQ ID NO: 60; a CDR2 comprising the amino acid sequence of SEQ ID NO: 132; and a CDR3 comprising the amino acid sequence of SEQ ID NO: 204; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-PD-1 sdAb moiety comprising a CDR1 comprising the amino acid sequence of SEQ ID NO: 60; a CDR2 comprising the amino acid sequence of SEQ ID NO: 132; and a CDR3 comprising the amino acid sequence of SEQ ID NO: 204. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized.

In some embodiments, there is provided an anti-PD-1 sdAb moiety comprising a CDR1 comprising the amino acid sequence of SEQ ID NO: 61, or a variant thereof comprising up to about 3 (such as about any of 1, 2, or 3) amino acid substitutions; a CDR2 comprising the amino acid sequence of SEQ ID NO: 133, or a variant thereof comprising up to about 3 (such as about any of 1, 2, or 3) amino acid substitutions; and a CDR3 comprising the amino acid sequence of SEQ ID NO: 205, or a variant thereof comprising up to about 3 (such as about any of 1, 2, or 3) amino acid substitutions. In some embodiments, there is provided an anti-PD-1 sdAb moiety comprising a CDR1 comprising the amino acid sequence of SEQ ID NO: 61; a CDR2 comprising the amino acid sequence of SEQ ID NO: 133; and a CDR3 comprising the amino acid sequence of SEQ ID NO: 205; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-PD-1 sdAb moiety comprising a CDR1 comprising the amino acid sequence of SEQ ID NO: 61; a CDR2 comprising the amino acid sequence of SEQ ID NO: 133; and a CDR3 comprising the amino acid sequence of SEQ ID NO: 205. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized.

In some embodiments, there is provided an anti-PD-1 sdAb moiety comprising a CDR1 comprising the amino acid sequence of SEQ ID NO: 62, or a variant thereof comprising up to about 3 (such as about any of 1, 2, or 3) amino acid substitutions; a CDR2 comprising the amino acid sequence of SEQ ID NO: 134, or a variant thereof comprising up to about 3 (such as about any of 1, 2, or 3) amino acid substitutions; and a CDR3 comprising the amino acid sequence of SEQ ID NO: 206, or a variant thereof comprising up to about 3 (such as about any of 1, 2, or 3) amino acid substitutions. In some embodiments, there is provided an anti-PD-1 sdAb moiety comprising a CDR1 comprising the amino acid sequence of SEQ ID NO: 62; a CDR2 comprising the amino acid sequence of SEQ ID NO: 134; and a CDR3 comprising the amino acid sequence of SEQ ID NO: 206; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-PD-1 sdAb moiety comprising a CDR1 comprising the amino acid sequence of SEQ ID NO: 62; a CDR2 comprising the amino acid sequence of SEQ ID NO: 134; and a CDR3 comprising the amino acid sequence of SEQ ID NO: 206. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized.

In some embodiments, there is provided an anti-PD-1 sdAb moiety comprising a CDR1 comprising the amino acid sequence of SEQ ID NO: 63, or a variant thereof comprising up to about 3 (such as about any of 1, 2, or 3) amino acid substitutions; a CDR2 comprising the amino acid sequence of SEQ ID NO: 135, or a variant thereof comprising up to about 3 (such as about any of 1, 2, or 3) amino acid substitutions; and a CDR3 comprising the amino acid sequence of SEQ ID NO: 207, or a variant thereof comprising up to about 3 (such as about any of 1, 2, or 3) amino acid substitutions. In some embodiments, there is provided an anti-PD-1 sdAb moiety comprising a CDR1 comprising the amino acid sequence of SEQ ID NO: 63; a CDR2 comprising the amino acid sequence of SEQ ID NO: 135; and a CDR3 comprising the amino acid sequence of SEQ ID NO: 207; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-PD-1 sdAb moiety comprising a CDR1 comprising the amino acid sequence of SEQ ID NO: 63; a CDR2 comprising the amino acid sequence of SEQ ID NO: 135; and a CDR3 comprising the amino acid sequence of SEQ ID NO: 207. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized.

In some embodiments, there is provided an anti-PD-1 sdAb moiety comprising a CDR1 comprising the amino acid sequence of SEQ ID NO: 64, or a variant thereof comprising up to about 3 (such as about any of 1, 2, or 3) amino acid substitutions; a CDR2 comprising the amino acid sequence of SEQ ID NO: 136, or a variant thereof comprising up to about 3 (such as about any of 1, 2, or 3) amino acid substitutions; and a CDR3 comprising the amino acid sequence of SEQ ID NO: 208, or a variant thereof comprising up to about 3 (such as about any of 1, 2, or 3) amino acid substitutions. In some embodiments, there is provided an anti-PD-1 sdAb moiety comprising a CDR1 comprising the amino acid sequence of SEQ ID NO: 64; a CDR2 comprising the amino acid sequence of SEQ ID NO: 136; and a CDR3 comprising the amino acid sequence of SEQ ID NO: 208; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-PD-1 sdAb moiety comprising a CDR1 comprising the amino acid sequence of SEQ ID NO: 64; a CDR2 comprising the amino acid sequence of SEQ ID NO: 136; and a CDR3 comprising the amino acid sequence of SEQ ID NO: 208. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized.

In some embodiments, there is provided an anti-PD-1 sdAb moiety comprising a CDR1 comprising the amino acid sequence of SEQ ID NO: 65, or a variant thereof comprising up to about 3 (such as about any of 1, 2, or 3) amino acid substitutions; a CDR2 comprising the amino acid sequence of SEQ ID NO: 137, or a variant thereof comprising up to about 3 (such as about any of 1, 2, or 3) amino acid substitutions; and a CDR3 comprising the amino acid sequence of SEQ ID NO: 209, or a variant thereof comprising up to about 3 (such as about any of 1, 2, or 3) amino acid substitutions. In some embodiments, there is provided an anti-PD-1 sdAb moiety comprising a CDR1 comprising the amino acid sequence of SEQ ID NO: 65; a CDR2 comprising the amino acid sequence of SEQ ID NO: 137; and a CDR3 comprising the amino acid sequence of SEQ ID NO: 209; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-PD-1 sdAb moiety comprising a CDR1 comprising the amino acid sequence of SEQ ID NO: 65; a CDR2 comprising the amino acid sequence of SEQ ID NO: 137; and a CDR3 comprising the amino acid sequence of SEQ ID NO: 209. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized.

In some embodiments, there is provided an anti-PD-1 sdAb moiety comprising a CDR1 comprising the amino acid sequence of SEQ ID NO: 66, or a variant thereof comprising up to about 3 (such as about any of 1, 2, or 3) amino acid substitutions; a CDR2 comprising the amino acid sequence of SEQ ID NO: 138, or a variant thereof comprising up to about 3 (such as about any of 1, 2, or 3) amino acid substitutions; and a CDR3 comprising the amino acid sequence of SEQ ID NO: 210, or a variant thereof comprising up to about 3 (such as about any of 1, 2, or 3) amino acid substitutions. In some embodiments, there is provided an anti-PD-1 sdAb moiety comprising a CDR1 comprising the amino acid sequence of SEQ ID NO: 66; a CDR2 comprising the amino acid sequence of SEQ ID NO: 138; and a CDR3 comprising the amino acid sequence of SEQ ID NO: 210; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-PD-1 sdAb moiety comprising a CDR1 comprising the amino acid sequence of SEQ ID NO: 66; a CDR2 comprising the amino acid sequence of SEQ ID NO: 138; and a CDR3 comprising the amino acid sequence of SEQ ID NO: 210. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized.

In some embodiments, there is provided an anti-PD-1 sdAb moiety comprising a CDR1 comprising the amino acid sequence of SEQ ID NO: 67, or a variant thereof comprising up to about 3 (such as about any of 1, 2, or 3) amino acid substitutions; a CDR2 comprising the amino acid sequence of SEQ ID NO: 139, or a variant thereof comprising up to about 3 (such as about any of 1, 2, or 3) amino acid substitutions; and a CDR3 comprising the amino acid sequence of SEQ ID NO: 211, or a variant thereof comprising up to about 3 (such as about any of 1, 2, or 3) amino acid substitutions. In some embodiments, there is provided an anti-PD-1 sdAb moiety comprising a CDR1 comprising the amino acid sequence of SEQ ID NO: 67; a CDR2 comprising the amino acid sequence of SEQ ID NO: 139; and a CDR3 comprising the amino acid sequence of SEQ ID NO: 211; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-PD-1 sdAb moiety comprising a CDR1 comprising the amino acid sequence of SEQ ID NO: 67; a CDR2 comprising the amino acid sequence of SEQ ID NO: 139; and a CDR3 comprising the amino acid sequence of SEQ ID NO: 211. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized.

In some embodiments, there is provided an anti-PD-1 sdAb moiety comprising a CDR1 comprising the amino acid sequence of SEQ ID NO: 68, or a variant thereof comprising up to about 3 (such as about any of 1, 2, or 3) amino acid substitutions; a CDR2 comprising the amino acid sequence of SEQ ID NO: 140, or a variant thereof comprising up to about 3 (such as about any of 1, 2, or 3) amino acid substitutions; and a CDR3 comprising the amino acid sequence of SEQ ID NO: 212, or a variant thereof comprising up to about 3 (such as about any of 1, 2, or 3) amino acid substitutions. In some embodiments, there is provided an anti-PD-1 sdAb moiety comprising a CDR1 comprising the amino acid sequence of SEQ ID NO: 68; a CDR2 comprising the amino acid sequence of SEQ ID NO: 140; and a CDR3 comprising the amino acid sequence of SEQ ID NO: 212; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-PD-1 sdAb moiety comprising a CDR1 comprising the amino acid sequence of SEQ ID NO: 68; a CDR2 comprising the amino acid sequence of SEQ ID NO: 140; and a CDR3 comprising the amino acid sequence of SEQ ID NO: 212. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized.

In some embodiments, there is provided an anti-PD-1 sdAb moiety comprising a CDR1 comprising the amino acid sequence of SEQ ID NO: 69, or a variant thereof comprising up to about 3 (such as about any of 1, 2, or 3) amino acid substitutions; a CDR2 comprising the amino acid sequence of SEQ ID NO: 141, or a variant thereof comprising up to about 3 (such as about any of 1, 2, or 3) amino acid substitutions; and a CDR3 comprising the amino acid sequence of SEQ ID NO: 213, or a variant thereof comprising up to about 3 (such as about any of 1, 2, or 3) amino acid substitutions. In some embodiments, there is provided an anti-PD-1 sdAb moiety comprising a CDR1 comprising the amino acid sequence of SEQ ID NO: 69; a CDR2 comprising the amino acid sequence of SEQ ID NO: 141; and a CDR3 comprising the amino acid sequence of SEQ ID NO: 213; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-PD-1 sdAb moiety comprising a CDR1 comprising the amino acid sequence of SEQ ID NO: 69; a CDR2 comprising the amino acid sequence of SEQ ID NO: 141; and a CDR3 comprising the amino acid sequence of SEQ ID NO: 213. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized.

In some embodiments, there is provided an anti-PD-1 sdAb moiety comprising a CDR1 comprising the amino acid sequence of SEQ ID NO: 70, or a variant thereof comprising up to about 3 (such as about any of 1, 2, or 3) amino acid substitutions; a CDR2 comprising the amino acid sequence of SEQ ID NO: 142, or a variant thereof comprising up to about 3 (such as about any of 1, 2, or 3) amino acid substitutions; and a CDR3 comprising the amino acid sequence of SEQ ID NO: 214, or a variant thereof comprising up to about 3 (such as about any of 1, 2, or 3) amino acid substitutions. In some embodiments, there is provided an anti-PD-1 sdAb moiety comprising a CDR1 comprising the amino acid sequence of SEQ ID NO: 70; a CDR2 comprising the amino acid sequence of SEQ ID NO: 142; and a CDR3 comprising the amino acid sequence of SEQ ID NO: 214; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-PD-1 sdAb moiety comprising a CDR1 comprising the amino acid sequence of SEQ ID NO: 70; a CDR2 comprising the amino acid sequence of SEQ ID NO: 142; and a CDR3 comprising the amino acid sequence of SEQ ID NO: 214. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized.

In some embodiments, there is provided an anti-PD-1 sdAb moiety comprising a CDR1 comprising the amino acid sequence of SEQ ID NO: 71, or a variant thereof comprising up to about 3 (such as about any of 1, 2, or 3) amino acid substitutions; a CDR2 comprising the amino acid sequence of SEQ ID NO: 143, or a variant thereof comprising up to about 3 (such as about any of 1, 2, or 3) amino acid substitutions; and a CDR3 comprising the amino acid sequence of SEQ ID NO: 215, or a variant thereof comprising up to about 3 (such as about any of 1, 2, or 3) amino acid substitutions. In some embodiments, there is provided an anti-PD-1 sdAb moiety comprising a CDR1 comprising the amino acid sequence of SEQ ID NO: 71; a CDR2 comprising the amino acid sequence of SEQ ID NO: 143; and a CDR3 comprising the amino acid sequence of SEQ ID NO: 215; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-PD-1 sdAb moiety comprising a CDR1 comprising the amino acid sequence of SEQ ID NO: 71; a CDR2 comprising the amino acid sequence of SEQ ID NO: 143; and a CDR3 comprising the amino acid sequence of SEQ ID NO: 215. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized.

In some embodiments, there is provided an anti-PD-1 sdAb moiety comprising a CDR1 comprising the amino acid sequence of SEQ ID NO: 72, or a variant thereof comprising up to about 3 (such as about any of 1, 2, or 3) amino acid substitutions; a CDR2 comprising the amino acid sequence of SEQ ID NO: 144, or a variant thereof comprising up to about 3 (such as about any of 1, 2, or 3) amino acid substitutions; and a CDR3 comprising the amino acid sequence of SEQ ID NO: 216, or a variant thereof comprising up to about 3 (such as about any of 1, 2, or 3) amino acid substitutions. In some embodiments, there is provided an anti-PD-1 sdAb moiety comprising a CDR1 comprising the amino acid sequence of SEQ ID NO: 72; a CDR2 comprising the amino acid sequence of SEQ ID NO: 144; and a CDR3 comprising the amino acid sequence of SEQ ID NO: 216; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-PD-1 sdAb moiety comprising a CDR1 comprising the amino acid sequence of SEQ ID NO: 72; a CDR2 comprising the amino acid sequence of SEQ ID NO: 144; and a CDR3 comprising the amino acid sequence of SEQ ID NO: 216. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized.

The anti-PD-1 sdAb moiety may comprise one or more "hallmark residues" in one or more of the FR sequences. In some embodiments, the anti-PD-1 sdAb moiety comprises a $V_HH$ domain comprising the amino acid sequence of any one of the following: a-1) the amino acid residue at position 37 is selected from the group consisting of F, Y, L, I, and V (such as F, Y or V, or such as F); a-2) the amino acid residue at position 44 is selected from the group consisting of A, G, E, D, G, Q, R, S, and L (such as E, Q, or G, or such as E); a-3) the amino acid residue at position 45 is selected from the group consisting of L, R, and C (such as L or R); a-4) the amino acid residue at position 103 is selected from the group consisting of W, R, G, and S (such as W, G, or R, or such as W); and a-5) the amino acid residue at position 108 is Q; or b-1) the amino acid residue at position 37 is selected from the group consisting of F, Y, L, I, and V (such as F, V or Y, or such as F); b-2) the amino acid residue at position 44 is selected from the group consisting of E, Q, and G; b-3) the amino acid residue at position 45 is R; b-4) the amino acid residue at position 103 is selected from the group consisting of W, R, and S (such as W); and b-5) the amino acid residue at position 108 is selected from the group consisting of Q and L (such as Q); wherein the amino acid position is according to Kabat numbering. It should be noted that these "hallmark residues" at amino acid positions 37, 44, 45, 103 and 108 according to Kabat numbering apply to anti-PD-1 sdAb moieties of natural $V_HH$ sequences, and can be substituted during humanization. For example, Q at amino acid position 108 according to Kabat numbering can be optionally humanized to L. Other humanized substitutions will be clear to those skilled in the art. For example, potentially useful humanizing substitutions can be determined by comparing the FR sequences of a naturally occurring $V_HH$ with the corresponding FR sequences of one or more closely related human $V_H$, then introducing one or more of such potentially useful humanizing substitutions into said $V_HH$ using methods known in the art (also as described herein). The resulting humanized $V_HH$ sequences can be tested for their PD-1 binding affinity, for stability, for ease and level of expression, and/or for other desired properties. Possible residue substitutions may also come from an antibody $V_H$ domain wherein the $V_H/V_L$ interface comprises one or more highly charged amino acid residues. The anti-PD-1 sdAb moiety described herein can be partially or fully humanized. Preferably, the resulting humanized anti-PD-1 sdAb binds to PD-1 with $K_d$, $K_{on}$, and $K_{off}$ as described herein.

In some embodiments, there is provided an anti-PD-1 sdAb moiety comprising a $V_HH$ domain comprising the amino acid sequence of any one of SEQ ID NOs: 289-324, or a variant thereof having at least about 80% (such as at least about any of 80%, 85%, 90%, 91%, 92%, 93%, 94%, 95%, 96%, 97%, 98%, or 99%) sequence identify to any one of SEQ ID NOs: 289-324. In some embodiments, there is provided an anti-PD-1 sdAb moiety comprising a $V_HH$ domain comprising the amino acid sequence of any one of SEQ ID NOs: 289-324, or a variant thereof comprising up to about 3 (such as about any of 1, 2, or 3) amino acid substitutions in the $V_HH$ domain. In some embodiments, the anti-PD-1 sdAb moiety comprising the $V_HH$ domain comprising the amino acid sequence of any one of SEQ ID NOs: 289-324, or a variant thereof comprises amino acid substitutions in CDRs, such as the CDR1, and/or the CDR2, and/or the CDR3 of any one of SEQ ID NOs: 289-324. In some embodiments, the anti-PD-1 sdAb moiety comprising the $V_HH$ domain comprising the amino acid sequence of any one of SEQ ID NOs: 289-324, or a variant thereof comprises CDR1, CDR2, and CDR3 of any one of SEQ ID NOs: 289-324, and the amino acid substitutions are in FRs, such as the FR1, and/or the FR2, and/or the FR3, and/or the FR4 of any one of SEQ ID NOs: 289-324. In some embodiments, the anti-PD-1 sdAb moiety comprising the $V_HH$ domain comprising the amino acid sequence of any one of SEQ ID NOs: 289-324, or a variant thereof comprises amino acid substitutions in both CDRs and FRs. In some embodiments, there is provided an anti-PD-1 sdAb moiety comprising a $V_HH$ domain comprising the amino acid sequence of any one of SEQ ID NOs: 289-324. In some embodiments, there is provided an anti-PD-1 sdAb moiety comprising CDR1, CDR2, and CDR3 of any one of SEQ ID NO: 289-324. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized.

In some embodiments, there is provided an anti-PD-1 sdAb moiety (hereinafter referred to as "competing anti-PD-1 sdAb moiety" or "competing anti-PD-1 sdAb") or anti-PD-1 construct comprising an anti-PD-1 sdAb moiety (hereinafter referred to as "competing anti-PD-1 construct") that specifically binds to PD-1 competitively with any one of the anti-PD-1 sdAb moiety described herein. In some embodiments, competitive binding may be determined using an ELISA assay. In some embodiments, there is provided an anti-PD-1 sdAb moiety (or an anti-PD-1 construct comprising an anti-PD-1 sdAb moiety) that specifically binds to PD-1 competitively with an anti-PD-1 sdAb moiety comprising the amino acid sequence of any one of SEQ ID NOs: 289-324. In some embodiments, there is provided an anti-PD-1 sdAb moiety (or an anti-PD-1 construct comprising an anti-PD-1 sdAb moiety) that specifically binds to PD-1 competitively with an anti-PD-1 sdAb moiety comprising a CDR1 comprising the amino acid sequence of any one of SEQ ID NOs: 37-72; a CDR2 comprising the amino acid sequence of any one of SEQ ID NOs: 109-144; and a CDR3 comprising the amino acid sequence of any one of SEQ ID NOs: 181-216. In some embodiments, the $K_d$ of the binding between the competing anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the competing anti-PD-1 sdAb moiety is camelid, chimeric, Single-Domain Antibodies Exemplary sdAbs include, but are not limited to, heavy chain variable domains from heavy-chain only antibodies (e.g., $V_HH$ (Variable domain of the heavy chain of the Heavy chain antibody) in Camelidae or $V_{NAR}$ (Variable domain of the shark New Antigen Receptor) in cartilaginous fish), binding molecules naturally devoid of light chains, single domains (such as $V_H$ or $V_L$) derived from conventional 4-chain antibodies, humanized heavy-chain only antibodies, human single-domain antibodies produced by transgenic mice or rats expressing human heavy chain segments, and engineered domains and single domain scaffolds other than those derived from antibodies. The sdAbs may be derived from any species including, but not limited to mouse, rat, human, camel, llama, lamprey, fish, shark, goat, rabbit, and bovine. sdAbs contemplated herein also include naturally occurring sdAb molecules from species other than Camelidae and sharks.

In some embodiments, the sdAb is derived from a naturally occurring single-domain antigen binding molecule known as heavy chain antibody devoid of light chains (also referred herein as "heavy chain-only antibodies", or "HCAb"). Such single domain molecules are disclosed in WO 94/04678 and Hamers-Casterman, C. et al. (1993) *Nature* 363:446-448, for example. For clarity reasons, the variable domain derived from a heavy chain molecule naturally devoid of light chain is known herein as a $V_HH$ to distinguish it from the conventional $V_H$ of four chain immunoglobulins. Such a $V_HH$ molecule can be derived from antibodies raised in *Camelidae* species, for example, camel, llama, vicuna, dromedary, alpaca and guanaco. Other species besides *Camelidae* may produce heavy chain molecules naturally devoid of light chain, and such $V_HH$s are within the scope of the present application.

In some embodiments, the sdAb is derived from a variable region of the immunoglobulin found in cartilaginous fish. For example, the sdAb can be derived from the immunoglobulin isotype known as Novel Antigen Receptor (NAR) found in the serum of shark. Methods of producing single domain molecules derived from a variable region of NAR ("IgNARs") are described in WO 03/014161 and Streltsov (2005) *Protein Sci.* 14:2901-2909.

In some embodiments, the sdAb is recombinant, CDR-grafted, humanized, camelized, de-immunized and/or in vitro generated (e.g., selected by phage display). In some embodiments, the amino acid sequence of the framework regions may be altered by "camelization" of specific amino acid residues in the framework regions. Camelization refers to the replacing or substitution of one or more amino acid residues in the amino acid sequence of a (naturally occurring) $V_H$ domain from a conventional 4-chain antibody by one or more of the amino acid residues that occur at the corresponding position(s) in a $V_HH$ domain of a heavy chain antibody. This can be performed in a manner known per se, which will be clear to the skilled person, for example on the basis of the further description herein. Such "camelizing" substitutions are preferably inserted at amino acid positions that form and/or are present at the $V_H$—$V_L$ interface, and/or at the so-called *Camelidae* hallmark residues, as defined herein (see for example WO 94/04678, Davies and Riechmann FEBS Letters 339: 285-290, 1994; Davies and Riechmann Protein Engineering 9 (6): 531-537, 1996; Riechmann J. Mol. Biol. 259: 957-969, 1996; and Riechmann and Muyldermans J. Immunol. Meth. 231: 25-38, 1999).

In some embodiments, the sdAb is a human sdAb produced by transgenic mice or rats expressing human heavy chain segments. See, e.g., US20090307787A1, U.S. Pat. No. 8,754,287, US20150289489A1, US20100122358A1, and WO2004049794. In some embodiments, the sdAb is affinity-matured.

In some embodiments, naturally occurring $V_HH$ domains against a particular antigen or target, can be obtained from (naïve or immune) libraries of *Camelid* $V_HH$ sequences. Such methods may or may not involve screening such a library using said antigen or target, or at least one part, fragment, antigenic determinant or epitope thereof using one or more screening techniques known per se. Such libraries and techniques are for example described in WO 99/37681, WO 01/90190, WO 03/025020 and WO 03/035694. Alternatively, improved synthetic or semi-synthetic libraries derived from (naïve or immune) $V_HH$ libraries may be used, such as $V_HH$ libraries obtained from (naïve or immune)

V$_H$H libraries by techniques such as random mutagenesis and/or CDR shuffling, as for example described in WO 00/43507.

In some embodiments, the sdAbs are generated from conventional 4-chain antibodies. See, for example, EP 0 368 684, Ward et al. (Nature 1989 Oct. 12; 341 (6242): 544-6), Holt et al., Trends Biotechnol., 2003, 21(11):484-490; WO 06/030220; and WO 06/003388.

Because of the unique properties of sdAbs, using V$_H$H domains as single antigen-binding proteins or as antigen-binding domains (i.e. as part of a larger protein or polypeptide) offers a number of significant advantages over the conventional V$_H$ and V$_L$, scFv and conventional antibody fragments (such as Fab or (Fab')$_2$): 1) only a single domain is required to bind an antigen with high affinity, so there is no need to have a second domain, nor to assure that these two domains are present in the correct spatial conformation and configuration (e.g. no need to pair the heavy chain and light chain during folding, no need to use a specially designed linker such as for scFv); 2) V$_H$H domains and other sdAbs can be expressed from a single gene and require no post-translational folding or modifications; 3) V$_H$H domains and other sdAbs can be easily engineered into multivalent and/or multispecific formats (such as those described in the present application); 4) V$_H$H domains and other sdAbs are highly soluble and do not have a tendency to aggregate (as with the mouse-derived "dAbs" described by Ward et al., Nature. 1989 Oct. 12; 341(6242):544-6); 5) V$_H$H domains and other sdAbs are highly stable against heat, pH, proteases and other denaturing agents or conditions; 6) V$_H$H domains and other sdAbs are easy and relatively cheap to prepare (even on a large production scale), such as using microbial fermentation, there is no need to use mammalian expression system (required by production of, for example, conventional antibody fragments); 7) V$_H$H domains and other sdAbs are relatively small (approximately 15 kDa, or 10 times smaller than a conventional IgG) compared to conventional 4-chain antibodies and antigen-binding fragments thereof, thus have high(er) tissue penetration ability, such as for solid tumors and other dense tissues; and 8) V$_H$H domains and other sdAbs can exhibit so-called "cavity-binding properties" (due to their extended CDR3 loop compared to that of conventional V$_H$ domains) and can therefore access targets and epitopes not accessible to conventional 4-chain antibodies and antigen-binding fragments thereof, for example, it has been shown that V$_H$H domains and other sdAbs can inhibit enzymes (see for example WO1997049805; Transue et al., Proteins. 1998 Sep. 1; 32(4):515-22; Lauwereys et al., EMBO J. 1998 Jul. 1; 17(13):3512-20).

PD-1

The terms "programmed cell death protein 1", "PD-1", "PD-1 antigen", "PD-1 epitope", and "Programmed Death 1" are used interchangeably, and include variants, isoforms, species homologs of human PD-1, and analogs having at least one common epitope with PD-1.

The amino acid sequence of human PD-1 is disclosed at Genbank Accession Number NP_005009. The region of amino acids 1-20 is the leader peptide; 21-170 is the extracellular domain; 171-191 is the transmembrane domain; and 192-288 is the cytoplasmic domain.

A particular human PD-1 sequence will generally be at least 90% identical in amino acids sequence to human PD-1 of Genbank Accession Number NP_005009 and contains amino acid residues that identify the amino acid sequence as being human when compared to PD-1 amino acid sequences of other species (e.g., murine). In some embodiments, a human PD-1 may be at least about 95%, 96%, 97%, 98%, or 99% identical in amino acid sequence to the human PD-1 of Genbank Accession Number NP_005009. In some embodiments, a human PD-1 sequence will display no more than 10 amino acid differences from the human PD-1 of Genbank Accession Number NP 005009. In some embodiments, the human PD-1 may display no more than 5, 4, 3, 2, or 1 amino acid difference from the human PD-1 of Genbank Accession Number NP_005009. Percent identity can be determined as described herein. In some embodiments, a human PD-1 sequence may differ from the human PD-1 of Genbank Accession Number NP_005009 by having, for example, conserved mutations or mutations in non-conserved regions and the PD-1 has substantially the same biological function as the human PD-1 of Genbank Accession Number NP_005009. For example, a biological function of human PD-1 is having an epitope in the extracellular domain of PD-1 that is specifically bound by an anti-PD-1 construct of the instant disclosure or a biological function of human PD-1 is modulation of T cell activity. In some embodiments, the anti-PD-1 sdAb moiety described herein specifically recognizes a PD-1 polypeptide with 100% amino acid sequence identity to the human PD-1 of Genbank Accession Number NP_005009. In some embodiments, the anti-PD-1 sdAb moiety described herein specifically recognizes a PD-1 polypeptide comprising an amino acid sequence of SEQ ID NO: 361 or 362.

In some embodiments, the anti-PD-1 sdAb moiety may cross-react with PD-1 from species other than human, or other proteins which are structurally related to human PD-1 (e.g., human PD-1 homologs). In some embodiments, the anti-PD-1 sdAb moiety is completely specific for human PD-1 and not exhibit species or other types of cross-reactivity. In some embodiments, the anti-PD-1 sdAb moiety specifically recognizes a soluble isoform of human PD-1. In some embodiments, the anti-PD-1 sdAb moiety specifically recognizes a membrane-bound isoform of human PD-1 (e.g., SEQ ID NO: 361).

In some embodiments, the anti-PD-1 sdAb moiety described herein specifically recognizes the extracellular domain (ECD) of PD-1. In some embodiments, the anti-PD-1 sdAb moiety specifically recognizes the N-terminal portion of the PD-1 ECD. In some embodiments, the anti-PD-1 sdAb moiety specifically recognizes the C-terminal portion of the PD-1 ECD. In some embodiments, the anti-PD-1 sdAb moiety specifically recognizes the middle portion of the PD-1 ECD. In some embodiments, the ECD of PD-1 specifically recognized by the anti-PD-1 sdAb moiety is at least about 95%, 96%, 97%, 98%, or 99% identical in amino acid sequence to the ECD of the human PD-1 of Genbank Accession Number NP_005009. In some embodiments, the ECD of PD-1 specifically recognized by the anti-PD-1 sdAb moiety is 100% identical in amino acid sequence to the ECD of the human PD-1 of Genbank Accession Number NP_005009. In some embodiments, the anti-PD-1 sdAb moiety specifically recognizes a PD-1 polypeptide comprising an amino acid sequence of SEQ ID NO: 362.

Antibody Affinity

Binding specificity of the antibody or antigen-binding domain can be determined experimentally by methods known in the art. Such methods comprise, but are not limited to Western blots, ELISA-, RIA-, ECL-, IRMA-, EIA-, BIAcore-tests and peptide scans.

In some embodiments, the $K_d$ of the binding between the anti-PD-1 sdAb moiety and PD-1 is about $10^{-5}$ M to about $10^{-6}$ M, about $10^{-6}$ M to about $10^{-7}$ M, about $10^{-7}$ M to about $10^{-8}$ M, about $10^{-8}$ M to about $10^{-9}$ M, about $10^{-9}$ M to about $10^{-10}$ M, about $10^{-10}$ M to about $10^{-11}$ M, about $10^{-11}$ M to about $10^{-12}$ M, about $10^{-5}$ M to about $10^{-12}$ M, about $10^{-6}$ M to about $10^{-12}$ M, about $10^{-7}$ M to about $10^{-12}$ M, about 10 M to about $10^{-12}$ M, about $10^{-9}$ M to about $10^{-12}$ M, about $10^{-10}$ M to about $10^{-12}$ M, about $10^{-5}$ M to about $10^{-11}$ M, about $10^{-7}$ M to about $10^{-11}$ M, about $10^{-8}$ M to about $10^{-11}$ M, about $10^{-9}$ M to about $10^{-11}$ M, about $10^{-5}$ M to about $10^{-10}$ M, about $10^{-7}$ M to about $10^{-10}$ M, about $10^{-8}$ M to about $10^{-10}$ M, about $10^{-5}$ M to about $10^{-9}$ M, about $10^{-7}$ M to about $10^{-9}$ M, about $10^{-5}$ M to about $10^{-8}$ M, or about $10^{-6}$ M to about $10^{-8}$ M.

In some embodiments, the $K_{on}$ of the binding between the anti-PD-1 sdAb moiety and PD-1 is about $10^2$ $M^{-1}$ $s^{-1}$ to about $10^4$ $M^{-1}$ $s^{-1}$, about $10^4$ $M^{-1}$ $s^{-1}$ to about $10^6$ $M^{-1}$ $s^{-1}$, about $10^6$ $M^{-1}$ $s^{-1}$ to about $10^7$ $M^{-1}$ $s^{-1}$, about $10^2$ $M^{-1}$ $s^{-1}$ to about $10^7$ $M^{-1}$ $s^{-1}$, about $10^3$ $M^{-1}$ $s^{-1}$ to about $10^7$ $M^{-1}$ $s^{-1}$, about $10^4$ $M^{-1}$ $s^{-1}$ to about $10^7$ $M^{-1}$ $s^{-1}$, about $10^5$ $M^{-1}$ $s^{-1}$ to about $10^7$ $M^{-1}$ $s^{-1}$, about $10^3$ $M^{-1}$ $s^{-1}$ to about $10^6$ $M^{-1}$ $s^{-1}$, or about $10^4$ $M^{-1}$ $s^{-1}$ to about $10^6$ $M^{-1}$ $s^{-1}$.

In some embodiments, the $K_{off}$ of the binding between the anti-PD-1 sdAb moiety and PD-1 is about 1 $s^{-1}$ to about $10^{-2}$ $s^{-1}$, about $10^{-2}$ $s^{-1}$ to about $10^{-4}$ $s^{-1}$, about $10^{-4}$ $s^{-1}$ to about $10^{-5}$ $s^{-1}$, about $10^{-5}$ $s^{-1}$ to about $10^{-6}$ $s^{-1}$ about 1 $s^{-1}$ to about $10^{-6}$ $s^{-1}$ about $10^{-2}$ $s^{-1}$ to about $10^{-6}$ $s^{-1}$ about $10^{-3}$ $s^{-1}$ to about $10^{-6}$ $s^{-1}$, about $10^{-4}$ $s^{-1}$ to about $10^{-6}$ $s^{-1}$, about $10^{-2}$ $s^{-1}$ to about $10^{-5}$ $s^{-1}$, or about $10^{-3}$ $s^{-1}$ to about $10^{-5}$ $s^{-1}$.

In some embodiments, the $EC_{50}$ of the anti-PD-1 sdAb moiety is less than 10 nM in an amplified luminescent proximity homogeneous assay (AlphaLISA). In some embodiments, the $EC_{50}$ of the anti-PD-1 sdAb moiety is less than 500 nM in an inhibition of ligand binding by FACS analysis (competition binding assay), or cell based cytokine release assay. In some embodiments, the $EC_{50}$ of the anti-PD-1 sdAb moiety is less than 1 nM (such as about 0.001 nM to about 0.01 nM, about 0.01 nM to about 0.1 nM, about 0.1 nM to about 1 nM, etc.), about 1 nM to about 10 nM, about 10 nM to about 50 nM, about 50 nM to about 100 nM, about 100 nM to about 200 nM, about 200 nM to about 300 nM, about 300 nM to about 400 nM, or about 400 nM to about 500 nM.

In some embodiments, the $IC_{50}$ of the anti-PD-1 sdAb moiety is less than 10 nM in an AlphaLISA. In some embodiments, the $IC_{50}$ of the anti-PD-1 sdAb moiety is less than 500 nM in an inhibition of ligand binding by FACS analysis (competition binding assay), or cell based cytokine release assay. In some embodiments, the $IC_{50}$ of the anti-PD-1 sdAb moiety is less than 1 nM (such as about 0.001 nM to about 0.01 nM, about 0.01 nM to about 0.1 nM, about 0.1 nM to about 1 nM, etc.), about 1 nM to about 10 nM, about 10 nM to about 50 nM, about 50 nM to about 100 nM, about 100 nM to about 200 nM, about 200 nM to about 300 nM, about 300 nM to about 400 nM, or about 400 nM to about 500 nM.

Chimeric or Humanized Antibodies

In some embodiments, the anti-PD-1 sdAb moiety provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a camelid species, such as llama) and a human constant region. In a further example, a chimeric antibody is a "class switched" antibody in which the class or subclass has been changed from that of the parent antibody. Chimeric antibodies include antigen-binding fragments thereof.

In some embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer*, 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA*, 89:4285 (1992); and Presta et al. *J. Immunol.*, 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

In some embodiments, the anti-PD-1 sdAbs are modified, such as humanized, without diminishing the native affinity of the domain for antigen and while reducing its immunogenicity with respect to a heterologous species. For example, the amino acid residues of the antibody variable domain ($V_HH$) of an llama antibody can be determined, and one or more of the *Camelid* amino acids, for example, in the framework regions, are replaced by their human counterpart as found in the human consensus sequence, without that polypeptide losing its typical character, i.e. the humanization does not significantly affect the antigen binding capacity of the resulting polypeptide. Humanization of *Camelid* single-domain antibodies requires the introduction and mutagenesis of a limited amount of amino acids in a single polypeptide chain. This is in contrast to humanization of scFv, Fab', (Fab')$_2$ and IgG, which requires the introduction of amino acid changes in two chains, the light and the heavy chain and the preservation of the assembly of both chains.

sdAbs comprising a $V_HH$ domain can be humanized to have human-like sequences. In some embodiments, the FR regions of the $V_HH$ domain used herein comprise at least about any one of 50%, 60%, 70%, 80%, 90%, 95% or more of amino acid sequence homology to human VH framework regions. One exemplary class of humanized $V_HH$ domains is characterized in that the $V_HH$s carry an amino acid from the group consisting of glycine, alanine, valine, leucine, isoleucine, proline, phenylalanine, tyrosine, tryptophan, methionine, serine, threonine, asparagine, or glutamine at position 45, such as, for example, L45 and a tryptophan at position 103, according to the Kabat numbering. As such, polypeptides belonging to this class show a high amino acid sequence homology to human VH framework regions and said polypeptides might be administered to a human directly without expectation of an unwanted immune response therefrom, and without the burden of further humanization.

Another exemplary class of humanized Camelid single-domain antibodies has been described in WO 03/035694 and contains hydrophobic FR2 residues typically found in conventional antibodies of human origin or from other species, but compensating this loss in hydrophilicity by the charged arginine residue on position 103 that substitutes the conserved tryptophan residue present in $V_H$ from double-chain antibodies. As such, peptides belonging to these two classes show a high amino acid sequence homology to human $V_H$ framework regions and said peptides might be administered to a human directly without expectation of an unwanted immune response therefrom, and without the burden of further humanization.

Human Antibodies

In some embodiments, the anti-PD-1 sdAb moiety provided herein is a human antibody (known as human domain antibody, or human DAb). Human antibodies can be produced using various techniques known in the art. Human antibodies are described generally in van Dijk and van de Winkel, Curr. Opin. Pharmacol. 5: 368-74 (2001), Lonberg, Curr. Opin. Immunol. 20:450-459 (2008), and Chen, Mol. Immunol. 47(4):912-21 (2010). Transgenic mice or rats capable of producing fully human single-domain antibodies (or DAb) are known in the art. See, e.g., US20090307787A1, U.S. Pat. No. 8,754,287, US20150289489A1, US20100122358A1, and WO2004049794.

Human antibodies (e.g., human DAbs) may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., U.S. Pat. Nos. 6,075,181 and 6,150,584 describing XENOMOUSE™ technology; U.S. Pat. No. 5,770,429 describing HuMAB® technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, e.g., by combining with a different human constant region.

Human antibodies (e.g., human DAbs) can also be made by hybridoma-based methods. Human myeloma and mouse-human heteromyeloma cell lines for the production of human monoclonal antibodies have been described (See, e.g., Kozbor J. Immunol., 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991)). Human antibodies generated via human B-cell hybridoma technology are also described in Li et al., Proc. Natl. Acad. Sci. USA, 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4): 265-268 (2006) (describing human-human hybridomas). Human hybridoma technology (Trioma technology) is also described in Vollmers and Brandlein, Histology and Histopathology, 20(3):927-937 (2005) and Vollmers and Brandlein, Methods and Findings in Experimental and Clinical Pharmacology, 27(3):185-91 (2005).

Human antibodies (e.g., human DAbs) may also be generated by isolating Fv clone variable domain sequences selected from human-derived phage display libraries. Such variable domain sequences may then be combined with a desired human constant domain. Techniques for selecting human antibodies from antibody libraries are described below.

One technique for obtaining $V_HH$ sequences directed against a particular antigen or target involves suitably immunizing a transgenic mammal that is capable of expressing heavy chain antibodies (i.e. so as to raise an immune response and/or heavy chain antibodies directed against said antigen or target), obtaining a suitable biological sample from said transgenic mammal that contains (nucleic acid sequences encoding) said $V_HH$ sequences (such as a blood sample, serum sample or sample of B-cells), and then generating $V_HH$ sequences directed against said antigen or target, starting from said sample, using any suitable technique known per se (such as any of the methods described herein or a hybridoma technique). For example, for this purpose, the heavy chain antibody-expressing mice and the further methods and techniques described in WO 02/085945, WO 04/049794 and WO 06/008548 and Janssens et al., Proc. Natl. Acad. Sci. USA. 2006 Oct. 10; 103(41):15130-5 can be used. For example, such heavy chain antibody expressing mice can express heavy chain antibodies with any suitable (single) variable domain, such as (single) variable domains from natural sources (e.g. human (single) variable domains, Camelid (single) variable domains or shark (single) variable domains), as well as for example synthetic or semi-synthetic (single) variable domains.

Library-Derived Antibodies

Antibodies of the present application may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in Methods in Molecular Biology 178:1-37 (O'Brien et al., ed., Human Press, Totowa, N.J., 2001) and further described, e.g., in the McCafferty et al., Nature 348:552-554; Clackson et al., Nature 352: 624-628 (1991); Marks et al., J. Mol. Biol. 222: 581-597 (1992); Marks and Bradbury, in Methods in Molecular Biology 248:161-175 (Lo, ed., Human Press, Totowa, N.J., 2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004). Methods for constructing single-domain antibody libraries have been described, for example, see U.S. Pat. No. 7,371,849.

In certain phage display methods, repertoires of $V_H$ and $V_L$ genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Repertoires of $V_HH$ genes can be similarly cloned by PCR, recombined randomly in phage libraries, and screened for antigen-binding phage. Phage typically display antibody fragments, either as scFv fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al., *EMBO J,* 12: 725-734 (1993). Finally, naïve libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

Biological Activities

The biological activity of anti-PD-1 sdAb moiety described herein can be determined by measuring its half maximal effective concentration ($EC_{50}$), which is a measure of the effectiveness of an antibody in binding to its target, or half maximal inhibitory concentration ($IC_{50}$), which is a measure of the effectiveness of an antibody in inhibiting a specific biological or biochemical function (such as inhibiting the binding between PD-1 and PD-L1/PD-L2). For example, here $EC_{50}$ can be used to indicate the effective concentration of anti-PD-1 sdAb needed to bind 50% PD-1 on cell surface, $IC_{50}$ can be used to indicate the effective concentration of anti-PD-1 sdAb needed to neutralize 50% of PD-1 bioactivity in vitro. $EC_{50}$ also represents the plasma concentration required for obtaining 50% of a maximum effect in vivo. $EC_{50}$ or $IC_{50}$ can be measured by assays known in the art, for example, bioassays such as FACS binding analysis, inhibition of ligand binding by FACS analysis (competition binding assay), cell-based cytokine release assay, or amplified luminescent proximity homogeneous assay (AlphaLISA).

For example, the blockade of ligand binding can be studied using flow cytometry (also see Example 1). CHO cells expressing human PD-1 can be dissociated from adherent culture flasks and mixed with varying concentrations of anti-PD-1 sdAb for test, and a constant concentration of labeled-PD-L1 protein or labeled-PD-L2 protein (such as biotin-labeled human PD-L1-Fc protein or biotin-labeled human PD-L2-Fc protein). An anti-PD-1 antibody positive control can be employed, such as Keytruda®. The mixture is equilibrated for 30 minutes at room temperature, washed three times with FACS buffer (PBS containing 1% BSA). Then, an antibody specifically recognizing the labeled PD-L1 or PD-L2 protein of constant concentration (such as PE/Cy5 Streptavidin secondary antibody) is added and incubated for 15 minutes at room temperature. Cells are washed with FACS buffer and analyzed by flow cytometry. Data can be analyzed with Prism (GraphPad Software, San Diego, Calif.) using non-linear regression to calculate $IC_{50}$. The results from the competition assay can demonstrate the ability of anti-PD-1 sdAbs in inhibiting the interaction between labeled-PD-L1/PD-L2 and PD-1.

The biological activity of anti-PD-1 sdAb moiety can also be tested by PD-1-based blockade assay for cytokine release (also see Example 1). PD-1 signaling typically has a greater effect on cytokine production than on cellular proliferation, with significant effects on IFN-γ, TNF-α and IL-2 production. Thus, blockade of PD-1 pathways by anti-PD-1 antibodies can be studied using a variety of bioassays that monitor T cell proliferation, IFN-γ release, or IL-2 secretion. PD-1 mediated inhibitory signaling also depends on the strength of the TCR signaling, with greater inhibition delivered at low levels of TCR stimulation. This reduction can be overcome by costimulation through CD28 (Freeman et al., J. Exp. Med. 192: 1027-34 (2000)) or the presence of IL-2 (Carter et al., Eur. J. Immunol. 32: 634-43 (2002)). PD-L1 and PD-L2 have been shown to downregulate T cell activation upon binding to PD-1 (Freeman et al., J. Exp. Med. 192: 1027-34 (2000)) or the presence of IL-2 (Carter et al., Eur. J. Immunol. 32: 634-43 (2002)).

For examples, PD-1 Effector Cells (Jurkat cell stably transfected with human PD-1 protein and NFAT luciferase) and CHO-K1/human CD274 (CHO-K1 stably expressing human PD-L1) are mixed in wells. Anti-PD-1 sdAbs are added into each well at different concentrations. No antibody can be used as a background control. Negative control (such as human IgG4) and positive control (such as Keytruda®) can be employed. After 24-hour incubation in 37° C./5% $CO_2$ incubator, medium is taken from each testing well for IL-2 secretion measurement (Cisbio). $EC_{50}$ value for each test antibody is measured, which will reflect the ability of the test anti-PD-1 sdAb in blocking the interaction between PD-1 and PD-L1 on Jurkat cells (PD-1/PD-L1 interaction inhibits T-cell IL-2 production).

The biological activity of anti-PD-1 sdAb moiety can also be tested by PD-1-based blockade assay for luciferase reporter activity (also see Example 1). The effector cells contain a luciferase construct that is induced upon disruption of the PD-1/PD-L1 receptor-ligand interaction. For example, PD-1 Effector Cells (Jurkat cell stably transfected with human PD-1 protein and NFAT luciferase) can be plated overnight and then incubated with a serial dilution of anti-PD-1 construct comprising anti-PD-1 sdAb, followed by addition of PD-L1 expressing cells (CHO-K1/human CD274) at a suitable E: T ratio. After 6 hours induction at 37° C., 5% $CO_2$, Bio-Glo™ Luciferase Assay Reagent can be added and luminescence can be determined. The results can demonstrate the ability of anti-PD-1 sdAbs in inhibiting the interaction between PD-L1 and PD-1.

In some embodiments, the anti-PD-1 sdAb moiety blocks or antagonizes signals transduced by the PD-1 receptor. In some embodiments, the anti-PD-1 sdAb moiety can bind to an epitope on PD-1 so as to inhibit PD-1 from interacting with PD-L1/PD-L2. In some embodiments, the anti-PD-1 sdAb moiety can reduce the binding of PD-1 to PD-L1/PD-L2 by at least about any of 5%, 10%, 20%, 25%, 30%, 40%, 50%, 60%, 70%, 75%, 80%, 90%, 95%, 99% or 99.9% under conditions in which the ratio of antibody combining site to PD-1 ligand binding site is greater than 1:1 and the concentration of antibody is greater than $10^{-8}$ M.

(II) Construct Comprising the Anti-PD-1 sdAb Moiety

The anti-PD-1 construct comprising the anti-PD-1 sdAb moiety can be of any possible format.

In some embodiments, the anti-PD-1 construct comprising the anti-PD-1 sdAb moiety may further comprise additional polypeptide sequences, such as one or more antibody moieties (or antigen binding portions), or Fc fragment of immunoglobulin. Such additional polypeptide sequences may or may not change or otherwise influence the (biological) properties of the anti-PD-1 sdAb, and may or may not add further functionality to the anti-PD-1 sdAb described herein. In some embodiments, the additional polypeptide sequences confer one or more desired properties or functionalities to the anti-PD-1 sdAb of the present invention.

In some embodiments, the additional polypeptide sequences may comprise a second antibody moiety or second antigen binding portion (such as sdAb, scFv, Fab, full-length antibody, etc.) that specifically recognizes a second epitope. In some embodiments, the second epitope is from PD-1. In some embodiments, the second epitope is not from PD-1. In some embodiments, the second antibody moiety (or second antigen binding portion) specifically recognizes the same epitope on PD-1 as the anti-PD-1 sdAb described herein. In some embodiments, the second antibody moiety (or second antigen binding portion) specifically recognizes a different epitope on PD-1 as the anti-PD-1 sdAb described herein. In some embodiments, the anti-PD-1 construct comprises two or more anti-PD-1-sdAb moieties described herein linked together via optional linkers (such as peptide linkers, e.g., any of those disclosed in the "Peptide linkers" section below). The two or more anti-PD-1-sdAb moieties linked together can be the same or different. In some embodiments, the optional peptide linker comprises the amino acid sequence of any one of SEQ ID NOs: 367-376.

In some embodiments, the additional polypeptide sequences may comprise a second antibody moiety or second antigen binding portion (such as sdAb, scFv, Fab, full-length antibody, etc.) that specifically recognizes CTLA-4. In some embodiments, the anti-PD-1 construct comprises one or more anti-PD-1-sdAb moieties described herein and one or more anti-CTLA-4 sdAb linked together via optional linkers (such as peptide linkers, e.g., any of those disclosed in the "peptide linkers" section below). The one or more anti-PD-1-sdAb moieties linked together can be the same or different, the one or more anti-CTLA-4-sdAbs linked together can be the same or different. The anti-CTLA-4 sdAb can be of any sequence, such as any of those disclosed in PCT/CN2017/105506 and PCT/CN2016/101777, which are incorporated herein by reference in their entirety. In some embodiments, the anti-CTLA-4 sdAb comprises the amino acid sequence of A34311VH11, AS07014VH11, or AS07189TKDVH11. The anti-PD-1 construct comprising the anti-PD-1 sdAb moiety described herein and anti-CTLA-4 sdAb can be of any format, for example, from N- to C-terminus: (anti-CTLA-4 sdAb1)-$L_1$-(anti-CTLA-4 sdAb2)-$L_2$-(anti-PD-1 sdAb), (anti-CTLA-4 sdAb1)-$L_1$-(anti-PD-1 sdAb)-$L_2$-(anti-CTLA-4 sdAb2), (anti-PD-1 sdAb)-$L_1$-(anti-CTLA-4 sdAb1)-$L_2$-(anti-CTLA-4 sdAb2), (anti-PD-1 sdAb1)-$L_1$-(anti-PD-1 sdAb2)-$L_2$-(anti-CTLA-4 sdAb), (anti-PD-1 sdAb1)-$L_1$-(anti-CTLA-4 sdAb)-$L_2$-(anti-PD-1 sdAb2), (anti-CTLA-4 sdAb)-$L_1$-(anti-PD-1 sdAb1)-$L_2$-(anti-PD-1 sdAb2), etc. ($L_1$ and $L_2$ can be the same or different optional linker, such as optional peptide linker). In some embodiments, the optional peptide linker comprises the amino acid sequence of any one of SEQ ID NOs: 367-376.

In some embodiments, the additional polypeptide sequences may increase the antibody construct half-life, solubility, or absorption, reduce immunogenicity or toxicity, eliminate or attenuate undesirable side effects, and/or confer other advantageous properties to and/or reduce undesired properties of the anti-PD-1 construct of the invention, compared to the anti-PD-1 sdAb described herein per se. Some non-limiting examples of such additional polypeptide sequences are serum proteins, such as human serum albumin (HSA; see e.g. WO 00/27435) or haptenic molecules (e.g. haptens that are recognized by circulating antibodies, see e.g. WO 98/22141). It was shown that linking fragments of immunoglobulins (such as $V_H$ domains) to serum albumin or fragments thereof may increase antibody half-life (see e.g. WO 00/27435 and WO 01/077137). Thus, in some embodiments, the anti-PD-1 construct of the present invention may comprise an anti-PD-1 sdAb moiety described herein linked to serum albumin (or to a suitable fragment thereof), optionally via a suitable linker (such as peptide linker). In some embodiments, the anti-PD-1 sdAb moiety described herein can be linked to a fragment of serum albumin at least comprising serum albumin domain III (see PCT/EP2007/002817). The anti-PD-1 sdAb-HSA fusion protein can be of any format, such as (sdAb) HSA (n is an integer of at least 1), sdAb-HSA-sdAb, etc. In some embodiments, the optional peptide linker comprises the amino acid sequence of any one of SEQ ID NOs: 367-376.

Anti-PD-1 Heavy Chain-Only Antibody (HCAb)

In some embodiments, the isolated anti-PD-1 construct is a heavy chain-only antibody (HCAb) comprising the anti-PD-1 sdAb moiety described herein. In some embodiments, the anti-PD-1 sdAb moiety described herein can be linked to one or more (preferably human) $C_H2$ and/or $C_H3$ domains, e.g., an Fc fragment, optionally via a linker sequence, to increase its half-life in vivo.

Figure 26A:
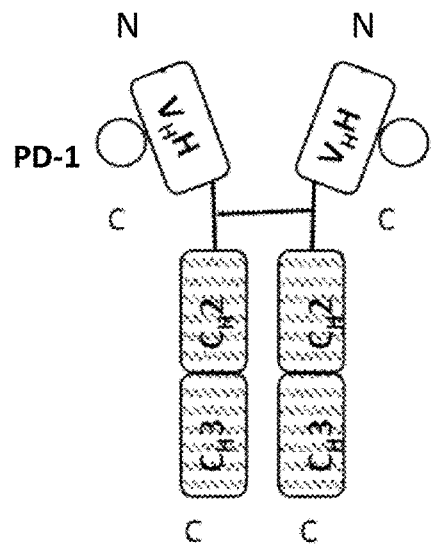
FIGS. 26A-26B depict schematic structure of exemplary anti-PD-1 HCAbs.
Figure 26B:
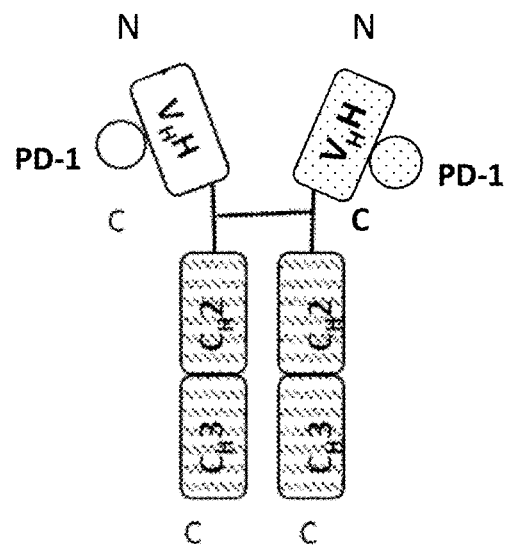

Thus in some embodiments, the isolated anti-PD-1 construct is an anti-PD-1 HCAb comprising an anti-PD-1 sdAb moiety described herein fused to an Fc fragment of an immunoglobulin, such as IgA, IgD, IgE, IgG, and IgM. In some embodiments, the anti-PD-1 HCAb comprises an Fc fragment of IgG, such as any of IgG1, IgG2, IgG3, or IgG4. In some embodiments, the Fc fragment is a human Fc, such as human IgG1 (hIgG1) Fc, hIgG2 Fc, or hIgG4 Fc. In some embodiments, the Fc fragment is effectorless, with reduced, minimized, or eliminated antibody effector functions such as ADCC, CDC, and/or ADCP (antibody-dependent cellular phagocytosis). For example, in some embodiments, the effectorless Fc comprises an N297A or DANA mutation (D265A+N297A) in the $C_H2$ region. In some embodiments, the effectorless Fc comprises K322A and L234A/L235A (LALA) mutations. In some embodiments, the Fc fragment is an effectorless (inert) IgG1 Fc, such as effectorless hIgG1 Fc. In some embodiments, the Fc fragment is a human IgG4 Fc (S228P). In some embodiments, the Fc fragment comprises the amino acid sequence of any one of SEQ ID NOs: 363-365. In some embodiments, the anti-PD-1 HCAb is monomeric. In some embodiments, the anti-PD-1 HCAb is dimeric. In some embodiments, the anti-PD-1 HCAb is multispecific and multivalent (such as bispecific and bivalent), e.g., comprising two or more different anti-PD-1 sdAb moieties described herein (exemplified as FIG. 26B). In some embodiments, the anti-PD-1 HCAb is monospecific and multivalent (e.g., bivalent; exemplified as FIG. 26A).

In some embodiments, the anti-PD-1 sdAb moiety and the Fc fragment are optionally connected by a peptide linker. In some embodiments, the peptide linker is a human IgG1 hinge (SEQ ID NO: 369). In some embodiments, the peptide linker is a mutated human IgG1 hinge (SEQ ID NO: 368). In some embodiments, the peptide linker is a human IgG4 hinge (SEQ ID NO: 367). In some embodiments, the peptide linker is a hIgG2 hinge. In some embodiments, the peptide linker comprises the amino acid sequence of any one of SEQ ID NOs: 367-376, such as SEQ ID NO: 371, 375, or 376.

Thus in some embodiments, there is provided an isolated anti-PD-1 HCAb comprising an sdAb moiety specifically recognizing PD-1, wherein the anti-PD-1 sdAb moiety comprises a CDR1 comprising the amino acid sequence of any one of SEQ ID NOs: 37-72, or a variant thereof comprising up to about 3 (such as about any of 1, 2, or 3) amino acid substitutions; a CDR2 comprising the amino acid sequence of any one of SEQ ID NOs: 109-144, or a variant thereof comprising up to about 3 (such as about any of 1, 2, or 3) amino acid substitutions; and a CDR3 comprising the amino acid sequence of any one of SEQ ID NOs: 181-216, or a variant thereof comprising up to about 3 (such as about any of 1, 2, or 3) amino acid substitutions, and wherein the anti-PD-1 sdAb moiety is fused to an Fc fragment of an immunoglobulin via an optional linker. In some embodiments, there is provided an isolated anti-PD-1 HCAb comprising an sdAb moiety specifically recognizing PD-1, wherein the sdAb moiety comprises a CDR1 comprising the amino acid sequence of any one of SEQ ID NOs: 37-72; a CDR2 comprising the amino acid sequence of any one of SEQ ID NOs: 109-144; and a CDR3 comprising the amino acid sequence of any one of SEQ ID NOs: 181-216; or a variant thereof comprising up to about 3 (such as about any of 1, 2, or 3) amino acid substitutions in the CDR regions, and wherein the anti-PD-1 sdAb moiety is fused to an Fc fragment of an immunoglobulin via an optional linker. In some embodiments, the amino acid substitutions are in CDR1 and/or CDR2. In some embodiments, there is provided an anti-PD-1 HCAb comprising an sdAb moiety specifically recognizing PD-1, wherein the sdAb moiety comprises a CDR1 comprising the amino acid sequence of any one of SEQ ID NOs: 37-72; a CDR2 comprising the amino acid sequence of any one of SEQ ID NOs: 109-144; and a CDR3 comprising the amino acid sequence of any one of SEQ ID NOs: 181-216, and wherein the anti-PD-1 sdAb moiety is fused to an Fc fragment of an immunoglobulin via an optional linker. In some embodiments, there is provided an isolated anti-PD-1 HCAb comprising an sdAb moiety specifically recognizing PD-1, wherein the sdAb moiety comprises a $V_HH$ domain comprising the amino acid sequence of any one of SEQ ID NOs: 289-324, or a variant thereof having at least about 80% (such as at least about any of 80%, 85%, 90%, 91%, 92%, 93%, 94%, 95%, 96%, 97%, 98%, or 99%) sequence identify to any one of SEQ ID NOs: 289-324, and wherein the anti-PD-1 sdAb moiety is fused to an Fc fragment of an immunoglobulin via an optional linker. In some embodiments, there is provided an isolated anti-PD-1 HCAb comprising a sdAb moiety specifically recognizing PD-1, wherein the sdAb moiety comprises a $V_HH$ domain comprising the amino acid sequence of any one of SEQ ID NOs: 289-324, or a variant thereof comprising up to about 3 (such as about any of 1, 2, or 3) amino acid substitutions in the $V_HH$ domain, and wherein the anti-PD-1 sdAb moiety is fused to an Fc fragment of an immunoglobulin via an optional linker. In some embodiments, the amino acid substitutions in the $V_HH$ domain are in CDRs, such as the CDR1, and/or the CDR2, and/or the CDR3 of any one of SEQ ID NOs: 289-324. In some embodiments, the amino acid substitutions in the $V_HH$ domain are in FRs, such as the FR1, and/or the FR2, and/or the FR3, and/or the FR4 of any one of SEQ ID NOs: 289-324. In some embodiments, the amino acid substitutions are in both CDRs and FRs of any one of SEQ ID NOs: 289-324. In some embodiments, there is provided an isolated anti-PD-1 HCAb comprising an sdAb moiety specifically recognizing PD-1, wherein the sdAb moiety comprises a $V_HH$ domain comprising the amino acid sequence of any one of SEQ ID NOs: 289-324, and wherein the anti-PD-1 sdAb moiety is fused to an Fc fragment of an immunoglobulin via an optional linker. In some embodiments, there is provided an isolated anti-PD-1 HCAb comprising an sdAb moiety specifically recognizing PD-1, wherein the sdAb moiety comprises CDR1, CDR2, and CDR3 of any one of SEQ ID NOs: 289-324, and wherein the anti-PD-1 sdAb moiety is fused to an Fc fragment of an immunoglobulin via an optional linker. In some embodiments, there is provided an isolated anti-PD-1 HCAb comprising two sdAb moieties specifically recognizing PD-1, wherein each anti-PD-1 sdAb moiety comprises a CDR1 comprising the amino acid sequence of any one of SEQ ID NOs: 37-72, or a variant thereof comprising up to about 3 (such as about any of 1, 2, or 3) amino acid substitutions; a CDR2 comprising the amino acid sequence of any one of SEQ ID NOs: 109-144, or a variant thereof comprising up to about 3 (such as about any of 1, 2, or 3) amino acid substitutions; and a CDR3 comprising the amino acid sequence of any one of SEQ ID NOs: 181-216, or a variant thereof comprising up to about 3 (such as about any of 1, 2, or 3) amino acid substitutions, and wherein the C-terminus of each anti-PD-1 sdAb is fused to the N-terminus of an Fc fragment of an immunoglobulin via an optional linker. In some embodiments, the two anti-PD-1 sdAb moieties are the same (exemplified as FIG. 26A). In some embodiments, the two anti-PD-1 sdAb moieties are different (exemplified as FIG. 26B). In some embodiments, the Fc fragment is a human IgG1 Fc, effectorless human IgG1 Fc, hIgG2 Fc, human IgG4 Fc, or hIgG4 Fc (S228P). In some embodiments, the Fc fragment comprises the amino acid sequence of any one of SEQ ID NOs: 363-365. In some embodiments, the anti-PD-1 HCAb is monomeric. In some embodiments, the anti-PD-1 HCAb is dimeric. In some embodiments, the anti-PD-1 sdAb moiety and the Fc fragment are optionally connected by a peptide linker. In some embodiments, the peptide linker comprises the amino acid sequence of any one of SEQ ID NOs: 367-376. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized.

In some embodiments, there is provided an isolated anti-PD-1 HCAb comprising the amino acid sequence of any one of SEQ ID NOs: 325-360.

In some embodiments, there is also provided an isolated anti-PD-1 HCAb (hereinafter referred to as "competing anti-PD-1 HCAb") that specifically binds to PD-1 competitively with any one of the isolated anti-PD-1 HCAbs, anti-PD-1 sdAbs, or anti-PD-1 constructs comprising the anti-PD-1 sdAb moiety described herein. Competitive binding may be determined using an ELISA assay. For example, in some embodiments, there is provided an isolated anti-PD-1 HCAb that specifically binds to PD-1 competitively with an isolated anti-PD-1 HCAb comprising the amino acid sequence of any one of SEQ ID NOs: 325-360. In some embodiments, there is provided an isolated anti-PD-1 HCAb that specifically binds to PD-1 competitively with an anti-PD-1 HCAb comprising an anti-PD-1 sdAb moiety comprising a CDR1 comprising the amino acid sequence of any one of SEQ ID NOs: 37-72; a CDR2 comprising the amino acid sequence of any one of SEQ ID NOs: 109-144; and a CDR3 comprising the amino acid sequence of any one of SEQ ID NOs: 181-216. In some embodiments, there is provided an isolated anti-PD-1 HCAb that specifically binds to PD-1 competitively with an anti-PD-1 sdAb moiety (or an anti-PD-1 construct comprising an anti-PD-1 sdAb moiety)

comprising a CDR1 comprising the amino acid sequence of any one of SEQ ID NOs: 37-72; a CDR2 comprising the amino acid sequence of any one of SEQ ID NOs: 109-144; and a CDR3 comprising the amino acid sequence of any one of SEQ ID NOs: 181-216. In some embodiments, the Fc fragment of the competing anti-PD-1 HCAb comprises the amino acid sequence of any one of SEQ ID NOs: 363-365. In some embodiments, the $K_d$ of the binding between the competing anti-PD-1 HCAb and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the competing anti-PD-1 HCAb is camelid, chimeric, human, partially humanized, or fully humanized.

Multivalent and/or Multispecific Antibodies

In some embodiments, the isolated anti-PD-1 construct comprises an anti-PD-1 sdAb moiety described herein fused to one or more other antibody moiety or antigen binding portion (such as an antibody moiety that specifically recognizes another epitope). The one or more other antibody moiety can be of any antibody or antibody fragment format, such as a full-length antibody, a Fab, a Fab', a (Fab')$_2$, an Fv, an scFv, an scFv-scFv, a minibody, a diabody, or an sdAb. In some embodiments, the one or more antibody moiety (or antigen binding portion) comprises a heavy chain variable domain ($V_H$) and a light chain variable domain ($V_L$). For a review of certain antibody fragments, see Hudson et al. Nat. Med. 9:129-134 (2003). For a review of scFv fragments, see, e.g., Pluckthün, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046. For a review of multispecific antibodies, see Weidle et al., Cancer Genomics Proteomics, 10(1):1-18, 2013; Geering and Fussenegger, Trends Biotechnol., 33(2):65-79, 2015; Stamova et al., Antibodies, 1(2):172-198, 2012. Diabodies are antibody fragments with two antigen-binding sites that may be bivalent or bispecific. See, for example, EP 404,097; WO 1993/01161; Hudson et al., Nat. Med. 9:129-134 (2003); and Hollinger et al., Proc. Natl. Acad. Sci. USA 90: 6444-6448 (1993). Triabodies and tetrabodies are also described in Hudson et al., Nat. Med. 9:129-134 (2003). Antibody fragments can be made by various techniques, including but not limited to proteolytic digestion of an intact antibody as well as production by recombinant host cells (e.g. E. coli or phage), as described herein.

Techniques for making multispecific antibodies include, but are not limited to, recombinant co-expression of two immunoglobulin heavy chain-light chain pairs having different specificities (see Milstein and Cuello, Nature 305: 537 (1983)), WO 93/08829, and Traunecker et al., EMBO J. 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., Science, 229: 81 (1985)); using leucine zippers to produce bi-specific antibodies (see, e.g., Kostelny et al., J. Immunol., 148(5):1547-1553 (1992)); using "diabody" technology for making bispecific antibody fragments (see, e.g., Hollinger et al., Proc. Natl. Acad. Sci. USA, 90:6444-6448 (1993)); and using single-chain Fv (sFv) dimers (see, e.g., Gruber et al., J. Immunol., 152:5368 (1994)); and preparing trispecific antibodies as described, e.g., in Tutt et al. J. Immunol. 147: 60 (1991); and creating polypeptides comprising tandem single-domain antibodies (see, e.g., U.S. Patent Application No. 20110028695; and Conrath et al. J. Biol. Chem., 2001; 276(10):7346-50). Engineered antibodies with three or more functional antigen binding sites, including "Octopus antibodies," are also included herein (see, e.g., US 2006/0025576A1).

Peptide Linkers

In some embodiments, the anti-PD-1 sdAb and the other one or more antibody moieties (such as a full-length antibody, sdAb, or an antigen binding portion comprising a $V_H$ and a $V_L$) within the anti-PD-1 construct can be optionally connected by a peptide linker. The length, the degree of flexibility and/or other properties of the peptide linker(s) used in the anti-PD-1 construct may have some influence on properties, including but not limited to the affinity, specificity or avidity for one or more particular antigens or epitopes. For example, longer peptide linkers may be selected to ensure that two adjacent domains do not sterically interfere with one another. In some embodiment, a peptide linker comprises flexible residues (such as glycine and serine) so that the adjacent domains are free to move relative to each other. For example, a glycine-serine doublet can be a suitable peptide linker.

The peptide linker can be of any suitable length. In some embodiments, the peptide linker is at least about any of 1, 2, 3, 4, 5, 6, 7, 8, 9, 10, 11, 12, 13, 14, 15, 16, 17, 18, 19, 20, 25, 30, 35, 40, 50, 75, 100 or more amino acids long. In some embodiments, the peptide linker is no more than about any of 100, 75, 50, 40, 35, 30, 25, 20, 19, 18, 17, 16, 15, 14, 13, 12, 11, 10, 9, 8, 7, 6, 5 or fewer amino acids long. In some embodiments, the length of the peptide linker is any of about 1 amino acid to about 10 amino acids, about 1 amino acid to about 20 amino acids, about 1 amino acid to about 30 amino acids, about 5 amino acids to about 15 amino acids, about 10 amino acids to about 25 amino acids, about 5 amino acids to about 30 amino acids, about 10 amino acids to about 30 amino acids long, about 30 amino acids to about 50 amino acids, about 50 amino acids to about 100 amino acids, or about 1 amino acid to about 100 amino acids.

The peptide linker may have a naturally occurring sequence, or a non-naturally occurring sequence. For example, a sequence derived from the hinge region of heavy chain only antibodies may be used as the linker. See, for example, WO1996/34103. In some embodiments, the peptide linker is a human IgG1 hinge (SEQ ID NO: 369). In some embodiments, the peptide linker is a mutated human IgG1 hinge (SEQ ID NO: 368). In some embodiments, the peptide linker is a human IgG4 hinge (SEQ ID NO: 367). In some embodiments, the peptide linker is a hIgG2 hinge. In some embodiments, the peptide linker is a flexible linker. Exemplary flexible linkers include glycine polymers (G)$_n$ (SEQ ID NO: 372), glycine-serine polymers (including, for example, (GS)$_n$ (SEQ ID NO: 373), (GSGGS)$_n$ (SEQ ID NO: 374), (GGGS)$_n$ (SEQ ID NO: 375), and (GGGGS)$_n$ (SEQ ID NO: 376), where n is an integer of at least one), glycine-alanine polymers, alanine-serine polymers, and other flexible linkers known in the art. In some embodiments, the peptide linker comprises the amino acid sequence of SEQ ID NO: 370 (GGGGSGGGS) or 371 (GGGGSGGGGSGGGGS).

In some embodiments, the anti-PD-1 construct comprising an anti-PD-1 sdAb moiety described herein and one or more other antibody moiety (such as a full-length antibody, sdAb, or an antigen binding portion comprising a $V_H$ and a $V_L$) is monospecific. In some embodiments, the anti-PD-1 construct comprising an anti-PD-1 sdAb moiety described herein and one or more other antibody moiety (such as a full-length antibody, sdAb, or an antigen binding portion comprising a $V_H$ and a $V_L$) is multispecific (such as bispecific). Multispecific molecules are molecules that have binding specificities for at least two different epitopes (e.g., bispecific antibodies have binding specificities for two epitopes). Multispecific molecules with more than two valencies and/or specificities are also contemplated. For example, trispecific antibodies can be prepared. Tutt et al. *J. Immunol.* 147: 60 (1991). It is to be appreciated that one of skill in the art could select appropriate features of individual multispecific molecules described herein to combine with one another to form a multispecific anti-PD-1 construct of the invention.

In some embodiments, the anti-PD-1 construct is multivalent but monospecific, i.e., the anti-PD-1 construct comprises an anti-PD-1 sdAb moiety described herein and at least a second antibody moiety (such as a full-length antibody, sdAb, or an antigen binding portion comprising a $V_H$ and a $V_L$) specifically recognizing the same PD-1 epitope as the anti-PD-1 sdAb moiety described herein. In some embodiments, the one or more antibody moiety that specifically recognizes the same PD-1 epitope as the anti-PD-1 sdAb moiety described herein may comprise the same CDRs and/or the same $V_H H$ amino acid sequence as the anti-PD-1 sdAb moiety. For example, the anti-PD-1 construct may comprise two or more anti-PD-1 sdAb moieties described herein, wherein the two or more anti-PD-1 sdAb moieties are the same, and are optionally connected by peptide linker(s). In some embodiments, the peptide linker comprises the amino acid sequence of any one of SEQ ID NOs: 367-376.

In some embodiments, the anti-PD-1 construct is multivalent and multispecific (e.g., bispecific), i.e., the anti-PD-1 construct comprises an anti-PD-1 sdAb moiety described herein and at least a second antibody moiety (such as a full-length antibody, sdAb, or an antigen binding portion comprising a $V_H$ and a $V_L$) specifically recognizing a second antigen other than PD-1, or a different PD-1 epitope recognized by the anti-PD-1 sdAb moiety described herein. In some embodiments, the second antibody moiety is an sdAb, such as anti-PD-1 sdAb, or anti-CTLA-4 sdAb (such as any of those disclosed in PCT/CN2017/105506 and PCT/CN2016/101777, which are incorporated herein by reference in their entirety). In some embodiments, the second antibody moiety specifically recognizes human serum albumin (HSA). In some embodiments, the anti-PD-1 sdAb moiety described herein is fused to the N-terminus and/or C-terminus of the second antibody moiety. In some embodiments, the anti-PD-1 construct is trivalent and bispecific. In some embodiments, the anti-PD-1 construct comprises two anti-PD-1 sdAb moieties described herein and a second antibody moiety (such as an anti-HSA sdAb, anti-CTLA-4 sdAb), wherein the second antibody moiety is between the two anti-PD-1 sdAb moieties. In some embodiments, the antibody moieties are optionally connected by peptide linker(s). In some embodiments, the peptide linker comprises the amino acid sequence of any one of SEQ ID NOs: 367-376.

The monospecific or multispecific anti-PD-1 construct comprising two or more anti-PD-1 sdAb moieties may have increase avidity compared to that of a single anti-PD-1 sdAb moiety described herein.

Bispecific Antibodies Comprising an Anti-PD-1 sdAb Moiety Fused to a Full-Length Antibody In some embodiments, the anti-PD-1 construct comprises an anti-PD-1 sdAb moiety described herein fused to a second antibody moiety, wherein the second antibody moiety is a full-length antibody consisting of two heavy chains and two light chains (such as full-length antibody specifically recognizing TIGIT, LAG-3, TIM-3, CTLA-4, or PD-1 (e.g., a second PD-1 epitope different from that recognized by the anti-PD-1 sdAb moiety described herein)). In some embodiments, the anti-PD-1 sdAb moiety and the full-length antibody are connected via an optional linker, such as a peptide linker.

Thus in some embodiments, there is provided an isolated anti-PD-1 construct comprising an sdAb moiety specifically recognizing PD-1 and a full-length antibody (such as full-length antibody specifically recognizing TIGIT, LAG-3, TIM-3, CTLA-4, or PD-1 (e.g., a second PD-1 epitope different from that recognized by the anti-PD-1 sdAb moiety described herein)), wherein the anti-PD-1 sdAb moiety comprises a CDR1 comprising the amino acid sequence of any one of SEQ ID NOs: 37-72, or a variant thereof comprising up to about 3 (such as about any of 1, 2, or 3) amino acid substitutions; a CDR2 comprising the amino acid sequence of any one of SEQ ID NOs: 109-144, or a variant thereof comprising up to about 3 (such as about any of 1, 2, or 3) amino acid substitutions; and a CDR3 comprising the amino acid sequence of any one of SEQ ID NOs: 181-216, or a variant thereof comprising up to about 3 (such as about any of 1, 2, or 3) amino acid substitutions. In some embodiments, there is provided an isolated anti-PD-1 construct comprising an sdAb moiety specifically recognizing PD-1 and a full-length antibody (such as full-length antibody specifically recognizing TIGIT, LAG-3, TIM-3, CTLA-4, or PD-1 (e.g., a second PD-1 epitope different from that recognized by the anti-PD-1 sdAb moiety described herein)), wherein the anti-PD-1 sdAb moiety comprises a CDR1 comprising the amino acid sequence of any one of SEQ ID NOs: 37-72, or a variant thereof comprising up to about 3 (such as about any of 1, 2, or 3) amino acid substitutions; a CDR2 comprising the amino acid sequence of any one of SEQ ID NOs: 109-144, or a variant thereof comprising up to about 3 (such as about any of 1, 2, or 3) amino acid substitutions; and a CDR3 comprising the amino acid sequence of any one of SEQ ID NOs: 181-216, or a variant thereof comprising up to about 3 (such as about any of 1, 2, or 3) amino acid substitutions; and wherein the N-terminus of the anti-PD-1 sdAb moiety is fused to the C-terminus of at least one of the heavy chains of the full-length antibody (exemplified as FIG. 17). In some embodiments, there is provided an isolated anti-PD-1 construct comprising an sdAb moiety specifically recognizing PD-1 and a full-length antibody (such as full-length antibody specifically recognizing TIGIT, LAG-3, TIM-3, CTLA-4, or PD-1 (e.g., a second PD-1 epitope different from that recognized by the anti-PD-1 sdAb moiety described herein)), wherein the anti-PD-1 sdAb moiety comprises a CDR1 comprising the amino acid sequence of any one of SEQ ID NOs: 37-72, or a variant thereof comprising up to about 3 (such as about any of 1, 2, or 3) amino acid substitutions; a CDR2 comprising the amino acid sequence of any one of SEQ ID NOs: 109-144, or a variant thereof comprising up to about 3 (such as about any of 1, 2, or 3) amino acid substitutions; and a CDR3 comprising the amino acid sequence of any one of SEQ ID NOs: 181-216, or a variant thereof comprising up to about 3 (such as about any of 1, 2, or 3) amino acid substitutions; and wherein the C-terminus of the anti-PD-1 sdAb moiety is fused to the N-terminus of at least one of the heavy chains of the full-length antibody (exemplified as FIG. 16). In some embodiments, there is provided an isolated anti-PD-1 construct comprising an sdAb moiety specifically recognizing PD-1 and a full-length antibody (such as full-length antibody specifically recognizing TIGIT, LAG-3, TIM-3, CTLA-4, or PD-1 (e.g., a second PD-1 epitope different from that recognized by the anti-PD-1 sdAb moiety described herein)), wherein the anti-PD-1 sdAb moiety comprises a CDR1 comprising the amino acid sequence of any one of SEQ ID NOs: 37-72, or a variant thereof comprising up to about 3 (such as about any of 1, 2, or 3) amino acid substitutions; a CDR2 comprising the amino acid sequence of any one of SEQ ID NOs: 109-144, or a variant thereof comprising up to about 3 (such as about any of 1, 2, or 3) amino acid substitutions; and a CDR3 comprising the amino acid sequence of any one of SEQ ID NOs: 181-216, or a variant thereof comprising up to about 3 (such as about any of 1, 2, or 3) amino acid substitutions; and wherein the N-terminus of the anti-PD-1 sdAb moiety is fused to the C-terminus of at least one of the light chains of the full-length antibody (exemplified as FIG. 19). In some embodiments, there is provided an isolated anti-PD-1 construct comprising an sdAb moiety specifically recognizing PD-1 and a full-length antibody (such as full-length antibody specifically recognizing TIGIT, LAG-3, TIM-3, CTLA-4, or PD-1 (e.g., a second PD-1 epitope different from that recognized by the anti-PD-1 sdAb moiety described herein)), wherein the anti-PD-1 sdAb moiety comprises a CDR1 comprising the amino acid sequence of any one of SEQ ID NOs: 37-72, or a variant thereof comprising up to about 3 (such as about any of 1, 2, or 3) amino acid substitutions; a CDR2 comprising the amino acid sequence of any one of SEQ ID NOs: 109-144, or a variant thereof comprising up to about 3 (such as about any of 1, 2, or 3) amino acid substitutions; and a CDR3 comprising the amino acid sequence of any one of SEQ ID NOs: 181-216, or a variant thereof comprising up to about 3 (such as about any of 1, 2, or 3) amino acid substitutions; and wherein the C-terminus of the anti-PD-1 sdAb moiety is fused to the N-terminus of at least one of the light chains of the full-length antibody (exemplified as FIG. 18). In some embodiments, there is provided an isolated anti-PD-1 construct comprising four sdAb moieties specifically recognizing PD-1 and a full-length antibody (such as full-length antibody specifically recognizing TIGIT, LAG-3, TIM-3, CTLA-4, or PD-1 (e.g., a second PD-1 epitope different from that recognized by the anti-PD-1 sdAb moiety described herein)), wherein each anti-PD-1 sdAb moiety comprises a CDR1 comprising the amino acid sequence of any one of SEQ ID NOs: 37-72, or a variant thereof comprising up to about 3 (such as about any of 1, 2, or 3) amino acid substitutions; a CDR2 comprising the amino acid sequence of any one of SEQ ID NOs: 109-144, or a variant thereof comprising up to about 3 (such as about any of 1, 2, or 3) amino acid substitutions; and a CDR3 comprising the amino acid sequence of any one of SEQ ID NOs: 181-216, or a variant thereof comprising up to about 3 (such as about any of 1, 2, or 3) amino acid substitutions; and wherein the C-terminus of the anti-PD-1 sdAb moiety is fused to the N-terminus of both heavy and light chains of the full-length antibody (exemplified as FIG. 20). In some embodiments, there is provided an isolated anti-PD-1 construct comprising four sdAb moieties specifically recognizing PD-1 and a full-length antibody (such as full-length antibody specifically recognizing TIGIT, LAG-3, TIM-3, CTLA-4, or PD-1 (e.g., a second PD-1 epitope different from that recognized by the anti-PD-1 sdAb moiety described herein)), wherein each anti-PD-1 sdAb moiety comprises a CDR1 comprising the amino acid sequence of any one of SEQ ID NOs: 37-72, or a variant thereof comprising up to about 3 (such as about any of 1, 2, or 3) amino acid substitutions; a CDR2 comprising the amino acid sequence of any one of SEQ ID NOs: 109-144, or a variant thereof comprising up to about 3 (such as about any of 1, 2, or 3) amino acid substitutions; and a CDR3 comprising the amino acid sequence of any one of SEQ ID NOs: 181-216, or a variant thereof comprising up to about 3 (such as about any of 1, 2, or 3) amino acid substitutions; wherein two anti-PD-1 sdAb moieties are fused together via a first optional linker, and the other two anti-PD-1 sdAb moieties are fused together via a second optional linker, and wherein the C-terminus of each set of the two anti-PD-1 sdAb fusion is fused to the N-terminus of each heavy chain of the full-length antibody via a third and fourth optional linkers (exemplified as FIG. 21). In some embodiments, the four anti-PD-1 sdAb moieties are identical. In some embodiments, the four anti-PD-1 sdAb moieties are different. In some embodiments, the anti-PD-1 sdAb moiety comprises a CDR1 comprising the amino acid sequence of any one of SEQ ID NOs: 37-72; a CDR2 comprising the amino acid sequence of any one of SEQ ID NOs: 109-144; and a CDR3 comprising the amino acid sequence of any one of SEQ ID NOs: 181-216. In some embodiments, the anti-PD-1 sdAb moiety comprises a $V_HH$ domain comprising the amino acid sequence of any one of SEQ ID NOs: 289-324. In some embodiments, the anti-PD-1 sdAb moiety comprises CDR1, CDR2, and CDR3 of any one of SEQ ID NOs: 289-324. In some embodiments, the Fc fragment of the full-length antibody is hIgG1 Fc, effectorless hIgG1 Fc, hIgG2 Fc, hIgG4 Fc, or hIgG4 Fc (S228P). In some embodiments, the Fc fragment of the full-length antibody comprises the amino acid sequence of any one of SEQ ID NOs: 363-365. In some embodiments, the full-length antibody is an activator of a stimulatory immune checkpoint molecule. In some embodiments, the full-length antibody is an immune checkpoint inhibitor, such as an inhibitor of TIGIT, LAG-3, TIM-3, CTLA-4, or PD-1 (e.g., an antibody that specifically recognizes a second PD-1 epitope different from that recognized by the anti-PD-1 sdAb moiety described herein). In some embodiments, the full-length antibody is an anti-TIGIT antibody. In some embodiments, the anti-TIGIT antibody comprises a $V_H$ comprising HC-CDR1, HC-CDR2, and HC-CDR3 of the amino acid sequence of SEQ ID NO: 377, and a $V_L$ comprising LC-CDR1, LC-CDR2, and LC-CDR3 of the amino acid sequence of SEQ ID NO: 378. In some embodiments, the anti-TIGIT antibody comprises a heavy chain comprising the amino acid sequence of SEQ ID NO: 377, and a light chain comprising the amino acid sequence of SEQ ID NO: 378. In some embodiments, the anti-TIGIT antibody is tiragolumab. In some embodiments, the full-length antibody is an anti-LAG-3 antibody. In some embodiments, the anti-LAG-3 antibody comprises a $V_H$ comprising HC-CDR1, HC-CDR2, and HC-CDR3 of the amino acid sequence of SEQ ID NO: 379, and a $V_L$ comprising LC-CDR1, LC-CDR2, and LC-CDR3 of the amino acid sequence of SEQ ID NO: 380. In some embodiments, the anti-LAG-3 antibody comprises a heavy chain comprising the amino acid sequence of SEQ ID NO: 379, and a light chain comprising the amino acid sequence of SEQ ID NO: 380. In some embodiments, the anti-LAG-3 antibody is relatlimab. In some embodiments, the full-length antibody is an anti-TIM-3 antibody. In some embodiments, the anti-TIM-3 antibody comprises a $V_H$ comprising HC-CDR1, HC-CDR2, and HC-CDR3 of the amino acid sequence of SEQ ID NO: 381, and a $V_L$ comprising LC-CDR1, LC-CDR2, and LC-CDR3 of the amino acid sequence of SEQ ID NO: 382. In some embodiments, the anti-TIM-3 antibody comprises a heavy chain comprising the amino acid sequence of SEQ ID NO: 381, and a light chain comprising the amino acid sequence of SEQ ID NO: 382. In some embodiments, the anti-TIM-3 antibody is MBG453. In some embodiments, the full-length antibody is an anti-CTLA-4 antibody. In some embodiments, the anti-CTLA-4 antibody comprises a $V_H$ comprising HC-CDR1, HC-CDR2, and HC-CDR3 of the amino acid sequence of SEQ ID NO: 383, and a $V_L$ comprising LC-CDR1, LC-CDR2, and LC-CDR3 of the amino acid sequence of SEQ ID NO: 384. In some embodiments, the anti-CTLA-4 antibody comprises a heavy chain comprising the amino acid sequence of SEQ ID NO: 383, and a light chain comprising the amino acid sequence of SEQ ID NO: 384. In some embodiments, the anti-CTLA-4 antibody is ipilimumab (e.g., Yervoy®). In some embodiments, the full-length antibody is an anti-PD-1 antibody (e.g., specifically recognizes a second PD-1 epitope different from that recognized by the anti-PD-1 sdAb moiety described herein). In some embodiments, the anti-PD-1 full-length antibody comprises a $V_H$ comprising HC-CDR1, HC-CDR2, and HC-CDR3 of the amino acid sequence of SEQ ID NO: 385, and a $V_L$ comprising LC-CDR1, LC-CDR2, and LC-CDR3 of the amino acid sequence of SEQ ID NO: 386. In some embodiments, the anti-PD-1 full-length antibody comprises a heavy chain comprising the amino acid sequence of SEQ ID NO: 385, and a light chain comprising the amino acid sequence of SEQ ID NO: 386. In some embodiments, the anti-PD-1 full-length antibody is pembrolizumab (e.g., Keytruda®) or nivolumab (e.g., Opdivo®). In some embodiments, the anti-PD-1 sdAb moiety and the full-length antibody are optionally connected by a peptide linker. In some embodiments, the peptide linker comprises the amino acid sequence of any one of SEQ ID NOs: 367-376. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized.

TIGIT

T cell immunoreceptor with Ig and ITIM domains (TIGIT, also known as Vstm3 or WUCAM) is an immune receptor belonging to the CD28 family. TIGIT exerts its inhibitory immune checkpoint function via several mechanisms. First, upon binding to its major ligand CD155 (PVR), the subsequent phosphorylation of TIGIT in its ITIM domain transduces inhibitory signals to downregulate IFN-γ expression in T cells and NK cells via NF-κB pathway. Second, as TIGIT interacts with PVR at higher affinity than with CD226, it competes with CD226 and attenuates the stimulatory signal transduced by CD226. Third, PVR binding to TIGIT on dendritic cells may lead to upregulation of IL-10 expression and downregulation of IL-12 expression, therefore impairing the anti-tumor immune response of dendritic cells. Lastly, recent research indicated that TIGIT can directly bind to CD226 in cis to inhibit CD226 dimerization, which is required for T cell activation. Therefore, TIGIT acts as an important negative regulator in immune responses in infection and cancer, and blockade of TIGIT signaling has been proposed as an approach to enhance T cell and NK cell immunity for cancer treatment. Exemplary anti-TIGIT antibodies that can be applied in the present application include, but are not limited to, tiragolumab.

The construct comprising bispecificity against TIGIT and PD-1 will be hereinafter referred to as "anti-TIGIT/PD-1 antibody", "anti-TIGIT/PD-1 construct", "PD-1×TIGIT antibody", or "PD-1×TIGIT BABP".

LAG-3

LAG-3 (Lymphocyte Activating Gene-3, CD223) works to suppress an immune response by action to Tregs, as well as direct effects on CD8+ T cells (Huang et al., 2004, Immunity. 21(4):503-13; Grosso et al., 2007, J Clin Invest. 117(11):3383-92). Exemplary anti-LAG-3 antibodies that can be applied in the present application include, but are not limited to, relatlimab (BMS-986016).

The construct comprising bispecificity against LAG-3 and PD-1 will be hereinafter referred to as "anti-LAG-3/PD-1 antibody", "anti-LAG-3/PD-1 construct", "PD-1×LAG-3 antibody", or "PD-1×LAG-3 BABP".

TIM-3

T-cell immunoglobulin and mucin-domain containing-3 (TIM-3) is also known as Hepatitis A virus cellular receptor 2 (HAVCR2). It is an immune checkpoint molecule which has been associated with the inhibition of lymphocyte activity and in some cases induction of lymphocyte anergy (Pardoll D. Nature Reviews 2012 April Vol. 12: 252). TIM-3 is a receptor for galectin 9 (GALS), which is up-regulated in various types of cancers, including breast cancers. TIM-3 has been identified as another important inhibitory receptor expressed by exhausted CD8+ T cells. In mouse models of cancer, it has been shown that the most dysfunctional tumor-infiltrating CD8+ T cells actually co-express PD-1 and TIM-3. Exemplary anti-TIM-3 antibodies that can be applied in the present application include, but are not limited to, MBG453.

The construct comprising bispecificity against TIM-3 and PD-1 will be hereinafter referred to as "anti-TIM-3/PD-1 antibody", "anti-TIM-3/PD-1 construct", "PD-1×TIM-3 antibody", or "PD-1×TIM-3 BABP".

CTLA-4

Cytotoxic T-Lymphocyte-Associated protein 4 (CTLA-4, or CD152) is a homolog of CD28, and is known as an inhibitory immune checkpoint molecule up-regulated on activated T-cells. CTLA-4 also binds to B7-1 and B7-2, but with greater affinity than CD28. The interaction between B7 and CTLA-4 dampens T cell activation, which constitutes an important mechanism of tumor immune escape. Anti-CTLA-4 antibody therapy has shown promise in a number of cancers, such as melanoma. Exemplary anti-CTLA-4 antibodies that can be applied in the present application include, but are not limited to, ipilimumab (e.g., Yervoy®).

The construct comprising bispecificity against CTLA-4 and PD-1 will be hereinafter referred to as "anti-CTLA-4/PD-1 antibody", "anti-CTLA-4/PD-1 construct", "PD-1×CTLA-4 antibody", or "PD-1×CTLA-4 BABP".

PD-1

In some embodiments, the second antibody moiety is a full-length antibody consisting of two heavy chains and two light chains that specifically recognizes another epitope of PD-1, different from the PD-1 epitope recognized by the anti-PD-1 sdAb moiety described herein. In some embodiments, fusing an anti-PD-1 sdAb moiety described herein with an anti-PD-1 full-length antibody that specifically recognizes a different PD-1 epitope will increase antibody potency. Exemplary anti-PD-1 antibodies that can be applied in the present application include, but are not limited to, pembrolizumab (e.g., Keytruda®) and nivolumab (e.g., Opdivo®).

The construct comprising bispecificity against PD-1 will be hereinafter referred to as "anti-PD-1/PD-1 antibody", "anti-PD-1/PD-1 construct", "PD-1×PD-1 antibody", or "PD-1×PD-1 BABP".

In some embodiments, there is also provided an anti-PD-1 construct comprising an sdAb moiety specifically recognizing PD-1 (hereinafter referred to as "competing anti-PD-1 construct") that specifically binds to PD-1 competitively with any one of the anti-PD-1 constructs described herein (such as anti-PD-1 sdAb moiety, anti-PD-1 sdAb-Fc fusion protein (e.g., anti-PD-1 HCAb), multispecific or monospecific anti-PD-1 construct comprising an anti-PD-1 sdAb moiety descried herein, e.g., PD-1×TIGIT BABP, PD-1× LAG-3 BABP, PD-1×TIM-3 BABP, PD-1×CTLA-4 BABP, or PD-1×PD-1 BABP described herein).

Anti-PD-1 Multispecific Antigen Binding Proteins (MABPs)

In some embodiments, there is provided an isolated anti-PD-1 construct comprising an anti-PD-1 sdAb moiety described herein fused to a full-length antibody or antigen binding fragment that comprises a $V_H$ and a $V_L$, wherein the anti-PD-1 construct is multispecific (hereinafter referred to as "multispecific anti-PD-1 construct" or "anti-PD-1 multispecific antigen binding protein (MABP)"). In some embodiments, the anti-PD-1 MABP is bispecific (hereinafter referred to as "bispecific anti-PD-1 construct" or "anti-PD-1 bispecific antigen binding protein (BABP)"). The anti-PD-1 sdAb moiety specifically binds PD-1 that is distinct from the target(s) recognized by the full-length antibody or antigen binding fragment comprising a $V_H$ and a $V_L$, thereby conferring a broadened targeting capability. Due to the small size of the sdAb, in some embodiments the anti-PD-1 MABPs (e.g., anti-PD-1 BABPs) described herein can have similar molecular weight and pharmacokinetic properties compared to those of the full-length antibody or antigen binding fragment component. For example, an anti-PD-1 MABP can be designed by fusing one or more anti-PD-1 sdAb moieties to a monoclonal antibody with proven clinical efficacy and safety to provide increased clinical benefits and desirable pharmacokinetic properties without impeding the expressibility of the multispecific construct. In some embodiments, the one or more anti-PD-1 sdAb moiety described herein is fused to the full-length antibody or antigen binding fragment by an optional peptide linker. The anti-PD-1 MABPs (e.g., anti-PD-1 BABPs) described herein can be adopted to target a variety of disease-related epitope or antigen combinations besides PD-1, such as PD-1 with the combination of immune checkpoint molecules, cell surface antigens (such as tumor antigens), or pro-inflammatory molecules, thereby providing agents that are useful for treating a variety of diseases and conditions, such as cancer, inflammation, and autoimmune diseases. The anti-PD-1 MABP (e.g., anti-PD-1 BABPs) can be of any format, such as those disclosed in PCT/CN2017/093644, which is incorporated herein by reference in their entirety.

Exemplary Anti-PD-1 MABPs and BABPs

In some embodiments, the anti-PD-1 MABP (e.g., BABP) comprises (a) a first antigen binding portion comprising an sdAb moiety specifically recognizing PD-1 described herein, and (b) a second antigen binding portion comprising a $V_H$ and a $V_L$, wherein the $V_H$ and $V_L$ together form an antigen-binding site that specifically binds TIGIT, wherein the first antigen binding portion and the second antigen binding portion are fused to each other (herein after referred to as "PD-1×TIGIT MABP" or "PD-1×TIGIT BABP"). In some embodiments, the anti-PD-1 MABP (e.g., BABP) comprises (a) a first antigen binding portion comprising an sdAb moiety specifically recognizing PD-1 described herein, and (b) a second antigen binding portion comprising a $V_H$ and a $V_L$, wherein the $V_H$ and $V_L$ together form an antigen-binding site that specifically binds LAG-3, wherein the first antigen binding portion and the second antigen binding portion are fused to each other (herein after referred to as "PD-1×LAG-3 MABP" or "PD-1×LAG-3 BABP"). In some embodiments, the anti-PD-1 MABP (e.g., BABP) comprises (a) a first antigen binding portion comprising an sdAb moiety specifically recognizing PD-1 described herein, and (b) a second antigen binding portion comprising a $V_H$ and a $V_L$, wherein the $V_H$ and $V_L$ together form an antigen-binding site that specifically binds TIM-3, wherein the first antigen binding portion and the second antigen binding portion are fused to each other (herein after referred to as "PD-1×TIM-3 MABP" or "PD-1×TIM-3 BABP"). In some embodiments, the anti-PD-1 MABP (e.g., BABP) comprises (a) a first antigen binding portion comprising an sdAb moiety specifically recognizing PD-1 described herein, and (b) a second antigen binding portion comprising a $V_H$ and a $V_L$, wherein the $V_H$ and $V_L$ together form an antigen-binding site that specifically binds CTLA-4, wherein the first antigen binding portion and the second antigen binding portion are fused to each other (herein after referred to as "PD-1×CTLA-4 MABP" or "PD-1×CTLA-4 BABP"). In some embodiments, the anti-PD-1 MABP (e.g., BABP) comprises (a) a first antigen binding portion comprising an sdAb moiety specifically recognizing PD-1 described herein, and (b) a second antigen binding portion comprising a $V_H$ and a $V_L$, wherein the $V_H$ and $V_L$ together form an antigen-binding site that specifically binds a second PD-1 epitope different from that recognized by the anti-PD-1 sdAb moiety described herein, wherein the first antigen binding portion and the second antigen binding portion are fused to each other (herein after referred to as "PD-1× PD-1 MABP" or "PD-1×PD-1 BABP").

Figure 17:
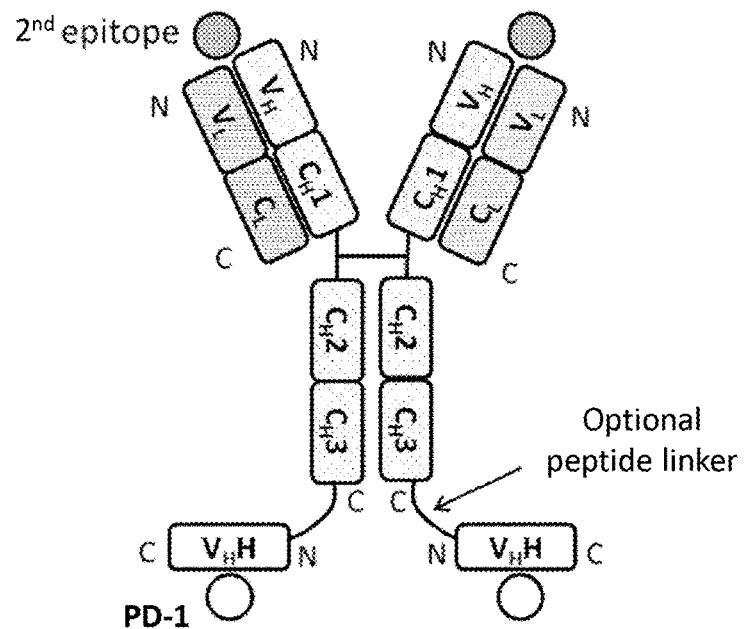
FIG. 17 depicts a schematic structure of an exemplary BABP comprising a monospecific full-length antibody having two identical heavy chains and two identical light chains, and two identical anti-PD-1 sdAbs, wherein the N-terminus of each anti-PD-1 sdAb is fused to the C-terminus of one heavy chain via an optional peptide linker. The two anti-PD-1 sdAbs specifically bind a first epitope (PD-1). The full-length antibody has two antigen binding sites that specifically bind a second epitope. For example, the BABP can consist of four polypeptide chains with structures from the N-terminus to the C-terminus as follows: (1) $V_L$—$C_L$; (2) $V_H$—$C_H1$-$C_H2$-$C_H3$-$V_H H$; (3) $V_H$—$C_H1$-$C_H2$-$C_H3$-$V_H H$; and (4) $V_L$—$C_L$, wherein $V_H$ and $V_L$ of polypeptide chains (1) and (2) forms an antigen binding site that specifically binds a first copy of the second epitope, $V_H$ and $V_L$ of polypeptide chains (3) and (4) forms an antigen binding site that specifically binds a second copy of the second epitope, and each $V_H H$ specifically binds a copy of the first epitope (PD-1). In alternative formats, each anti-PD-1 sdAb may be omitted, or replaced with two identical or different anti-PD-1 sdAbs fused to each other. The monospecific full-length antibody may be replaced with a bispecific full-length antibody to further expand binding specificity.

In some embodiments, there is provided an anti-PD-1 BABP comprising: (a) a first polypeptide comprising from N-terminus to C-terminus: $V_H$—$C_H1$-$C_H2$-$C_H3$-anti-PD-1 sdAb moiety; and (b) a second polypeptide comprising from N-terminus to C-terminus: $V_L$—$C_L$, wherein $V_H$ and $V_L$ forms an antigen binding site that specifically binds a second epitope (e.g., TIGIT, LAG-3, TIM-3, CTLA-4, PD-1 (such as a second PD-1 epitope different from that recognized by the anti-PD-1 sdAb moiety described herein)), and wherein the anti-PD-1 sdAb moiety comprises a CDR1 comprising the amino acid sequence of any one of SEQ ID NOs: 37-72, or a variant thereof comprising up to about 3 (such as about any of 1, 2, or 3) amino acid substitutions; a CDR2 comprising the amino acid sequence of any one of SEQ ID NOs: 109-144, or a variant thereof comprising up to about 3 (such as about any of 1, 2, or 3) amino acid substitutions; and a CDR3 comprising the amino acid sequence of any one of SEQ ID NOs: 181-216, or a variant thereof comprising up to about 3 (such as about any of 1, 2, or 3) amino acid substitutions. In some embodiments, the anti-PD-1 sdAb comprises a CDR1 comprising the amino acid sequence of any one of SEQ ID NOs: 37-72; a CDR2 comprising the amino acid sequence of any one of SEQ ID NOs: 109-144; and a CDR3 comprising the amino acid sequence of any one of SEQ ID NOs: 181-216. In some embodiments, the anti-PD-1 sdAb moiety comprises a $V_H$H domain comprising the amino acid sequence of any one of SEQ ID NO: 289-324. In some embodiments, $V_H$ and $V_L$ form an antigen binding site that specifically binds TIGIT. In some embodiments, the $V_H$ and $V_L$ domains are derived from tiragolumab. In some embodiments, the $V_H$ comprises HC-CDR1, HC-CDR2, and HC-CDR3 of the amino acid sequence of SEQ ID NO: 377, and $V_L$ comprises LC-CDR1, LC-CDR2, and LC-CDR3 of the amino acid sequence of SEQ ID NO: 378. In some embodiments, $V_H$ and $V_L$ form an antigen binding site that specifically binds LAG-3. In some embodiments, the $V_H$ and $V_L$ domains are derived from relatlimab. In some embodiments, the $V_H$ comprises HC-CDR1, HC-CDR2, and HC-CDR3 of the amino acid sequence of SEQ ID NO: 379, and $V_L$ comprises LC-CDR1, LC-CDR2, and LC-CDR3 of the amino acid sequence of SEQ ID NO: 380. In some embodiments, $V_H$ and $V_L$ form an antigen binding site that specifically binds TIM-3. In some embodiments, the $V_H$ and $V_L$ domains are derived from MBG453. In some embodiments, the $V_H$ comprises HC-CDR1, HC-CDR2, and HC-CDR3 of the amino acid sequence of SEQ ID NO: 381 and $V_L$ comprises LC-CDR1, LC-CDR2, and LC-CDR3 of the amino acid sequence of SEQ ID NO: 382. In some embodiments, $V_H$ and $V_L$ form an antigen binding site that specifically binds CTLA-4. In some embodiments, the $V_H$ and $V_L$ domains are derived from ipilimumab (e.g., Yervoy®). In some embodiments, the $V_H$ comprises HC-CDR1, HC-CDR2, and HC-CDR3 of the amino acid sequence of SEQ ID NO: 383 and $V_L$ comprises LC-CDR1, LC-CDR2, and LC-CDR3 of the amino acid sequence of SEQ ID NO: 384. In some embodiments, $V_H$ and $V_L$ form an antigen binding site that specifically binds PD-1 (such as a second PD-1 epitope different from that recognized by the anti-PD-1 sdAb moiety described herein). In some embodiments, the $V_H$ and $V_L$ domains are derived from pembrolizumab (e.g., Keytruda®) or nivolumab (e.g., Opdivo®). In some embodiments, the $V_H$ comprises HC-CDR1, HC-CDR2, and HC-CDR3 of the amino acid sequence of SEQ ID NO: 385 and $V_L$ comprises LC-CDR1, LC-CDR2, and LC-CDR3 of the amino acid sequence of SEQ ID NO: 386. In some embodiments, the $C_H3$ and anti-PD-1 sdAb moiety are fused to each other optionally via a peptide linker, such as a peptide linker comprising the amino acid sequence of any one of SEQ ID NOs: 367-376. In some embodiments, the $C_H2$ and $C_H3$ domains are derived from IgG1 Fc, effectorless IgG1 Fc, IgG2 Fc, IgG4 Fc, or IgG4 Fc (S228P), e.g., any of SEQ ID NOs: 363-365. In some embodiments, the anti-PD-1 BABP comprises two identical copies of the first polypeptide and two identical copies of the second polypeptide. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized. In some embodiments, the PD-1 BABP has the structure as shown in FIG. 17.

Figure 16:
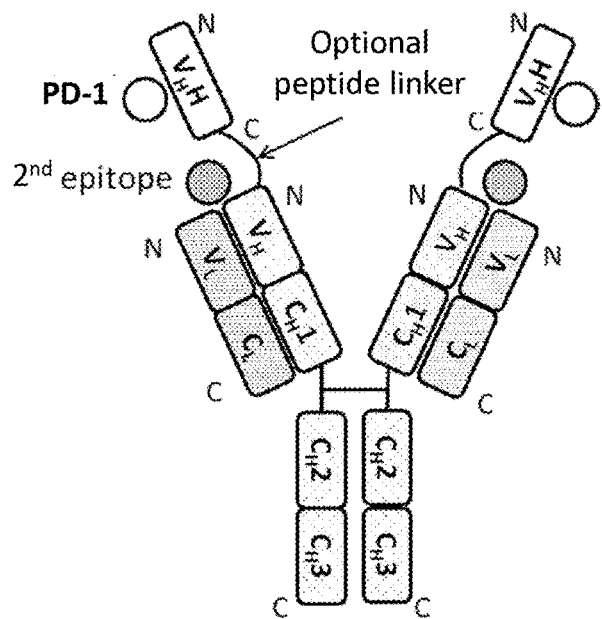
FIG. 16 depicts a schematic structure of an exemplary BABP comprising a monospecific full-length antibody having two identical heavy chains and two identical light chains, and two identical anti-PD-1 sdAbs, wherein the C-terminus of each anti-PD-1 sdAb is fused to the N-terminus of one heavy chain via an optional peptide linker. The two anti-PD-1 sdAbs specifically bind a first epitope (PD-1). The full-length antibody has two antigen binding sites that specifically bind a second epitope. For example, the BABP can consist of four polypeptide chains with structures from the N-terminus to the C-terminus as follows: (1) $V_L$—$C_L$; (2) $V_HH$—$V_H$—$C_H1$-$C_H2$-$C_H3$; (3) $V_HH$—$V_H$—$C_H1$-$C_H2$-$C_H3$; and (4) $V_L$—$C_L$, wherein $V_H$ and $V_L$ of polypeptide chains (1) and (2) forms an antigen binding site that specifically binds a first copy of the second epitope, $V_H$ and $V_L$ of polypeptide chains (3) and (4) forms an antigen binding site that specifically binds a second copy of the second epitope, and each $V_H H$ specifically binds a copy of the first epitope (PD-1). In alternative formats, each anti-PD-1 sdAb may be omitted, or replaced with two identical or different anti-PD-1 sdAbs fused to each other. The monospecific full-length antibody may be replaced with a bispecific full-length antibody to further expand binding specificity.

In some embodiments, there is provided an anti-PD-1 BABP comprising: (a) a first polypeptide comprising from N-terminus to C-terminus: anti-PD-1 sdAb moiety-$V_H$—$C_H1$-$C_H2$-$C_H3$; and (b) a second polypeptide comprising from N-terminus to C-terminus: $V_L$—$C_L$, wherein $V_H$ and $V_L$ forms an antigen binding site that specifically binds a second epitope (e.g., TIGIT, LAG-3, TIM-3, CTLA-4, PD-1 (such as a second PD-1 epitope different from that recognized by the anti-PD-1 sdAb moiety described herein)), and wherein the anti-PD-1 sdAb moiety comprises a CDR1 comprising the amino acid sequence of any one of SEQ ID NOs: 37-72, or a variant thereof comprising up to about 3 (such as about any of 1, 2, or 3) amino acid substitutions; a CDR2 comprising the amino acid sequence of any one of SEQ ID NOs: 109-144, or a variant thereof comprising up to about 3 (such as about any of 1, 2, or 3) amino acid substitutions; and a CDR3 comprising the amino acid sequence of any one of SEQ ID NOs: 181-216, or a variant thereof comprising up to about 3 (such as about any of 1, 2, or 3) amino acid substitutions. In some embodiments, the anti-PD-1 sdAb moiety comprises a CDR1 comprising the amino acid sequence of any one of SEQ ID NOs: 37-72; a CDR2 comprising the amino acid sequence of any one of SEQ ID NOs: 109-144; and a CDR3 comprising the amino acid sequence of any one of SEQ ID NOs: 181-216. In some embodiments, the anti-PD-1 sdAb moiety comprises a $V_HH$ domain comprising the amino acid sequence of any one of SEQ ID NO: 289-324. In some embodiments, $V_H$ and $V_L$ form an antigen binding site that specifically binds TIGIT. In some embodiments, the $V_H$ and $V_L$ domains are derived from tiragolumab. In some embodiments, the $V_H$ comprises HC-CDR1, HC-CDR2, and HC-CDR3 of the amino acid sequence of SEQ ID NO: 377, and $V_L$ comprises LC-CDR1, LC-CDR2, and LC-CDR3 of the amino acid sequence of SEQ ID NO: 378. In some embodiments, $V_H$ and $V_L$ form an antigen binding site that specifically binds LAG-3. In some embodiments, the $V_H$ and $V_L$ domains are derived from relatlimab. In some embodiments, the $V_H$ comprises HC-CDR1, HC-CDR2, and HC-CDR3 of the amino acid sequence of SEQ ID NO: 379, and $V_L$ comprises LC-CDR1, LC-CDR2, and LC-CDR3 of the amino acid sequence of SEQ ID NO: 380. In some embodiments, $V_H$ and $V_L$ form an antigen binding site that specifically binds TIM-3. In some embodiments, the $V_H$ and $V_L$ domains are derived from MBG453. In some embodiments, the $V_H$ comprises HC-CDR1, HC-CDR2, and HC-CDR3 of the amino acid sequence of SEQ ID NO: 381 and $V_L$ comprises LC-CDR1, LC-CDR2, and LC-CDR3 of the amino acid sequence of SEQ ID NO: 382. In some embodiments, $V_H$ and $V_L$ form an antigen binding site that specifically binds CTLA-4. In some embodiments, the $V_H$ and $V_L$ domains are derived from ipilimumab (e.g., Yervoy®). In some embodiments, the $V_H$ comprises HC-CDR1, HC-CDR2, and HC-CDR3 of the amino acid sequence of SEQ ID NO: 383 and $V_L$ comprises LC-CDR1, LC-CDR2, and LC-CDR3 of the amino acid sequence of SEQ ID NO: 384. In some embodiments, $V_H$ and $V_L$ form an antigen binding site that specifically binds PD-1 (such as a second PD-1 epitope different from that recognized by the anti-PD-1 sdAb moiety described herein). In some embodiments, the $V_H$ and $V_L$ domains are derived from pembrolizumab (e.g., Keytruda®) or nivolumab (e.g., Opdivo®). In some embodiments, the $V_H$ comprises HC-CDR1, HC-CDR2, and HC-CDR3 of the amino acid sequence of SEQ ID NO: 385 and $V_L$ comprises LC-CDR1, LC-CDR2, and LC-CDR3 of the amino acid sequence of SEQ ID NO: 386. In some embodiments, the $V_H$ and the anti-PD-1 sdAb moiety are fused to each other optionally via a peptide linker, such as a peptide linker comprising the amino acid sequence of any one of SEQ ID NOs: 367-376. In some embodiments, the $C_H2$ and $C_H3$ domains are derived from IgG1 Fc, effectorless IgG1 Fc, IgG2 Fc, IgG4 Fc, or IgG4 Fc (S228P), e.g., any of SEQ ID NOs: 363-365. In some embodiments, the anti-PD-1 BABP comprises two identical copies of the first polypeptide and two identical copies of the second polypeptide. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized. In some embodiments, the PD-1 BABP has the structure as shown in FIG. 16.

In some embodiments, there is provided an anti-PD-1 BABP comprising: (a) a first polypeptide comprising from N-terminus to C-terminus: $V_H$—$C_H1$-$C_H2$-$C_H3$; and (b) a second polypeptide comprising from N-terminus to C-terminus: $V_L$—$C_L$-anti-PD-1 sdAb moiety, wherein $V_H$ and $V_L$ forms an antigen binding site that specifically binds a second epitope (e.g., TIGIT, LAG-3, TIM-3, CTLA-4, PD-1 (such as a second PD-1 epitope different from that recognized by the anti-PD-1 sdAb moiety described herein)), and wherein the anti-PD-1 sdAb moiety comprises a CDR1 comprising the amino acid sequence of any one of SEQ ID NOs: 37-72, or a variant thereof comprising up to about 3 (such as about any of 1, 2, or 3) amino acid substitutions; a CDR2 comprising the amino acid sequence of any one of SEQ ID NOs: 109-144, or a variant thereof comprising up to about 3 (such as about any of 1, 2, or 3) amino acid substitutions; and a CDR3 comprising the amino acid sequence of any one of SEQ ID NOs: 181-216, or a variant thereof comprising up to about 3 (such as about any of 1, 2, or 3) amino acid substitutions. In some embodiments, the anti-PD-1 sdAb moiety comprises a CDR1 comprising the amino acid sequence of any one of SEQ ID NOs: 37-72; a CDR2 comprising the amino acid sequence of any one of SEQ ID NOs: 109-144; and a CDR3 comprising the amino acid sequence of any one of SEQ ID NOs: 181-216. In some embodiments, the anti-PD-1 sdAb moiety comprises a $V_HH$ domain comprising the amino acid sequence of any one of SEQ ID NO: 289-324. In some embodiments, $V_H$ and $V_L$ form an antigen binding site that specifically binds TIGIT. In some embodiments, the $V_H$ and $V_L$ domains are derived from tiragolumab. In some embodiments, the $V_H$ comprises HC-CDR1, HC-CDR2, and HC-CDR3 of the amino acid sequence of SEQ ID NO: 377, and $V_L$ comprises LC-CDR1, LC-CDR2, and LC-CDR3 of the amino acid sequence of SEQ ID NO: 378. In some embodiments, $V_H$ and $V_L$ form an antigen binding site that specifically binds LAG-3. In some embodiments, the $V_H$ and $V_L$ domains are derived from relatlimab. In some embodiments, the $V_H$ comprises HC-CDR1, HC-CDR2, and HC-CDR3 of the amino acid sequence of SEQ ID NO: 379, and $V_L$ comprises LC-CDR1, LC-CDR2, and LC-CDR3 of the amino acid sequence of SEQ ID NO: 380. In some embodiments, $V_H$ and $V_L$ form an antigen binding site that specifically binds TIM-3. In some embodiments, the $V_H$ and $V_L$ domains are derived from MBG453. In some embodiments, the $V_H$ comprises HC-CDR1, HC-CDR2, and HC-CDR3 of the amino acid sequence of SEQ ID NO: 381 and $V_L$ comprises LC-CDR1, LC-CDR2, and LC-CDR3 of the amino acid sequence of SEQ ID NO: 382. In some embodiments, $V_H$ and $V_L$ form an antigen binding site that specifically binds CTLA-4. In some embodiments, the $V_H$ and $V_L$ domains are derived from ipilimumab (e.g., Yervoy®). In some embodiments, the $V_H$ comprises HC-CDR1, HC-CDR2, and HC-CDR3 of the amino acid sequence of SEQ ID NO: 383 and $V_L$ comprises LC-CDR1, LC-CDR2, and LC-CDR3 of the amino acid sequence of SEQ ID NO: 384. In some embodiments, $V_H$ and $V_L$ form an antigen binding site that specifically binds PD-1 (such as a second PD-1 epitope different from that recognized by the anti-PD-1 sdAb moiety described herein). In some embodiments, the $V_H$ and $V_L$ domains are derived from pembrolizumab (e.g., Keytruda®) or nivolumab (e.g., Opdivo®). In some embodiments, the $V_H$ comprises HC-CDR1, HC-CDR2, and HC-CDR3 of the amino acid sequence of SEQ ID NO: 385 and $V_L$ comprises LC-CDR1, LC-CDR2, and LC-CDR3 of the amino acid sequence of SEQ ID NO: 386. In some embodiments, the $C_L$ and the anti-PD-1 sdAb moiety are fused to each other optionally via a peptide linker, such as a peptide linker comprising the amino acid sequence of any one of SEQ ID NOs: 367-376. In some embodiments, the $C_H2$ and $C_H3$ domains are derived from IgG1 Fc, effectorless IgG1 Fc, IgG2 Fc, IgG4 Fc, or IgG4 Fc (S228P), e.g., any of SEQ ID NOs: 363-365.

Figure 19:
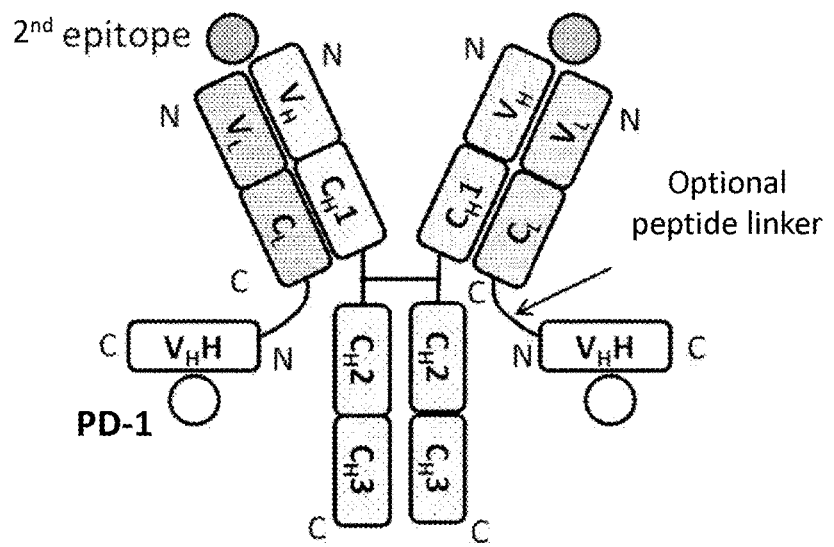
FIG. 19 depicts a schematic structure of an exemplary BABP comprising a monospecific full-length antibody having two identical heavy chains and two identical light chains, and two identical anti-PD-1 sdAbs, wherein the N-terminus of each anti-PD-1 sdAb is fused to the C-terminus of one light chain via an optional peptide linker. The two anti-PD-1 sdAbs specifically bind a first epitope. The full-length antibody has two antigen binding sites that specifically bind a second epitope. For example, the BABP can consist of four polypeptide chains with structures from the N-terminus to the C-terminus as follows: (1) $V_L$—$C_L$—$V_H H$; (2) $V_H$—$C_H1$-$C_H2$-$C_H3$; (3) $V_H$—$C_H1$-$C_H2$-$C_H3$; and (4) $V_L$—$C_L$—$V_H H$, wherein $V_H$ and $V_L$ of polypeptide chains (1) and (2) forms an antigen binding site that specifically binds a first copy of the second epitope, $V_H$ and $V_L$ of polypeptide chains (3) and (4) forms an antigen binding site that specifically binds a second copy of the second epitope, and each $V_H H$ specifically binds a copy of the first epitope (PD-1). In alternative formats, each anti-PD-1 sdAb may be omitted, or replaced with two identical or different anti-PD-1 sdAbs fused to each other. The monospecific full-length antibody may be replaced with a bispecific full-length antibody to further expand binding specificity.

In some embodiments, the anti-PD-1 BABP comprises two identical copies of the first polypeptide and two identical copies of the second polypeptide. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized. In some embodiments, the PD-1 BABP has the structure as shown in FIG. 19.

Figure 18:
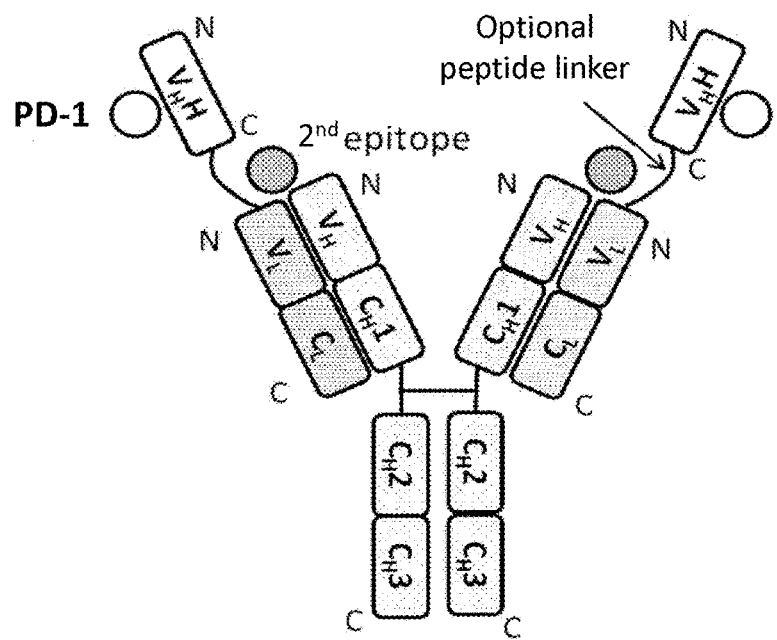
FIG. 18 depicts a schematic structure of an exemplary BABP comprising a monospecific full-length antibody having two identical heavy chains and two identical light chains, and two identical anti-PD-1 sdAbs, wherein the C-terminus of each anti-PD-1 sdAb is fused to the N-terminus of one light chain via an optional peptide linker. The two anti-PD-1 sdAbs specifically bind a first epitope (PD-1). The full-length antibody has two antigen binding sites that specifically bind a second epitope. For example, the BABP can consist of four polypeptide chains with structures from the N-terminus to the C-terminus as follows: (1) $V_H H$—$V_L$—$C_L$; (2) $V_H$—$C_H1$-$C_H2$-$C_H3$; (3) $V_H$—$C_H1$-$C_H2$-$C_H3$; and (4) $V_H H$—$V_L$—$C_L$, wherein $V_H$ and $V_L$ of polypeptide chains (1) and (2) forms an antigen binding site that specifically binds a first copy of the second epitope, $V_H$ and $V_L$ of polypeptide chains (3) and (4) forms an antigen binding site that specifically binds a second copy of the second epitope, and each $V_H H$ specifically binds a copy of the first epitope (PD-1). In alternative formats, each anti-PD-1 sdAb may be omitted, or replaced with two identical or different anti-PD-1 sdAbs fused to each other. The monospecific full-length antibody may be replaced with a bispecific full-length antibody to further expand binding specificity.

In some embodiments, there is provided an anti-PD-1 BABP comprising: (a) a first polypeptide comprising from N-terminus to C-terminus: $V_H$—$C_H1$-$C_H2$-$C_H3$; and (b) a second polypeptide comprising from N-terminus to C-terminus: anti-PD-1 sdAb moiety-$V_L$—$C_L$, wherein $V_H$ and $V_L$ forms an antigen binding site that specifically binds a second epitope (e.g., TIGIT, LAG-3, TIM-3, CTLA-4, PD-1 (such as a second PD-1 epitope different from that recognized by the anti-PD-1 sdAb moiety described herein)), and wherein the anti-PD-1 sdAb moiety comprises a CDR1 comprising the amino acid sequence of any one of SEQ ID NOs: 37-72, or a variant thereof comprising up to about 3 (such as about any of 1, 2, or 3) amino acid substitutions; a CDR2 comprising the amino acid sequence of any one of SEQ ID NOs: 109-144, or a variant thereof comprising up to about 3 (such as about any of 1, 2, or 3) amino acid substitutions; and a CDR3 comprising the amino acid sequence of any one of SEQ ID NOs: 181-216, or a variant thereof comprising up to about 3 (such as about any of 1, 2, or 3) amino acid substitutions. In some embodiments, the anti-PD-1 sdAb moiety comprises a CDR1 comprising the amino acid sequence of any one of SEQ ID NOs: 37-72; a CDR2 comprising the amino acid sequence of any one of SEQ ID NOs: 109-144; and a CDR3 comprising the amino acid sequence of any one of SEQ ID NOs: 181-216. In some embodiments, the anti-PD-1 sdAb moiety comprises a $V_HH$ domain comprising the amino acid sequence of any one of SEQ ID NO: 289-324. In some embodiments, $V_H$ and $V_L$ form an antigen binding site that specifically binds TIGIT. In some embodiments, the $V_H$ and $V_L$ domains are derived from tiragolumab. In some embodiments, the $V_H$ comprises HC-CDR1, HC-CDR2, and HC-CDR3 of the amino acid sequence of SEQ ID NO: 377, and $V_L$ comprises LC-CDR1, LC-CDR2, and LC-CDR3 of the amino acid sequence of SEQ ID NO: 378. In some embodiments, $V_H$ and $V_L$ form an antigen binding site that specifically binds LAG-3. In some embodiments, the $V_H$ and $V_L$ domains are derived from relatlimab. In some embodiments, the $V_H$ comprises HC-CDR1, HC-CDR2, and HC-CDR3 of the amino acid sequence of SEQ ID NO: 379, and $V_L$ comprises LC-CDR1, LC-CDR2, and LC-CDR3 of the amino acid sequence of SEQ ID NO: 380. In some embodiments, $V_H$ and $V_L$ form an antigen binding site that specifically binds TIM-3. In some embodiments, the $V_H$ and $V_L$ domains are derived from MBG453. In some embodiments, the $V_H$ comprises HC-CDR1, HC-CDR2, and HC-CDR3 of the amino acid sequence of SEQ ID NO: 381 and $V_L$ comprises LC-CDR1, LC-CDR2, and LC-CDR3 of the amino acid sequence of SEQ ID NO: 382. In some embodiments, $V_H$ and $V_L$ form an antigen binding site that specifically binds CTLA-4. In some embodiments, the $V_H$ and $V_L$ domains are derived from ipilimumab (e.g., Yervoy®). In some embodiments, the $V_H$ comprises HC-CDR1, HC-CDR2, and HC-CDR3 of the amino acid sequence of SEQ ID NO: 383 and $V_L$ comprises LC-CDR1, LC-CDR2, and LC-CDR3 of the amino acid sequence of SEQ ID NO: 384. In some embodiments, $V_H$ and $V_L$ form an antigen binding site that specifically binds PD-1 (such as a second PD-1 epitope different from that recognized by the anti-PD-1 sdAb moiety described herein). In some embodiments, the $V_H$ and $V_L$ domains are derived from pembrolizumab (e.g., Keytruda®) or nivolumab (e.g., Opdivo®). In some embodiments, the $V_H$ comprises HC-CDR1, HC-CDR2, and HC-CDR3 of the amino acid sequence of SEQ ID NO: 385 and $V_L$ comprises LC-CDR1, LC-CDR2, and LC-CDR3 of the amino acid sequence of SEQ ID NO: 386. In some embodiments, the $V_L$ and the anti-PD-1 sdAb moiety are fused to each other optionally via a peptide linker, such as a peptide linker comprising the amino acid sequence of any one of SEQ ID NOs: 367-376. In some embodiments, the $C_H2$ and $C_H3$ domains are derived from IgG1 Fc, effectorless IgG1 Fc, IgG2 Fc, IgG4 Fc, or IgG4 Fc (S228P), e.g., any of SEQ ID NOs: 363-365. In some embodiments, the anti-PD-1 BABP comprises two identical copies of the first polypeptide and two identical copies of the second polypeptide. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized. In some embodiments, the PD-1 BABP has the structure as shown in FIG. 18.

Figure 20:
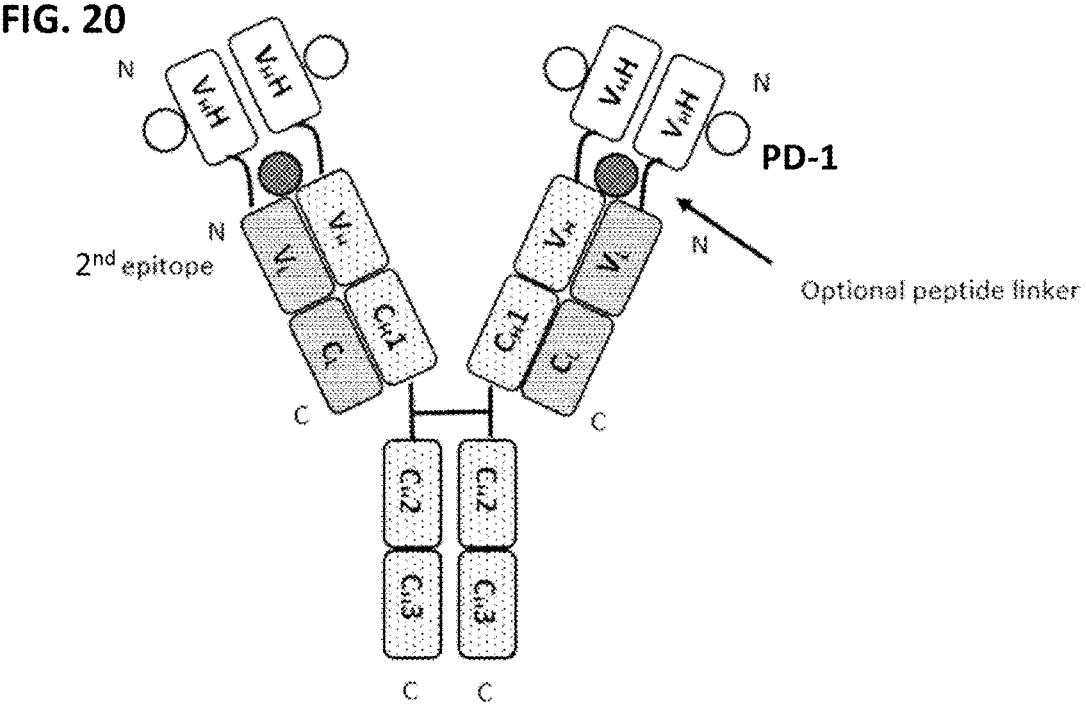
FIG. 20 depicts a schematic structure of an exemplary BABP comprising a monospecific full-length antibody having two identical heavy chains and two identical light chains, and four identical anti-PD-1 sdAbs, wherein the C-terminus of each anti-PD-1 sdAb is fused to the N-terminus of heavy chain or light chain of the monospecific full-length antibody via an optional peptide linker. Each anti-PD-1 sdAb specifically binds to a first epitope (PD-1). The full-length antibody has two antigen binding sites that each specifically binds a second epitope. For example, the BABP can consist of four polypeptide chains with structures from the N-terminus to the C-terminus as follows: (1) $V_H H$—$V_L$—$C_L$; (2) $V_H H$—$V_H$—$C_H1$-$C_H2$-$C_H3$; (3) $V_H H$—$V_H$—$C_H1$-$C_H2$-$C_H3$; and (4) $V_H H$—$V_L$—$C_L$, wherein $V_H$ and $V_L$ of polypeptide chains (1) and (2) forms an antigen binding site that specifically binds a first copy of the second epitope, $V_H$ and $V_L$ of polypeptide chains (3) and (4) forms an antigen binding site that specifically binds a second copy of the second epitope, and each $V_H H$ specifically binds a copy of the first epitope (PD-1). In alternative formats, each anti-PD-1 sdAb may be omitted, or replaced with two identical or different anti-PD-1 sdAbs fused to each other. The monospecific full-length antibody may be replaced with a bispecific full-length antibody to further expand binding specificity.

In some embodiments, there is provided an anti-PD-1 MABP (e.g., BABP) comprising: (a) a first polypeptide comprising from N-terminus to C-terminus: anti-PD-1 sdAb1 moiety-$V_H$—$C_H1$-$C_H2$-$C_H3$; and (b) a second polypeptide comprising from N-terminus to C-terminus: anti-PD-1 sdAb2 moiety-$V_L$—$C_L$, wherein $V_H$ and $V_L$ forms an antigen binding site that specifically binds a second epitope (e.g., TIGIT, LAG-3, TIM-3, CTLA-4, PD-1 (such as a second PD-1 epitope different from that recognized by the anti-PD-1 sdAb moiety described herein)), and wherein the anti-PD-1 sdAb1 moiety and the anti-PD-1 sdAb2 moiety each comprises a CDR1 comprising the amino acid sequence of any one of SEQ ID NOs: 37-72, or a variant thereof comprising up to about 3 (such as about any of 1, 2, or 3) amino acid substitutions; a CDR2 comprising the amino acid sequence of any one of SEQ ID NOs: 109-144, or a variant thereof comprising up to about 3 (such as about any of 1, 2, or 3) amino acid substitutions; and a CDR3 comprising the amino acid sequence of any one of SEQ ID NOs: 181-216, or a variant thereof comprising up to about 3 (such as about any of 1, 2, or 3) amino acid substitutions. In some embodiments, the anti-PD-1 sdAb1 moiety and the anti-PD-1 sdAb2 moiety each comprises a CDR1 comprising the amino acid sequence of any one of SEQ ID NOs: 37-72; a CDR2 comprising the amino acid sequence of any one of SEQ ID NOs: 109-144; and a CDR3 comprising the amino acid sequence of any one of SEQ ID NOs: 181-216. In some embodiments, the anti-PD-1 sdAb1 moiety and the anti-PD-1 sdAb2 moiety each comprises a $V_HH$ domain comprising the amino acid sequence of any one of SEQ ID NO: 289-324. In some embodiments, the anti-PD-1 sdAb1 moiety and the anti-PD-1 sdAb2 moiety are the same. In some embodiments, the anti-PD-1 sdAb1 moiety and the anti-PD-1 sdAb2 moiety are different. In some embodiments, $V_H$ and $V_L$ form an antigen binding site that specifically binds TIGIT. In some embodiments, the $V_H$ and $V_L$ domains are derived from tiragolumab. In some embodiments, the $V_H$ comprises HC-CDR1, HC-CDR2, and HC-CDR3 of the amino acid sequence of SEQ ID NO: 377, and $V_L$ comprises LC-CDR1, LC-CDR2, and LC-CDR3 of the amino acid sequence of SEQ ID NO: 378. In some embodiments, $V_H$ and $V_L$ form an antigen binding site that specifically binds LAG-3. In some embodiments, the $V_H$ and $V_L$ domains are derived from relatlimab. In some embodiments, the $V_H$ comprises HC-CDR1, HC-CDR2, and HC-CDR3 of the amino acid sequence of SEQ ID NO: 379, and $V_L$ comprises LC-CDR1, LC-CDR2, and LC-CDR3 of the amino acid sequence of SEQ ID NO: 380. In some embodiments, $V_H$ and $V_L$ form an antigen binding site that specifically binds TIM-3. In some embodiments, the $V_H$ and $V_L$ domains are derived from MBG453. In some embodiments, the $V_H$ comprises HC-CDR1, HC-CDR2, and HC-CDR3 of the amino acid sequence of SEQ ID NO: 381 and $V_L$ comprises LC-CDR1, LC-CDR2, and LC-CDR3 of the amino acid sequence of SEQ ID NO: 382. In some embodiments, $V_H$ and $V_L$ form an antigen binding site that specifically binds CTLA-4. In some embodiments, the $V_H$ and $V_L$ domains are derived from ipilimumab (e.g., Yervoy®). In some embodiments, the $V_H$ comprises HC-CDR1, HC-CDR2, and HC-CDR3 of the amino acid sequence of SEQ ID NO: 383 and $V_L$ comprises LC-CDR1, LC-CDR2, and LC-CDR3 of the amino acid sequence of SEQ ID NO: 384. In some embodiments, $V_H$ and $V_L$ form an antigen binding site that specifically binds PD-1 (such as a second PD-1 epitope different from that recognized by the anti-PD-1 sdAb moiety described herein). In some embodiments, the $V_H$ and $V_L$ domains are derived from pembrolizumab (e.g., Keytruda®) or nivolumab (e.g., Opdivo®). In some embodiments, the $V_H$ comprises HC-CDR1, HC-CDR2, and HC-CDR3 of the amino acid sequence of SEQ ID NO: 385 and $V_L$ comprises LC-CDR1, LC-CDR2, and LC-CDR3 of the amino acid sequence of SEQ ID NO: 386. In some embodiments, the $V_L$ and anti-PD-1 sdAb2 moiety are fused to each other optionally via a peptide linker, such as a peptide linker comprising the amino acid sequence of any one of SEQ ID NOs: 367-376. In some embodiments, the $V_H$ and anti-PD-1 sdAb 1 moiety are fused to each other optionally via a peptide linker, such as a peptide linker comprising the amino acid sequence of any one of SEQ ID NOs: 367-376. In some embodiments, the $C_H2$ and $C_H3$ domains are derived from IgG1 Fc, effectorless IgG1 Fc, IgG2 Fc, IgG4 Fc, or IgG4 Fc (S228P), e.g., any of SEQ ID NOs: 363-365. In some embodiments, the anti-PD-1 MABP (e.g., BABP) comprises two identical copies of the first polypeptide and two identical copies of the second polypeptide. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized. In some embodiments, the PD-1 MABP (e.g., BABP) has the structure as shown in FIG. 20.

Figure 21:
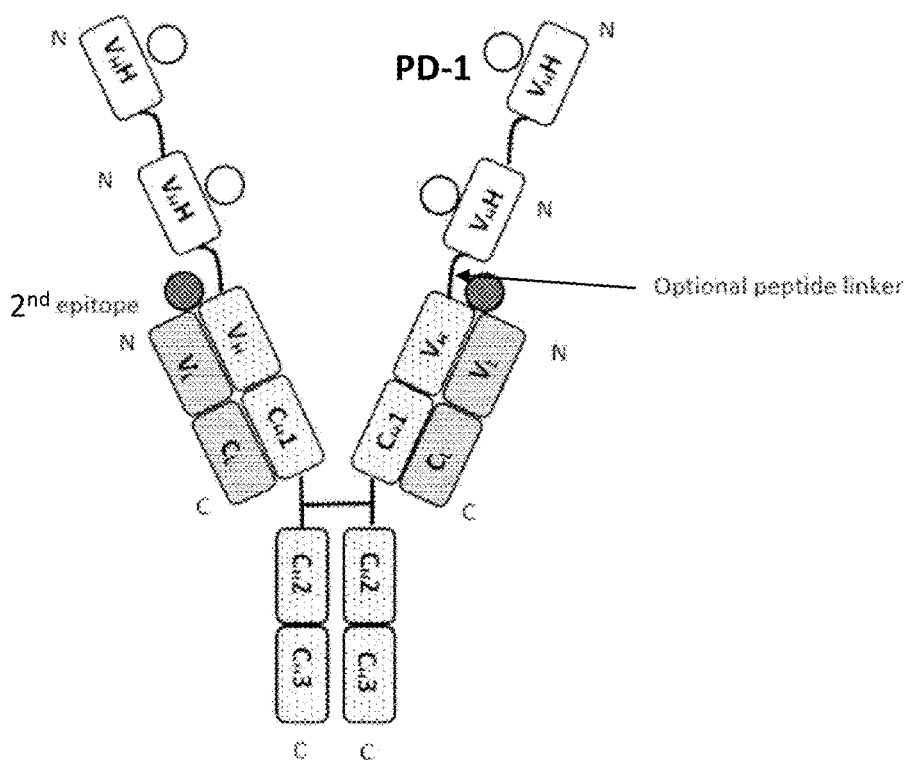
FIG. 21 depicts a schematic structure of an exemplary BABP comprising a monospecific full-length antibody having two identical heavy chains and two identical light chains, and four identical anti-PD-1 sdAbs, wherein fused to the N-terminus of each heavy chain are two identical anti-PD-1 sdAbs, the two anti-PD-1 sdAbs are fused to each other via an optional peptide linker, and the two anti-PD-1 sdAbs are fused to the N-terminus of each heavy chain via an optional peptide linker. Each anti-PD-1 sdAb specifically binds a first epitope (PD-1). The full-length antibody has two antigen binding sites that each specifically binds a second epitope. For example, the BABP can consist of four polypeptide chains with structures from the N-terminus to the C-terminus as follows: (1) $V_L$—$C_L$; (2) $V_H H$—$V_H H$—$V_H$—$C_H1$-$C_H2$-$C_H3$; (3) $V_H H$—$V_H H$—$V_H$—$C_H1$-$C_H2$-$C_H3$; and (4) $V_L$—$C_L$, wherein $V_H$ and $V_L$ of polypeptide chains (1) and (2) forms an antigen binding site that specifically binds a first copy of the second epitope, $V_H$ and $V_L$ of polypeptide chains (3) and (4) forms an antigen binding site that specifically binds a second copy of the second epitope, and each $V_H H$ specifically binds a copy of the first epitope (PD-1). In alternative formats, each anti-PD-1 sdAb may be omitted, or replaced with two identical or different anti-PD-1 sdAbs fused to each other. The monospecific full-length antibody may be replaced with a bispecific full-length antibody to further expand binding specificity.

In some embodiments, there is provided an anti-PD-1 MABP (e.g., BABP) comprising: (a) a first polypeptide comprising from N-terminus to C-terminus: anti-PD-1 sdAb1 moiety-anti-PD-1 sdAb2 moiety-$V_H$—$C_H1$-$C_H2$-$C_H3$; and (b) a second polypeptide comprising from N-terminus to C-terminus: $V_L$—$C_L$, wherein $V_H$ and $V_L$ forms an antigen binding site that specifically binds a second epitope (e.g., TIGIT, LAG-3, TIM-3, CTLA-4, PD-1 (such as a second PD-1 epitope different from that recognized by the anti-PD-1 sdAb moiety described herein)), and wherein the anti-PD-1 sdAb1 moiety and the anti-PD-1 sdAb2 moiety each comprises a CDR1 comprising the amino acid sequence of any one of SEQ ID NOs: 37-72, or a variant thereof comprising up to about 3 (such as about any of 1, 2, or 3) amino acid substitutions; a CDR2 comprising the amino acid sequence of any one of SEQ ID NOs: 109-144, or a variant thereof comprising up to about 3 (such as about any of 1, 2, or 3) amino acid substitutions; and a CDR3 comprising the amino acid sequence of any one of SEQ ID NOs: 181-216, or a variant thereof comprising up to about 3 (such as about any of 1, 2, or 3) amino acid substitutions. In some embodiments, the anti-PD-1 sdAb1 moiety and the anti-PD-1 sdAb2 moiety each comprises a CDR1 comprising the amino acid sequence of any one of SEQ ID NOs: 37-72; a CDR2 comprising the amino acid sequence of any one of SEQ ID NOs: 109-144; and a CDR3 comprising the amino acid sequence of any one of SEQ ID NOs: 181-216. In some embodiments, the anti-PD-1 sdAb1 moiety and the anti-PD-1 sdAb2 moiety each comprises a $V_HH$ domain comprising the amino acid sequence of any one of SEQ ID NOs: 289-324. In some embodiments, the anti-PD-1 sdAb1 moiety and the anti-PD-1 sdAb2 moiety are the same. In some embodiments, the anti-PD-1 sdAb1 moiety and the anti-PD-1 sdAb2 moiety are different. In some embodiments, $V_H$ and $V_L$ form an antigen binding site that specifically binds TIGIT. In some embodiments, the $V_H$ and $V_L$ domains are derived from tiragolumab. In some embodiments, the $V_H$ comprises HC-CDR1, HC-CDR2, and HC-CDR3 of the amino acid sequence of SEQ ID NO: 377, and $V_L$ comprises LC-CDR1, LC-CDR2, and LC-CDR3 of the amino acid sequence of SEQ ID NO: 378. In some embodiments, $V_H$ and $V_L$ form an antigen binding site that specifically binds LAG-3. In some embodiments, the $V_H$ and $V_L$ domains are derived from relatlimab. In some embodiments, the $V_H$ comprises HC-CDR1, HC-CDR2, and HC-CDR3 of the amino acid sequence of SEQ ID NO: 379, and $V_L$ comprises LC-CDR1, LC-CDR2, and LC-CDR3 of the amino acid sequence of SEQ ID NO: 380. In some embodiments, $V_H$ and $V_L$ form an antigen binding site that specifically binds TIM-3. In some embodiments, the $V_H$ and $V_L$ domains are derived from MBG453. In some embodiments, the $V_H$ comprises HC-CDR1, HC-CDR2, and HC-CDR3 of the amino acid sequence of SEQ ID NO: 381 and $V_L$ comprises LC-CDR1, LC-CDR2, and LC-CDR3 of the amino acid sequence of SEQ ID NO: 382. In some embodiments, $V_H$ and $V_L$ form an antigen binding site that specifically binds CTLA-4. In some embodiments, the $V_H$ and $V_L$ domains are derived from ipilimumab (e.g., Yervoy®). In some embodiments, the $V_H$ comprises HC-CDR1, HC-CDR2, and HC-CDR3 of the amino acid sequence of SEQ ID NO: 383 and $V_L$ comprises LC-CDR1, LC-CDR2, and LC-CDR3 of the amino acid sequence of SEQ ID NO: 384. In some embodiments, $V_H$ and $V_L$ form an antigen binding site that specifically binds PD-1 (such as a second PD-1 epitope different from that recognized by the anti-PD-1 sdAb moiety described herein). In some embodiments, the $V_H$ and $V_L$ domains are derived from pembrolizumab (e.g., Keytruda®) or nivolumab (e.g., Opdivo®). In some embodiments, the $V_H$ comprises HC-CDR1, HC-CDR2, and HC-CDR3 of the amino acid sequence of SEQ ID NO: 385 and $V_L$ comprises LC-CDR1, LC-CDR2, and LC-CDR3 of the amino acid sequence of SEQ ID NO: 386. In some embodiments, the anti-PD-1 sdAb 1 moiety and the anti-PD-1 sdAb2 moiety, and/or the $V_H$ and anti-PD-1 sdAb2 moiety, are fused to each other optionally via a peptide linker, such as a peptide linker comprising the amino acid sequence of any one of SEQ ID NOs: 367-376. In some embodiments, the $C_H2$ and $C_H3$ domains are derived from IgG1 Fc, effectorless IgG1 Fc, IgG2 Fc, IgG4 Fc, or IgG4 Fc (S228P), e.g., any of SEQ ID NOs: 363-365. In some embodiments, the anti-PD-1 MABP (e.g., BABP) comprises two identical copies of the first polypeptide and two identical copies of the second polypeptide. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized. In some embodiments, the PD-1 MABP (e.g., BABP) has the structure as shown in FIG. 21.

Figure 22:
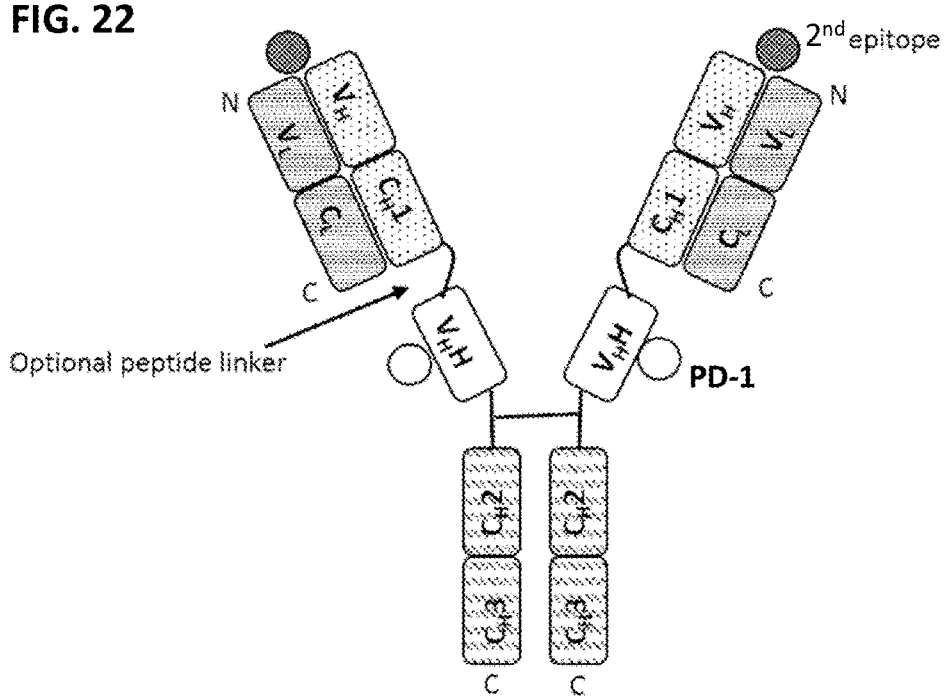
FIG. 22 depicts a schematic structure of an exemplary BABP comprising two identical antigen-binding (Fab) fragments, two identical anti-PD-1 sdAbs, and an Fc region, wherein the N-terminus of each anti-PD-1 sdAb is fused to the C-terminus of the $C_H1$ region of the Fab fragment via an optional peptide linker and the C-terminus of each anti-PD-1 sdAb is fused to the N-terminus of the $C_H2$ region of the Fc region. Each anti-PD-1 sdAb specifically binds a first epitope (PD-1). Each Fab fragment specifically binds a second epitope. For example, the BABP can consist of four polypeptide chains with structures from the N-terminus to the C-terminus as follows: (1) $V_L$—$C_L$; (2) $V_H$—$C_H1$-$V_HH$—$C_H2$-$C_H3$; (3) $V_H$—$C_H1$-$V_HH$—$C_H2$-$C_H3$; and (4) $V_L$—$C_L$, wherein $V_H$ and $V_L$ of polypeptide chains (1) and (2) forms an antigen binding site that specifically binds a first copy of the second epitope, $V_H$ and $V_L$ of polypeptide chains (3) and (4) forms an antigen binding site that specifically binds a second copy of the second epitope, and each $V_HH$ specifically binds a copy of the first epitope (PD-1). In alternative formats, each anti-PD-1 sdAb may be omitted, or replaced with two identical or different anti-PD-1 sdAbs fused to each other. In alternative formats, to expand specificity, the two Fab fragments can specifically bind different epitopes, and/or the $V_HH$ fragments can specifically bind different epitopes.

In some embodiments, there is provided an anti-PD-1 BABP comprising: (a) a first polypeptide comprising from N-terminus to C-terminus: $V_H$—$C_H$1-anti-PD-1 sdAb moiety-$C_H$2-$C_H$3; and (b) a second polypeptide comprising from N-terminus to C-terminus: $V_L$—$C_L$, wherein $V_H$ and $V_L$ forms an antigen binding site that specifically binds a second epitope (e.g., TIGIT, LAG-3, TIM-3, CTLA-4, PD-1 (such as a second PD-1 epitope different from that recognized by the anti-PD-1 sdAb moiety described herein)), and wherein the anti-PD-1 sdAb moiety comprises a CDR1 comprising the amino acid sequence of any one of SEQ ID NOs: 37-72, or a variant thereof comprising up to about 3 (such as about any of 1, 2, or 3) amino acid substitutions; a CDR2 comprising the amino acid sequence of any one of SEQ ID NOs: 109-144, or a variant thereof comprising up to about 3 (such as about any of 1, 2, or 3) amino acid substitutions; and a CDR3 comprising the amino acid sequence of any one of SEQ ID NOs: 181-216, or a variant thereof comprising up to about 3 (such as about any of 1, 2, or 3) amino acid substitutions. In some embodiments, the anti-PD-1 sdAb moiety comprises a CDR1 comprising the amino acid sequence of any one of SEQ ID NOs: 37-72; a CDR2 comprising the amino acid sequence of any one of SEQ ID NOs: 109-144; and a CDR3 comprising the amino acid sequence of any one of SEQ ID NOs: 181-216. In some embodiments, the anti-PD-1 sdAb moiety comprises a $V_HH$ domain comprising the amino acid sequence of any one of SEQ ID NO: 289-324. In some embodiments, $V_H$ and $V_L$ form an antigen binding site that specifically binds TIGIT. In some embodiments, the $V_H$ and $V_L$ domains are derived from tiragolumab. In some embodiments, the $V_H$ comprises HC-CDR1, HC-CDR2, and HC-CDR3 of the amino acid sequence of SEQ ID NO: 377, and $V_L$ comprises LC-CDR1, LC-CDR2, and LC-CDR3 of the amino acid sequence of SEQ ID NO: 378. In some embodiments, $V_H$ and $V_L$ form an antigen binding site that specifically binds LAG-3. In some embodiments, the $V_H$ and $V_L$ domains are derived from relatlimab. In some embodiments, the $V_H$ comprises HC-CDR1, HC-CDR2, and HC-CDR3 of the amino acid sequence of SEQ ID NO: 379, and $V_L$ comprises LC-CDR1, LC-CDR2, and LC-CDR3 of the amino acid sequence of SEQ ID NO: 380. In some embodiments, $V_H$ and $V_L$ form an antigen binding site that specifically binds TIM-3. In some embodiments, the $V_H$ and $V_L$ domains are derived from MBG453. In some embodiments, the $V_H$ comprises HC-CDR1, HC-CDR2, and HC-CDR3 of the amino acid sequence of SEQ ID NO: 381 and $V_L$ comprises LC-CDR1, LC-CDR2, and LC-CDR3 of the amino acid sequence of SEQ ID NO: 382. In some embodiments, $V_H$ and $V_L$ form an antigen binding site that specifically binds CTLA-4. In some embodiments, the $V_H$ and $V_L$ domains are derived from ipilimumab (e.g., Yervoy®). In some embodiments, the $V_H$ comprises HC-CDR1, HC-CDR2, and HC-CDR3 of the amino acid sequence of SEQ ID NO: 383 and $V_L$ comprises LC-CDR1, LC-CDR2, and LC-CDR3 of the amino acid sequence of SEQ ID NO: 384. In some embodiments, $V_H$ and $V_L$ form an antigen binding site that specifically binds PD-1 (such as a second PD-1 epitope different from that recognized by the anti-PD-1 sdAb moiety described herein). In some embodiments, the $V_H$ and $V_L$ domains are derived from pembrolizumab (e.g., Keytruda®) or nivolumab (e.g., Opdivo®). In some embodiments, the $V_H$ comprises HC-CDR1, HC-CDR2, and HC-CDR3 of the amino acid sequence of SEQ ID NO: 385 and $V_L$ comprises LC-CDR1, LC-CDR2, and LC-CDR3 of the amino acid sequence of SEQ ID NO: 386. In some embodiments, the $C_H1$ and the anti-PD-1 sdAb moiety are fused to each other optionally via a peptide linker, such as a peptide linker comprising the amino acid sequence of any one of SEQ ID NOs: 367-376. In some embodiments, the $C_H2$ and $C_H3$ domains are derived from IgG1 Fc, effectorless IgG1 Fc, IgG2 Fc, IgG4 Fc, or IgG4 Fc (S228P), e.g., any of SEQ ID NOs: 363-365. In some embodiments, the anti-PD-1 BABP comprises two identical copies of the first polypeptide and two identical copies of the second polypeptide. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized. In some embodiments, the PD-1 BABP has the structure as shown in FIG. 22.

Figure 23:
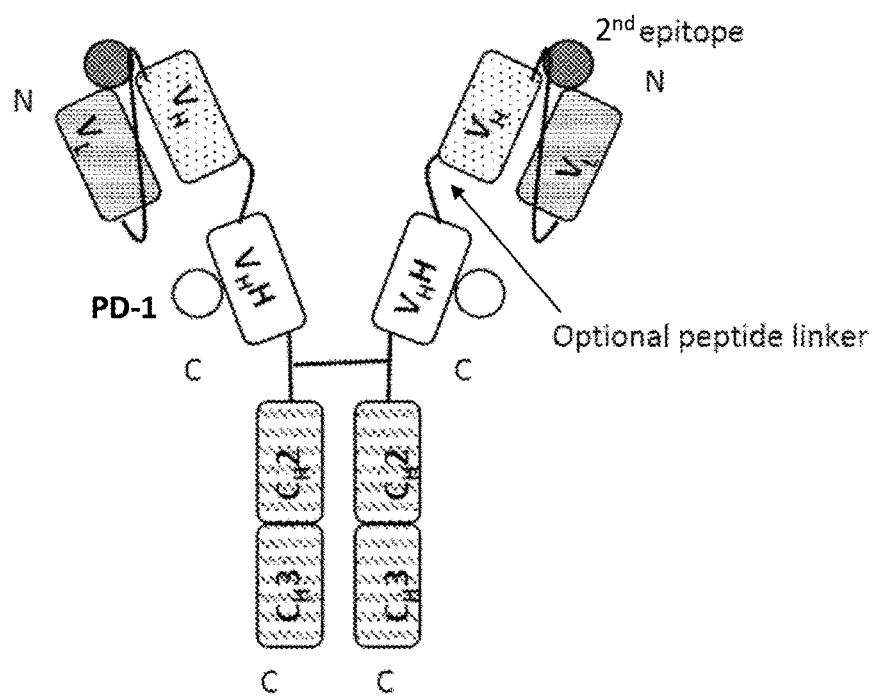
FIG. 23 depicts a schematic structure of an exemplary BABP comprising two identical single chain variable fragments (scFvs), two identical anti-PD-1 sdAbs, and an Fc region, wherein the N-terminus of each anti-PD-1 sdAb is fused to the C-terminus of an scFv via an optional peptide linker and the C-terminus of each anti-PD-1 sdAb is fused to the N-terminus of the Fc region. Each anti-PD-1 sdAb specifically binds a first epitope (PD-1). Each scFv specifically binds a second epitope. For example, the BABP can consist of two polypeptide chains each with a structure from the N-terminus to the C-terminus as follows: $V_L$—$V_H$—$V_HH$—$C_H2$-$C_H3$, wherein $V_H$ and $V_L$ of each polypeptide chain forms a scFv domain that specifically binds a copy of the second epitope, and each $V_HH$ specifically binds a copy of the first epitope (PD-1). In alternative formats, the scFv domain can comprise from the N-terminus to the C-terminus: $V_H$—$V_L$. In alternative formats, each anti-PD-1 sdAb may be omitted, or replaced with two identical or different anti-PD-1 sdAbs fused to each other. Additionally, to expand specificity, the two scFvs can specifically bind different epitopes, and/or the $V_HH$ fragments can specifically bind different epitopes.

In some embodiments, there is provided an anti-PD-1 BABP comprising a polypeptide comprising from N-terminus to C-terminus: $V_L$—$V_H$-anti-PD-1 sdAb moiety-$C_H2$-$C_H3$, wherein the $V_L$ and $V_H$ together forms an scFv that specifically binds a second epitope (e.g., TIGIT, LAG-3, TIM-3, CTLA-4, PD-1 (such as a second PD-1 epitope different from that recognized by the anti-PD-1 sdAb moiety described herein)), and wherein the anti-PD-1 sdAb moiety comprises a CDR1 comprising the amino acid sequence of any one of SEQ ID NOs: 37-72, or a variant thereof comprising up to about 3 (such as about any of 1, 2, or 3) amino acid substitutions; a CDR2 comprising the amino acid sequence of any one of SEQ ID NOs: 109-144, or a variant thereof comprising up to about 3 (such as about any of 1, 2, or 3) amino acid substitutions; and a CDR3 comprising the amino acid sequence of any one of SEQ ID NOs: 181-216, or a variant thereof comprising up to about 3 (such as about any of 1, 2, or 3) amino acid substitutions. In some embodiments, there is provided an anti-PD-1 BABP comprising a polypeptide comprising from N-terminus to C-terminus: $V_H$—$V_L$-anti-PD-1 sdAb moiety-$C_H2$-$C_H3$, wherein the $V_L$ and $V_H$ together forms an scFv that specifically binds a second epitope (e.g., TIGIT, LAG-3, TIM-3, CTLA-4, PD-1 (such as a second PD-1 epitope different from that recognized by the anti-PD-1 sdAb moiety described herein)), and wherein the anti-PD-1 sdAb moiety comprises a CDR1 comprising the amino acid sequence of any one of SEQ ID NOs: 37-72, or a variant thereof comprising up to about 3 (such as about any of 1, 2, or 3) amino acid substitutions; a CDR2 comprising the amino acid sequence of any one of SEQ ID NOs: 109-144, or a variant thereof comprising up to about 3 (such as about any of 1, 2, or 3) amino acid substitutions; and a CDR3 comprising the amino acid sequence of any one of SEQ ID NOs: 181-216, or a variant thereof comprising up to about 3 (such as about any of 1, 2, or 3) amino acid substitutions. In some embodiments, the anti-PD-1 sdAb moiety comprises a CDR1 comprising the amino acid sequence of any one of SEQ ID NOs: 37-72; a CDR2 comprising the amino acid sequence of any one of SEQ ID NOs: 109-144; and a CDR3 comprising the amino acid sequence of any one of SEQ ID NOs: 181-216. In some embodiments, the anti-PD-1 sdAb moiety comprises a $V_H H$ domain comprising the amino acid sequence of any one of SEQ ID NO: 289-324. In some embodiments, the scFv (or the $V_L$ and $V_H$ that form the scFv) specifically binds TIGIT. In some embodiments, the scFv (or the $V_L$ and $V_H$ that form the scFv) is derived from tiragolumab. In some embodiments, the $V_H$ comprises HC-CDR1, HC-CDR2, and HC-CDR3 of the amino acid sequence of SEQ ID NO: 377, and $V_L$ comprises LC-CDR1, LC-CDR2, and LC-CDR3 of the amino acid sequence of SEQ ID NO: 378. In some embodiments, the scFv (or the $V_L$ and $V_H$ that form the scFv) specifically binds LAG-3. In some embodiments, the scFv (or the $V_L$ and $V_H$ that form the scFv) is derived from relatlimab. In some embodiments, the $V_H$ comprises HC-CDR1, HC-CDR2, and HC-CDR3 of the amino acid sequence of SEQ ID NO: 379, and $V_L$ comprises LC-CDR1, LC-CDR2, and LC-CDR3 of the amino acid sequence of SEQ ID NO: 380. In some embodiments, the scFv (or the $V_L$ and $V_H$ that form the scFv) specifically binds TIM-3. In some embodiments, the scFv (or the $V_L$ and $V_H$ that form the scFv) is derived from MBG453. In some embodiments, the $V_H$ comprises HC-CDR1, HC-CDR2, and HC-CDR3 of the amino acid sequence of SEQ ID NO: 381 and $V_L$ comprises LC-CDR1, LC-CDR2, and LC-CDR3 of the amino acid sequence of SEQ ID NO: 382. In some embodiments, the scFv (or the $V_L$ and $V_H$ that form the scFv) specifically binds CTLA-4. In some embodiments, the scFv (or the $V_L$ and $V_H$ that form the scFv) is derived from ipilimumab (e.g., Yervoy®). In some embodiments, the $V_H$ comprises HC-CDR1, HC-CDR2, and HC-CDR3 of the amino acid sequence of SEQ ID NO: 383 and $V_L$ comprises LC-CDR1, LC-CDR2, and LC-CDR3 of the amino acid sequence of SEQ ID NO: 384. In some embodiments, the scFv (or the $V_L$ and $V_H$ that form the scFv) specifically binds PD-1 (such as a second PD-1 epitope different from that recognized by the anti-PD-1 sdAb moiety described herein). In some embodiments, the scFv (or the $V_L$ and $V_H$ that form the scFv) is derived from pembrolizumab (e.g., Keytruda®) or nivolumab (e.g., Opdivo®). In some embodiments, the $V_H$ comprises HC-CDR1, HC-CDR2, and HC-CDR3 of the amino acid sequence of SEQ ID NO: 385 and $V_L$ comprises LC-CDR1, LC-CDR2, and LC-CDR3 of the amino acid sequence of SEQ ID NO: 386. In some embodiments, the $V_H$ and $V_L$ that forms the scFv, and/or the scFv and the anti-PD-1 sdAb moiety, are fused to each other optionally via a peptide linker, such as a peptide linker comprising the amino acid sequence of any one of SEQ ID NOs: 367-376. In some embodiments, the $C_H2$ and $C_H3$ domains are derived from IgG1 Fc, effectorless IgG1 Fc, IgG2 Fc, IgG4 Fc, or IgG4 Fc (S228P), e.g., any of SEQ ID NOs: 363-365. In some embodiments, the anti-PD-1 BABP comprises two identical copies of the polypeptide. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized. In some embodiments, the PD-1 BABP has the structure as shown in FIG. 23.

Figure 24:
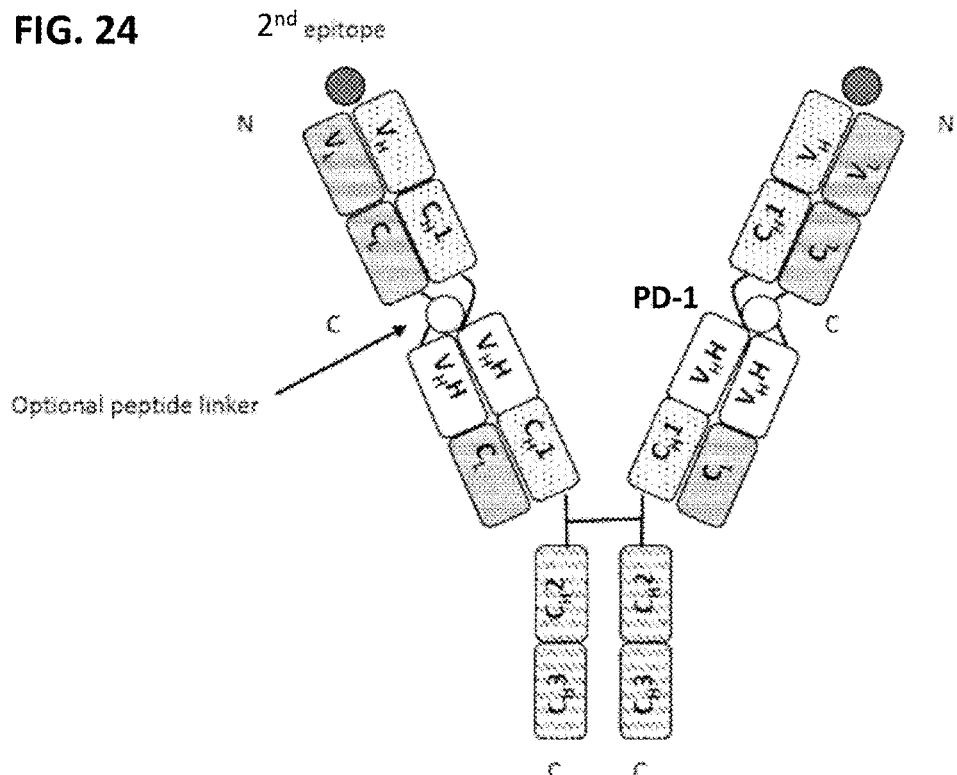
FIG. 24 depicts a schematic structure of an exemplary BABP comprising two identical Fab fragments, two identical Fab-like fragments each comprising two $V_HH$ fragments, and an Fc region. In each Fab-like fragment, the $V_H$ and $V_L$ regions are each replaced by an anti-PD-1 sdAb. Each Fab-like fragment specifically binds a first epitope (PD-1). Each Fab fragment specifically binds a second epitope. For example, the BABP can consist of four polypeptide chains with structures from the N-terminus to the C-terminus as follows: (1) $V_L$—$C_L$—$V_HH$—$C_L$; (2) $V_H$—$C_H1$-$V_HH$—$C_H1$-$C_H2$-$C_H3$; (3) $V_H$—$C_H1$-$V_HH$—$C_H1$-$C_H2$-$C_H3$; and (4) $V_L$—$C_L$—$V_HH$—$C_L$, wherein $V_H$ and $V_L$ of polypeptide chains (1) and (2) forms an antigen binding site that specifically binds a first copy of the second epitope, $V_H$ and $V_L$ of polypeptide chains (3) and (4) forms an antigen binding site that specifically binds a second copy of the second epitope, and each $V_HH$ specifically binds a copy of the first epitope (PD-1). In alternative formats, to expand specificity, the two Fab fragments can specifically bind different epitopes, and/or the Fab-like fragments can specifically bind different epitopes (e.g., different epitopes from PD-1).

In some embodiments, there is provided an anti-PD-1 MABP (e.g., BABP) comprising: (a) a first polypeptide comprising from N-terminus to C-terminus: $V_H$—$C_H1$-anti-PD-1 sdAb1 moiety-$C_H1$-$C_H2$-$C_H3$; and (b) a second polypeptide comprising from N-terminus to C-terminus: $V_L$—$C_L$-anti-PD-1 sdAb2 moiety-$C_L$, wherein $V_H$ and $V_L$ forms an antigen binding site that specifically binds a second epitope (e.g., TIGIT, LAG-3, TIM-3, CTLA-4, PD-1 (such as a second PD-1 epitope different from that recognized by the anti-PD-1 sdAb moiety described herein)), and wherein the anti-PD-1 sdAb1 moiety and the anti-PD-1 sdAb2 moiety each comprises a CDR1 comprising the amino acid sequence of any one of SEQ ID NOs: 37-72, or a variant thereof comprising up to about 3 (such as about any of 1, 2, or 3) amino acid substitutions; a CDR2 comprising the amino acid sequence of any one of SEQ ID NOs: 109-144, or a variant thereof comprising up to about 3 (such as about any of 1, 2, or 3) amino acid substitutions; and a CDR3 comprising the amino acid sequence of any one of SEQ ID NOs: 181-216, or a variant thereof comprising up to about 3 (such as about any of 1, 2, or 3) amino acid substitutions. In some embodiments, the anti-PD-1 sdAb1 moiety and the anti-PD-1 sdAb2 moiety each comprises a CDR1 comprising the amino acid sequence of any one of SEQ ID NOs: 37-72; a CDR2 comprising the amino acid sequence of any one of SEQ ID NOs: 109-144; and a CDR3 comprising the amino acid sequence of any one of SEQ ID NOs: 181-216. In some embodiments, the anti-PD-1 sdAb1 moiety and the anti-PD-1 sdAb2 moiety each comprises a $V_H H$ domain comprising the amino acid sequence of any one of SEQ ID NOs: 289-324. In some embodiments, the anti-PD-1 sdAb1 moiety and the anti-PD-1 sdAb2 moiety are the same. In some embodiments, the anti-PD-1 sdAb1 moiety and the anti-PD-1 sdAb2 moiety are different. In some embodiments, $V_H$ and $V_L$ form an antigen binding site that specifically binds TIGIT. In some embodiments, the $V_H$ and $V_L$ domains are derived from tiragolumab. In some embodiments, the $V_H$ comprises HC-CDR1, HC-CDR2, and HC-CDR3 of the amino acid sequence of SEQ ID NO: 377, and $V_L$ comprises LC-CDR1, LC-CDR2, and LC-CDR3 of the amino acid sequence of SEQ ID NO: 378. In some embodiments, $V_H$ and $V_L$ form an antigen binding site that specifically binds LAG-3. In some embodiments, the $V_H$ and $V_L$ domains are derived from relatlimab. In some embodiments, the $V_H$ comprises HC-CDR1, HC-CDR2, and HC-CDR3 of the amino acid sequence of SEQ ID NO: 379, and $V_L$ comprises LC-CDR1, LC-CDR2, and LC-CDR3 of the amino acid sequence of SEQ ID NO: 380. In some embodiments, $V_H$ and $V_L$ form an antigen binding site that specifically binds TIM-3. In some embodiments, the $V_H$ and $V_L$ domains are derived from MBG453. In some embodiments, the $V_H$ comprises HC-CDR1, HC-CDR2, and HC-CDR3 of the amino acid sequence of SEQ ID NO: 381 and $V_L$ comprises LC-CDR1, LC-CDR2, and LC-CDR3 of the amino acid sequence of SEQ ID NO: 382. In some embodiments, $V_H$ and $V_L$ form an antigen binding site that specifically binds CTLA-4. In some embodiments, the $V_H$ and $V_L$ domains are derived from ipilimumab (e.g., Yervoy®). In some embodiments, the $V_H$ comprises HC-CDR1, HC-CDR2, and HC-CDR3 of the amino acid sequence of SEQ ID NO: 383 and $V_L$ comprises LC-CDR1, LC-CDR2, and LC-CDR3 of the amino acid sequence of SEQ ID NO: 384. In some embodiments, $V_H$ and $V_L$ form an antigen binding site that specifically binds PD-1 (such as a second PD-1 epitope different from that recognized by the anti-PD-1 sdAb moiety described herein). In some embodiments, the $V_H$ and $V_L$ domains are derived from pembrolizumab (e.g., Keytruda®) or nivolumab (e.g., Opdivo®). In some embodiments, the $V_H$ comprises HC-CDR1, HC-CDR2, and HC-CDR3 of the amino acid sequence of SEQ ID NO: 385 and $V_L$ comprises LC-CDR1, LC-CDR2, and LC-CDR3 of the amino acid sequence of SEQ ID NO: 386. In some embodiments, the $C_H 1$ and the anti-PD-1 sdAb1 moiety, and/or $C_L$ and the anti-PD-1 sdAb2 moiety, are fused to each other optionally via a peptide linker, such as a peptide linker comprising the amino acid sequence of any one of SEQ ID NOs: 367-376. In some embodiments, the $C_H 2$ and $C_H 3$ domains are derived from IgG1 Fc, effectorless IgG1 Fc, IgG2 Fc, IgG4 Fc, or IgG4 Fc (S228P), e.g., any of SEQ ID NOs: 363-365. In some embodiments, the anti-PD-1 MABP (e.g., BABP) comprises two identical copies of the first polypeptide and two identical copies of the second polypeptide. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized. In some embodiments, the PD-1 MABP (e.g., BABP) has the structure as shown in FIG. 24.

Figure 25:
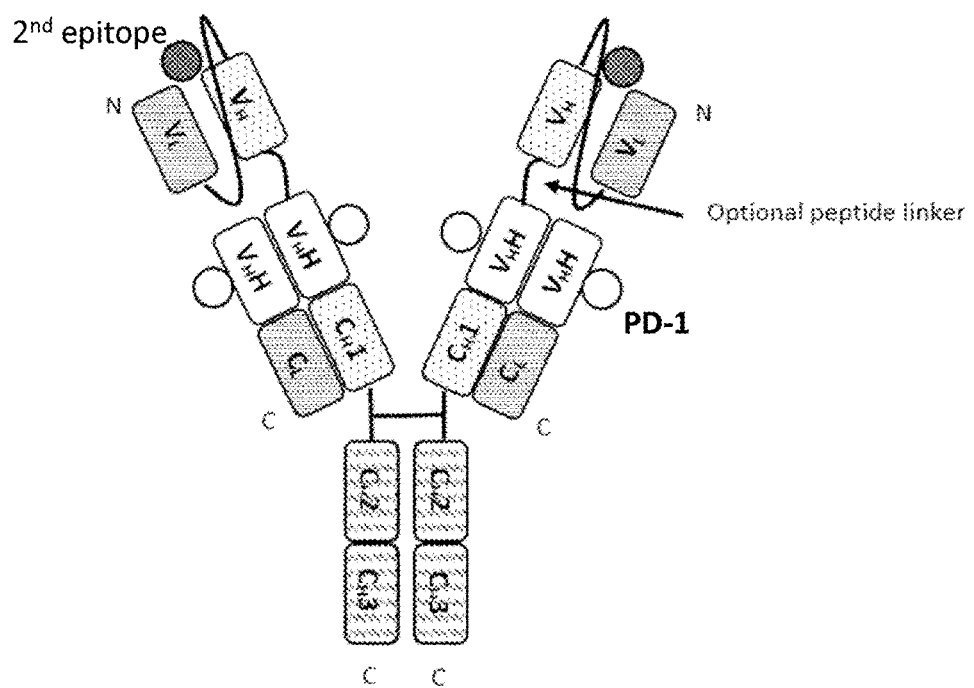
FIG. 25 depicts a schematic structure of an exemplary BABP comprising two identical scFvs, two identical Fab-like fragments each comprising two $V_HH$ fragments, and an Fc region. In each Fab-like fragment, the $V_H$ and $V_L$ regions are each replaced by an anti-PD-1 sdAb. Each Fab-like fragment specifically binds a first epitope (PD-1). Each scFv specifically binds a second epitope. For example, the BABP can consist of four polypeptide chains with structures from the N-terminus to the C-terminus as follows: (1) $V_HH$—$C_L$; (2) $V_L$—$V_H$—$V_HH$—$C_H1$-$C_H2$-$C_H3$; (3) $V_H$—$V_H$—$V_HH$—$C_H1$-$C_H2$-$C_H3$; and (4) $V_HH$—$C_L$, wherein $V_H$ and $V_L$ of polypeptide chains (2) and (3) each forms an scFv that specifically binds a copy of the second epitope, and each $V_HH$ specifically binds a copy of the first epitope (PD-1). In alternative formats, the C-terminus of the scFv may be fused to the N-terminus of the chain in the Fab-like fragment comprising $V_HH$—$C_L$; and/or the scFv domain can comprise from the N-terminus to the C-terminus: $V_H$—$V_L$. Additionally, to expand specificity, the two scFvs can specifically bind different epitopes, and/or the $V_HH$ fragments can specifically bind different epitopes (e.g., different epitopes from PD-1).

In some embodiments, there is provided an anti-PD-1 MABP (e.g., BABP) comprising: (a) a first polypeptide comprising from N-terminus to C-terminus: $V_L$—$V_H$-anti-PD-1 sdAb1 moiety-$C_H 2$-$C_H 3$; and (b) a second polypeptide comprising from N-terminus to C-terminus: anti-PD-1 sdAb2 moiety-$C_L$, wherein the $V_L$ and $V_H$ that forms the scFv specifically binds a second epitope (e.g., TIGIT, LAG-3, TIM-3, CTLA-4, PD-1 (such as a second PD-1 epitope different from that recognized by the anti-PD-1 sdAb moiety described herein)), and wherein the anti-PD-1 sdAb 1 moiety and the anti-PD-1 sdAb2 moiety each comprises a CDR1 comprising the amino acid sequence of any one of SEQ ID NOs: 37-72, or a variant thereof comprising up to about 3 (such as about any of 1, 2, or 3) amino acid substitutions; a CDR2 comprising the amino acid sequence of any one of SEQ ID NOs: 109-144, or a variant thereof comprising up to about 3 (such as about any of 1, 2, or 3) amino acid substitutions; and a CDR3 comprising the amino acid sequence of any one of SEQ ID NOs: 181-216, or a variant thereof comprising up to about 3 (such as about any of 1, 2, or 3) amino acid substitutions. In some embodiments, there is provided an anti-PD-1 MABP (e.g., BABP) comprising: (a) a first polypeptide comprising from N-terminus to C-terminus: $V_H$—$V_L$-anti-PD-1 sdAb1 moiety-$C_H 2$-$C_H 3$; and (b) a second polypeptide comprising from N-terminus to C-terminus: anti-PD-1 sdAb2 moiety-$C_L$, wherein the $V_L$ and $V_H$ that forms the scFv specifically binds a second epitope (e.g., TIGIT, LAG-3, TIM-3, CTLA-4, PD-1 (such as a second PD-1 epitope different from that recognized by the anti-PD-1 sdAb moiety described herein)), and wherein the anti-PD-1 sdAb 1 moiety and the anti-PD-1 sdAb2 moiety each comprises a CDR1 comprising the amino acid sequence of any one of SEQ ID NOs: 37-72, or a variant thereof comprising up to about 3 (such as about any of 1, 2, or 3) amino acid substitutions; a CDR2 comprising the amino acid sequence of any one of SEQ ID NOs: 109-144, or a variant thereof comprising up to about 3 (such as about any of 1, 2, or 3) amino acid substitutions; and a CDR3 comprising the amino acid sequence of any one of SEQ ID NOs: 181-216, or a variant thereof comprising up to about 3 (such as about any of 1, 2, or 3) amino acid substitutions. In some embodiments, the anti-PD-1 sdAb1 moiety and the anti-PD-1 sdAb2 moiety each comprises a CDR1 comprising the amino acid sequence of any one of SEQ ID NOs: 37-72; a CDR2 comprising the amino acid sequence of any one of SEQ ID NOs: 109-144; and a CDR3 comprising the amino acid sequence of any one of SEQ ID NOs: 181-216. In some embodiments, the anti-PD-1 sdAb1 moiety and the anti-PD-1 sdAb2 moiety each comprises a $V_H H$ domain comprising the amino acid sequence of any one of SEQ ID NOs: 289-324. In some embodiments, the anti-PD-1 sdAb 1 moiety and the anti-PD-1 sdAb2 moiety are the same. In some embodiments, the anti-PD-1 sdAb 1 moiety and the anti-PD-1 sdAb2 moiety are different. In some embodiments, the scFv (or the $V_L$ and $V_H$ that form the scFv) specifically binds TIGIT. In some embodiments, the scFv (or the V$_L$ and V$_H$ that form the scFv) is derived from tiragolumab. In some embodiments, the V$_H$ comprises HC-CDR1, HC-CDR2, and HC-CDR3 of the amino acid sequence of SEQ ID NO: 377, and V$_L$ comprises LC-CDR1, LC-CDR2, and LC-CDR3 of the amino acid sequence of SEQ ID NO: 378. In some embodiments, the scFv (or the V$_L$ and V$_H$ that form the scFv) specifically binds LAG-3. In some embodiments, the scFv (or the V$_L$ and V$_H$ that form the scFv) is derived from relatlimab. In some embodiments, the V$_H$ comprises HC-CDR1, HC-CDR2, and HC-CDR3 of the amino acid sequence of SEQ ID NO: 379, and V$_L$ comprises LC-CDR1, LC-CDR2, and LC-CDR3 of the amino acid sequence of SEQ ID NO: 380. In some embodiments, the scFv (or the V$_L$ and V$_H$ that form the scFv) specifically binds TIM-3. In some embodiments, the scFv (or the V$_L$ and V$_H$ that form the scFv) is derived from MBG453. In some embodiments, the V$_H$ comprises HC-CDR1, HC-CDR2, and HC-CDR3 of the amino acid sequence of SEQ ID NO: 381 and V$_L$ comprises LC-CDR1, LC-CDR2, and LC-CDR3 of the amino acid sequence of SEQ ID NO: 382. In some embodiments, the scFv (or the V$_L$ and V$_H$ that form the scFv) specifically binds CTLA-4. In some embodiments, the scFv (or the V$_L$ and V$_H$ that form the scFv) is derived from ipilimumab (e.g., Yervoy®). In some embodiments, the V$_H$ comprises HC-CDR1, HC-CDR2, and HC-CDR3 of the amino acid sequence of SEQ ID NO: 383 and V$_L$ comprises LC-CDR1, LC-CDR2, and LC-CDR3 of the amino acid sequence of SEQ ID NO: 384. In some embodiments, the scFv (or the V$_L$ and V$_H$ that form the scFv) specifically binds PD-1 (such as a second PD-1 epitope different from that recognized by the anti-PD-1 sdAb moiety described herein). In some embodiments, the scFv (or the V$_L$ and V$_H$ that form the scFv) is derived from pembrolizumab (e.g., Keytruda®) or nivolumab (e.g., Opdivo®). In some embodiments, the V$_H$ comprises HC-CDR1, HC-CDR2, and HC-CDR3 of the amino acid sequence of SEQ ID NO: 385 and V$_L$ comprises LC-CDR1, LC-CDR2, and LC-CDR3 of the amino acid sequence of SEQ ID NO: 386. In some embodiments, the V$_H$ and V$_L$ that forms the scFv, and/or the scFv and the anti-PD-1 sdAb1 moiety, are fused to each other optionally via a peptide linker, such as a peptide linker comprising the amino acid sequence of any one of SEQ ID NOs: 367-376. In some embodiments, the C$_H$2 and C$_H$3 domains are derived from IgG1 Fc, effectorless IgG1 Fc, IgG2 Fc, IgG4 Fc, or IgG4 Fc (S228P), e.g., any of SEQ ID NOs: 363-365. In some embodiments, the anti-PD-1 MABP (e.g., BABP) comprises two identical copies of the first polypeptide and two identical copies of the second polypeptide. In some embodiments, the K$_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized. In some embodiments, the PD-1 MABP (e.g., BABP) has the structure as shown in FIG. 25.

In some embodiments, there is also provided an anti-PD-1 MABP (e.g., BABP) comprising an sdAb moiety specifically recognizing PD-1 (hereinafter referred to as "competing anti-PD-1 construct", "competing anti-PD-1 MABP", or "competing anti-PD-1 BABP") that specifically binds to PD-1 competitively with any one of the anti-PD-1 construct described herein (such as anti-PD-1 sdAb moiety, anti-PD-1 sdAb-Fc fusion protein (e.g., HCAb), multispecific (e.g., bispecific) or monospecific anti-PD-1 construct comprising an anti-PD-1 sdAb moiety descried herein, e.g., anti-PD-1/ TIGIT, anti-PD-1/LAG-3, anti-PD-1/TIM-3, anti-PD-1/ CTLA-4, or anti-PD-1/PD-1 constructs (e.g., MABP or BABP) described herein).

(III) Anti-PD-1 Construct Antibody Variants

In some embodiments, amino acid sequence variants of the anti-PD-1 construct (e.g., anti-PD-1 sdAb moiety, anti-PD-1 sdAb-Fc fusion protein (e.g., HCAb), anti-PD-1 MABP/BABP) provided herein are contemplated. For example, it may be desirable to improve the binding affinity and/or other biological properties of the antibody. Amino acid sequence variants of an antibody may be prepared by introducing appropriate modifications into the nucleic acid sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, Deletion and Variants

In some embodiments, antibody variants having one or more amino acid substitutions are provided. Sites of interest for substitutional mutagenesis include the HVRs (or CDRs) and FRs. Conservative substitutions are shown in Table 2 under the heading of "Preferred substitutions." More substantial changes are provided in Table 2 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 2

Amino acid substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; and (6) aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001)). In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In some embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or CDRs. In some embodiments of the variant $V_HH$ sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

b) Glycosylation Variants

In some embodiments, an isolated anti-PD-1 construct provided herein is altered to increase or decrease the extent to which the construct is glycosylated. Addition or deletion of glycosylation sites to an antibody may be conveniently accomplished by altering the amino acid sequence such that one or more glycosylation sites is created or removed.

Where the anti-PD-1 construct comprises an Fc region (e.g., anti-PD-1 sdAb-Fc fusion protein (e.g., HCAb), PD-1×TIGIT MABP, PD-1×LAG-3 MABP, PD-1×TIM-3 MABP, PD-1×CTLA-4 MABP, or PD-1×PD-1 MABP), the carbohydrate attached thereto may be altered. Native antibodies produced by mammalian cells typically comprise a branched, biantennary oligosaccharide that is generally attached by an N-linkage to Asn297 of the $C_H2$ domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an anti-PD-1 construct of the present application may be made in order to create antibody variants with certain improved properties.

In some embodiments, anti-PD-1 construct antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g., complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Patent Application No. US 2003/0157108 A1, Presta, L; and WO 2004/056312 A1, Adams et al., especially at Example 11), and knockout cell lines, such as alpha-1,6-fucosyltransferase gene, *FUT8*, knockout CHO cells (see, e.g., Yamane-Ohnuki et al. Biotech. Bioeng. 87: 614 (2004); Kanda, Y. et al., *Biotechnol. Bioeng.*, 94(4):680-688 (2006); and WO2003/085107).

Anti-PD-1 construct variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In some embodiments, one or more amino acid modifications may be introduced into the Fc region of the anti-PD-1 construct provided herein (e.g., anti-PD-1 sdAb-Fc fusion protein (e.g., HCAb), PD-1×TIGIT MABP, PD-1×LAG-3 MABP, PD-1×TIM-3 MABP, PD-1×CTLA-4 MABP, or PD-1×PD-1 MABP), thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In some embodiments, the present application contemplates an anti-PD-1 construct (e.g., anti-PD-1 sdAb-Fc fusion protein (e.g., HCAb), PD-1×TIGIT MABP, PD-1×LAG-3 MABP, PD-1×TIM-3 MABP, PD-1×CTLA-4 MABP, or PD-1×PD-1 MABP) variant that possesses some but not all effector functions, which make it a desirable candidate for applications in which the half-life of the anti-PD-1 construct in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 2 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and Cyto-Tox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103: 2738-2743 (2004)). FcRn binding and in vivo clearance/half-life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In some embodiments, an anti-PD-1 construct variant comprises an Fc region with one or more amino acid substitutions which improve ADCC, e.g., substitutions at positions 298, 333, and/or 334 of the Fc region (EU numbering of residues).

Anti-PD-1 constructs (such as anti-PD-1 sdAb-Fc fusion protein (e.g., HCAb), anti-PD-1 sdAb fused to a full-length antibody, or anti-PD-1 MABP/BABP described herein) comprising any of the Fc variants described herein, or combinations thereof, are contemplated.

d) Cysteine Engineered Antibody Variants

In some embodiments, it may be desirable to create cysteine engineered anti-PD-1 constructs, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In some embodiments, any one or more of the following residues may be substituted with cysteine: A118 (EU numbering) of the heavy chain; and S400 (EU numbering) of the heavy chain Fc region. Cysteine engineered anti-PD-1 constructs may be generated as described, e.g., in U.S. Pat. No. 7,521,541.

III. Pharmaceutical Compositions

Further provided by the present application are pharmaceutical compositions comprising any one of the anti-PD-1 constructs comprising a sdAb specifically recognizing PD-1 as described herein (such as anti-PD-1 sdAb, anti-PD-1 sdAb-Fc fusion protein (e.g., HCAb), anti-PD-1/TIGIT bispecific antibody (e.g., PD-1×TIGIT BABP), anti-PD-1/LAG-3 bispecific antibody (e.g., PD-1×LAG-3 BABP), anti-PD-1/TIM-3 bispecific antibody (e.g., PD-1×TIM-3 BABP), anti-PD-1/CTLA-4 bispecific antibody (e.g., PD-1×CTLA-4 BABP), or anti-PD-1/PD-1 bispecific antibody (e.g., PD-1×PD-1 BABP)), and optionally a pharmaceutically acceptable carrier. Pharmaceutical compositions can be prepared by mixing an anti-PD-1 construct described herein having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions.

The pharmaceutical composition is preferably to be stable, in which the anti-PD-1 construct comprising anti-PD-1 sdAb moiety described here essentially retains its physical and chemical stability and integrity upon storage. Various analytical techniques for measuring protein stability are available in the art and are reviewed in *Peptide and Protein Drug Delivery*, 247-301, Vincent Lee Ed., Marcel Dekker, Inc., New York, N.Y., Pubs. (1991) and Jones, A. *Adv. Drug Delivery Rev.* 10: 29-90 (1993).

In order for the pharmaceutical compositions to be used for in vivo administration, they must be sterile. The pharmaceutical composition may be rendered sterile by filtration through sterile filtration membranes. The pharmaceutical compositions herein generally are placed into a container having a sterile access port, for example, an intravenous solution bag or vial having a stopper pierceable by a hypodermic injection needle.

The route of administration is in accordance with known and accepted methods, such as by single or multiple bolus or infusion over a long period of time in a suitable manner, e.g., injection or infusion by subcutaneous, intravenous, intraperitoneal, intramuscular, intra-arterial, intralesional or intraarticular routes, topical administration, inhalation or by sustained release or extended-release means. In some embodiments, the pharmaceutical composition is administered locally, such as intratumorally.

The pharmaceutical compositions herein may also contain more than one active compound as necessary for the particular indication being treated, preferably those with complementary activities that do not adversely affect each other. Alternatively, or in addition, the composition may comprise a cytotoxic agent, chemotherapeutic agent, cytokine, immunosuppressive agent, or growth inhibitory agent. Such molecules are suitably present in combination in amounts that are effective for the purpose intended.

IV. Methods of Treating PD-1-Related Diseases

The anti-PD-1 construct comprising an sdAb moiety specifically recognizing PD-1 as described herein (such as anti-PD-1 sdAb, anti-PD-1 sdAb-Fc fusion protein (e.g., HCAb), anti-PD-1/TIGIT bispecific antibody (e.g., PD-1×TIGIT BABP), anti-PD-1/LAG-3 bispecific antibody (e.g., PD-1×LAG-3 BABP), anti-PD-1/TIM-3 bispecific antibody (e.g., PD-1×TIM-3 BABP), anti-PD-1/CTLA-4 bispecific antibody (e.g., PD-1×CTLA-4 BABP), or anti-PD-1/PD-1 bispecific antibody (e.g., PD-1×PD-1 BABP)), and the compositions (such as pharmaceutical compositions) thereof are useful for a variety of applications, such as in diagnosis, molecular assays, and therapy.

One aspect of the invention provides a method of treating a PD-1 related disease or a condition in an individual in need thereof, comprising administering to the individual an effective amount of a pharmaceutical composition comprising the anti-PD-1 construct described herein. In some embodiments, the PD-1 related disease is cancer, such as solid tumor (e.g., colon cancer). In some embodiments, the PD-1-related disease is pathogenic infection, such as viral infection. In some embodiments, the PD-1-related disease is an immune-related disease. In some embodiments, immune-related disease is associated with a T cell dysfunctional disorder. In some embodiments, the T cell dysfunctional disorder is characterized by T cell anergy or decreased ability to secrete cytokines, proliferate or execute cytolytic activity. In some embodiments, the T cell dysfunctional disorder is characterized by T cell exhaustion. In some embodiments, the T cells are CD4+ and CD8+ T cells. In some embodiments, the immune-related disease is selected from the group consisting of unresolved acute infection, chronic infection, and tumor immunity. In some embodiments, an anti-PD-1 construct described herein may be for use in increasing, enhancing, or stimulating an immune response or function in a subject in need thereof. In some embodiments, the PD-1-related disease (e.g., cancer, immune-related disease) is partially resistant to immune checkpoint molecule monoblockade (e.g., partially resistant to anti-TIGIT, LAG-3, TIM-3, CTLA-4, or PD-1 antibody monotherapy treatment).

The present invention contemplates, in part, anti-PD-1 protein constructs (such as anti-PD-1 sdAb, anti-PD-1 sdAb-Fc fusion protein (e.g., HCAb), anti-PD-1/TIGIT bispecific antibody (e.g., PD-1×TIGIT BABP), anti-PD-1/LAG-3 bispecific antibody (e.g., PD-1×LAG-3 BABP), anti-PD-1/TIM-3 bispecific antibody (e.g., PD-1×TIM-3 BABP), anti-PD-1/CTLA-4 bispecific antibody (e.g., PD-1×CTLA-4 BABP), or anti-PD-1/PD-1 bispecific antibody (e.g., PD-1×PD-1 BABP)), nucleic acid molecules or vectors encoding thereof, host cells comprising nucleic acid molecules or vectors encoding thereof, that can be administered either alone or in any combination with another therapy, and in at least some aspects, together with a pharmaceutically acceptable carrier or excipient. In some embodiments, prior to administration of the anti-PD-1 construct, they may be combined with suitable pharmaceutical carriers and excipients that are well known in the art. The compositions prepared according to the disclosure can be used for the treatment or delaying of worsening of cancer, or increasing, enhancing, or stimulating an immune response or function in a subject in need thereof.

In some embodiments, there is provided a method of treating a PD-1-related disease (e.g., cancer, immune-related disease such as that associated with a T cell dysfunctional disorder) comprising administering to the individual an effective amount of a pharmaceutical composition comprising an isolated anti-PD-1 construct comprising an sdAb moiety specifically recognizing PD-1 (such as anti-PD-1 sdAb, anti-PD-1 sdAb-Fc fusion protein (e.g., HCAb), anti-PD-1/TIGIT bispecific antibody (e.g., PD-1×TIGIT BABP), anti-PD-1/LAG-3 bispecific antibody (e.g., PD-1×LAG-3 BABP), anti-PD-1/TIM-3 bispecific antibody (e.g., PD-1×TIM-3 BABP), anti-PD-1/CTLA-4 bispecific antibody (e.g., PD-1×CTLA-4 BABP), or anti-PD-1/PD-1 bispecific antibody (e.g., PD-1×PD-1 BABP)), wherein the anti-PD-1 sdAb moiety comprises a CDR1 comprising the amino acid sequence of any one of SEQ ID NOs: 37-72, or a variant thereof comprising up to about 3 (such as about any of 1, 2, or 3) amino acid substitutions; a CDR2 comprising the amino acid sequence of any one of SEQ ID NOs: 109-144, or a variant thereof comprising up to about 3 (such as about any of 1, 2, or 3) amino acid substitutions; and a CDR3 comprising the amino acid sequence of any one of SEQ ID NOs: 181-216, or a variant thereof comprising up to about 3 (such as about any of 1, 2, or 3) amino acid substitutions; and optionally a pharmaceutical acceptable carrier. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized. In some embodiments, the anti-PD-1 sdAb moiety comprises a $V_HH$ domain comprising the amino acid sequence of any one of SEQ ID NOs: 289-324. In some embodiments, the PD-1-related disease is cancer. In some embodiments, the cancer is a solid tumor (such as colon cancer). In some embodiments, the PD-1-related disease is an immune-related disease. In some embodiments, immune-related disease is associated with a T cell dysfunctional disorder. In some embodiments, the T cell dysfunctional disorder is characterized by T cell anergy or decreased ability to secrete cytokines, proliferate or execute cytolytic activity. In some embodiments, the T cell dysfunctional disorder is characterized by T cell exhaustion. In some embodiments, the immune-related disease is selected from the group consisting of unresolved acute infection, chronic infection, and tumor immunity. In some embodiments, the PD-1-related disease (e.g., cancer, immune-related disease) is partially resistant to immune checkpoint inhibitor monotherapy (e.g., partially resistant to anti-TIGIT, LAG-3, TIM-3, CTLA-4, or PD-1 antibody monotherapy treatment). In some embodiments, the method further comprises administering to the individual an additional therapy (e.g., cancer therapy, such as surgery, radiation, chemotherapy, immunotherapy, hormone therapy, or a combination thereof). In some embodiments, the additional therapy is immunotherapy, e.g., by administering to the individual an effective amount of a second pharmaceutical composition comprising an immunomodulator. In some embodiments, the immunomodulator is an immune checkpoint inhibitor, e.g., anti-TIGIT, anti-LAG-3, anti-TIM-3, anti-CTLA-4, anti-PD-1, or anti-PD-L1 antibody. In some embodiments, the pharmaceutical composition is administered systemically (such as intravenously or intraperitoneally). In some embodiments, the pharmaceutical composition is administered locally (such as intratumorally). In some embodiments, the individual is a human. In some embodiments, the method of treating cancer has one or more of the following biological activities: (1) killing cancer cells (including bystander killing); (2) inhibiting proliferation of cancer cells; (3) inducing immune response in a tumor; (4) reducing tumor size; (5) alleviating one or more symptoms in an individual having cancer; (6) inhibiting tumor metastasis; (7) prolonging survival; (8) prolonging time to cancer progression; and (9) preventing, inhibiting, or reducing the likelihood of the recurrence of a cancer. In some embodiments, the method of killing cancer cells mediated by the pharmaceutical composition described herein can achieve a tumor cell death rate of at least about any of 40%, 50%, 60%, 70%, 80%, 90%, 95%, or more. In some embodiments, the method of killing cancer cells mediated by the pharmaceutical composition described herein can achieve a bystander tumor cell (e.g., uninfected by oncolytic VV encoding the anti-PD-1 construct) death rate of at least about any of 10%, 20%, 30%, 40%, 50%, 60%, 70%, 80%, 90%, 95%, or more. In some embodiments, the method of reducing tumor size mediated by the pharmaceutical composition described herein can reduce at least about 10% (including for example at least about any of 20%, 30%, 40%, 60%, 70%, 80%, 90%, or 100%) of the tumor size. In some embodiments, the method of inhibiting tumor metastasis mediated by the pharmaceutical composition described herein can inhibit at least about 10% (including for example at least about any of 20%, 30%, 40%, 60%, 70%, 80%, 90%, or 100%) of the metastasis. In some embodiments, the method of prolonging survival of an individual (such as a human) mediated by the pharmaceutical composition described herein can prolongs the survival of the individual by at least any of 1, 2, 3, 4, 5, 6, 7, 8, 9, 10, 11, 12, 18, or 24 months. In some embodiments, the method of prolonging time to cancer progression mediated by the pharmaceutical composition described herein can prolongs the time to cancer progression by at least any of 1, 2, 3, 4, 5, 6, 7, 8, 9, 10, 11, or 12 weeks. In some embodiments, the method of treating immune-related disease can increase, enhance, or stimulate an immune response or function in a subject. In some embodiments, the immune response or function is increased, enhanced, and/or stimulated by activating effector cells (e.g., T cells, e.g., CD8+ and/or CD4+ T cells), expanding (increasing) an effector cell population, and/or killing target cells (e.g., target tumor cells) in the subject.

In some embodiments, the method is suitable for treating cancers with aberrant PD-1 or PD-L1/PD-L2 expression, activity and/or signaling include, by way of non-limiting example, hematological cancer and/or solid tumors. Some cancers whose growth may be inhibited using the antibodies of the invention include cancers typically responsive to immunotherapy. Non-limiting examples of cancers for treatment include melanoma (e.g., metastatic malignant melanoma), renal cancer (e.g. clear cell carcinoma), prostate cancer (e.g. hormone refractory prostate adenocarcinoma), breast cancer, colon cancer and lung cancer (e.g. non-small cell lung cancer), gastric cancer, ovarian cancer, and glioblastoma. Additionally, the invention includes refractory or recurrent malignancies whose growth may be inhibited using the antibodies of the invention. Examples of other cancers that may be treated using the antibodies of the invention include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The present invention is also useful for treatment of metastatic cancers, especially metastatic cancers that express PD-1 or PD-L1/PD-L2. In some embodiments, the cancer with aberrant PD-1 or PD-L1/PD-L2 expression, activity and/or signaling is partially resistant to PD-1 mono-blockade (e.g., partially resistant to anti-PD-1 antibody monotherapy treatment), or partially resistant to immune checkpoint inhibitor monotherapy (e.g., anti-TIGIT, LAG-3, TIM-3, CTLA-4 antibody monotherapy treatment). In such case, anti-PD-1 MABPs (e.g., BABPs) such as PD-1×TIGIT, PD-1×LAG-3, PD-1×TIM-3, PD-1× CTLA-4, or PD-1×PD-1 MABPs (e.g., BABPs) described herein can be used.

The methods described herein are suitable for treating a variety of cancers, including both solid cancer and liquid cancer. The methods are applicable to cancers of all stages, including early stage cancer, non-metastatic cancer, primary cancer, advanced cancer, locally advanced cancer, metastatic cancer, or cancer in remission. The methods described herein may be used as a first therapy, second therapy, third therapy, or combination therapy with other types of cancer therapies known in the art, such as chemotherapy, surgery, hormone therapy, radiation, gene therapy, immunotherapy (such as T-cell therapy or administering immunomodulators), bone marrow transplantation, stem cell transplantation, targeted therapy, cryotherapy, ultrasound therapy, photodynamic therapy, radio-frequency ablation or the like, in an adjuvant setting or a neoadjuvant setting (i.e., the method may be carried out before the primary/definitive therapy). In some embodiments, the method is used to treat an individual who has previously been treated. In some embodiments, the cancer has been refractory to prior therapy. In some embodiments, the method is used to treat an individual who has not previously been treated. In some embodiments, the cancer is partially resistant to immune checkpoint inhibitor monotherapy (e.g., partially resistant to anti-TIGIT, LAG-3, TIM-3, CTLA-4, or PD-1 antibody monotherapy treatment).

Thus in some embodiments, there is provided a method of treating cancer (such as carcinoma or adenocarcinoma, such as cancers with aberrant PD-1 expression, activity and/or signaling, and/or cancers with aberrant TIGIT/LAG-3/TIM-3/CTLA-4 expression, activity and/or signaling), comprising administering to the individual an effective amount of a pharmaceutical composition comprising an anti-PD-1 construct (e.g., PD-1×TIGIT, PD-1×LAG-3, PD-1×TIM-3, PD-1×CTLA-4, PD-1×PD-1 MABP or BABP corresponding to the aberrant TIGIT/LAG-3/TIM-3/CTLA-4/PD-1 expression, activity and/or signaling) comprising: (a) a first antigen binding portion comprising an anti-PD-1 sdAb moiety comprising a CDR1 comprising the amino acid sequence of any one of SEQ ID NOs: 37-72, or a variant thereof comprising up to about 3 (such as about any of 1, 2, or 3) amino acid substitutions; a CDR2 comprising the amino acid sequence of any one of SEQ ID NOs: 109-144, or a variant thereof comprising up to about 3 (such as about any of 1, 2, or 3) amino acid substitutions; and a CDR3 comprising the amino acid sequence of any one of SEQ ID NOs: 181-216, or a variant thereof comprising up to about 3 (such as about any of 1, 2, or 3) amino acid substitutions, and (b) a second antigen binding portion comprising a $V_H$ and a $V_L$, wherein the $V_H$ and $V_L$ together form an antigen-binding site that specifically binds a second immune checkpoint molecule (e.g., TIGIT, LAG-3, TIM-3, CTLA-4, PD-1 (such as a second PD-1 epitope different from that recognized by the anti-PD-1 sdAb moiety described herein)), wherein the first antigen binding portion is fused to the second antigen binding portion; and optionally a pharmaceutical acceptable carrier. In some embodiments the second antigen binding portion comprises a heavy chain comprising a $V_H$ and light chain comprising a $V_L$. In some embodiments, the first antigen binding portion is fused to the second antigen binding portion at the N-terminus of the heavy chain, the N-terminus of the light chain, the N-terminus of the Fc region, the C-terminus of the heavy chain, or the C-terminus of the light chain. In some embodiments, the second antigen binding portion comprises a full-length 4-chain antibody or antigen binding fragment thereof (e.g., Fab or scFv). In some embodiments, the first antigen binding portion is fused to the C-terminus of the second antigen binding portion comprising a Fab or an scFv. In some embodiments, the first and second antigen binding portions are fused optionally via a peptide linker, such as a peptide linker comprising the amino acid sequence of any one of SEQ ID NOs: 367-376. In some embodiments, the second antigen binding portion comprises an Fc fragment (e.g. derived from IgG4, IgG2, or IgG1). In some embodiments, the Fc fragment of comprises the amino acid sequence of any one of SEQ ID NOs: 363-365. In some embodiments, there is provided a method of treating a cancer (such as carcinoma or adenocarcinoma, such as cancers with aberrant PD-1 expression, activity and/or signaling, and/or cancers with aberrant TIGIT/LAG-3/TIM-3/CTLA-4 expression, activity and/or signaling), comprising administering to the individual an effective amount of a pharmaceutical composition comprising an isolated anti-PD-1 construct comprising an sdAb moiety specifically recognizing PD-1 fused to a full-length antibody (e.g., antibody specifically recognizing TIGIT, LAG-3, TIM-3, CTLA-4, or PD-1 (such as a second PD-1 epitope different from that recognized by the anti-PD-1 sdAb moiety described herein), corresponding to the aberrant TIGIT/LAG-3/TIM-3/CTLA-4/PD-1 expression), wherein the anti-PD-1 sdAb moiety comprises a CDR1 comprising the amino acid sequence of any one of SEQ ID NOs: 37-72, or a variant thereof comprising up to about 3 (such as about any of 1, 2, or 3) amino acid substitutions; a CDR2 comprising the amino acid sequence of any one of SEQ ID NOs: 109-144, or a variant thereof comprising up to about 3 (such as about any of 1, 2, or 3) amino acid substitutions; and a CDR3 comprising the amino acid sequence of any one of SEQ ID NOs: 181-216, or a variant thereof comprising up to about 3 (such as about any of 1, 2, or 3) amino acid substitutions; and optionally a pharmaceutical acceptable carrier. In some embodiments, the $V_H$ and $V_L$ domains are derived from tiragolumab. In some embodiments, the $V_H$ comprises HC-CDR1, HC-CDR2, and HC-CDR3 of the amino acid sequence of SEQ ID NO: 377, and $V_L$ comprises LC-CDR1, LC-CDR2, and LC-CDR3 of the amino acid sequence of SEQ ID NO: 378. In some embodiments, the full-length antibody is an anti-TIGIT antibody comprising a heavy chain comprising the amino acid sequence of SEQ ID NO: 377, and a light chain comprising the amino acid sequence of SEQ ID NO: 378. In some embodiments, the $V_H$ and $V_L$ domains are derived from relatlimab. In some embodiments, the $V_H$ comprises HC-CDR1, HC-CDR2, and HC-CDR3 of the amino acid sequence of SEQ ID NO: 379, and $V_L$ comprises LC-CDR1, LC-CDR2, and LC-CDR3 of the amino acid sequence of SEQ ID NO: 380. In some embodiments, the full-length antibody is an anti-LAG-3 antibody comprising a heavy chain comprising the amino acid sequence of SEQ ID NO: 379, and a light chain comprising the amino acid sequence of SEQ ID NO: 380. In some embodiments, the $V_H$ and $V_L$ domains are derived from MBG453. In some embodiments, the $V_H$ comprises HC-CDR1, HC-CDR2, and HC-CDR3 of the amino acid sequence of SEQ ID NO: 381, and $V_L$ comprises LC-CDR1, LC-CDR2, and LC-CDR3 of the amino acid sequence of SEQ ID NO: 382. In some embodiments, the full-length antibody is an anti-TIM-3 antibody comprising a heavy chain comprising the amino acid sequence of SEQ ID NO: 381, and a light chain comprising the amino acid sequence of SEQ ID NO: 382. In some embodiments, the $V_H$ and $V_L$ domains are derived from ipilimumab (e.g., Yervoy®). In some embodiments, the $V_H$ comprises HC-CDR1, HC-CDR2, and HC-CDR3 of the amino acid sequence of SEQ ID NO: 383, and $V_L$ comprises LC-CDR1, LC-CDR2, and LC-CDR3 of the amino acid sequence of SEQ ID NO: 384. In some embodiments, the full-length antibody is an anti-CTLA-4 antibody comprising a heavy chain comprising the amino acid sequence of SEQ ID NO: 383, and a light chain comprising the amino acid sequence of SEQ ID NO: 384. In some embodiments, the $V_H$ and $V_L$ domains are derived from pembrolizumab (e.g., Keytruda®) or nivolumab (e.g., Opdivo®). In some embodiments, the $V_H$ comprises HC-CDR1, HC-CDR2, and HC-CDR3 of the amino acid sequence of SEQ ID NO: 385, and $V_L$ comprises LC-CDR1, LC-CDR2, and LC-CDR3 of the amino acid sequence of SEQ ID NO: 386. In some embodiments, the full-length antibody is an anti-PD-1 antibody comprising a heavy chain comprising the amino acid sequence of SEQ ID NO: 385, and a light chain comprising the amino acid sequence of SEQ ID NO: 386. In some embodiments, the $K_d$ of the binding between the anti-PD-1 sdAb moiety and PD-1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-1 sdAb moiety is camelid, chimeric, human, partially humanized, or fully humanized. In some embodiments, the N-terminus of the anti-PD-1 sdAb moiety is fused to the C-terminus of at least one of the heavy chains of the full-length antibody. In some embodiments, the C-terminus of the anti-PD-1 sdAb moiety is fused to the N-terminus of at least one of the heavy chains of the full-length antibody. In some embodiments, the N-terminus of the anti-PD-1 sdAb moiety is fused to the C-terminus of at least one of the light chains of the full-length antibody. In some embodiments, the C-terminus of the anti-PD-1 sdAb moiety is fused to the N-terminus of at least one of the light chains of the full-length antibody. In some embodiments, the anti-PD-1 construct comprises four anti-PD-1 sdAb moieties, wherein the C-terminus of each anti-PD-1 sdAb moiety is fused to the N-terminus of each chain of the full-length antibody. In some embodiments, the anti-PD-1 construct comprises four anti-PD-1 sdAb moieties, wherein two anti-PD-1 sdAb moieties are fused together, which is further fused to the N-terminus of each heavy chain of the full-length antibody. In some embodiments, the anti-PD-1 sdAb moiety comprises a $V_HH$ domain comprising the amino acid sequence of any one of SEQ ID NO: 289-324. In some embodiments, the anti-PD-1 sdAb moiety and the full length antibody are optionally connected by a peptide linker (such as peptide linker comprising the amino acid sequence of any one of SEQ ID NOs: 367-376). In some embodiments, the cancer is a solid tumor (such as colon cancer). In some embodiments, the pharmaceutical composition is administered systemically (such as intravenously or intraperitoneally). In some embodiments, the pharmaceutical composition is administered locally (such as intratumorally). In some embodiments, the method further comprises administering to the individual an additional cancer therapy (such as surgery, radiation, chemotherapy, immunotherapy, hormone therapy, or a combination thereof). In some embodiments, the individual is a human. In some embodiments, the cancer is partially resistant to immune checkpoint molecule monoblockade (e.g., partially resistant to anti-PD-1 antibody, anti-TIGIT antibody, anti-LAG-3 antibody, anti-TIM-3 antibody, or anti-CTLA-4 antibody monotherapy treatment).

Dosages and desired drug concentrations of pharmaceutical compositions of the present application may vary depending on the particular use envisioned. The determination of the appropriate dosage or route of administration is well within the skill of an ordinary artisan Animal experiments provide reliable guidance for the determination of effective doses for human therapy. Interspecies scaling of effective doses can be performed following the principles laid down by Mordenti, J. and Chappell, W. "The Use of Interspecies Scaling in Toxicokinetics," In *Toxicokinetics and New Drug Development*, Yacobi et al., Eds, Pergamon Press, New York 1989, pp. 42-46.

The pharmaceutical compositions of the present application, including but not limited to reconstituted and liquid formulations, are administered to an individual in need of treatment with the anti-PD-1 construct described herein (such as anti-PD-1 sdAb, anti-PD-1 sdAb-Fc fusion protein (e.g., HCAb), anti-PD-1/TIGIT bispecific antibody (e.g., PD-1×TIGIT BABP), anti-PD-1/LAG-3 bispecific antibody (e.g., PD-1×LAG-3 BABP), anti-PD-1/TIM-3 bispecific antibody (e.g., PD-1×TIM-3 BABP), anti-PD-1/CTLA-4 bispecific antibody (e.g., PD-1×CTLA-4 BABP), or anti-PD-1/PD-1 bispecific antibody (e.g., PD-1×PD-1 BABP)), preferably a human, in accord with known methods, such as intravenous administration as a bolus or by continuous infusion over a period of time, by intramuscular, intraperitoneal, intracerobrospinal, subcutaneous, intravenous (i.v.), intra-articular, intrasynovial, intrathecal, oral, topical, or inhalation routes. A reconstituted formulation can be prepared by dissolving a lyophilized anti-PD-1 construct described herein in a diluent such that the protein is dispersed throughout. Exemplary pharmaceutically acceptable (safe and non-toxic for administration to a human) diluents suitable for use in the present application include, but are not limited to, sterile water, bacteriostatic water for injection (BWFI), a pH buffered solution (e.g. phosphate-buffered saline), sterile saline solution, Ringer's solution or dextrose solution, or aqueous solutions of salts and/or buffers.

In some embodiments, the pharmaceutical compositions are administered to the individual by subcutaneous (i.e. beneath the skin) administration. For such purposes, the pharmaceutical compositions may be injected using a syringe. However, other devices for administration of the pharmaceutical compositions are available such as injection devices; injector pens; auto-injector devices, needleless devices; and subcutaneous patch delivery systems. In some embodiments, the pharmaceutical compositions are administered to the individual intravenously. In some embodiments, the pharmaceutical composition is administered to an individual by infusion, such as intravenous infusion. Infusion techniques for immunotherapy are known in the art (see, e.g., Rosenberg et al., New Eng. J. of Med. 319: 1676 (1988)).

V. Methods of Preparation

The anti-PD-1 construct described herein (such as anti-PD-1 sdAb, anti-PD-1 sdAb-Fc fusion protein (e.g., HCAb), anti-PD-1/TIGIT bispecific antibody (e.g., PD-1×TIGIT BABP), anti-PD-1/LAG-3 bispecific antibody (e.g., PD-1×LAG-3 BABP), anti-PD-1/TIM-3 bispecific antibody (e.g., PD-1×TIM-3 BABP), anti-PD-1/CTLA-4 bispecific antibody (e.g., PD-1×CTLA-4 BABP), or anti-PD-1/PD-1 bispecific antibody (e.g., PD-1×PD-1 BABP) may be prepared using any methods known in the art or as described herein. Also see Examples 1-3. In some embodiments, there is provided a method of producing an anti-PD-1 construct, comprising: (a) culturing a host cell comprising an isolated nucleic acid or vector encoding the anti-PD-1 construct described herein under conditions effective to express the encoded anti-PD-1 construct; and (b) obtaining the expressed anti-PD-1 construct from said host cell. In some embodiments, the method of step (a) further comprises producing a host cell comprising the isolated nucleic acid or vector encoding the anti-PD-1 construct described herein.

Methods of preparing sdAbs have been described. See, for example, Els Pardon et al., *Nature Protocol*, 2014; 9(3): 674. sdAbs (such as $V_HHs$) may be obtained using methods known in the art such as by immunizing a *Camelid* species (such as camel or llama) and obtaining hybridomas therefrom, or by cloning a library of single-domain antibodies using molecular biology techniques known in the art and subsequent selection by ELISA with individual clones of unselected libraries or by using phage display.

For recombinant production of the sdAbs, the nucleic acids encoding the single-domain antibodies are isolated and inserted into a replicable vector for further cloning (amplification of the DNA) or for expression. DNA encoding the single-domain antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, preferred host cells are of either prokaryotic or eukaryotic (generally mammalian) origin. In some embodiments, the isolated nucleic acid encoding the anti-PD-1 construct described herein comprises the nucleic acid sequence of any one of SEQ ID NOs: 253-288.

I. Recombinant Production in Eukaryotic Cells

For eukaryotic expression, the vector components generally include, but are not limited to, one or more of the following, a signal sequence, an origin of replication, one or more marker genes, and enhancer element, a promoter, and a transcription termination sequence.

a) Signal Sequence Component

A vector for use in a eukaryotic host may also an insert that encodes a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. In mammalian cell expression, mammalian signal sequences as well as viral secretory leaders, for example, the herpes simplex gD signal, are available.

The DNA for such precursor region is ligated in reading frame to DNA encoding the antibodies of the present application.

b) Origin of Replication

Generally, the origin of replication component is not needed for mammalian expression vectors (the SV40 origin may typically be used only because it contains the early promoter).

c) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up nucleic acid encoding the antibodies of the present application, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with the polypeptide encoding-DNA sequences, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

d) Promoter Component

Expression and cloning vectors usually contain a promoter that is recognized by the host organism and is operably linked to the nucleic acid encoding the desired polypeptide sequences. Virtually all eukaryotic genes have an AT-rich region located approximately 25 to 30 based upstream from the site where transcription is initiated. Another sequence found 70 to 80 bases upstream from the start of the transcription of many genes is a CNCAAT region where N may be any nucleotide. At the 3' end of most eukaryotic is an AATAAA sequence that may be the signal for addition of the poly A tail to the 3' end of the coding sequence. All of these sequences may be inserted into eukaryotic expression vectors.

Other promoters suitable for use with prokaryotic hosts include the phoA promoter, -lactamase and lactose promoter systems, alkaline phosphatase promoter, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the antibodies.

Polypeptide transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., *Nature* 297:598-601 (1982) on expression of human-interferon cDNA in mouse cells under the control of a thymidine kinase promoter from herpes simplex virus. Alternatively, the Rous Sarcoma Virus long terminal repeat can be used as the promoter.

e) Enhancer Element Component

Transcription of a DNA encoding the antibodies of the present application by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (100-270 bp), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the polypeptide encoding sequence, but is preferably located at a site 5' from the promoter.

f) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the polypeptide-encoding mRNA. One useful transcription termination component is the bovine growth hormone polyadenylation region. See WO94/11026 and the expression vector disclosed therein.

g) Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/−DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for antibodies production and cultured in conventional nutrient media modified as appropriate for inducing promoters, selecting transformants, or amplifying the genes encoding the desired sequences.

h) Culturing the Host Cells

The host cells used to produce the antibodies of the present application may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

i) Protein Purification

When using recombinant techniques, the antibodies can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., Bio/Technology 10:163-167 (1992) describe a procedure for isolating antibodies which are secreted to the periplasmic space of E. coli. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The protein composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify the antibodies that are based on human immunoglobulins containing 1, 2, or 4 heavy chains (Lindmark et al., J. Immunol. Meth. 62:1-13 (1983)). Protein G is recommended for all mouse isotypes and for human 3 (Guss et al., EMBO J. 5:15671575 (1986)). The matrix to which the affinity ligand is attached is most often agarose, but other matrices are available. Mechanically stable matrices such as controlled pore glass or poly(styrene-divinyl)benzene allow for faster flow rates and shorter processing times than can be achieved with agarose. Where the antibody comprises a $C_H3$ domain, the Bakerbond ABXTMresin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

2. Polyclonal Antibodies

Polyclonal antibodies are generally raised in animals by multiple subcutaneous (s.c.) or intraperitoneal (i.p.) injections of the relevant antigen and an adjuvant. It may be useful to conjugate the relevant antigen to a protein that is immunogenic in the species to be immunized, e.g., keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are independently lower alkyl groups. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The animals are immunized against the antigen, immunogenic conjugates, or derivatives by combining, e.g., 100 μg or 5 μg or the protein or conjugate (for rabbits or mice, respectively) with 3 volumes of Freund's complete adjuvant and injecting the solution intradermally at multiple sites. One month later, the animals are boosted with 1/5 to 1/10 the original amount of peptide or conjugate in Freund's complete adjuvant by subcutaneous injection at multiple sites. Seven to fourteen days later, the animals are bled and the serum is assayed for antibody titer. Animals are boosted until the titer plateaus. Conjugates also can be made in recombinant cell culture as protein fusions. Also, aggregating agents such as alum are suitable to enhance the immune response. Also see Example 1 for immunization in Camels.

VI. Articles of Manufacture and Kits

Further provided are kits and articles of manufacture comprising any of the isolated anti-PD-1 constructs (such as anti-PD-1 sdAb, anti-PD-1 sdAb-Fc fusion protein (e.g., HCAb), anti-PD-1/TIGIT bispecific antibody (e.g., PD-1× TIGIT BABP), anti-PD-1/LAG-3 bispecific antibody (e.g., PD-1×LAG-3 BABP), anti-PD-1/TIM-3 bispecific antibody (e.g., PD-1×TIM-3 BABP), anti-PD-1/CTLA-4 bispecific antibody (e.g., PD-1×CTLA-4 BABP), or anti-PD-1/PD-1 bispecific antibody (e.g., PD-1×PD-1 BABP)), isolated nucleic acids or vectors encoding thereof, or isolated host cells comprising the isolated nucleic acids or vectors encoding the anti-PD-1 constructs described herein. In some embodiments, a kit is provided which comprises any one of the pharmaceutical compositions described herein and preferably provides instructions for its use.

The kits of the present application are in suitable packaging. Suitable packaging includes, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The kits may include multiple unit doses of the pharmaceutical composition and instructions for use, packaged in quantities sufficient for storage and use in pharmacies, for example, hospital pharmacies and compounding pharmacies.

EXAMPLES

The examples below are intended to be purely exemplary of the invention and should therefore not be considered to limit the invention in any way. The following examples and detailed description are offered by way of illustration and not by way of limitation.

Example 1: Generation of Anti-PD-1 sdAbs and Anti-PD-1 HCAbs

Immunization

Two Camels were immunized with recombinant PD-1 extracellular domain (ECD) protein (Accession #NP_005009.2, SEQ ID NO: 362) under all current animal welfare regulations. For immunization, the antigen was formulated as an emulsion with CFA (primary immunization) or IFA (boost immunization). The antigen was administered by double-spot injections intramuscularly at the neck. Each animal received two injections of the emulsion, containing 100 μg of PD-1 ECD and 4 subsequent injections containing 50 μg of antigen at weekly intervals. At different time points during immunization, 10 ml blood samples were collected from the animal and sera were prepared. The induction of an antigen specific humoral immune response was verified using the serum samples in an ELISA-based experiment with immobilized PD-1 ECD protein (FIGS. 1A-1B and FIGS. 2A-2B). Five days after the last immunization, a blood sample of 200 ml was collected. Peripheral blood lymphocytes (PBLs), as the genetic source of the camelid heavy chain immunoglobulins (HCAbs), were isolated from the 200 ml blood sample using a Ficoll-Paque gradient (Amersham Biosciences), yielding $5 \times 10^8$ PBLs. The maximal diversity of antibodies is expected to be equal to the number of sampled B-lymphocytes, which is about 20% of the number of PBLs ($1 \times 10^8$). The fraction of heavy-chain antibodies in camel is up to 20% of the number of B-lymphocytes. Therefore, the maximal diversity of HCAbs in the 200 ml blood sample is calculated as $2 \times 10^7$ different molecules.

Library Construction and Binders Selection

RNA extracted from PBLs and lymph node was used as starting material for RT-PCR to amplify sdAb encoding gene fragments. These fragments were cloned into an in-house phagemid vector. The vector encodes a C-terminal His6 tag in frame with the sdAb coding sequence. The library size is more than $1 \times 10^9$. The library phage was prepared according to a standard protocol and stored after filter sterilization at 4° C. for further use.

Selections were carried out with the above libraries using solid-phase panning as well as cell-based panning Colonies were picked and grown in 96 deep well plates (1 ml volume) and induced by adding IPTG and 0.1% Triton for sdAb expression in the supernatant. The supernatant was analyzed for their ability to bind to PD-1 ECD protein (by ELISA) and PD-1 stable cell line (by FACS). The positive binders were sequenced and the unique clones were selected for further characterization (Table 3).

SdAb Production

The selected His6-tagged sdAbs were purified from periplasmic extracts by AKTA. The NTA resin was processed according to the manufacturer's instructions. Periplasmic extracts prepared were incubated with the resin for 30 min at RT on a rotator. The resin was washed with PBS and transferred to a column. The packed resin was washed with 15 mM Imidazole. SdAbs were eluted from the column using 150 mM Imidazole. The eluted fractions were analyzed by spotting on Hybond Membrane and visualized with Ponceau. Fractions containing protein were pooled and dialyzed against PBS. Dialyzed protein was collected, filter sterilized, concentration determined and stored at −20° C.

To determine the purity, protein samples were analyzed on a 12% SDS-PAGE gel. 10 μl Laemmli sample buffer was added to 10 μl (2 μg) purified protein, then the sample was heated for 10 minutes at 95° C., cooled and loaded onto a 12% SDS-PAGE gel. The gel was processed according to general procedures and stained with Coomassie Brilliant Blue (CBB). The purification data was summarized in FIG. 28.

Affinity Measurements of sdAbs by Surface Plasmon Resonance (SPR)

Figure 3A:
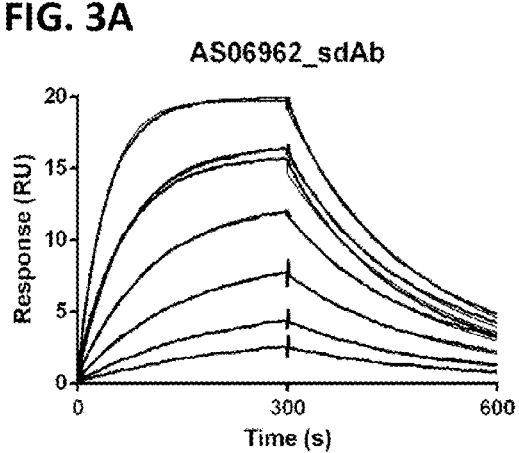
FIGS. 3A-3F depict the affinities of selected six camelid sdAbs measured by surface plasma resonance. The $k_{on}$, $k_{off}$ and $K_D$ values are summarized in FIG. 3G.
Figure 3B:
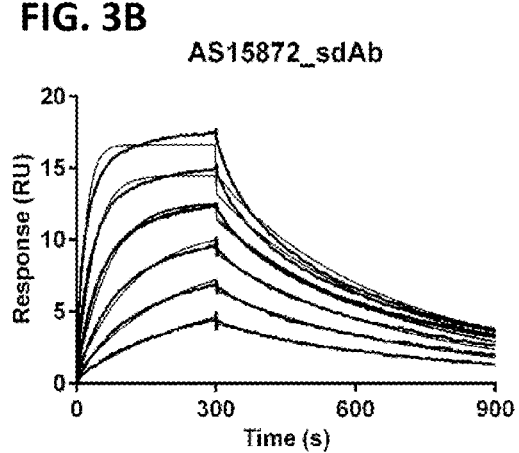
Figure 3C:
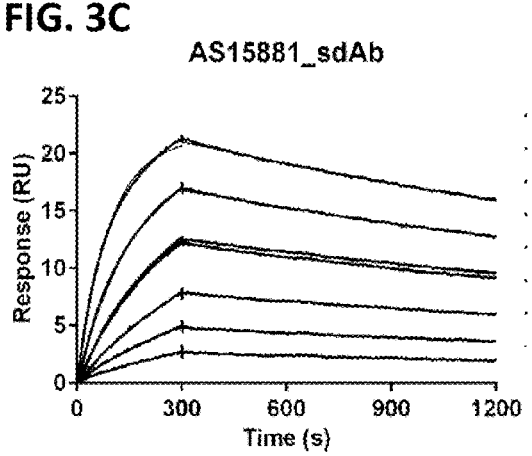
Figure 3D:
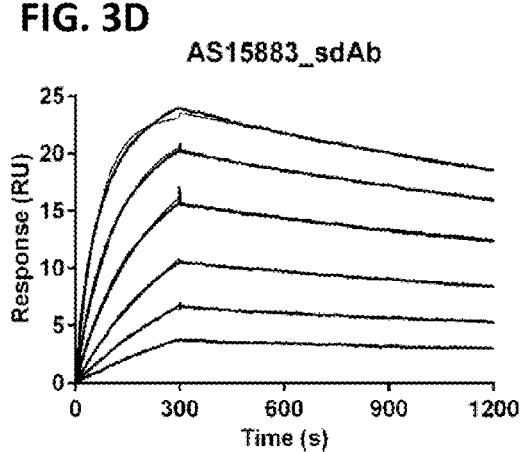
Figure 3E:
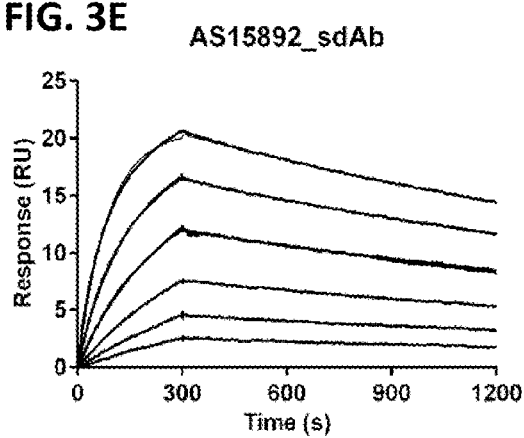
Figure 3F:
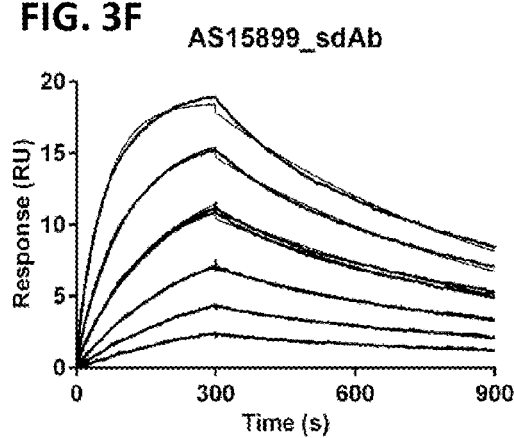
Figures 3G, 4A, 4B:
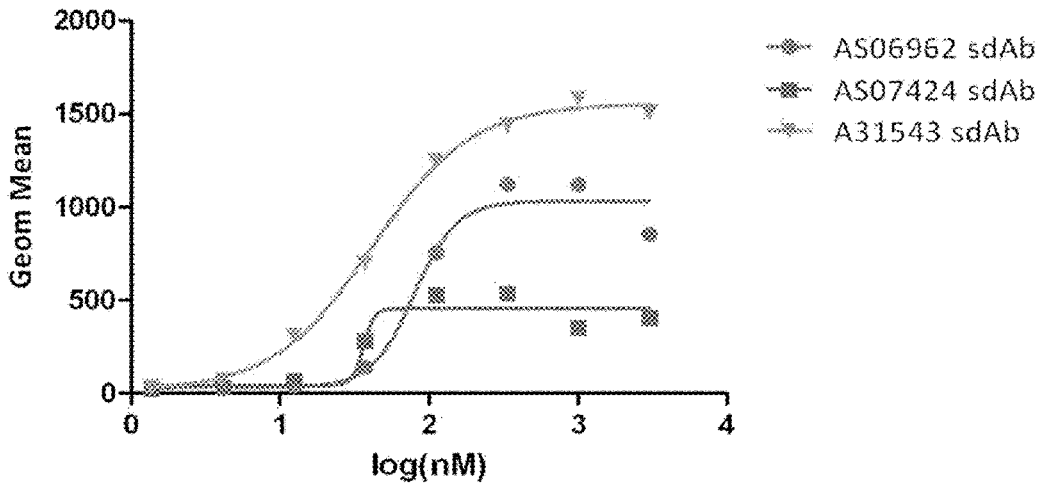
FIGS. 4A-4B depict binding abilities of generated sdAbs to human PD-1 expressing cells.

Binding kinetics of sdAbs were determined by SPR on a BIAcore T200 instrument (GE Healthcare). Briefly, PD-1 ECD was amine-coupled to a CM5 sensor chip at a density of about 50 RU. 5 concentrations of the sdAbs with 3-fold serial dilutions (starting from 2 nM to 162 nM) were injected over the coated sensor chip. Flow rate was 30 μl/min in all experiments. Association phase was 5 min, and dissociation phase was 5, 10 or 15 min. The chip was regenerated using Glycine/HCl pH 1.5. Binding curves at different concentrations of sdAbs were fitted to a 1:1 Langmuir binding model to calculate the kinetic parameters $k_{on}$, $k_{off}$ and $K_D$ (see FIGS. 3A-3F for sdAb affinity data). Sensorgram processing and data analysis was performed with Biacore T200 Evaluation Software (GE Healthcare). The affinity parameters were summarized in FIG. 3G.

Binding to PD-1 Expressed on Cells by FACS Analysis

Binding of sdAb to PD-1 expressed on CHO cells is determined using a fluorescence-activated cell sorting (FACS)-based assay. CHO cells expressing human PD-1 were dissociated from adherent culture flasks and mixed with varying concentrations of antibodies (both in a 96-well plate). The mixture was equilibrated for 30 minutes at room temperature, washed three times with FACS buffer (PBS containing 1% BSA). Secondary antibody fluorescein isothiocyanate (FITC)-conjugated anti-human kappa antibody (Jackson ImmunoResearch) was then added and incubated for 15 minutes at room temperature. Cells were washed again with FACS buffer and analyzed by flow cytometry. Data were analyzed with Prism (GraphPad Software, San Diego, Calif.) using non-linear regression, and $EC_{50}$ values were calculated. As can be seen from FIGS. 4A-4B, the FACS binding assays demonstrated that A31543, AS06962, and AS07424 sdAbs can bind to PD-1 at low concentrations (1-10 µg/ml).

Inhibition of Ligand Binding by FACS Analysis

Figures 5A, 5B, 6A:
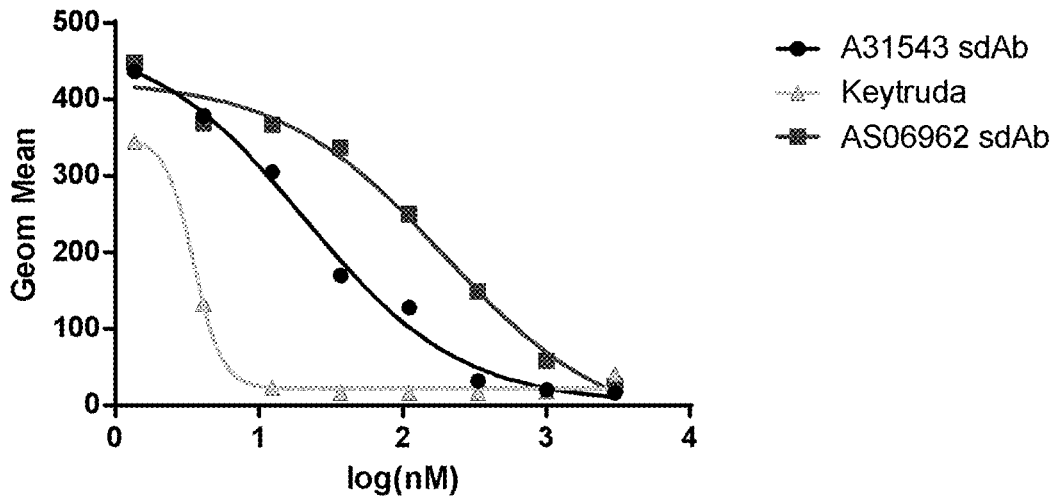
FIGS. 5A-5B depict ligand competition activity evaluation of generated sdAbs measured by flow cytometry.
Figure 6B:
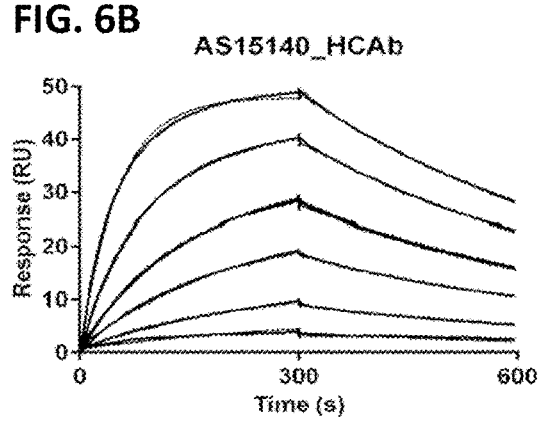
Figure 6C:
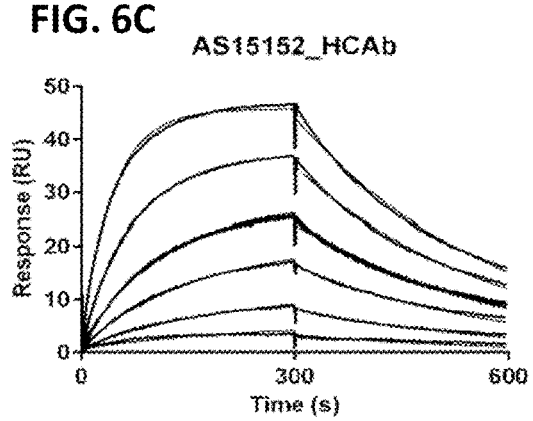
Figure 6D:
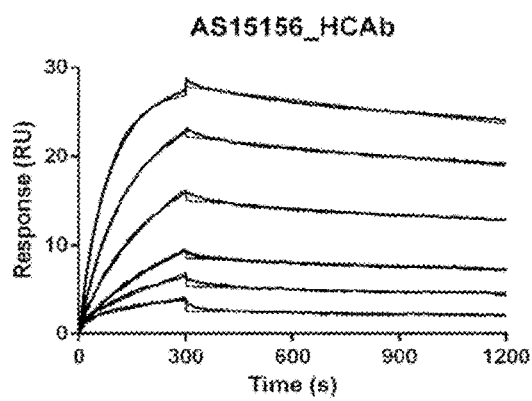
Figure 6E:
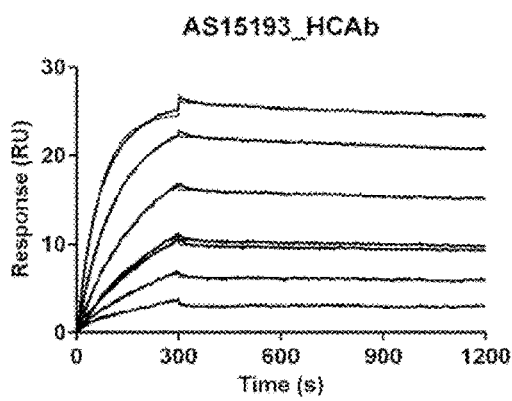
Figure 6F:
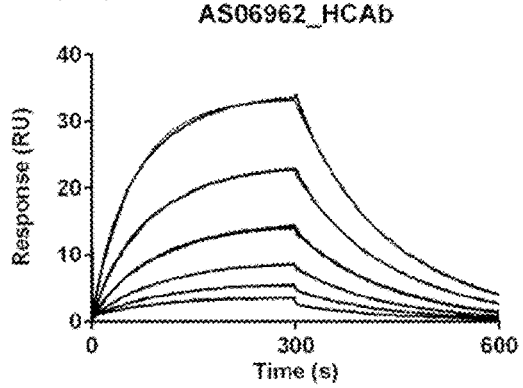
Figure 6G:
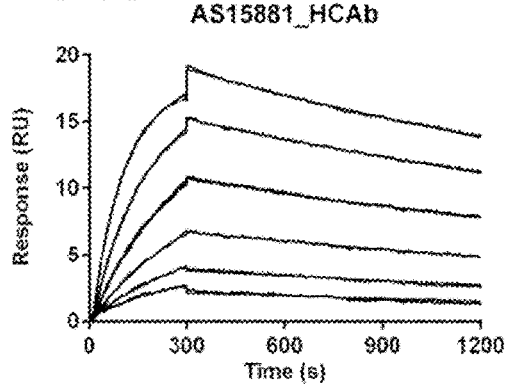

Blockade of ligand binding was studied using flow cytometry. For anti-PD-1 sdAbs evaluation, CHO cells expressing human PD-1 were dissociated from adherent culture flasks and mixed with varying concentrations of antibodies and a constant concentration of biotin-labeled human PD-L1/Fc or human PD-L2/Fc protein (both in a 96-well plate). Keytruda® was used as an anti-PD-1 antibody positive control. The mixture was equilibrated for 30 minutes at room temperature, washed three times with FACS buffer (PBS containing 1% BSA). PE/Cy5 Streptavidin secondary antibody was then added and incubated for 15 minutes at room temperature. Cells were washed again with FACS buffer and analyzed by flow cytometry (FIG. 5A). Data were analyzed with Prism (GraphPad Software, San Diego, Calif.) using non-linear regression, and $IC_{50}$ values were calculated (FIG. 5B).

HCAb Construction, Production and Characterization

SdAbs with functional activities and slow off-rate from the above studies were selected for HCAb construction and production. DNA sequences of selected sdAbs were fused with DNA sequences of human IgG4 Fc (S228P) to make HCAb constructs. The HCAb constructs were transfected into CHO cell for HCAb expression. Secreted HCAbs in the condition medium were purified by protein A column. The purification data was summarized in FIG. 29.

Affinity Measurements of HCAbs by Surface Plasmon Resonance (SPR)

Binding kinetics of anti-PD-1 camelid HCAbs were determined using a SPR biosensor, Biacore T200 (GE Healthcare). Antibody was immobilized on the sensor chip through Fc capture method at a density of about 50 RU. 5 concentrations of human PD-1-His antigen with 3-fold serial dilutions (starting from 3 nM to 243 nM) were injected over the coated sensor chip. Flow rate was 30 µl/min in all experiments. The chip was regenerated using Glycine/HCl pH 1.5. Binding curves at different concentrations of PD-1-His antigen were fitted to a 1:1 Langmuir binding model to calculate the kinetic parameters $k_{on}$, $k_{off}$ and $K_D$ (see FIGS. 6B-6K for HCAb affinity data). Keytruda® was used as an experimental control (FIG. 6L). Sensorgram processing and data analysis was performed with Biacore T200 Evaluation Software (GE Healthcare). The affinity parameters were summarized in FIG. 6A.

As can be seen in FIGS. 6A-6L, the selected HCAbs (AS15140_HCAb, AS15152_HCAb, AS15156_HCAb, AS15193_HCAb, AS06962_HCAb, AS15881_HCAb, AS15883_HCAb, AS15892_HCAb, AS15899_HCAb, and AS25170_HCAb) show comparable binding affinities to Keytruda®.

Figure 7A:
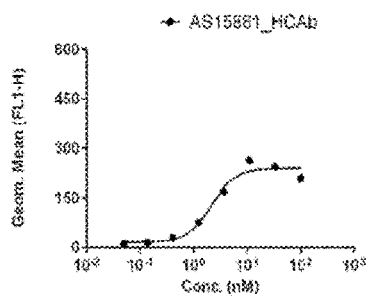
Figure 7B:
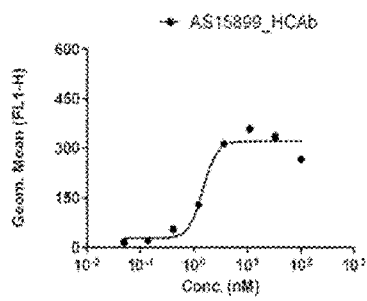
Figure 7C:
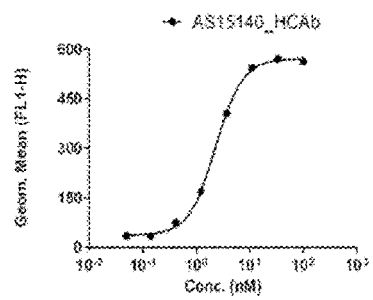
Figure 7D:
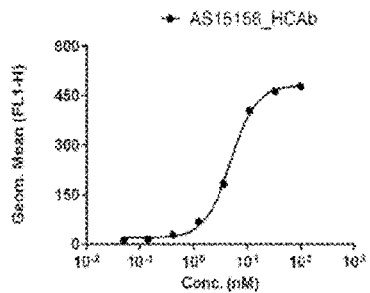
Figure 7E:
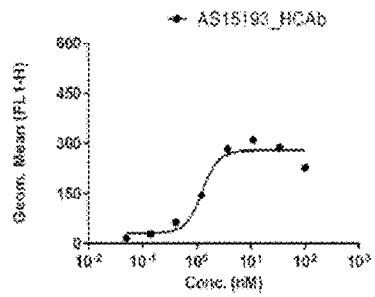
Figure 7F:
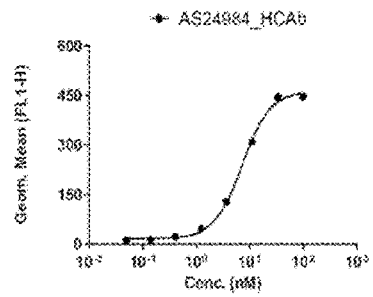
Figure 7G:
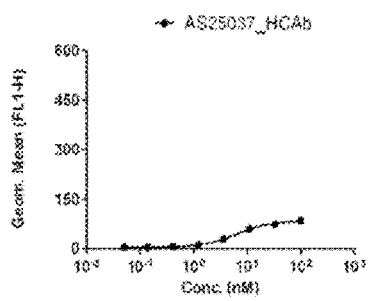
Figure 7H:
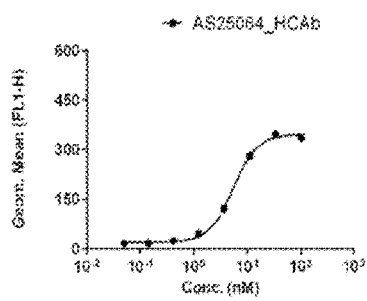
Figure 7I:
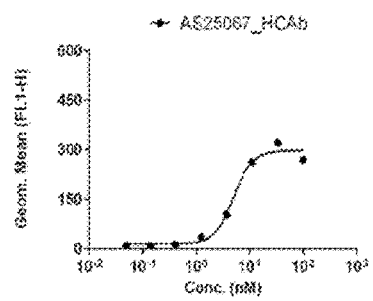
Figure 7J:
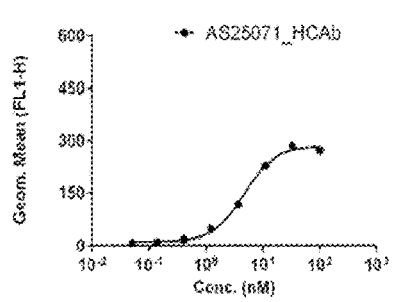
Figure 7K:
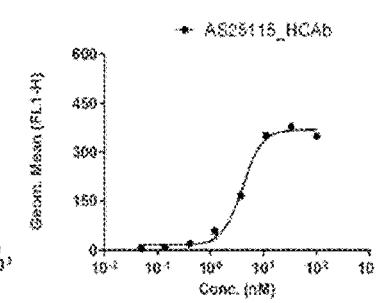
Figure 7L:
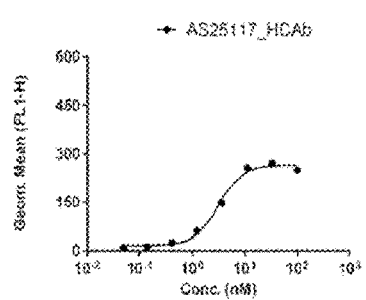
Figure 7M:
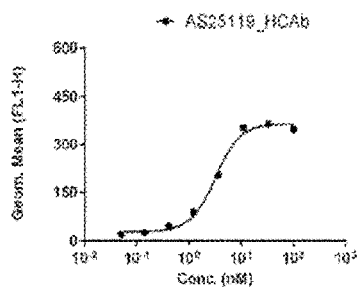
Figure 7N:
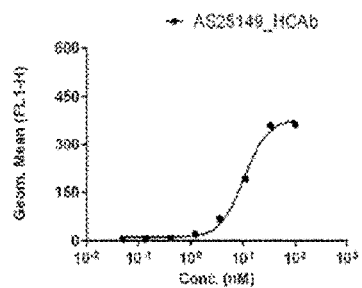
Figure 7O:
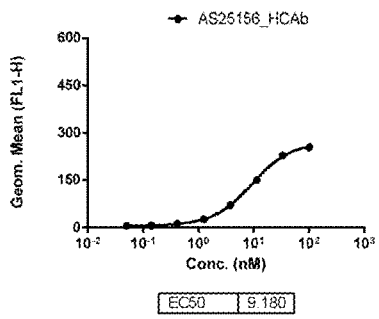
Figure 7P:
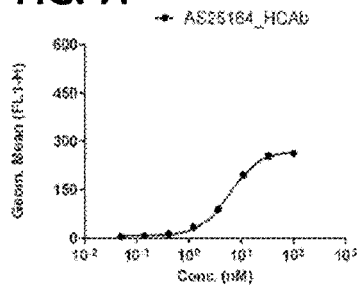
Figure 7Q:
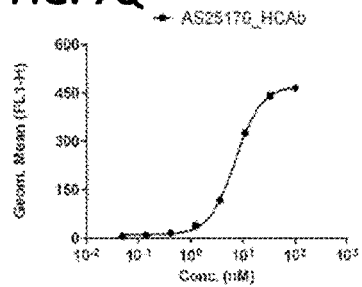
Figure 7R:
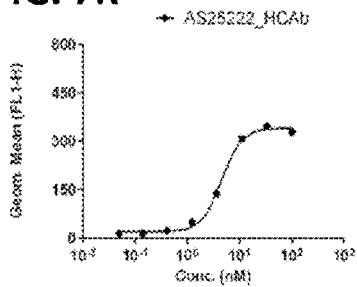
Figure 7S:
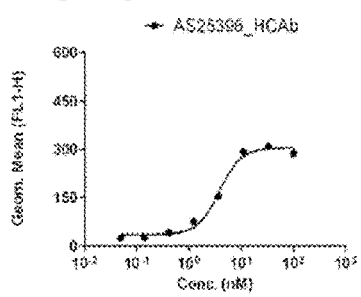
Figure 7T:
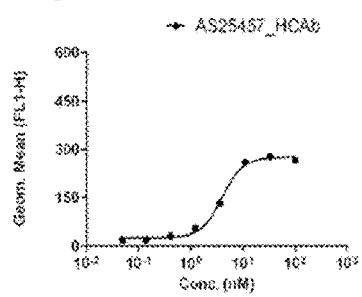
Figure 7U:
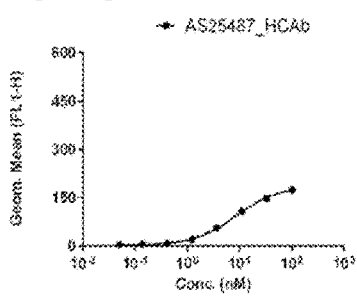
Figure 7V:
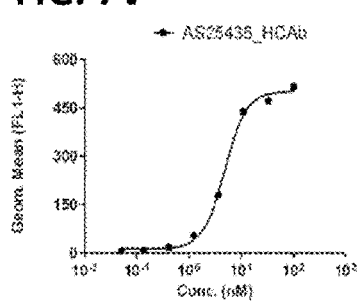
Figure 7W:
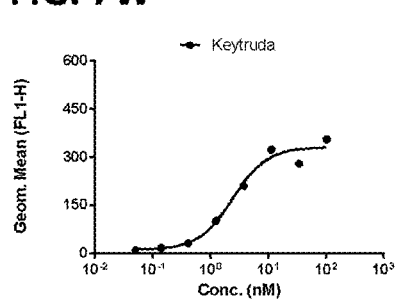

Binding of HCAbs to PD-1 Expressed on Cells by FACS Analysis 22 purified anti-PD-1 HCAbs were tested for their binding abilities to PD-1 expressed on CHO cells as described above (FIGS. 7A-7V). Keytruda® was used as an experimental control (FIG. 7W). $EC_{50}$ were summarized in FIG. 7X. As can be seen from FIGS. 7A-7X, the FACS binding assays demonstrated all 22 HCAbs exhibited good binding to PD-1 on cell surface.

Figure 8A:
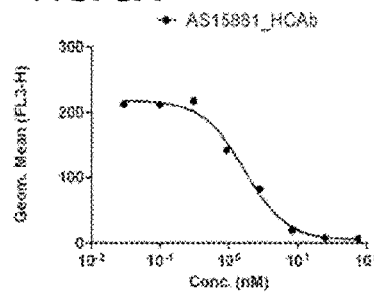
Figure 8B:
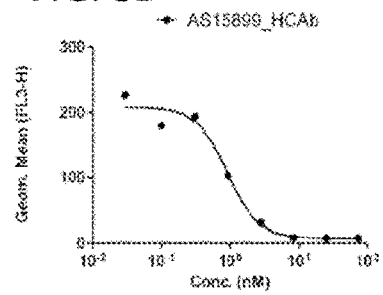
Figure 8C:
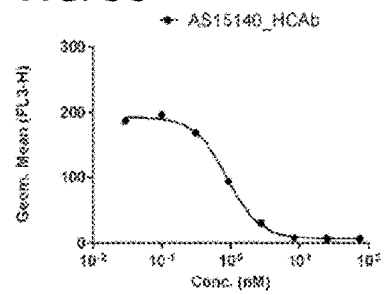
Figure 8D:
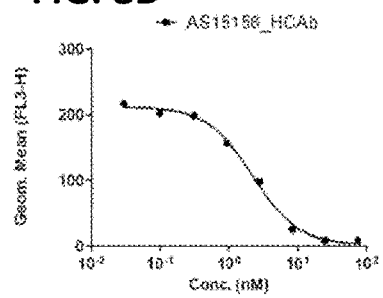
Figure 8E:
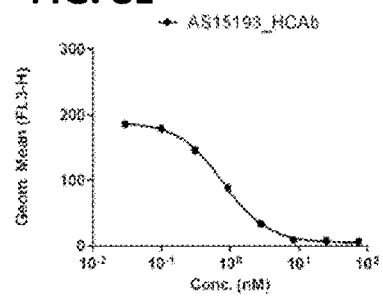
Figure 8F:
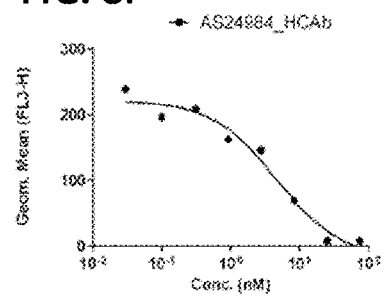
Figure 8G:
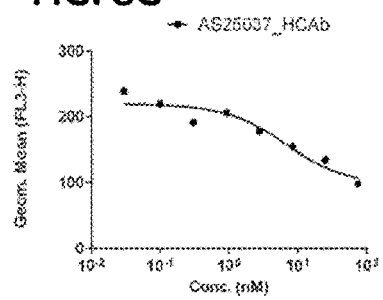
Figure 8H:
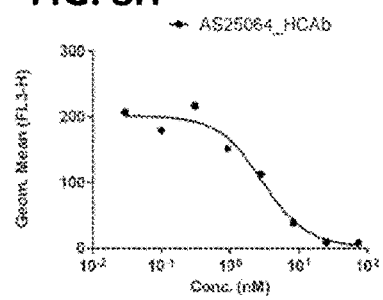
Figure 8I:
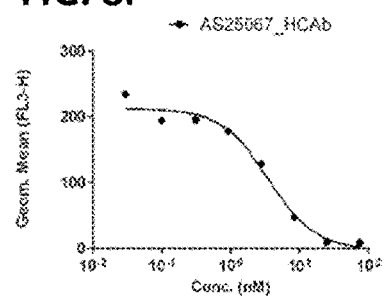
Figure 8J:
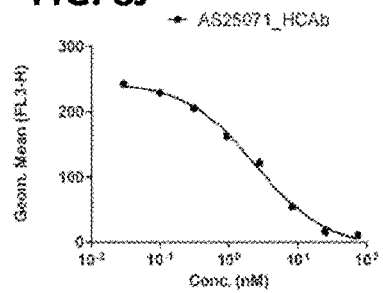
Figure 8K:
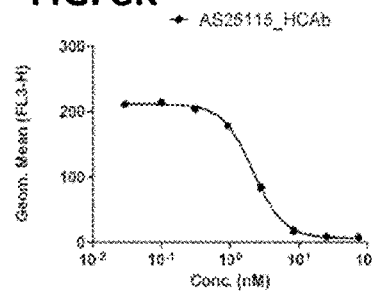
Figure 8L:
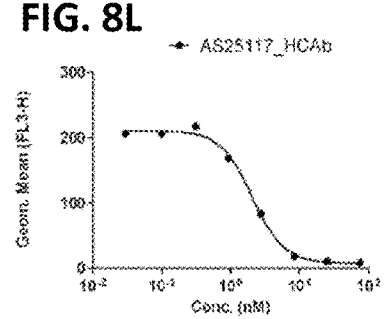
Figure 8M:
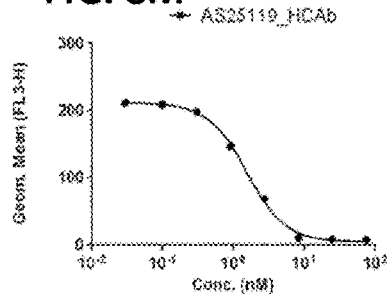
Figure 8N:
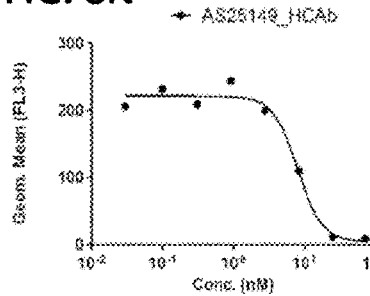
Figure 8O:
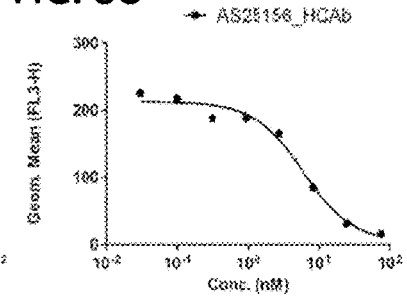
Figure 8P:
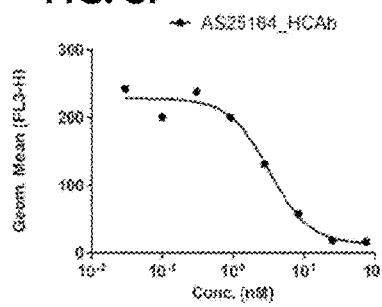
Figure 8Q:
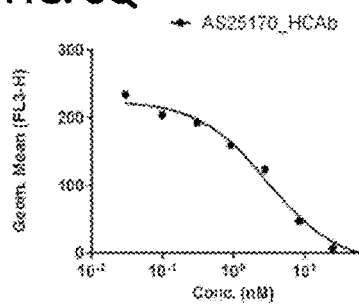
Figure 8R:
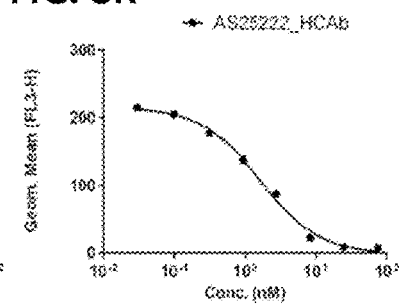
Figure 8S:
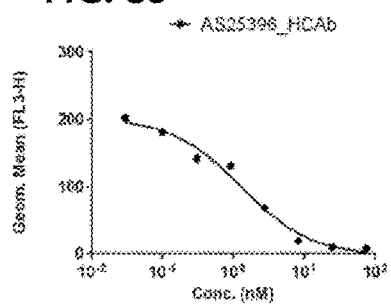
Figure 8T:
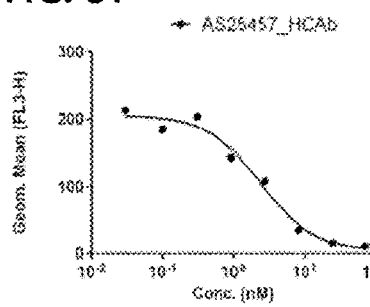
Figure 8U:
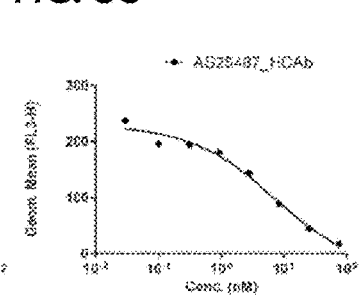
Figure 8V:
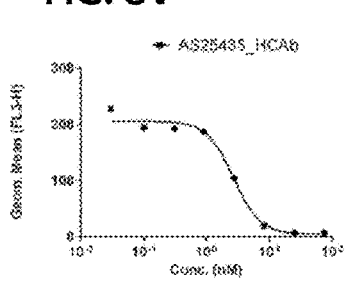
Figure 8W:
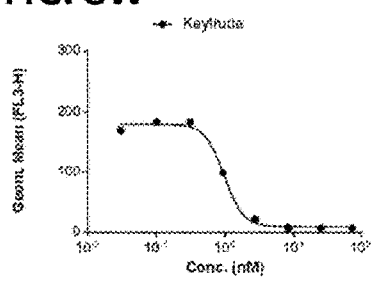
Figure 12A:
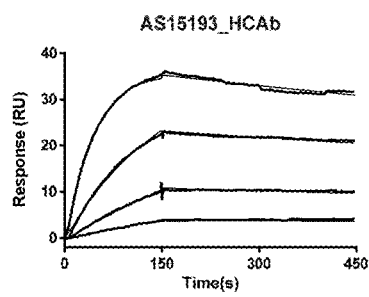
FIGS. 12A-12E depict the affinities of four humanized HCAbs (FIGS. 12B-12E) and the parent HCAb (AS15193_HCAb, FIG. 12A) measured by surface plasma resonance. The $k_{on}$, $k_{off}$ and $K_D$ values are summarized in FIG. 12F.
Figure 12B:
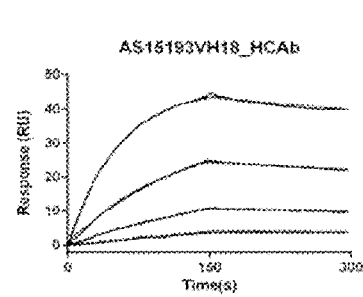
Figure 12C:
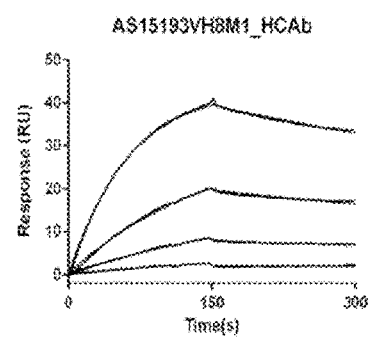
Figure 12D:
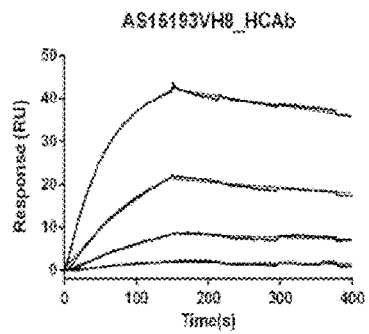
Figure 12E:
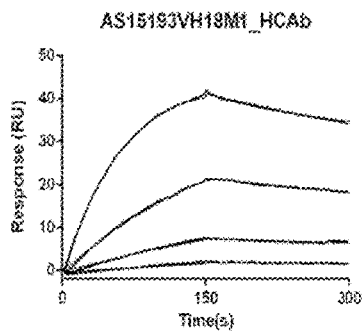

Inhibition of Ligand Binding by FACS Analysis 22 purified anti-PD-1 HCAbs were tested for their abilities to inhibit PD-1 and PD-L1 binding by FACS analysis, similarly as described in above (FIGS. 8A-8V). Keytruda® was used as an experimental control (FIG. 8W). $IC_{50}$ were summarized in FIG. 8X. As can be seen from FIGS. 8A-8X, the competition assays demonstrated the ability of anti-PD-1 HCAbs in efficiently inhibiting PD-1/PD-L1 interactions at low concentrations (1-10 µg/ml). And according to $IC_{50}$ of the FACS data, all 22 HCAbs showed good ligand competition activity.

PD-1 Based Functional Blockade Assay

CHO-K1 cells stably expressing PD-L1 and Jurkat effector cells are used to assess PD-1 blockade for anti-PD-1 HCAbs evaluation. The effector cells contain a luciferase construct that is induced upon disruption of the PD-1/PD-L1 receptor-ligand interaction, such as when the PD-L1 expressing cells are mixed with effector cells expressing PD-1. Thus, the efficacy of inhibiting the interaction of PD-L1 on CHO-K1 stable cells with PD-1 on effector cells by anti-PD-1 HCAbs can be assessed by measuring luciferase reporter activity. The assay is performed as follows.

On day one, PD-L1 expressing CHO-K1 cells were thawed in a 37° C. water bath until cells were just thawed (about 3-4 minutes), and 0.5 mL of thawed cells were transferred to 14.5 mL cell recovery medium (10% FBS/F-12). The cell suspension was mixed well by gently inverting the tube 1-2 times. The cell suspension was then transferred to a sterile reagent reservoir, and dispensed into assay plates with 25 µL of cell suspension per well. 100 µL of assay medium was added per well as blank control. 100 µL of cell recovery medium was added per well for wells serving as blank control. The plates were then lidded and incubated overnight in a $CO_2$ incubator at 37° C.

Next, PD-1 Jurkat effector cells were thawed in a 37° C. water bath until cells were just thawed (about 3-4 minutes). The cell suspension was gently mixed in the vial by pipetting up and down, and 0.5 mL of the cells was added to 5.9 mL assay buffer. The cell suspension was mixed well by gently inverting the tube 1-2 times. The cells were spinned down then transferred to a sterile reagent reservoir in 200 µL assay buffer, and 40 µL of the buffer with cells was dispensed to each well containing the various concentration of anti-PD-1 HCAb or control antibody (starting from 1 µM with 3-fold dilution, total 8 concentrations). Then 160 µL of PD-L1 CHO-K1 cells were added into each well. The plates were lidded and incubated for six hours at 37° C. in a $CO_2$ incubator.

The Luciferase Assay System was reconstituted by transferring one bottle of Buffer to the bottle containing Substrate. The system was stored at room temperature and shielded from light for same day use. After 6 hours induction, assay plates were removed from the $CO_2$ incubator and equilibrated at ambient temperature for 5-10 min. 80 μL of reagent was added to each well. The plates were incubated for 5-10 min at ambient temperature. Luminescence was measured in GloMax® Discover System (Promega, Madison, Wis.) or a plate reader with glow-type luminescence reading capabilities.

Luminescence is expressed as Relative Light Unit (RLU). The RLU values of wells having diluted HCAbs or Keytruda® control was normalized to the RLU of no antibody to provide Fold of Luciferase Induction. Data were graphed as Fold of RLU Induction versus Log 10 concentration of HCAb antibody (or Keytruda® control). The data were fitted to a curve and $EC_{50}$ of each HCAb and control anti-PD-1 antibody Keytruda® was determined using curve fitting software such as GraphPad Prism (FIGS. 9A-9G). $EC_{50}$ data were summarized in FIG. 9H.

PD-1 inhibition by the antibodies can also be studied by determining IL-2 secretion level in mixed lymphocyte reactions (MLR) comprising target cells expressing PD-1 and activated T cells, with anti-PD-1 HCAbs provided at various concentrations.

Human CD4+ T cells and allogeneic monocytes were purified from PBMC using the isolation kits (Miltenyl Biotec). Monocytes were induced into dendritic cells. Each well contained $10^5$ CD4+ T cells and $10^4$ allogeneic dendritic cells with a final working volume of 200 Anti-PD-1 HCAbs were added into each well at different concentrations. No antibody was used as a background control. Human IgG4 was used as a negative control (not shown), and Keytruda® was used as the positive anti-PD-1 antibody control. After 72-hour incubation in 37° C./5% $CO_2$ incubator, 100 μl medium was taken from each testing well for IL-2 secretion measurement (Cisbio). Antibody concentration-dependent secretion of IL-2 in the MLRs was used to extract an $EC_{50}$ value for anti-PD-1 activity of the anti-PD-1 antibodies (FIGS. 10A-10C), and compared with the $EC_{50}$ value of the full-length PD-1 antibody Keytruda® (FIG. 10D). The $EC_{50}$ of MLR assay were summarized in FIG. 10E. Consistent with the FACS-based ligand competition assay results (FIGS. 8A-8X), the functional activities of three selected HCAbs in targeting PD-1 were comparable to their monoclonal antibody Keytruda® by MLR.

Example 2: Anti-PD-1 sdAb Humanization and Characterization

Humanization of Anti-PD-1 sdAbs

Protein sequence of AS15193 sdAb was aligned with the 3 closest human germline sequences sharing the highest degree of homology. The best human germline sequences were selected as human acceptor. Homology model was made. According to the model analysis data, residues potentially critical for antigen binding or antibody scaffold formation were left untouched while the rest were selected for conversion into the human counterpart. Three panels of sequence optimized variants were generated and selected based on binding, stability and functional activity data. Four variants (AS15193VH8, AS15193VH8M1, AS15193VH18 and AS15193VH18M1) were selected based on binding and off-rate ranking data. The camelid parent sdAb, the humanized variants and the human acceptor sequences were aligned in FIG. 11. Humanized sdAbs are indicated with "VH" in their names.

Example 3: Humanized HCAb Construction, Production and Characterization 4 sdAbs (AS15193VH8, AS15193VH8M1, AS15193VH18 and AS15193VH18M1) with functional activities and slow off-rate from the above off-rate ranking study using BIAcore T200 in Example 2 (data not shown) were selected for HCAb construction and production. DNA sequences of the selected sdAbs were fused with DNA sequence of human IgG4 Fc (S228P) to make humanized HCAb constructs. The HCAb constructs were transfected into CHO cell for HCAb expression. Secreted HCAbs in the condition medium were purified by protein A column.

Affinity Measurements of Humanized HCAbs by Surface Plasmon Resonance (SPR)

Binding kinetics of anti-PD-1 humanized HCAbs were determined using an SPR biosensor, Biacore T200 (GE Healthcare). Antibody was immobilized on the sensor chip through Fc capture method, as mentioned in Example 1. Antigen PD-1-His protein was used as the analyte (4 concentrations of human PD-1-His antigen with 3-fold serial dilutions (starting from 1 nM to 27 nM)). Dissociation ($k_d$) and association ($k_a$) rate constants were obtained using Biacore T200 evaluation software (FIGS. 12A-12E). The apparent equilibrium dissociation constants ($K_D$) were calculated from the ratio of $k_d$ over $k_a$. Data were summarized in FIG. 12F. According to the data, the binding affinities of humanized HCAbs (AS15193VH8_HCAb, AS15193VH8M1_HCAb, AS15193VH18_HCAb and AS15193VH18M1_HCAb) were close to its parental HCAb (AS15193_HCAb), suggesting that antibody affinity was maintained after humanization.

Binding of Humanized HCAbs to PD-1 Expressed on Cells by FACS Analysis

Figure 13A:
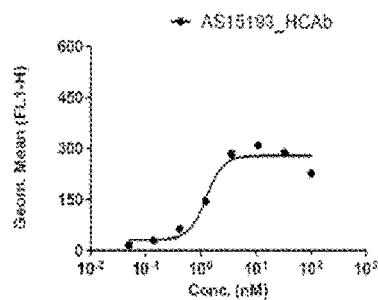
FIGS. 13A-13E depict binding abilities of four humanized HCAbs (FIGS. 13B-13E) and the parent HCAb (AS15193_HCAb, FIG. 13A) to human PD-1 expressing cells. EC$_{50}$ is summarized in FIG. 13F.
Figure 13B:
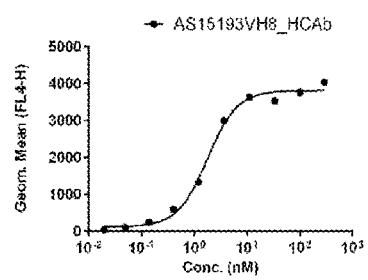
Figure 13C:
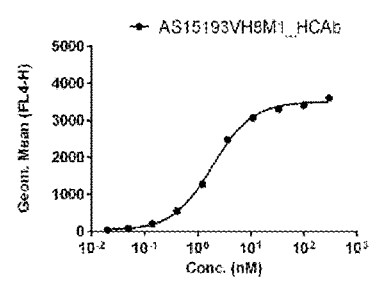
Figure 13D:
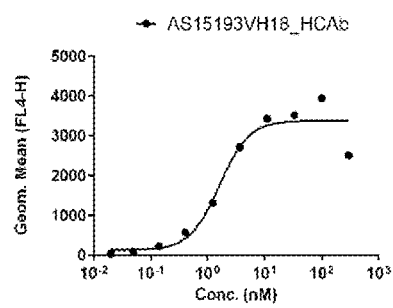
Figure 13E:
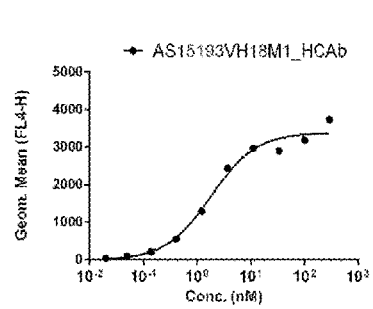

Purified humanized anti-PD-1 HCAbs were tested for their binding abilities to PD-1 expressed on CHO cells, as described in Example 1. As can be seen from FIGS. 13A-13E, the FACS binding assays demonstrated that various humanized HCAbs exhibited comparable binding ability to parental AS15193_HCAb. FACS binding $EC_{50}$ data were summarized in FIG. 13F. Consistent with the above binding affinity result, the humanized HCAbs (AS15193VH8_HCAb, AS15193VH8M1_HCAb, AS15193VH18_HCAb, and AS15193VH18M1_HCAb) also showed comparable binding ability to its parental AS15193_HCAb.

Inhibition of Ligand Binding by FACS Analysis

Purified humanized anti-PD-1 HCAbs were tested for their abilities to inhibit PD-1/PD-L1 binding by FACS analysis, as described in Example 1. As can be seen from FIGS. 14A-14E, the competition assays demonstrated the ability of humanized anti-PD-1 HCAbs in efficiently inhibiting PD-1/PD-L1 interactions at low concentrations (1-10 μg/ml). And according to $IC_{50}$ of the FACS data (FIG. 14F), 4 humanized HCAbs showed comparable ligand blocking activity to their parental AS15193_HCAb.

PD-1 Based Functional Blockade Assay

PD-1 inhibition by the 4 humanized HCAbs was studied by IL-2-based luciferase repeater assay, as described in Example 1. Antibody concentration-dependent activation of IL-2 reporter was used to extract an $EC_{50}$ value for anti-PD-1 activity of the humanized anti-PD-1 HCAbs, and compared with the $EC_{50}$ value of the parent AS15193_HCAb (FIGS. 15A-15E). Consistent with the FACS-based ligand competition assay results, the functional activities of 4 humanized HCAbs were comparable to their parental AS15193_HCAb. Data were summarized in FIG. 15F.

In Vivo Activity of Humanized HCAbs

In the studies presented here, the efficacy of PD-1 humanized HCAb blockade against murine tumor model was investigated. Inhibition of the PD-1/PD-L1 interaction is proposed to exert a therapeutic effect by restoring anti-tumor CD8+ T cell responses, thus the preclinical efficacy study was conducted in syngeneic murine tumor model in which the immune system of the host is fully intact. The human PD-1 transgenic mice was used.

Figure 27:
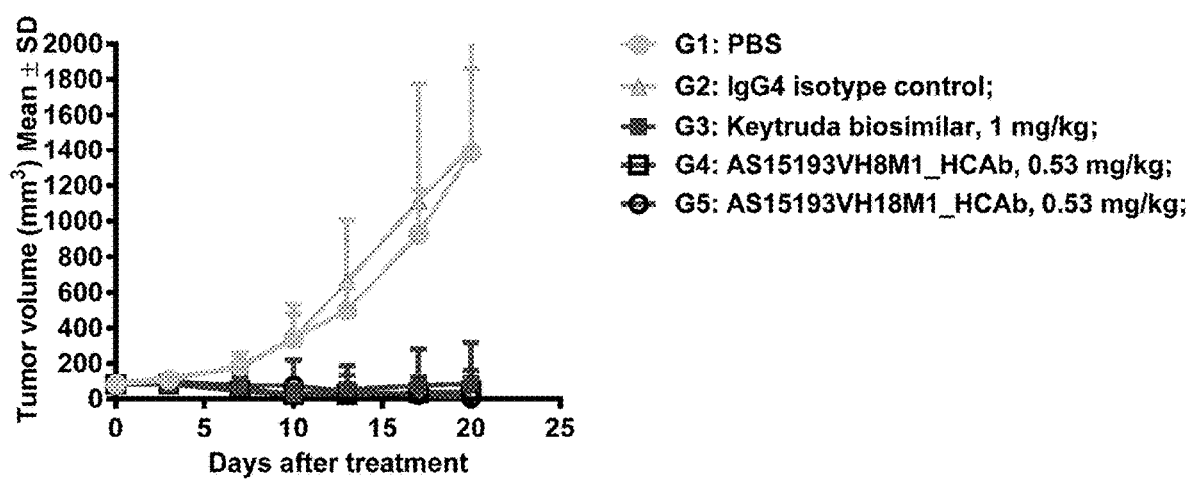
FIG. 27 depicts the in vivo efficacy study of two humanized HCAbs AS15193VH8M1_HCAb and AS15193VH18M1_HCAb.

In this study, mice were inoculated subcutaneously in the right flank with $1 \times 10^6$ human PD-L1 overexpression MC38 colon carcinoma cells. When tumors reached a mean volume of ~100 $mm^3$, mice were sorted into treatment groups (n=5) (defined as study day 0). 2 humanized anti-PD-1 HCAbs tested in this study: AS15193VH8M1_HCAb and AS15193VH18M1_HCAb. Groups were administered benchmark antibody Keytruda (1 mg/kg) or humanized HCAbs (0.53 mg/kg) intravenously twice a week for 2 weeks. 2 control groups were treated with 1 ml/kg of PBS or 1 mg/kg of human IgG4 isotype control. Tumors were measured twice weekly for the study duration. All treatment groups demonstrated significant efficacy (P<0.050) when compared to the control groups (FIG. 27). These observations support that anti-PD-1 therapy as an effective strategy for driving anti-tumor CD8+ T cell responses.

TABLE 3

SEQUENCE LISTING
Anti-PD-1 sdAb SEQ ID NOs

| | SEQ ID NO: FR1 | | SEQ ID NO: CDR1 | | SEQ ID NO: FR2 | | SEQ ID NO: CDR2 | | SEQ ID NO: FR3 | | SEQ ID NO: CDR3 | | SEQ ID NO: FR4 |
|---|---|---|---|---|---|---|---|---|---|---|---|---|---|
| A31543 | 1 | QVQLVESGGGKVQPGGSLRLSCAAS | 37 | GGTLDYYAIG | 73 | WFRQAPGKEREAVS | 109 | CISSSDGSTYYADSVKG | 145 | RFTISRDNAKNTVYLQMNSLKPGDTAVYHCAT | 181 | DRACGSSWLGAES | 217 | WAQGTQVTVSS |
| AS06962 | 2 | QVHLVDSGGGLVQPGGSLRLSCAAS | 38 | GSITSRNTMG | 74 | WYRQVPGKQRELVA | 110 | LIATFVTHYADSVKG | 146 | RFTISRDNARKMVFLEMNSLQPEDTGAYYCYV | 182 | DVSPY | 218 | WGRGTQVTVSS |
| AS15090 | 3 | QVQLVESGGGSVQAGGSLRLSCAAS | 39 | GYTYIPNCMA | 75 | WFRQAPGKEREGVT | 111 | LIFTGDGTSTYVDSVKG | 147 | RFTISQDNAKNTVYLQMNSLKPEDTALYYCAA | 183 | AERCGSNDRISFWGISY | 219 | WGQGTQVTVSS |
| AS15140 | 4 | QVQLVESGGGSVQAGGSLRLSCTAS | 40 | AYTYSNICLG | 76 | WLRQAPGGGLEAVA | 112 | TIYIADQTSYYADSVKG | 148 | RFRISKDAAKNAVYLQMSSLRPEDTAMYYCAS | 184 | RYGSTCGEYLADYTS | 220 | RAQGTQVTVSS |
| AS15152 | 5 | QMQLVESGGGSVQAGGSLRLSCAVS | 41 | GYIYNRNFMG | 77 | WFRQAPGKEREGVA | 113 | AIYTGGPYTYYTDSVQG | 149 | RFTISQDNTKNTVYLQMNSLKPEDTAMYYCVS | 185 | DLSDGTWDQGRWNY | 221 | WGQGTQVTVSS |
| AS15156 | 6 | QVQLVESGGGSAQAGGSLRLSCAVS | 42 | GYIYNRNFMG | 78 | WFRQVPGKVREGVA | 114 | AIYTGTERTYYADSVKG | 150 | RFTISQDNAKNTVYLQMNSLKPEDTAMYYCVA | 186 | DLRDGTWDTGVWNT | 222 | WGQGTQVTVSS |
| AS15193 | 7 | QIQLVESGGGSAQAGGSLRLSCVVS | 43 | GNIYNRNFMG | 79 | WFRQAPGKVREGVA | 115 | AIYTGTSRTYYADSVKG | 151 | RFTISQDNAKNTVYLQMNSLKPEDTAMYYCAA | 187 | DLRDGFWDTGVWNT | 223 | WGQGTQVTVSS |
| AS15872 | 8 | QVQLVESGGGLVQPGGSLTLSCAAS | 44 | GFTFSTAAMS | 80 | WVRQVPEEGLEWVA | 116 | SIDSSGSRTYYAGSVKG | 152 | RFTISRDNAKNTLYLQLNSLKAEDTAMYYCAK | 188 | DHMSWLP | 224 | RGQGTQVTVSS |
| AS15881 | 9 | QVQLVESGGGSVQAGGSLRLSCAAS | 45 | GFTDSSYCGA | 81 | WFRQVPGKEREGVA | 117 | IIDRYGGTMYKDSVKG | 153 | RFTISKDTAKNILYLQMNSLKLEDTAMYYCAA | 189 | AEYRGSSCDAESGY | 225 | WGQGTQVTVSS |
| AS15883 | 10 | QVHLMESGGGSVQAGGSLTLSCAAS | 46 | VFTDSNYCMA | 82 | WFRQVPGKEREGVA | 118 | IIDRYGGTMYKDSVKG | 154 | RFTISKDTAKNILYLQMNSLKLEDTAMYYCAA | 190 | AGYRGSSCDADSGY | 226 | WGQGTQVTVSS |
| AS15892 | 11 | QIQLVESGGGSVQAGGSLRLSCAAS | 47 | GFTDSSYCGA | 83 | WFRQVPGKEREGVA | 119 | IIDRYGGTMYKDSVKG | 155 | RFTISKDTAKNILYLQMNSLKLEDTAMYYCAA | 191 | AEYRGSSCDAESGY | 227 | WGQGTQVTVSS |

TABLE 3-continued

SEQUENCE LISTING
Anti-PD-1 sdAb SEQ ID NOs

| | SEQ ID NO: FR1 | | SEQ ID NO: CDR1 | | SEQ ID NO: FR2 | | SEQ ID NO: CDR2 | | SEQ ID NO: FR3 | | SEQ ID NO: CDR3 | | SEQ ID NO: FR4 |
|---|---|---|---|---|---|---|---|---|---|---|---|---|---|
| AS15899 | 12 | QVQLVES GGGSVQA GGSLRLS CAAS | 48 | GYTA GSLC MG | 84 | WFRQA PGKERE GVA | 120 | AIYTGGGS TYYADSV KG | 156 | RFTISQDNAKNT VYLQMNSLKPE DTAQYYCGA | 192 | GSREDYCD RGYIYDH | 228 | WGQGT QVTVS S |
| AS17049 | 13 | QVKLVES GGGSVQA GGYLRLS CAAS | 49 | GDTN NLNF RG | 85 | WFRQA PGKERE GVA | 121 | VITHSGST YYAESVK G | 157 | RFTISQDLAKNT MYLQMNSLKPE DTAMYYCAA | 193 | ADVWRIS WSFVPELF SY | 229 | WGQGT QVTVS S |
| AS17118 | 14 | QVQLVES GGGSVQA GGSLRLS CAGS | 50 | GFTFN NYAM G | 86 | WFRQA PGKERE GIA | 122 | GIWTGGGS TYYADSV KG | 158 | RFTISEDVAKNT VYLQMDSLKPE DTAMYYCAA | 194 | ERWDYSD WRRLKRG DYNY | 230 | WGQGT QVTVS S |
| AS24984 | 15 | QVHLMES GGGSVPS GGSLRLS CAVS | 51 | GSGY SYSR GCFA | 87 | WFQQR PGKERE GVA | 123 | IINMDGHT RYSDSVQ G | 159 | RFIISQDKAKNTL HLQMNTLRPDD TAMYYCAY | 195 | DRSQCYVL SDRLRLPG TFSD | 231 | WGQGT QVTVS S |
| AS25037 | 16 | EVQLAES GGGSVQA GGSLKLS CLAS | 52 | QWISS DCGM A | 88 | WYRQA PGKERE LVS | 124 | RISSDDTT TYADSVK G | 160 | RFTISQDSAKNT LYLQMNKLKTE DTGVYYCAA | 196 | EAKSTITSL CYPLNY | 232 | WGQGT QVTVS S |
| AS25064 | 17 | QVQLVES GGGSVQA GGSLRLT CAAT | 53 | GYSW RPDC MG | 89 | WYRQA AEKER EGVA | 125 | VIDADGIT SYADAAK G | 161 | RFTISRDNNKITL YLQMLKPDDTG MYVCVV | 197 | GWRVSSG GNCQFND Y | 233 | WGQGT QVTVS S |
| AS25067 | 18 | QVHLMES GGGAVQT GGSLRLS CAVS | 54 | GISISP DCMG | 90 | WFRQA PGKKR EAVT | 126 | TIFANTGS ARYGDSV KG | 162 | RFTSSQGNAKNT LYLQMDSVKLD DTGTYYCAA | 198 | RFTGGDCF DHQPLA | 234 | WRFWG QGTQV TVSS |
| AS25071 | 19 | EVQLAES GGGSVQS GGSLRLS CAVS | 55 | GSGY SYSR GCFA | 91 | WFQQR PGKERE GVA | 127 | IINSDGHT AYSDSVQ G | 163 | RFIISQDKAKNTL YLQMNSLKPDD TAMYYCAY | 199 | DRSQCYVL RDRLRLPD TFTD | 235 | WGQGT QVTVS S |
| AS25115 | 20 | QVHLVES GGASVQA GGSLRLS CAAT | 56 | AYTA SNYC MG | 92 | WFRQS PGKERE AVA | 128 | SINDDGVT SYADSVK G | 164 | RFTISQDSAKKT LYLQMNRLKPE DTAMYYCAA | 200 | TPDGYCYA ERLSRWRY EF | 236 | WGQGT QVTVS S |
| AS25117 | 21 | EVQLAES GGGSVQA GGSLRLS CVIS | 57 | GTSIS PDCM G | 93 | WFRQA PGKKR EAVM | 129 | SIFTNTGST RYGDSVK G | 165 | RFTSSQGNAKNT LYLQMDSLKLD DTATYYCAA | 201 | RYTGGDCF NLEPLAWR F | 237 | WGQGT QVTVS S |
| AS25119 | 22 | QVQLVES GGGSVQA GGPLRLT CAAT | 58 | GYSW RPDC MG | 94 | WYRQA AEKER EGVA | 130 | VIDADGIT SYADAAK G | 166 | RFTISRDNNNITL YLQMLKPDDTG MYVCVI | 202 | GWRVSSG GNCQFND Y | 238 | WGQGT QVTVS S |
| AS25149 | 23 | QVQLVES GGGSVQS GGSLKLS CAVS | 59 | GSGY SYSR GCFA | 95 | WFQQR PGKERE GVA | 131 | IINSDGHT RYSDSVQ G | 167 | RFIISQDKAKNTL YLQMNSLKPDD AAMYYCAY | 203 | DRNQCYV LLDRLRLP GTFSD | 239 | WGQGT QVTVS S |
| AS25156 | 24 | EVQLVES GGGSVQS GGSLRLS CAVS | 60 | GSGY SYSR GCFA | 96 | WFQQR PGKERE GVA | 132 | IINSDGHT RYSDSVQ G | 168 | RFIISQDKAKNTL YLQMNSLKPDD TAMYYCAY | 204 | DCSQCYVL RDRLRLPD TFTD | 240 | WGQGT QVTVS S |
| AS25164 | 25 | EVQLVES GGGSVQS GGSLRLS CAVS | 61 | GSGY SYNR GCFA | 97 | WFQQR PGKERE GVA | 133 | IINSDGHTT YGDSVQG | 169 | RFIISQDKAKNTL DLQMNSLKPDD TAMYYCAY | 205 | DRNQCYV LRDRLRLP DTFTD | 241 | WGQGT QVTVS S |

TABLE 3-continued

SEQUENCE LISTING
Anti-PD-1 sdAb SEQ ID NOs

| SEQ ID NO: | FR1 | SEQ ID NO: | CDR1 | SEQ ID NO: | FR2 | SEQ ID NO: | CDR2 | SEQ ID NO: | FR3 | SEQ ID NO: | CDR3 | SEQ ID NO: | FR4 |
|---|---|---|---|---|---|---|---|---|---|---|---|---|---|
| AS25170 | 26 QVKLVESGGGLVQSGGSLRLSCAVS | 62 | GSGYSYSRGCFA | 98 | WFQQRPGKEREGVA | 134 | IINMDGHTMYSDLAQG | 170 | RFIISQDKAKNTLYLQMNSLKPDDTAMYYCAY | 206 | DRDQCYVLRDRLRLPDTFND | 242 | WGQGTQVTVSS |
| AS25222 | 27 QIQLVESGGGSVQAGGSLRLSCAVT | 63 | GISISPDCMG | 99 | WFRQAPGKKREAVA | 135 | TIFTNTASTRYGDSVKG | 171 | RFTSSQGNGKNTLYLQMDSLNVDDTATYYCAA | 207 | RYTGGNCFNLEPLAWHF | 243 | WGQGTQVTVSS |
| AS25396 | 28 QVHLMESGGGSVQAGGSLRLSCVVS | 64 | GISISPDCMG | 100 | WFRQAPGKKREAVA | 136 | TIFTNTRRTRYGDSVKG | 172 | RVTSSQGNAKNTLYLKMDNLRHDDTATYYCAA | 208 | RYTGGDCFNLDPLSWRF | 244 | WGQGTQVTVSS |
| AS25457 | 29 QVQLVESGGGSVQAGGSLRLSCAVS | 65 | GISISPDCMG | 101 | WFRQAPGKKREAVA | 137 | TIFTNTRSTRYGDSVKG | 173 | RFTSSQGNAKNTLYLQMDSLKLDDTATYYCAA | 209 | RYTGGDCFNLEPVAWRF | 245 | WGQGTQVTVSS |
| AS25487 | 30 EVQLVESGGGLVQPGGSLRLSCAAS | 66 | GFTFSVWSMS | 102 | WVRQAPGEGLEWVS | 138 | TITGSGAQTYYASSRG | 174 | RFTTSRDNAKNTVYLQMNSLKSDDTAVYYCER | 210 | GNGQTAMEALINPP | 246 | ERPGTQVTVSS |
| AS25095 | 31 QVQLVESGGGLMQPGGSLRLSCAAS | 67 | GFTFSSYWMY | 103 | WVRQAPGKGLEWVS | 139 | VINRAGDSAWYADSVTG | 175 | RFTISRDNAKNTVYLQMDSLKPEDTAMYYCAA | 211 | DSRGYGGDWYKLLSDFNY | 247 | CGQGTQVTVSS |
| AS25435 | 32 QVQLVESGGGSVQAGGSLRLSCAAT | 68 | AYTASFYCMG | 104 | WFRQAPGKEREAVA | 140 | SINDDGVTMYADSVKG | 176 | QFTISQDSATKTLYLQMNRLKPEDTAMYYCAA | 212 | TPEGYCYAERLSTWRYTF | 248 | WGQGTQVTVSS |
| AS15193VH8 | 33 EVQLVESGGGLVQPGGSLRLSCAVS | 69 | GNIYNRNFMG | 105 | WFRQAPGKGLEGVS | 141 | AIYTGTSRTYYADSVKG | 177 | RFTISRDNSKNTVYLQMNSLRAEDTAVYYCAA | 213 | DLRDGFWDTGVWNT | 249 | WGQGTLVTVSS |
| AS15193VH8M1 | 34 EVQLVESGGGLVQPGGSLRLSCAVS | 70 | GNIYNRNFMG | 106 | WFRQAPGKGLEGVS | 142 | AIYTGTSRTYYADSVKG | 178 | RFTISRDNSKNTVYLQMNSLRAEDTAVYYCAA | 214 | DLREGFWDTGVWNT | 250 | WGQGTLVTVSS |
| AS15193VH18 | 35 EVQLVESGGGLVQPGGSLRLSCAVS | 71 | GNIYNRNFMG | 107 | WFRQAPGKGREGVS | 143 | AIYTGTSRTYYADSVKG | 179 | RFTISRDNAKNTVYLQMNSLRPEDTAVYYCAA | 215 | DLRDGFWDTGVWNT | 251 | WGQGTLVTVSS |
| AS15193VH18M1 | 36 EVQLVESGGGLVQPGGSLRLSCAVS | 72 | GNIYNRNFMG | 108 | WFRQAPGKGREGVS | 144 | AIYTGTSRTYYADSVKG | 180 | RFTISRDNAKNTVYLQMNSLRPEDTAVYYCAA | 216 | DLREGFWDTGVWNT | 252 | WGQGTLVTVSS |

SEQ ID NO: 253 (A31543 sdAb nucleic acid sequence)
CAGGTACAGCTGGTGGAGTCTGGGGGAGGCAAGGTGCAGCCTGGGGGGTCTCTGAGACTCTCCT
GTGCAGCCTCTGGAGGCACTTTGGATTATTATGCCATAGGCTGGTTCCGCCAGGCCCCAGGGAAG
GAGCGCGAGGCCGTGTCATGTATTAGTAGTAGCGATGGTAGCACATACTATGCAGACTCCGTGAA
GGGCCGATTCACCATCTCCAGAGACAATGCCAAGAACACGGTGTATCTTCAAATGAACAGCCTG
AAACCTGGGGACACGGCCGTTTATCACTGTGCGACAGATCGGCGTGCGGTAGTAGCTGGTTAG
GGGCCGAATCATGGGCCCAGGGGACCCAGGTCACCGTCTCCTCA SEQ ID NO: 254 (AS06962 sdAb nucleic acid sequence)
CAGGTGCACCTGGTGGATTCTGGGGGAGGCTTGGTGCAGCCTGGGGGGTCTCTGAGACTCTCCTG
TGCAGCCTCTGGAAGCATCACCAGTAGAAATACCATGGGCTGGTACCGGCAGGTTCAGGGGAAG
CAGCGCGAATTGGTCGCGCTAATTGCGACTTTTGTCACACATTATGCGGACTCCGTGAAGGGCCG
ATTCACCATCTCCAGAGATAACGCCAGGAAGATGGTGTTTAGAGATGAACAGCCTGCAACCTG
AGGACACGGGCGCGTATTATTGTTATGTCGATGTCTCGCCCTATTGGGGCCGGGGGACCCAGGTC
ACCGTCTCCTCA TABLE 3-continued SEQUENCE LISTING
Anti-PD-1 sdAb SEQ ID NOs

| SEQ ID NO: FR1 | SEQ ID NO: CDR1 | SEQ ID NO: FR2 | SEQ ID NO: CDR2 | SEQ ID NO: FR3 | SEQ ID NO: CDR3 | SEQ ID NO: FR4 |
|---|---|---|---|---|---|---|

SEQ ID NO: 255 (AS15090 sdAb nucleic acid sequence)
CAGGTGCAACTGGTGGAGTCTGGGGGAGGCTCGGTGCAGGCTGGAGGGTCTCTGAGACTCTCCT
GTGCAGCCTCTGGATACACCTATATTCCCAACTGCATGGCCTGGTTCCGCCAGGCTCCAGGGAAG
GAGCGCGAGGGGGTCACACTTATTTTTACTGGTGATGGTACCTCAACCTATGTCGACTCCGTGAA
GGGCCGATTCACCATCTCCCAAGACAACGCCAAGAACACGGTGTATCTGCAAATGAACAGCCTG
AAACCCGAGGACACTGCCTTGTACTACTGTGCGGCAGCCGAACGTTGTAGTGGTTCAAACGACAG
AATATCCTTTTGGGGAATTAGCTACTGGGGCCAGGGGACCCAGGTCACCGTCTCCTCA SEQ ID NO: 256 (AS15140 sdAb nucleic acid sequence)
CAGGTGCAACTGGTGGAGTCTGGGGGAGGCTCGGTGCAGGCTGGGGGGTCTTTGAGACTCTCCTG
TACAGCCTCTGCATACACCTACAGTAACATCTGTTTGGGCTGGCTCCGCCAGGCTCCAGGGGGGG
GGCTCGAGGCTGTCGCAACGATTTATATTGCGGATCAGACATCATACTATGCCGACTCCGTGAAG
GGCCGATTCCGCATCTCTAAAGACGCCGCCAAGAACGCGGTGTATCTGCAAATGAGCAGCCTGA
GACCTGAGGACACTGCCATGTACTACTGTGCGTCCCGGTACGGTAGTACCTGCGGCAATATTTA
GCTGACTATACCTCCCGGGCCCAGGGGACCCAGGTCACCGTCTCCTCA SEQ ID NO: 257 (AS15152 sdAb nucleic acid sequence)
CAGATGCAGCTGGTGGAGTCTGGGGGAGGCTCGGTGCAGGCTGGAGGGTCTCTGAGACTCTCTTG
TGCAGTCTCTGGATACATCTACAATCGCAACTTCATGGGCTGGTTCCGCCAGGCTCCCGGGAAGG
AGCGCGAGGGGGTCGCGGCTATTTATACTGGTGGCCCATACACATACTATACCGACTCCGTGCAG
GGCCGATTCACCATCTCCCAAGACAACACCAAGAACACGGTGTATCTGCAAATGAACAGCCTGA
AACCTGAGGACACTGCCATGTATTACTGTGTGTCAGATCTTTCGGACGGTACTTGGGACCAGGGC
CGATGGAACTACTGGGGCCAGGGGACCCAGGTCACCGTCTCCTCA SEQ ID NO: 258 (AS15156 sdAb nucleic acid sequence)
CAGGTGCAACTGGTGGAGTCTGGGGGAGGCTCGGCGCAGGCTGGAGGGTCTCTGAGACTCTCCT
GTGCAGTCTCTGGATACATTTACAATCGTAACTTCATGGGCTGGTTCCGCCAGGTTCCAGGAAAG
GTGCGCGAGGGGGTCGCAGCAATTTATACTGGTACTGAACGCACGTACTATGCCGACTCCGTGAA
GGGCCGATTCACCATCTCCCAAGACAACGCCAAGAACACGGTGTATCTGCAGATGAATAGTCTG
AAACCTGAGGACACTGCCATGTACTACTGTGTGGCGGATTTGCGGGATGGTACTTGGGATACGGG
CGTATGGAACACCTGGGGCCAGGGGACCCAGGTCACCGTCTCCTCA SEQ ID NO: 259 (AS15193 sdAb nucleic acid sequence)
CAGATTCAGCTGGTGGAGTCTGGGGGAGGCTCGGCGCAGGCTGGAGGGTCTCTGAGACTCTCCTG
TGTAGTCTCTGGAAACATCTACAATCGTAACTTCATGGGCTGGTTCCGCCAGGCTCCAGGGAAGG
TGCGCGAGGGGGTCGCAGCAATTTATACTGGTACTAGTCGCACGTACTATGCCGACTCCGTGAAG
GGCCGATTCACCATCTCCCAAGACAACGCCAAGAATACGGTGTATCTGCAAATGAATAGTCTGAA
ACCTGAGGACACTGCCATGTACTACTGTGCGCGGATTTGCGGGATGGTTTCTGGGATACGGGCG
TATGGAACACCTGGGGCAGGGGACCCAGGTCACCGTCTCCTCA SEQ ID NO: 260 (AS15872 sdAb nucleic acid sequence)
CAGGTGCAACTGGTGGAGTCTGGGGGAGGCTTGGTGCAGCCTGGGGGGTCTCTGACACTCTCCTG
TGCAGCCTCTGGATTCACGTTCAGTACCGCCGCCATGAGCTGGGTCCGCCAGGTTCGCAGAGGAGG
GACTCGAGTGGGTCGCATCTATTGATAGTAGTGGTAGTCGCACATACTATGCGGGCTCCGTGAAG
GGCCGATTCACCATCTCCAGAGACAACGCCAAGAACACGCTGTATTTGCAATTGAACAGCCTGAA
AGCTGAGGACACGGCCATGTATTACTGTCAAAAGATCACATGAGCTGGTTGCCGCGGGCCAG
GGGACCCAGGTCACCGTCTCCTCA SEQ ID NO: 261 (AS15881 sdAb nucleic acid sequence)
CAGGTGCAACTGGTGGAGTCTGGGGGAGGATCGGTGCAGGCTGGAGGGTCTCTGAGACTCTCCT
GTGCAGCCTCTGGATTCACCGACAGTTCGTACTGCGGGGCCTGGTTTCGCCAGGTTCCAGGGAAG
GAGCGCGAGGGGGTCGCGATTATCGATAGATATGGTGGGACAATGTACAAAGACTCCGTGAAGG
GCCGATTCACCATCTCCAAAGACACTGCCAAGAATATTCTGTATCTGCAAATGAACAGCCTGAAA
CTTGAGGACACTGCCATGTACTACTGTGCGGCAGCCGAATATCGAGGCTCTTCGTGTGACGCGGA
GAGTGGCTACTGGGGCCAGGGGACCCAGGTCACCGTCTCCTCA SEQ ID NO: 262 (AS15883 sdAb nucleic acid sequence)
CAGGTGCACCTGATGGAGTCTGGGGGAGGTTCGGTGCAGGCTGGAGGGTCCCTGACTCTCTCCTG
TGCAGCCTCTGTATTCACCGACAGTAACTACTGCATGGCCTGGTTCCGCCAGGTTCCAGGGAAGG
AGCGCGAGGGGGTCGCAATTATCGATAGATATGGTGGTACGATGTACAAAGACTCCGTGAAGGG
CCGATTCACCATCTCCAAAGACACTGCCAAGAATATTCTGTATCTGCAAATGAACAGCCTGAAAC
TTGAGGACACTGCCATGTACTACTGTGCGGCAGCCGGGTATCGAGGCTCTTCGTGTGACGCGGAT
AGTGGCTACTGGGGCCAGGGGACCCAGGTCACCGTCTCCTCA SEQ ID NO: 263 (AS15892 sdAb nucleic acid sequence)
CAGATTCAGCTGGTGGAGTCTGGGGGAGGATCGGTGCAGGCTGGAGGGTCTCTGAGACTCTCCTG
TGCAGCCTCTGGATTCACCGACAGTTCGTACTGCGGGGCCTGGTTTCGCCAGGTTCCAGGGAAGG
AGCGCGAGGGGGTCGCGATTATCGATAGATATGGTGGGACAATGTACAAAGACTCCGTGAAGGG
CCGATTCACCATCTCCAAAGACACTGCCAAGAATATTCTGTATCTGCAAATGAACAGCCTGAAAC
TTGAGGACACTGCCATGTACTACTGTGCGGCAGCCGAATATCGAGGCTCTTCGTGTGACGCGGAG
AGTGGCTACTGGGGCCAGGGGACCCAGGTCACCGTCTCCTCA TABLE 3-continued SEQUENCE LISTING
Anti-PD-1 sdAb SEQ ID NOs

| SEQ ID NO: FR1 | SEQ ID NO: CDR1 | SEQ ID NO: FR2 | SEQ ID NO: CDR2 | SEQ ID NO: FR3 | SEQ ID NO: CDR3 | SEQ ID NO: FR4 |
| --- | --- | --- | --- | --- | --- | --- |

SEQ ID NO: 264 (AS15899 sdAb nucleic acid sequence)
CAGGTGCAACTGGTGGAGTCTGGGGGAGGCTCGGTGCAGGCTGGAGGGTCTCTGAGACTCTCCT
GTGCAGCCTCTGGATACACCGCCGGTAGCCTCTGCATGGGCTGGTTCCGCCAGGCTCCAGGGAAG
GAGCGCGAGGGGGTCGCAGCTATTTATACTGGTGGTGGTAGCACATACTATGCCGACTCCGTGAA
GGGCCGATTCACCATCTCCCAAGACAACGCCAAGAACACGGTGTATCTGCAAATGAACAGCCTG
AAACCTGAGGACACTGCCCAGTACTACTGCGGGGCGGGTAGTAGGGAAGACTACTGCGACAGGG
GTTACATCTATGATCACTGGGGCCAGGGGACCCAGGTCACCGTCTCCTCA SEQ ID NO: 265 (AS17049 sdAb nucleic acid sequence)
CAGGTGAAGTTAGTGGAGTCTGGGGGAGGCTCGGTGCAGGCTGGAGGGTACCTGAGACTCTCCT
GTGCAGCCTCTGGAGACACCAACAACTTGAACTTCAGGGGCTGGTTCCGCCAGGCTCCAGGGAA
GGAGCGCGAGGGGGTCGCAGTTATCACTCACTCTGGTAGCACATACTATGCCGAATCCGTGAAG
GGCCGATTCACCATCTCCCAAGACCTCGCCAAGAACACGATGTATCTGCAAATGAACAGTCTGAA
ACCTGAGGACACTGCTATGTACTACTGTGCGGCAGCAGATGTGGCGTATTAGCTGGTCCTTTG
TTCCGGAACTCTTTAGTTACTGGGGCCAGGGGACCCAGGTCACCGTCTCCTCA SEQ ID NO: 266 (AS17118 sdAb nucleic acid sequence)
CAGGTGCAGCTGGTGGAGTCTGGGGGAGGCTCGGTGCAGGCTGGAGGGTCTCTGAGACTCTCTTG
TGCAGGCTCTGGATTTACCTTCAATAACTACGCCATGGGCTGGTTCCGCCAGGCTCCAGGGAAGG
AGCGCGAGGGAATCGCGGGAATTTGGACTGGTGGTGGTAGTACATACTATGCCGACTCCGTGAA
GGGCCGATTCACCATCTCCGAAGACGTCGCCAAGAACACGGTGTATCTGCAAATGGACAGCCTG
AAACCTGAGGACACTGCCATGTACTACTGTGCGGCCGAGCGCTGGGACTATAGCGACTGGCGAC
GCCTAAAGAGGGGGGACTATAACTACTGGGGCCAGGGGACCCAGGTCACCGTCTCCTCA SEQ ID NO: 267 (AS24984 sdAb nucleic acid sequence)
CAGGTGCACCTGATGAGTCTGGGGGAGGGTCGGTGCCGTCTGGAGGGTCTCTGAGACTCTCCTG
TGCAGTCTCTGGATCTGGATACAGCTATAGTCGCGGCTGCTTCGCATGGTTCCAGCAGCGTCCAG
GGAAGGAGCGCGAGGGGGTCGCAATTATTAATATGGATGGGCACACAAGATACTCAGACTCCGT
GCAGGGCCGATTCATCATCTCCCAAGACAAGGCCAAGAACACACTACATCTGCAAATGAACACC
CTGAGACCTGACGACACGGCCATGTATTACTGTGCGTACGATCGCAGTCAGTGTTACGTGCTAAG
CGACCGCTTACGCCTCCAGGTACCTTTAGTGACTGGGGCCAGGGGACCCAGGTCACCGTCTCCT
CA SEQ ID NO: 268 (AS25037 sdAb nucleic acid sequence)
GAGGTGCAACTGGCGGAGTCTGGGGGAGGCTCGGTGCAGGCTGGAGGGTCTCTGAAACTCTCCT
GTTTAGCCTCGCAATGGATCAGTAGTGATTGCGAATGGCCTGGTACCGCCAGGCTCCAGGGAAG
GAGCGCGAATTGGTCTCACGCATTAGTAGTGATGATACCACAACCTATGCAGACTCCGTGAAGGG
CCGATTCACCATCTCCCAAGACAGTGCCAAGAACACGCTGTATCTGCAAATGAACAAGCTGAAA
ACTGAAGACACGGGCGTGTATTATTGTGCGGCAGAAGCCAAGAGCACTATAACGAGCCTGTGCT
ACCCCTTGAACTACTGGGGCCAGGGGACCCAGGTCACCGTCTCCTCA SEQ ID NO: 269 (AS25064 sdAb nucleic acid sequence)
CAGGTGCAGCTGGTGGAGTCTGGGGGAGGCTCCGTGCAGGCTGGAGGGTCTCTGAGACTCACCT
GTGCAGCCACTGGATACTCTTGGAGACCCGACTGCATGGGCTGGTACCGCCAGGCTGCAGAGAA
GGAGCGCGAGGGGGTCGCAGTTATTGATGCTGATGGTATCACAAGCTACGCAGACGCCGCGAAG
GGCCGATTCACCATCTCCCGAGACAACAACAAGATCACTCTATATCTGCAAATGCTGAAACCTGA
CGACACTGGCATGTACGTCTGTGTGGTAGGATGGAGAGTAAGCAGTGGTGGTAACTGCCAATTCA
ATGACTACTGGGGTCAGGGGACCCAGGTCACCGTCTCCTCA SEQ ID NO: 270 (AS25067 sdAb nucleic acid sequence)
CAGGTGCACCTGATGGAGTCTGGGGGAGGCGCGGTGCAGACCGGAGGGTCTCTGAGGCTCTCCT
GTGCAGTATCGGGAATCTCCATCAGTCCAGACTGCATGGGCTGGTTCCGCCAGGCTCCAGGGAAG
AAGCGCGAGGCGGTCACGACAATTTTTGCTAATACTGGTAGCGCGCGCTATGGCGACTCCGTGAA
GGGCCGATTCACCAGCTCCAAGGCAACGCCAAGAATACGCTGTATCTGCAAATGGACAGCGTG
AAACTTGATGACACTGGCACGTACTACTGTGCGGCACGGTTTACGGGGGGTGACTGCTTTGATCA
TCAGCCATTGGCGTGGCGCTTCTGGGGCCAGGGGACCCAGGTCACCGTCTCCTCA SEQ ID NO: 271 (AS25071 sdAb nucleic acid sequence)
GAGGTGCAACTGGCGGAGTCTGGGGGAGGGTCGGTGCAGTCTGGAGGGTCTCTGAGACTCTCCT
GTGCAGTCTCTGGATCTGGATACAGCTATAGTCGCGGCTGCTTCGCGTGGTTCCAGCAGCGTCCA
GGAAAGGAGCGCGAGGGGGTCGCAATTATTAATAGTGATGGGCACACAGCATACTCAGACTCCG
TGCAGGGCCGATTCATCATCTCCCAAGACAAGGCCAAGAACACACTATATCTGCAAATGAACAG
CCTGAAACCTGACGACACGGCCATGTATTACTGTGCGTACGATCGCAGTCAGTGTTACGTGCTTC
GCGACCGCTTACGCCTCCCAGATACCTTTACTGACTGGGGCCAGGGGACCCAGGTCACCGTCTCC
TCA SEQ ID NO: 272 (AS25115 sdAb nucleic acid sequence)
CAGGTGCACCTGGTGGAGTCTGGGGGAGCCTCGGTGCAGGCTGGAGGGTCTCTGAGACTCTCCTG
TGCAGCCACTGCGTACACCGCCAGTAATTATTGCATGGGCTGGTTCCGCCAGTCTCCAGGGAAGG
AGCGCGAGGCAGTCGCAAGTATTAATGATGACGGCGTCACAAGCTACGCAGACTCCGTGAAGGG
CCGATTCACCATCTCCCAAGACAGCGCCAAGAAGACTCTGTATCTCCAAATGAACCGCCTGAAAC
CTGAGGACACTGCCATGTACTACTGTGCGGCCACCCCGGATGTTACTGCTACGCCAGAGACTT
TCCCGGTGGAGATATGAGTTCTGGGGCCAGGGGACCCAGGTCACCGTCTCCTCA TABLE 3-continued SEQUENCE LISTING
Anti-PD-1 sdAb SEQ ID NOs

| SEQ ID NO: FR1 | SEQ ID NO: CDR1 | SEQ ID NO: FR2 | SEQ ID NO: CDR2 | SEQ ID NO: FR3 | SEQ ID NO: CDR3 | SEQ ID NO: FR4 |
|---|---|---|---|---|---|---|

SEQ ID NO: 273 (AS25117 sdAb nucleic acid sequence)
GAGGTGCAGCTGGCGGAGTCTGGGGGAGGCTCGGTGCAGGCTGGAGGGTCTCTGAGGCTCTCCT
GTGTAATATCAGGAACCTCCATCAGTCCAGACTGCATGGGCTGGTTCCGCCAGGCTCCAGGGAAG
AAGCGCGAGGCAGTCATGAGTATTTTTACAAATACTGGTAGCACGCGCTATGGCGACTCCGTGAA
GGGCCGATTCACCAGCTCCCAAGGCAACGCCAAGAATACGCTGTATCTGCAAATGGACAGCTTG
AAACTTGATGACACTGCCACGTACTACTGTGCGGCCCGGTATACGGGGGGTGACTGCTTTAATCT
TGAACCATTGGCGTGGCGCTTCTGGGGCCAGGGGACCCAGGTCACCGTCTCCTCA SEQ ID NO: 274 (AS25119 sdAb nucleic acid sequence)
CAGGTTCAGCTGGTGGAGTCTGGGGGAGGCTCCGTGCAGGCTGGAGGGCCTCTGAGACTCACCT
GTGCAGCCACTGGATACTCTTGGAGACCCGACTGCATGGGCTGGTACCGCCAGGCTGCAGAGAA
GGAGCGCGAGGGGGTCGCAGTTATTGATGCTGATGGTATCACAAGTTACGCAGACGCCGCGAAG
GGCCGATTCACCATCTCCCGAGACAACAACAACATCACTCTATATCTGCAAATGCTGAAACCTGA
CGACACTGGCATGTACGTCTGTGTGATAGGATGGAGAGTAAGCAGTGGTGGTAACTGCCAATTCA
ATGACTACTGGGGTCAGGGGACCCAGGTCACCGTCTCCTCA SEQ ID NO: 275 (AS25149 sdAb nucleic acid sequence)
CAGGTTCAGCTGGTGGAGTCTGGGGGAGGGTCGGTGCAGTCTGGAGGGTCTCTGAAACTCTCCTG
TGCAGTCTCTGGATCTGGATACAGCTATAGTCGCGGCTGCTTCGCATGGTTCCAACAGCGTCCAG
GGAAGGAGCGCGAGGGGGTCGCAATTATTAATAGCGATGGACACACAAGATACTCAGACTCCGT
GCAGGGCCGATTCATCATCTCCCAAGACAAGGCCAAGAACACACTATATCTCCAAATGAACAGC
CTGAAACCTGACGACGCGGCCATGTATTACTGTGCGTACGATCGCAATCAGTGTTACGTTCTTCTC
GACCGCTTACGCCTCCCAGGTACCTTTAGTGACTGGGGCCAGGGGACCCAGGTCACCGTCTCCTC
A SEQ ID NO: 276 (AS25164 sdAb nucleic acid sequence)
GAGGTGCAGCTGGTGGAGTCTGGGGGAGGGTCGGTGCAGTCTGGAGGGTCTCTGAGACTCTCCT
GTGCAGTCTCTGGATCTGGATACAGCTATAATCGCGGCTGCTTCGCGTGGTTCCAGCAGCGTCCA
GGGAAGGAGCGCGAGGGGGTCGCAATTATTAATAGCGATGGGCACACAACGTACGGAGACTCCG
TGCAGGGCCGATTCATCATCTCCCAAGACAAGGCCAAGAACACACTAGATCTGCAAATGAACAG
CCTGAAACCTGACGACACGGCCATGTATTACTGTGCGTACGATCGCAATCAGTGTTACGTGCTTC
GCGACCGCTTACGCCTCCCAGATACCTTTACTGACTGGGGCCAGGGGACCCAGGTCACCGTCTCC
TCA SEQ ID NO: 277 (AS25170 sdAb nucleic acid sequence)
CAGGTGAAGTTGGTGGAGTCTGGGGGAGGGTTGGTGCAGTCTGGAGGGTCTCTGAGACTCTCCTG
TGCAGTCTCTGGATCTGGATACAGCTATAGTCGCGGCTGCTTCGCATGGTTCCAGCAGCGTCCAG
GGAAGGAGCGCGAGGGGGTCGCAATTATTAATATGGATGGACACACAATGTACTCAGACTTGGC
GCAGGGCCGATTCATCATCTCCCAAGACAAGGCCAAGAACACACTATATCTGCAAATGAACAGC
CTGAAACCTGACGACACGGCCATGTATTACTGTGCGTACGATCGCGATCAGTGTTACGTACTTCG
GGACCGCTTACGCCTCCCAGATACCTTTAATGACTGGGGCCAGGGGACCCAGGTCACCGTCTCCT
CA SEQ ID NO: 278 (AS25222 sdAb nucleic acid sequence)
CAGATTCAGCTGGTGGAGTCTGGGGGAGGCTCGGTGCAGGCTGGAGGGTCTCTGAGGCTCTCCTG
TGCAGTCACAGGAATCTCCATCAGTCCAGACTGCATGGGCTGGTTCCGCCAGGCTCCAGGGAAG
AAGCGCGAGGCAGTCGCGACTATTTTTACTAATACTGCGAGCACGCGCTATGGCGACTCCGTGAA
GGGCCGATTCACCAGCTCCCAAGGGAACGGCAAGAATACGCTGTATCTGCAAATGGACAGCTTG
AACGTTGATGACACTGCCACGTACTACTGTGCGGCCCGCTATACGGGGGGTAACTGCTTTAATCT
TGAGCCATTGGCGTGGCACTTCTGGGGCCAGGGGACCCAGGTCACCGTCTCCTCA SEQ ID NO: 279 (AS25396 sdAb nucleic acid sequence)
CAGGTGCACCTGATGGAGTCTGGGGGAGGCTCGGTGCAGGCTGGAGGGTCTCTGAGGCTCTCCT
GTGTAGTATCAGGAATCTCCATCAGTCCAGACTGTATGGGTGGTTCCGCCAGGCTCCAGGGAAGA
AGCGCGAGGCAGTCGCGACTATTTTTACTAATACTCGTAGGACGCGCTATGGCGACTCGGTGAAG
GGCCGAGTCACCAGCTCCCAAGGCAACGCCAAGAATACGCTGTATCTAAAAATGGACAACTTGA
GGCACGATGACACTGCCACGTACTACTGTGCGGCCCGGTATACGGGGGGTGACTGCTTTAATCTT
GACCCATTGTCCTGGCGCTTCTGGGGCCAGGGGACCCAGGTCACCGTCTCCTCA SEQ ID NO: 280 (AS25457 sdAb nucleic acid sequence)
CAGGTGCAGCTGGTGGAGTCTGGGGGAGGCTCGGTGCAGGCTGGAGGGTCTCTGAGGCTCTCCT
GTGCAGTATCAGGAATCTCCATCAGTCCAGACTGCATGGGCTGGTTCCGCCAGGCTCCAGGGAAG
AAGCGCGAGGCAGTCGCGACTATTTTTACTAATACTCGTAGCACGCGCTATGGCGACTCCGTGAA
GGGCCGATTCACCAGCTCCCAAGGCAACGCCAAGAATACGCTGTATCTGCAAATGGACAGCTTG
AAACTTGATGACACTGCCACGTACTACTGTGCGGCCCGGTATACGGGGGGTGACTGCTTTAATCT
TGAGCCTGTGGCGTGGCGCTTCTGGGGCCAGGGGACCCAGGTCACCGTCTCCTCA SEQ ID NO: 281 (AS25487 sdAb nucleic acid sequence)
GAGGTGCAGCTGGTGGAGTCTGGGGGAGGCTTGGTGCAGCCTGGGGGGTCTCTGAGACTCTCCTG
TGCAGCCTCTGGCTTCACCTTCAGTGTTTGGTCGATGTCCTGGGTCCGCCAGGCTCCAGGGGAGG
GACTCGAGTGGGTCTCAACTATCACTGGGAGTGGCGCACAAACATATTATGCAAGCTCAGTGAG
GGGCCGATTCACCACCTCCAGAGACAACGCCAAGAACACGGTATATCTGCAAATGAACAGCCTG TABLE 3-continued SEQUENCE LISTING
Anti-PD-1 sdAb SEQ ID NOs

| SEQ ID NO: FR1 | SEQ ID NO: CDR1 | SEQ ID NO: FR2 | SEQ ID NO: CDR2 | SEQ ID NO: FR3 | SEQ ID NO: CDR3 | SEQ ID NO: FR4 |
|---|---|---|---|---|---|---|

AAATCTGACGACACGGCCGTGTATTATTGTGAGAGAGGAAATGGTCAGACTGCTATGGAGGCTCT
CATTAACCCGCCCGAGCGTCCGGGGACCCAGGTCACCGTCTCCTCA

SEQ ID NO: 282 (AS25095 sdAb nucleic acid sequence)
CAGGTGCAGCTGGTGGAGTCTGGGGGAGGCTTGATGCAGCCTGGGGGGTCTTTGAGACTCTCCTG
TGCAGCCTCTGGATTCACCTTCAGTAGTTACTGGATGTACTGGGTCCGCCAGGCTCCAGGGAAGG
GGCTTGAGTGGGTCTCGGTTATTAATAGAGCTGGTGATTCCGCCTGGTATGCAGACTCAGTGACG
GGCCGATTCACCATCTCCAGAGACAACGCCAAGAACACGGTGTATCTGCAAATGGACAGCCTGA
AACCTGAGGACACGGCCATGTACTACTGTGCGGCAGACTCGAGGGGGTACGGTGGTGACTGGTA
CAAGCTCCTCTCAGACTTTAATTATTGCGGCCAGGGGACCCAGGTCACCGTCTCCTCA SEQ ID NO: 283 (AS25435 sdAb nucleic acid sequence)
CAGGTGCAGCTGGTGGAGTCTGGGGGAGGCTCGGTGCAGGCTGGAGGGTCTCTGAGACTCTCCT
GTGCAGCCACTGCGTACACCGCCAGTTTCTACTGCATGGGCTGGTTCCGCCAGGCTCCAGGGAAG
GAGCGCGAGGCGGTCGCAAGTATTAATGATGACGGCGTCACAATGTACGCAGACTCCGTGAAGG
GCCAATTCACCATCTCCCAAGACAGCGCCACGAAGACTCTGTATCTGCAAATGAACCGCCTGAAA
CCTGAGGACACCGCCATGTACTACTGTGCGGCCACCCCGGAAGGTTACTGCTACGCCAGAGACT
TTCCACGTGGAGATATACGTTCTGGGGCCAGGGGACCCAGGTCACCGTCTCCTCA SEQ ID NO: 284 (AS25156 sdAb nucleic acid sequence)
GAGGTGCAGCTGGTGGAGTCTGGGGGAGGGTCGGTGCAGTCTGGAGGGTCTCTGAGACTCTCCT
GTGCAGTCTCTGGATCTGGATACAGCTATAGTCGCGGCTGCTTCGCGTGGTTCCAGCAGCGTCCA
GGAAAGGAGCGCGAGGGGGTCGCAATTATTAATAGCGATGGCCACACAAGATACTCAGACTCCG
TGCAGGGCCGATTCATCATCTCCCAAGACAAGGCCAAGAACACACTATATCTGCAAATGAACAG
CCTGAAACCTGACGACACGGCCATGTATTACTGTGCGTACGATTGCAGTCAGTGTTACGTGCTTC
GCGACCGCTTACGCCTCCCAGATACCTTTACTGACTGGGGCCAGGGGACCCAGGTCACCGTCTCC
TCA SEQ ID NO: 285 (AS15193VH8 sdAb nucleic acid sequence)
GAGGTGCAGCTGGTGGAGAGCGGAGGAGGACTGGTGCAGCCAGGAGGCTCTCTGAGACTGTCCT
GCGCCGTGAGCGGCAACATCTACAACAGAAATTTCATGGGATGGTTTAGGCAGGCTCCTGGCAA
GGGACTGGAGGGCGTGTCCGCCATCTATACCGGCACATCTCGCACCTACTATGCTGACTCCGTGA
AGGGCAGGTTCACCATCTCTCGGGATAACTCCAAGAATACAGTGTACCTGCAGATGAACTCTCTG
AGGGCCGAGGACACAGCCGTGTACTATTGTGCCGCTGACCTGCGGGATGGCTTTTGGGATACCGG
CGTGTGGAATACATGGGGCCAGGGCACCCTGGTGACAGTGTCCAGC SEQ ID NO: 286 (AS15193VH8M1 sdAb nucleic acid sequence)
GAGGTGCAGCTGGTGGAGAGCGGAGGAGGACTGGTGCAGCCAGGAGGCTCTCTGAGACTGTCCT
GCGCCGTGAGCGGCAACATCTACAACAGAAATTTCATGGGATGGTTTAGGCAGGCTCCTGGCAA
GGGACTGGAGGGCGTGTCCGCCATCTATACCGGCACATCTCGCACCTACTATGCTGACTCCGTGA
AGGGCAGGTTCACCATCTCTCGGGATAACTCCAAGAATACAGTGTACCTGCAGATGAACTCTCTG
AGGGCCGAGGACACAGCCGTGTACTATTGTGCCGCTGACCTGCGGGAGGGCTTTTGGGATACCGG
CGTGTGGAATACATGGGCCCAGGGCACCCTGGTGACAGTGTCCAGC SEQ ID NO: 287 (AS15193VH18 sdAb nucleic acid sequence)
GAGGTGCAGCTGGTGGAGTCCGGAGGAGGACTGGTGCAGCCAGGAGGCTCTCTGAGGCTGTCCT
GCGCCGTGAGCGGAAACATCTACAACAGAAATTTCATGGGATGGTTTAGGCAGGCTCCTGGCAA
GGGAAGGGAGGGCGTGTCTGCTATCTATACCGGCACATCCAGGACCTACTATGCCGACAGCGTG
AAGGGCAGGTTCACCATCTCTCGGATAACGCTAAGAATACAGTGTACCTGCAGATGAACTCCCT
GCGGCCAGAGGACACAGCCGTGTACTATTGTGCCGCTGACCTGAGAGATGGCTTTTGGGATACCGG
GCGTGTGGAATACATGGGCCCAGGGCACCCTGGTGACAGTGTCCAGC SEQ ID NO: 288 (AS15193VH18M1 sdAb nucleic acid sequence)
GAGGTGCAGCTGGTGGAGTCCGGAGGAGGACTGGTGCAGCCAGGAGGCTCTCTGAGGCTGTCCT
GCGCCGTGAGCGGAAACATCTACAACAGAAATTTCATGGGATGGTTTAGGCAGGCTCCTGGCAA
GGGAAGGGAGGGCGTGTCTGCTATCTATACCGGCACATCCAGGACCTACTATGCCGACAGCGTG
AAGGGCAGGTTCACCATCTCTCGGGATAACGCTAAGAATACAGTGTACCTGCAGATGAACTCCCT
GCGGCCAGAGGACACAGCCGTGTACTATTGTGCCGCTGACCTGAGAGAGGGCTTTTGGGATACC
GGCGTGTGGAATACATGGGCCCAGGGCACCCTGGTGACAGTGTCCAGC SEQ ID NO: 289 (A31543 sdAb amino acid sequence; CDRs are
underlined)
QVQLVESGGGKVQPGGSLRLSCAAS<u>GGTLDYYAIG</u>WFRQAPGKEREAVS<u>CISSSDGSTYYADSVKGR</u>
FTISRDNAKNTVYLQMNSLKPGDTAVYHCAT<u>DRACGSSWLGAES</u>WAQGTQVTVSS SEQ ID NO: 290 (AS06962 sdAb amino acid sequence; CDRs are
underlined)
QVHLVDSGGGLVQPGGSLRLSCAAS<u>GSITSRNTMG</u>WYRQVPGKQRELVA<u>LIATFVTHYADSVKGRFT</u>
ISRDNARKMVFLEMNSLQPEDTGAYYCYV<u>DVSPYW</u>GRGTQVTVSS TABLE 3-continued SEQUENCE LISTING
Anti-PD-1 sdAb SEQ ID NOs

| SEQ ID NO: FR1 | SEQ ID NO: CDR1 | SEQ ID NO: FR2 | SEQ ID NO: CDR2 | SEQ ID NO: FR3 | SEQ ID NO: CDR3 | SEQ ID NO: FR4 |
| --- | --- | --- | --- | --- | --- | --- |

SEQ ID NO: 291 (AS15090 sdAb amino acid sequence; CDRs are underlined)
QVQLVESGGGSVQAGGSLRLSCAAS<u>GYTYIPNCMA</u>WFRQAPGKEREGVT<u>LIFTGDGTSTYVDSVKGR</u>
FTISQDNAKNTVYLQMNSLKPEDTALYYCAA<u>AERCSGSNDRISFWGISY</u>WGQGTQVTVSS SEQ ID NO: 292 (AS15140 sdAb amino acid sequence; CDRs are underlined)
QVQLVESGGGSVQAGGSLRLSCTAS<u>AYTYSNICLG</u>WLRQAPGGGLEAVA<u>TIYIADQTSYYADSVKGR</u>
FRISKDAAKNAVYLQMSSLRPEDTAMYYCAS<u>RYGSTCGEYLADYTSRA</u>QGTQVTVSS SEQ ID NO: 293 (AS15152 sdAb amino acid sequence; CDRs are underlined)
QMQLVESGGGSVQAGGSLRLSCAVS<u>GYIYNRNFMG</u>WFRQAPGKEREGVA<u>AIYTGGPYTYYTDSVQG</u>
RFTISQDNTKNTVYLQMNSLKPEDTAMYYCVS<u>DLSDGTWDQGRWNY</u>WGQGTQVTVSS SEQ ID NO: 294 (AS15156 sdAb amino acid sequence; CDRs are underlined)
QVQLVESGGGSAQAGGSLRLSCAVS<u>GYIYNRNFMG</u>WFRQVPGKVREGVA<u>AIYTGTERTYYADSVKG</u>
RFTISQDNAKNTVYLQMNSLKPEDTAMYYCVA<u>DLRDGTWDTGVWNT</u>WGQGTQVTVSS SEQ ID NO: 295 (AS15193 sdAb amino acid sequence; CDRs are underlined)
QIQLVESGGGSAQAGGSLRLSCVVS<u>GNIYNRNFMG</u>WFRQAPGKVREGVA<u>AIYTGTSRTYYADSVKG</u>
RFTISQDNAKNTVYLQMNSLKPEDTAMYYCAA<u>DLRDGFWDTGVWNT</u>WGQGTQVTVSS SEQ ID NO: 296 (AS15872 sdAb amino acid sequence; CDRs are underlined)
QVQLVESGGGLVQPGGSLTLSCAAS<u>GFTFSTAAMS</u>WVRQVPEEGLEWVAS<u>IDSSGSRTYYAGSVKGR</u>
FTISRDNAKNTLYLQLNSLKAEDTAMYYCAK<u>DHMSWLPR</u>GQGTQVTVSS SEQ ID NO: 297 (AS15881 sdAb amino acid sequence; CDRs are underlined)
QVQLVESGGGSVQAGGSLRLSCAAS<u>GFTDSSYCGA</u>WFRQVPGKEREGVA<u>IIDRYGGTMYKDSVKGR</u>
FTISKDTAKNILYLQMNSLKLEDTAMYYCAA<u>AEYRGSSCDAESGY</u>WGQGTQVTVSS SEQ ID NO: 298 (AS15883 sdAb amino acid sequence; CDRs are underlined)
QVHLMESGGGSVQAGGSLTLSCAAS<u>VFTDSNYCMA</u>WFRQVPGKEREGVA<u>IIDRYGGTMYKDSVKG</u>
RFTTSKDTAKNILYLQMNSLKLEDTAMYYCAA<u>AGYRGSSCDADSGY</u>WGQGTQVTVSS SEQ ID NO: 299 (AS15892 sdAb amino acid sequence; CDRs are underlined)
QIQLVESGGGSVQAGGSLRLSCAAS<u>GFTDSSYCGA</u>WFRQVPGKEREGVA<u>IIDRYGGTMYKDSVKGRF</u>
TISKDTAKNILYLQMNSLKLEDTAMYYCAA<u>AEYRGSSCDAESGY</u>WGQGTQVTVSS SEQ ID NO: 300 (AS15899 sdAb amino acid sequence; CDRs are underlined)
QVQLVESGGGSVQAGGSLRLSCAAS<u>GYTAGSLCMG</u>WFRQAPGKEREGVA<u>AIYTGGGSTYYADSVK</u>
GRFTISQDNAKNTVYLQMNSLKPEDTAQYYCAG<u>SREDYCDRGYIYDH</u>WGQGTQVTVSS SEQ ID NO: 301 (AS17049 sdAb amino acid sequence; CDRs are underlined)
QVKLVESGGGSVQAGGYLRLSCAAS<u>GDTNNLNFRG</u>WFRQAPGKEREGVA<u>VITHSGSTYYAESVKGR</u>
FTISQDLAKNTMYLQMNSLKPEDTAMYYCAA<u>ADVWRISWSFVPELFSY</u>WGQGTQVTVSS SEQ ID NO: 302 (AS17118 sdAb amino acid sequence; CDRs are underlined)
QVQLVESGGGSVQAGGSLRLSCAGS<u>GFTFNNYAMG</u>WFRQAPGKEREGIA<u>GIWTGGGSTYYADSVKG</u>
RFTISEDVAKNTVYLQMDSLKPEDTAMYYCAA<u>ERWDYSDWRRLKRGDYNY</u>WGQGTQVTVSS SEQ ID NO: 303 (AS24984 sdAb amino acid sequence; CDRs are underlined)
QVHLMESGGGSVPSGGSLRLSCAVS<u>GSGYSYSRGCFA</u>WFQQRPGKEREGVA<u>IINMDGHTRYSDSVQG</u>
RFIISQDKAKNTLHLQMNTLRPDDTAMYYCAY<u>DRSQCYVLSDRLRLPGTFSD</u>WGQGTQVTVSS SEQ ID NO: 304 (AS25037 sdAb amino acid sequence; CDRs are underlined)
EVQLAESGGGSVQAGGSLKLSCLAS<u>QWISSDCGMA</u>WYRQAPGKERELVS<u>RISSDDTTTYADSVKGRF</u>
TISQDSAKNTLYLQMNKLKTEDTGVYYCAA<u>EAKSTITSLCYPLNY</u>WGQGTQVTVSS TABLE 3-continued SEQUENCE LISTING
Anti-PD-1 sdAb SEQ ID NOs

| SEQ ID NO: FR1 | SEQ ID NO: CDR1 | SEQ ID NO: FR2 | SEQ ID NO: CDR2 | SEQ ID NO: FR3 | SEQ ID NO: CDR3 | SEQ ID NO: FR4 |
|---|---|---|---|---|---|---|

SEQ ID NO: 305 (AS25064 sdAb amino acid sequence; CDRs are underlined)
QVQLVESGGGSVQAGGSLRLTCAAT<u>GYSWRPDCMG</u>WYRQAAEKEREGVA<u>VIDADGITSYADAAKG</u>
RFTISRDNNKITLYLQMLKPDDTGMYVCVV<u>GWRVSSGGNCQFNDY</u>WGQGTQVTVSS SEQ ID NO: 306 (AS25067 sdAb amino acid sequence; CDRs are underlined)
QVHLMESGGAVQTGGSLRLSCAVS<u>GISISPDCMG</u>WFRQAPGKKREAVT<u>TIFANTGSARYGDSVKGR</u>
FTSSQGNAKNTLYLQMDSVKLDDTGTYYCAA<u>RFTGGDCFDHQPLAW</u>RFWGQGTQVTVSS SEQ ID NO: 307 (AS25071 sdAb amino acid sequence; CDRs are underlined)
EVQLAESGGGSVQSGGSLRLSCAVS<u>GSGYSYSRGCFA</u>WFQQRPGKEREGVA<u>IINSDGHTAYSDSVQG</u>
RFIISQDKAKNTLYLQMNSLKPDDTAMYYCAY<u>DRSQCYVLRDRLRLPDTFTD</u>WGQGTQVTVSS SEQ ID NO: 308 (AS25115 sdAb amino acid sequence; CDRs are underlined)
QVHLVESGGASVQAGGSLRLSCAAT<u>AYTASNYCMG</u>WFRQSPGKEREAVA<u>SINDDGVTSYADSVKGR</u>
FTISQDSAKKTLYLQMNRLKPEDTAMYYCAA<u>TPDGYCYAERLSRWRYEF</u>WGQGTQVTVSS SEQ ID NO: 309 (AS25117 sdAb amino acid sequence; CDRs are underlined)
EVQLAESGGGSVQAGGSLRLSCVIS<u>GTSISPDCMG</u>WFRQAPGKKREAVM<u>SIFTNTGSTRYGDSVKGRF</u>
TSSQGNAKNTLYLQMDSLKLDDTATYYCAA<u>RYTGGDCFNLEPLAW</u>RFWGQGTQVTVSS SEQ ID NO: 310 (AS25119 sdAb amino acid sequence; CDRs are underlined)
QVQLVESGGGSVQAGGPLRLTCAAT<u>GYSWRPDCMG</u>WYRQAAEKEREGVA<u>VIDADGITSYADAAKG</u>
RFTISRDNNNITLYLQMLKPDDTGMYVCVI<u>GWRVSSGGNCQFNDY</u>WGQGTQVTVSS SEQ ID NO: 311 (AS25149 sdAb amino acid sequence; CDRs are underlined)
QVQLVESGGGSVQSGGSLKLSCAVS<u>GSGYSYSRGCFA</u>WFQQRPGKEREGVA<u>IINSDGHTRYSDSVQG</u>
RFIISQDKAKNTLYLQMNSLKPDDAAMYYCAY<u>DRNQCYVLLDRLRLPGTFSD</u>WGQGTQVTVSS SEQ ID NO: 312 (AS25156 sdAb amino acid sequence; CDRs are underlined)
EVQLVESGGGSVQSGGSLRLSCAVS<u>GSGYSYSRGCFA</u>WFQQRPGKEREGVA<u>IINSDGHTRYSDSVQG</u>
RFIISQDKAKNTLYLQMNSLKPDDTAMYYCAY<u>DCSQCYVLRDRLRLPDTFTD</u>WGQGTQVTVSS SEQ ID NO: 313 (AS25164 sdAb amino acid sequence; CDRs are underlined)
EVQLVESGGGSVQSGGSLRLSCAVS<u>GSGYSYNRGCFA</u>WFQQRPGKEREGVA<u>IINSDGHTTYGDSVQG</u>
RFIISQDKAKNTLDLQMNSLKPDDTAMYYCAY<u>DRNQCYVLRDRLRLPDTFTD</u>WGQGTQVTVSS SEQ ID NO: 314 (AS25170 sdAb amino acid sequence; CDRs are underlined)
QVKLVESGGGLVQSGGSLRLSCAVS<u>GSGYSYSRGCFA</u>WFQQRPGKEREGVA<u>IINMDGHTMYSDLAQ</u>
GRFIISQDKAKNTLYLQMNSLKPDDTAMYYCAY<u>DRDQCYVLRDRLRLPDTFND</u>WGQGTQVTVSS SEQ ID NO: 315 (AS25222 sdAb amino acid sequence; CDRs are underlined)
QIQLVESGGGSVQAGGSLRLSCAVT<u>GISISPDCMG</u>WFRQAPGKKREAVA<u>TIFTNTASTRYGDSVKGRF</u>
TSSQGNGKNTLYLQMDSLNVDDTATYYCAA<u>RYTGGNCFNLEPLAWH</u>FWGQGTQVTVSS SEQ ID NO: 316 (AS25396 sdAb amino acid sequence; CDRs are underlined)
QVHLMESGGGSVQAGGSLRLSCVVS<u>GISISPDCMG</u>WFRQAPGKKREAVA<u>TIFTNTRRTRYGDSVKGR</u>
VTSSQGNAKNTLYLKMDNLRHDDTATYYCAA<u>RYTGGDCFNLDPLSWR</u>FWGQGTQVTVSS SEQ ID NO: 317 (AS25457 sdAb amino acid sequence; CDRs are underlined)
QVQLVESGGGSVQAGGSLRLSCAVS<u>GISISPDCMG</u>WFRQAPGKKREAVA<u>TIFTNTRSTRYGDSVKGRF</u>
TSSQGNAKNTLYLQMDSLKLDDTATYYCAA<u>RYTGGDCFNLEPVAWR</u>FWGQGTQVTVSS SEQ ID NO: 318 (AS25487 sdAb amino acid sequence; CDRs are underlined)
EVQLVESGGGLVQPGGSLRLSCAAS<u>GFTFSVWSMS</u>WVRQAPGEGLEWVS<u>TITGSGAQTYYASSVRG</u>
RFTTSRDNAKNTVYLQMNSLKSDDTAVYYCER<u>GNGQTAMEALINPPERPG</u>TQVTVSS TABLE 3-continued SEQUENCE LISTING
Anti-PD-1 sdAb SEQ ID NOs

| SEQ ID NO: FR1 | SEQ ID NO: CDR1 | SEQ ID NO: FR2 | SEQ ID NO: CDR2 | SEQ ID NO: FR3 | SEQ ID NO: CDR3 | SEQ ID NO: FR4 |
|---|---|---|---|---|---|---|

SEQ ID NO: 319 (AS25095 sdAb amino acid sequence; CDRs are
underlined)
QVQLVESGGGLMQPGGSLRLSCAAS GFTFSSYWMY WVRQAPGKGLEWVS VINRAGDSAWYADSVT
GRFTISRDNAKNTVYLQMDSLKPEDTAMYYCAA DSRGYGGDWYKLLSDFNY CGQGTQVTVSS SEQ ID NO: 320 (AS25435 sdAb amino acid sequence; CDRs are
underlined)
QVQLVESGGGSVQAGGSLRLSCAAT AYTASFYCMG WFRQAPGKEREAVAS INDDGVTMYADSVKG
QFTISQDSATKTLYLQMNRLKPEDTAMYYCAA TPEGYCYAERLSTWRYTF WGQGTQVTVSS SEQ ID NO: 321 (AS15193VH8 sdAb amino acid sequence; CDRs are
underlined)
EVQLVESGGGLVQPGGSLRLSCAVS GNIYNRNFMG WFRQAPGKGLEGVS AIYTGTSRTYYADSVKG
RFTISRDNSKNTVYLQMNSLRAEDTAVYYCAA DLRDGFWDTGVWNT WGQGTLVTVSS SEQ ID NO: 322 (AS15193VH8M1 sdAb amino acid sequence; CDRs are
underlined)
EVQLVESGGGLVQPGGSLRLSCAVS GNIYNRNFMG WFRQAPGKGLEGVS AIYTGTSRTYYADSVKG
RFTISRDNSKNTVYLQMNSLRAEDTAVYYCAA DLREGFWDTGVWNT WGQGTLVTVSS SEQ ID NO: 323 (AS15193VH18 sdAb amino acid sequence; CDRs are
underlined)
EVQLVESGGGLVQPGGSLRLSCAVS GNIYNRNFMG WFRQAPGKGREGVS AIYTGTSRTYYADSVKG
RFTISRDNAKNTVYLQMNSLRPEDTAVYYCAA DLRDGFWDTGVWNT WGQGTLVTVSS SEQ ID NO: 324 (AS15193VH18M1 sdAb amino acid sequence; CDRs are
underlined)
EVQLVESGGGLVQPGGSLRLSCAVS GNIYNRNFMG WFRQAPGKGREGVS AIYTGTSRTYYADSVKG
RFTISRDNAKNTVYLQMNSLRPEDTAVYYCAA DLREGFWDTGVWNT WGQGTLVTVSS SEQ ID NO: 325 (A31543 HCAb amino acid sequence; CDRs are
underlined, linker is bolded)
QVQLVESGGGKVQPGGSLRLSCAAS GGTLDYYAIG WFRQAPGKEREAVS CISSSDGSTYYADSVKGR
FTISRDNAKNTVYLQMNSLKPGDTAVYHCAT DRACGSSWLGAES WAQGTQVTVSS**ESKYGPPCPPC
P**APEFLGGPSVFLFPPKPKDTLMISRTPEVTCVVVDVSQEDPEVQFNWYVDGVEVHNAKTKPREEQF
NSTYRVVSVLTVLHQDWLNGKEYKCKVSNKGLPSSIEKTISKAKGQPREPQVYTLPPSQEEMTKNQV
SLTCLVKGFYPSDIAVEWESNGQPENNYKTTPPVLDSDGSFFLYSRLTVDKSRWQEGNVFSCSVMHE
ALHNHYTQKSLSLSLGK SEQ ID NO: 326 (AS06962 HCAb amino acid sequence; CDRs are
underlined, linker is bolded)
QVHLVDSGGGLVQPGGSLRLSCAAS GSITSRNTMG WYRQVPGKQRELVA LIATFVTHYADSVKGRFT
ISRDNARKMVFLEMNSLQPEDTGAYYCYVD DVSPYW GRGTQVTVSSESKYGPPCPPCAPEFLGGPS
VFLFPPKPKDTLMISRTPEVTCVVVDVSQEDPEVQFNWYVDGVEVHNAKTKPREEQFNSTYRVVSVL
TVLHQDWLNGKEYKCKVSNKGLPSSIEKTISKAKGQPREPQVYTLPPSQEEMTKNQVSLTCLVKGFY
PSDIAVEWESNGQPENNYKTTPPVLDSDGSFFLYSRLTVDKSRWQEGNVFSCSVMHEALHNHYTQKS
LSLSLGK SEQ ID NO: 327 (AS15090 HCAb amino acid sequence; CDRs are
underlined, linker is bolded)
QVQLVESGGGSVQAGGSLRLSCAAS GYTYIPNCMA WFRQAPGKEREGVTL IFTGDGTSTY VDSVKGR
FTISQDNAKNTVYLQMNSLKPEDTALYYCAA AERCSGSNDRISFWGISY WGQGTQVTVSS**ESKYGPP
C**CPPCPAPEFLGGPSVFLFPPKPKDTLMISRTPEVTCVVVDVSQEDPEVQFNWYVDGVEVHNAKTKPR
EEQFNSTYRVVSVLTVLHQDWLNGKEYKCKVSNKGLPSSIEKTISKAKGQPREPQVYTLPPSQEEMTK
NQVSLTCLVKGFYPSDIAVEWESNGQPENNYKTTPPVLDSDGSFFLYSRLTVDKSRWQEGNVFSCSV
MHEALHNHYTQKSLSLSLGK SEQ ID NO: 328 (AS15140 HCAb amino acid sequence; CDRs are
underlined, linker is bolded)
QVQLVESGGGSVQAGGSLRLSCTAS AYTYSNICLG WLRQAPGGGLEAVA TIYIADQTSYYADSVKGR
FRISKDAAKNAVYLQMSSLRPEDTAMYYCAS RYGSTCGEYLADYTSRAQGTQVTVSS**ESKYGPPC
PCP**APEFLGGPSVFLFPPKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPREPQVYTLPPSQEEMTKN
QVSLTCLVKGFYPSDTAVEWESNGQPENNYKTTPPVLDSDGSFFLYSRLTVDKSRWQEGNVFSCSVM
HEALHNHYTQKSLSLSLGK SEQ ID NO: 329 (AS15152 HCAb amino acid sequence; CDRs are
underlined, linker is bolded)
QMQLVESGGGSVQAGGSLRLSCAVS GYIYNRNFMG WFRQAPGKEREGVA AIYTGGPYTYYTDSVQG
RFTISQDNTKNTVYLQMNSLKPEDTAMYYCVS DLSDGTWDQGRWNY WGQGTQVTVSS**ESKYGPPC
PPCP**APEFLGGPSVFLFPPKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPREPQVYTLPPSQEEMTKN TABLE 3-continued SEQUENCE LISTING
Anti-PD-1 sdAb SEQ ID NOs

| SEQ ID NO: FR1 | SEQ ID NO: CDR1 | SEQ ID NO: FR2 | SEQ ID NO: CDR2 | SEQ ID NO: FR3 | SEQ ID NO: CDR3 | SEQ ID NO: FR4 |
|---|---|---|---|---|---|---|

QVSLTCLVKGFYPSDIAVEWESNGQPENNYKTTPPVLDSDGSFFLYSRLTVDKSRWQEGNVFSCSVM
HEALHNHYTQKSLSLSLGK

SEQ ID NO: 330 (AS15156 HCAb amino acid sequence; CDRs are
underlined, linker is bolded)
QVQLVESGGGSAQAGGSLRLSCAVS<u>GYIYNRNFMG</u>WFRQVPGKVREGVA<u>AIYTGTERTYYADSVKG</u>
RFTISQDNAKNTVYLQMNSLKPEDTAMYYCVA<u>DLRDGTWDTGVWNT</u>WGQGTQVTVSSESKYGPP
CPPCPAPEFLGGPSVFLFPPKPKDTLMISRTPEVTCVVVDVSQEDPEVQFNWYVDGVEVHNAKTKPR
EEQFNSTYRVVSVLTVLHQDWLNGKEYKCKVSNKGLPSSIEKTISKAKGQPREPQVYTLPPSQEEMTK
NQVSLTCLVKGFYPSDIAVEWESNGQPENNYKTTPPVLDSDGSFFLYSRLTVDKSRWQEGNVFSCSV
MHEALHNHYTQKSLSLSLGK SEQ ID NO: 331 (AS15193 HCAb amino acid sequence; CDRs are
underlined, linker is bolded)
QIQLVESGGGSAQAGGSLRLSCVVS<u>GNIYNRNFMG</u>WFRQAPGKVREGVA<u>AIYTGTSRTYYADSVKG</u>
RFTISQDNAKNTVYLQMNSLKPEDTAMYYCAA<u>DLRDGFWDTGVWNT</u>WGQGTQVTVSSESKYGPP
CPPCPAPEFLGGPSVFLFPPKPKDTLMISRTPEVTCVVVDVSQEDPEVQFNWYVDGVEVHNAKTKPR
EEQFNSTYRVVSVLTVLHQDWLNGKEYKCKVSNKGLPSSIEKTISKAKGQPREPQVYTLPPSQEEMTK
NQVSLTCLVKGFYPSDIAVEWESNGQPENNYKTTPPVLDSDGSFFLYSRLTVDKSRWQEGNVFSCSV
MHEALHNHYTQKSLSLSLGK SEQ ID NO: 332 (AS15872 HCAb amino acid sequence; CDRs are
underlined, linker is bolded)
QVQLVESGGGLVQPGGSLTLSCAAS<u>GFTFSTAAMS</u>WVRQVPEEGLEWVAS<u>IDSSGSRTYYAGSVKGR</u>
FTISRDNAKNTLYLQLNSLKAEDTAMYYCAK<u>DHMSWLPR</u>GQGTQVTVSSESKYGPPCPPCPAPEFL
GGPSVFLFPPKPKDTLMISRTPEVTCVVVDVSQEDPEVQFNWYVDGVEVHNAKTKPREEQFNSTYRV
VSVLTVLHQDWLNGKEYKCKVSNKGLPSSIEKTISKAKGQPREPQVYTLPPSQEEMTKNQVSLTCLV
KGFYPSDIAVEWESNGQPENNYKTTPPVLDSDGSFFLYSRLTVDKSRWQEGNVFSCSVMHEALHNHY
TQKSLSLSLGK SEQ ID NO: 333 (AS15881 HCAb amino acid sequence; CDRs are
underlined, linker is bolded)
QVQLVESGGGSVQAGGSLRLSCAAS<u>GFTDSSYCGA</u>WFRQVPGKEREGVA<u>IIDRYGGTMYKDSVKGR</u>
FTISKDTAKNILYLQMNSLKLEDTAMYYCAA<u>AEYRGSSCDAESGYW</u>GQGTQVTVSSESKYGPPCPP
CPAPEFLGGPSVFLFPPKPKDTLMISRTPEVTCVVVDVSQEDPEVQFNWYVDGVEVHNAKTKPREEQ
FNSTYRVVSVLTVLHQDWLNGKEYKCKVSNKGLPSSIEKTISKAKGQPREPQVYTLPPSQEEMTKNQ
VSLTCLVKGFYPSDIAVEWESNGQPENNYKTTPPVLDSDGSFFLYSRLTVDKSRWQEGNVFSCSVMH
EALHNHYTQKSLSLSLGK SEQ ID NO: 334 (AS15883 HCAb amino acid sequence; CDRs are
underlined, linker is bolded)
QVHLMESGGGSVQAGGSLTLSCAAS<u>VFTDSNYCMA</u>WFRQVPGKEREGVA<u>IIDRYGGTMYKDSVKG</u>
RFTISKDTAKNILYLQMNSLKLEDTAMYYCAA<u>AYRGSSCDASGYW</u>GQGTQVTVSSESKYGPPCP
PCPAPEFLGGPSVFLFPPKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPREPQVYTLPPSQEEMTKN
QVSLTCLVKGFYPSDIAVEWESNGQPENNYKTTPPVLDSDGSFFLYSRLTVDKSRWQEGNVFSCSVM
HEALHNHYTQKSLSLSLGK SEQ ID NO: 335 (AS15892 HCAb amino acid sequence; CDRs are
underlined, linker is bolded)
QIQLVESGGGSVQAGGSLRLSCAAS<u>GFTDSSYCGA</u>WFRQVPGKEREGVA<u>IIDRYGGTMYKDSVKGRF</u>
TISKDTAKNILYLQMNSLKLEDTAMYYCAA<u>AEYRGSSCDAESGYW</u>GQGTQVTVSSESKYGPPCPPC
PAPEFLGGPSVFLFPPKPKDTLMISRTPEVTCVVVDVSQEDPEVQFNWYVDGVEVHNAKTKPREEQF
NSTYRVVSVLTVLHQDWLNGKEYKCKVSNKGLPSSIEKTISKAKGQPREPQVYTLPPSQEEMTKNQV
SLTCLVKGFYPSDIAVEWESNGQPENNYKTTPPVLDSDGSFFLYSRLTVDKSRWQEGNVFSCSVMHE
ALHNHYTQKSLSLSLGK SEQ ID NO: 336 (AS15899 HCAb amino acid sequence; CDRs are
underlined, linker is bolded)
QVQLVESGGGSVQAGGSLRLSCAAS<u>GYTAGSLCMG</u>WFRQAPGKEREGVA<u>AIYTGGGSTYYADSVK</u>
GRFTISQDNAKNTVYLQMNSLKPEDTAQYYCGA<u>GSREDYCDRGYTYDHW</u>GQGTQVTVSSESKYGPP
CPPCPAPEFLGGPSVFLFPPKPKDTLMISRTPEVTCVVVDVSQEDPEVQFNWYVDGVEVHNAKTKPR
EEQFNSTYRVVSVLTVLHQDWLNGKEYKCKVSNKGLPSSIEKTISKAKGQPREPQVYTLPPSQEEMTK
NQVSLTCLVKGFYPSDIAVEWESNGQPENNYKTTPPVLDSDGSFFLYSRLTVDKSRWQEGNVFSCSV
MHEALHNHYTQKSLSLSLGK SEQ ID NO: 337 (AS17049 HCAb amino acid sequence; CDRs are
underlined, linker is bolded)
QVKLVESGGGSVQAGGYLRLSCAAS<u>GDTNNLNFRG</u>WFRQAPGKEREGVA<u>VITHSGSTYYAESVKGR</u>
FTISQDLAKNTMYLQMNSLKPEDTAMYYCAA<u>ADVWRISWSFVPELFSYW</u>GQGTQVTVSSESKYGPP
CPPCPAPEFLGGPSVFLFPPKPKDTLMISRTPEVTCVVVDVSQEDPEVQFNWYVDGVEVHNAKTKPR
EEQFNSTYRVVSVLTVLHQDWLNGKEYKCKVSNKGLPSSIEKTISKAKGQPREPQVYTLPPSQEEMTK TABLE 3-continued SEQUENCE LISTING
Anti-PD-1 sdAb SEQ ID NOs

| SEQ ID NO: FR1 | SEQ ID NO: CDR1 | SEQ ID NO: FR2 | SEQ ID NO: CDR2 | SEQ ID NO: FR3 | SEQ ID NO: CDR3 | SEQ ID NO: FR4 |
| --- | --- | --- | --- | --- | --- | --- |

NQVSLTCLVKGFYPSDIAVEWESNGQPENNYKTTPPVLDSDGSFFLYSRLTVDKSRWQEGNVFSCSV
MHEALHNHYTQKSLSLSLGK

SEQ ID NO: 338 (AS17118 HCAb amino acid sequence; CDRs are
underlined, linker is bolded)
QVQLVESGGGSVQAGGSLRLSCAGS<u>GFTFNNYAMG</u>WFRQAPGKEREGIA<u>GIWTGGGSTYYADSVKG</u>
RFTISEDVAKNTVYLQMDSLKPEDTAMYYCAA<u>ERWDYSDWRRLKRGDYNY</u>WGQGTQVTVSSESK
YGPPCPPCPAPEFLGGPSVFLFPPKPKDTLMISRTPEVTCVVVDVSQEDPEVQFNWYVDGVEVHNAK
TKPREEQFNSTYRVVSVLTVLHQDWLNGKEYKCKVSNKGLPSSIEKTISKAKGQPREPQVYTLPPSQE
EMTKNQVSLTCLVKGFYPSDIAVEWESNGQPENNYKTTPPVLDSDGSFFLYSRLTVDKSRWQEGNVF
SCSVMHEALHNHYTQKSLSLSLGK SEQ ID NO: 339 (AS24984 HCAb amino acid sequence; CDRs are
underlined, linker is bolded)
QVHLMESGGGSVPSGGSLRLSCAVS<u>GSGYSYSRGCFAW</u>FQQRPGKEREGVAI<u>INMDGHTRYSDSVQG</u>
RFIISQDKAKNTLHLQMNTLRPDDTAMYYCAY<u>DRSQCYVLSDRLRLPGTFSD</u>WGQGTQVTVSSESK
YGPPCPPCPAPEFLGGPSVFLFPPKPKDTLMISRTPEVTCVVVDVSQEDPEVQFNWYVDGVEVHNAK
TKPREEQFNSTYRVVSVLTVLHQDWLNGKEYKCKVSNKGLPSSIEKTISKAKGQPREPQVYTLPPSQE
EMTKNQVSLTCLVKGFYPSDIAVEWESNGQPENNYKTTPPVLDSDGSFFLYSRLTVDKSRWQEGNVF
SCSVMHEALHNHYTQKSLSLSLGK SEQ ID NO: 340 (AS25037 HCAb amino acid sequence; CDRs are
underlined, linker is bolded)
EVQLAESGGGSVQAGGSLKLSCLAS<u>QWISSDCGMA</u>WYRQAPGKERELVS<u>RISSDDTTTYADSVKGRF</u>
TISQDSAKNTLYLQMNKLKTEDTGVYYCAA<u>EAKSTITSLCYPLNY</u>WGQGTQVTVSSESKYGPPCPPC
PAPEFLGGPSVFLFPPKPKDTLMISRTPEVTCVVVDVSQEDPEVQFNWYVDGVEVHNAKTKPREEQF
NSTYRVVSVLTVLHQDWLNGKEYKCKVSNKGLPSSIEKTISKAKGQPREPQVYTLPPSQEEMTKNQV
SLTCLVKGFYPSDIAVEWESNGQPENNYKTTPPVLDSDGSFFLYSRLTVDKSRWQEGNVFSCSVMHE
ALHNHYTQKSLSLSLGK SEQ ID NO: 341 (AS25064 HCAb amino acid sequence; CDRs are
underlined, linker is bolded)
QVQLVESGGGSVQAGGSLRLTCAAT<u>GYSWRPDCMG</u>WYRQAAEKEREGVAV<u>IDADGITSYADAAKG</u>
RFTISRDNNKITLYLQMLKPDDTGMYVCVV<u>GWRVSSGGNCQFNDY</u>WGQGTQVTVSSESKYGPPCP
PCPAPEFLGGPSVFLFPPKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPREPQVYTLPPSQEEMTKN
QVSLTCLVKGFYPSDIAVEWESNGQPENNYKTTPPVLDSDGSFFLYSRLTVDKSRWQEGNVFSCSVM
HEALHNHYTQKSLSLSLGK SEQ ID NO: 342 (AS25067 HCAb amino acid sequence; CDRs are
underlined, linker is bolded)
QVHLMESGGGAVQTGGSLRLSCAVS<u>GISISPDCMG</u>WFRQAPGKKREAVT<u>TIFANTGSARYGDSVKGR</u>
FTSSGNAKNTLYLQMDSVKLDDTGTYYCAA<u>RFTGGDCFDHQPLAW</u>RFWGQGTQVTVSSESKYGP
PCPPCPAPEFLGGPSVFLFPPKPKDTLMISRTPEVTCVVVDVSQEDPEVQFNWYVDGVEVHNAKTKP
REEQFNSTYRVVSVLTVLHQDWLNGKEYKCKVSNKGLPSSIEKTISKAKGQPREPQVYTLPPSQEEMT
KNQVSLTCLVKGFYPSDIAVEWESNGQPENNYKTTPPVLDSDGSFFLYSRLTVDKSRWQEGNVFSCS
VMHEALHNHYTQKSLSLSLGK SEQ ID NO: 343 (AS25071 HCAb amino acid sequence; CDRs are
underlined, linker is bolded)
EVQLAESGGGSVQSGGSLRLSCAVS<u>GSGYSYSRGCFAW</u>FQQRPGKEREGVAI<u>INSDGHTAYSDSVQG</u>
RFIISQDKAKNTLYLQMNSLKPDDTAMYYCAY<u>DRSQCYVLRDRLRLPDTFTD</u>WGQGTQVTVSSESK
YGPPCPPCPAPEFLGGPSVFLFPPKPKDTLMISRTPEVTCVVVDVSQEDPEVQFNWYVDGVEVHNAK
TKPREEQFNSTYRVVSVLTVLHQDWLNGKEYKCKVSNKGLPSSIEKTISKAKGQPREPQVYTLPPSQE
EMTKNQVSLTCLVKGFYPSDIAVEWESNGQPENNYKTTPPVLDSDGSFFLYSRLTVDKSRWQEGNVF
SCSVMHEALHNHYTQKSLSLSLGK SEQ ID NO: 344 (AS25115 HCAb amino acid sequence; CDRs are
underlined, linker is bolded)
QVHLVESGGASVQAGGSLRLSCAAT<u>AYTASNYCMG</u>WFRQSPGKEREAVA<u>SINDDGVTSYADSVKGR</u>
FTISQDSAKKTLYLQMNRLKPEDTAMYYCAA<u>TPDGYCYAERLSRWRYEF</u>WGQGTQVTVSSESKYGP
PCPPCPAPEFLGGPSVFLFPPKPKDTLMISRTPEVTCVVVDVSQEDPEVQFNWYVDGVEVHNAKTKP
REEQFNSTYRVVSVLTVLHQDWLNGKEYKCKVSNKGLPSSIEKTISKAKGQPREPQVYTLPPSQEEMT
KNQVSLTCLVKGFYPSDIAVEWESNGQPENNYKTTPPVLDSDGSFFLYSRLTVDKSRWQEGNVFSCS
VMHEALHNHYTQKSLSLSLGK SEQ ID NO: 345 (AS25117 HCAb amino acid sequence; CDRs are
underlined, linker is bolded)
EVQLAESGGGSVQAGGSLRLSCVIS<u>GTSISPDCMG</u>WFRQAPGKKREAVM<u>SIFTNTGSTRYGDSVKGRF</u>
TSSQGNAKNTLYLQMDSLKLDDTATYYCAA<u>RYTGGDCFNLEPLAWRF</u>WGQGTQVTVSSESKYGPP
CPPCPAPEFLGGPSVFLFPPKPKDTLMISRTPEVTCVVVDVSQEDPEVQFNWYVDGVEVHNAKTKPR
EEQFNSTYRVVSVLTVLHQDWLNGKEYKCKVSNKGLPSSIEKTISKAKGQPREPQVYTLPPSQEEMTK TABLE 3-continued SEQUENCE LISTING
Anti-PD-1 sdAb SEQ ID NOs

| SEQ ID NO: FR1 | SEQ ID NO: CDR1 | SEQ ID NO: FR2 | SEQ ID NO: CDR2 | SEQ ID NO: FR3 | SEQ ID NO: CDR3 | SEQ ID NO: FR4 |
| --- | --- | --- | --- | --- | --- | --- |

NQVSLTCLVKGFYPSDIAVEWESNGQPENNYKTTPPVLDSDGSFFLYSRLTVDKSRWQEGNVFSCSV
MHEALHNHYTQKSLSLSLGK

SEQ ID NO: 346 (AS25119 HCAb amino acid sequence; CDRs are
underlined, linker is bolded)
QVQLVESGGGSVQAGGPLRLTCAAT<u>GYSWRPDCMG</u>WYRQAAEKEREGVA<u>VIDADGITSYADAAKG</u>
RFTISRDNNNITLYLQMLKPDDTGMYVCVI<u>GWRVSSGGNCQFNDY</u>WGQGTQVTVSS**ESKYGPPCPP
CP**APEFLGGPSVFLFPPKPKDTLMISRTPEVTCVVVDVSQEDPEVQFNWYVDGVEVHNAKTKPREEQ
FNSTYRVVSVLTVLHQDWLNGKEYKCKVSNKGLPSSIEKTISKAKGQPREPQVYTLPPSQEEMTKNQ
VSLTCLVKGFYPSDIAVEWESNGQPENNYKTTPPVLDSDGSFFLYSRLTVDKSRWQEGNVFSCSVMH
EALHNHYTQKSLSLSLGK SEQ ID NO: 347 (AS25149 HCAb amino acid sequence; CDRs are
underlined, linker is bolded)
QVQLVESGGGSVQSGGSLKLSCAVS<u>GSGYSYSRGCFA</u>WFQQRPGKEREGVAI<u>INSDGHTRYSDSVQG</u>
RFIISQDKAKNTLYLQMNSLKPDDAAMYYCAY<u>DRNQCYVLLDRLRLPGTFSDW</u>GQGTQVTVSS**ESK
YGPPCPPCP**APEFLGGPSVFLFPPKPKDTLMISRTPEVTCVVVDVSQEDPEVQFNWYVDGVEVHNAK
TKPREEQFNSTYRVVSVLTVLHQDWLNGKEYKCKVSNKGLPSSIEKTISKAKGQPREPQVYTLPPSQE
EMTKNQVSLTCLVKGFYPSDIAVEWESNGQPENNYKTTPPVLDSDGSFFLYSRLTVDKSRWQEGNVF
SCSVMHEALHNHYTQKSLSLSLGK SEQ ID NO: 348 (AS25156 HCAb amino acid sequence; CDRs are
underlined, linker is bolded)
EVQLVESGGGSVQSGGSLRLSCAVS<u>GSGYSYSRGCFA</u>WFQQRPGKEREGVAI<u>INSDGHTRYSDSVQG</u>
RFIISQDKAKNTLYLQMNSLKPDDTAMYYCAY<u>DCSQCYVLRDRLRLPDTFTDW</u>GQGTQVTVSS**ESK
YGPPCPPCP**APEFLGGPSVFLFPPKPKDTLMISRTPEVTCVVVDVSQEDPEVQFNWYVDGVEVHNAK
TKPREEQFNSTYRVVSVLTVLHQDWLNGKEYKCKVSNKGLPSSIEKTISKAKGQPREPQVYTLPPSQE
EMTKNQVSLTCLVKGFYPSDIAVEWESNGQPENNYKTTPPVLDSDGSFFLYSRLTVDKSRWQEGNVF
SCSVMHEALHNHYTQKSLSLSLGK SEQ ID NO: 349 (AS25164 HCAb amino acid sequence; CDRs are
underlined, linker is bolded)
EVQLVESGGGSVQSGGSLRLSCAVS<u>GSGYSYNRGCFA</u>WFQQRPGKEREGVAI<u>INSDGHTTYGDSVQG</u>
RFIISQDKAKNTLDLQMNSLKPDDTAMYYCAY<u>DRNQCYVLRDRLRLPDTFTDW</u>GQGTQVTVSS**ESK
YGPPCPPCP**APEFLGGPSVFLFPPKPKDTLMISRTPEVTCVVVDVSQEDPEVQFNWYVDGVEVHNAK
TKPREEQFNSTYRVVSVLTVLHQDWLNGKEYKCKVSNKGLPSSIEKTISKAKGQPREPQVYTLPPSQE
EMTKNQVSLTCLVKGFYPSDIAVEWESNGQPENNYKTTPPVLDSDGSFFLYSRLTVDKSRWQEGNVF
SCSVMHEALHNHYTQKSLSLSLGK SEQ ID NO: 350 (AS25170 HCAb amino acid sequence; CDRs are
underlined, linker is bolded)
QVKLVESGGGLVQSGGSLRLSCAVS<u>GSGYSYSRGCFA</u>WFQQRPGKEREGVAI<u>INMDGHTMYSDLAQ</u>
GRFIISQDKAKNTLYLQMNSLKPDDTAMYYCAY<u>DRDQCYVLRDRLRLPDTFNDW</u>GQGTQVTVSS**ES
KYGPPCPPCP**APEFLGGPSVFLFPPKPKDTLMISRTPEVTCVVVDVSQEDPEVQFNWYVDGVEVHNA
KTKPREEQFNSTYRVVSVLTVLHQDWLNGKEYKCKVSNKGLPSSIEKTISKAKGQPREPQVYTLPPSQ
EEMTKNQVSLTCLVKGFYPSDIAVEWESNGQPENNYKTTPPVLDSDGSFFLYSRLTVDKSRWQEGNV
FSCSVMHEALHNHYTQKSLSLSLGK SEQ ID NO: 351 (AS25222 HCAb amino acid sequence; CDRs are
underlined, linker is bolded)
QIQLVESGGGSVQAGGSLRLSCAVT<u>GISISPDCMG</u>WFRQAPGKKREAVAT<u>IFTNTASTRYGDSVKGRF</u>
TSSQGNGKNTLYLQMDSLNVDDTATYYCAA<u>RYTGGNCFNLEPLAWH</u>FWGQGTQVTVSS**ESKYGPP
CPPCP**APEFLGGPSVFLFPPKPKDTLMISRTPEVTCVVVDVSQEDPEVQFNWYVDGVEVHNAKTKPR
EEQFNSTYRVVSVLTVLHQDWLNGKEYKCKVSNKGLPSSIEKTISKAKGQPREPQVYTLPPSQEEMTK
NQVSLTCLVKGFYPSDIAVEWESNGQPENNYKTTPPVLDSDGSFFLYSRLTVDKSRWQEGNVFSCSV
MHEALHNHYTQKSLSLSLGK SEQ ID NO: 352 (AS25396 HCAb amino acid sequence; CDRs are
underlined, linker is bolded)
QVHLMESGGGSVQAGGSLRLSCVVS<u>GISISPDCMG</u>WFRQAPGKKREAVAT<u>IFTNTRRTRYGDSVKGR</u>
VTSSQGNAKNTLYLKMDNLRHDDTATYYCAA<u>RYTGGDCFNLDPLSWRF</u>WGQGTQVTVSS**ESKYGP
PCPPCP**APEFLGGPSVFLFPPKPKDTLMISRTPEVTCVVVDVSQEDPEVQFNWYVDGVEVHNAKTKP
REEQFNSTYRVVSVLTVLHQDWLNGKEYKCKVSNKGLPSSIEKTISKAKGQPREPQVYTLPPSQEEMT
KNQVSLTCLVKGFYPSDIAVEWESNGQPENNYKTTPPVLDSDGSFFLYSRLTVDKSRWQEGNVFSCS
VMHEALHNHYTQKSLSLSLGK SEQ ID NO: 353 (AS25457 HCAb amino acid sequence; CDRs are
underlined, linker is bolded)
QVQLVESGGGSVQAGGSLRLSCAVS<u>GISISPDCMG</u>WFRQAPGKKREAVAT<u>IFTNTRSTRYGDSVKGRF</u>
TSSQGNAKNTLYLQMDSLKLDDTATYYCAA<u>RYTGGDCFNLEPVAWRF</u>WGQGTQVTVSS**ESKYGPP
CPPCP**APEFLGGPSVFLFPPKPKDTLMISRTPEVTCVVVDVSQEDPEVQFNWYVDGVEVHNAKTKPR
EEQFNSTYRVVSVLTVLHQDWLNGKEYKCKVSNKGLPSSIEKTISKAKGQPREPQVYTLPPSQEEMTK TABLE 3-continued SEQUENCE LISTING
Anti-PD-1 sdAb SEQ ID NOs

| SEQ ID NO: FR1 | SEQ ID NO: CDR1 | SEQ ID NO: FR2 | SEQ ID NO: CDR2 | SEQ ID NO: FR3 | SEQ ID NO: CDR3 | SEQ ID NO: FR4 |
|---|---|---|---|---|---|---|

NQVSLTCLVKGFYPSDIAVEWESNGQPENNYKTTPPVLDSDGSFFLYSRLTVDKSRWQEGNVFSCSV
MHEALHNHYTQKSLSLSLGK

SEQ ID NO: 354 (AS25487 HCAb amino acid sequence; CDRs are
underlined, linker is bolded)
EVQLVESGGGLVQPGGSLRLSCAAS<u>GFTFSVWSMS</u>WVRQAPGEGLEWVS<u>TITGSGAQTYYASSVRG</u>
RFTTSRDNAKNTVYLQMNSLKSDDTAVYYCER<u>GNGQTAMEALINPP</u>ERPGTQVTVSS**ESKYGPPCPP
CP**APEFLGGPSVFLFPPKPKDTLMISRTPEVTCVVVDVSQEDPEVQFNWYVDGVEVHNAKTKPREEQ
FNSTYRVVSVLTVLHQDWLNGKEYKCKVSNKGLPSSIEKTISKAKGQPREPQVYTLPPSQEEMTKNQ
VSLTCLVKGFYPSDIAVEWESNGQPENNYKTTPPVLDSDGSFFLYSRLTVDKSRWQEGNVFSCSVMH
EALHNHYTQKSLSLSLGK SEQ ID NO: 355 (AS25095 HCAb amino acid sequence; CDRs are
underlined, linker is bolded)
QVQLVESGGGLMQPGGSLRLSCAAS<u>GFTFSSYWMY</u>WVRQAPGKGLEWVS<u>VINRAGDSAWYADSVT</u>
GRFTISRDNAKNTVYLQMDSLKPEDTAMYYCAAD<u>SRGYGGDWYKLLSDFNY</u>CGQGTQVTVSS**ESK
YGPPCPCP**APEFLGGPSVFLFPPKPKDTLMISRTPEVTCVVVDVSQEDPEVQFNWYVDGVEVHNAK
TKPREEQFNSTYRVVSVLTVLHQDWLNGKEYKCKVSNKGLPSSIEKTISKAKGQPREPQVYTLPPSQE
EMTKNQVSLTCLVKGFYPSDIAVEWESNGQPENNYKTTPPVLDSDGSFFLYSRLTVDKSRWQEGNVF
SCSVMHEALHNHYTQKSLSLSLGK SEQ ID NO: 356 (AS25435 HCAb amino acid sequence; CDRs are
underlined, linker is bolded)
QVQLVESGGGSVQAGGSLRLSCAAT<u>AYTASFYCMG</u>WFRQAPGKEREAVAS<u>INDDGVTMYADSVKG</u>
QFTISQDSATKTLYLQMNRLKPEDTAMYYCAA<u>TPEGYCYAERLSTWRYTF</u>WGQGTQVTVSS**ESKYG
PPCPPCP**APEFLGGPSVFLFPPKPKDTLMISRTPEVTCVVVDVSQEDPEVQFNWYVDGVEVHNAKTK
PREEQFNSTYRVVSVLTVLHQDWLNGKEYKCKVSNKGLPSSIEKTISKAKGQPREPQVYTLPPSQEEM
TKNQVSLTCLVKGFYPSDIAVEWESNGQPENNYKTTPPVLDSDGSFFLYSRLTVDKSRWQEGNVFSCS
VMHEALHNHYTQKSLSLSLGK SEQ ID NO: 357 (AS15193VH8 HCAb amino acid sequence; CDRs are
underlined, linker is bolded)
EVQLVESGGGLVQPGGSLRLSCAVS<u>GNIYNRNFMG</u>WFRQAPGKGLEGVS<u>AIYTGTSRTYYADSVKG</u>
RFTISRDNSKNTVYLQMNSLRAEDTAVYYCAA<u>DLRDGFWDTGVWNT</u>WGQGTLVTVSS**ESKYGPPC
PPCP**APEVLGGPSVFLFPPKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPREPQVYTLPPSQEEMTKN
QVSLTCLVKGFYPSDIAVEWESNGQPENNYKTTPPVLDSDGSFFLYSRLTVDKSRWQEGNVFSCSVM
HEALHNHYTQKSLSLSLGK SEQ ID NO: 358 (AS15193VH8M1 HCAb amino acid sequence; CDRs are
underlined, linker is bolded)
EVQLVESGGGLVQPGGSLRLSCAVS<u>GNIYNRNFMG</u>WFRQAPGKGLEGVS<u>AIYTGTSRTYYADSVKG</u>
RFTISRDNSKNTVYLQMNSLRAEDTAVYYCAA<u>DLREGFWDTGVWNT</u>WGQGTLVTVSS**ESKYGPPC
PPCP**APEFLGGPSVFLFPPKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPREPQVYTLPPSQEEMTKN
QVSLTCLVKGFYPSDIAVEWESNGQPENNYKTTPPVLDSDGSFFLYSRLTVDKSRWQEGNVFSCSVM
HEALHNHYTQKSLSLSLGK SEQ ID NO: 359 (AS15193VH18 HCAb amino acid sequence; CDRs are
underlined, linker is bolded)
EVQLVESGGGLVQPGGSLRLSCAVS<u>GNIYNRNFMG</u>WFRQAPGKGREGVS<u>AIYTGTSRTYYADSVKG</u>
RFTISRDNAKNTVYLQMNSLRPEDTAVYYCAA<u>DLRDGFWDTGVWNT</u>WGQGTLVTVSS**ESKYGPPC
PPCP**APEFLGGPSVFLFPPKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPREPQVYTLPPSQEEMTKN
QVSLTCLVKGFYPSDIAVEWESNGQPENNYKTTPPVLDSDGSFFLYSRLTVDKSRWQEGNVFSCSVM
HEALHNHYTQKSLSLSLGK SEQ ID NO: 360 (AS15193VH18M1 HCAb amino acid sequence; CDRs are
underlined, linker is bolded)
EVQLVESGGGLVQPGGSLRLSCAVS<u>GNIYNRNFMG</u>WFRQAPGKGREGVS<u>AIYTGTSRTYYADSVKG</u>
RFTISRDNAKNTVYLQMNSLRPEDTAVYYCAA<u>DLREGFWDTGVWNT</u>WGQGTLVTVSS**ESKYGPPC
PPCP**APEFLGGPSVFLFPPKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPREPQVYTLPPSQEEMTKN
QVSLTCLVKGFYPSDIAVEWESNGQPENNYKTTPPVLDSDGSFFLYSRLTVDKSRWQEGNVFSCSVM
HEALHNHYTQKSLSLSLGK SEQ ID NO: 361 (human PD-1 amino acid sequence, excluding the
leader peptide)
PGWFLDSPDRPWNPPTFSPALLVVTEGDNATFTCSFSNTSESFVLNWYRMSPSNQTDKLAAFPEDRSQ
PGQDCRFRVTQLPNGRDFHMSVVRARRNDSGTYLCGAISLAPKAQIKESLRAELRVTERRAEVPTAHP
SPSPRPAGQFQTLVVGVVGGLLGSLVLLVWVLAVICSRAARGTIGARRTGQPLKEDPSAVPVFSVDYG
ELDFQWREKTPEPPVPCVPEQTEYATIVFPSGMGTSSPARRGSADGPRSAQPLRPEDGHCSWPL TABLE 3-continued SEQUENCE LISTING
Anti-PD-1 sdAb SEQ ID NOs

| SEQ ID NO: FR1 | SEQ ID NO: CDR1 | SEQ ID NO: FR2 | SEQ ID NO: CDR2 | SEQ ID NO: FR3 | SEQ ID NO: CDR3 | SEQ ID NO: FR4 |
|---|---|---|---|---|---|---|

SEQ ID NO: 362 (extracellular domain of human PD-1 amino acid sequence)
PGWFLDSPDRPWNPPTFSPALLVVTEGDNATFTCSFSNTSESFVLNWYRMSPSNQTDKLAAFPEDRSQ
PGQDCRFRVTQLPNGRDFHMSVVRARRNDSGTYLCGAISLAPKAQIKESLRAELRVTERRAEVPTAHP
SPSPRPAGQFQTLV SEQ ID NO: 363 (IgG4 Fc amino acid sequence)
APEFLGGPSVFLFPPKPKDTLMISRTPEVTCVVVDVSQEDPEVQFNWYVDGVEVHNAKTKPREEQFNS
TYRVVSVLTVLHQDWLNGKEYKCKVSNKGLPSSIEKTISKAKGQPREPQVYTLPPSQEEMTKNQVSL
TCLVKGFYPSDIAVEWESNGQPENNYKTTPPVLDSDGSFFLYSRLTVDKSRWQEGNVFSCSVMHEAL
HNHYTQKSLSLSLGK SEQ ID NO: 364 (IgG1 inert Fc amino acid sequence)
APELLGGPSVFLFPPKPKDTLMISRTPEVTCVVVDVSHEDPEVKFNWYVDGVEVHNAKTKPREEQYA
STYRVVSVLTVLHQDWLNGKEYKCKVSNKALPAPIEKTISKAKGQPREPQVYTLPPSREEMTKNQVS
LTCLVKGFYPSDIAVEWESNGQPENNYKTTPPVLDSDGSFFLYSKLTVDKSRWQQGNVFSCSVMHEA
LHNHYTQKSLSLSPGK SEQ ID NO: 365 (IgG1 Fc amino acid sequence)
APELLGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSRDELTKNQVSL
TCLVKGFYPSDIAVEWESNGQPENNYKTTPPVLDSDGSFFLYSKLTVDKSRWQQGNVFSCSVMHEAL
HNHYTQKSLSLSPGK SEQ ID NO: 366 (human acceptor amino acid sequence)
QVQLVESGGGVVQPGGSLRLSCAASGFTFSSYGMHWVRQAPGKGLEWVSVIYSGGSSTYYADSVKG
RFTISRDNSKNTLYLQMNSLRAEDTAVYYCAK SEQ ID NO: 367 (human IgG4 (hIgG4) hinge amino acid sequence)
ESKYGPPCPPCP SEQ ID NO: 368 (mutated human IgG1 (hIgG1) hinge amino acid sequence)
EPKSSDKTHTSPPSP SEQ ID NO: 369 (human IgG1 (hIgG1) hinge amino acid sequence)
EPKSCDKTHTCPPCP SEQ ID NO: 370 (linker peptide (9GS) amino acid sequence)
GGGGSGGGS SEQ ID NO: 371 (linker peptide amino acid sequence)
GGGGSGGGGSGGGGS SEQ ID NO: 372 (linker peptide amino acid sequence, n is an integer of at least one)
$(G)_n$ SEQ ID NO: 373 (linker peptide amino acid sequence, n is an integer of at least one)
$(GS)_n$ SEQ ID NO: 374 (linker peptide amino acid sequence, n is an integer of at least one)
$(GSGGS)_n$ SEQ ID NO: 375 (linker peptide amino acid sequence, n is an integer of at least one)
$(GGGS)_n$ SEQ ID NO: 376 (Linker peptide amino acid sequence, n is an integer of at least one)
$(GGGGS)_n$ SEQ ID NO: 377 (anti-TIGIT mAb tiragolumab heavy chain amino acid sequence)
EVQLQQSGPGLVKPSQTLSLTCAISGDSVSSNSAAWNWIRQSPSRGLEWLGKTYYRFKWYSDYAVSV
KGRITINPDTSKNQFSLQLNSVTPEDTAVFYCTRESSTTYDLLAGPFDYWGQGTLVTVSSASTKGPSVFP
LAPSSKSTSGGTAALGCLVKDYFPEPVTVSWNSGALTSGVHTFPAVLQSSGLYSLSSVVTVPSSSLGTQ
TYICNVNHKPSNTKVDKKVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPA
PIEKTISKAKGQPREPQVYTLPPSREEMTKNQVSLTCLVKGFYPSDIAVEWESNGQPENNYKTTPPVLD
SDGSFFLYSKLTVDKSRWQQGNVFSCSVMHEALHNHYTQKSLSLSPGK TABLE 3-continued SEQUENCE LISTING
Anti-PD-1 sdAb SEQ ID NOs

| SEQ ID NO: FR1 | SEQ ID NO: CDR1 | SEQ ID NO: FR2 | SEQ ID NO: CDR2 | SEQ ID NO: FR3 | SEQ ID NO: CDR3 | SEQ ID NO: FR4 |
|---|---|---|---|---|---|---|

SEQ ID NO: 378 (anti-TIGIT mAb tiragolumab light chain amino acid sequence)
DIVMTQSPDSLAVSLGERATINCKSSQTVLYSSNNKKYLAWYQQKPGQPPNLLIYWASTRESGVPDRE
SGSGSGTDFTLTISSLQAEDVAVYYCQQYYSTPFTFGPGTKVEIKRTVAAPSVFIFPPSDEQLKSGTASV
VCLLNNFYPREAKVQWKVDNALQSGNSQESVTEQDSKDSTYSLSSTLTLSKADYEKHKVYACEVTH
QGLSSPVTKSFNRGEC SEQ ID NO: 379 (anti-LAG-3 mAb relatlimab heavy chain amino acid sequence)
QVQLQQWGAGLLKPSETLSLTCAVYGGSFSDYYWNWIRQPPGKGLEWIGEINHRGSTNSNPSLKSRV
TLSLDTSKNQFSLKLRSVTAADTAVYYCAFGYSDYEYNWFDPWGQGTLVTVSSASTKGPSVFPLAPC
SRSTSESTAALGCLVKDYFPEPVTVSWNSGALTSGVHTFPAVLQSSGLYSLSSVVTVPSSSLGTKTYTC
NVDHKPSNTKVDKRVESKYGPPCPPCPAPEFLGGPSVFLFPPKPKDTLMISRTPEVTCVVVDVSQEDPE
VQFNWYVDGVEVHNAKTKPREEQFNSTYRVVSVLTVLHQDWLNGKEYKCKVSNKGLPSSIEKTISK
AKGQPREPQVYTLPPSQEEMTKNQVSLTCLVKGFYPSDIAVEWESNGQPENNYKTTPPVLDSDGSFFL
YSRLTVDKSRWQEGNVFSCSVMHEALHNHYTQKSLSLSLG SEQ ID NO: 380 (anti-LAG-3 mAb relatlimab light chain amino acid sequence)
EIVLTQSPATLSLSPGERATLSCRASQSISSYLAWYQQKPGQAPRLLIYDASNRATGIPARFSGSGSGTD
FTLTISSLEPEDFAVYYCQQRSNWPLTFGQGTNLEIKRTVAAPSVFIFPPSDEQLKSGTASVVCLLNNFY
PREAKVQWKVDNALQSGNSQESVTEQDSKDSTYSLSSTLTLSKADYEKHKVYACEVTHQGLSSPVTK
SFNRGEC SEQ ID NO: 381 (anti-TIM-3 mAb MBG453 heavy chain amino acid sequence)
QVQLVQSGAEVKKPGASVKVSCKASGYTFTSYNMHWVRQAPGQGLEWIGDIYPGQGDTSYNQKFK
GRATMTADKSTSTVYMELSSLRSEDTAVYYCARVGGAFPMDYWGQGTLVTVSSASTKGPSVFPLAP
CSRSTSESTAALGCLVKDYFPEPVTVSWNSGALTSGVHTFPAVLQSSGLYSLSSVVTVPSSSLGTKTYT
CNVDHKPSNTKVDKRVESKYGPPCPPCPAPEFLGGPSVFLFPPKPKDTLMISRTPEVTCVVVDVSQEDP
EVQFNWYVDGVEVHNAKTKPREEQFNSTYRVVSVLTVLHQDWLNGKEYKCKVSNKGLPSSIEKTIS
KAKGQPREPQVYTLPPSQEEMTKNQVSLTCLVKGFYSDIAVEWESNGQPENNYKTTPPVLDSDGSFF
LYSRLTVDKSRWQEGNVFSCSVMHEALHNHYTQKSLSLSLGK SEQ ID NO: 382 (anti-TIM-3 mAb MBG453 light chain amino acid sequence)
DIVLTQSPDSLAVSLGERATINCRASESVEYYGTSLMQWYQQKPGQPPKLLIYAASNVESGVPDRFSG
SGSGTDFTLTISSLQAEDVAVYYCQQSRKDPSTFGGGTKVEIKRTVAAPSVFIFPPSDEQLKSGTASVV
CLLNNFYPREAKVQWKVDNALQSGNSQESVTEQDSKDSTYSLSSTLTLSKADYEKHKVYACEVTHQ
GLSSPVTKSFNRGEC SEQ ID NO: 383 (anti-CTLA-4 mAb Ipilimumab heavy chain amino acid sequence)
QVQLVESGGGVVQPGRSLRLSCAASGFTFSSYTMHWVRQAPGKGLEWVTFISYDGNNKYYADSVKG
RFTISRDNSKNTLYLQMNSLRAEDTAIYYCARTGWLGPFDYWGQGTLVTVSSASTKGPSVFPLAPSSK
STSGGTAALGCLVKDYFPEPVTVSWNSGALTSGVHTFPAVLQSSGLYSLSSVVTVPSSSLGTQTYICN
VNHKPSNTKVDKRVEPKSCDKTHTCPPCPAPELLGGPSVFLFPPKPKDTLMTSRTPEVTCVVVDVSHE
DPEVKFNWYVDGVEVHNAKTKPREEQYNSTYRVVSVLTVLHQDWLNGKEYKCKVSNKALPAPIEK
TISKAKGQPREPQVYTLPPSRDELTKNQVSLTCLVKGFYPSDIAVEWESNGQPENNYKTTPPVLDSDG
SFFLYSKLTVDKSRWQQGNVFSCSVMHEALHNHYTQKSLSLSPGK SEQ ID NO: 384 (anti-CTLA-4 mAb Ipilimumab light chain amino acid sequence)
EIVLTQSPGTLSLSPGERATLSCRASQSVGSSYLAWYQQKPGQAPRLLIYGAFSRATGIPDRFSGSGSGT
DFTLTISRLEPEDFAVYYCQQYGSSPWTFGQGTKVEIKRTVAAPSVFIFPPSDEQLKSGTASVVCLLNN
FYPREAKVQWKVDNALQSGNSQESVTEQDSKDSTYSLSSTLTLSKADYEKHKVYACEVTHQGLSSPV
TKSFNRGEC SEQ ID NO: 385 (anti-PD-1 mAb Pembrolizumab (IgG4 S228P) heavy chain amino acid sequence)
QVQLVQSGVEVKKPGASVKVSCKASGYTFTNYYMYWVRQAPGQGLEWMGGINPSNGGTNFNEKFK
NRVTLTTDSSTTTAYMELKSLQFDDTAVYYCARRDYRFDMGFDYWGQGTTVTVSSASTKGPSVFPL
APCSRSTSESTAALGCLVKDYFPEPVTVSWNSGALTSGVHTFPAVLQSSGLYSLSSVVTVPSSSLGTKT
YTCNVDHKPSNTKVDKRVESKYGPPCPPCPAPEFLGGPSVFLFPPKPKDTLMISRTPEVTCVVVDVSQ
EDPEVQFNWYVDGVEVHNAKTKPREEQFNSTYRVVSVLTVLHQDWLNGKEYKCKVSNKGLPSSIEK
TISKAKGQPREPQVYTLPPSQEEMTKNQVSLTCLVKGFYPSDIAVEWESNGQPENNYKTTPPVLDSDG
SFFLYSRLTVDKSRWQEGNVFSCSVMHEALHNHYTQKSLSLSLGK SEQ ID NO: 386 (anti-PD-1 mAb Pembrolizumab (IgG4 S228P) light chain amino acid sequence)
EIVLTQSPATLSLSPGERATLSCRASKGVSTSGYSYLHWYQQKPGQAPRLLIYLASYLESGVPARFSGS
GSGTDFTLTISSLEPEDFAVYYCQHSRDLPLTFGGGTKVEIKRTVAAPSVFIFPPSDEQLKSGTASVVCL

TABLE 3-continued

SEQUENCE LISTING
Anti-PD-1 sdAb SEQ ID NOs

| SEQ ID NO: FR1 | SEQ ID NO: CDR1 | SEQ ID NO: FR2 | SEQ ID NO: CDR2 | SEQ ID NO: FR3 | SEQ ID NO: CDR3 | SEQ ID NO: FR4 |
|---|---|---|---|---|---|---|

LNNFYPREAKVQWKVDNALQSGNSQESVTEQDSKDSTYSLSSTLTLSKADYEKHKVYACEVTHQGL
SSPVTKSFNRGEC

---

What is claimed is:

1. An isolated anti-programmed cell death protein 1 (anti-PD-1) construct comprising a single-domain antibody (sdAb) moiety specifically recognizing PD-1 (anti-PD-1 sdAb moiety), wherein the anti-PD-1 sdAb moiety comprises any one of the following:
   (1) a CDR1 comprising the amino acid sequence of SEQ ID NO: 70, a CDR2 comprising the amino acid sequence of SEQ ID NO: 142, and a CDR3 comprising the amino acid sequence of SEQ ID NO: 214; or
   (2) a CDR1 comprising the amino acid sequence of SEQ ID NO: 43, a CDR2 comprising the amino acid sequence of SEQ ID NO: 115, and a CDR3 comprising the amino acid sequence of SEQ ID NO: 187.

2. The isolated anti-PD-1 construct of claim 1, wherein the anti-PD-1 sdAb moiety comprises a $V_H H$ domain comprising the amino acid sequence of any one of SEQ ID NOs: 295 and 321-324.

3. The isolated anti-PD-1 construct of claim 1, wherein the anti-PD-1 sdAb moiety is camelid, chimeric, partially humanized, or fully humanized.

4. The isolated anti-PD-1 construct of claim 1, wherein the isolated anti-PD-1 construct is a heavy chain-only antibody (HCAb) comprising the anti-PD-1 sdAb moiety fused to an Fc fragment via a linker.

5. The isolated anti-PD-1 construct of claim 4, wherein the HCAb is dimeric.

6. The isolated anti-PD-1 construct of claim 4, wherein the Fc fragment is a human IgG1 (hIgG1) Fc, an hIgG1 Fc comprising an effectorless mutation, an hIgG4 Fc, or an hIgG4 Fc (S228P).

7. The isolated anti-PD-1 construct of claim 4, wherein the linker comprises the amino acid sequence of any one of SEQ ID NOs: 367-376.

8. The isolated anti-PD-1 construct of claim 4, wherein the HCAb comprises the amino acid sequence of any one of SEQ ID NOs: 331 and 357-360.

9. The isolated anti-PD-1 construct of claim 1, wherein the isolated anti-PD-1 construct further comprises a second antibody moiety specifically recognizing a second epitope.

10. The isolated anti-PD-1 construct of claim 9, wherein the anti-PD-1 sdAb moiety and the second antibody moiety are connected by a peptide linker.

11. The isolated anti-PD-1 construct of claim 10, wherein the peptide linker comprises the amino acid sequence of any one of SEQ ID NOs: 367-376.

12. The isolated anti-PD-1 construct of claim 9, wherein the second antibody moiety is a full-length antibody consisting of two heavy chains and two light chains.

13. The isolated anti-PD-1 construct of claim 12, wherein the Fc fragment of the heavy chain is an hIgG1 Fc, an hIgG1 Fc comprising an effectorless mutation, an hIgG4 Fc, or an hIgG4 Fc (S228P).

14. The isolated anti-PD-1 construct of claim 12, wherein the isolated anti-PD-1 construct comprises a configuration selected from the group consisting of:

(a) the N-terminus of the anti-PD-1 sdAb moiety is fused to the C-terminus of one of the heavy chains of the full-length antibody;
(b) the C-terminus of the anti-PD-1 sdAb moiety is fused to the N-terminus of one of the heavy chains of the full-length antibody;
(c) the N-terminus of the anti-PD-1 sdAb moiety is fused to the C-terminus of one of the light chains of the full-length antibody;
(d) the C-terminus of the anti-PD-1 sdAb moiety is fused to the N-terminus of one of the light chains of the full-length antibody;
(e) the isolated anti-PD-1 construct comprises four anti-PD-1 sdAb moieties, wherein the C-terminus of the first anti-PD-1 sdAb moiety is fused to the N-terminus of the first heavy chain of the full-length antibody, the C-terminus of the second anti-PD-1 sdAb moiety is fused to the N-terminus of the second heavy chain of the full-length antibody, the C-terminus of the third anti-PD-1 sdAb moiety is fused to the N-terminus of the first light chain of the full-length antibody, and the C-terminus of the fourth anti-PD-1 sdAb moiety is fused to the N-terminus of the second light chain of the full-length antibody;
(f) the isolated anti-PD-1 construct comprises four anti-PD-1 sdAb moieties, wherein the C-terminus of the first anti-PD-1 sdAb moiety is fused to the N-terminus of the second anti-PD-1 sdAb moiety, and the C-terminus of the second anti-PD-1 sdAb moiety is fused to the N-terminus of the first heavy chain of the full-length antibody, the C-terminus of the third anti-PD-1 sdAb moiety is fused to the N-terminus of the fourth anti-PD-1 sdAb moiety, and the C-terminus of the fourth anti-PD-1 sdAb moiety is fused to the N-terminus of the second heavy chain of the full-length antibody;
(g) the isolated anti-PD-1 construct comprises two anti-PD-1 sdAb moieties, wherein the N-terminus of the first anti-PD-1 sdAb moiety is fused to the C-terminus of the first heavy chain of the full-length antibody, and the N-terminus of the second anti-PD-1 sdAb moiety is fused to the C-terminus of the second heavy chain of the full-length antibody;
(h) the isolated anti-PD-1 construct comprises two anti-PD-1 sdAb moieties, wherein the C-terminus of the first anti-PD-1 sdAb moiety is fused to the N-terminus of the first heavy chain of the full-length antibody, and the C-terminus of the second anti-PD-1 sdAb moiety is fused to the N-terminus of the second heavy chain of the full-length antibody;
(i) the isolated anti-PD-1 construct comprises two anti-PD-1 sdAb moieties, wherein the N-terminus of the first anti-PD-1 sdAb moiety is fused to the C-terminus of the first light chain of the full-length antibody, and the N-terminus of the second anti-PD-1 sdAb moiety is fused to the C-terminus of the second light chain of the full-length antibody; and (j) the isolated anti-PD-1 construct comprises two anti-PD-1 sdAb moieties, wherein the C-terminus of the first anti-PD-1 sdAb moiety is fused to the N-terminus of the first light chain of the full-length antibody, and the C-terminus of the second anti-PD-1 sdAb moiety is fused to the N-terminus of the second light chain of the full-length antibody.

15. The isolated anti-PD-1 construct of claim 12, wherein the full-length antibody specifically recognizes TIGIT (anti-TIGIT full-length antibody), and wherein the anti-TIGIT full-length antibody comprises:
   (a) HC-CDR1, HC-CDR2, and HC-CDR3 of a heavy chain comprising the amino acid sequence of SEQ ID NO: 377, and LC-CDR1, LC-CDR2, and LC-CDR3 of a light chain comprising the amino acid sequence of SEQ ID NO: 378; or
   (b) a heavy chain comprising the amino acid sequence of SEQ ID NO: 377, and a light chain comprising the amino acid sequence of SEQ ID NO: 378.

16. An isolated anti-PD-1 construct comprising an anti-PD-1 sdAb moiety, wherein the anti-PD-1 sdAb moiety comprises CDR1, CDR2, and CDR3 of any one of SEQ ID NOs: 295 and 321-324.

\* \* \* \* \*